US011623924B2

(12) United States Patent
Bandarage et al.

(10) Patent No.: US 11,623,924 B2
(45) Date of Patent: Apr. 11, 2023

(54) MODULATORS OF ALPHA-1 ANTITRYPSIN

(71) Applicant: Vertex Pharmaceuticals Incorporated, Boston, MA (US)

(72) Inventors: Upul Keerthi Bandarage, Lexington, MA (US); Cavan McKeon Bligh, Melrose, MA (US); Michael John Boyd, Sharon, MA (US); Diane M. Boucher, South Hamilton, MA (US); Michael Aaron Brodney, Newton, MA (US); Veronique Damagnez, Boston, MA (US); Lev Tyler Dewey Fanning, San Marcos, CA (US); Mary Elizabeth Eccles, Cambridge, MA (US); Robert Francis Fimognari, Jr., Brookline, MA (US); Kevin James Gagnon, Burlington, MA (US); Pedro M. Garcia Barrantes, Melrose, MA (US); Simon Giroux, Cambridge, MA (US); Ronald Lee Grey, Jr., Mansfield, MA (US); Amy Beth Hall, Wellesley Hills, MA (US); Sarah Carol Hood, Worchester, MA (US); Dennis James Hurley, San Marcos, CA (US); Joshua Kennedy Hussey, Pepperell, MA (US); Mac Arthur Johnson, Jr., Derry, NH (US); Peter Jones, Sharon, MA (US); Sarathy Kesavan, Quincy, MA (US); Adam Looker, Aurburndale, MA (US); Brad D. Maxwell, Holliston, MA (US); John Patrick Maxwell, Hingham, MA (US); Ales Medek, Winchester, MA (US); Mettachit Navamal, Belmont, MA (US); Philippe Marcel Nuhant, Dorchester, MA (US); Setu Roday, Arlington, MA (US); Stefanie Roeper, Medford, MA (US); Rupa Sawant, Wayland, MA (US); Yi Shi, Natick, MA (US); Rebecca Jane Swett, Somerville, MA (US); Qing Tang, Boxborough, MA (US); Timothy Lewis Tapley, Cardiff, CA (US); Stephen A. Thomson, Del Mar, CA (US); Michael Waldo, Grafton, MA (US); Jinwang Xu, Framingham, MA (US); Kevin Michael Cottrell, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 16/593,118

(22) Filed: Oct. 4, 2019

(65) Prior Publication Data

US 2021/0179587 A1 Jun. 17, 2021

Related U.S. Application Data

(60) Provisional application No. 62/768,662, filed on Nov. 16, 2018, provisional application No. 62/742,148, filed on Oct. 5, 2018.

(51) Int. Cl.

| | |
|---|---|
| ***C07D 403/04*** | (2006.01) |
| ***C07D 519/00*** | (2006.01) |

(52) U.S. Cl.

CPC ......... *C07D 403/04* (2013.01); *C07D 519/00* (2013.01); *C07B 2200/05* (2013.01); *C07B 2200/13* (2013.01)

(58) Field of Classification Search

None

See application file for complete search history.

(56) References Cited

U.S. PATENT DOCUMENTS

| | | | |
|---|---|---|---|
| 2001/0051620 | A1 | 12/2001 | Berger et al. |
| 2003/0097000 | A1 | 5/2003 | Bovy et al. |
| 2016/0083363 | A1 | 3/2016 | Hamm et al. |
| 2020/0361939 | A1 | 11/2020 | Bandarage et al. |
| 2021/0260036 | A1 | 8/2021 | Bozic et al. |

FOREIGN PATENT DOCUMENTS

| | | | |
|---|---|---|---|
| CN | 107698505 | A | 2/2018 |
| CN | 110776459 | A | 2/2020 |
| EP | 0 465 398 | A2 | 1/1992 |
| EP | 1 396 488 | A1 | 3/2004 |
| EP | 3 699 179 | A1 | 8/2020 |
| JP | 2000-72751 | A | 3/2000 |
| JP | 2000-281654 | A | 10/2000 |
| WO | WO 2000/075114 | A1 | 12/2000 |
| WO | WO 2001/044197 | A2 | 6/2001 |
| WO | WO 2002/008224 | A1 | 1/2002 |
| WO | WO 2002/094790 | A1 | 11/2002 |
| WO | WO 2006/093823 | A1 | 9/2006 |
| WO | WO 2011/056222 | A1 | 5/2011 |

(Continued)

OTHER PUBLICATIONS

Grant & Hackh's Chemical Dictionary (5th Ed. 1987) at p. 148.*
Chemical Abstract Registry No. 2103889-64-9, indexed in the Registry File on STN CAS Online Jul. 27, 2017.*
Chemical Abstract Registry No. 1516110-75-0, indexed in the Registry File on STN CAS Online Jan. 10, 2014.*
Donawade, Dundappa S.et al., "Synthesis and antimicrobial activity of novel linearly fused 5-substituted-7-acetyl-2, 6-dimethyloxazolo [4,5-j] indoles", *Indian Journal of Chemistry*, Section B, Council of Scientific and Industrial Research, vol. 46B, Apr. 1, 2007, pp. 690-693.

(Continued)

*Primary Examiner* — Po-Chih Chen
(74) *Attorney, Agent, or Firm* — Finnegan, Henderson, Farabow, Garrett & Dunner, LLP

(57) ABSTRACT

Novel compounds, compositions, and methods of using and preparing the same, which may be useful for treating alpha-1 antitrypsin deficiency (AATD).

15 Claims, 17 Drawing Sheets
(15 of 17 Drawing Sheet(s) Filed in Color)

(56) References Cited

FOREIGN PATENT DOCUMENTS

| | | | |
|---|---|---|---|
| WO | WO 2011/110852 | A1 | 9/2011 |
| WO | WO 2016/154051 | A1 | 9/2016 |
| WO | WO 2017/197240 | | 11/2017 |
| WO | WO 2019/076336 | | 4/2019 |
| WO | WO 2019/089667 | A1 | 5/2019 |
| WO | WO 2019/116302 | A1 | 6/2019 |
| WO | WO 2019/149522 | A1 | 8/2019 |
| WO | WO 2019/243841 | A1 | 12/2019 |
| WO | WO 2020/033288 | A1 | 2/2020 |
| WO | WO 2020/081257 | A1 | 4/2020 |
| WO | WO 2020/247160 | A1 | 12/2020 |
| WO | WO 2021/067584 | A1 | 4/2021 |
| WO | WO 2021/155087 | A1 | 8/2021 |
| WO | WO 2021/203007 | A1 | 10/2021 |
| WO | WO 2021/203010 | A1 | 10/2021 |
| WO | WO 2021/203014 | A1 | 10/2021 |
| WO | WO 2021/203023 | A1 | 10/2021 |
| WO | WO 2021/203025 | A1 | 10/2021 |
| WO | WO 2021/203028 | A1 | 10/2021 |
| WO | WO 2022/026372 | A2 | 2/2022 |

OTHER PUBLICATIONS

Forbes, I.T. et al., "Synthesis, Biological Activity, and Molecular Modeling Studies of Selective 5-HT2C/2B Receptor Antagonists", *Journal of Medicinal Chemistry*, American Chemical Society, vol. 39, No. 25, Jan. 1, 1996, pp. 4966-4977.

International Search Report from International Application No. PCT/US2019/054681, dated Mar. 30, 2020.

Jiang, Hui, et al., Multiple Roles of the Pyrimidyl Group in the Rhodium-Catalyzed Regioselective Synthesis and Functionalization of Indole-3-carboxylic Acid Esters, *Advanced Synthesis & Catalysis*, vol. 358, No. 2, Jan. 21, 2016, pp. 188-194.

Maity, Soumitra et al., "A Visible-Light-Mediated Oxidative C?N Bond Formation/Aromatization Cascade: Photocatalytic Preparation of N-Arylindoles", *Angewandte Chemie, International Edition*, vol. 51, No. 38, Sep. 17, 2012, pp. 9562-9566.

Mali, Raghao S. et al., "Useful Syntheses of Pyrano- and Pyridoindoles", *Organic Preparations and Procedures International: The New Journal for Organic Synthesis*, vol. 26, No. 5, Oct. 1, 1994, pp. 573-577.

Meti, Puttavva et al., "Regioselective synthesis of dipyrrolopyrazine (DPP) Derivatives via metal free and metal catalyzed amination and investigation of their optical and thermal properties", *RSC Advances*, vol. 7, No. 29, Jan. 1, 2017, pp. 18120-18131.

Saccarello, Maria Luisa et al., "Á New Synthesis of 1-Alkyl-3-aminoindoles", *Synthesis*, vol. 1979, No. 09, Jan. 1, 1979, pp. 727-729.

Song, Xia et al., "Regioselective Synthesis of 2-Alkenylindoles and 2-Alkenylindole-3-carboxylates through the Cascade Reactions of N-Nitrosoanilines with Propargyl Alcohols", *Journal of Organic Chemistry*, vol. 83, No. 15, Aug. 3, 2018, pp. 8509-8521.

Vertex Provides Update on its Clinical Programs Targeting Alpha-1 Antitrypsin Deficiency, VERTEX (Oct. 14, 2020), https://news.vrtx.com/press-release/vertex-provides-update-its-clinical-programs-targeting-alpha-1-antitrypsin-deficiency (4 pages).

Vertex Announces Primary Endpoint Achieved in Phase 2 Study of VX-864 in Alpha-1 Antitrypsin Deficiency, VERTEX (Jun. 10, 2021), https://news.vrtx.com/press-release/vertex-announces-primary-endpoint-achieved-phase-2-study-vx-864-alpha-1-antitrypsin (5 pages).

American Thoracic Society & European Respiratory Society (2003) "American Thoracic Society/European Respiratory Society Statement: Standards for the Diagnosis and Management of Individuals with Alpha-1 Antitrypsin Deficiency," *Am J Respir Crit Care Med.*, 168:818-900.

Balle, T. et al. (2003) "Synthesis and Structure-Affinity Relationship Investigations of 5-Aminomethyl and 5-Carbamoyl Analogues of the Antipsychotic Sertindole. A New Class of Selective α1 Adrenoceptor Antagonists," *Bioorg. Med. Chem.*, 11:1065-1078.

Bergin, D.A. et al. (2014) "The circulating proteinase inhibitor alpha-1 antitrypsin regulates neutrophil degranulation and autoimmunity," *Sci Transl Med.*, 6(217):217ra1 (70 pages).

Fregonese, F. & J. Stolk (2008) "Hereditary alpha-1-antitrypsin deficiency and its clinical consequences," *Orphanet J. Rare Dis.*, 3:16 (9 pages).

Geraghty, P. et al. (Dec. 2014), "α1-Antitrypsin Activates Protein Phosphatase 2A to Counter Lung Inflammatory Responses," *Am J Respir Crit Care Med*, 190(11):1229-1242.

Gadaginamath, G.S. et al. (2000) "Chemoselective Reaction of 3,6-Diacetylindole Towards Hydroxylamine: Synthesis and Antimicrobial Activity of Novel Isoxazolo[4,5-f]indole Derivatives," *Rev. Roum. Chim.*, 45(10):929-933.

Ghorai, J. et al. (2016) "Cobalt(III)-Catalyzed Intramolecular Cross-Dehydrogenative C—H/X—H Coupling: Efficient Synthesis of Indoles and Benzofurans," *Chem. Eur. J.*, 22:16042-16046.

Ghorai, J. et al. (2018) "Divergent Functionalization of N-Alkyl-2-alkenylanilines: Efficient Synthesis of Substituted Indoles and Quinolines," *Chem. Asian J.*, 13(17):2499-2504.

Gosai, S. et al. (Nov. 2010) "Automated High-Content Live Animal Drug Screening Using C. elegans Expressing the Aggregation Prone Serpin αI-antitrypsin Z," *PLoS One*, 5(11):e15460 (16 pages).

International Search Report and Written Opinion for International Application No. PCT/US2020/032832, dated Oct. 27, 2020 (17 pages).

International Search Report and Written Opinion for International Application No. PCT/US2020/053777, dated Mar. 4, 2021 (11 pages).

International Search Report and Written Opinion for International Application No. PCT/US2021/015614, dated Apr. 29, 2021 (9 pages).

International Search Report and Written Opinion for International Application No. PCT/US2021/025616, dated Jun. 14, 2021 (12 pages).

International Search Report and Written Opinion for International Application No. PCT/US2021/025623, dated Jun. 14, 2021 (18 pages).

International Search Report and Written Opinion for International Application No. PCT/US2021/025597, dated Jun. 16, 2021 (13 pages).

Kamat, A.G. et al. (Mar. 1994), "Synthesis and Antimicrobial Activity of Furoindole Derivatives," *Indian J. Chem. Sect. B*, 33B(3):255-259.

Ogushi, F. et al. (1987) "Z-type α1-antitrypsin is less competent than M1-type α1-antitrypsin as an inhibitor of neutrophil elastase," *J Clin Invest.*, 80(5):1366-1374.

Piitulainen, E. & H.A. Tanash (2015), "The Clinical Profile of Subjects Included in the Swedish National Register on Individuals with Severe Alpha 1-Antitrypsin deficiency," *COPD*, 12(S1):36-41.

Tanash, H.A. et al. (2016) "Cause-specific mortality in individuals with severe alpha 1-antitrypsin deficiency in comparison with the general population in Sweden," *International Journal of COPD*, 2016(11):1663-1669.

Wen, W. et al. (2014) "Substituted indoles as selective protease activated receptor 4 (PAR-4) antagonists: Discovery and SAR of ML354," *Bioorg. Med. Chem. Lett.*, http://dx.doi.org/10.1016/j.bmcl.2014.08.021.

U.S. Appl. No. 17/060,945, filed Oct. 1, 2020, by Bozic et al.

U.S. Appl. No. 17/162,129, filed Jan. 29, 2021, by Bozic et al.

Akhapkina V.I. et al. "Fundamental bases of modulatory concept and classification of modulatory drugs" Russian Medical Journal, Issue 19, 2012, pp. 933-951 (Relevance statement only).

Belikov, V.G. "Pharmaceutical Chemistry", textbook, 2007, Moscow, MEDpress-inform, pp. 27-29 (Relevance statement only).

Chou, Tiny-Chao, "Drug Combination Studies and Their Synergy Quantification Using the Chou-Talalay Method", Cancer Res; 70(2), 2010, pp. 440-446.

Harkevich, D.A. Pharmacology/Textbook, 2010, 10th edition, pp. 72-82(Relevance statement only).

Kummerer, K.Pharmaceuticals in the environment, Annual Review of Environment and Resources, 2010, V.35, p. 57-75.

(56) References Cited

OTHER PUBLICATIONS

Kuznetsova, G.A. Methodological instructions, Irkutsk State University, Department of General Physics, 2005, p. 3, p. 2(Relevance statement only).
Mashkovsky, M.D. Drugs, 14th edition, vol. 1. Moscow., 2001, p. 11 (Relevance statement only).

* cited by examiner

MODULATORS OF ALPHA-1 ANTITRYPSIN

This application claims the benefit of U.S. Provisional Application No. 62/742,148, filed on Oct. 5, 2018, and of U.S. Provisional Application No. 62/768,662, filed on Nov. 16, 2018, the contents of each of which are incorporated by reference in their entirety.

The disclosure provides compounds that are capable of modulating alpha-1 antitypsin (AAT) activity and methods of treating alpha-1 antitrypsin deficiency (AATD) by administering one or more such compounds.

AATD is a genetic disorder characterized by low circulating levels of AAT. While treatments for AATD are improving, there is currently no cure. AAT is produced primarily in the liver and secreted into the blood. AAT inhibits a number of serine proteases secreted by inflammatory cells (most notably neutrophil elastase [NE]) and thus protects organs such as the lung from protease-induced damage, especially during periods of inflammation.

The mutation most commonly associated with AATD involves a substitution of lysine for glutamic acid (E342K) in the SERPINA1 gene that encodes the AAT protein. This mutation, known as the Z mutation, leads to misfolding of the translated protein, which polymerizes within cells and is not secreted into the bloodstream. Consequently, circulating AAT levels in individuals homozygous for the Z mutation (PiZZ) are markedly reduced; only approximately 15% of mutant Z AAT protein folds correctly and is secreted by the cell. An additional consequence of the Z mutation is that the secreted Z-AAT has reduced activity compared to wild-type protein, with 40% to 80% of normal antiprotease activity (American thoracic society/European respiratory society, Am J Respir Crit Care Med. 2003; 168(7):818-900; and Ogushi et al. J Clin Invest. 1987; 80(5):1366-74).

The accumulation of polymerized Z-AAT protein within hepatocytes causes cytotoxicity that can result in cirrhosis or liver cancer later in life and neonatal liver disease in 12% of patients. This accumulation may spontaneously remit but can be fatal in a small number of children. The deficiency of circulating AAT results in unregulated protease activity that degrades lung tissue over time, resulting in emphysema, a form of chronic obstructive pulmonary disease (COPD). This effect is severe in PiZZ individuals and typically manifests in middle age, resulting in a decline in quality of life and shortened lifespan (mean 68 years of age) (Tanash et al. Int J Chron Obstruct Pulm Dis. 2016; 11:1663-9). The effect is most pronounced in PiZZ individuals who smoke, resulting in an even further shortened lifespan (58 years). Piitulainen and Tanash, COPD 2015; 12(1):36-41. PiZZ individuals account for the majority of those with clinically relevant AATD lung disease. Accordingly, there is a need for additional and effective treatments for AATD.

A milder form of AATD is associated with a mutation known as the SZ mutation, which results in clinically significant lung disease but not liver disease. Fregonese and Stolk, Orphanet J Rare Dis. 2008; 33:16. As with the ZZ mutation, the deficiency of circulating AAT in subjects with the SZ mutation results in unregulated protease activity that degrades lung tissue over time and can result in emphysema, particularly in smokers.

The current standard of care for AAT deficient individuals who have or show signs of developing significant lung or liver disease is augmentation therapy or enzyme replacement therapy. Augmentation therapy involves administration of a pooled, purified human plasma protein concentrate to augment the missing AAT. Although infusions of the plasma protein have been shown to improve survival or slow the rate of emphysema progression, augmentation therapy is often not sufficient under challenging conditions. Similarly, although enzyme replacement therapy shows promise in delaying progression of disease, only 2% of the administered drug reaches the lungs. In addition, replacement enzyme therapy requires weekly visits for treatment. Thus, there is a continuing need for new and more effective treatments for AATD.

One aspect of the invention provides compounds of Formulae I, 1-6, 3-4, 3-5, 3-6, 4-3, 5-3, 6-4, 7-4, 8-4, 12-1, 12-2, II, and III as well as tautomers of those compounds, pharmaceutically acceptable salts of those compounds and their tautomers, and deuterated derivatives of any of the foregoing that can be employed in the treatment of AATD. For example, compounds of Formula I can be depicted as:

(I)

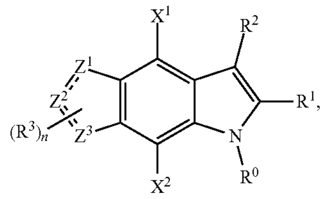

wherein:

$R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy;

(ii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iii) $R^2$ is chosen from:
hydrogen,
cyano,
halogens,
alkylamide groups,
$C_1$-$C_8$ linear, branched, and cyclic alkyl groups optionally substituted with an oxo group,
a $C_1$-$C_8$ linear, branched, and cyclic alkoxy group,
a 5- or 6-membered heteroaryl group,
a cyano group,
an amino group,
an aminoalkyl group,
an alkylamide group,
an alkylsulfonyl group,
an alkylsulfonamide group,
an alkylsulfoxide group,
a group

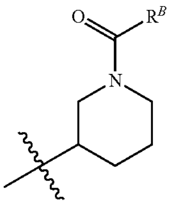
or
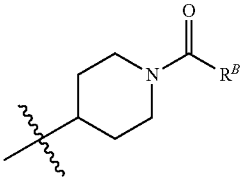

wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group,
a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group,
a

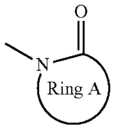

group wherein the Ring A is chosen from 4-8 membered rings optionally comprising one or two heteroatoms in addition to the Ring A nitrogen, or
a carboxylic acid group esterified with a uronic acid,
$C_2$-$C_6$ linear, branched, and cyclic alkenyl groups,
$C_2$-$C_6$ linear, branched, and cyclic alkynyl groups,
A-$CO_2R^4$ groups wherein A is optionally present and if present is chosen from
$C_1$-$C_8$ linear, branched, and cyclic alkyl and alkoxy groups,
$C_2$-$C_6$ linear, branched, and cyclic alkenyl groups,
$C_3$-$C_8$ cycloalkyl linked to $C_1$-$C_8$ linear or branched alkyl groups,
$C_1$-$C_8$ linear or branched alkyl linked to $C_3$-$C_8$ cycloalkyl groups,
$C_3$-$C_8$ cycloalkyl linked to $C_3$-$C_8$ cycloalkyl groups,
$C_1$-$C_8$ linear, branched, and cyclic alkyl linked to $C_3$-$C_8$ cycloalkyl linked to
a $C_1$-$C_8$ linear, branched, and cyclic alkyl groups,
wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and
wherein $R^4$ is chosen from hydrogen, $C_1$-$C_8$ linear, branched, and cyclic alkyl groups, and $C_2$-$C_6$ linear, branched, and cyclic alkenyl groups,
A-$C(O)NH_2$ groups wherein A is optionally present and if present is chosen from
$C_1$-$C_8$ linear, branched, and cyclic alkyl and alkoxy groups,
$C_2$-$C_6$ linear, branched, and cyclic alkenyl groups,
$C_3$-$C_8$ cycloalkyl linked to $C_1$-$C_8$ linear or branched alkyl groups,
$C_1$-$C_8$ linear or branched alkyl linked to $C_3$-$C_8$ cycloalkyl groups,
$C_3$-$C_8$ cycloalkyl linked to $C_3$-$C_8$ cycloalkyl groups,
$C_1$-$C_8$ linear, branched, and cyclic alkyl linked to $C_3$-$C_8$ cycloalkyl linked to
a $C_1$-$C_8$ linear, branched, and cyclic alkyl groups,
wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and
wherein $R^4$ is chosen from hydrogen, $C_1$-$C_8$ linear, branched, and cyclic alkyl groups, and $C_2$-$C_6$ linear, branched, and cyclic alkenyl groups,
$C(O)NR^6R^7$ wherein $R^6$ and $R^7$ are independently chosen from hydrogen,
$C_1$-$C_8$ linear, branched, and cyclic alkyl groups,
$C_2$-$C_6$ linear, branched, and cyclic alkenyl groups,
4- to 8-membered heterocycles optionally substituted by one or more substituents chosen from cyano, halogens, $C_1$-$C_8$ linear, branched, and cyclic alkyl groups, and $C_2$-$C_6$ linear, branched, and cyclic alkenyl groups,
or $R^6$ and $R^7$ together with the nitrogen to which they are attached form a 4-8 membered ring optionally comprising one or two heteroatoms in addition to the nitrogen to which they are attached, and which ring is optionally substituted with a substituent chosen from halogens, cyano, hydroxy, and $C_1$-$C_6$ linear, branched, and cyclic alkyl groups,
$SO_2R^5$ groups wherein $R^5$ is chosen from $C_1$-$C_8$ linear, branched, and cyclic alkyl groups, and $C_2$-$C_6$ linear, branched, and cyclic alkenyl groups, and

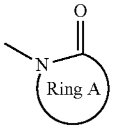

groups wherein the Ring A is a 4-8 membered ring optionally comprising one or two heteroatoms in addition to the Ring A nitrogen;
(iv) $X^1$ and $X^2$ are independently chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(v) each ⎓ represents a single or double bond, provided that no more than one ⎓ is a double bond;

(vi) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 halogens;

(vii) n is an integer chosen from 0, 1, 2, and 3; and (viii) $Z^1$, $Z^2$, and $Z^3$ are independently chosen from carbon, nitrogen, sulfur, and oxygen, wherein when $Z^1$, $Z^2$, and/or $Z^3$ are carbon or nitrogen, the valences of carbon and nitrogen are completed with hydrogen atoms, $C_1$-$C_8$ linear, branched, and cyclic alkyls, or cyano. For example, compounds of Formula II can be depicted as:

(II)

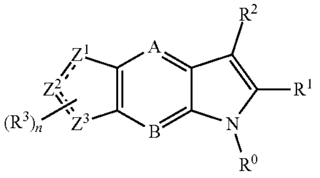

a tautomer thereof, a pharmaceutically acceptable salt of any of the foregoing, or a deuterated derivative of any of the foregoing;

wherein:

(i) A and B are each independently chosen from N and C—$X^1$ (ii) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy;

(iii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iv) $R^2$ is chosen from:

hydrogen, cyano, halogens, alkylamide groups, $C_1$-$C_8$ linear, branched, and cyclic alkyl groups optionally substituted with an oxo group, a $C_1$-$C_8$ linear, branched, and cyclic alkoxy group, a 5- or 6-membered heteroaryl group, a cyano group, an amino group, an aminoalkyl group, an alkylamide group, an alkylsulfonyl group, an alkylsulfonamide group, an alkylsulfoxide group, a group

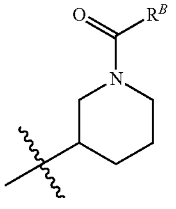

or

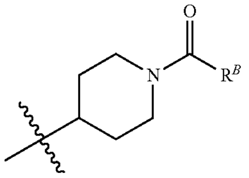

wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group, a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group.

a

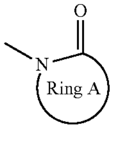

group wherein the Ring A is chosen from 4-8 membered rings optionally comprising one or two heteroatoms in addition to the Ring A nitrogen, and/or a carboxylic acid group esterified with a uronic acid, $C_2$-$C_6$ linear, branched, and cyclic alkenyl groups, $C_2$-$C_6$ linear, branched, and cyclic alkynyl groups, A-$CO_2R^4$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, A-C(O)$NH_2$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, C(O)$NR^6R^7$ wherein $R^6$ and $R^7$ are independently chosen from hydrogen, $C_1$-$C_8$ linear, branched, and cyclic alkyl groups, $C_2$-$C_6$ linear, branched, and cyclic alkenyl groups, 4- to 8-membered heterocycles optionally substituted by one or more substituents chosen from cyano, halogens, $C_1$-$C_8$ linear, branched, and cyclic alkyl groups, and $C_2$-$C_6$ linear, branched, and cyclic alkenyl groups, or $R^6$ and $R^7$ together with the nitrogen to which they are attached form a 4-8 membered ring optionally comprising one or two heteroatoms in addition to the nitrogen to which they are attached, and which ring is optionally substituted with a substituent chosen from halogens, cyano, hydroxy, and $C_1$-$C_6$ linear, branched, and cyclic alkyl groups, $SO_2R^5$ groups wherein $R^5$ is chosen from $C_1$-$C_8$ linear, branched, and cyclic alkyl groups, and $C_2$-$C_6$ linear, branched, and cyclic alkenyl groups, and

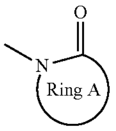

groups wherein the Ring A is a 4-8 membered ring optionally comprising one or two heteroatoms in addition to the Ring A nitrogen;

(v) $X^1$ is chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(vi) each ═══ represents a single or double bond, provided that no more than one ═══ is a double bond;

(vii) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 halogens;

(viii) n is an integer chosen from 0, 1, 2, and 3; and (ix) $Z^1$, $Z^2$, and $Z^3$ are independently chosen from carbon, nitrogen, sulfur, and oxygen, wherein when $Z^1$, $Z^2$, and/or $Z^3$ are carbon or nitrogen, the valences of carbon and nitrogen are completed with hydrogen atoms, $C_1$-$C_8$ linear, branched, and cyclic alkyls, or cyano.

For example, compounds of Formula III can be depicted as:

(III)

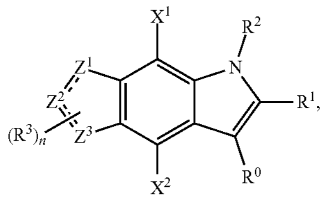

a tautomer thereof, a pharmaceutically acceptable salt of any of the foregoing, or a deuterated derivative of any of the foregoing;

wherein:

(i) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy;

(ii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iii) $R^2$ is chosen from:

hydrogen, cyano, halogens, alkylamide groups, $C_1$-$C_8$ linear, branched, and cyclic alkyl groups optionally substituted with an oxo group, a $C_1$-$C_8$ linear, branched, and cyclic alkoxy group, a 5- or 6-membered heteroaryl group, a cyano group, an amino group, an aminoalkyl group, an alkylamide group, an alkylsulfonyl group, an alkylsulfonamide group, an alkylsulfoxide group, a group

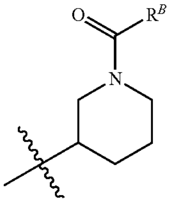

or

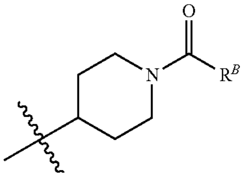

wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group, a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group.

a

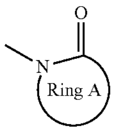

group wherein the Ring A is chosen from 4-8 membered rings optionally comprising one or two heteroatoms in addition to the Ring A nitrogen, and/or a carboxylic acid group esterified with a uronic acid, $C_2$-$C_6$ linear, branched, and cyclic alkenyl groups, $C_2$-$C_6$ linear, branched, and cyclic alkynyl groups, A-$CO_2R^4$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, A-C(O)$NH_2$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, C(O)$NR^6R^7$ wherein $R^6$ and $R^7$ are independently chosen from hydrogen, $C_1$-$C_8$ linear, branched, and cyclic alkyl groups, $C_2$-$C_6$ linear, branched, and cyclic alkenyl groups, 4- to 8-membered heterocycles optionally substituted by one or more substituents chosen from cyano, halogens, $C_1$-$C_8$ linear, branched, and cyclic alkyl groups, and $C_2$-$C_6$ linear, branched, and cyclic alkenyl groups, or $R^6$ and $R^7$ together with the nitrogen to which they are attached form a 4-8 membered ring optionally comprising one or two heteroatoms in addition to the nitrogen to which they are attached, and which ring is optionally substituted with a substituent chosen from halogens, cyano, hydroxy, and $C_1$-$C_6$ linear, branched, and cyclic alkyl groups, $SO_2R^5$ groups wherein $R^5$ is chosen from $C_1$-$C_8$ linear, branched, and cyclic alkyl groups, and $C_2$-$C_6$ linear, branched, and cyclic alkenyl groups, and

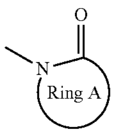

groups wherein the Ring A is a 4-8 membered ring optionally comprising one or two heteroatoms in addition to the Ring A nitrogen;

(iv) $X^1$ and $X^2$ are independently chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(v) each $\equiv$ represents a single or double bond, provided that no more than one $\equiv$ is a double bond;

(vi) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 halogens;

(vii) n is an integer chosen from 0, 1, 2, and 3; and (viii) $Z^1$, $Z^2$, and $Z^3$ are independently chosen from carbon, nitrogen, sulfur, and oxygen, wherein when $Z^1$, $Z^2$, and/or $Z^3$ are carbon or nitrogen, the valences of carbon and nitrogen are completed with hydrogen atoms, $C_1$-$C_8$ linear, branched, and cyclic alkyls, or cyano.

In one aspect of the invention the compounds of Formulae I, II, and III are selected from Compounds 1-215, as well as tautomers of those compounds, pharmaceutically acceptable salts of those compounds and their tautomers, and deuterated derivatives of any of the foregoing that can be employed in the treatment of AATD.

In some embodiments, the invention provides pharmaceutical compositions comprising at least one compound of selected from compounds of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing. In some embodiments, the pharmaceutical compositions may comprise a compound selected from Compounds 1-215, tautomers of those compounds, pharmaceutically acceptable salts of those compounds and their tautomers, and deuterated derivatives of any of the foregoing. These compositions may further include at least one additional active pharmaceutical ingredient and/or at least one carrier.

Another aspect of the invention provides methods of treating AATD comprising administering to a subject in need thereof, at least one compound of selected from compounds of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing or a pharmaceutical composition comprising the at least one compound. In some embodiments, the methods comprise administering a compound selected from Compounds 1-215, tautomers of those compounds, pharmaceutically acceptable salts of those compounds and their tautomers, and deuterated derivatives of any of the foregoing.

In some embodiments, the methods of treatment include administration of at least one additional active agent to the subject in need thereof, either in the same pharmaceutical composition as the at least one compound of selected from compounds of Formulae I, 1-6, 3-4, 3-5, 3-6, 4-3, 5-3, 6-4, 7-4, 8-4, 12-1, 12-2, II, and III tautomers of those compounds, pharmaceutically acceptable salts of those compounds and their tautomers, and deuterated derivatives of any of the foregoing, or as separate compositions. In some embodiments, the methods comprise administering a compound selected from Compounds 1-215, tautomers of those compounds, pharmaceutically acceptable salts of those compounds and their tautomers, and deuterated derivatives of any of the foregoing with at least one additional active agent either in the same pharmaceutical composition or in a separate composition. In some embodiments, the subject in need of treatment carries the ZZ mutation. In some embodiments, the subject in need of treatment carries the SZ mutation.

In some embodiments, the methods of treatment include administration of at least one additional active agent to the subject in need thereof, either in the same pharmaceutical composition as the at least one compound of selected from compounds of Formulae I, 1-6, 3-4, 3-5, 3-6, 4-3, 5-3, 6-4, 7-4, 8-4, 12-1, 12-2, II, and III tautomers of those compounds, pharmaceutically acceptable salts of those compounds and their tautomers, and deuterated derivatives of any of the foregoing, or as separate compositions, wherein the additional active agent is alpha-1 antitrypsin protein (AAT) from the blood plasma of healthy human donors. In some embodiments, the methods comprise administering a compound selected from Compounds 1-215, tautomers of those compounds, pharmaceutically acceptable salts of those compounds and their tautomers, and deuterated derivatives of any of the foregoing with at least one additional active agent either in the same pharmaceutical composition or in a separate composition, wherein the additional active agent is alpha-1 antitrypsin protein (AAT) from the blood plasma of healthy human donors.

In some embodiments, the methods of treatment include administration of at least one additional active agent to the subject in need thereof, either in the same pharmaceutical composition as the at least one compound of selected from compounds of Formulae I, 1-6, 3-4, 3-5, 3-6, 4-3, 5-3, 6-4, 7-4, 8-4, 12-1, 12-2, II, and III tautomers of those compounds, pharmaceutically acceptable salts of those compounds and their tautomers, and deuterated derivatives of any of the foregoing, or as separate compositions, wherein the additional active agent is recombinant AAT. In some embodiments, the methods comprise administering a compound selected from Compounds 1-215, tautomers of those compounds, pharmaceutically acceptable salts of those compounds and their tautomers, and deuterated derivatives of any of the foregoing with at least one additional active agent either in the same pharmaceutical composition or in a separate composition, wherein the additional active agent is recombinant AAT.

Also provided are methods of modulating AAT, comprising administering to a subject in need thereof, at least one compound of selected from compounds of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing or a pharmaceutical composition comprising the at least one compound, tautomer, salt, or deuterated derivative. In some embodiments, the methods of modulating AAT comprise administering at least one compound selected from Compounds 1-215, tautomers of those compounds, pharmaceutically acceptable salts of those compounds and their tautomers, and deuterated derivatives of any of the foregoing or a pharmaceutical composition comprising the at least one compound, tautomer, salt, or deuterated derivative.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

I. Definitions

Figure 1:
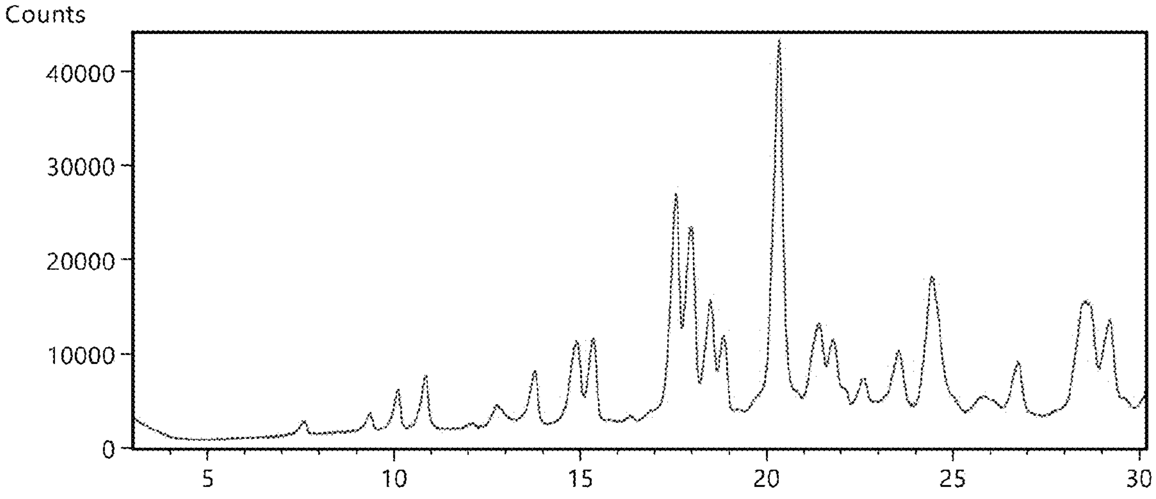
FIG. 1 depicts an XRPD diffractogram of a mixture of crystalline Form A of Compound 32 and crystalline Form C of Compound 32

The term "AAT" as used herein means alpha-1 antitrypsin or a mutation thereof, including, but not limited to, the AAT gene mutations such as Z mutations. As used herein, "Z-AAT" means AAT mutants which have the Z mutation.

As used herein, "mutations" can refer to mutations in the SERPINA1 gene (the gene encoding AAT) or the effect of alterations in the gene sequence on the AAT protein. A "SERPINA1 gene mutation" refers to a mutation in the SERPINA1 gene, and an "AAT protein mutation" refers to a mutation that results in an alteration in the amino acid sequence of the AAT protein. A genetic defect or mutation, or a change in the nucleotides in a gene in general, results in a mutation in the AAT protein translated from that gene.

As used herein, a patient who is "homozygous" for a particular gene mutation has the same mutation on each allele.

As used herein, a patient who has the PiZZ genotype is a patient who is homozygous for the Z mutation in the AAT protein.

The term "AATD" as used herein means alpha-1 antitrypsin deficiency, which is a genetic disorder characterized by low circulating levels of AAT.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

Compounds of the invention may optionally be substituted with one or more substituents. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from a specific compound of this disclosure only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$ are within the scope of this disclosure.

Unless otherwise indicated, structures depicted herein are also meant to include all isomeric forms of the structure, e.g., racemic mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of a compound that exist together in equilibrium, and are readily interchanged by migration of an atom or group within the molecule.

"Stereoisomer" refers to both enantiomers and diastereomers.

As used herein, "deuterated derivative" refers to a compound having the same chemical structure as a reference compound, but with one or more hydrogen atoms replaced by a deuterium atom ("D"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of a compound of the invention, at least one hydrogen is replaced with deuterium at well above its natural isotopic abundance (which is typically about 0.015%). In some embodiments, the deuterated derivatives of the invention have an isotopic enrichment factor for each deuterium atom, of at least 3500 (52.5% deuterium incorporation at each designated deuterium) at least 4500, (67.5% deuterium incorporation), at least 5000 (75% deuterium incorporation) at least 5500 (82.5% deuterium incorporation), at least 6000 (90% deuterium incorporation), at lease 6333.3 (95% deuterium incorporation, at least 6466.7 (97% deuterium incorporation, or at least 6600 (99% deuterium incorporation).

The term "isotopic enrichment factor" as used herein means the ratio between the isotopic abundance and the natural abundance of a specified isotope.

The term "alkyl," or "aliphatic" as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic that has a single point of attachment to the rest of the molecule. Unless otherwise specified, alkyl groups contain 1-20 alkyl carbon atoms. In some embodiments, alkyl groups contain 1-10 aliphatic carbon atoms. In other embodiments, alkyl groups contain 1-8 aliphatic carbon atoms. In still other embodiments, alkyl groups contain 1-6 alkyl carbon atoms, in other embodiments alkyl groups contain 1-4 alkyl carbon atoms, and in yet other embodiments alkyl groups contain 1-3 alkyl carbon atoms. Nonlimiting examples of alkyl groups include, but are not limited to, linear or branched, substituted or unsubstituted alkyl, alkenyl, alkynyl groups and hybrids thereof, such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The terms "cycloalkyl," "carbocycle," "cycloaliphatic," or "cyclic alkyl" refer to a spirocyclic or monocyclic $C_{3-8}$ hydrocarbon or a spirocyclic, bicyclic, bridged bicyclic, tricyclic, or bridged tricyclic $C_{8-14}$ hydrocarbon that is completely saturated or that contains one or more units of unsaturation, but which is not aromatic, wherein any individual ring in said bicyclic ring system has 3-7 members.

The term "heteroalkyl," or "heteroaliphatic" as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "alkenyl" as used herein, means a straight-chain (i.e., unbranched), branched, substituted or unsubstituted hydrocarbon chain that contains one or more units of saturation, or a monocyclic hydrocarbon or bicyclic hydrocarbon that contains one or more units of unsaturation, but which is not aromatic (referred to herein as, "cyclic alkenyl").

The term "heterocycle", "heterocyclyl", "heterocycloaliphatic", or "heterocyclic" as used herein means non-aromatic, monocyclic, bicyclic, or tricyclic ring systems in which one or more ring members is an independently chosen heteroatom. In some embodiments, the "heterocycle", "heterocyclyl", "heterocycloaliphatic", or "heterocyclic" group has three to fourteen ring members in which one or more ring members is a heteroatom independently chosen from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, wherein one carbon of the alkyl group is replaced by an oxygen ("alkoxy") or sulfur ("thioalkyl") atom, respectively, provided that the oxygen and sulfur atoms are linked between two carbon atoms. A "cyclic alkoxy" refers to a monocyclic, spirocyclic, bicyclic, bridged bicyclic, tricyclic, or bridged tricyclic hydrocarbon that contains at least one alkoxy group, but is not aromatic. Non-limiting examples of cyclic alkyoxy groups include tetrahydropyranyl, tetrahydrofuranyl, oxetanyl, 8-oxabicyclo[3.2.1]octanyl, and oxepanyl.

The terms "haloalkyl" and "haloalkoxy" means an alkyl or alkoxy, as the case may be, which is substituted with one or more halogen atoms. The term "halogen" or means F, Cl, Br, or I. Examples of haloalkyls include $-CHF_2$, $-CH_2F$, $-CF_3$, $-CF_2-$, or perhaloalkyl, such as, $-CF_2CF_3$.

The term "aminoalkyl" means an alkyl group which is substituted with or contains an amino group. As used herein, an "amino" refers to a group which is a primary, secondary, or tertiary amine.

The term "alkylsulfoxide" means an alkyl group in which a carbon of said alkyl group is replaced by or substituted with a sulfoxide group. A "cyclic alkylsulfoxide" refers to a monocyclic hydrocarbon or bicyclic hydrocarbon that contains one or more alkylsulfoxides, but is not aromatic. As used herein, "sulfoxide" means a sulfinyl (i.e., —S(O)—) which is attached to two carbon atoms.

The term "alkylsulfinamide" means an alkyl group in which a carbon of said alkyl group is replaced by or substituted with a sulfinamide group. As used herein, "sulfinamide" refers to —S(O)—, in which the sulfur atom is independently attached to an amine group and attached to carbon.

The term "alkylsulfonyl" means an alkyl group in which a carbon of said alkyl group is replaced by or substituted with a sulfonyl group. As used herein, "sulfonyl" refers to $-S(O)_2-$, wherein the sulfur is attached to a carbon and also attached to a different carbon.

The term "alkylsulfonamide" means an alkyl group in which a carbon of said alkyl group is replaced by or substituted with a sulfonamide group. As used herein, a "sulfonamide" refers to a $-S(O)_2-$ wherein the sulfur is attached to an amine group and also attached to carbon.

The term "alkylamide" means an alkyl group in which a carbon of said alkyl group is replaced with an amide. As used herein, "amide" refers to a carbonyl (i.e., —C(O)—) that is attached to an amine group and also attached to carbon.

As used herein, an "oxo" group refers to =O.

As used herein, a "cyano" or "nitrile" groups refers to —C≡N.

As used herein, a "hydroxy" group refers to —OH.

"Tert" and "t-" each refer to tertiary.

As used herein, "aromatic groups" or "aromatic rings" refer to chemical groups that contain conjugated, planar ring systems with delocalized pi electron orbitals comprised of [4n+2] p orbital electrons, wherein n is an integer ranging from 0 to 6. Nonlimiting examples of aromatic groups include aryl and heteroaryl groups.

The term "aryl" used alone or as part of a larger moiety as in "arylalkyl", "arylalkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" also refers to heteroaryl ring systems as defined herein below. Nonlimiting examples of aryl groups include phenyl rings.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members.

An aryl (including arylalkyl, arylalkoxy, aryloxyalkyl and the like) or heteroaryl (including heteroarylalkyl and heteroarylalkoxy and the like) group may contain one or more substituents.

An alkyl group, or a non-aromatic heterocyclic ring may contain one or more substituents.

Examples of useful protecting groups for nitrogen-containing groups, such as amine groups, include, for example, t-butyl carbamate (Boc), benzyl (Bn), tetrahydropyranyl (THP), 9-fluorenylmethyl carbamate (Fmoc) benzyl carbamate (Cbz), acetamide, trifluoroacetamide, triphenylmethylamine, benzylideneamine, and p-toluenesulfonamide. Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis, 3rd Edition* (John Wiley & Sons, New York, 1999).

Examples of suitable solvents that may be used in this disclosure include, but not limited to, water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Examples of suitable bases that may be used in this disclosure include, but not limited to, 1,8-diazabicyclo [5.4.0]undec-7-ene (DBU), potassium tert-butoxide (KOtBu), sodium tert-butoxide (NaOtBu), sodium tert-amylate (NaOt-Amyl), potassium carbonate ($K_2CO_3$), N-methylmorpholine (NMM), triethylamine ($Et_3N$; TEA), diisopropyl-ethyl amine ($i-Pr_2EtN$; DIPEA), pyridine, potassium hydroxide (KOH), sodium hydroxide (NaOH), lithium hydroxide (LiOH) and sodium methoxide (NaOMe; $NaOCH_3$).

The disclosure includes pharmaceutically acceptable salts of the compounds of the invention. A salt of a compound of is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences,* 1977, 66, 1-19. For example, Table 1 of that article provides the following pharmaceutically acceptable salts:

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucos amine salts.

The terms "patient" and "subject" are used interchangeably and refer to an animal including a human.

The terms "effective dose" and "effective amount" are used interchangeably herein and refer to that amount of a compound that produces the desired effect for which it is administered (e.g., improvement in AATD or a symptom of AATD, lessening the severity of AATD or a symptom of AATD, and/or reducing the rate of onset or incidence of AATD or a symptom of AATD). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the term "treatment" and its cognates refer to improving AATD or its symptoms in a subject, delaying the onset of AATD or its symptoms in a subject, or lessening the severity of AATD or its symptoms in a subject. "Treatment" and its cognates as used herein, include, but are not limited to the following: improved liver and/or spleen function, lessened jaundice, improved lung function, lessened lung diseases and/or pulmonary exacerbations (e.g., emphysema), lessened skin disease (e.g., necrotizing panniculitis), increased growth in children, improved appetite, and reduced fatigue. Improvements in or lessening the severity of any of these symptoms can be readily assessed according to methods and techniques known in the art or subsequently developed.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

Any one or more of the compounds of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing may be administered once daily, twice daily, or three times daily for the treatment of AATD. In some embodiments, the any one or more compounds are selected from Compounds 1-215, tautomers of those compounds, pharmaceutically acceptable salts of those compounds and their tautomers, and deuterated derivatives of any of the foregoing. In some embodiments, at least one compound chosen from compounds of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing is administered once daily. In some embodiments, a compound selected from Compounds 1-215, tautomers of those compounds, pharmaceutically acceptable salts of those compounds and their tautomers, and deuterated derivatives of any of the foregoing is administered once daily. In some embodiments, at least one compound chosen from compounds of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing are administered twice daily. In some embodiments, a compound selected from Compounds 1-215, tautomers of those compounds, pharmaceutically acceptable salts of those compounds and their tautomers, and deuterated derivatives of any of the foregoing is administered twice daily. In some embodiments, at least one compound chosen from compounds of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing are administered three times daily. In some embodiments, a compound selected from Compounds 1-215, tautomers of those compounds, pharmaceutically acceptable salts of those compounds and their tautomers, and deuterated derivatives of any of the foregoing is administered three times daily.

Any one or more of the compounds of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing may be administered in combination with AAT augmentation therapy or AAT replacement therapy for the treatment of AATD. In some embodiments, the any one or more compounds are selected from Compounds 1-215, tautomers of those compounds, pharmaceutically acceptable salts of those compounds and their tautomers, and deuterated derivatives of any of the foregoing.

As used herein, "AAT augmentation therapy" refers to the use of alpha-1 antitrypsin protein (AAT) from the blood plasma of healthy human donors to augment (increase) the alpha-1 antitrypsin levels circulating in the blood. "AAT replacement therapy" refers to administration of recombinant AAT.

In some embodiments, 10 mg to 1,500 mg, 100 mg to 1800 mg, 100 mg to 500 mg, 200 mg to 600 mg, 200 mg to 800 mg, 400 mg to 2,000 mg, 400 mg to 2,500 mg or 400 mg to 600 mg of a compound of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, or deuterated derivatives of such compound, tautomer, or salt are administered once daily, twice daily, or three times daily. In some embodiments, 10 mg to 1,500 mg, 100 mg to 1800 mg, 100 mg to 500 mg, 200 mg to 600 mg, 200 mg to 800 mg, 400 mg to 2000 mg, or 400 mg to 600 mg of a compound selected from Compounds 1-215, tautomers of those compounds, pharmaceutically acceptable salts of those compounds and their tautomers, or deuterated derivatives of such compound, tautomer, or salt are administered once daily, twice daily, or three times daily.

One of ordinary skill in the art would recognize that, when an amount of a compound is disclosed, the relevant amount of a pharmaceutically acceptable salt form of the compound is an amount equivalent to the concentration of the free base of the compound. It is noted that the disclosed amounts of the compounds, tautomers, pharmaceutically acceptable salts, and deuterated derivatives are based upon the free base form of the reference compound. For example, "10 mg of at least one compound chosen from compounds of Formula (I) and pharmaceutically acceptable salts thereof" includes 10 mg of a compound of Formula (I) and a concentration of a pharmaceutically acceptable salt of compounds of Formula (I) equivalent to 10 mg of compounds of Formula (I).

As used herein, the term "ambient conditions" means room temperature, open air condition and uncontrolled humidity condition.

As used herein, the terms "crystalline form" and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, solid state nuclear magnetic resonance (SSNMR), differential scanning calorimetry (DSC), dynamic vapor sorption (DVS), and/or thermogravimetric analysis (TGA). Accordingly, as used herein, the terms "crystalline Form [X] of Compound ([Y])" and "crystalline Form [C] of a [pharmaceutically acceptable] salt of Compound ([Y])" refer to unique crystalline forms that can be identified and distinguished from each other by one or more characterization techniques including, for example, X-ray powder diffraction (XRPD), single crystal X-ray diffraction, SSNMR, differential scanning calorimetry (DSC), dynamic vapor sorption (DVS), and/or thermogravimetric analysis (TGA). In some embodiments, the novel crystalline forms are characterized by an X-ray powder diffractogram having one or more signals at one or more specified two-theta values (° 2θ).

As used herein, the terms "solvate" refers to a crystal form comprising one or more molecules of a compound of the present disclosure and, incorporated into the crystal lattice, one or more molecules of a solvent or solvents in stoichiometric or nonstoichiometric amounts. When the solvent is water, the solvate is referred to as a "hydrate".

As used herein, the term "SSNMR" refers to the analytical characterization method of solid state nuclear magnetic resonance. SSNMR spectra can be recorded at ambient conditions on any magnetically active isotope present in the sample. The typical examples of active isotopes for small molecule active pharmaceutical ingredients include $^{1}H$, $^{2}H$, $^{13}C$, $^{19}F$, $^{31}P$, $^{15}N$, $^{14}N$, $^{35}Cl$, $^{11}B$, $^{7}Li$, $^{17}O$, $^{23}Na$, $^{79}Br$, and $^{195}Pt$.

As used herein, the term "XRPD" refers to the analytical characterization method of X-ray powder diffraction. XRPD patterns can be recorded at ambient conditions in transmission or reflection geometry using a diffractometer.

As used herein, the terms "X-ray powder diffractogram," "X-ray powder diffraction pattern," "XRPD pattern" interchangeably refer to an experimentally obtained pattern plotting signal positions (on the abscissa) versus signal intensities on the ordinate). For an amorphous material, an X-ray powder diffractogram may include one or more broad signals; and for a crystalline material, an X-ray powder diffractogram may include one or more signals, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . . " and/or "a signal at at least . . . two-theta value(s) chosen from . . . ."

A "signal" or "peak" as used herein refers to a point in the XRPD pattern where the intensity as measured in counts is at a local. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta," "a signal at [a] two-theta value[ ] of . . . " and/or "a signal at at least . . . two-theta value(s) chosen from . . . " refer to X-ray reflection positions as measured and observed in X-ray powder diffraction experiments (° 2θ).

The repeatability of the angular values is in the range of ±0.2° 2θ, i.e., the angular value can be at the recited angular value +0.2 degrees two-theta, the angular value −0.2 degrees two-theta, or any value between those two end points (angular value +0.2 degrees two-theta and angular value −0.2 degrees two-theta).

The terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

The term "X-ray powder diffractogram having a signal at . . . two-theta values" as used herein refers to an XRPD pattern that contains X-ray reflection positions as measured and observed in X-ray powder diffraction experiments (° 2θ).

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order.

For example, an amorphous material is a solid material having no sharp characteristic signal(s) in its X-ray power diffractogram (i.e., is not crystalline as determined by XRPD). Instead, one or more broad peaks (e.g., halos) appear in its diffractogram. Broad peaks are characteristic of an amorphous solid. See, e.g., US 2004/0006237 for a comparison of diffractograms of an amorphous material and crystalline material. In addition, the widths of signals in $^{13}C$ NMR and $^{19}F$ NMR spectra of amorphous material are typically substantially broader than those in $^{13}C$ NMR and $^{19}F$ NMR spectra of crystalline material.

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (° 2θ) referred to herein) generally mean that value reported ±0.2 degrees 2θ of the reported value, an art-recognized variance.

As used herein, an SSNMR spectrum is "substantially similar to that in [a particular] Figure" when at least 90%, such as at least 95%, at least 98%, or at least 99%, of the signals in the two spectra overlap. In determining "substantial similarity," one of ordinary skill in the art will understand that there may be variation in the intensities and/or signal positions in SSNMR spectra even for the same crystalline form. Thus, those of ordinary skill in the art will understand that the signal maximum values in SSNMR spectra (in ppm) referred to herein generally mean that value reported ±0.2 ppm of the reported value, an art-recognized variance.

As used herein, a crystalline form is "substantially pure" when it accounts for an amount by weight equal to or greater than 90% of the sum of all solid form(s) in a sample as determined by a method in accordance with the art, such as quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample.

As used herein, the term "DSC" refers to the analytical method of Differential Scanning calorimetry.

As used herein, the term "TGA" refers to the analytical method of Thermo Gravimetric (or thermogravimetric) Analysis.

II. Compounds and Compositions

In some embodiments, a compound of the invention is a compound of Formula I:

(I)

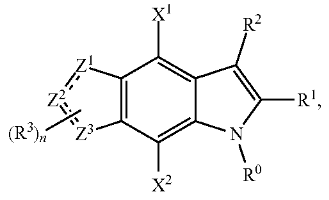

a tautomer thereof, a pharmaceutically acceptable salt of said compound or tautomer, or a deuterated derivative of any of the foregoing; wherein:

(i) $R^0$ is chosen from
(a) $C_1$-$C_8$ linear, branched, and cyclic alkyl groups, wherein the alkyl group is optionally substituted with 1-4 $R^A$; and
(b) 5- to 10-membered aromatic rings optionally substituted with 1-4 $R^A$,
wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents chosen from halogens and methoxy;
(ii) $R^1$ is chosen from
(a) $C_1$-$C_8$ linear, branched, and cyclic alkyl groups, wherein the alkyl group is optionally substituted with 1-4 substituents chosen from
halogens,
cyano, and
$C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, and
(b) $C_1$-$C_8$ linear, branched, and cyclic alkoxy groups optionally substituted with 1-4 substituents chosen from
halogens,
cyano, and
$C_1$-$C_6$ linear, branched, and cyclic alkyl groups that are optionally substituted with 1-4 halogens;
(iii) $R^2$ is chosen from:
hydrogen,
cyano,
halogens,
$C_1$-$C_8$ linear, branched, and cyclic alkyl groups optionally substituted with an oxo group,
$C_2$-$C_6$ linear, branched, and cyclic alkenyl groups,
A-$CO_2R^4$ groups wherein A is optionally present and if present is chosen from
$C_1$-$C_8$ linear, branched, and cyclic alkyl and alkoxy groups,
$C_2$-$C_6$ linear, branched, and cyclic alkenyl groups,
$C_3$-$C_5$ cycloalkyl linked to $C_1$-$C_8$ linear or branched alkyl groups,
$C_1$-$C_8$ linear or branched alkyl linked to $C_3$-$C_5$ cycloalkyl groups,
$C_3$-$C_5$ cycloalkyl linked to $C_3$-$C_5$ cycloalkyl groups,
$C_1$-$C_8$ linear, branched, and cyclic alkyl linked to $C_3$-$C_5$ cycloalkyl linked to
a $C_1$-$C_8$ linear, branched, and cyclic alkyl groups,
wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and
wherein $R^4$ is chosen from hydrogen, $C_1$-$C_8$ linear, branched, and cyclic alkyl groups, and $C_2$-$C_6$ linear, branched, and cyclic alkenyl groups,
$C(O)NR^6R^7$ wherein $R^6$ and $R^7$ are independently chosen from
hydrogen,
$C_1$-$C_8$ linear, branched, and cyclic alkyl groups,
$C_2$-$C_6$ linear, branched, and cyclic alkenyl groups,
4- to 8-membered heterocycles optionally substituted by one or more substituents chosen from cyano, halogens,
$C_1$-$C_8$ linear, branched, and cyclic alkyl groups, and
$C_2$-$C_6$ linear, branched, and cyclic alkenyl groups,
or $R^6$ and $R^7$ together with the nitrogen to which they are attached form a 4-8 membered ring optionally comprising one or two heteroatoms in addition to the nitrogen to which they are attached, and which ring is optionally substituted with a substituent chosen from halogens, cyano, hydroxy, and $C_1$-$C_6$ linear, branched, and cyclic alkyl groups,
$SO_2R^5$ groups wherein $R^5$ is chosen from $C_1$-$C_8$ linear, branched, and cyclic alkyl groups, and $C_2$-$C_6$ linear, branched, and cyclic alkenyl groups, and

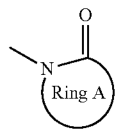

groups wherein the Ring A is a 4-8 membered ring optionally comprising one or two heteroatoms in addition to the Ring A nitrogen;
(iv) $X^1$ and $X^2$ are independently chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;
(v) each ═══ represents a single or double bond, provided that no more than one ═══ is a double bond;
(vi) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 halogens;
(vii) n is an integer chosen from 0, 1, 2, and 3; and
(viii) $Z^1$, $Z^2$, and $Z^3$ are independently chosen from carbon, nitrogen, sulfur, and oxygen, wherein when $Z^1$, $Z^2$, and/or $Z^3$ are carbon or nitrogen, the valences of carbon and nitrogen are completed with hydrogen atoms.

In some embodiments, a compound of the invention is a compound of Formula II:

(II)

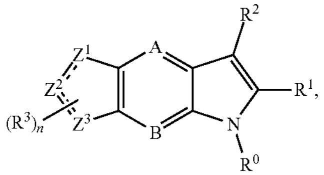

a tautomer thereof, a pharmaceutically acceptable salt of said compound or tautomer, or a deuterated derivative of any of the foregoing; wherein:
(i) A and B are each independently chosen from N and C—$X^1$ (ii) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy;

(iii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iv) $R^2$ is chosen from:

hydrogen, cyano, halogens, alkylamide groups, $C_1$-$C_8$ linear, branched, and cyclic alkyl groups optionally substituted with an oxo group, a $C_1$-$C_8$ linear, branched, and cyclic alkoxy group, a 5- or 6-membered heteroaryl group, a cyano group, an amino group, an aminoalkyl group, an alkylamide group, an alkylsulfonyl group, an alkylsulfonamide group, an alkylsulfoxide group, a group

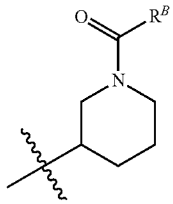

or

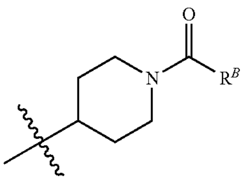

wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group, a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group.

a

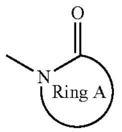

group wherein the Ring A is chosen from 4-8 membered rings optionally comprising one or two heteroatoms in addition to the Ring A nitrogen, and a carboxylic acid group esterified with a uronic acid, $C_2$-$C_6$ linear, branched, and cyclic alkenyl groups, A-$CO_2R^4$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, A-C(O)$NH_2$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, $C(O)NR^6R^7$ wherein $R^6$ and $R^7$ are independently chosen from hydrogen, $C_1$-$C_8$ linear, branched, and cyclic alkyl groups, $C_2$-$C_6$ linear, branched, and cyclic alkenyl groups, 4- to 8-membered heterocycles optionally substituted by one or more substituents chosen from cyano, halogens, $C_1$-$C_8$ linear, branched, and cyclic alkyl groups, and $C_2$-$C_6$ linear, branched, and cyclic alkenyl groups, or $R^6$ and $R^7$ together with the nitrogen to which they are attached form a 4-8 membered ring optionally comprising one or two heteroatoms in addition to the nitrogen to which they are attached, and which ring is optionally substituted with a substituent chosen from halogens, cyano, hydroxy, and $C_1$-$C_6$ linear, branched, and cyclic alkyl groups, $SO_2R^5$ groups wherein $R^5$ is chosen from $C_1$-$C_8$ linear, branched, and cyclic alkyl groups, and $C_2$-$C_6$ linear, branched, and cyclic alkenyl groups, and

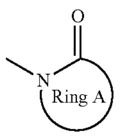

groups wherein the Ring A is a 4-8 membered ring optionally comprising one or two heteroatoms in addition to the Ring A nitrogen;

(v) $X^1$ is chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(vi) each ═══ represents a single or double bond, provided that no more than one ═══ is a double bond;

(vii) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 halogens;

(viii) n is an integer chosen from 0, 1, 2, and 3; and (ix) $Z^1$, $Z^2$, and $Z^3$ are independently chosen from carbon, nitrogen, sulfur, and oxygen, wherein when $Z^1$, $Z^2$, and/or $Z^3$ are carbon or nitrogen, the valences of carbon and nitrogen are completed with hydrogen atoms, $C_1$-$C_8$ linear, branched, and cyclic alkyls, or cyano.

In some embodiments, a compound of the invention is a compound of Formula III:

(III)

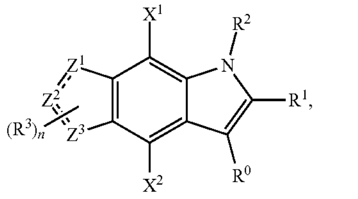

a tautomer thereof, a pharmaceutically acceptable salt of said compound or tautomer, or a deuterated derivative of any of the foregoing; wherein:

(i) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy;

(ii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iii) $R^2$ is chosen from:

hydrogen, cyano, halogens, alkylamide groups, $C_1$-$C_8$ linear, branched, and cyclic alkyl groups optionally substituted with an oxo group, a $C_1$-$C_8$ linear, branched, and cyclic alkoxy group, a 5- or 6-membered heteroaryl group, a cyano group, an amino group, an aminoalkyl group, an alkylamide group, an alkylsulfonyl group, an alkylsulfonamide group, an alkylsulfoxide group, a group

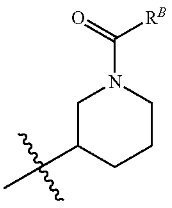

or

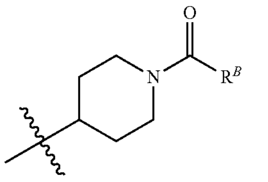

wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group, a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group.

a

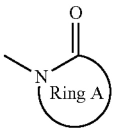

group wherein the Ring A is chosen from 4-8 membered rings optionally comprising one or two heteroatoms in addition to the Ring A nitrogen, and a carboxylic acid group esterified with a uronic acid, $C_2$-$C_6$ linear, branched, and cyclic alkenyl groups, A-$CO_2R^4$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, A-C(O)$NH_2$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, C(O)$NR^6R^7$ wherein $R^6$ and $R^7$ are independently chosen from hydrogen, $C_1$-$C_8$ linear, branched, and cyclic alkyl groups, $C_2$-$C_6$ linear, branched, and cyclic alkenyl groups, 4- to 8-membered heterocycles optionally substituted by one or more substituents chosen from cyano, halogens, $C_1$-$C_8$ linear, branched, and cyclic alkyl groups, and $C_2$-$C_6$ linear, branched, and cyclic alkenyl groups, or $R^6$ and $R^7$ together with the nitrogen to which they are attached form a 4-8 membered ring optionally comprising one or two heteroatoms in addition to the nitrogen to which they are attached, and which ring is optionally substituted with a substituent chosen from halogens, cyano, hydroxy, and $C_1$-$C_6$ linear, branched, and cyclic alkyl groups, $SO_2R^5$ groups wherein $R^5$ is chosen from $C_1$-$C_8$ linear, branched, and cyclic alkyl groups, and $C_2$-$C_6$ linear, branched, and cyclic alkenyl groups, and

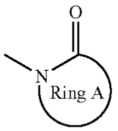

groups wherein the Ring A is a 4-8 membered ring optionally comprising one or two heteroatoms in addition to the Ring A nitrogen;

(iv) $X^1$ and $X^2$ are independently chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(v) each ═══ represents a single or double bond, provided that no more than one ═══ is a double bond;

(vi) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 halogens;

(vii) n is an integer chosen from 0, 1, 2, and 3; and (viii) $Z^1$, $Z^2$, and $Z^3$ are independently chosen from carbon, nitrogen, sulfur, and oxygen, wherein when $Z^1$, $Z^2$, and/or $Z^3$ are carbon or nitrogen, the valences of carbon and nitrogen are completed with hydrogen atoms, $C_1$-$C_8$ linear, branched, and cyclic alkyls, or cyano.

In some embodiments, $R^0$ is chosen from heteroaryl rings.

In some embodiments, $R^0$ is phenyl.

In some embodiments, $R^0$ is substituted with 1-2 substituents. In some embodiments, the 1-2 substituents are independently chosen from halogens and $C_1$-$C_4$ alkyl groups.

In some embodiments, $R^0$ is substituted with a fluorine and/or a methyl group.

In some embodiments, $R^1$ is chosen from $C_1$-$C_3$ linear and branched alkyl groups and $C_4$-$C_6$ cyclic alkyl groups.

In some embodiments, $R^1$ is chosen from $C_6$ cyclic alkyl groups wherein 1 carbon atom is replaced by a heteroatom.

In some embodiments, $R^1$ is chosen from:

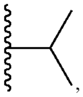, 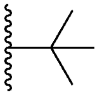, 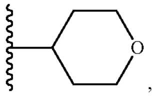, 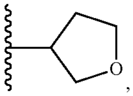,

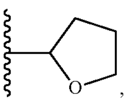, 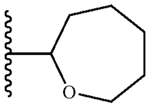, 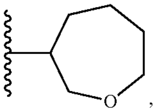,

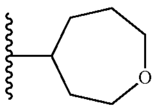, 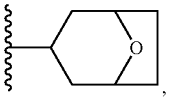, and 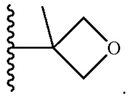.

In some embodiments, at least one of $Z^1$, $Z^2$, and $Z^3$ is nitrogen. In some embodiments, two of $Z^1$, $Z^2$, and $Z^3$ are nitrogen and the other is chosen from carbon and nitrogen.

In some embodiments, the compound of the invention is a compound of any one of Formulae I, 1-6, 3-4, 3-5, 3-6, 4-3, 5-3, 6-4, 7-4, 8-4, 12-1, 12-2, II, and III 1-6

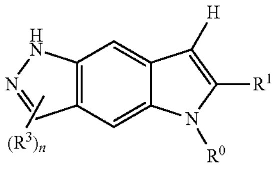

3-4

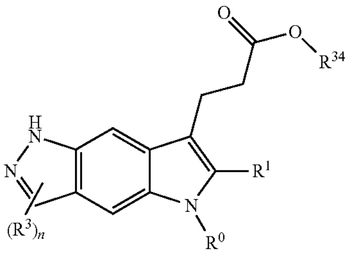

3-5

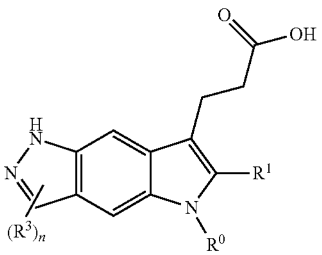

-continued 3-6

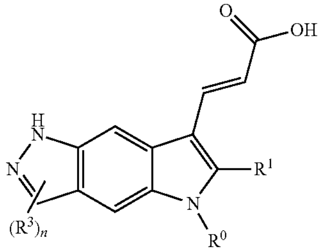

4-3

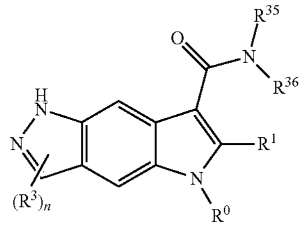

5-3

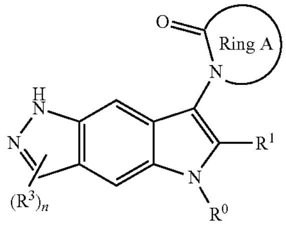

6-4

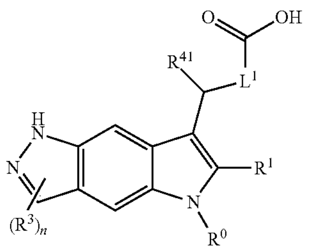

7-4

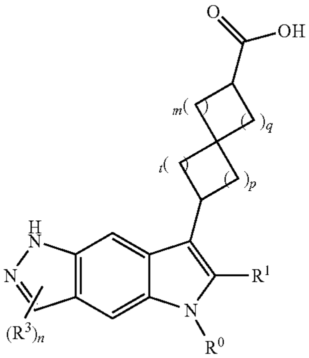

8-4

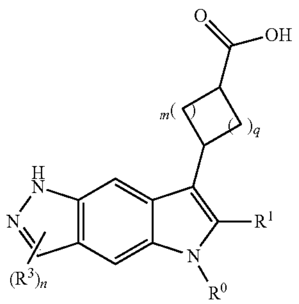

-continued 12-1

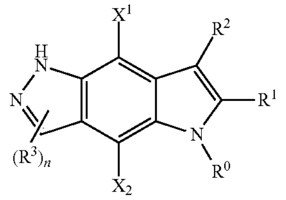

12-2

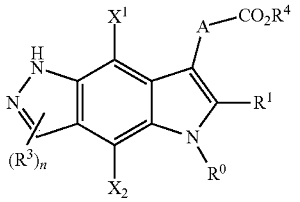

a tautomer thereof, a pharmaceutically acceptable salts of such compound or tautomer, or a deuterated derivative of any of the foregoing, wherein:

$R^0$, $R^1$, $R^2$, $R^3$, $R^4$, $X^1$, $X^2$, A, and n are defined for compounds of Formula (I), $R^{34}$ is selected from $C_1$-$C_6$ linear, branched, and cyclic alkyl groups;

$R^{35}$ and $R^{36}$ are selected from $C_1$-$C_6$ linear, branched, and cyclic alkyl groups; or $R^{35}$ and $R^{36}$, taken together with the N atom to which they are bound, form a 4 to 6 membered ring, optionally substituted with $C_1$-$C_6$ linear, branched, and cyclic alkyl groups;

$R^{41}$ is selected from H, $C_1$-$C_6$ linear, branched, and cyclic alkyl groups, (e.g., Me, Et, and i-Pr);

$L^1$ is chosen from:

$C_1$-$C_8$ linear, branched, and cyclic alkyl groups,
$C_2$-$C_6$ linear, branched, and cyclic alkenyl groups,
$C_3$-$C_8$ cycloalkyl linked to $C_1$-$C_8$ linear or branched alkyl groups,
$C_1$-$C_8$ linear or branched alkyl linked to $C_3$-$C_8$ cycloalkyl groups,
$C_3$-$C_8$ cycloalkyl linked to $C_3$-$C_8$ cycloalkyl groups,
$C_1$-$C_8$ linear, branched, and cyclic alkyl linked to $C_3$-$C_8$ cycloalkyl linked to
a $C_1$-$C_8$ linear, branched, and cyclic alkyl groups, wherein up to 3 carbon atoms of $L^1$ are optionally substituted with 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, m is an integer chosen from 0-3, and q is an integer chosen from 0-3, provided that:
(i) if m is 0, then q is at least 1; and
(ii) if q is 0, then m is at least 1; and t is an integer chosen from 0-3, and p is an integer chosen from 0-3, provided that:
(i) if t is 0, then p is at least 2; and
(ii) if p is 0, then t is at least 2.

In some embodiments, the compound of the invention is selected from Compounds 1-215 depicted in Table 1. A wavy line in a compound in Table 1 (i.e., ) depicts a bond between two atoms and indicates a position of mixed stereochemistry for a collection of molecules, such as a racemic mixture, cis/trans isomers, or (E)/(Z) isomers. An asterisk adjacent to an atom (e.g.,

in a compound in Table 1, indicates a stereogenic center of an unassigned, single stereoisomer in the molecule. A pound symbol (#) next to carbon atom indicates that the carbon atom is replaced with $^{13}C$.

TABLE 1

| Compounds 1-215 | |
|---|---|
| 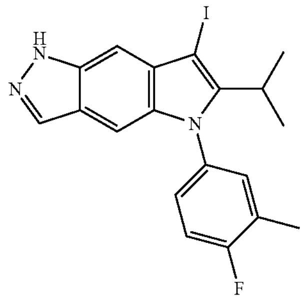 [SMILES: Cc1cc(-n2c(C(C)C)c(I)c3cc4[nH]ncc4cc32)ccc1F] | 1 |
| 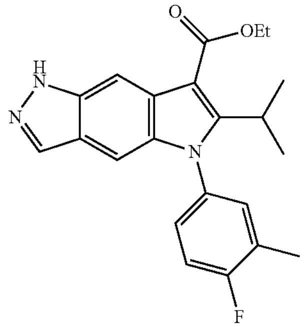 [SMILES: CCOC(=O)c1c(C(C)C)n(-c2ccc(F)c(C)c2)c2cc3cn[nH]c3cc12] | 2 |
| 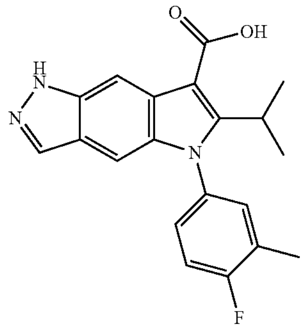 [SMILES: Cc1cc(-n2c(C(C)C)c(C(=O)O)c3cc4[nH]ncc4cc32)ccc1F] | 3 |
| 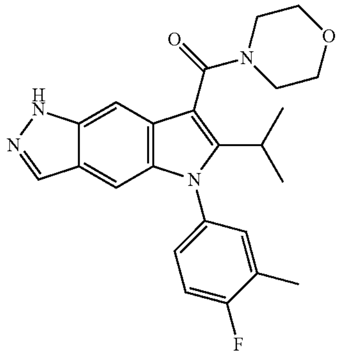 [SMILES: Cc1cc(-n2c(C(C)C)c(C(=O)N3CCOCC3)c3cc4[nH]ncc4cc32)ccc1F] | 4 |

TABLE 1-continued
| Compounds 1-215 |
| --- |
| 5 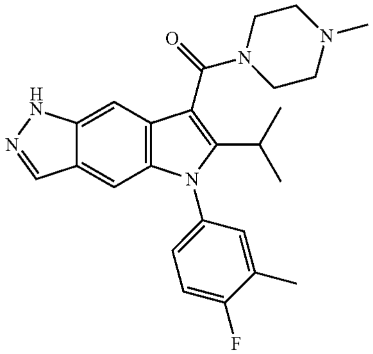 [SMILES: Cc1cc(-n2c(C(C)C)c(C(=O)N3CCN(C)CC3)c3cc4[nH]ncc4cc32)ccc1F] |
| 6 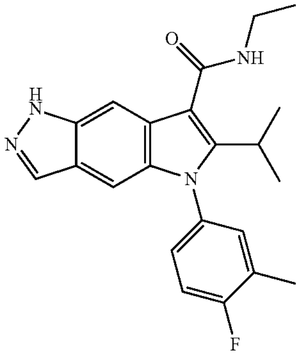 [SMILES: CCNC(=O)c1c(C(C)C)n(-c2ccc(F)c(C)c2)c2cc3cn[nH]c3cc12] |
| 7 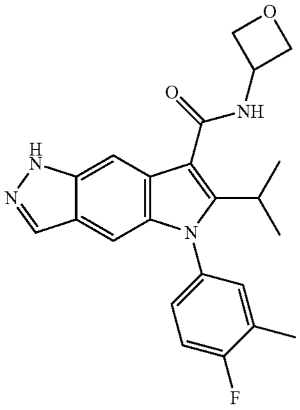 [SMILES: Cc1cc(-n2c(C(C)C)c(C(=O)NC3COC3)c3cc4[nH]ncc4cc32)ccc1F] |
| 8 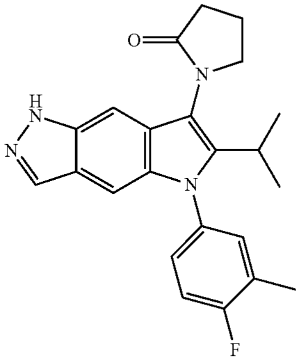 [SMILES: Cc1cc(-n2c(C(C)C)c(N3CCCC3=O)c3cc4[nH]ncc4cc32)ccc1F] |
TABLE 1-continued
| Compounds 1-215 |
| --- |
| 9 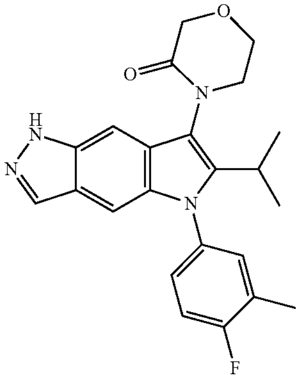 [SMILES: Cc1cc(-n2c(C(C)C)c(N3CCOCC3=O)c3cc4[nH]ncc4cc32)ccc1F] |
| 10 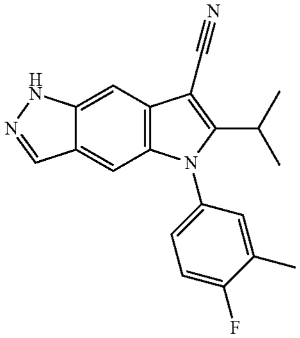 [SMILES: Cc1cc(-n2c(C(C)C)c(C#N)c3cc4[nH]ncc4cc32)ccc1F] |
| 11 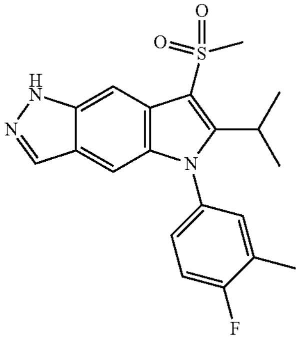 [SMILES: Cc1cc(-n2c(C(C)C)c(S(C)(=O)=O)c3cc4[nH]ncc4cc32)ccc1F] |
| 12 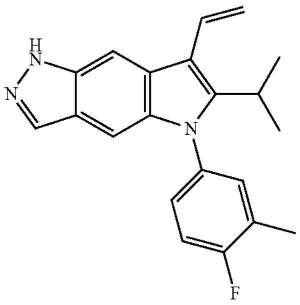 [SMILES: C=Cc1c(C(C)C)n(-c2ccc(F)c(C)c2)c2cc3cn[nH]c3cc12] |

TABLE 1-continued
| Compounds 1-215 |
|---|
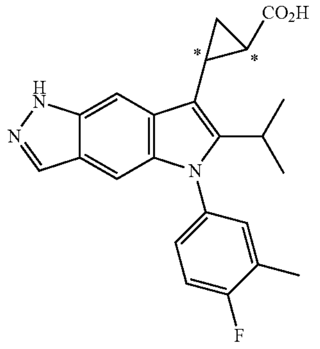
13
[TRANS ENANT-1]
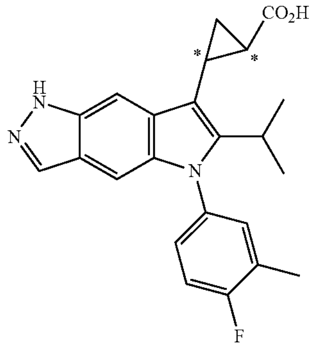
14
[TRANS ENANT-2]
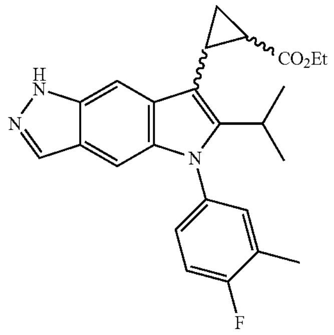 [SMILES: CCOC(=O)C1CC1c1c(C(C)C)n(-c2ccc(F)c(C)c2)c2cc3cn[nH]c3cc12]
15
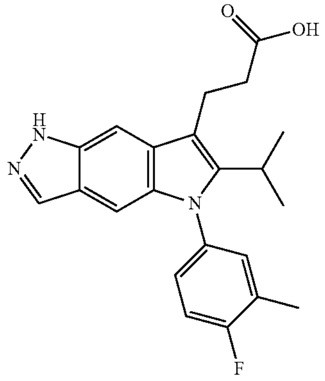 [SMILES: Cc1cc(-n2c(C(C)C)c(CCC(=O)O)c3cc4[nH]ncc4cc32)ccc1F]
16
TABLE 1-continued
| Compounds 1-215 |
|---|
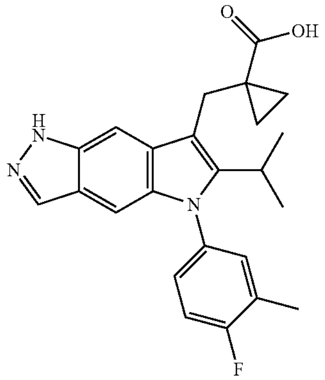 [SMILES: Cc1cc(-n2c(C(C)C)c(CC3(C(=O)O)CC3)c3cc4[nH]ncc4cc32)ccc1F]
17
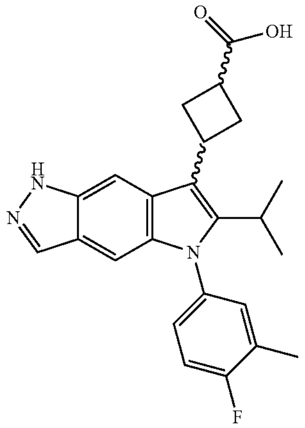 [SMILES: Cc1cc(-n2c(C(C)C)c(C3CC(C(=O)O)C3)c3cc4[nH]ncc4cc32)ccc1F]
18
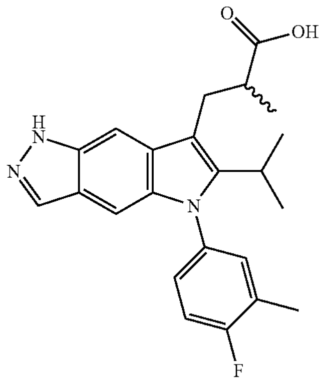
19
[RAC]

TABLE 1-continued
| Compounds 1-215 |
| --- |
20
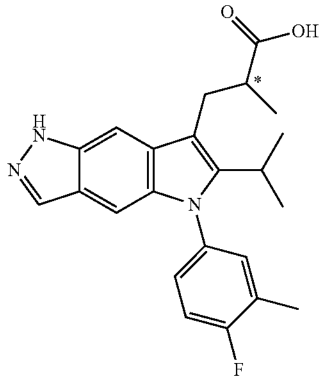
[ENANT-1]
21
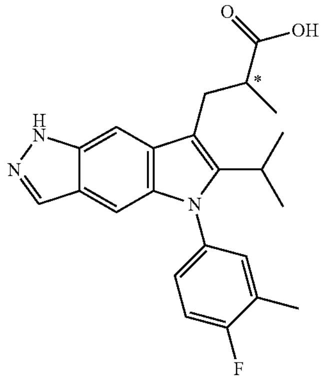
[ENANT-2]
22
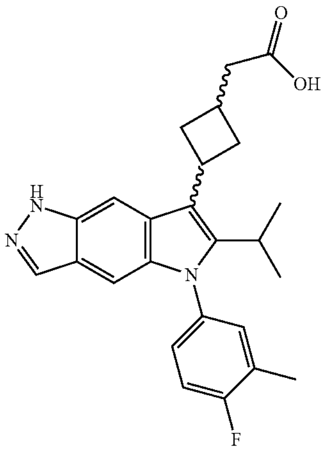 [SMILES: Cc1cc(-n2c(C(C)C)c(C3CC(CC(=O)O)C3)c3cc4[nH]ncc4cc32)ccc1F]
TABLE 1-continued
| Compounds 1-215 |
| --- |
23
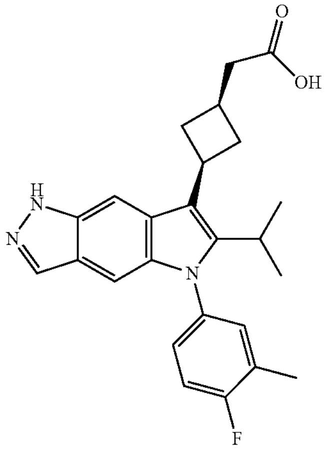 [SMILES: Cc1cc(-n2c(C(C)C)c([C@H]3C[C@@H](CC(=O)O)C3)c3cc4[nH]ncc4cc32)ccc1F]
24
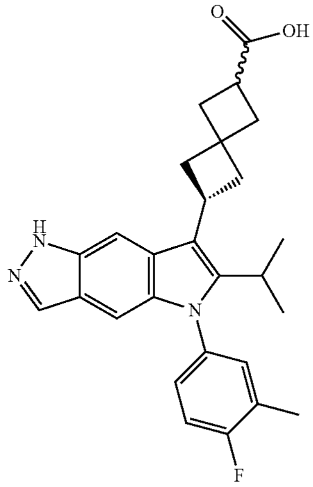
[RAC]
25
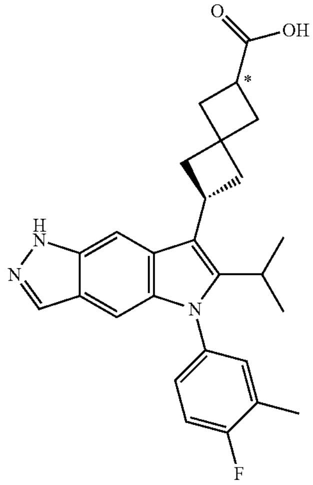
[ENANT-1]

TABLE 1-continued
| Compounds 1-215 |
|---|
26
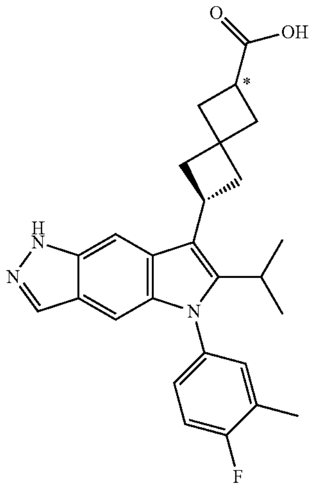
[ENANT-2]
27
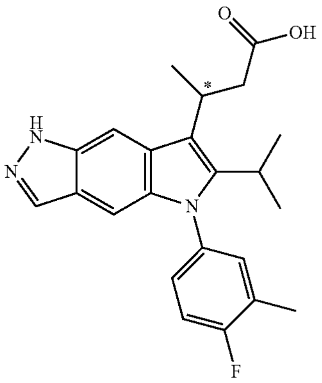
[ENANT-1]
28
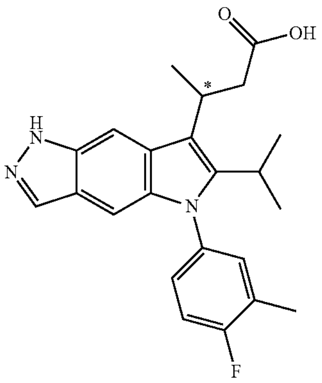
[ENANT-2]
TABLE 1-continued
| Compounds 1-215 |
|---|
29
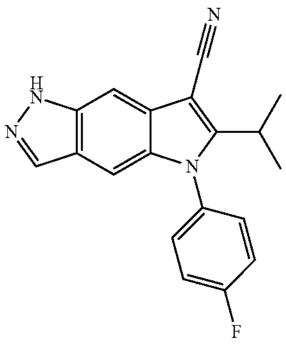 [SMILES: CC(C)c1c(C#N)c2cc3[nH]ncc3cc2n1-c1ccc(F)cc1]
30
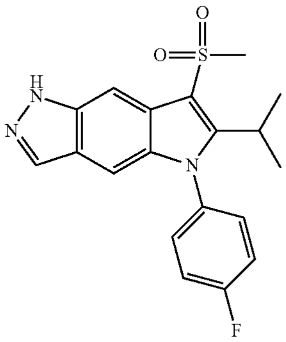 [SMILES: CC(C)c1c(S(C)(=O)=O)c2cc3[nH]ncc3cc2n1-c1ccc(F)cc1]
31
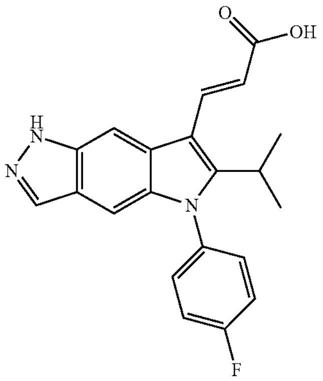 [SMILES: CC(C)c1c(/C=C/C(=O)O)c2cc3[nH]ncc3cc2n1-c1ccc(F)cc1]
32
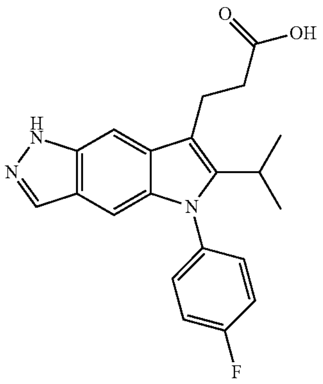 [SMILES: CC(C)c1c(CCC(=O)O)c2cc3[nH]ncc3cc2n1-c1ccc(F)cc1]

TABLE 1-continued
Compounds 1-215
33
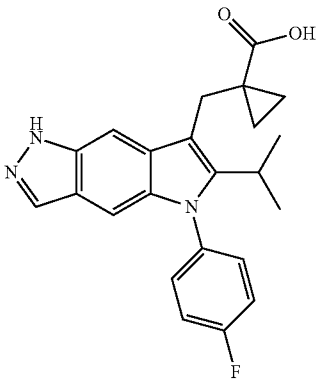 [SMILES: CC(C)c1c(CC2(C(=O)O)CC2)c2cc3[nH]ncc3cc2n1-c1ccc(F)cc1]
34
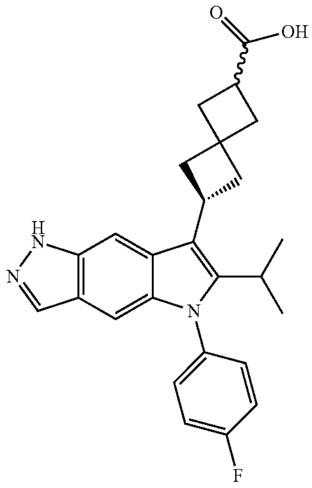
[RAC]
35
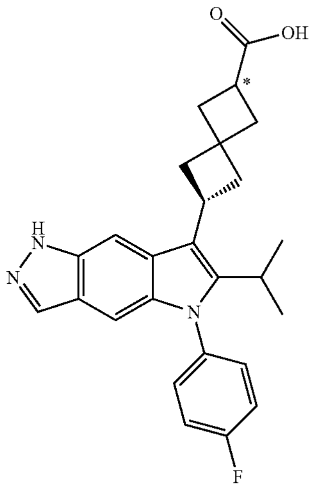
[ENANT-1]
TABLE 1-continued
Compounds 1-215
36
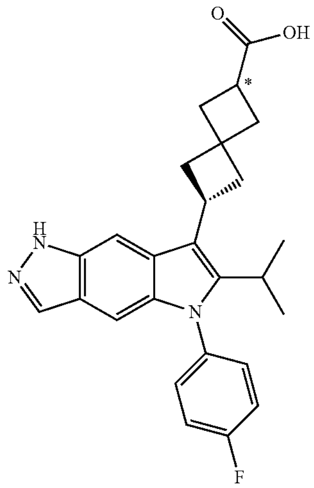
[ENANT-2]
37
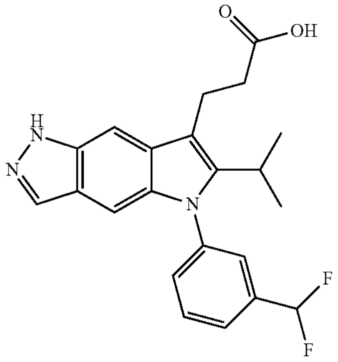 [SMILES: CC(C)c1c(CCC(=O)O)c2cc3[nH]ncc3cc2n1-c1cccc(C(F)F)c1]
38
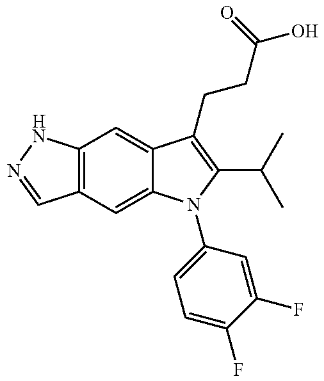 [SMILES: CC(C)c1c(CCC(=O)O)c2cc3[nH]ncc3cc2n1-c1ccc(F)c(F)c1]
39
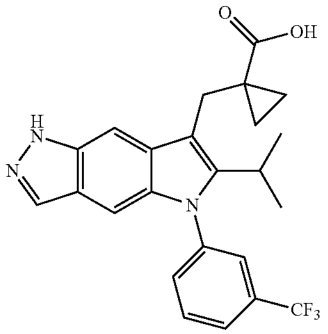 [SMILES: CC(C)c1c(CC2(C(=O)O)CC2)c2cc3[nH]ncc3cc2n1-c1cccc(C(F)(F)F)c1]

TABLE 1-continued
| Compounds 1-215 |
| --- |
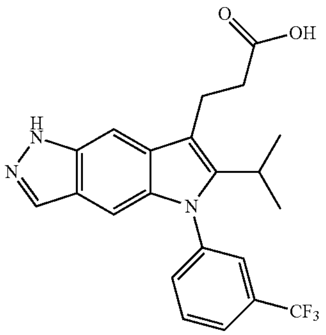 [SMILES: CC(C)c1c(CCC(=O)O)c2cc3[nH]ncc3cc2n1-c1cccc(C(F)(F)F)c1]
40
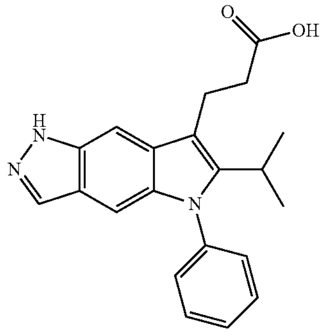 [SMILES: CC(C)c1c(CCC(=O)O)c2cc3[nH]ncc3cc2n1-c1ccccc1]
41
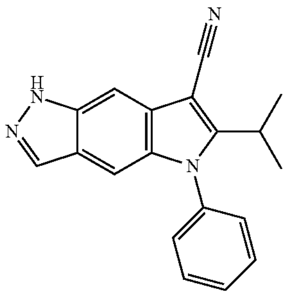 [SMILES: CC(C)c1c(C#N)c2cc3[nH]ncc3cc2n1-c1ccccc1]
42
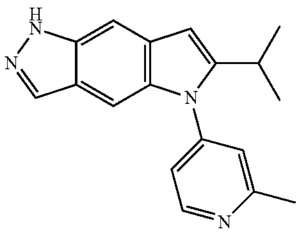 [SMILES: Cc1cc(-n2c(C(C)C)cc3cc4[nH]ncc4cc32)ccn1]
43
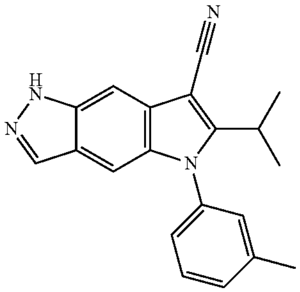 [SMILES: Cc1cccc(-n2c(C(C)C)c(C#N)c3cc4[nH]ncc4cc32)c1]
44
TABLE 1-continued
| Compounds 1-215 |
| --- |
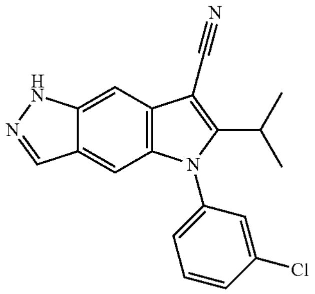 [SMILES: CC(C)c1c(C#N)c2cc3[nH]ncc3cc2n1-c1cccc(Cl)c1]
45
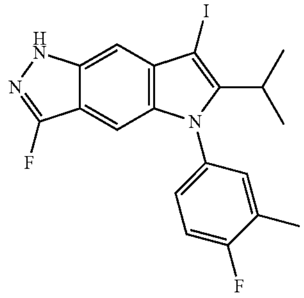 [SMILES: Cc1cc(-n2c(C(C)C)c(I)c3cc4[nH]nc(F)c4cc32)ccc1F]
46
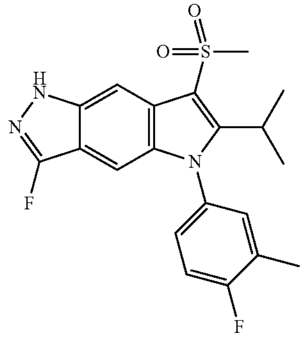 [SMILES: Cc1cc(-n2c(C(C)C)c(S(C)(=O)=O)c3cc4[nH]nc(F)c4cc32)ccc1F]
47
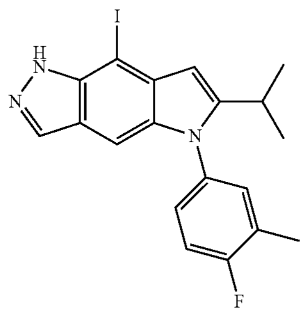
48
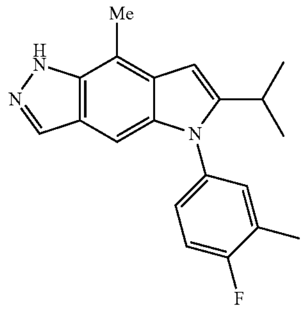
49

TABLE 1-continued
| Compounds 1-215 |
| --- |
| 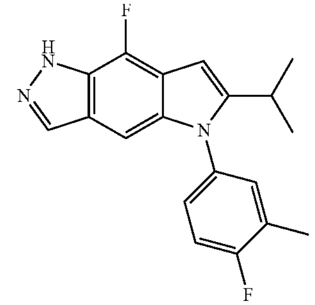 [SMILES: Cc1cc(-n2c(C(C)C)cc3c(I)c4[nH]ncc4cc32)ccc1F] 50 |
| 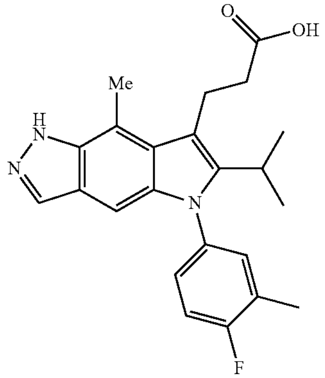 [SMILES: Cc1cc(-n2c(C(C)C)c(CCC(=O)O)c3c(C)c4[nH]ncc4cc32)ccc1F] 51 |
| 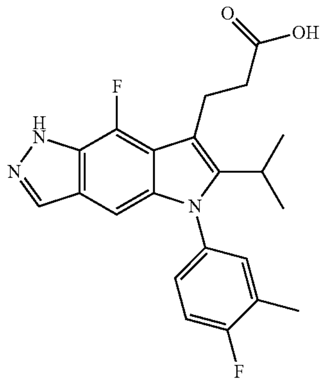 [SMILES: Cc1cc(-n2c(C(C)C)c(CCC(=O)O)c3c(F)c4[nH]ncc4cc32)ccc1F] 52 |
| 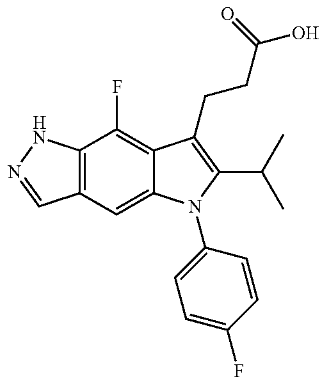 [SMILES: CC(C)c1c(CCC(=O)O)c2c(F)c3[nH]ncc3cc2n1-c1ccc(F)cc1] 53 |
TABLE 1-continued
| Compounds 1-215 |
| --- |
| 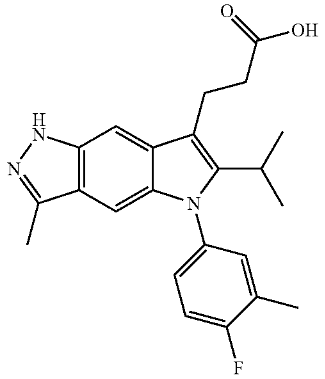 [SMILES: Cc1cc(-n2c(C(C)C)c(CCC(=O)O)c3cc4[nH]nc(C)c4cc32)ccc1F] 54 |
| 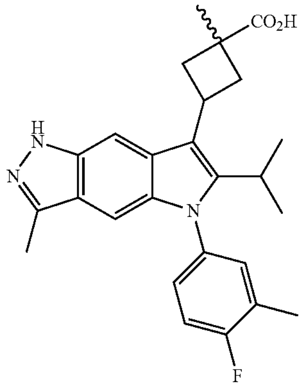 [SMILES: Cc1cc(-n2c(C(C)C)c(C3CC(C)(C(=O)O)C3)c3cc4[nH]nc(C)c4cc32)ccc1F] 55 |
| 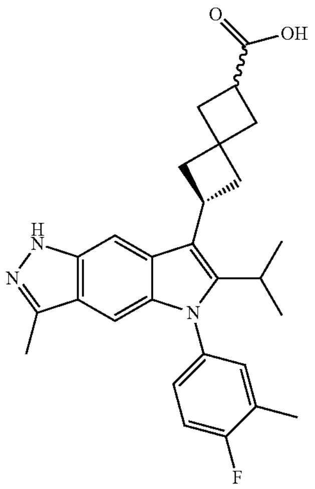 [Rac] 56 |

TABLE 1-continued
| Compounds 1-215 |
|---|
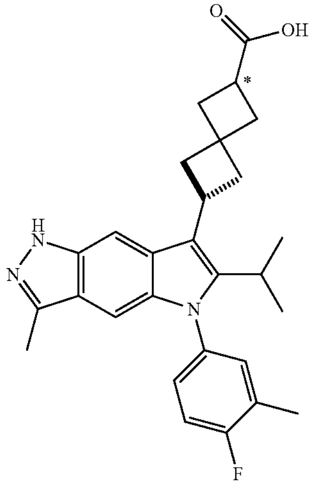
57
[ENANT-1]
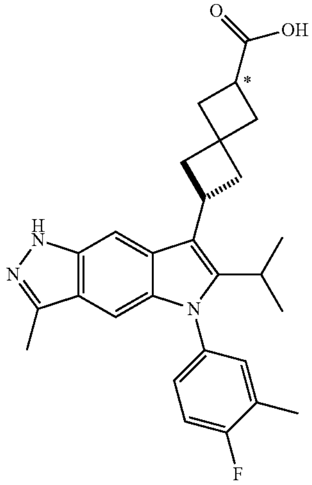
58
[ENANT-2]
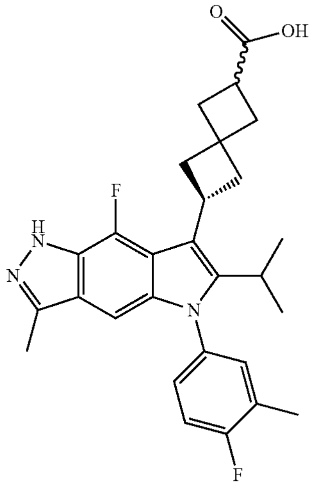
59
[Rac]
TABLE 1-continued
| Compounds 1-215 |
|---|
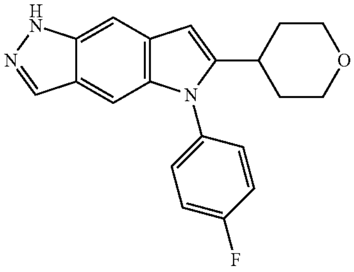 [SMILES: Fc1ccc(-n2c(C3CCOCC3)cc3cc4[nH]ncc4cc32)cc1]
60
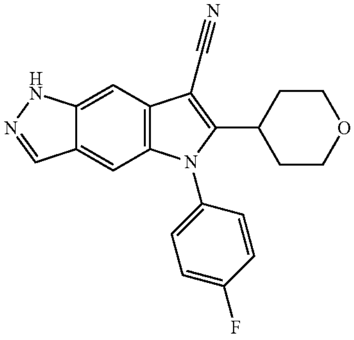 [SMILES: N#Cc1c(C2CCOCC2)n(-c2ccc(F)cc2)c2cc3cn[nH]c3cc12]
61
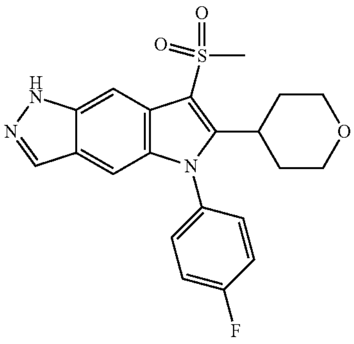 [SMILES: CS(=O)(=O)c1c(C2CCOCC2)n(-c2ccc(F)cc2)c2cc3cn[nH]c3cc12]
62
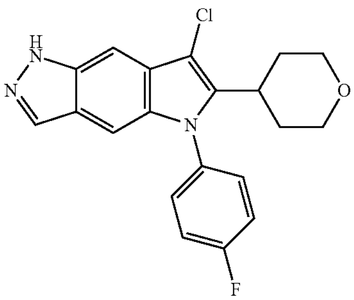 [SMILES: Fc1ccc(-n2c(C3CCOCC3)c(Cl)c3cc4[nH]ncc4cc32)cc1]
63

TABLE 1-continued
| Compounds 1-215 |
|---|
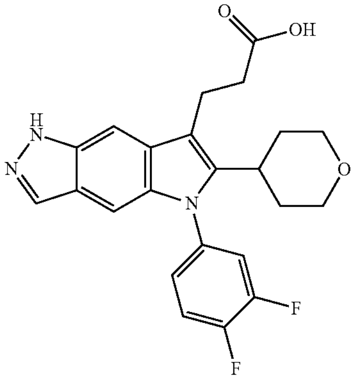
64
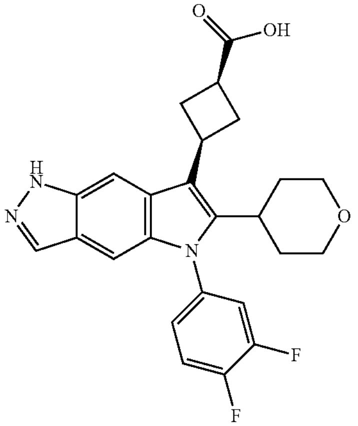 [SMILES: O=C(O)[C@H]1C[C@@H](c2c(C3CCOCC3)n(-c3ccc(F)c(F)c3)c3cc4cn[nH]c4cc32)C1]
65
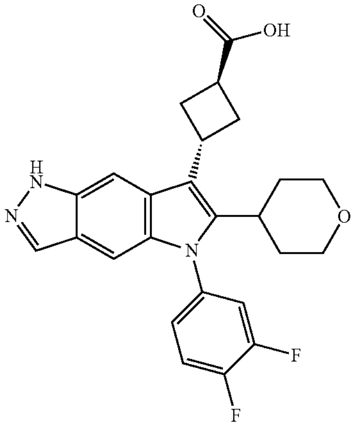 [SMILES: O=C(O)[C@H]1C[C@H](c2c(C3CCOCC3)n(-c3ccc(F)c(F)c3)c3cc4cn[nH]c4cc32)C1]
66
TABLE 1-continued
| Compounds 1-215 |
|---|
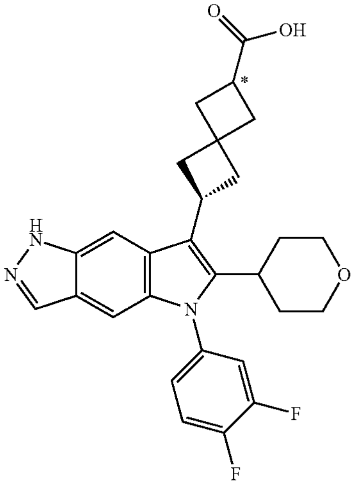
67
[ENANT-1]
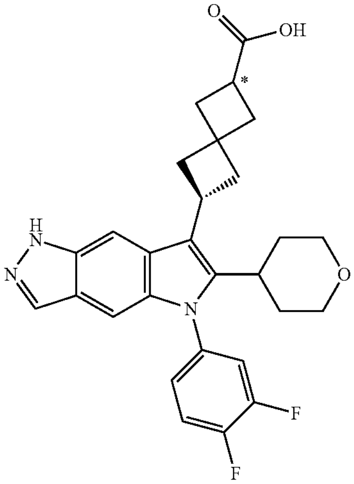
68
[ENANT-2]
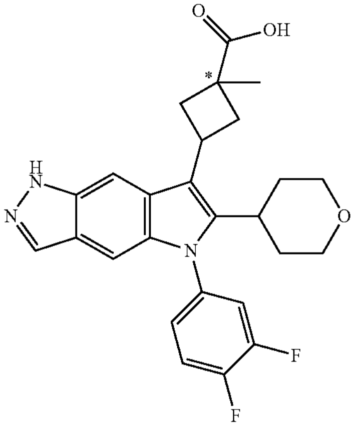
69
[Isomer-1]

TABLE 1-continued
Compounds 1-215
70
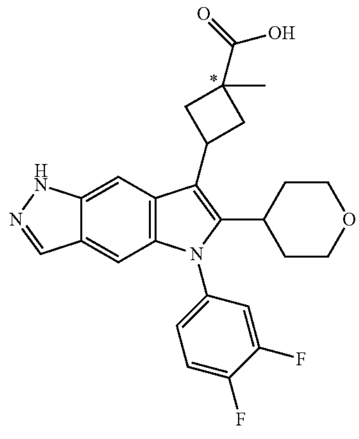
[Isomer-2]
71
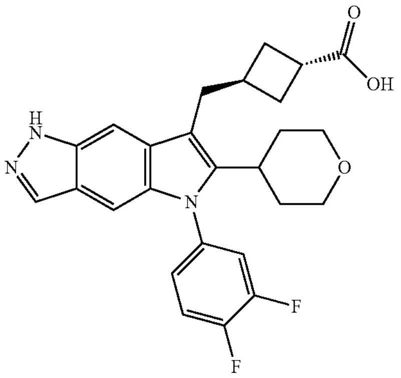
72
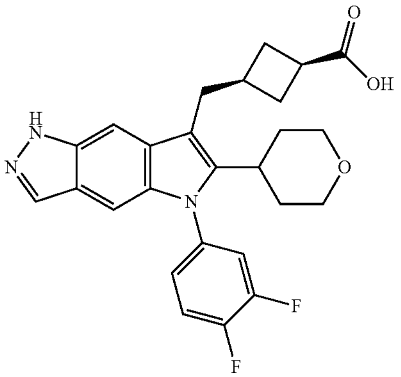
73
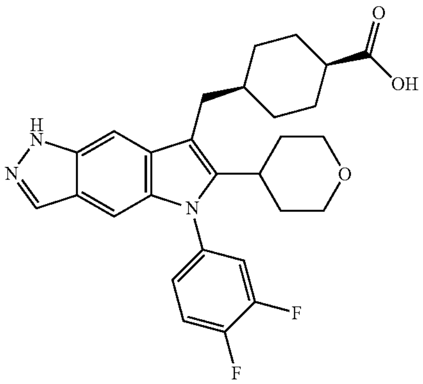 [SMILES: O=C(O)[C@H]1CC[C@@H](Cc2c(C3CCOCC3)n(-c3ccc(F)c(F)c3)c3cc4cn[nH]c4cc23)CC1]
TABLE 1-continued
Compounds 1-215
74
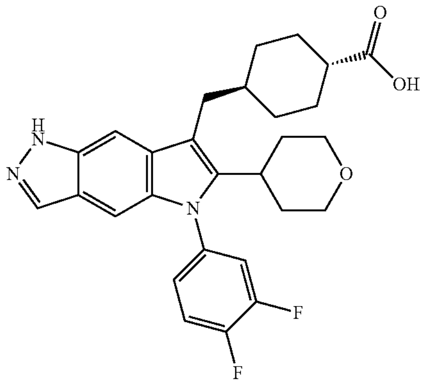
75
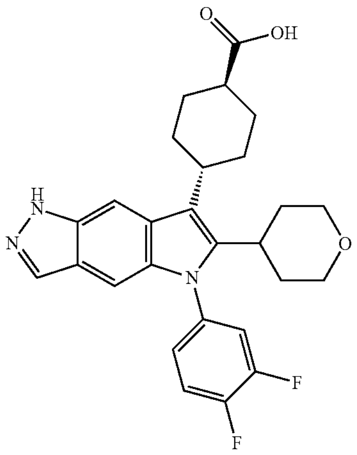 [SMILES: O=C(O)[C@H]1CC[C@H](c2c(C3CCOCC3)n(-c3ccc(F)c(F)c3)c3cc4cn[nH]c4cc32)CC1]
76
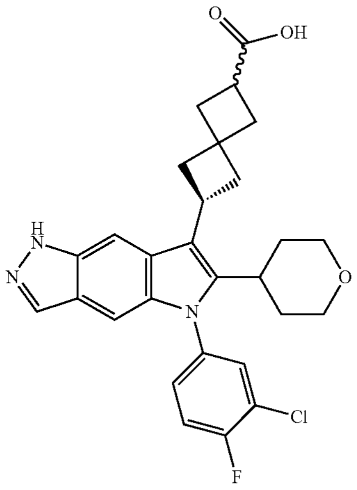
[RAC]

TABLE 1-continued
Compounds 1-215
77
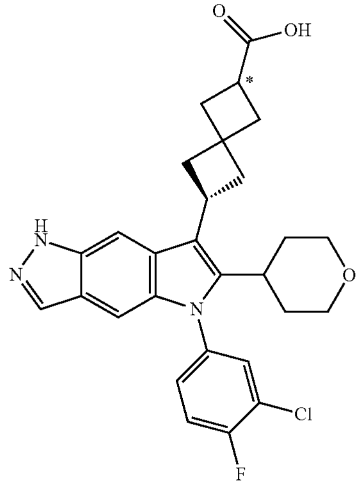
[ENANT-1]
78
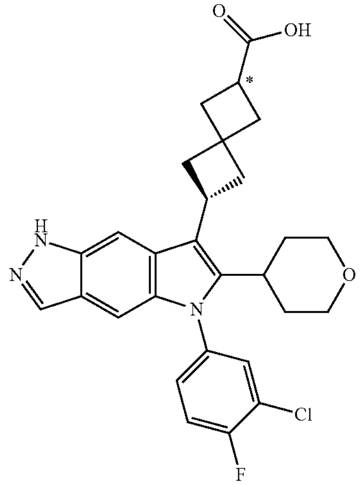
[ENANT-2]
79
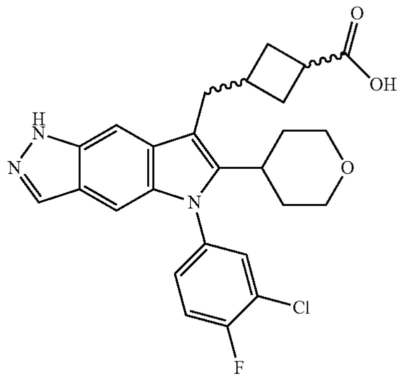
80
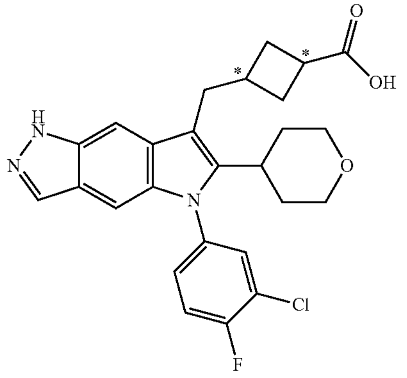
[Isomer-1]
81
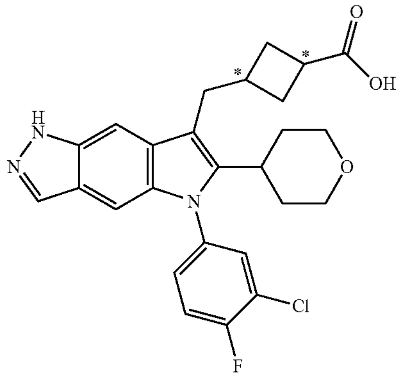
[Isomer-2]
82
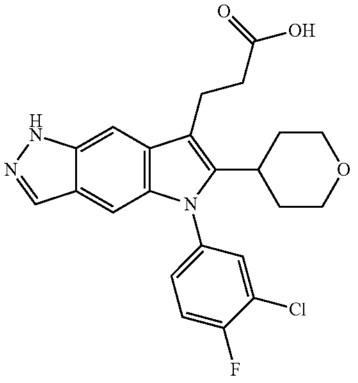 [SMILES: O=C(O)CCc1c(C2CCOCC2)n(-c2ccc(F)c(Cl)c2)c2cc3cn[nH]c3cc12]
83
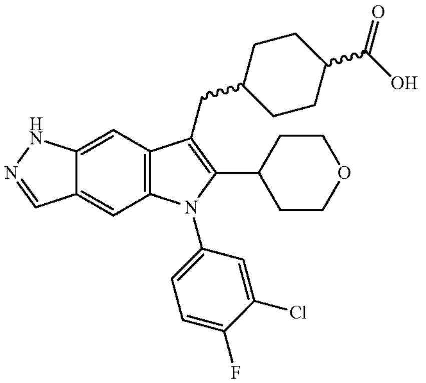 [SMILES: O=C(O)C1CCC(Cc2c(C3CCOCC3)n(-c3ccc(F)c(Cl)c3)c3cc4cn[nH]c4cc23)CC1]

TABLE 1-continued
| Compounds 1-215 |
|---|
84
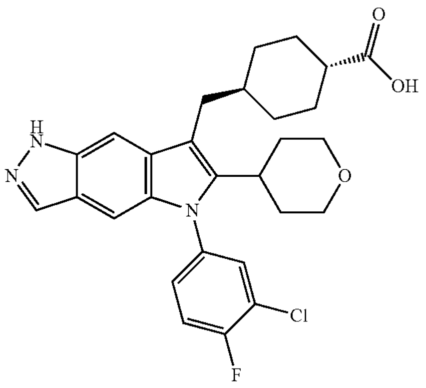 [SMILES: O=C(O)[C@H]1CC[C@H](Cc2c(C3CCOCC3)n(-c3ccc(F)c(Cl)c3)c3cc4cn[nH]c4cc23)CC1]
85
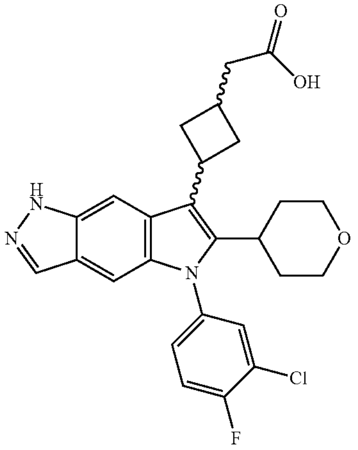 [SMILES: O=C(O)CC1CC(c2c(C3CCOCC3)n(-c3ccc(F)c(Cl)c3)c3cc4cn[nH]c4cc23)C1]
86
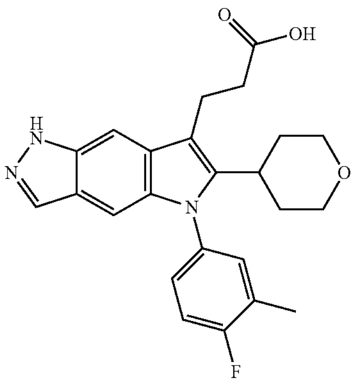 [SMILES: Cc1cc(-n2c(C3CCOCC3)c(CCC(=O)O)c3cc4[nH]ncc4cc32)ccc1F]
TABLE 1-continued
| Compounds 1-215 |
|---|
87
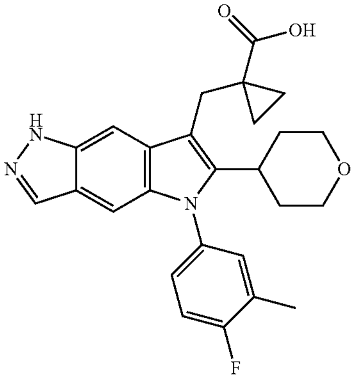 [SMILES: Cc1cc(-n2c(C3CCOCC3)c(CC3(C(=O)O)CC3)c3cc4[nH]ncc4cc32)ccc1F]
88
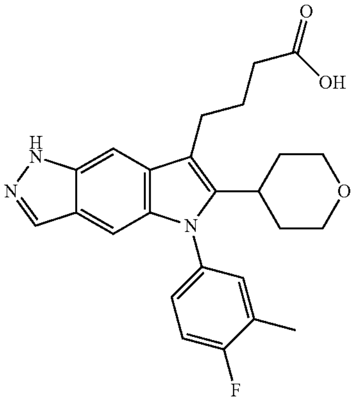 [SMILES: Cc1cc(-n2c(C3CCOCC3)c(CCCC(=O)O)c3cc4[nH]ncc4cc32)ccc1F]
89
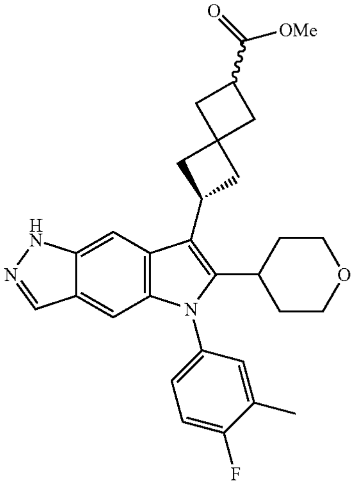
[RAC]

TABLE 1-continued
Compounds 1-215
90
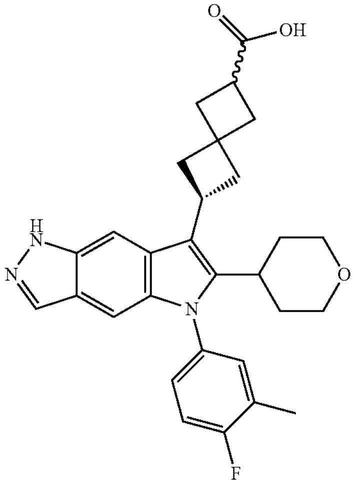
[RAC]
91
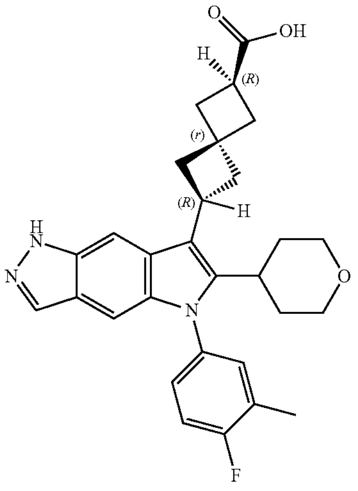
[ENANT-1]
92
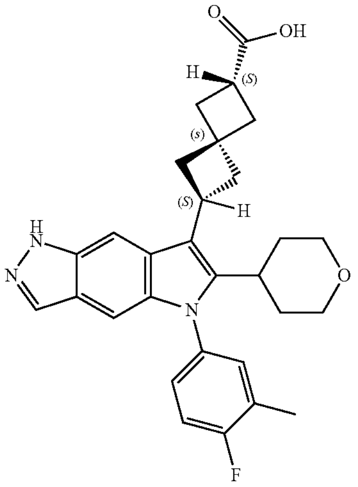
[ENANT-2]
TABLE 1-continued
Compounds 1-215
93
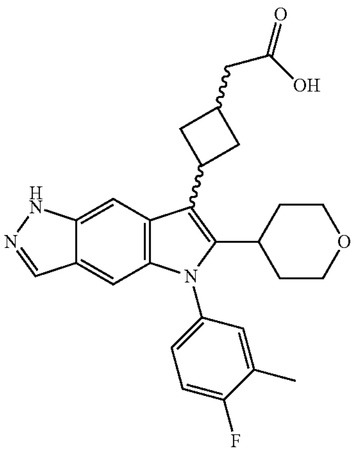 [SMILES: Cc1cc(-n2c(C3CCOCC3)c(C3CC(CC(=O)O)C3)c3cc4[nH]ncc4cc32)ccc1F]
94
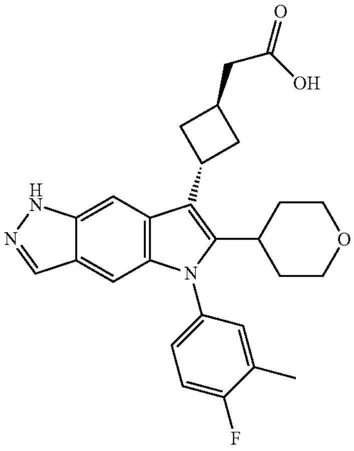 [SMILES: Cc1cc(-n2c(C3CCOCC3)c([C@H]3C[C@H](CC(=O)O)C3)c3cc4[nH]ncc4cc32)ccc1F]
95
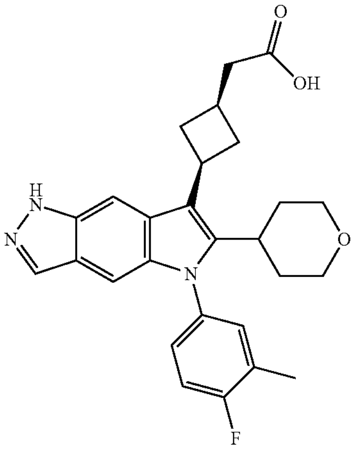 [SMILES: Cc1cc(-n2c(C3CCOCC3)c([C@H]3C[C@@H](CC(=O)O)C3)c3cc4[nH]ncc4cc32)ccc1F]

TABLE 1-continued
Compounds 1-215
96
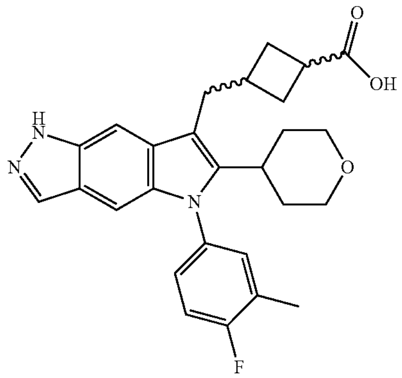 [SMILES: Cc1cc(-n2c(C3CCOCC3)c(CC3CC(C(=O)O)C3)c3cc4[nH]ncc4cc32)ccc1F]
97
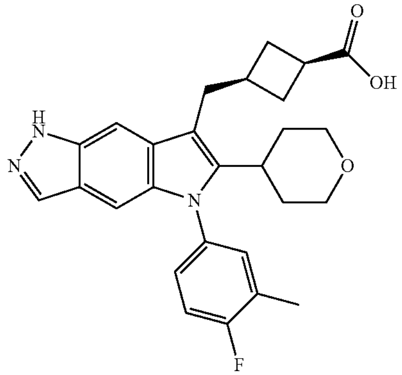 [SMILES: Cc1cc(-n2c(C3CCOCC3)c(C[C@H]3C[C@@H](C(=O)O)C3)c3cc4[nH]ncc4cc32)ccc1F]
98
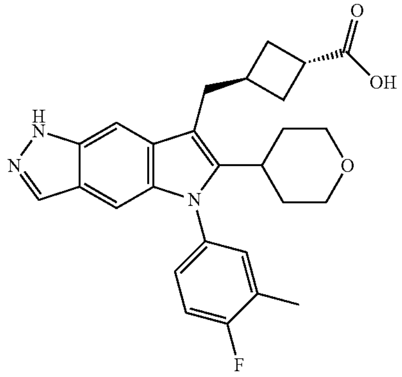 [SMILES: Cc1cc(-n2c(C3CCOCC3)c(C[C@H]3C[C@H](C(=O)O)C3)c3cc4[nH]ncc4cc32)ccc1F]
99
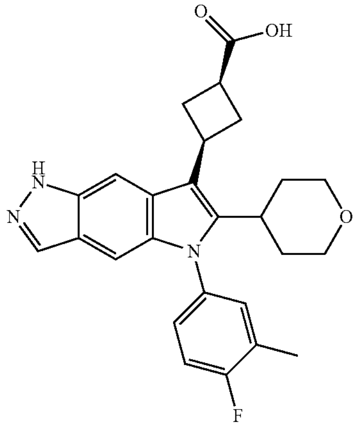 [SMILES: Cc1cc(-n2c(C3CCOCC3)c([C@H]3C[C@@H](C(=O)O)C3)c3cc4[nH]ncc4cc32)ccc1F]
100
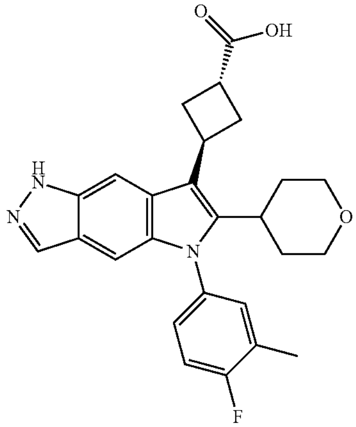 [SMILES: Cc1cc(-n2c(C3CCOCC3)c([C@H]3C[C@H](C(=O)O)C3)c3cc4[nH]ncc4cc32)ccc1F]
101
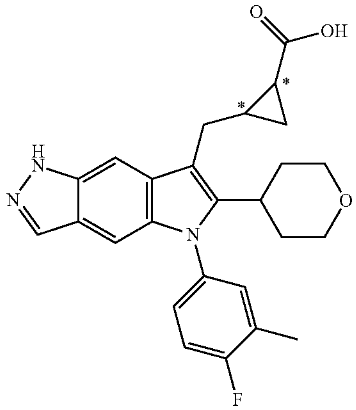
[TRANS-ENANT-1]
102
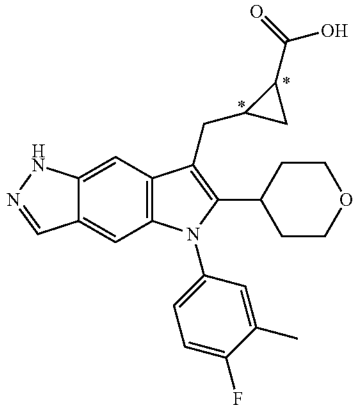
[TRANS-ENANT-2]

TABLE 1-continued
Compounds 1-215
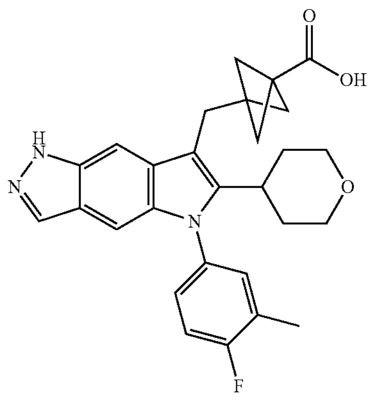 [SMILES: Cc1cc(-n2c(C3CCOCC3)c(CC34CC(C(=O)O)(C3)C4)c3cc4[nH]ncc4cc32)ccc1F]
103
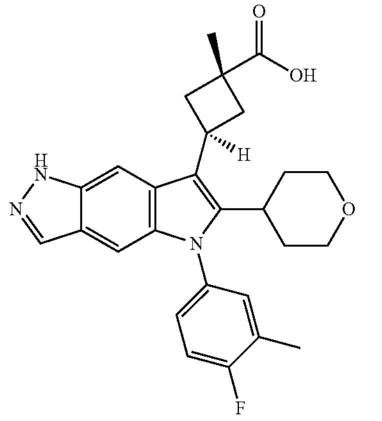 [SMILES: Cc1cc(-n2c(C3CCOCC3)c([C@H]3C[C@](C)(C(=O)O)C3)c3cc4[nH]ncc4cc32)ccc1F]
104
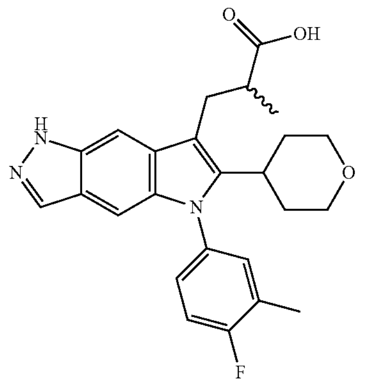
105
[Rac]
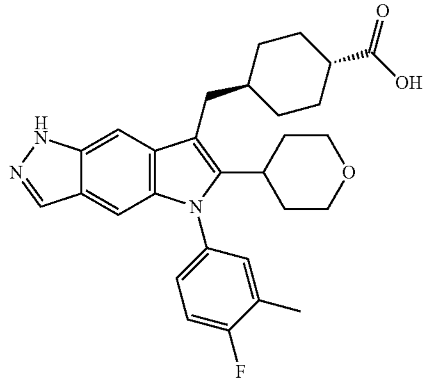 [SMILES: Cc1cc(-n2c(C3CCOCC3)c(C[C@H]3CC[C@H](C(=O)O)CC3)c3cc4[nH]ncc4cc32)ccc1F]
106
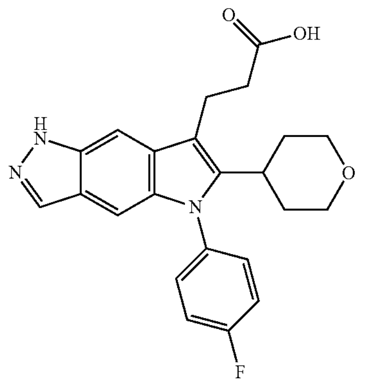 [SMILES: O=C(O)CCc1c(C2CCOCC2)n(-c2ccc(F)cc2)c2cc3cn[nH]c3cc12]
107
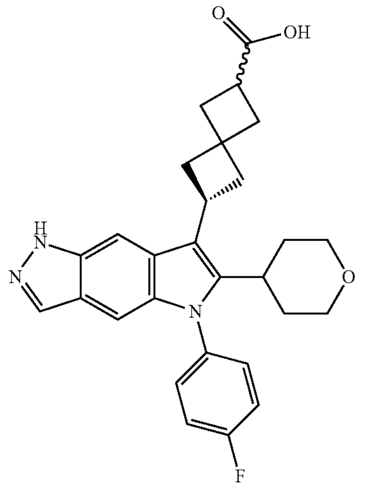
108
[RAC]

TABLE 1-continued
| Compounds 1-215 |
|---|
| 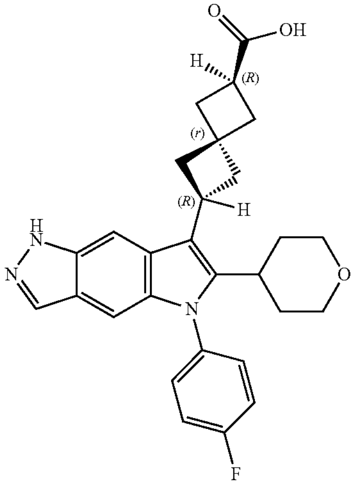 109 |
| [ENANT-1] |
| 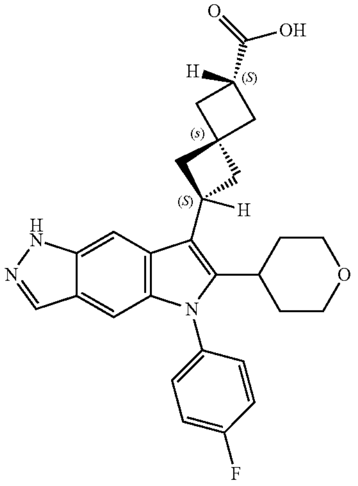 110 |
| [ENANT-2] |
| 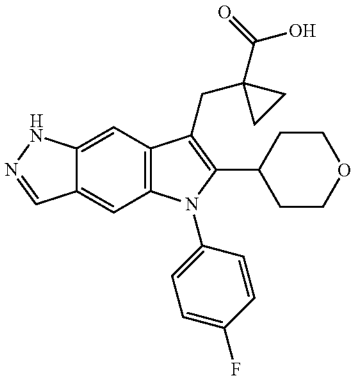 [SMILES: O=C(O)C1(Cc2c(C3CCOCC3)n(-c3ccc(F)cc3)c3cc4cn[nH]c4cc23)CC1] 111 |
TABLE 1-continued
| Compounds 1-215 |
|---|
| 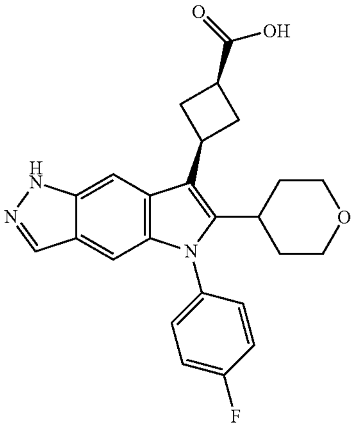 [SMILES: O=C(O)[C@H]1C[C@@H](c2c(C3CCOCC3)n(-c3ccc(F)cc3)c3cc4cn[nH]c4cc32)C1] 112 |
| 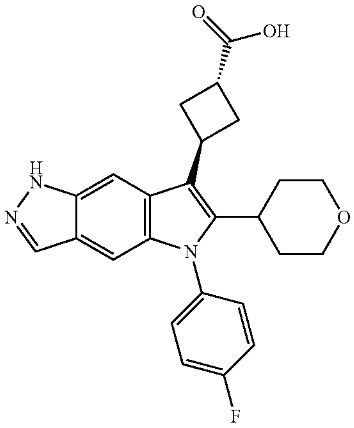 [SMILES: O=C(O)[C@H]1C[C@H](c2c(C3CCOCC3)n(-c3ccc(F)cc3)c3cc4cn[nH]c4cc32)C1] 113 |
| 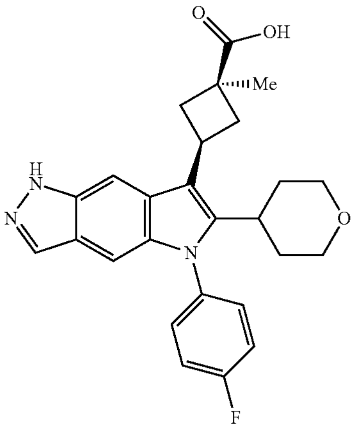 [SMILES: C[C@]1(C(=O)O)C[C@@H](c2c(C3CCOCC3)n(-c3ccc(F)cc3)c3cc4cn[nH]c4cc32)C1] 114 |

TABLE 1-continued
Compounds 1-215
115
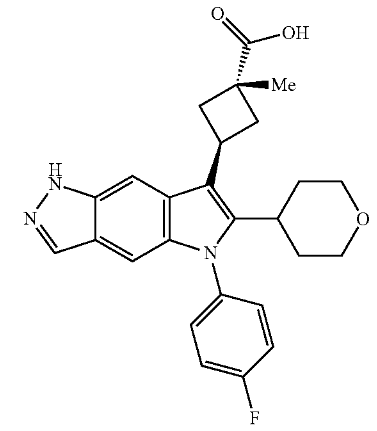 [SMILES: C[C@]1(C(=O)O)C[C@H](c2c(C3CCOCC3)n(-c3ccc(F)cc3)c3cc4cn[nH]c4cc32)C1]
116
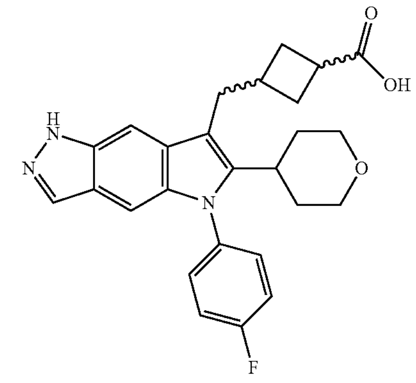 [SMILES: O=C(O)C1CC(Cc2c(C3CCOCC3)n(-c3ccc(F)cc3)c3cc4cn[nH]c4cc23)C1]
117
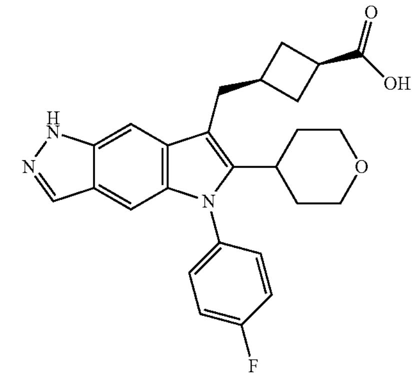 [SMILES: O=C(O)[C@H]1C[C@@H](Cc2c(C3CCOCC3)n(-c3ccc(F)cc3)c3cc4cn[nH]c4cc23)C1]
118
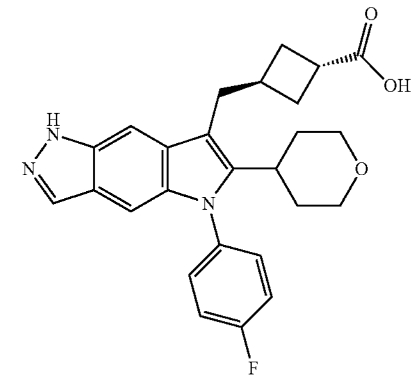 [SMILES: O=C(O)[C@H]1C[C@H](Cc2c(C3CCOCC3)n(-c3ccc(F)cc3)c3cc4cn[nH]c4cc23)C1]
TABLE 1-continued
Compounds 1-215
119
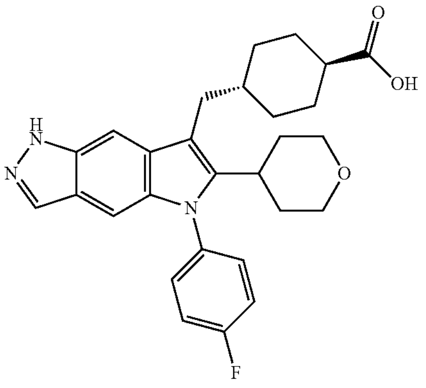 [SMILES: O=C(O)[C@H]1CC[C@H](Cc2c(C3CCOCC3)n(-c3ccc(F)cc3)c3cc4cn[nH]c4cc23)CC1]
120
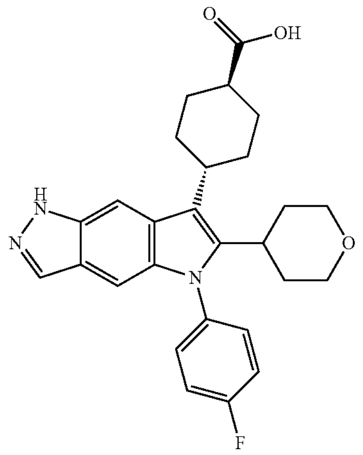 [SMILES: O=C(O)[C@H]1CC[C@H](c2c(C3CCOCC3)n(-c3ccc(F)cc3)c3cc4cn[nH]c4cc32)CC1]
121
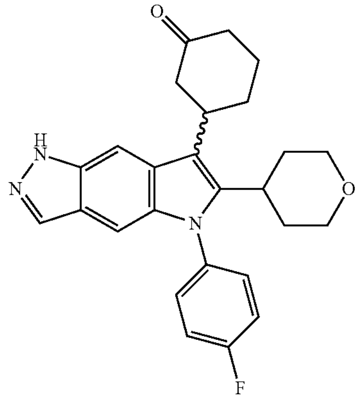
[RAC]

TABLE 1-continued
Compounds 1-215
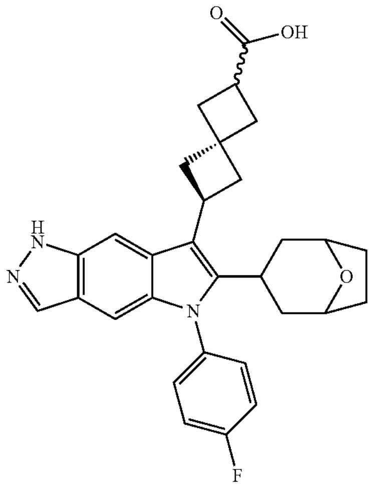
122
[RAC]
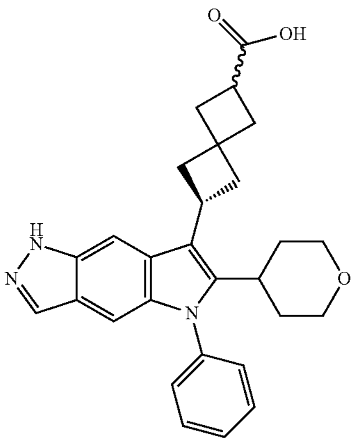
123
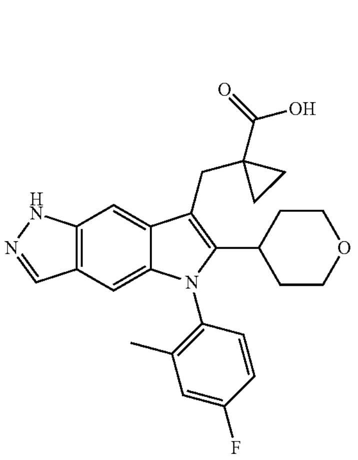 [SMILES: Cc1cc(F)ccc1-n1c(C2CCOCC2)c(CC2(C(=O)O)CC2)c2cc3[nH]ncc3cc21]
124
TABLE 1-continued
Compounds 1-215
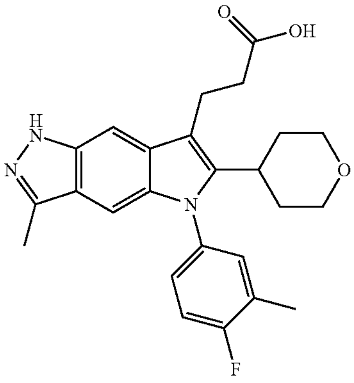 [SMILES: Cc1cc(-n2c(C3CCOCC3)c(CCC(=O)O)c3cc4[nH]nc(C)c4cc32)ccc1F]
125
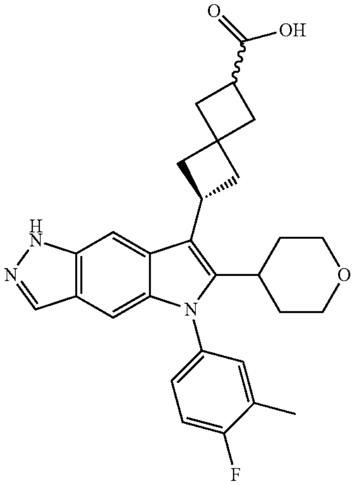
126
[Rac]
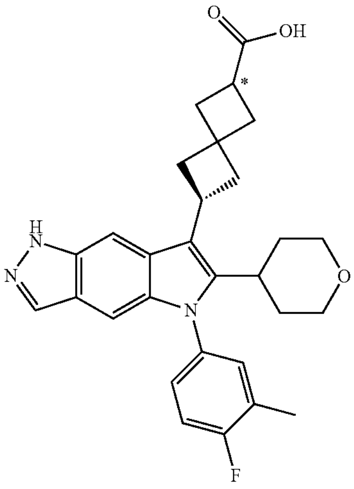
127
[ENANT-1]

TABLE 1-continued
Compounds 1-215
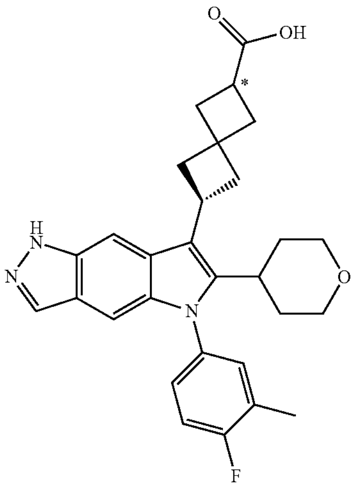
128
[ENANT-2]
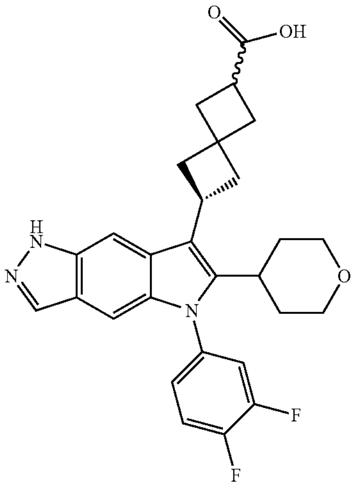
129
[RAC]
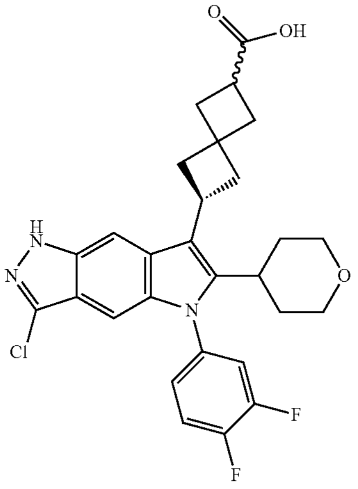
130
[RAC]
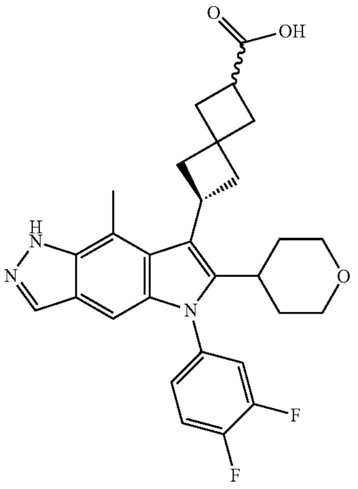
131
[RAC]
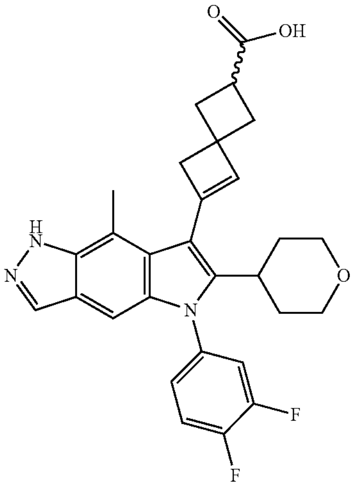
132
[RAC]
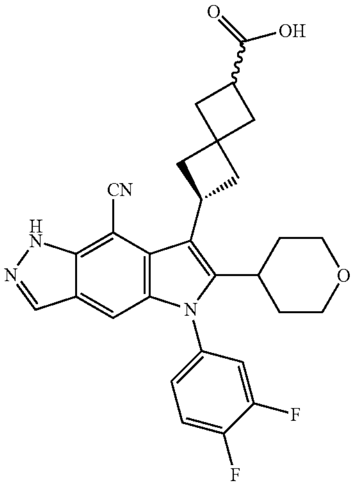
133
[RAC]

TABLE 1-continued
| Compounds 1-215 |
| --- |
| 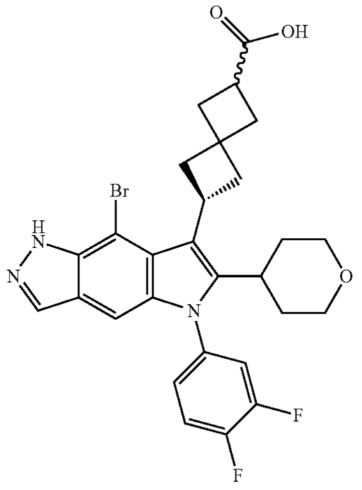 134 |
| [RAC] |
| 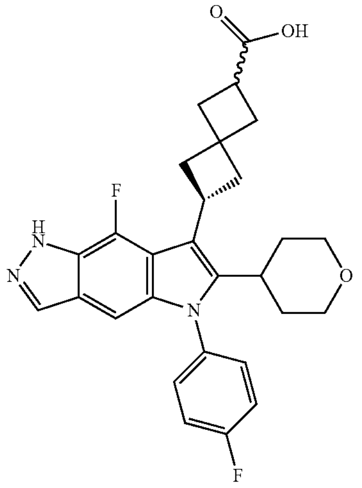 135 |
| [RAC] |
| 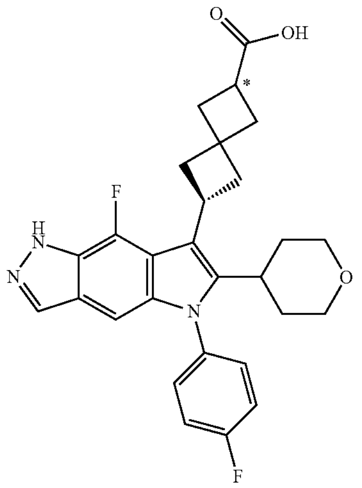 136 |
| [ENANT-1] |
TABLE 1-continued
| Compounds 1-215 |
| --- |
| 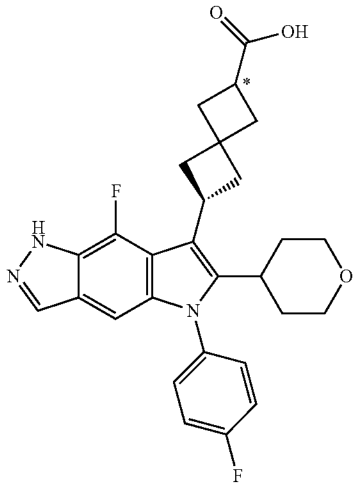 137 |
| [ENANT-2] |
| 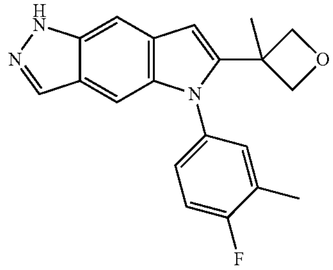 [SMILES: Cc1cc(-n2c(C3(C)COC3)cc3cc4[nH]ncc4cc32)ccc1F] 138 |
| 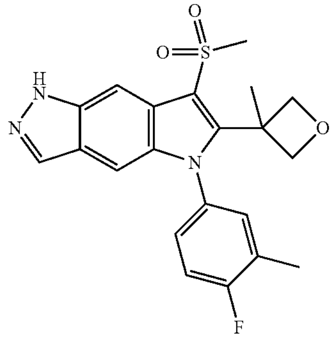 [SMILES: Cc1cc(-n2c(C3(C)COC3)c(S(C)(=O)=O)c3cc4[nH]ncc4cc32)ccc1F] 139 |

TABLE 1-continued
Compounds 1-215
140
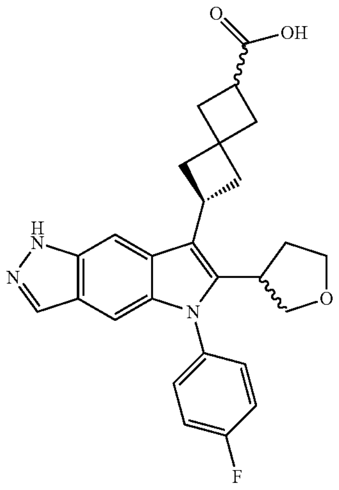
141
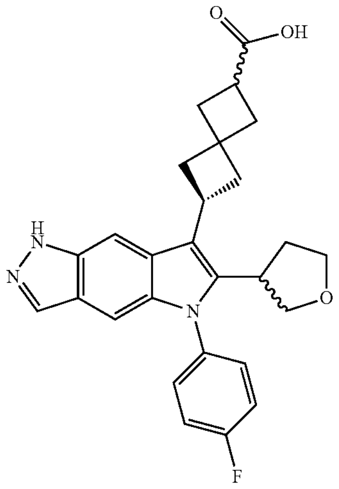
[DIAST MIX-1]
142
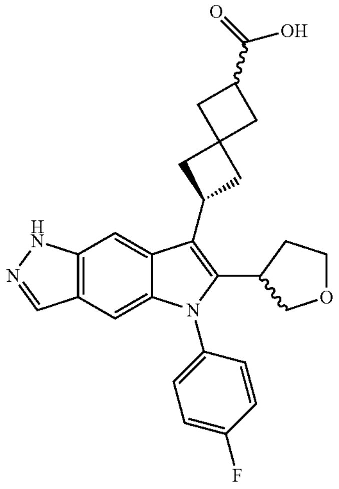
[DIAST MIX-2]
TABLE 1-continued
Compounds 1-215
143
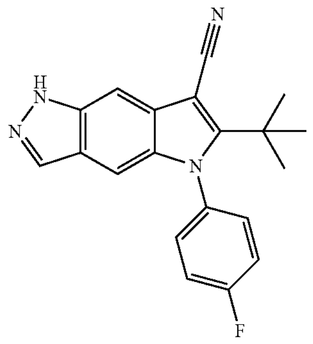 [SMILES: CC(C)(C)c1c(C#N)c2cc3[nH]ncc3cc2n1-c1ccc(F)cc1]
144
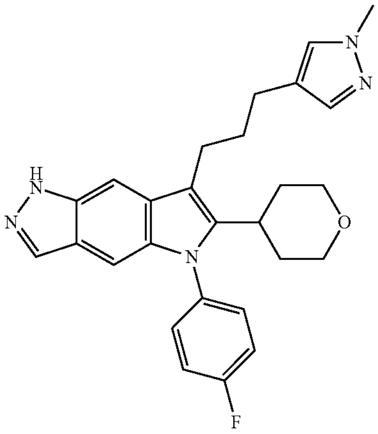 [SMILES: Cn1cc(CCCc2c(C3CCOCC3)n(-c3ccc(F)cc3)c3cc4cn[nH]c4cc23)cn1]
145
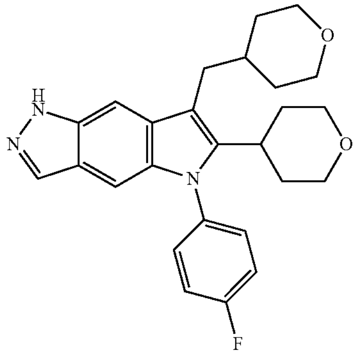 [SMILES: Fc1ccc(-n2c(C3CCOCC3)c(CC3CCOCC3)c3cc4[nH]ncc4cc32)cc1]
146
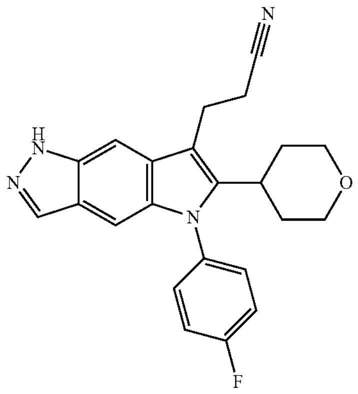 [SMILES: N#CCCc1c(C2CCOCC2)n(-c2ccc(F)cc2)c2cc3cn[nH]c3cc12]

TABLE 1-continued
| Compounds 1-215 |
| --- |
147
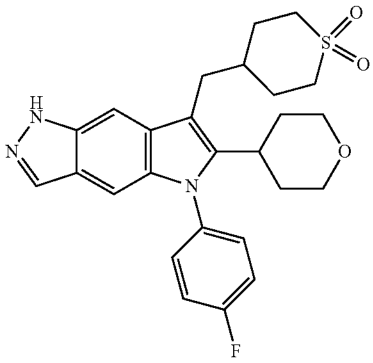 [SMILES: O=S1(=O)CCC(Cc2c(C3CCOCC3)n(-c3ccc(F)cc3)c3cc4cn[nH]c4cc23)CC1]
148
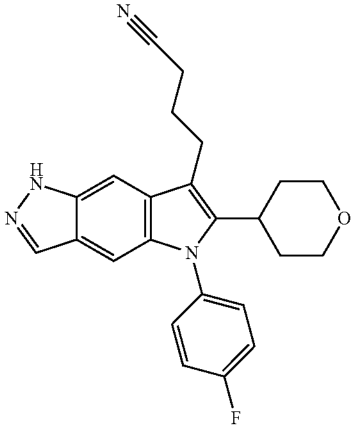 [SMILES: N#CCCCc1c(C2CCOCC2)n(-c2ccc(F)cc2)c2cc3cn[nH]c3cc12]
149
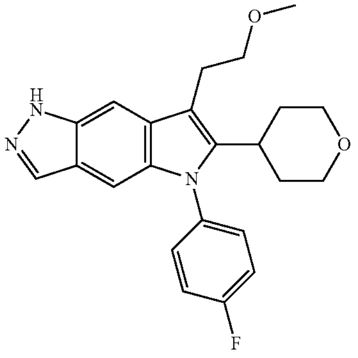 [SMILES: COCCc1c(C2CCOCC2)n(-c2ccc(F)cc2)c2cc3cn[nH]c3cc12]
TABLE 1-continued
| Compounds 1-215 |
| --- |
150
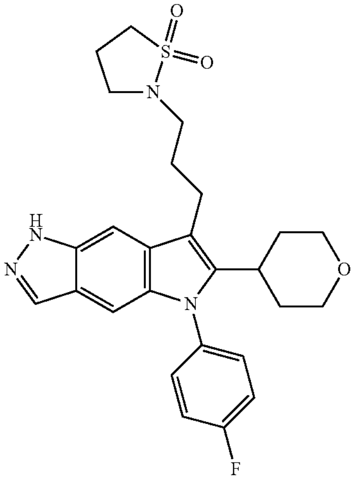 [SMILES: O=S1(=O)CCCN1CCCc1c(C2CCOCC2)n(-c2ccc(F)cc2)c2cc3cn[nH]c3cc12]
151
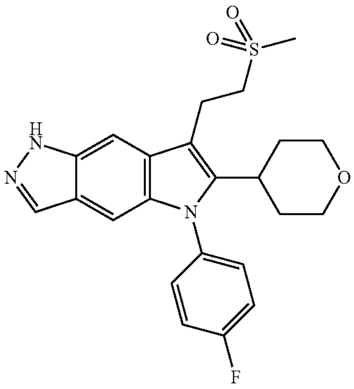 [SMILES: CS(=O)(=O)CCc1c(C2CCOCC2)n(-c2ccc(F)cc2)c2cc3cn[nH]c3cc12]
152
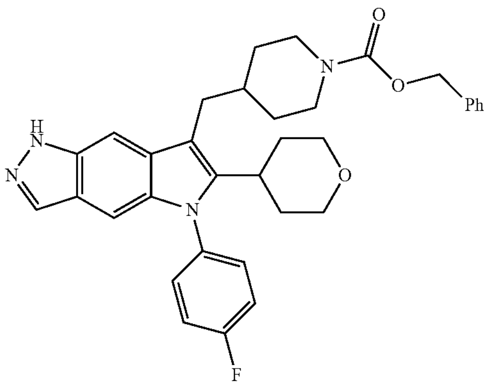 [SMILES: O=C(OCc1ccccc1)N1CCC(Cc2c(C3CCOCC3)n(-c3ccc(F)cc3)c3cc4cn[nH]c4cc23)CC1]

TABLE 1-continued
Compounds 1-215
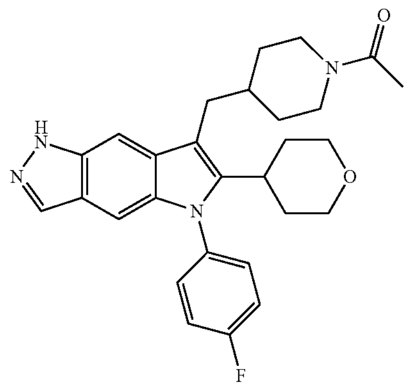 [SMILES: CC(=O)N1CCC(Cc2c(C3CCOCC3)n(-c3ccc(F)cc3)c3cc4cn[nH]c4cc23)CC1]
153
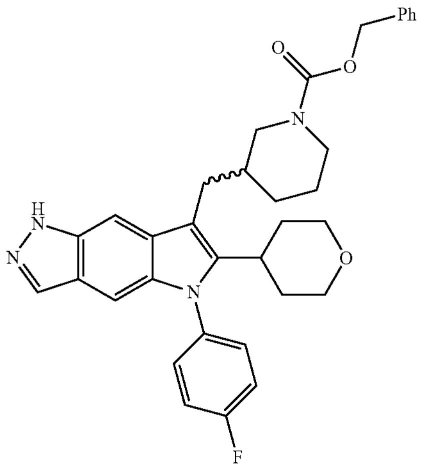 [SMILES: O=C(OCc1ccccc1)N1CCCC(Cc2c(C3CCOCC3)n(-c3ccc(F)cc3)c3cc4cn[nH]c4cc23)C1]
154
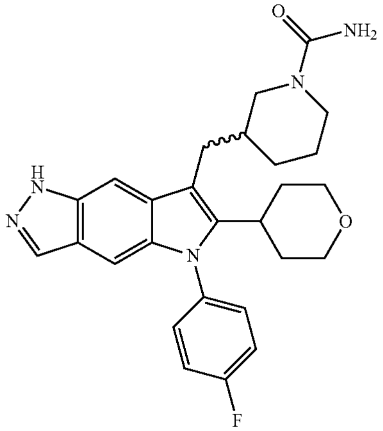 [SMILES: NC(=O)N1CCCC(Cc2c(C3CCOCC3)n(-c3ccc(F)cc3)c3cc4cn[nH]c4cc23)C1]
155
TABLE 1-continued
Compounds 1-215
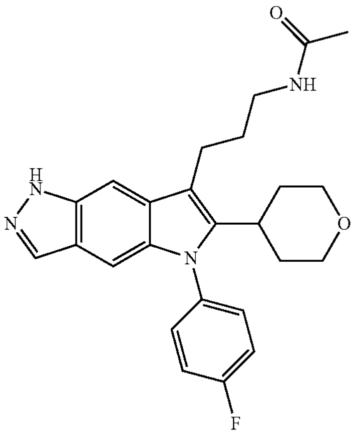 [SMILES: CC(=O)NCCCc1c(C2CCOCC2)n(-c2ccc(F)cc2)c2cc3cn[nH]c3cc12]
156
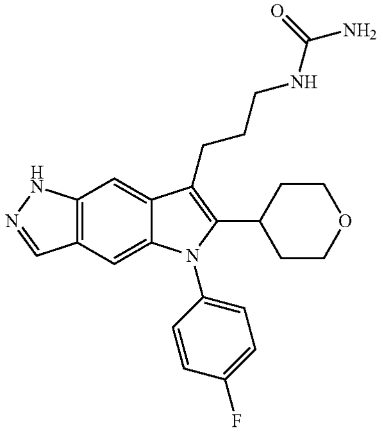 [SMILES: NC(=O)NCCCc1c(C2CCOCC2)n(-c2ccc(F)cc2)c2cc3cn[nH]c3cc12]
157
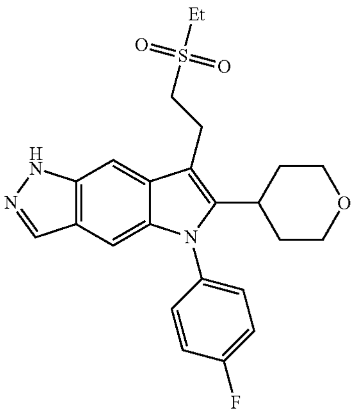 [SMILES: CCS(=O)(=O)CCc1c(C2CCOCC2)n(-c2ccc(F)cc2)c2cc3cn[nH]c3cc12]
158

TABLE 1-continued
| Compounds 1-215 |
| --- |
| 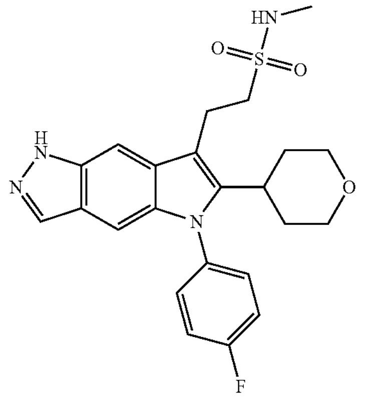 [SMILES: CNS(=O)(=O)CCc1c(C2CCOCC2)n(-c2ccc(F)cc2)c2cc3cn[nH]c3cc12] 159 |
| 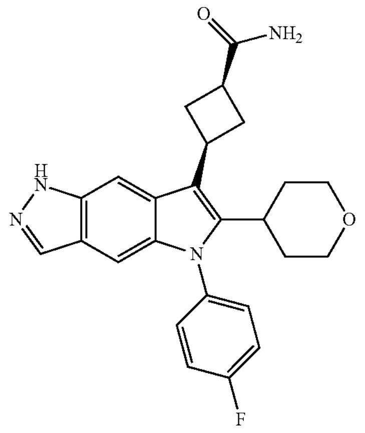 [SMILES: NC(=O)[C@H]1C[C@@H](c2c(C3CCOCC3)n(-c3ccc(F)cc3)c3cc4cn[nH]c4cc32)C1] 160 |
| 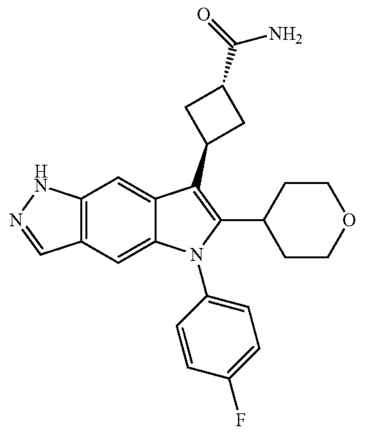 [SMILES: NC(=O)[C@H]1C[C@H](c2c(C3CCOCC3)n(-c3ccc(F)cc3)c3cc4cn[nH]c4cc32)C1] 161 |
TABLE 1-continued
| Compounds 1-215 |
| --- |
| 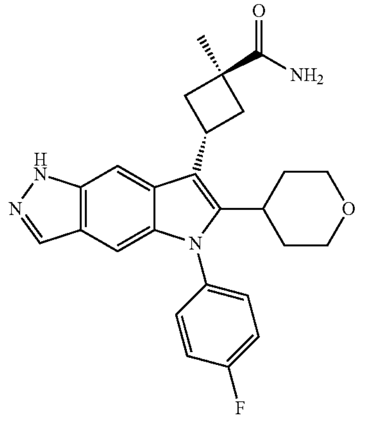 [SMILES: C[C@]1(C(N)=O)C[C@H](c2c(C3CCOCC3)n(-c3ccc(F)cc3)c3cc4cn[nH]c4cc32)C1] 162 |
| 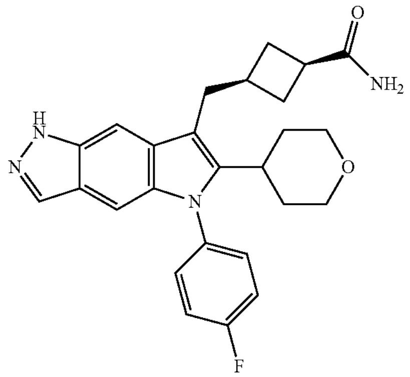 [SMILES: NC(=O)[C@H]1C[C@@H](Cc2c(C3CCOCC3)n(-c3ccc(F)cc3)c3cc4cn[nH]c4cc23)C1] 163 |
| 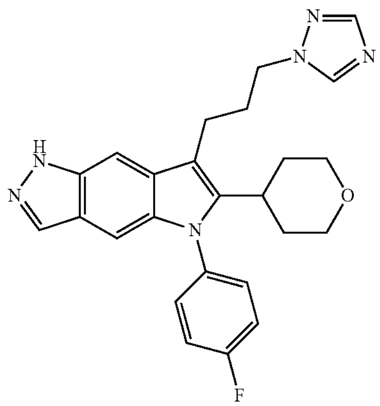 [SMILES: Fc1ccc(-n2c(C3CCOCC3)c(CCCn3cncn3)c3cc4[nH]ncc4cc32)cc1] 164 |
| 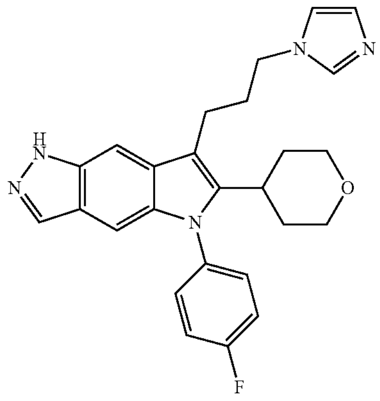 [SMILES: Fc1ccc(-n2c(C3CCOCC3)c(CCCn3ccnc3)c3cc4[nH]ncc4cc32)cc1] 165 |

TABLE 1-continued
Compounds 1-215
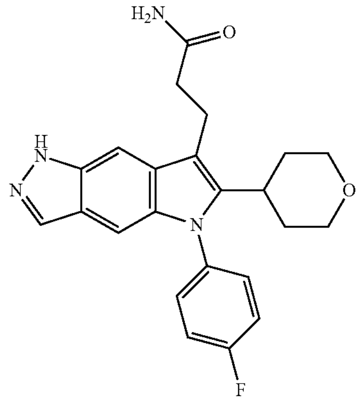 [SMILES: NC(=O)CCc1c(C2CCOCC2)n(-c2ccc(F)cc2)c2cc3cn[nH]c3cc12]
166
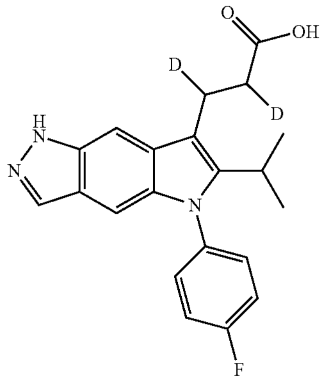 [SMILES: [2H]C(C(=O)O)C([2H])c1c(C(C)C)n(-c2ccc(F)cc2)c2cc3cn[nH]c3cc12]
167
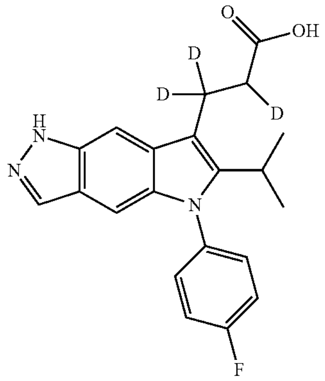 [SMILES: [2H]C(C(=O)O)C([2H])([2H])c1c(C(C)C)n(-c2ccc(F)cc2)c2cc3cn[nH]c3cc12]
168
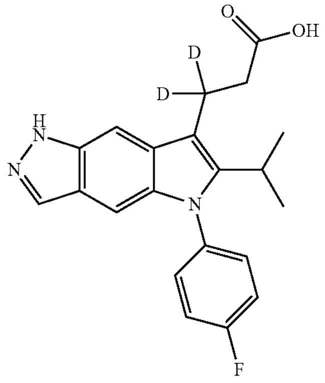 [SMILES: [2H]C([2H])(CC(=O)O)c1c(C(C)C)n(-c2ccc(F)cc2)c2cc3cn[nH]c3cc12]
169
TABLE 1-continued
Compounds 1-215
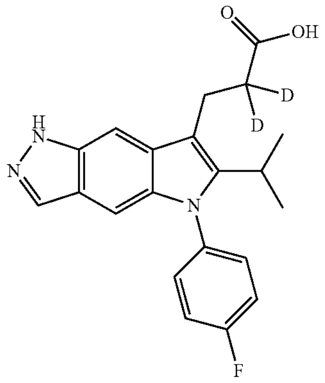 [SMILES: [2H]C([2H])(Cc1c(C(C)C)n(-c2ccc(F)cc2)c2cc3cn[nH]c3cc12)C(=O)O]
170
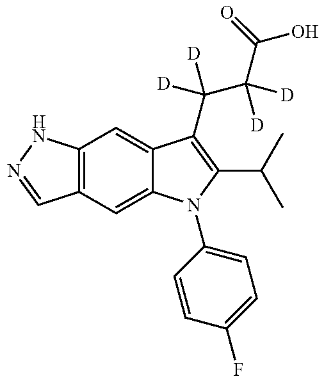 [SMILES: [2H]C([2H])(C(=O)O)C([2H])([2H])c1c(C(C)C)n(-c2ccc(F)cc2)c2cc3cn[nH]c3cc12]
171
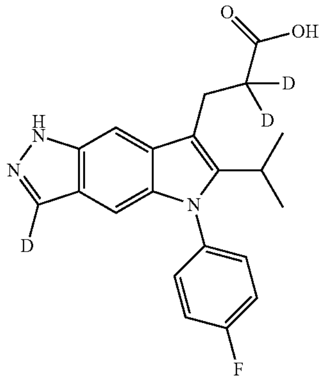 [SMILES: [2H]c1n[nH]c2cc3c(CC([2H])([2H])C(=O)O)c(C(C)C)n(-c4ccc(F)cc4)c3cc12]
172

TABLE 1-continued
| Compounds 1-215 |
|---|
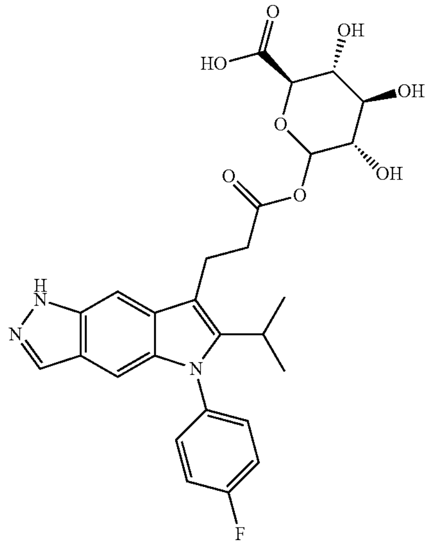 [SMILES: CC(C)c1c(CCC(=O)OC2O[C@@H](C(=O)O)[C@H](O)[C@@H](O)[C@@H]2O)c2cc3[nH]ncc3cc2n1-c1ccc(F)cc1]
173
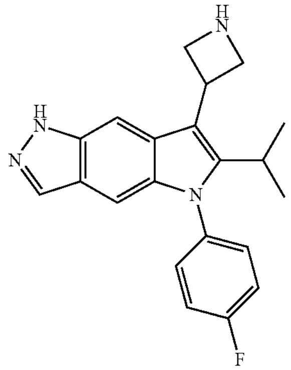 [SMILES: CC(C)c1c(C2CNC2)c2cc3[nH]ncc3cc2n1-c1ccc(F)cc1]
174
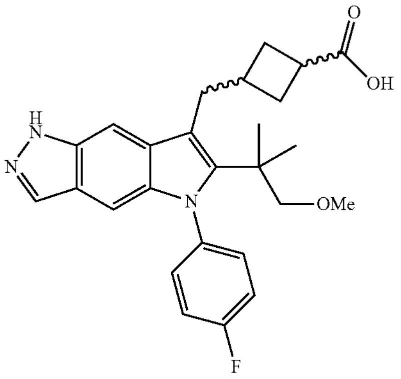 [SMILES: COCC(C)(C)c1c(CC2CC(C(=O)O)C2)c2cc3[nH]ncc3cc2n1-c1ccc(F)cc1]
175
TABLE 1-continued
| Compounds 1-215 |
|---|
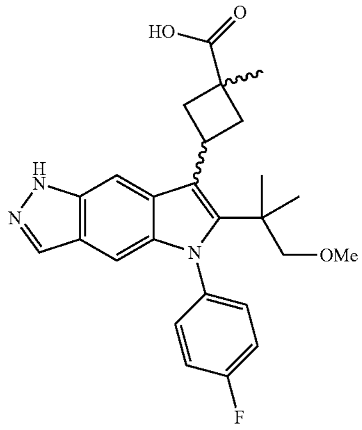 [SMILES: COCC(C)(C)c1c(C2CC(C)(C(=O)O)C2)c2cc3[nH]ncc3cc2n1-c1ccc(F)cc1]
176
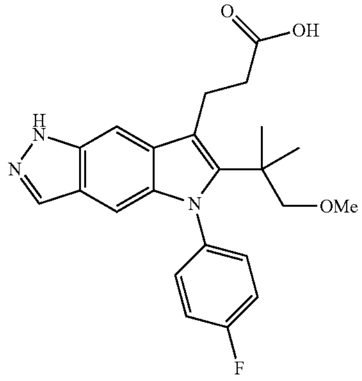 [SMILES: COCC(C)(C)c1c(CCC(=O)O)c2cc3[nH]ncc3cc2n1-c1ccc(F)cc1]
177
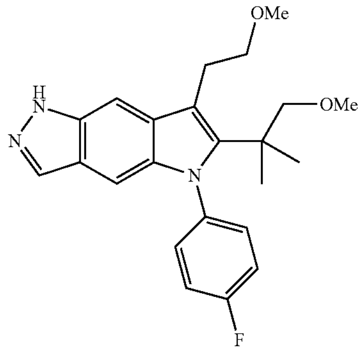 [SMILES: COCCc1c(C(C)(C)COC)n(-c2ccc(F)cc2)c2cc3cn[nH]c3cc12]
178
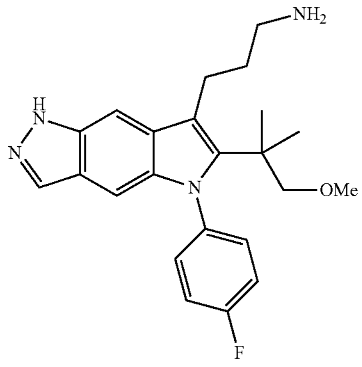 [SMILES: COCC(C)(C)c1c(CCCN)c2cc3[nH]ncc3cc2n1-c1ccc(F)cc1]
179

TABLE 1-continued
Compounds 1-215
180
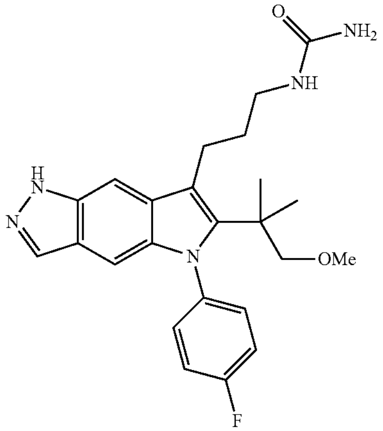 [SMILES: COCC(C)(C)c1c(CCCNC(N)=O)c2cc3[nH]ncc3cc2n1-c1ccc(F)cc1]
181
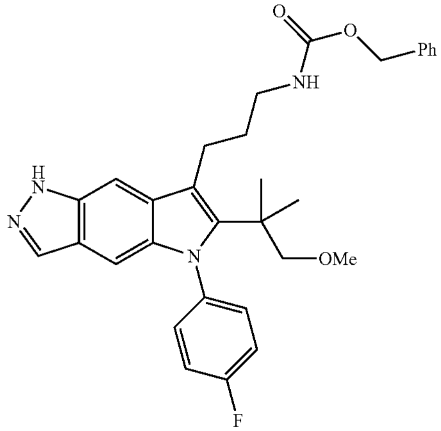 [SMILES: COCC(C)(C)c1c(CCCNC(=O)OCc2ccccc2)c2cc3[nH]ncc3cc2n1-c1ccc(F)cc1]
182
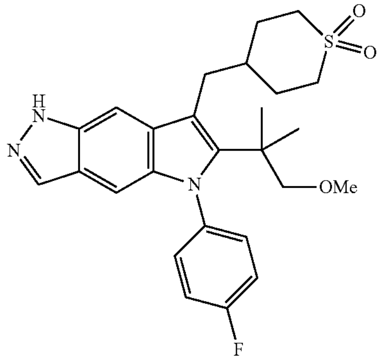 [SMILES: COCC(C)(C)c1c(CC2CCS(=O)(=O)CC2)c2cc3[nH]ncc3cc2n1-c1ccc(F)cc1]
183
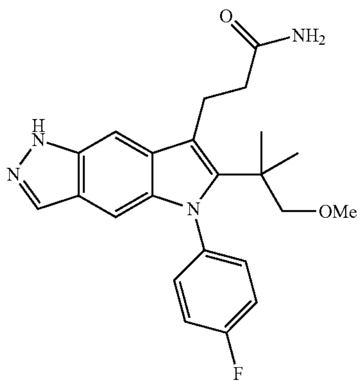 [SMILES: COCC(C)(C)c1c(CCC(N)=O)c2cc3[nH]ncc3cc2n1-c1ccc(F)cc1]
TABLE 1-continued
Compounds 1-215
184
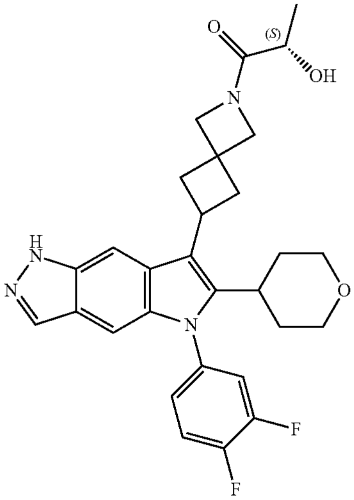
185
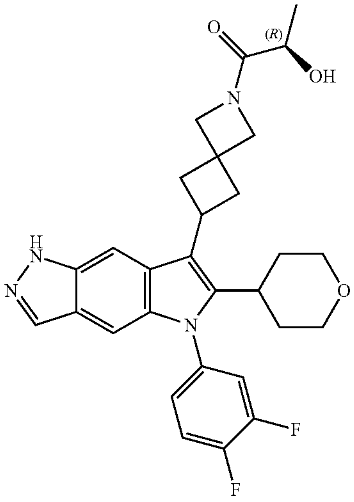
186
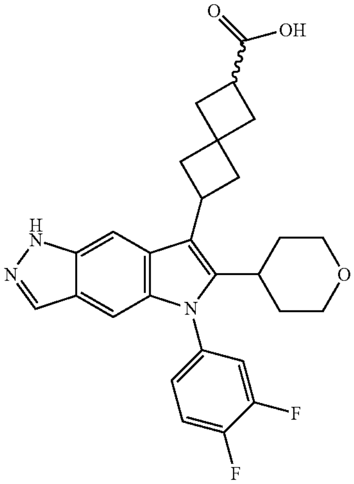 [SMILES: O=C(O)C1CC2(C1)CC(c1c(C3CCOCC3)n(-c3ccc(F)c(F)c3)c3cc4cn[nH]c4cc13)C2]

TABLE 1-continued
Compounds 1-215
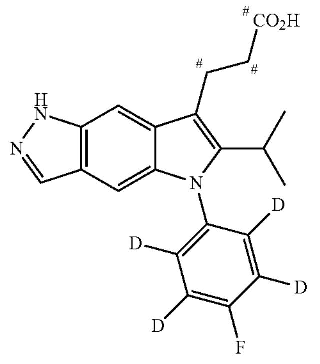
187
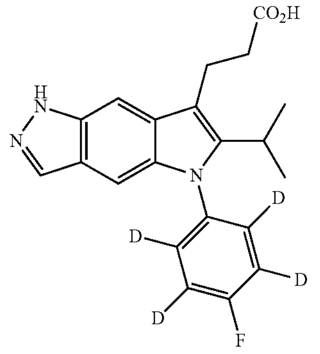 [SMILES: [2H]c1c([2H])c(-n2c(C(C)C)c(CCC(=O)O)c3cc4[nH]ncc4cc32)c([2H])c([2H])c1F]
188
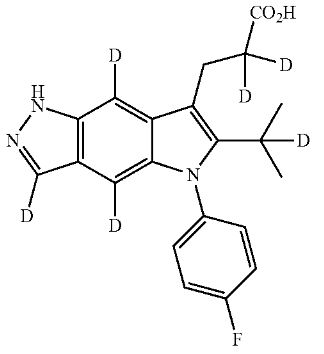 [SMILES: [2H]c1n[nH]c2c([2H])c3c(CC([2H])([2H])C(=O)O)c(C([2H])(C)C)n(-c4ccc(F)cc4)c3c([2H])c12]
189
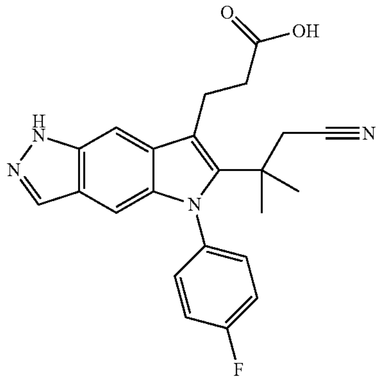 [SMILES: CC(C)(CC#N)c1c(CCC(=O)O)c2cc3[nH]ncc3cc2n1-c1ccc(F)cc1]
190
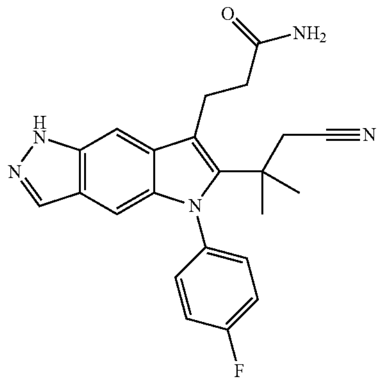 [SMILES: CC(C)(CC#N)c1c(CCC(N)=O)c2cc3[nH]ncc3cc2n1-c1ccc(F)cc1]
191
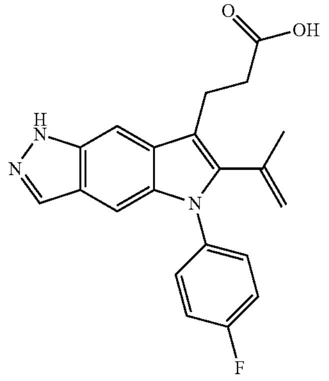 [SMILES: C=C(C)c1c(CCC(=O)O)c2cc3[nH]ncc3cc2n1-c1ccc(F)cc1]
192
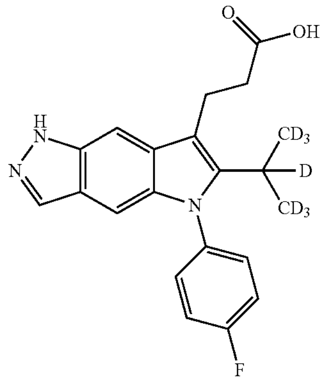 [SMILES: [2H]C([2H])([2H])C([2H])(c1c(CCC(=O)O)c2cc3[nH]ncc3cc2n1-c1ccc(F)cc1)C([2H])([2H])[2H]]
193
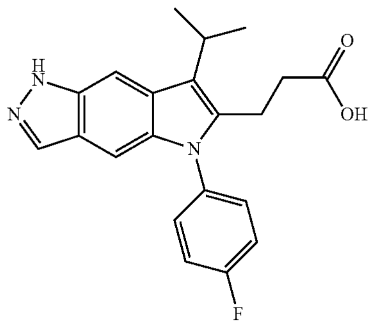 [SMILES: CC(C)c1c(CCC(=O)O)n(-c2ccc(F)cc2)c2cc3cn[nH]c3cc12]
194

TABLE 1-continued
| Compounds 1-215 |
|---|
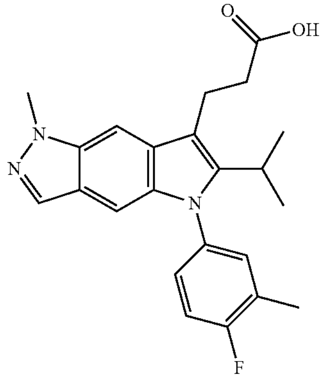 [SMILES: Cc1cc(-n2c(C(C)C)c(CCC(=O)O)c3cc4c(cnn4C)cc32)ccc1F]
195
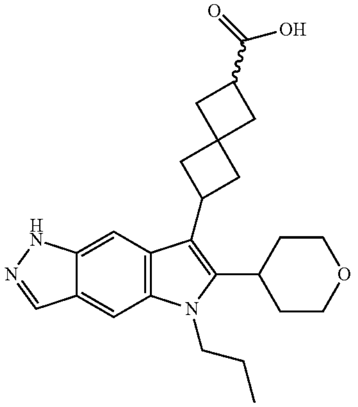 [SMILES: CCCn1c(C2CCOCC2)c(C2CC3(CC(C(=O)O)C3)C2)c2cc3[nH]ncc3cc21]
196
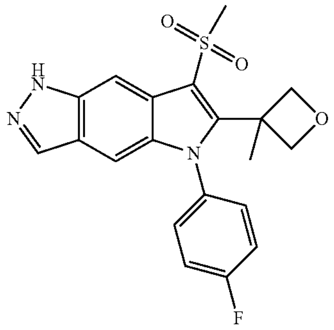 [SMILES: CC1(c2c(S(C)(=O)=O)c3cc4[nH]ncc4cc3n2-c2ccc(F)cc2)COC1]
197
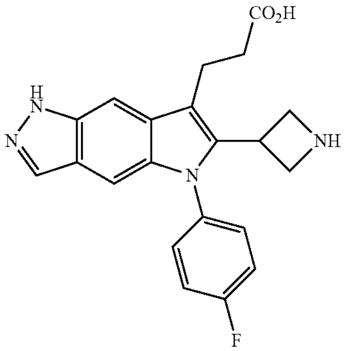 [SMILES: O=C(O)CCc1c(C2CNC2)n(-c2ccc(F)cc2)c2cc3cn[nH]c3cc12]
198
TABLE 1-continued
| Compounds 1-215 |
|---|
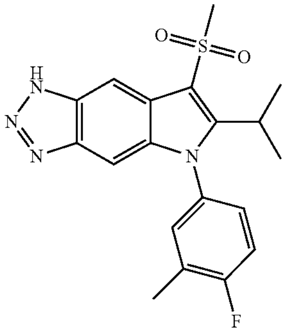 [SMILES: Cc1cc(-n2c(C(C)C)c(S(C)(=O)=O)c3cc4[nH]nnc4cc32)ccc1F]
199
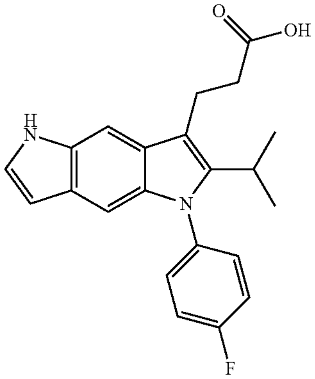 [SMILES: CC(C)c1c(CCC(=O)O)c2cc3[nH]ccc3cc2n1-c1ccc(F)cc1]
200
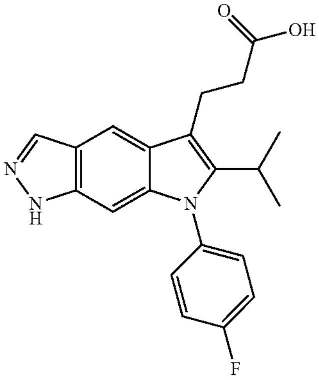 [SMILES: CC(C)c1c(CCC(=O)O)c2cc3cn[nH]c3cc2n1-c1ccc(F)cc1]
201
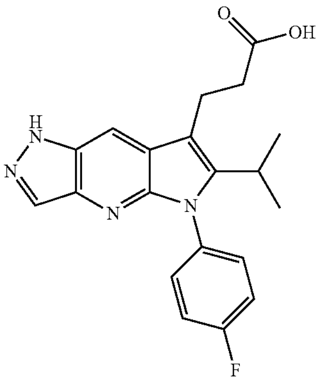 [SMILES: CC(C)c1c(CCC(=O)O)c2cc3[nH]ncc3nc2n1-c1ccc(F)cc1]
202

TABLE 1-continued
Compounds 1-215
203
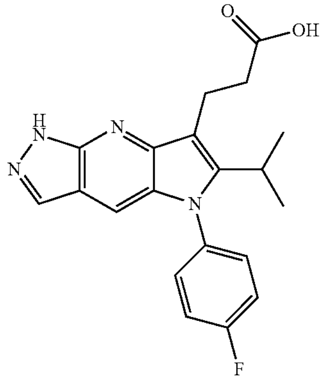 [SMILES: CC(C)c1c(CCC(=O)O)c2nc3[nH]ncc3cc2n1-c1ccc(F)cc1]
204
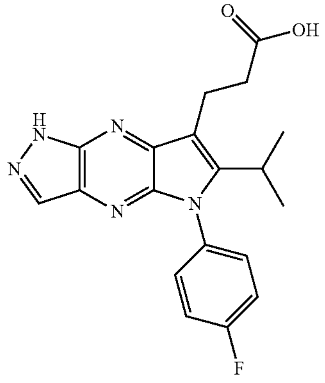 [SMILES: CC(C)c1c(CCC(=O)O)c2nc3[nH]ncc3nc2n1-c1ccc(F)cc1]
205
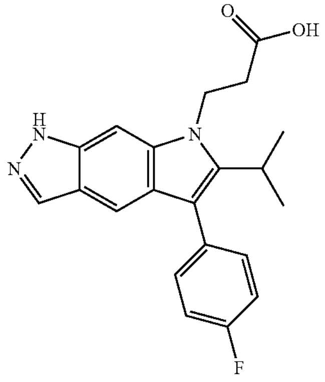 [SMILES: CC(C)c1c(-c2ccc(F)cc2)c2cc3cn[nH]c3cc2n1CCC(=O)O]
206
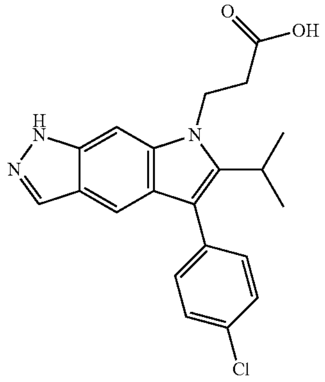 [SMILES: CC(C)c1c(-c2ccc(Cl)cc2)c2cc3cn[nH]c3cc2n1CCC(=O)O]
TABLE 1-continued
Compounds 1-215
207
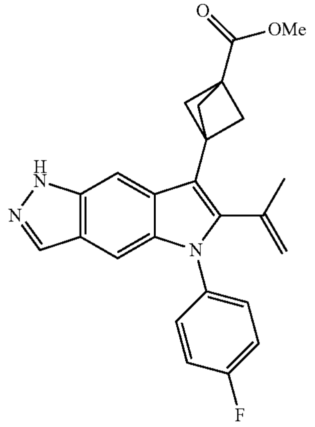 [SMILES: C=C(C)c1c(C23CC(C(=O)OC)(C2)C3)c2cc3[nH]ncc3cc2n1-c1ccc(F)cc1]
208
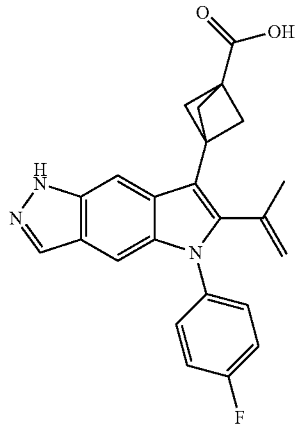 [SMILES: C=C(C)c1c(C23CC(C(=O)O)(C2)C3)c2cc3[nH]ncc3cc2n1-c1ccc(F)cc1]
209
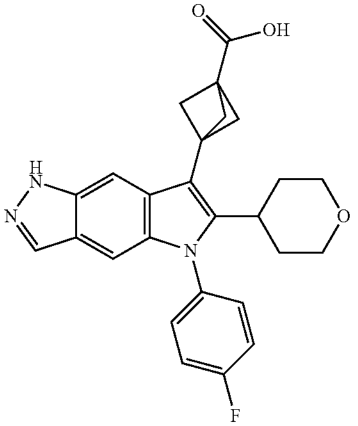 [SMILES: O=C(O)C12CC(c3c(C4CCOCC4)n(-c4ccc(F)cc4)c4cc5cn[nH]c5cc34)(C1)C2]

TABLE 1-continued

Compounds 1-215

210

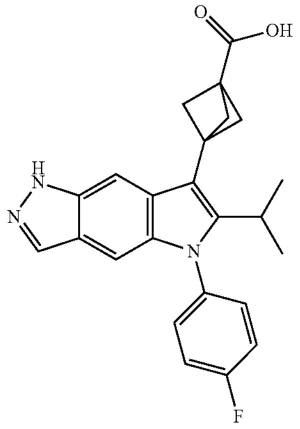 [SMILES: CC(C)c1c(C23CC(C(=O)O)(C2)C3)c2cc3[nH]ncc3cc2n1-c1ccc(F)cc1]

211

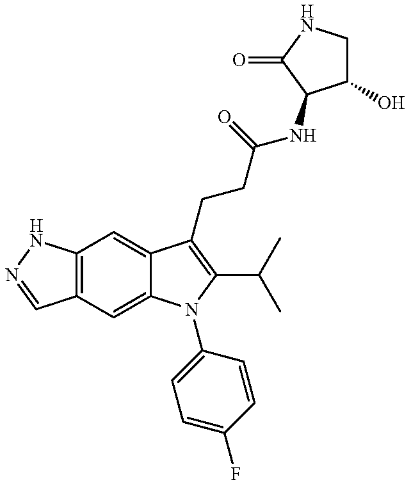 [SMILES: CC(C)c1c(CCC(=O)N[C@H]2C(=O)NC[C@@H]2O)c2cc3[nH]ncc3cc2n1-c1ccc(F)cc1]

212

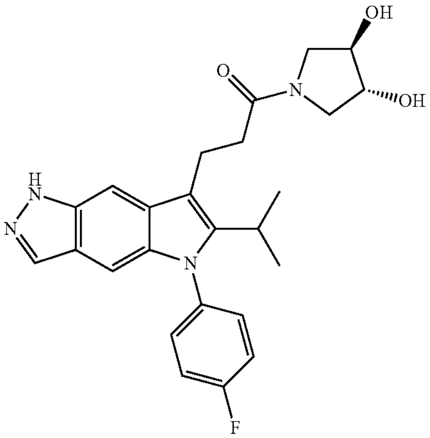 [SMILES: CC(C)c1c(CCC(=O)N2C[C@@H](O)[C@H](O)C2)c2cc3[nH]ncc3cc2n1-c1ccc(F)cc1]

TABLE 1-continued

Compounds 1-215

213

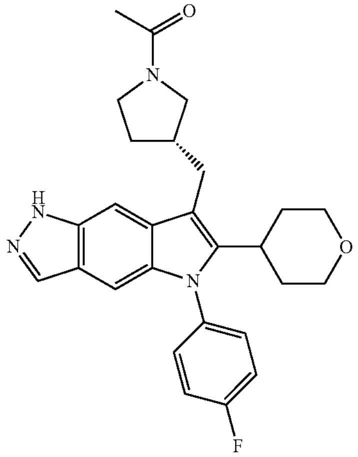 [SMILES: CC(=O)N1CC[C@@H](Cc2c(C3CCOCC3)n(-c3ccc(F)cc3)c3cc4cn[nH]c4cc23)C1]

214

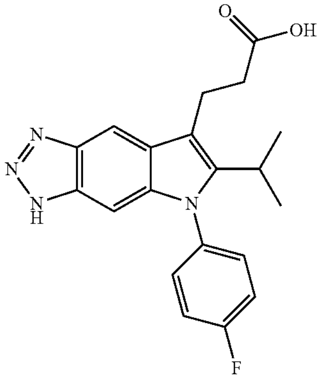 [SMILES: CC(C)c1c(CCC(=O)O)c2cc3nn[nH]c3cc2n1-c1ccc(F)cc1]

215

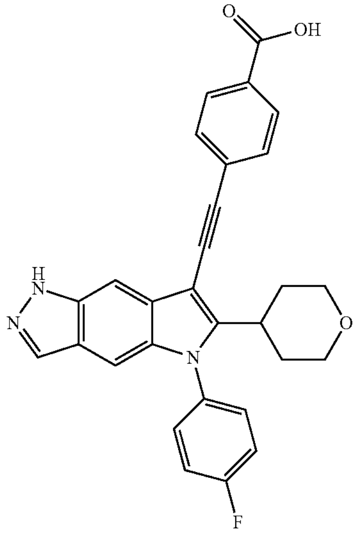 [SMILES: O=C(O)c1ccc(C#Cc2c(C3CCOCC3)n(-c3ccc(F)cc3)c3cc4cn[nH]c4cc23)cc1]

Some embodiments of the invention include derivatives of Compounds 1-215 or compounds of Formulae I, 1-6, 3-4, 3-5, 3-6, 4-3, 5-3, 6-4, 7-4, 8-4, 12-1, 12-2, II, and III. In some embodiments, the derivatives are silicon derivatives in which at least one carbon atom in a compound selected from Compounds 1-215 or compounds of Formulae I, 1-6, 3-4, 3-5, 3-6, 4-3, 5-3, 6-4, 7-4, 8-4, 12-1, 12-2, II, and III has been replaced by silicon. In some embodiments, the derivatives are boron derivatives, in which at least one carbon atom in a compound selected from Compounds 1-215 or compounds of Formulae I, 1-6, 3-4, 3-5, 3-6, 4-3, 5-3, 6-4, 7-4, 8-4, 12-1, 12-2, II, and III has been replaced by boron. In other embodiments, the derivatives are phosphate derivatives, in which at least one carbon atom in a compound selected from Compounds 1-215 or compounds of Formulae I, 1-6, 3-4, 3-5, 3-6, 4-3, 5-3, 6-4, 7-4, 8-4, 12-1, 12-2, II, and III has been replaced by phosphorus. Because the general properties of silicon, boron, and phosphorus are similar to those of carbon, replacement of carbon by silicon, boron, or phosphorus can result in compounds with similar biological activity to a carbon containing original compound.

In some embodiments, the derivative is a silicon derivative in which one carbon atom in a compound selected from Compounds 1-215 or compounds of Formulae I, 1-6, 3-4, 3-5, 3-6, 4-3, 5-3, 6-4, 7-4, 8-4, 12-1, 12-2, II, and III has been replaced by silicon. In other embodiments, two carbon atoms have been replaced by silicon. The carbon replaced by silicon may be a non-aromatic carbon. In some embodiments a quaternary carbon atom of a tert-butyl moiety such as in Compound 215, may be replaced by silicon. In some embodiments, the silicon derivatives of the invention may include one or more hydrogen atoms replaced by deuterium. For example, one or more hydrogens of a tert-butyl moiety in which the carbon has been replaced by silicon, may be replaced by deuterium. In other embodiments, a silicon derivative of a compound selected from Compounds 1-215 or compounds of I, 1-6, 3-4, 3-5, 3-6, 4-3, 5-3, 6-4, 7-4, 8-4, 12-1, 12-2, II, and III may have silicon incorporated into a heterocycle ring.

In some embodiments, examples of silicon derivatives of Compounds 1-215 or compounds of Formulae I, 1-6, 3-4, 3-5, 3-6, 4-3, 5-3, 6-4, 7-4, 8-4, 12-1, 12-2, II, and III include the following compounds:

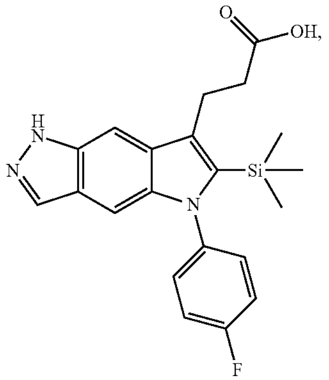

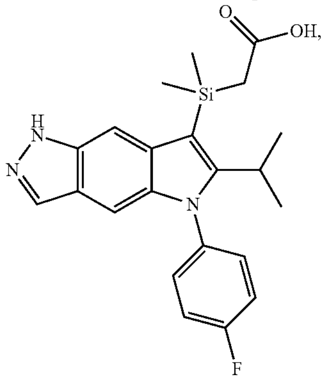

and

-continued

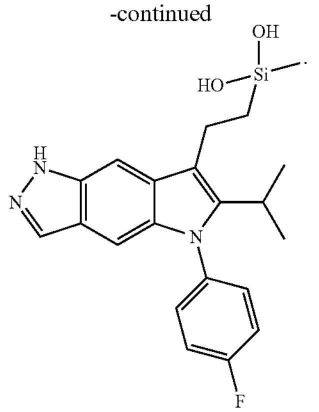

In some embodiments, examples of boron derivatives of Compounds 1-215 or compounds of Formulae I, 1-6, 3-4, 3-5, 3-6, 4-3, 5-3, 6-4, 7-4, 8-4, 12-1, 12-2, II, and III include the following compounds:

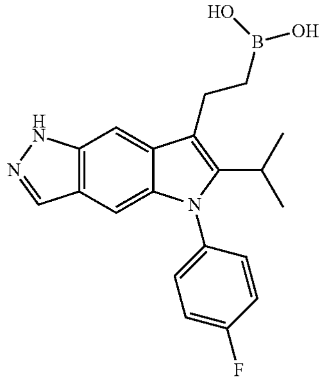

and

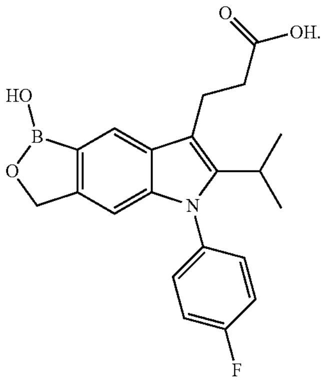

In some embodiments, examples of phosphate derivatives of Compounds 1-215 or compounds of Formulae I, 1-6, 3-4, 3-5, 3-6, 4-3, 5-3, 6-4, 7-4, 8-4, 12-1, 12-2, II, and III include the following compounds:

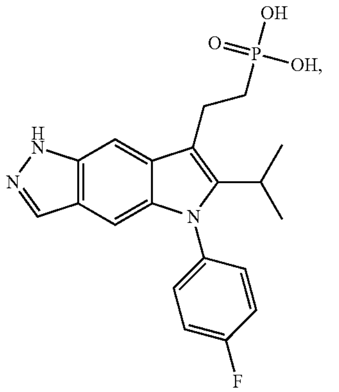

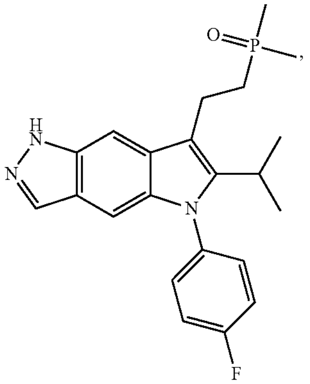

, and

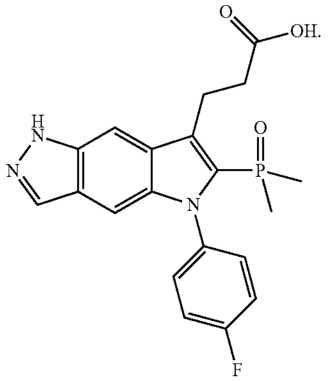

Solid Forms of Compounds

In some embodiments, Compound 32 is an amorphous solid. In some embodiments, Compound 32 is a crystalline solid. In some embodiments, Compound 32 is in the form of Crystalline Form A, Crystalline Form B, Crystalline Form C, Compound 32 monohydrochloride salt, Compound 32 hemi hydrochloride salt hemi hydrate, Compound 32 ethanol solvate, or a mixture of any two or more of the foregoing.

In some embodiments, Compound 32 is a crystalline solid consisting of Crystalline Form A and Crystalline Form C. In some embodiments, the crystalline solid consists of 1% to 99% Crystalline Form A relative to the total weight of the crystalline solid Compound 32. In some embodiments, the crystalline solid consists of 2% to 99% Crystalline Form A relative to the total weight of the crystalline solid Compound 32. In some embodiments, the crystalline solid consists of 5% to 99% Crystalline Form A relative to the total weight of the crystalline solid Compound 32. In some embodiments, the crystalline solid consists of 10% to 99% Crystalline Form A relative to the total weight of the crystalline solid Compound 32. In some embodiments, the crystalline solid consists of 15% to 99% Crystalline Form A relative to the total weight of the crystalline solid Compound 32. In some embodiments, the crystalline solid consists of 20% to 99% Crystalline Form A relative to the total weight of the crystalline solid Compound 32. In some embodiments, the crystalline solid consists of 25% to 99% Crystalline Form A relative to the total weight of the crystalline solid Compound 32. In some embodiments, the crystalline solid consists of 30% to 99% Crystalline Form A relative to the total weight of the crystalline solid Compound 32. In some embodiments, the crystalline solid consists of 35% to 99% Crystalline Form A relative to the total weight of the crystalline solid Compound 32. In some embodiments, the crystalline solid consists of 45% to 99% Crystalline Form A relative to the total weight of the crystalline solid Compound 32. In some embodiments, the crystalline solid consists of 50% to 99% Crystalline Form A relative to the total weight of the crystalline solid Compound 32. In some embodiments, the crystalline solid consists of 55% to 99% Crystalline Form A relative to the total weight of the crystalline solid Compound 32. In some embodiments, the crystalline solid consists of 60% to 99% Crystalline Form A relative to the total weight of the crystalline solid Compound 32. In some embodiments, the crystalline solid consists of 65% to 99% Crystalline Form A relative to the total weight of the crystalline solid Compound 32. In some embodiments, the crystalline solid consists of 70% to 99% Crystalline Form A relative to the total weight of the crystalline solid Compound 32. In some embodiments, the crystalline solid consists of 75% to 99% Crystalline Form A relative to the total weight of the crystalline solid Compound 32. In some embodiments, the crystalline solid consists of 80% to 99% Crystalline Form A relative to the total weight of the crystalline solid Compound 32. In some embodiments, the crystalline solid consists of 85% to 99% Crystalline Form A relative to the total weight of the crystalline solid Compound 32. In some embodiments, the crystalline solid consists of 90% to 99% Crystalline Form A relative to the total weight of the crystalline solid Compound 32. In some embodiments, the crystalline solid consists of 95% to 99% Crystalline Form A relative to the total weight of the crystalline solid Compound 32.

In some embodiments, the crystalline solid of Compound 32 consists of 1% to 99% Crystalline Form C relative to the total weight of the crystalline solid Compound 32. In some embodiments, the crystalline solid consists of 2% to 99% Crystalline Form C relative to the total weight of the crystalline solid Compound 32. In some embodiments, the crystalline solid consists of 5% to 99% Crystalline Form C relative to the total weight of the crystalline solid Compound 32. In some embodiments, the crystalline solid consists of 10% to 99% Crystalline Form C relative to the total weight of the crystalline solid Compound 32. In some embodiments, the crystalline solid consists of 15% to 99% Crystalline Form C relative to the total weight of the crystalline solid Compound 32. In some embodiments, the crystalline solid consists of 20% to 99% Crystalline Form C relative to the total weight of the crystalline solid Compound 32. In some embodiments, the crystalline solid consists of 25% to 99% Crystalline Form C relative to the total weight of the crystalline solid Compound 32. In some embodiments, the crystalline solid consists of 30% to 99% Crystalline Form C relative to the total weight of the crystalline solid Compound 32. In some embodiments, the crystalline solid consists of 35% to 99% Crystalline Form C relative to the total weight of the crystalline solid Compound 32. In some embodiments, the crystalline solid consists of 45% to 99% Crystalline Form C relative to the total weight of the crystalline solid Compound 32. In some embodiments, the crystalline solid consists of 50% to 99% Crystalline Form C relative to the total weight of the crystalline solid Compound 32. In some embodiments, the crystalline solid consists of 55% to 99% Crystalline Form C relative to the total weight of the crystalline solid Compound 32. In some embodiments, the crystalline solid consists of 60% to 99% Crystalline Form C relative to the total weight of the crystalline solid Compound 32. In some embodiments, the crystalline solid consists of 65% to 99% Crystalline Form C relative to the total weight of the crystalline solid Compound 32. In some embodiments, the crystalline solid consists of 70% to 99% Crystalline Form C relative to the total weight of the crystalline solid Compound 32. In some embodiments, the crystalline solid consists of 75% to 99% Crystalline Form C relative to the total weight of the crystalline solid Compound 32. In some embodiments, the crystalline solid consists of 80% to 99% Crystalline Form C relative to the total weight of the crystalline solid Compound 32. In some embodiments, the crystalline solid consists of 85% to 99% Crystalline Form C relative to the total weight of the crystalline solid Compound 32. In some embodiments, the crystalline solid consists of 90% to 99% Crystalline Form C relative to the total weight of the crystalline solid Compound 32. In some embodiments, the crystalline solid consists of 95% to 99% Crystalline Form C relative to the total weight of the crystalline solid Compound 32.

In some embodiments, Compound 32 is a crystalline solid comprising 60% to 99.9% Crystalline Form A relative to the total weight of the crystalline solid Compound 32 and 0.1% to 40% Crystalline Form C relative to the total weight of the crystalline solid Compound 32. In some embodiments, the crystalline solid comprises 70% to 95% Crystalline Form A relative to the total weight of the crystalline solid Compound 32 and 5% to 30% Crystalline Form C relative to the total weight of the crystalline solid Compound 32. In some embodiments, the crystalline solid comprises 80% to 90% Crystalline Form A relative to the total weight of the crystalline solid Compound 32 and 10% to 20% Crystalline Form C relative to the total weight of the crystalline solid Compound 32.

In some embodiments, Compound 32 is in the form of Crystalline Form A. In some embodiments, Compound 32 is in the form of substantially pure Crystalline Form A. In some embodiments, Crystalline Form A is characterized by an X-ray powder diffractogram substantially similar to that in FIG. 7. In some embodiments, Crystalline Form A is characterized by an X-ray powder diffractogram having a signal at at least two two-theta values chosen from 15.0±0.2, 15.4±0.2, 17.6±0.2, and 20.4±0.2. In some embodiments, Crystalline Form A is characterized by an X-ray powder diffractogram having a signal at at least three two-theta values chosen from 10.9±0.2, 15.0±0.2, 15.4±0.2, 17.6±0.2, 18.1±0.2, 18.6±0.2, and 20.4±0.2.

In some embodiments, Crystalline Form A is characterized by an X-ray powder diffractogram having a signal at at least three two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least four two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least five two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least six two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least seven two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least eight two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least nine two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least ten two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least eleven two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least twelve two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least thirteen two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least fourteen two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least fifteen two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least sixteen two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least seventeen two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least eighteen two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least nineteen two-theta values chosen from 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at 20.4±0.2, 17.6±0.2, 18.1±0.2, 18.6±0.2, 24.5±0.2, 29.3±0.2, 15.0±0.2, 28.8±0.2, 24.7±0.2, 15.4±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2 two-theta.

In some embodiments, Crystalline Form A is characterized by an X-ray powder diffractogram having a signal at at least two two-theta values chosen from 15.0±0.2, 15.4±0.2, 17.6±0.2, and 20.4±0.2 and at least one additional signal at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least two additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least three additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least four additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least five additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least six additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least seven additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least eight additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least nine additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least ten additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least eleven additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least twelve additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least thirteen additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least fourteen additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at at least two two-theta values chosen from 15.0±0.2, 15.4±0.2, 17.6±0.2, and 20.4±0.2 and at least fifteen additional signals at two-theta values chosen from 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2. In some embodiments, Crystalline Form A is characterized by an X-ray powder diffractogram having a signal at 15.0±0.2, 15.4±0.2, 17.6±0.2, 20.4±0.2, 18.1±0.2, 18.6±0.2, 24.5±0.2, 29.3±0.2, 28.8±0.2, 24.7±0.2, 21.5±0.2, 18.9±0.2, 13.8±0.2, 10.9±0.2, 21.9±0.2, 23.6±0.2, 28.5±0.2, 26.8±0.2, 22.7±0.2, and 10.2±0.2 two-theta.

In some embodiments, Crystalline Form A has a single crystal unit cell characterized as follows:

| Crystal System<br>Space Group | Monoclinic<br>$P2_1/c$ |
|---|---|
| a (Å) | 9.3 ± 0.1 |
| b (Å) | 22.8 ± 0.1 |
| c (Å) | 8.6 ± 0.1 |
| α (°) | 90 ± 0.1 |
| β (°) | 94.7 ± 0.1 |
| γ (°) | 90 ± 0.1 |
| V ($Å^3$) | 1813.5 ± 0.2 |
| Z/Z' | 4/1 |

In some embodiments, disclosed herein is a composition comprising Crystalline Form A of compound 32. In some embodiments, disclosed herein is a composition comprising Compound 32 in substantially pure Crystalline Form A. In some embodiments, disclosed herein is a composition comprising at least one active compound consisting essentially of Compound 32 in Crystalline Form A.

Figure 11:
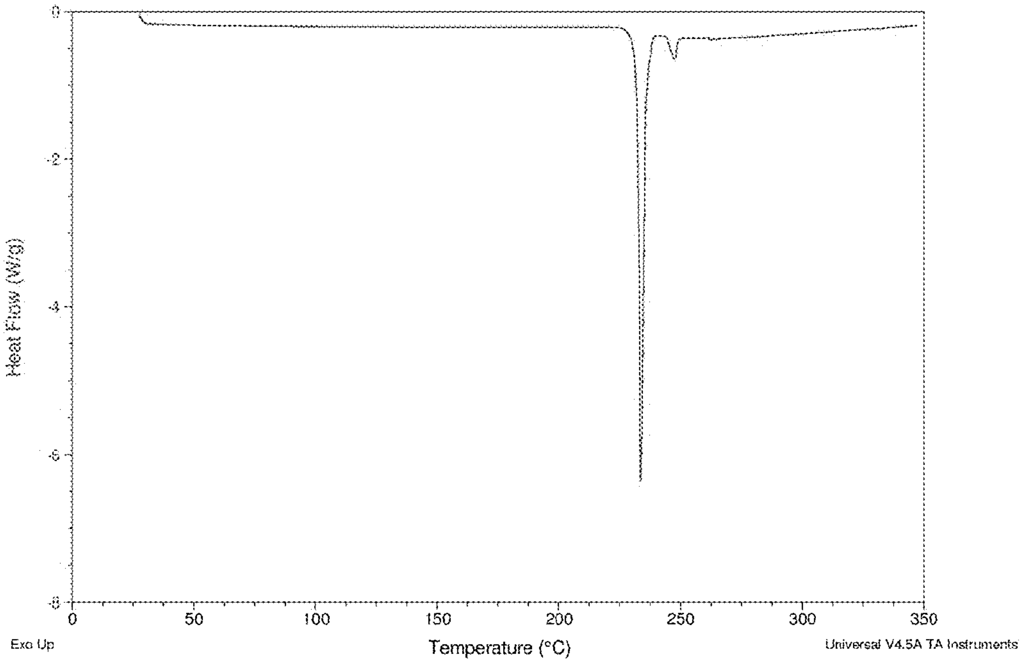
FIG. 11 depicts a DSC thermogram of Crystalline Form A of Compound 32.

In some embodiments, Crystalline Form A is characterized by a DSC substantially similar to that in FIG. 11. In some embodiments, Crystalline Form A is characterized by a DSC having a melting point at 234° C.

In some embodiments, Crystalline Form A is characterized by a $^{13}C$ NMR spectrum having a signal at at least one ppm values chosen from 137.1±0.2, 131.4±0.2, 121.7±0.2, 107.6±0.2, and 98.8±0.2 ppm. In some embodiments, Crystalline Form A is characterized by a $^{13}C$ NMR spectrum having a signal at at least two ppm values chosen from 137.1±0.2, 131.4±0.2, 121.7±0.2, 107.6±0.2, and 98.8±0.2 ppm. In some embodiments, Crystalline Form A is characterized by a $^{13}C$ NMR spectrum having a signal at at least three ppm values chosen from 137.1±0.2, 131.4±0.2, 121.7±0.2, 107.6±0.2, and 98.8±0.2 ppm. In some embodiments, Crystalline Form A is characterized by a $^{13}C$ NMR spectrum having a signal at at least four ppm values chosen from 137.1±0.2, 131.4±0.2, 121.7±0.2, 107.6±0.2, and 98.8±0.2 ppm. In some embodiments, Crystalline Form A is characterized by a $^{13}C$ NMR spectrum having a signal at 137.1±0.2, 131.4±0.2, 121.7±0.2, 107.6±0.2, and 98.8±0.2 ppm.

In some embodiments, Crystalline Form A is characterized by a $^{19}F$ NMR spectrum having a signal at −109.8±0.2 ppm.

In some embodiments, disclosed herein is Crystalline Form B of Compound 32. In some embodiments, Crystalline Form B is in substantially pure form. In some embodiments, Crystalline Form B is characterized by an X-ray powder diffractogram substantially similar to that in FIG. 13. In some embodiments, Crystalline Form B is characterized by an X-ray powder diffractogram having a signal at at least two two-theta values chosen from 10.0±0.2, 11.3±0.2, 12.2±0.2, and 20.7±0.2. In some embodiments, Crystalline Form B is characterized by an X-ray powder diffractogram having a signal at at least three two-theta values chosen from 7.8±0.2, 10.0±0.2, 11.3±0.2, 12.2±0.2, 16.0±0.2, and 20.7±0.2.

In some embodiments, Crystalline Form B is characterized by an X-ray powder diffractogram having a signal at at least two two-theta values chosen from 10.0±0.2, 11.3±0.2, 12.2±0.2, and 20.7±0.2 and at least one additional signal at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at at least two two-theta values chosen from 10.0±0.2, 11.3±0.2, 12.2±0.2, and 20.7±0.2 and at least two additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at at least three two-theta values chosen from 10.0±0.2, 11.3±0.2, 12.2±0.2, and 20.7±0.2 and at least one additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at at least two two-theta values chosen from 10.0±0.2, 11.3±0.2, 12.2±0.2, and 20.7±0.2 and at least four additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at at least two two-theta values chosen from 10.0±0.2, 11.3±0.2, 12.2±0.2, and 20.7±0.2 and at least five additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at at least two two-theta values chosen from 10.0±0.2, 11.3±0.2, 12.2±0.2, and 20.7±0.2 and at least six additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2.

In some embodiments, Crystalline Form B is characterized by an X-ray powder diffractogram having a signal at at least two two-theta values chosen from 10.0±0.2, 11.3±0.2, 12.2±0.2, and 20.7±0.2 and at least seven additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at at least two two-theta values chosen from 10.0±0.2, 11.3±0.2, 12.2±0.2, and 20.7±0.2 and at least eight additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at at least two two-theta values chosen from 10.0±0.2, 11.3±0.2, 12.2±0.2, and 20.7±0.2 and at least nine additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at at least two two-theta values chosen from 10.0±0.2, 11.3±0.2, 12.2±0.2, and 20.7±0.2 and at least ten additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at at least two two-theta values chosen from 10.0±0.2, 11.3±0.2, 12.2±0.2, and 20.7±0.2 and at least eleven additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at at least three two-theta values chosen from 10.0±0.2, 11.3±0.2, 12.2±0.2, and 20.7±0.2 and at least eleven additional signals at two-theta values chosen from 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2. In some embodiments, Crystalline Form B is characterized by an X-ray powder diffractogram having a signal at 10.0±0.2, 11.3±0.2, 12.2±0.2, 20.7±0.2, 21.3±0.2, 16.0±0.2, 20.3±0.2, 9.9±0.2, 22.7±0.2, 7.8±0.2, 20.5±0.2, 18.7±0.2, 23.4±0.2, 19.0±0.2, and 27.6±0.2 two-theta.

In some embodiments, disclosed herein is a composition comprising Crystalline Form B of compound 32. In some embodiments, disclosed herein is a composition comprising Compound 32 in substantially pure Crystalline Form B. In some embodiments, disclosed herein is a composition comprising at least one active compound consisting essentially of Compound 32 in Crystalline Form B.

Figure 17:
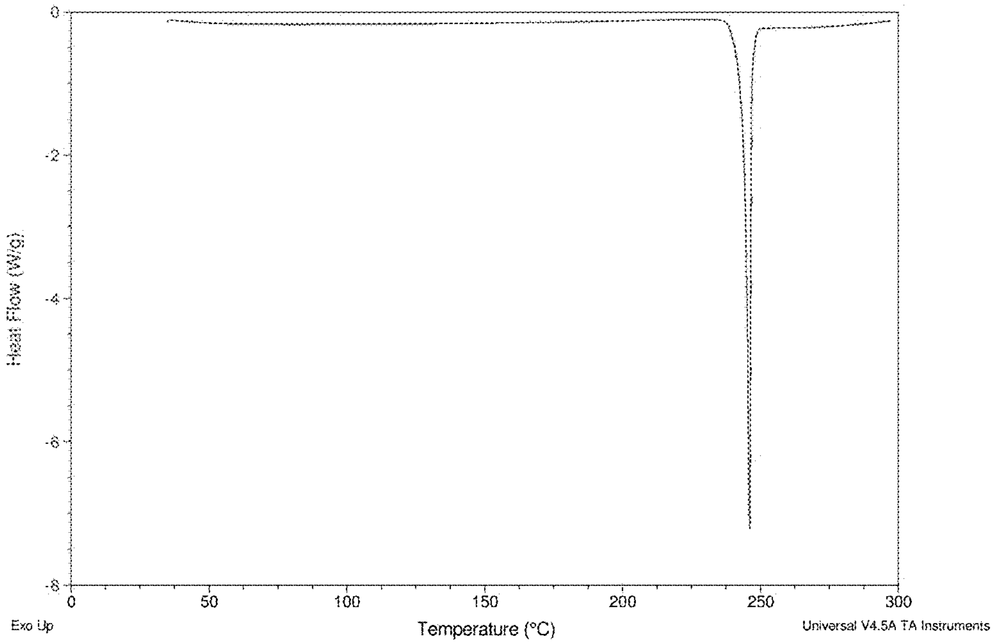
FIG. 17 depicts a DSC thermogram of Crystalline Form B of Compound 32.

In some embodiments, Crystalline Form B is characterized by a DSC substantially similar to that in FIG. 17. In some embodiments, Crystalline Form B is characterized by a DSC having a melting point at 246° C.

In some embodiments, Crystalline Form B is characterized by a $^{13}C$ NMR spectrum having a signal at at least three ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least four ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least five ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least six ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least seven ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least eight ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least nine ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least ten ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least eleven ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least twelve ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least thirteen ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least fourteen ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least fifteen ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least sixteen ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least seventeen ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm. In some embodiments, Crystalline Form B is characterized by a $^{13}C$ NMR spectrum having a signal at at least eighteen ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm.

In some embodiments, Crystalline Form B is characterized by a $^{19}F$ NMR spectrum having a signal at −112.0±0.2 and/or −117.6±0.2 ppm. In some embodiments, Crystalline Form B is characterized by a $^{19}F$ NMR spectrum having a signal at −112.0±0.2 and −117.6±0.2 ppm.

In some embodiments, disclosed herein is Crystalline Form C of Compound 32. In some embodiments, Crystalline Form C is in substantially pure form. In some embodiments, Crystalline Form C is characterized by an X-ray powder diffractogram substantially similar to that in FIG. 18. In some embodiments, Crystalline Form C is characterized by an X-ray powder diffractogram having a signal at at least two two-theta values chosen from 14.7±0.2, 14.9±0.2, and 17.0±0.2. In some embodiments, Crystalline Form C is characterized by an X-ray powder diffractogram having a signal at at least three two-theta values chosen from 13.1±0.2, 14.7±0.2, 14.9±0.2, 17.0±0.2, and 18.1±0.2.

In some embodiments, Crystalline Form C is characterized by an X-ray powder diffractogram having a signal at least two two-theta values chosen from 14.7±0.2, 14.9±0.2, and 17.0±0.2 and at least one additional signal at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least one additional signal at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least two additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least three additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least four additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least five additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least six additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least seven additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least eight additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least nine additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least ten additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least eleven additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least twelve additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at least two two-theta values chosen from 14.7±0.2, 14.9±0.2, and 17.0±0.2 and at least thirteen additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, 17.0±0.2, 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2 two-theta.

In some embodiments, Crystalline Form C is characterized by an X-ray powder diffractogram having a signal at 14.7±0.2, 14.9±0.2, and 17.0±0.2 two-theta and at least one additional signal at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least one additional signal at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least two additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least three additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least four additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least five additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least six additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least seven additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least eight additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least nine additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least ten additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least eleven additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least twelve additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, and 17.0±0.2 two-theta and at least thirteen additional signals at two-theta values chosen from 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2. In some embodiments, Crystalline Form C is characterized by an X-ray powder diffractogram having a signal at 14.7±0.2, 14.9±0.2, 17.0±0.2, 18.1±0.2, 13.1±0.2, 19.8±0.2, 22.0±0.2, 28.7±0.2, 20.8±0.2, 21.5±0.2, 25.0±0.2, 23.0±0.2, 24.5±0.2, 19.0±0.2, 10.2±0.2, and 15.6±0.2 two-theta.

In some embodiments, Crystalline Form C has a single crystal unit cell characterized as follows:

| Crystal System<br>Space Group | Orthorhombic<br>Pbca |
|---|---|
| a (Å) | 23.0 ± 0.1 |
| b (Å) | 8.5 ± 0.1 |
| c (Å) | 37.6 ± 0.1 |
| α (°) | 90 ± 0.1 |
| β (°) | 90 ± 0.1 |
| γ (°) | 90 ± 0.1 |
| V ($Å^3$) | 7349.7 ± 0.2 |
| Z/Z' | 6/2 |

In some embodiments, disclosed herein is a composition comprising Crystalline Form C of compound 32. In some embodiments, disclosed herein is a composition comprising Compound 32 in substantially pure Crystalline Form C. In some embodiments, disclosed herein is a composition comprising at least one active compound consisting essentially of Compound 32 in Crystalline Form C.

Figure 22:
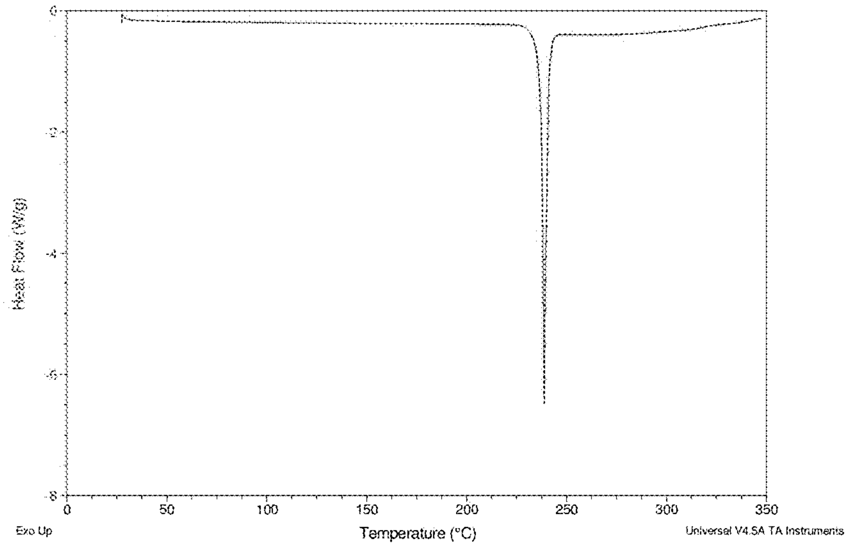
FIG. 22 depicts a thermogram of Crystalline Form C of Compound 32.

In some embodiments, Crystalline Form C is characterized by a DSC substantially similar to that in FIG. 22. In some embodiments, Crystalline Form C is characterized by a DSC having a melting point at 239° C.

In some embodiments, Crystalline Form C is characterized by a $^{13}C$ NMR spectrum having a signal at at least three ppm values chosen from 140.0±0.2, 137.5±0.2, 135.6±0.2, 133.7±0.2, 122.1±0.2, 121.4±0.2, 108.1±0.2, 99.2±0.2, 95.5±0.2, 22.7±0.2, and 20.6±0.2 ppm. In some embodiments, Crystalline Form C is characterized by a $^{13}C$ NMR spectrum having a signal at at least four ppm values chosen from 140.0±0.2, 137.5±0.2, 135.6±0.2, 133.7±0.2, 122.1±0.2, 121.4±0.2, 108.1±0.2, 99.2±0.2, 95.5±0.2, 22.7±0.2, and 20.6±0.2 ppm. In some embodiments, Crystalline Form C is characterized by a $^{13}C$ NMR spectrum having a signal at at least five ppm values chosen from 140.0±0.2, 137.5±0.2, 135.6±0.2, 133.7±0.2, 122.1±0.2, 121.4±0.2, 108.1±0.2, 99.2±0.2, 95.5±0.2, 22.7±0.2, and 20.6±0.2 ppm. In some embodiments, Crystalline Form C is characterized by a $^{13}C$ NMR spectrum having a signal at at least six ppm values chosen from 140.0±0.2, 137.5±0.2, 135.6±0.2, 133.7±0.2, 122.1±0.2, 121.4±0.2, 108.1±0.2, 99.2±0.2, 95.5±0.2, 22.7±0.2, and 20.6±0.2 ppm. In some embodiments, Crystalline Form C is characterized by a $^{13}C$ NMR spectrum having a signal at at least seven ppm values chosen from 140.0±0.2, 137.5±0.2, 135.6±0.2, 133.7±0.2, 122.1±0.2, 121.4±0.2, 108.1±0.2, 99.2±0.2, 95.5±0.2, 22.7±0.2, and 20.6±0.2 ppm. In some embodiments, Crystalline Form C is characterized by a $^{13}C$ NMR spectrum having a signal at at least eight ppm values chosen from 140.0±0.2, 137.5±0.2, 135.6±0.2, 133.7±0.2, 122.1±0.2, 121.4±0.2, 108.1±0.2, 99.2±0.2, 95.5±0.2, 22.7±0.2, and 20.6±0.2 ppm. In some embodiments, Crystalline Form C is characterized by a $^{13}C$ NMR spectrum having a signal at at least nine ppm values chosen from 140.0±0.2, 137.5±0.2, 135.6±0.2, 133.7±0.2, 122.1±0.2, 121.4±0.2, 108.1±0.2, 99.2±0.2, 95.5±0.2, 22.7±0.2, and 20.6±0.2 ppm. In some embodiments, Crystalline Form C is characterized by a $^{13}C$ NMR spectrum having a signal at at least ten ppm values chosen from 140.0±0.2, 137.5±0.2, 135.6±0.2, 133.7±0.2, 122.1±0.2, 121.4±0.2, 108.1±0.2, 99.2±0.2, 95.5±0.2, 22.7±0.2, and 20.6±0.2 ppm. In some embodiments, Crystalline Form C is characterized by a $^{13}$C NMR spectrum having a signal at at least eleven ppm values chosen from 140.0±0.2, 137.5±0.2, 135.6±0.2, 133.7±0.2, 122.1±0.2, 121.4±0.2, 108.1±0.2, 99.2±0.2, 95.5±0.2, 22.7±0.2, and 20.6±0.2 ppm.

In some embodiments, Crystalline Form C is characterized by a $^{19}$F NMR spectrum having a signal at −109.3±0.2 and/or −112.4±0.2 ppm. In some embodiments, Crystalline Form C is characterized by a $^{19}$F NMR spectrum having a signal at −109.3±0.2 and −112.4±0.2 ppm.

In some embodiments, disclosed herein is a composition comprising Crystalline Form A of Compound 32 and Crystalline Form C of Compound 32. In some embodiments, the composition comprising Crystalline Form A of Compound 32 and Crystalline Form C of Compound 32 is characterized by an X-ray powder diffractogram having a signal at at least three two-theta values chosen from 15.0±0.2, 15.4±0.2, 17.6±0.2, 18.0±0.2, and 20.3±0.2. In some embodiments, the composition comprising Crystalline Form A of Compound 32 and Crystalline Form C of Compound 32 is characterized by a DSC substantially similar to that in FIG. 5. In some embodiments, the composition comprising Crystalline Form A of Compound 32 and Crystalline Form C of Compound 32 is characterized by a DSC having a melting point at 237° C.

In some embodiments, the composition comprising Crystalline Form A of Compound 32 and Crystalline Form C of Compound 32 is characterized by a $^{13}$C NMR spectrum having a signal at at least three ppm values chosen from 140.1±0.2, 137.2±0.2, 131.5±0.2, 121.8±0.2, 107.7±0.2, and 98.9±0.2 ppm. In some embodiments, the composition comprising Crystalline Form A of Compound 32 and Crystalline Form C of Compound 32 is characterized by a $^{13}$C NMR spectrum having a signal at at least four ppm values chosen from 140.1±0.2, 137.2±0.2, 131.5±0.2, 121.8±0.2, 107.7±0.2, and 98.9±0.2 ppm. In some embodiments, the composition comprising Crystalline Form A of Compound 32 and Crystalline Form C of Compound 32 is characterized by a $^{13}$C NMR spectrum having a signal at at least five ppm values chosen from 140.1±0.2, 137.2±0.2, 131.5±0.2, 121.8±0.2, 107.7±0.2, and 98.9±0.2 ppm. In some embodiments, the composition comprising Crystalline Form A of Compound 32 and Crystalline Form C of Compound 32 is characterized by a $^{13}$C NMR spectrum having a signal at at least six ppm values chosen from 140.1±0.2, 137.2±0.2, 131.5±0.2, 121.8±0.2, 107.7±0.2, and 98.9±0.2 ppm.

In some embodiments, the composition comprising Crystalline Form A of Compound 32 and Crystalline Form C of Compound 32 is characterized by a $^{19}$F NMR spectrum having a signal at −109.7±0.2 and/or −112.5±0.2 ppm. In some embodiments, the composition comprising Crystalline Form A of Compound 32 and Crystalline Form C of Compound 32 is characterized by a $^{19}$F NMR spectrum having a signal at −109.7±0.2 and −112.5±0.2 ppm.

In some embodiments, disclosed herein is Compound 32 monohydrochloride salt. In some embodiments, Compound 32 monohydrochloride salt is a crystalline solid comprising more than one solid state form. In some embodiments, Compound 32 monohydrochloride salt is characterized by an X-ray powder diffractogram substantially similar to that in FIG. 29. In some embodiments, Compound 32 monohydrochloride salt 1 is characterized by an X-ray powder diffractogram having a signal at at least two two-theta values chosen from 17.8±0.2, 20.2±0.2, and 23.8±0.2. In some embodiments, Compound 32 monohydrochloride salt is characterized by an X-ray powder diffractogram having a signal at at least three two-theta values chosen from 9.3±0.2, 13.6±0.2, 17.8±0.2, 20.2±0.2, and 23.8±0.2.

In some embodiments, Compound 32 monohydrochloride salt is in the form of a single crystalline form having a single crystal unit cell characterized as follows:

| Crystal System<br>Space Group | Monoclinic<br>$P2_1/n$ |
|---|---|
| a (Å) | 12.2 ± 0.1 |
| b (Å) | 18.6 ± 0.1 |
| c (Å) | 18.0 ± 0.1 |
| α (°) | 90 ± 0.1 |
| β (°) | 102.0 ± 0.1 |
| γ (°) | 90 ± 0.1 |
| V (Å$^3$) | 3985 ± 0.2 |
| Z/Z' | 2/2 |

Figure 30:
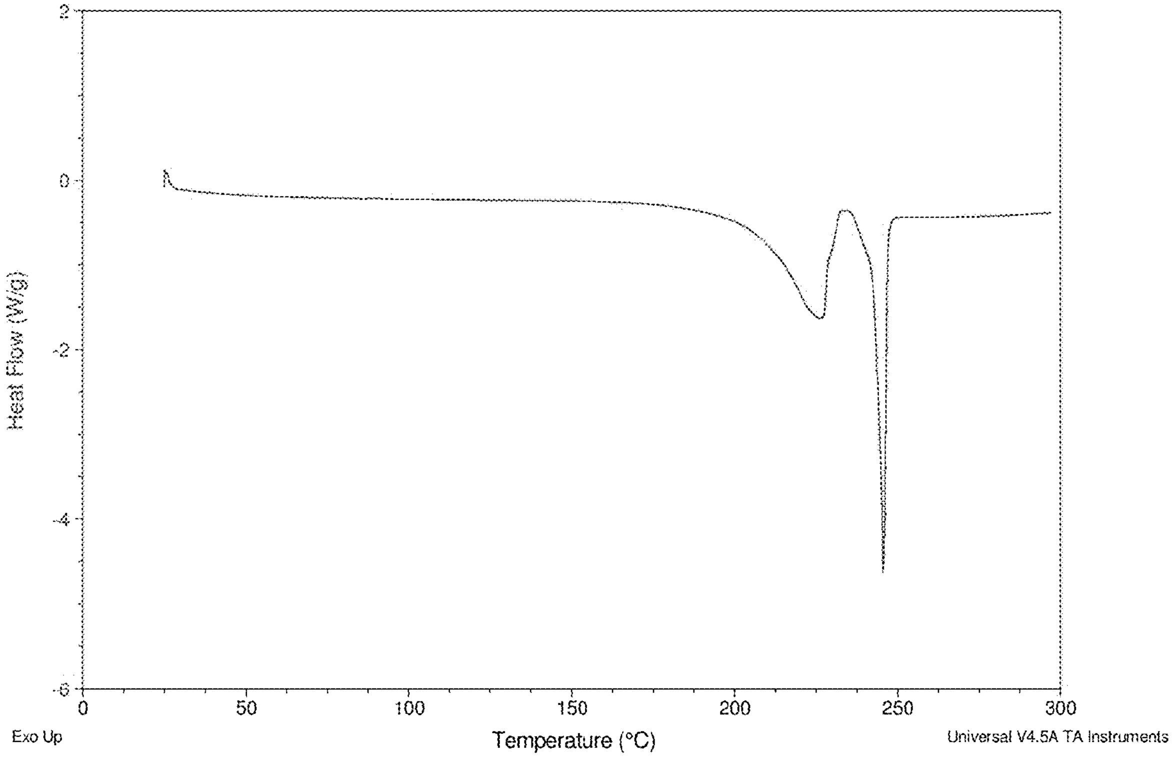
FIG. 30 depicts a DSC thermogram of Compound 32 Mono HCl Salt.

In some embodiments, Compound 32 monohydrochloride salt is characterized by a DSC substantially similar to at least one DSC in FIG. 30. In some embodiments, Compound 32 monohydrochloride salt is characterized by a DSC having at least one endotherm at ~226° C. and at least one endotherm at ~245° C.

In some embodiments, disclosed herein is Compound 32 hemi hydrochloride salt hemi hydrate. In some embodiments, Compound 32 hemihydrochloride hemihydrate is a crystalline solid comprising more than one solid state form. In some embodiments, Compound 32 hemihydrochloride hemihydrate in substantially pure form. In some embodiments, Compound 32 hemihydrochloride hemihydrate is characterized by an X-ray powder diffractogram substantially similar to that in FIG. 31. In some embodiments, Compound 32 hemihydrochloride hemihydrate is characterized by an X-ray powder diffractogram having a signal at at least two two-theta values chosen from 6.2±0.2, 8.8±0.2, and 16.4±0.2. In some embodiments, Compound 32 hemihydrochloride hemihydrate is characterized by an X-ray powder diffractogram having a signal at at least three two-theta values chosen from 6.2±0.2, 8.8±0.2, and 16.4±0.2, and 25.9±0.2. In some embodiments, Compound 32 hemihydrochloride hemihydrate is characterized by an X-ray powder diffractogram after air drying substantially similar to that in FIG. 32. In some embodiments, Compound 32 hemihydrochloride hemihydrate is characterized by an X-ray powder diffractogram after vacuum drying substantially similar to that in FIG. 33. In some embodiments, Compound 32 hemihydrochloride hemihydrate after vacuum drying is characterized by an X-ray powder diffractogram after air drying having a signal at at least four two-theta values chosen from 6.2±0.2, 8.8±0.2, 16.4±0.2, 19.8±0.2, 23.0±0.2, and 24.5±0.2. In some embodiments, Compound 32 hemihydrochloride hemihydrate is in the form of a single crystalline form having a single crystal unit cell characterized as follows:

| Crystal System<br>Space Group | Triclinic<br>P-1 |
|---|---|
| a (Å) | 10.4 ± 0.1 |
| b (Å) | 14.0 ± 0.1 |
| c (Å) | 14.3 ± 0.1 |
| α (°) | 102.2 ± 0.1 |
| β (°) | 91.7 ± 0.1 |
| γ (°) | 107.7 ± 0.1 |
| V (Å$^3$) | 1934 ± 0.2 |
| Z/Z' | 2/2 |

Figure 35:
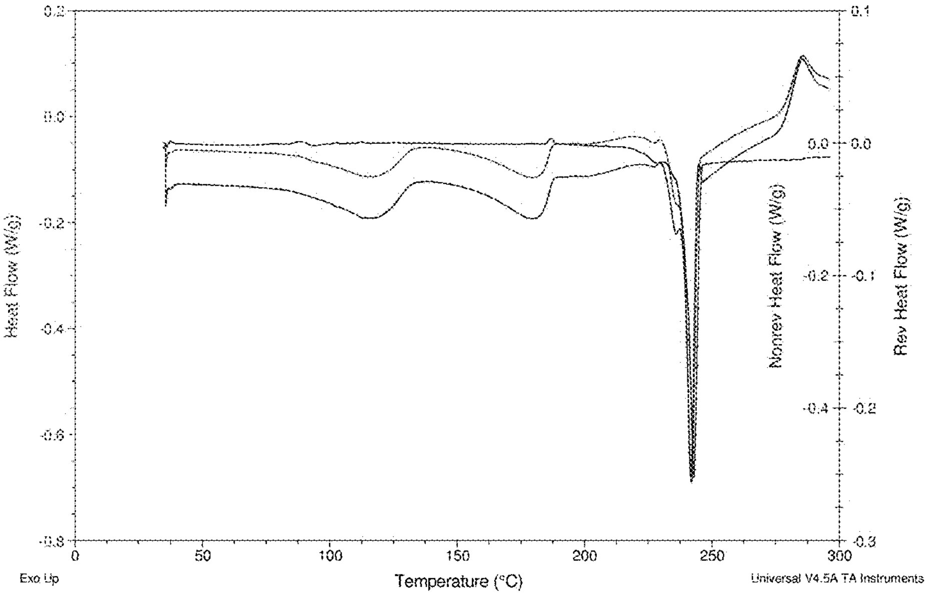
FIG. 35 depicts a DSC thermogram of Compound 32 Hemi HCl Hemi Salt Hydrate.

In some embodiments, Compound 32 hemihydrochloride hemihydrate is characterized by a DSC substantially similar to at least one DSC in FIG. 35. In some embodiments, Compound 32 hemihydrochloride hemihydrate is characterized by a DSC having a melting point at 250° C.

In some embodiments, disclosed herein is Compound 32 ethanol solvate. In some embodiments, Compound 32 ethanol solvate is characterized by an X-ray powder diffractogram substantially similar to that in FIG. 24. In some embodiments, Compound 32 ethanol solvate is characterized by an X-ray powder diffractogram having a signal at at least three two-theta values chosen from 9.8±0.2, 11.3±0.2, 20.5±0.2, and 24.1±0.2. In some embodiments, Compound 32 ethanol solvate has a single crystal unit cell characterized as follows:

| Crystal System<br>Space Group | Triclinic<br>P-1 |
|---|---|
| a (Å) | 92. ± 0.1 |
| b (Å) | 14.5 ± 0.1 |
| c (Å) | 15.5 ± 0.1 |
| α (°) | 73.6 ± 0.1 |
| β (°) | 75.7 ± 0.1 |
| γ (°) | 88.7 ± 0.1 |
| V ($Å^3$) | 1927 ± 0.2 |
| Z/Z' | 2/2 |

Figure 28:
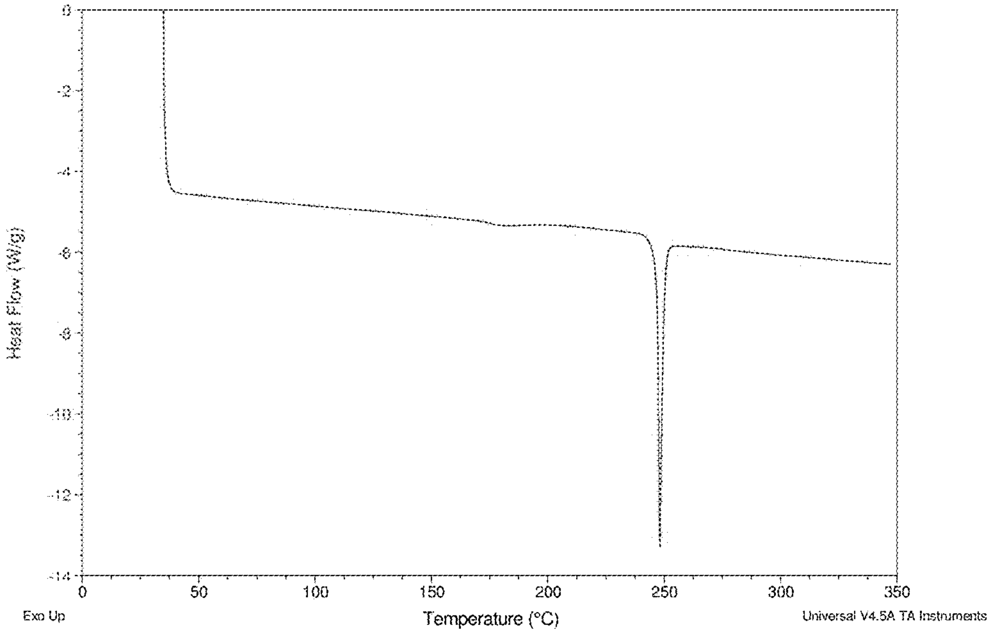
FIG. 28 depicts a DSC thermogram of Compound 32 ethanol solvate.

In some embodiments, Compound 32 ethanol solvate is characterized by a DSC substantially similar to that in FIG. 28. In some embodiments, Compound 32 ethanol solvate is characterized by a DSC having a melting point at 248° C.

In some embodiments, Compound 32 ethanol solvate is characterized by a $^{13}C$ NMR spectrum having a signal at at least three ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm. In some embodiments, Compound 32 ethanol solvate is characterized by a $^{13}C$ NMR spectrum having a signal at at four three ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm. In some embodiments, Compound 32 ethanol solvate is characterized by a $^{13}C$ NMR spectrum having a signal at at least five ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm. In some embodiments, Compound 32 ethanol solvate is characterized by a $^{13}C$ NMR spectrum having a signal at at least six ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm. In some embodiments, Compound 32 ethanol solvate is characterized by a $^{13}C$ NMR spectrum having a signal at at least seven ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm. In some embodiments, Compound 32 ethanol solvate is characterized by a $^{13}C$ NMR spectrum having a signal at at least eight ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm. In some embodiments, Compound 32 ethanol solvate is characterized by a $^{13}C$ NMR spectrum having a signal at at least nine ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm.

In some embodiments, Compound 32 ethanol solvate is characterized by a $^{13}C$ NMR spectrum having a signal at at least ten ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm. In some embodiments, Compound 32 ethanol solvate is characterized by a $^{13}C$ NMR spectrum having a signal at at least eleven ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm. In some embodiments, Compound 32 ethanol solvate is characterized by a $^{13}C$ NMR spectrum having a signal at at least twelve ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm.

In some embodiments, Compound 32 ethanol solvate is characterized by a $^{19}F$ NMR spectrum having a signal at −112.0±0.2 and/or −115.0±0.2 ppm. In some embodiments, Compound 32 ethanol solvate is characterized by a $^{19}F$ NMR spectrum having a signal at −112.0±0.2 and −115.0±0.2 ppm.

In some embodiments, Compound 32 is in Amorphous Form. In some embodiments, Amorphous Form of Compound 32 is characterized by a $^{13}C$ NMR spectrum having a signal at 146.5±0.2 and/or 120.6±0.2 ppm. In some embodiments, Amorphous Form of Compound 32 is characterized by a $^{13}C$ NMR spectrum having a signal at 146.5±0.2 and 120.6±0.2 ppm. In some embodiments, Amorphous Form of Compound 32 is characterized by a $^{19}F$ NMR spectrum having a signal at −113.3±0.2 ppm.

Another aspect of the invention provides pharmaceutical compositions comprising a compound according to any one formula chosen from Formulae I, 1-6, 3-4, 3-5, 3-6, 4-3, 5-3, 6-4, 7-4, 8-4, 12-1, 12-2, II, and III and Compounds 1-215, tautomers of those compounds, pharmaceutically acceptable salts of those compounds and their tautomers, and deuterated derivatives of any of the foregoing. In some embodiments, the pharmaceutical composition comprising at least one compound chosen from Formulae I, 1-6, 3-4, 3-5, 3-6, 4-3, 5-3, 6-4, 7-4, 8-4, 12-1, 12-2, II, and III and Compounds 1-215, tautomers of those compounds, pharmaceutically acceptable salts of those compounds and their tautomers, and deuterated derivatives of any of the foregoing is administered to a patient in need thereof.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure can be employed in combination therapies; that is, the pharmaceutical compositions described herein can further include at least one other active agent. Alternatively, a pharmaceutical composition comprising at least one compound of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing can be administered as a separate composition concurrently with, prior to, or subsequent to, a composition comprising at least one additional active agent. In some embodiments, a pharmaceutical composition comprising at least one compound selected from Compounds 1-215 tautomers of those compounds, pharmaceutically acceptable salts of those compounds and their tautomers, and deuterated derivatives of any of the foregoing can be administered as a separate composition concurrently with, prior to, or subsequent to, a composition comprising at least one additional active agent.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

In another aspect of the invention, the compounds and the pharmaceutical compositions, described herein, are used to treat AATD. In some embodiments, the subject in need of treatment with the compounds and compositions of the invention carries the ZZ mutation. In some embodiments, the subject in need of treatment with the compounds and compositions of the invention carries the SZ mutation.

In some embodiments, the methods of the invention comprise administering to a patient in need thereof a compound chosen from any of the compounds of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing. In some embodiments, the compound of Formula I is selected from Compounds 1-215, tautomers of those compounds, pharmaceutically acceptable salts of those compounds and their tautomers, and deuterated derivatives of any of the foregoing. In some embodiments, said patient in need thereof has a Z mutation in the alpha-1 antitrypsin gene. In some embodiments said patient in need thereof is homozygous for the Z-mutation in the alpha-1 antitrypsin gene.

Another aspect of the invention provides methods of modulating alpha-1 antitrypsin activity comprising the step of contacting said alpha-1-antitrypsin with at least one compound of Formulae I, 1-6, 3-4, 3-5, 3-6, 4-3, 5-3, 6-4, 7-4, 8-4, 12-1, 12-2, II, and III and tautomers of those compounds, pharmaceutically acceptable salts of those compounds and their tautomers, and deuterated derivatives of any of the foregoing. In some embodiments, the methods of modulating alpha-1 antitrypsin activity comprising the step of contacting said alpha-1-antitrypsin with at least one compound selected from Compounds 1-215, tautomers of those compounds, pharmaceutically acceptable salts of those compounds and their tautomers, and deuterated derivatives of any of the foregoing.

III. Preparation of Compounds

All the generic, subgeneric, and specific compound formulae disclosed herein are considered part of the invention.

A. Compounds of Formula I

The compounds of the invention may be made according to standard chemical practices or as described herein. Throughout the following synthetic schemes and in the descriptions for preparing compounds of Formulae I, 1-6, 3-4, 3-5, 3-6, 4-3, 5-3, 6-4, 7-4, 8-4, 12-1, 12-2, II, and III, Compounds 1-215, tautomers of those compounds, pharmaceutically acceptable salts of those compounds and their tautomers, and deuterated derivatives of any of the foregoing, the following abbreviations are used:

Abbreviations

BrettPhos Pd G4=dicyclohexyl-[3,6-dimethoxy-2-[2,4,6-tri (propan-2-yl)phenyl]phenyl]phosphane; methanesulfonic acid; N-methyl-2-phenylaniline; palladium CBzCl=Benzyl chloroformate DIPEA=N,N-Diisopropylethylamine or N-ethyl-N-isopropyl-propan-2-amine DMA=dimethyl acetamide DMAP=dimethylamino pyridine DME=dimethoxyethane DMF=dimethylformamide DMSO=dimethyl sulfoxide DTBPF=1,1'-Bis(di-tert-butylphosphino)ferrocene EtOAc=Ethyl Acetate HATU=[dimethylamino(triazolo[4,5-b]pyridin-3-yloxy) methylene]-dimethyl-ammonium (Phosphorus Hexafluoride Ion)

IPA=isopropyl alcohol

MeOH=MeOH

MP-TMT scavenger resin=a macroporous polystyrene-bound trimercaptotriazine, a resin bound equivalent of 2,4,6-trimercaptotriazine (TMT).

MTBE=Methyl tert-butyl ether

NMM=N-methyl morpholine

NMP=N-methyl pyrrolidine $Pd(dppf)_2Cl_2$=[1,1'-Bis(diphenylphosphino)ferrocene]dichloropalladium(II)

$PdCl_2(PPh_3)_2$=Bis(triphenylphosphine)palladium(II) dichloride

PTSA=p-Toluenesulfonic acid monohydrate

SFC=super critical fluid chromatography

SPhos Pd G3=(2-Dicyclohexylphosphino-2',6'-dimethoxybiphenyl) [2-(2'-amino-1,1'-biphenyl)]palladium(II) methanesulfonate T3P=2,4,6-Tripropyl-1,3,5,2,4,6-trioxatriphosphorinane-2,4,6-trioxide TBAF=Tetrabutylammonium fluoride tBuXPhos Pd G1=Chloro[2-(di-tert-butylphosphino)-2',4',6'-triisopropyl-1,1'-biphenyl][2-(2-aminoethyl)phenyl)]palladium(II) or t-BuXPhos palladium(II) phenethylamine chloride tBuXPhos Pd G3=[(2-Di-tert-butylphosphino-2',4',6'-triisopropyl-1,1'-biphenyl)-2-(2'-amino-1,1'-biphenyl)] palladium(II) methanesulfonate tBuXPhos Pd G4=ditert-butyl-[2-(2,4,6-triisopropylphenyl) phenyl]phosphane; dichloromethane; methanesulfonate; N-methyl-2-phenyl-aniline palladium (II)

TEA=triethylamine

TFA=trifluoroacetic acid

THF=tetrahydrofuran

THP=tetrahydropyran

TMSS=Tris(trimethylsilyl)silane

XPhos Pd G1=(2-Dicyclohexylphosphino-2',4',6'-triisopropyl-1,1'-biphenyl)[2-(2-aminoethyl)phenyl)]palladium(II) chloride or (XPhos) palladium(II) phenethylamine chloride In some embodiments, processes for preparing compounds of Formula I, tautomers, pharmaceutically acceptable salts of those compounds or tautomers, or deuterated derivatives of any of the foregoing, comprise reacting a compound of Formula I-1, tautomer, salt, or derivative thereof with a deprotection reagent as depicted in Scheme 1 below (wherein all variables are as defined for Formula I above):

Scheme 1

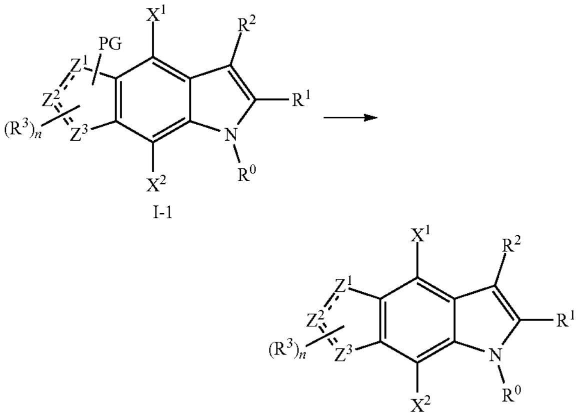

I-1

(I)

A protecting group is used (PG) when at least one of $Z^1$, $Z^2$, or $Z^3$ is nitrogen. In some embodiments, the PG is chosen from t-butyl carbamate (Boc), benzyl (Bn), tetrahydropyranyl (THP), 9-fluorenylmethyl carbamate (Fmoc) benzyl carbamate (Cbz), acetamide, trifluoroacetamide, triphenylmethylamine, benzylideneamine, and p-toluenesulfonamide.

Any suitable conditions, such as those for a deprotection reaction of a nitrogen atom, known in the art can be used. In some embodiments, the reaction depicted in Scheme 1 is performed in the presence of a base, such as a metal hydroxide (e.g., NaOH or KOH). In some embodiments, the reaction depicted in Scheme 1 is performed in the presence of a hydrogen source (e.g., $H_2$) and a hydrogenation catalyst (e.g., Pd on carbon). In some embodiments the reaction depicted in Scheme is performed in the presence of a hydride source (e.g., $SiEt_3H$) and/or a metal catalyst (e.g., Pd or Pt).

In some embodiments, as shown in Scheme 2, the processes for preparing compounds of Formula I, tautomers, salts, or deuterated derivatives thereof comprise reacting a compound of Formula I-2 or a salt thereof with an alkylating, acylating, aminating, cyanating and/or sulfonating agent to generate a compound of Formula I-1. In some embodiments, as shown in Scheme 2, the methods comprise reacting a compound of Formula I-2 with a halogenating agent to generate a compound of Formula I-2a. In some embodiments, as shown in Scheme 2, the methods comprise reacting a compound of Formula I-2a with an alkylating, acylating, aminating, and/or sulfinating agent to generate a compound of Formula I-1.

Scheme 2

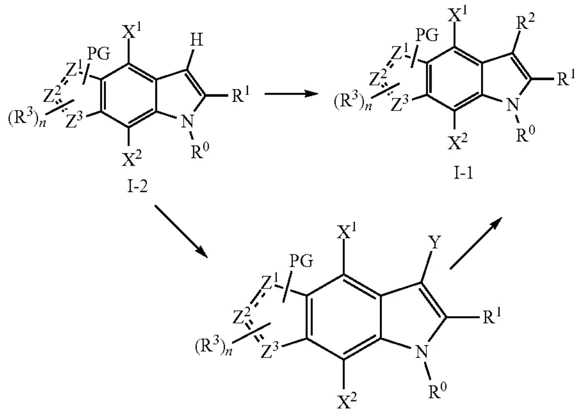

I-2

I-1

I-2a

Groups $R^0$, $R^1$, $R^2$, $R^3$, $X^1$, $X^2$, $Z^1$, $Z^2$, $Z^3$, n, and PG depicted in Scheme 2 are chosen from the described groups according to Formulae (I) and I-1, provided above. Y is selected from halogens (e.g., I, Br, or Cl).

Any suitable conditions, such as those for an alkylating, aminating, cyanating, carbonylating, halogenating, and/or sulfonating reaction of an heteroaryl ring, known in the art can be used for generating a compound of Formula I-1 from a compound of Formulae I-2 or I-2a. In some embodiments, the reaction generating a compound of Formula I-2a from a compound of Formula I-2 depicted in Scheme 2 is performed in the presence of a halogenating agent (e.g., N-iodosuccinimide). In some embodiments, the reaction generating a compound of Formula I-1 from a compound of Formulae I-2 depicted in Scheme 2 is performed in the presence of alkylating reagents (e.g., aldehydes, ketones, or acetals), acids (e.g., TFA or methanesulfonic acid), and/or reducing agents (e.g., triethylsilane). In some embodiments, said reaction is followed by hydrogenation in the presence of hydrogenation reagents (e.g., palladium on carbon and hydrogen gas). In some embodiments, the reaction generating a compound of Formula I-1 from a compound of Formulae I-2 or I-2a depicted in Scheme 2 is performed in the presence of aminating reagents (e.g., amine-containing molecules or amide-containing molecules and metal catalysts), cyanating reagents (e.g., N-cyano-4-methyl-N-phenyl-benzenesulfonamide), carbonylation reagents (e.g., carbon monoxide and BINAP-PdCl2), and/or sulfonating reagents (e.g., sodium methanesulfinate).

In some embodiments, as shown in Scheme 3, the processes for preparing compounds of Formula I, tautomers, salts, and deuterated derivatives thereof, comprise reacting a compound of Formula I-3 or a salt thereof with a protecting reagent to generate a compound of Formula I-2:

Scheme 3

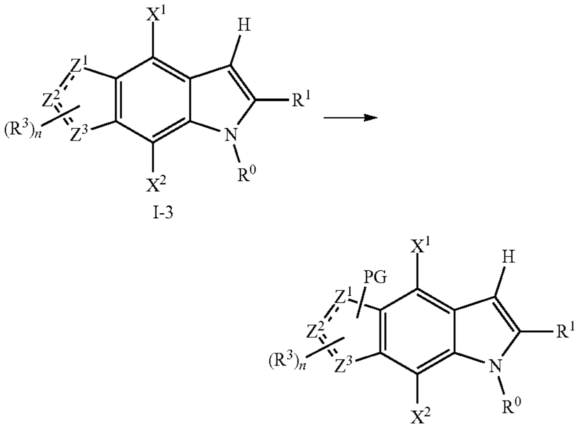

I-3

I-2 wherein all variables and PG depicted in Scheme 3 are defined as described above for Formulae (I) and I-1.

Any suitable conditions, such as those for a protection reaction of a nitrogen atom, known in the art can be used. For example, in some embodiments, the reaction depicted in Scheme 3 is performed in the presence of a nitrogen protecting reagent (e.g., benzyl chloroformate (Cbz-Cl) or di-tert-butyl dicarbonate anhydride (boc anyhydride)).

In some embodiments, as shown in Scheme 4, the processes for preparing compounds of Formula I, tautomers, salts, and deuterated derivatives thereof, comprise converting a compound of Formula I-4 or a salt thereof by an internal alkyne amine coupling to generate a compound of Formula I-3, a tautomer thereof, a pharmaceutically acceptable salt of any of the foregoing, or a deuterated derivative of any of the foregoing:

Scheme 4

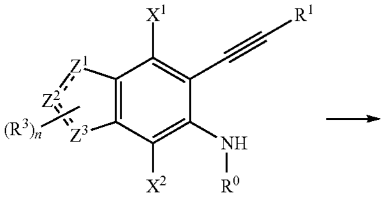

I-4

-continued

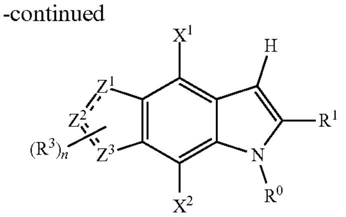

I-3 wherein all variables depicted in Scheme 4 are defined as described above for Formula (I).

Any suitable conditions, such as those for an alkyne amine coupling, known in the art can be used. For example, in some embodiments, the reaction depicted in Scheme 4 is performed in the presence of polar solvents (e.g., DMSO, MeOH, or AcOH). In some embodiments, the reaction depicted in Scheme 4 is performed with the presence of added heat.

In some embodiments, as shown in Scheme 5, the processes for preparing compounds of Formula I, tautomers, salts, and deuterated derivatives thereof, comprise reacting a compound of Formula I-5 or a salt thereof with a compound of Formula I-6 or a salt thereof to generate a compound of Formula I-4, a tautomer thereof, a pharmaceutically acceptable salt of any of the foregoing, or a deuterated derivative of any of the foregoing:

Scheme 5

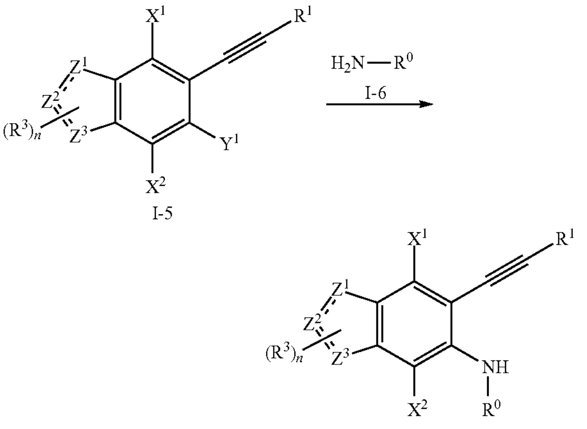

I-5

I-4 wherein variables depicted in Scheme 5 are defined as described above for Formula (I) and $Y^1$ is a halogen (e.g., I, Br, or Cl).

Any suitable conditions, such as those for amine coupling, known in the art can be used. For example, in some embodiments, the reaction depicted in Scheme 5 is performed in the presence of amine coupling reagents (e.g., 2-Di-tert-butylphosphino-2',4',6'-triisopropylbiphenyl Pd G1 (tBuXPhos Pd G1)). In some embodiments, the reaction depicted in Scheme 5 is performed in the presence of a base (e.g., sodium t-butoxide).

In some embodiments, as shown in Scheme 6, the processes for preparing compounds of Formula I, tautomers, salts, and deuterated derivatives thereof, comprise reacting a compound of Formula I-7 or a salt thereof with a compound of Formula I-8 or a salt thereof to generate a compound of Formula I-5, a tautomer thereof, a pharmaceutically acceptable salt of any of the foregoing, or a deuterated derivative of any of the foregoing:

Scheme 6

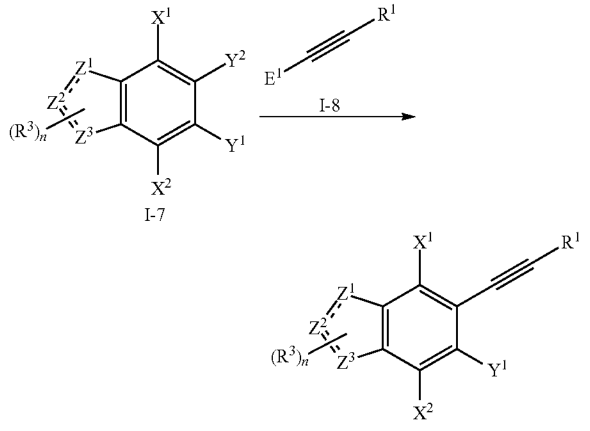

I-7

I-5 wherein variables depicted in Scheme 6 are defined as described above for Formula (I);

$Y^1$ and $Y^2$ are independently selected from halogens (e.g., I, Br, or $C_1$); and $E^1$ is hydrogen or trimethylsilyl.

Any suitable conditions, such as those for alkyne coupling, known in the art can be used. For example, in some embodiments, the reaction depicted in Scheme 6 is performed in the presence of coupling reagents (e.g., CuI or $Pd(PPh_3)_2Cl_2$). In some embodiments, the reaction depicted in Scheme 6 is performed in the presence of a base, such as triethylamine B. Compounds of Formulae (1-6), (3-4), (3-5), (3-6), (4-3), (5-3), (6-4), (7-4), (8-4), (12-1), and (12-2)

Scheme 7 provides processes for preparing compounds of Formulae 1-6 and 1-7, tautomers, salts, and deuterated derivatives thereof:

Scheme 7

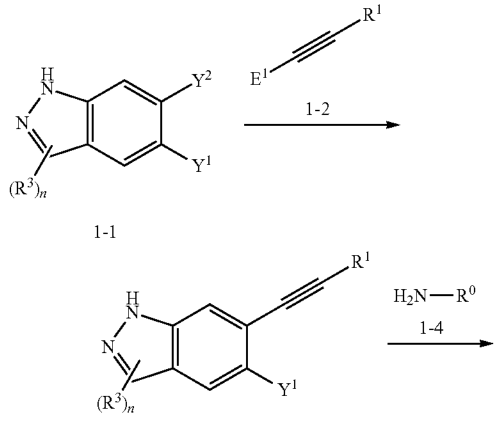

1-1

1-3

-continued

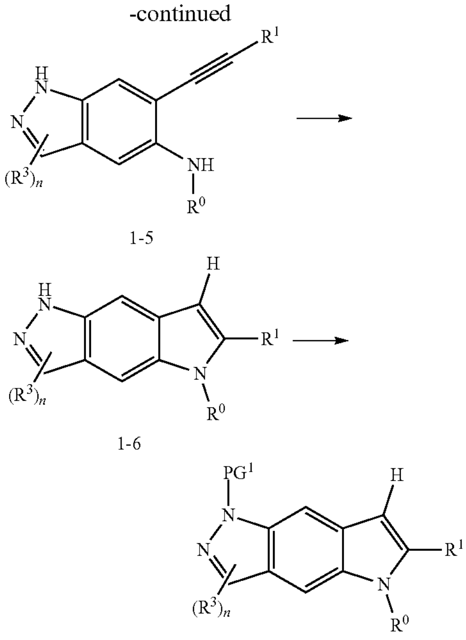

1-5

1-6

1-7 wherein variables $R^0$, $R^1$, $R^3$, and n depicted in Scheme 7 are as defined for Formula (I) above;

$Y^1$ and $Y^2$ are independently selected from halogens (e.g., I, Br, and Cl);

$PG^1$ is an amine protecting group, such as benzyloxycarbonyl; and $E^1$ is hydrogen or trimethylsilyl.

Any suitable conditions, such as those for alkyne coupling, known in the art can be used for converting a compound of Formula 1-1 and a compound of Formula 1-2 to a compound of Formula 1-3. For example, in some embodiments, the reaction is performed in the presence of coupling reagents (e.g., CuI or $Pd(PPh_3)_2Cl_2$). In some embodiments, the reaction is performed in the presence of a base, such as triethylamine Any suitable conditions, such as those for amine coupling, known in the art can be used for converting a compound of Formula 1-3 and a compound of Formula 1-4 to a compound of Formula 1-5. For example, in some embodiments, the reaction is performed in the presence of amine coupling reagents (e.g., 2-Di-tert-butylphosphino-2',4',6'-triisopropylbiphenyl Pd G1 (tBuXPhos Pd G1)). In some embodiments, the reaction is performed in the presence of a base (e.g., sodium t-butoxide)

Any suitable conditions, such as those for an alkyne amine coupling, known in the art can be used for converting a compound of Formula 1-5 to a compound of Formula 1-6. For example, in some embodiments, the reaction is performed in the presence of polar solvents (e.g., DMSO, MeOH, and AcOH). In some embodiments, the reaction is performed with the presence of added heat.

Any suitable conditions, such as those for a protection reaction of a nitrogen atom, known in the art can be used for converting a compound of Formula 1-6 to a compound of Formula 1-7. For example, in some embodiments, the reaction is performed in the presence of a nitrogen protecting reagent (e.g., benzyl chloroformate (Cbz-Cl), di-tert-butyl dicarbonate anhydride (boc anyhydride), or 3,4-dihydro-2H-pyran).

Scheme 8 provides processes for preparing compounds of Formulae 2-2, 2-3, 2-4, 2-5, and 2-6:

Scheme 8

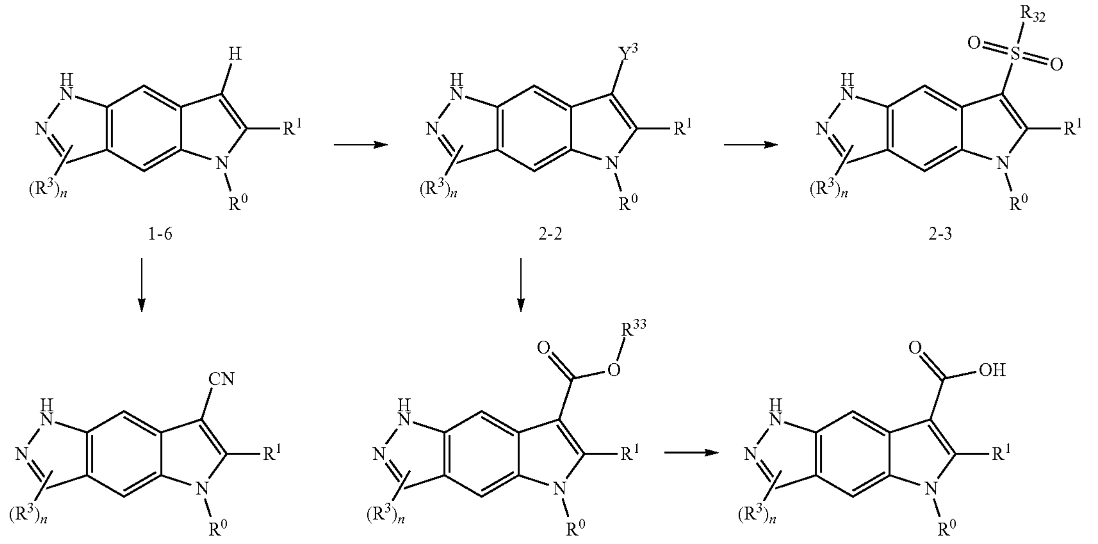
1-6
2-2
2-3
2-4
2-5
2-6 wherein variables $R^0$, $R^1$, $R^3$, and n depicted in Scheme 8 are as defined for Formula I above;

$Y^3$ is a halogen (e.g., I, Br, or $C_1$);

$R^{32}$ is selected from $C_1$-$C_6$ linear, branched, and cyclic alkyl groups; and $R^{33}$ is selected from $C_1$-$C_6$ linear, branched, and cyclic alkyl groups.

Any suitable conditions, such as those for a halogenation reaction of an aryl ring, known in the art can be used for converting a compound of Formula 1-6 to a compound of Formula 2-2. For example, in some embodiments, the reaction is performed in the presence of halogenating reagents (e.g., N-iodosuccinimide).

Any suitable conditions, such as those for a sulfonation reaction of an aryl halide, known in the art can be used for converting a compound of Formula 2-2 to a compound of Formula 2-3. For example, in some embodiments, the reaction is performed in the presence of sulfonating reagents (e.g., sodium methanesulfinate).

Any suitable conditions, such as those for a carbonylation reaction of an aryl halide, known in the art can be used for converting a compound of Formula 2-2 to a compound of Formula 2-5. For example, in some embodiments, the reaction is performed in the presence of carbonylation reagents (e.g., carbon monoxide and BINAP-$PdCl_2$).

Any suitable conditions, such as those for hydrolysis of an ester, known in the art can be used for converting a compound of Formula 2-5 to a compound of Formula 2-6. For example, in some embodiments, the reaction is performed in the presence of a base (e.g., LiOH or NaOH).

Any suitable conditions, such as those for a cyanating reaction of an aryl ring, known in the art can be used for converting a compound of Formula 1-6 to a compound of Formula 2-4. For example, in some embodiments, the reaction is performed in the presence of cyanating reagents (e.g., N-cyano-4-methyl-N-phenyl-benzenesulfonamide).

Scheme 9 provides processes preparing compounds of Formulae 3-3, 3-4, 3-5, and 3-6:

Scheme 9

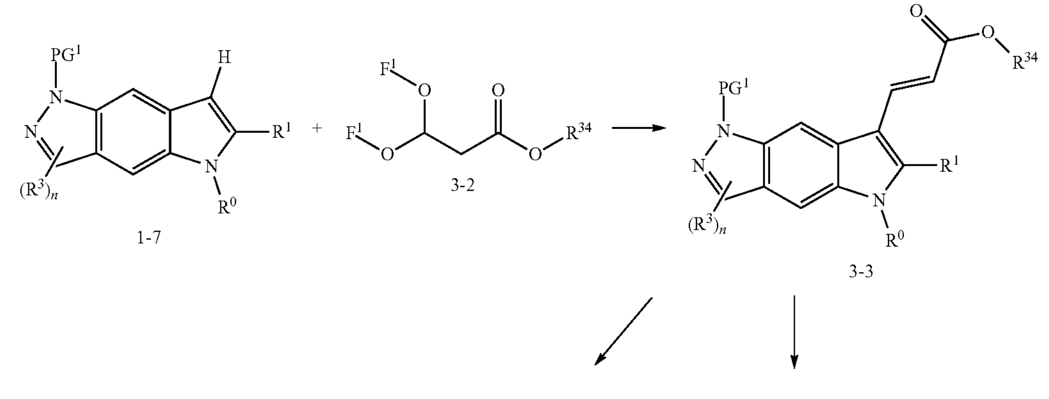
1-7
3-2
3-3

-continued

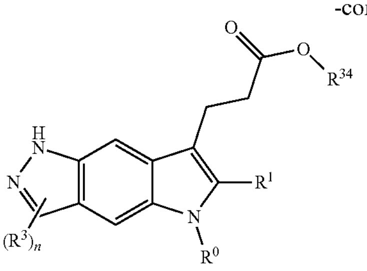

3-4

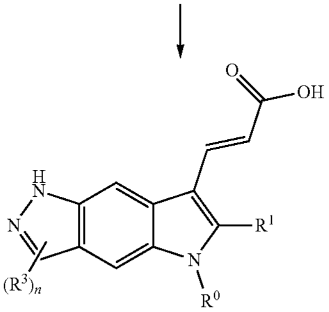

3-5

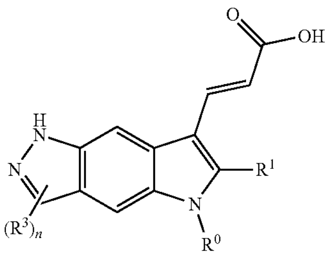

3-6 wherein variables $R^0$, $R^1$, $R^3$, and n depicted in Scheme 9 as defined for Formula (I) above;

$PG^1$ is an amine protecting group, such as benzyloxycarbonyl;

$F^1$ is an acetal protecting group (e.g., Me); and $R^{34}$ is selected from $C_1$-$C_6$ linear, branched, and cyclic alkyl groups.

Any suitable conditions, such as those for an aldol reaction with an aryl ring, known in the art can be used for reacting a compound of Formula 1-7 and a compound of Formula 3-2 to provide a compound of Formula 3-3. For example, in some embodiments, the reaction is performed in the presence of acid (e.g., methanesulfonic acid). In some embodiments, the reaction is performed in the presence of triethylsilane.

Any suitable conditions, such as those for a hydrogenation reaction of an olefin, known in the art can be used for reacting a compound of Formula 3-3 and to provide a compound of Formula 3-4. For example, in some embodiments, the reaction is performed in the presence of hydrogenation reagents (e.g., $H_2$ and Pd on carbon).

Any suitable conditions, such as those for hydrolysis of an ester, known in the art can be used for converting a compound of Formula 3-4 to a compound of Formula 3-5. For example, in some embodiments, the reaction is performed in the presence of a base (e.g., LiOH).

Any suitable conditions, such as those for hydrolysis of an ester, known in the art can be used for converting a compound of Formula 3-3 to a compound of Formula 3-6. For example, in some embodiments, the reaction is performed in the presence of a base (e.g., LiOH).

Scheme 10 provides a process for preparing compounds of Formula 4-3:

Scheme 10

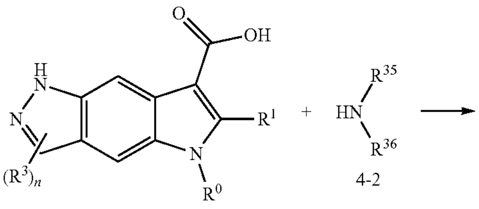

2-6

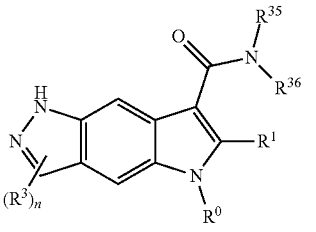

4-3 wherein variables $R^0$, $R^1$, $R^3$ are as defined for Formula I above; and wherein $R^{35}$ and $R^{36}$ are selected from C1-C6 linear, branched, and cyclic alkyl groups; or $R^{35}$ and $R^{36}$, taken together with the N atom to which they are bound, form a 4 to 6 membered ring, optionally substituted with C1-C6 linear, branched, and cyclic alkyl groups.

Any suitable conditions, such as those for formation of an amide from a carboxylic acid, known in the art can be used for reacting a compound of Formula 2-6 and a compound of Formula 4-2 to provide a compound of Formula 4-3. For example, in some embodiments, the reaction is performed in the presence of amide coupling reagents (e.g., HATU).

Scheme 11 provides a process for preparing compounds of Formula 5-3:

Scheme 11

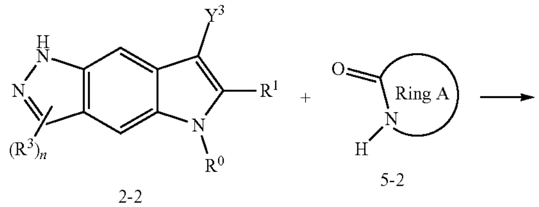

2-2

5-2

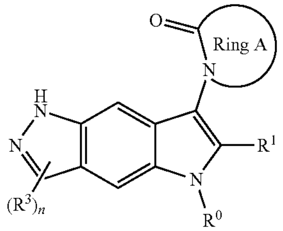

5-3 wherein variables $R^0$, $R^1$, $R^3$, n, and Ring A depicted in Scheme 11 are as defined for Formula I above and $Y^3$ is a halogen (e.g., I, Br, and Cl).

Any suitable conditions, such as those for coupling an N-containing ring with an aryl halide, known in the art can be used for reacting a compound of Formula 2-2 and a compound of Formula 5-2 to provide a compound of Formula 5-3. For example, in some embodiments, the reaction is performed in the presence of coupling reagents (e.g., CuI, N,N'-dimethylethane-1,2-diamine, and $K_3PO_4$).

Scheme 12 provides a process for preparing compounds of Formula 6-4:

Scheme 12

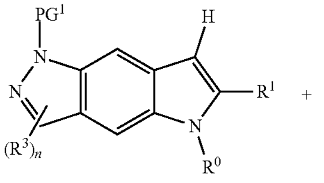

1-7

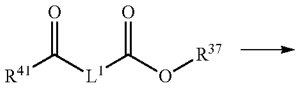

6-2

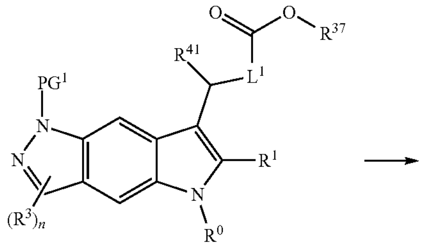

6-3

-continued

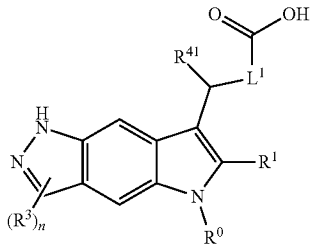

6-4 wherein variables $R^0$, $R^1$, $R^3$, and n depicted in Scheme 12 are as defined for Formula I above;

$PG^1$ is an amine protecting group, such as benzyloxycarbonyl;

$L^1$ is selected from $C_1$-$C_6$ linear, branched, and cyclic alkyl groups;

$R^{37}$ is selected from $C_1$-$C_6$ linear, branched, and cyclic alkyl groups, (e.g., Me, Et, and i-Pr); and $R^{41}$ is selected from H, $C_1$-$C_6$ linear, branched, and cyclic alkyl groups, (e.g., Me, Et, and i-Pr).

Any suitable conditions, such as those for an aldol reaction with an aryl ring, known in the art can be used for reacting a compound of Formula 1-7 and a compound of Formula 6-2 to provide a compound of Formula 6-3. For example, in some embodiments, the reaction is performed in the presence of acid (e.g., methanesulfonic acid).

Any suitable conditions, such as those for deprotection of a nitrogen protection group and hydrolysis of an ester, known in the art can be used for converting a compound of Formula 6-3 to a compound of Formula 6-4. For example, in some embodiments, the reaction is performed in the presence of base (e.g., LiOH). In some embodiments, the reaction is performed in the presence of hydrogenation reagents (e.g., $H_2$ and Pd on carbon).

Scheme 13 provide processes for preparing compounds of Formulae 7-3 and 7-4:

Scheme 13

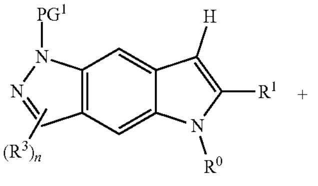

1-7

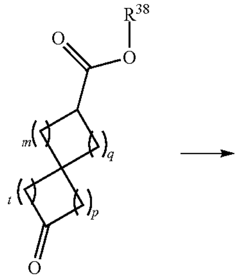

7-2

-continued

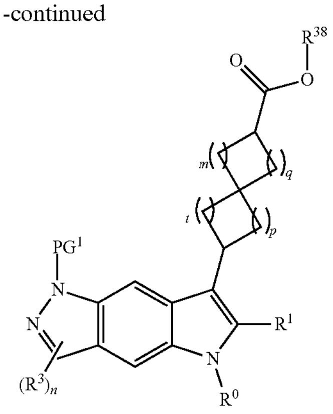

7-3

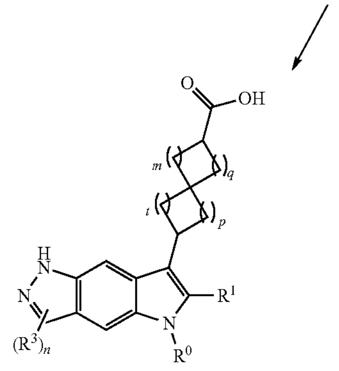

7-4 wherein variables $R^0$, $R^1$, $R^3$, and n depicted in Scheme 13 are as defined for Formula I above;

$PG^1$ is an amine protecting group, such as benzyloxycarbonyl;

m is an integer chosen from 0-3, and q is an integer chosen from 0-3, provided that:

(i) if m is 0, then q is at least 2 and (ii) if q is 0, then m is at least 2;

t is an integer chosen from 0-3, and p is an integer chosen from 0-3, provided that:

(i) if t is 0, then p is at least 2 and (ii) if p is 0, then t is at least 2; and $R^{38}$ is chosen from C1-C6 linear, branched, and cyclic alkyl groups.

Any suitable conditions, such as those for an aldol reaction with an aryl ring, known in the art can be used for reacting a compound of Formula 1-7 and a compound of Formula 7-2 to provide a compound of Formula 7-3. For example, in some embodiments, the reaction is performed in the presence of acid (e.g., trifluoroacetic acid and methanesulfonic acid).

Any suitable conditions, such as those for deprotection of a nitrogen protection group and hydrolysis of an ester, known in the art can be used for converting a compound of Formula 7-3 to a compound of Formula 7-4. For example, in some embodiments, the reaction is performed in the presence of base (e.g., LiOH). In some embodiments, the reaction is performed in the presence of hydrogenation reagents (e.g., H2 and Pd on carbon).

Scheme 14 provides a process for preparing compounds of Formulae 8-3 and 8-4:

Scheme 14

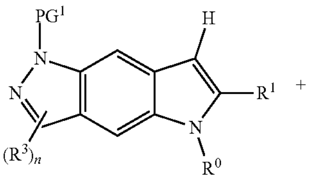

1-7

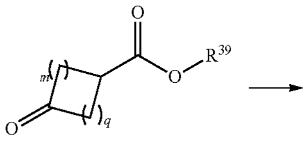

8-2

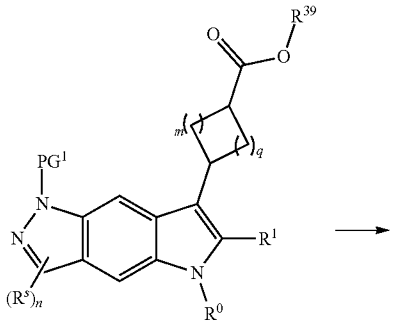

8-3

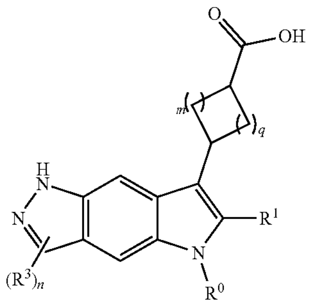

8-4 wherein variables $R^0$, $R^1$, $R^3$, and n depicted in Scheme 14 are as defined for Formula I above;

$PG^1$ is chosen an amine protecting group, such as benzyloxycarbonyl;

m is an integer chosen from 0-3, and q is an integer chosen from 0-3, provided that:

(i) if m is 0, then q is at least 2 and (ii) if q is 0, then m is at least 2; and $R^{39}$ is chosen from $C_1$-$C_6$ linear, branched, and cyclic alkyl groups.

Any suitable conditions, such as those for an aldol reaction with an aryl ring, known in the art can be used for reacting a compound of Formula 1-7 and a compound of Formula 8-2 to provide a compound of Formula 8-3. For example, in some embodiments, the reaction is performed in the presence of acid (e.g., trifluoroacetic acid and methanesulfonic acid).

Any suitable conditions, such as those for deprotection of a nitrogen protection group and hydrolysis of an ester, known in the art can be used for converting a compound of Formula 8-3 to a compound of Formula 8-4. For example, in some embodiments, the reaction is performed in the presence of base (e.g., LiOH). In some embodiments, the reaction is performed in the presence of hydrogenation reagents (e.g., $H_2$ and Pd on carbon).

Scheme 15 provides a process preparing compounds of Formula 9-3:

Scheme 15

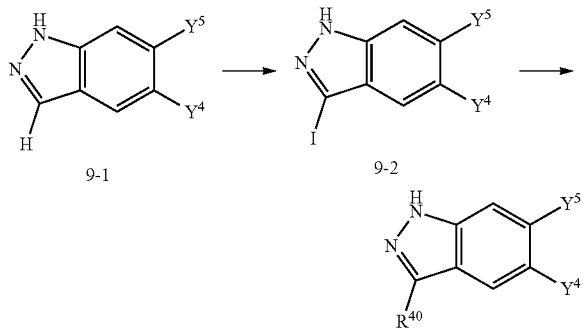

9-1 9-2 9-3 wherein in Scheme 15, $Y^4$ and $Y^5$ are independently selected from halogens; and $R^{40}$ is chosen from $C_1$-$C_6$ linear, branched, and cyclic alkyl groups.

Any suitable conditions, such as those for a iodination reaction of an aryl ring, known in the art can be used for converting a compound of Formula 9-1 to a compound of Formula 9-2. For example, in some embodiments, the reaction is performed in the presence of iodinating reagents (e.g., N-iodosuccinimide).

Any suitable conditions, such as those for a metal-catalyzed coupling reaction with an aryl halide ring, known in the art can be used for converting a compound of Formula 9-2 to a compound of Formula 9-3. For example, in some embodiments, the reaction is performed in the presence of an organometallic reagent (e.g., dimethyl zinc). In some embodiments, the reaction is performed in the presence of a catalyst (such as $Pd(dppf)_2Cl_2$). In some embodiments the reaction is performed in the presence of added heat.

Scheme 16 provides a process for preparing compounds of Formula 10-3:

Scheme 16

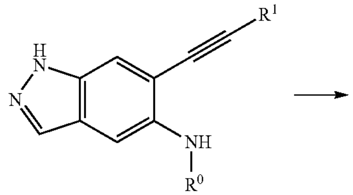

10-1

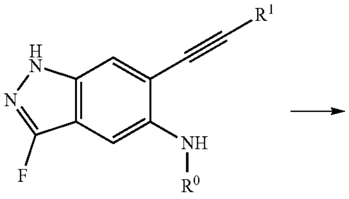

10-2

-continued

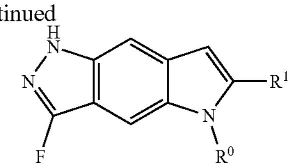

10-3 wherein variables $R^0$ and $R^1$ depicted in Scheme 16 are as defined for Formula I above.

Any suitable conditions, such as those for fluorination of an aryl ring, known in the art can be used for converting a compound of Formula 10-1 to a compound of Formula 10-2. For example, in some embodiments, the reaction is performed in the presence of a fluorinating agent (e.g., 1-Chloromethyl-4-fluoro-1,4-diazoniabicyclo[2.2.2]octane bis(tetrafluoroborate)). In some embodiments, the reaction is performed in the presence of added heat.

Any suitable conditions, such as those for an alkyne amine coupling, known in the art can be used for converting a compound of Formula 10-2 to a compound of Formula 10-3. For example, in some embodiments, the reaction is performed in the presence of polar solvents (e.g., DMSO, MeOH, and AcOH). In some embodiments, the reaction is performed with the presence of added heat.

Scheme 17 provide processes for preparing compounds of Formulae 11-4 and 11-6:

Scheme 17

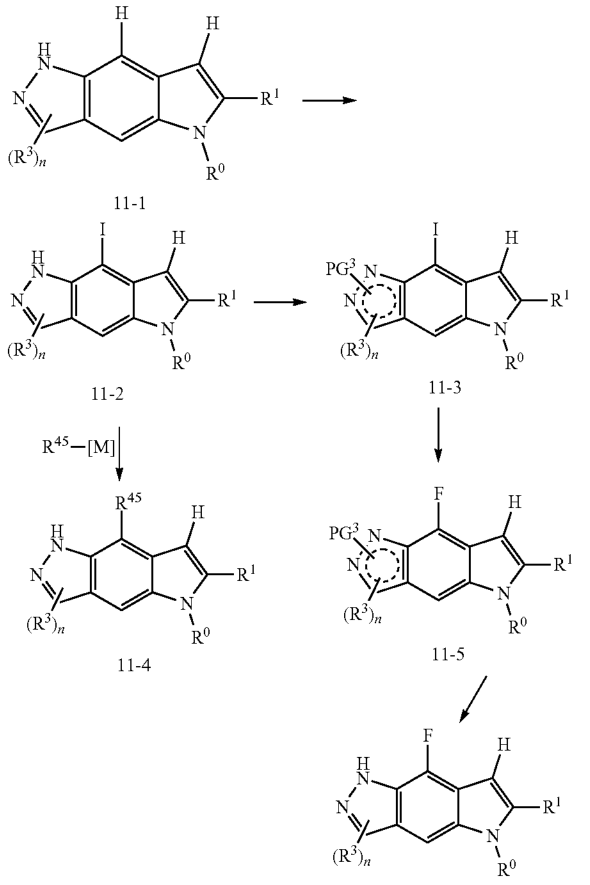

11-1 11-2 11-3 11-4 11-5 11-6 wherein variables $R^0$, $R^1$, $R^3$ and n depicted in Scheme 17 are as defined for Formula I above;

$PG^3$ is an amine protecting group;

$R^{45}$ is chosen from C1-C6 linear, branched, and cyclic alkyl groups; and

M is a metal such as zinc or boron.

Any suitable conditions, such as those for iodination of an aryl ring, known in the art can be used for converting a compound of Formula 11-1 to a compound of Formula 11-2. For example, in some embodiments, the reaction is performed in the presence of iodination reagents (e.g., N-iodo-succinimide).

Any suitable conditions, such as those for protecting an amine, known in the art can be used for converting a compound of Formula 11-2 to a compound of Formula 11-3. For example, in some embodiments, the reaction is performed in the presence of protecting reagents (e.g., Cbz-Cl).

Any suitable conditions, such as those for coupling with an aryl halide, known in the art can be used for reacting a compound of Formula 11-2 with $R^{45}$-[M] to a compound of Formula 11-4. In some embodiments, $R^{45}$-[M] is an organometallic reagent, such as dimethyl zinc.

Another aspect of the invention includes processes of preparing compounds of Formulae 12-1 and 12-2:

12-1

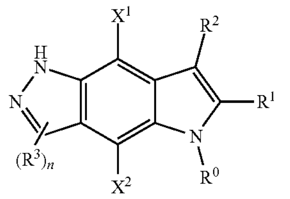

12-2

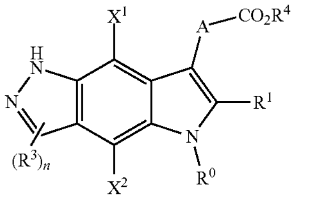

wherein variables $X^1$, $X^2$, $R^0$, $R^1$, $R^2$, $R^3$, $R^4$, A, and n depicted in Formulae 12-1 and 12-2 are as defined for Formula I above.

Any suitable conditions known to a person of ordinary skill art can be used to prepare compounds of Formulae 12-1 and 12-2, such as the processes described for preparing compounds of Formulae I, 1-6, 3-4, 3-5, 3-6, 4-3, 5-3, 6-4, 7-4, 8-4, 10-4, 11-4, and 11-6, and Compounds 1-215.

Scheme 18 provides processes for preparing compounds of Formula I-1 and Formula I from compounds of Formula 18-1.

Scheme 18

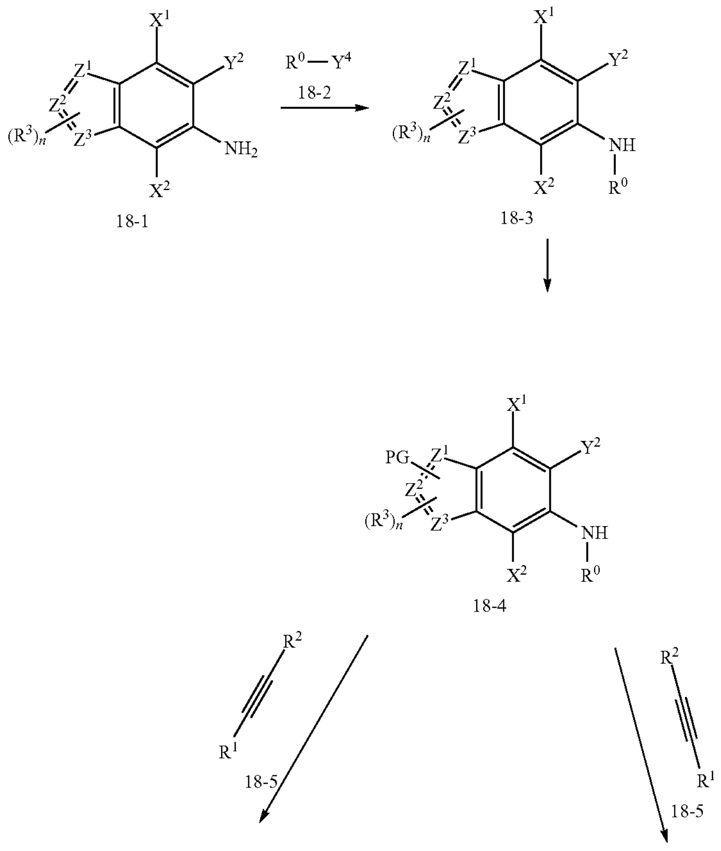

-continued

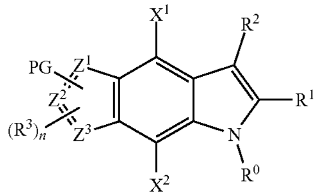

I-1

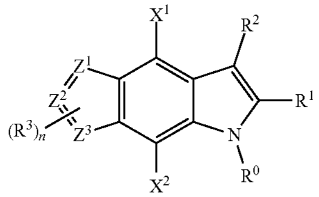

(I)

$Y^2$ is any suitable halogen (e.g. $C_1$, Br or I). $Y^4$ is a suitable halogen (e.g. Cl, Br or I). Other variables are defined as in Formula I. A compound of Formula 18-3 may be prepared by reacting a compound of Formula 18-1 and a compound of Formula 18-2. The reaction may be performed in the presence of a catalyst system (e.g. tBuXPhos Pd G4) and a base (e.g. NaOtBu). The reaction may be performed in a solvent such as tBuOH. Compounds of Formula 18-4 may be prepared from compounds of Formula 18-3 using any reagent appropriate for the protection of a nitrogen atom. In some embodiments, phenylsulfonyl chloride ($PhSO_2Cl$) in the presence of a base (e.g. KOtBu) may be used. Compounds of Formula I-1 and Formula I may be prepared by reacting compounds of Formula 18-4 with alkynes of Formula 18-5 in the presence of a catalyst (e.g. $Pd(P_tBu_3)_2$) and an amine base (e.g. N-methyldicyclohexylamine) In some embodiments, the reaction may be performed in a polar solvent such as 1,4-dioxane, with added heat (110° C.).

Compounds of Formula II may be prepared as depicted in Scheme 19.

Scheme 19

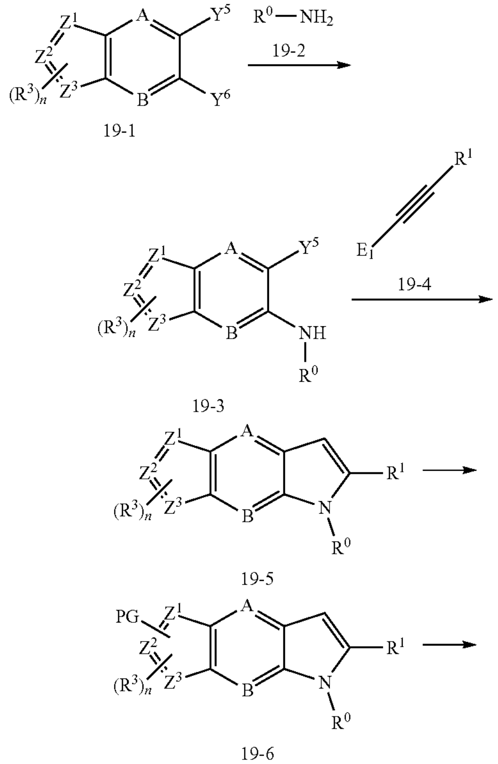

19-1, 19-3, 19-5, 19-6

-continued

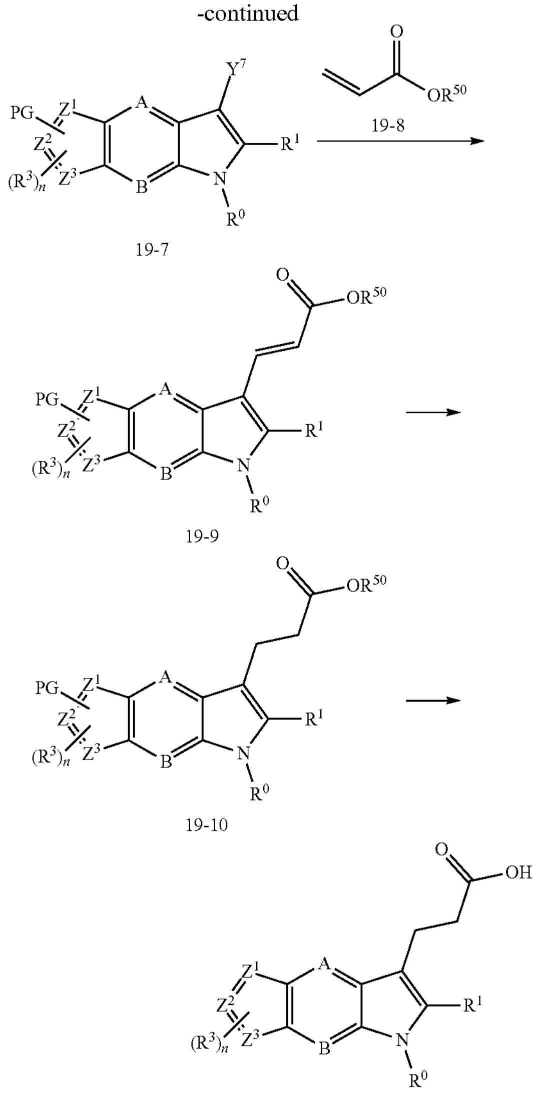

19-7, 19-9, 19-10, 19-11

$Y^6$ and $Y^7$ are suitable halogens (such as, for example, Br or I). $R^{50}$ is an alkyl group (such as, for example, methyl (Me), ethyl (Et), or tert-butyl (t-Bu)).

Any suitable condition, such as those for performing amination reactions may be used to react compounds of Formula 19-1 and amines of Formula 19-2 to give a compound of Formula 19-3. For example, the reaction may be performed in the presence of a catalyst (e.g. BrettPhos Pd G1, tBuXPhos Pd G4, BrettPhos Pd G4 or tBuXPhos Pd G1), a suitable base (e.g. NaOtBu), and a solvent such as THF, tBuOH or ethanol. Compounds of Formula 19-3 may be coupled to alkynes of Formula 19-4 using any suitable conditions for aryl halide to alkyne coupling known to those skilled in the art (e.g. Sonagashira coupling). In some embodiments, the reaction may be performed in the presence of CuI and $Pd(PPh_3)_2Cl_2$. In some embodiments, a base such as triethylamine or DIPEA may be used. In some alternative embodiments, bases such as KOH or CsF may be used. In some embodiments the reaction may be performed with added heat (70° C.). Compounds of Formula 19-6 may be prepared from 19-5 using a suitable protecting group reagent. For example, PivCl, SEM-Cl or $PhSO_2$—Cl may be used. The reaction may be performed in the presence of any suitable base (e.g. KOtBu or KOH). Compounds of Formula 19-7 may be prepared by reaction of compounds of Formula 19-6 with a halogenating agent (e.g N-iodosuccinimide or N-bromosuccinimide) in a solvent such as dichloromethane. Compounds of formula 19-9 may be prepared from 19-7 and 19-8 using any suitable method for the coupling of an aryl halide with an alkene. For example, in the presence of a catalyst system (e.g. $Pd(P_tBu_3)_2$. In some embodiments, the reaction is performed in the presence of a base (e.g. N-methyldicyclohexylamine, $KHCO_3$ or $K_2CO_3$). Any suitable conditions, such as those for a hydrogenation reaction of an olefin, known in the art can be used for reacting a compound of Formula 19-9 and to provide a compound of Formula 19-10. For example, in some embodiments, the reaction is performed in the presence of hydrogenation reagents (e.g., $H_2$ and Pd on carbon, or $NH_4HCO_2$ Pd on carbon). Any suitable conditions, such as those for hydrolysis of an ester, known in the art can be used for converting a compound of Formula 19-10 to a compound of Formula 19-11. For example, in some embodiments, the reaction is performed in the presence of a base (e.g., LiOH or NaOH).

Scheme 20 describes a method for preparation of compounds of formula III.

Scheme 20

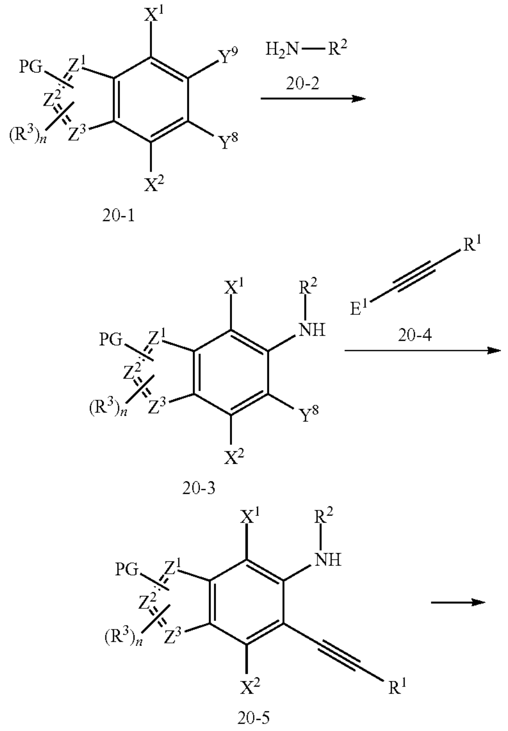

20-5

-continued

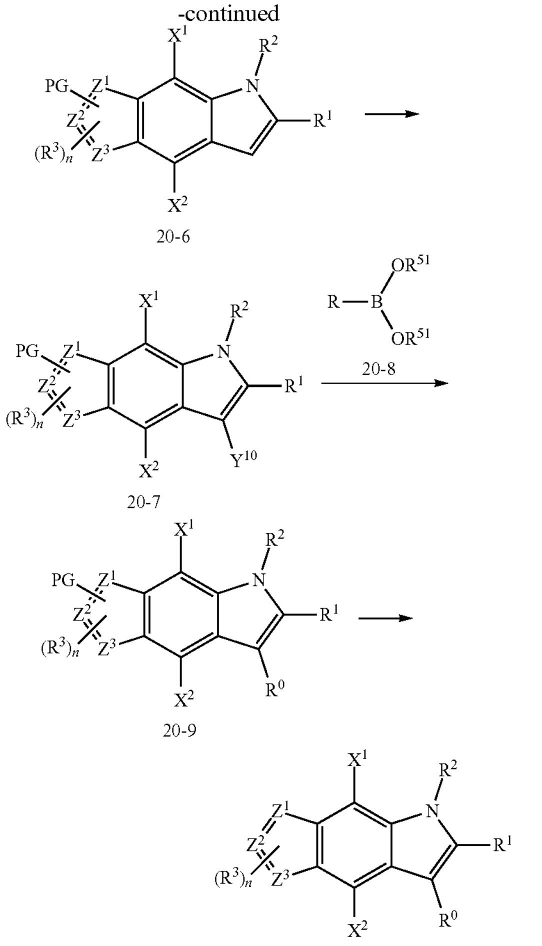

(III)

$Y^8$ and $Y^9$ are suitable halogens (e.g. Cl, Br or I). $Y^{10}$ is Br or I. $R^{51}$ is hydrogen (H), methyl (Me), alkyl, or alkyl linked as part of a ring as in a cyclic boronate ester. Any suitable method for reacting amines with an aryl halide may be used to prepare a compound of formula 20-3 from 20-1 and an amine for formula 20-2. In some embodiments, the reaction may be performed in the presences of a catalyst (e.g. $Pd_2(dba)_3$) and ligand such as BINAP, in the presence of a base (e.g. $Cs_2CO_3$). A compound of formula 20-5 may be prepared from 20-3 by Sonagashira coupling with an alkyne of Formula 20-4. In some embodiments, the reaction may be performed in the presence of $Pd(PhCN)_2Cl_2$, XPhos and a base such as $Cs_2CO_3$. Compounds of formula 20-6 may be prepared from compounds of formula 20-5 using any suitable method for the intramolecular cyclization of an amine onto an alkyne. In some examples, an Au catalyst such as [1,3-bis(2,6-diisopropylphenyl)imidazol-2-ylidene]-chloro-gold may be used. A reagent such as $AgBF_4$ may be present. The reaction may be performed in the presence of additional heat, (e.g. 60° C.). Compounds of formula 20-7 may be prepared by reacting a compound of Formula 20-6 with a halogenating agent (e.g N-iodosuccinimide or N-bromosuccinimide) in a solvent such as dichloromethane. Suzuki coupling of a boronic acid or boronic ester of formula 20-8 with an aryl halide of Formula 20-7 provides compounds of Formula 20-9. In some embodiments, a catalyst such as SPhos Pd G3 is used. In some embodiments, the reaction may be performed in the presence of a base (e.g.

$K_3PO_4$) in a polar solvent (e.g. 1,4-dioxane) at elevated temperature (80° C.). Compounds of Formula III may be prepared from compounds of Formula 20-9 using a suitable method for removal of a nitrogen protecting group. In some embodiments, for example, where the nitrogen protecting group is a pivaloyl, an aqueous solution of base (e.g. NaOH or KOH) in a polar solvent (e.g. a THF and MeOH mixture) may be used. The reaction may be performed with added heat (e.g. 55° C.).

In some embodiments, a method of preparing a compound of formula 32

32

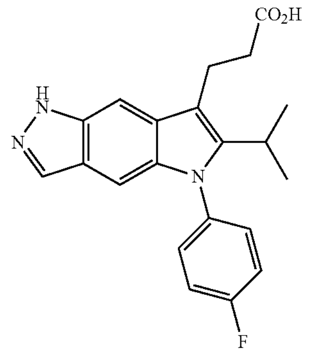

a pharmaceutically acceptable salt thereof, or a deuterated derivative of any of the foregoing is disclosed, the method comprising reacting a compound of formula C4

C4

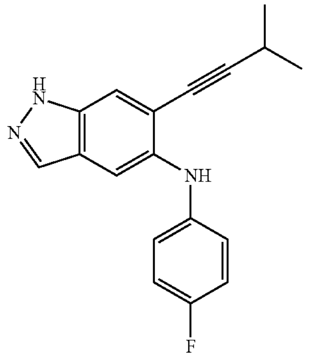

with at least one acid to produce a compound of formula S3

S3

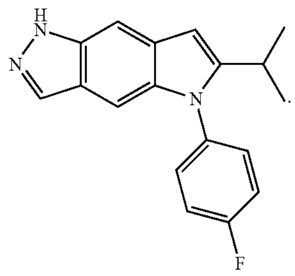

In some embodiments, the at least one acid is acetic acid.

In some embodiments, the method further comprises reacting the compound of formula S3 with benzyl chloroformate in the presence of at least one base to produce a compound of formula S4

S4

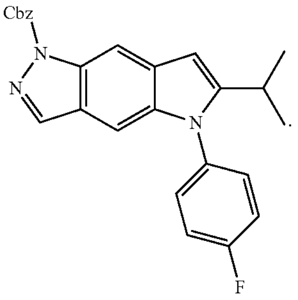

In some embodiments, the at least one base is chosen from potassium tert-butoxide, sodium tert-butoxide, sodium tert-amylate, and sodium methoxide.

In some embodiments, the method further comprises reacting the compound of formula S4 with methyl-3,3-dimethoxypropionate in the presence of at least one acid to produce a compound of formula C35

C35

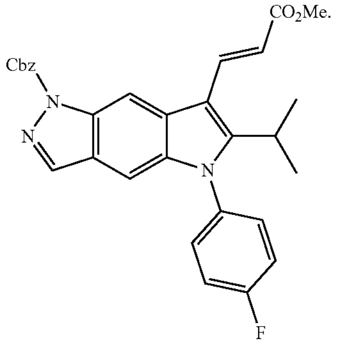

In some embodiments, the at least one acid is chosen from para-toluenesulfonic acid and para-toluenesulfonic acid hydrate.

In some embodiments, the method further comprises hydrogenating the compound of formula C35 to produce a compound of formula C36

C36

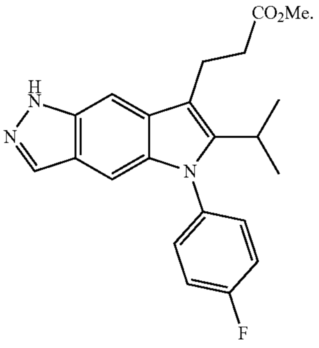

In some embodiments, the hydrogenation is performed using palladium on carbon and hydrogen gas. In some embodiments, the method further comprises hydrolyzing the compound of formula C36 to produce the compound of formula 32. In some embodiments, the hydrolysis comprises reacting the compound of formula C36 with at least one base and subsequent acidification with at least one acid. In some embodiments, the hydrolysis comprises reacting the compound of formula C36 with at least one base chosen from potassium hydroxide, sodium hydroxide, lithium hydroxide, and sodium methoxide and subsequent acidification with at least one acid. In some embodiments, the hydrolysis comprises reacting the compound of formula C36 with at least one base chosen from potassium hydroxide, sodium hydroxide, lithium hydroxide, and sodium methoxide and subsequent acidification with at least one acid chosen from acetic acid.

In some embodiments, the method further comprises reacting a compound of formula C7

C7

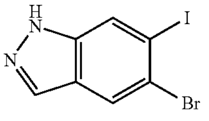

with 3-methyl-1-butyne in the presence of at least one coupling reagent and at least one base to produce a compound of formula C8

C8

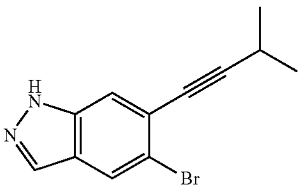

.

In some embodiments, the at least one coupling reagent is chosen from CuI and $Pd(PPh_3)_2Cl_2$. In some embodiments, the at least one base is chosen from triethylamine, diethylamine, diisopropylethylamine, and pyridine.

In some embodiments, the method further comprises reacting the compound of formula C8 with 4-fluoroaniline in the presence of a palladium catalyst and at least one base to produce the compound of formula C4. In some embodiments, the at least one base is chosen from potassium tert-butoxide, sodium tert-butoxide, sodium tert-amylate, and sodium methoxide.

In some embodiments, disclosed is a method of preparing a compound of formula 32

32

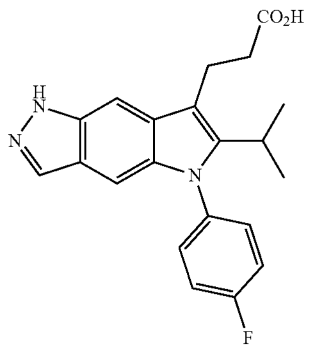

a pharmaceutically acceptable salt thereof, or a deuterated derivative of any of the foregoing, comprising:

(a) reacting a compound of formula C7

C7

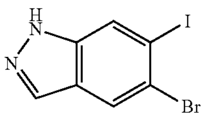

with 3-methyl-1-butyne in the presence of at least one coupling reagent and at least one base to produce a compound of formula C8

C8

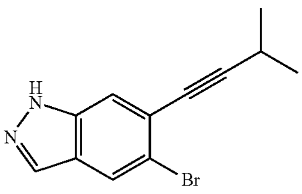

;

(b) reacting the compound of formula C8 with 4-fluoroaniline in the presence of a palladium catalyst and at least one base to produce a compound of formula C4

C4

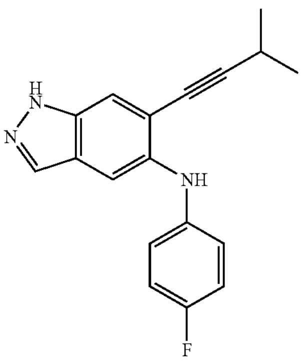

;

(c) reacting the compound of formula C4 with at least one acid to produce a compound of formula S3

S3

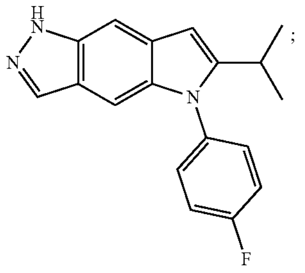

(d) reacting the compound of formula S3 with benzyl chloroformate in the presence of at least one base to produce a compound of formula S4

S4

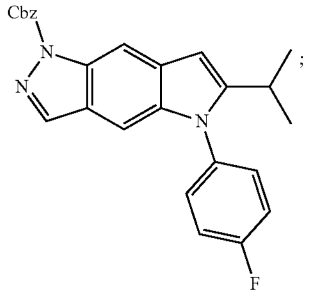

(e) reacting the compound of formula S4 with methyl-3,3-dimethoxypropionate in the presence of at least one acid to produce a compound of formula C35

C35

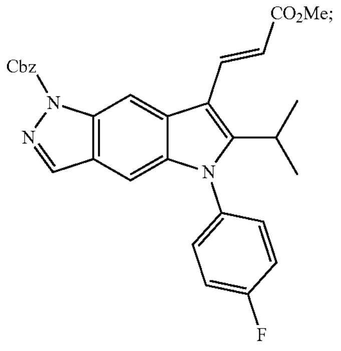

(f) hydrogenating the compound of formula C35 to produce a compound of formula C36

C36

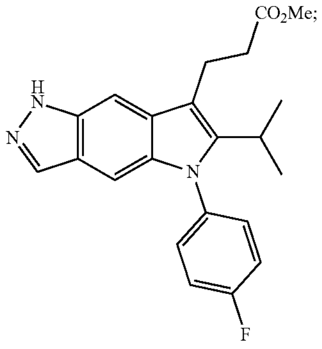

and (g) hydrolyzing the compound of formula C36 to produce the compound of formula 32.

In some embodiments, the at least one coupling reagent used in (a) is chosen from CuI and $Pd(PPh_3)_2Cl_2$. In some embodiments, the at least one base in (a) is chosen from triethylamine, diethylamine, diisopropylethylamine, and pyridine. In some embodiments, the at least one base in (b) is chosen from potassium tert-butoxide, sodium tert-butoxide, sodium tert-amylate, and sodium methoxide. In some embodiments, the at least one acid in (c) is acetic acid. In some embodiments, the at least one base in (d) is chosen from potassium tert-butoxide, sodium tert-butoxide, sodium tert-amylate, and sodium methoxide. In some embodiments, the at least one acid in (e) is chosen from para-toluenesulfonic acid and para-toluenesulfonic acid hydrate. In some embodiments, the hydrogenation in (f) is performed using palladium on carbon and hydrogen gas. In some embodiments, the hydrolysis in (g) comprises reacting the compound of formula C36 with at least one base and subsequent acidification with at least one acid. In some embodiments, the hydrolysis in (g) comprises reacting the compound of formula C36 with at least one base chosen from potassium hydroxide, sodium hydroxide, lithium hydroxide, and sodium methoxide and subsequent acidification with at least one acid. In some embodiments, the hydrolysis in (g) comprises reacting the compound of formula C36 with at least one base chosen from potassium hydroxide, sodium hydroxide, lithium hydroxide, and sodium methoxide and subsequent acidification with at least one acid chosen from acetic acid.

In some embodiments, disclosed is a method of preparing a compound of formula S3

S3

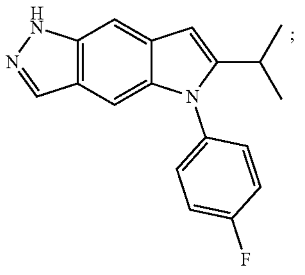

a salt thereof, or a deuterated derivative of any of the foregoing, comprising reacting a compound of formula C4

C4

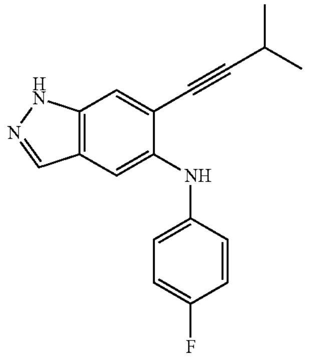

with at least one acid. In some embodiments, the at least one acid is acetic acid. In some embodiments, the compound of formula C4 is prepared by reacting a compound of formula C8

C8

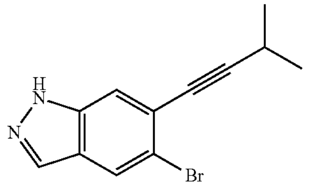

with 4-fluoroaniline in the presence of a palladium catalyst and at least one base. In some embodiments, the at least one base is chosen from potassium tert-butoxide, sodium tert-butoxide, sodium tert-amylate, and sodium methoxide. In some embodiments, the compound of formula C8 is prepared by reacting a compound of formula C7

C7

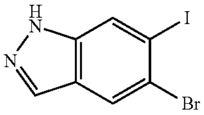

with 3-methyl-1-butyne in the presence of at least one coupling reagent and at least one base. In some embodiments, the at least one coupling reagent is chosen from CuI and $Pd(PPh_3)_2Cl_2$. In some embodiments, the at least one base is chosen from triethylamine, diethylamine, diisopropylethylamine, and pyridine.

In some embodiments, disclosed is a method of preparing a compound of formula S6

S6

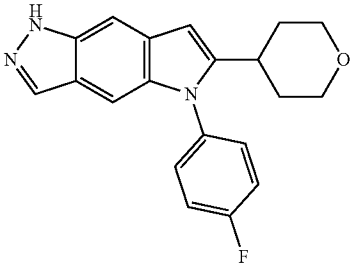

a salt thereof, or a deuterated derivative of any of the foregoing, comprising heating a solution comprising a compound of formula C15

C15

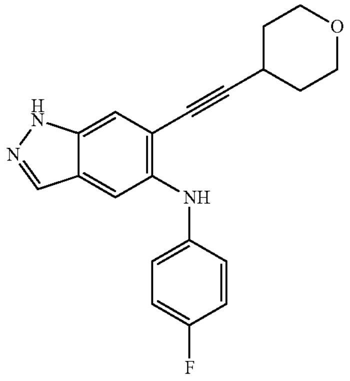

with at least one base. In some embodiments, the method further comprises reacting a compound of formula C14

C14

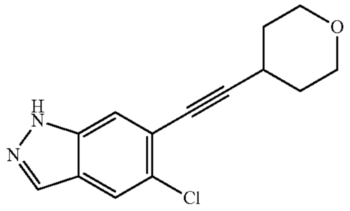

with 4-fluoroaniline, at least one base, and at least one palladium precatalyst to prepare the compound of formula S6. In some embodiments, the at least one base is sodium t-butoxide. In some embodiments, the at least one palladium precatalyst is BrettPhos Pd G4.

IV. Exemplary Embodiments

1. A compound of formula (I):

(I)

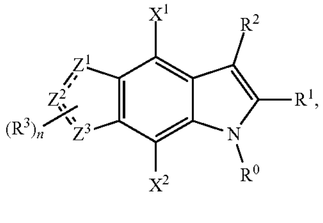

a tautomer thereof, a pharmaceutically acceptable salt of any of the foregoing, or a deuterated derivative of any of the foregoing;

wherein:

(i) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy;

(ii) $R^1$ is chosen from (a) $C_1$-$C_8$ linear, branched, and cyclic alkyl groups, wherein the alkyl group is optionally substituted with 1-4 substituents chosen from
halogens,
carboxylic acid,
cyano, and
$C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from
halogens,
cyano, and
$C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iii) $R^2$ is chosen from:
hydrogen,
cyano,
halogens,
alkylamide groups,
$C_1$-$C_8$ linear, branched, and cyclic alkyl groups optionally substituted with
an oxo group,
a $C_1$-$C_8$ linear, branched, and cyclic alkoxy group,
a 5- or 6-membered heteroaryl group,
a cyano group,
an amino group,
an aminoalkyl group,
an alkylamide group,
an alkylsulfonyl group,
an alkylsulfonamide group,
an alkylsulfoxide group,
a group

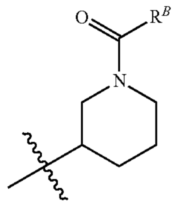

or

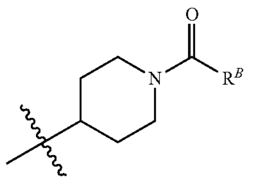

wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group, a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group.

a

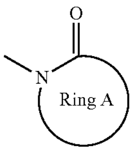

group wherein the Ring A is chosen from 4-8 membered rings optionally comprising one or two heteroatoms in addition to the Ring A nitrogen, and/or
a carboxylic acid group esterified with a uronic acid,
$C_2$-$C_6$ linear, branched, and cyclic alkenyl groups,
$C_2$-$C_6$ linear, branched, and cyclic alkynyl groups,
A-$CO_2R^4$ groups wherein A is optionally present and if present is chosen from
$C_1$-$C_8$ linear, branched, and cyclic alkyl and alkoxy groups,
$C_2$-$C_6$ linear, branched, and cyclic alkenyl groups,
$C_3$-$C_8$ cycloalkyl linked to $C_1$-$C_8$ linear or branched alkyl groups,
$C_1$-$C_8$ linear or branched alkyl linked to $C_3$-$C_8$ cycloalkyl groups,
$C_3$-$C_8$ cycloalkyl linked to $C_3$-$C_8$ cycloalkyl groups,
$C_1$-$C_8$ linear, branched, and cyclic alkyl linked to $C_3$-$C_8$ cycloalkyl linked to
a $C_1$-$C_8$ linear, branched, and cyclic alkyl groups,
wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and
wherein $R^4$ is chosen from hydrogen, $C_1$-$C_8$ linear, branched, and cyclic alkyl groups, and $C_2$-$C_6$ linear, branched, and cyclic alkenyl groups,
A-C(O)$NH_2$ groups wherein A is optionally present and if present is chosen from
$C_1$-$C_8$ linear, branched, and cyclic alkyl and alkoxy groups,
$C_2$-$C_6$ linear, branched, and cyclic alkenyl groups,
$C_3$-$C_8$ cycloalkyl linked to $C_1$-$C_8$ linear or branched alkyl groups,
$C_1$-$C_8$ linear or branched alkyl linked to $C_3$-$C_8$ cycloalkyl groups,
$C_3$-$C_8$ cycloalkyl linked to $C_3$-$C_8$ cycloalkyl groups,
$C_1$-$C_8$ linear, branched, and cyclic alkyl linked to $C_3$-$C_8$ cycloalkyl linked to
a $C_1$-$C_8$ linear, branched, and cyclic alkyl groups,
wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and
wherein $R^4$ is chosen from hydrogen, $C_1$-$C_8$ linear, branched, and cyclic alkyl groups, and $C_2$-$C_6$ linear, branched, and cyclic alkenyl groups, C(O)NR$^6$R$^7$ wherein R$^6$ and R$^7$ are independently chosen from
hydrogen,
$C_1$-$C_8$ linear, branched, and cyclic alkyl groups,
$C_2$-$C_6$ linear, branched, and cyclic alkenyl groups,
4- to 8-membered heterocycles optionally substituted by one or more substituents chosen from cyano, halogens,
$C_1$-$C_8$ linear, branched, and cyclic alkyl groups, and
$C_2$-$C_6$ linear, branched, and cyclic alkenyl groups,
or R$^6$ and R$^7$ together with the nitrogen to which they are attached form a 4-8 membered ring optionally comprising one or two heteroatoms in addition to the nitrogen to which they are attached, and which ring is optionally substituted with a substituent chosen from halogens, cyano, hydroxy, and $C_1$-$C_6$ linear, branched, and cyclic alkyl groups,
SO$_2$R$^5$ groups wherein R$^5$ is chosen from $C_1$-$C_8$ linear, branched, and cyclic alkyl groups, and $C_2$-$C_6$ linear, branched, and cyclic alkenyl groups, and

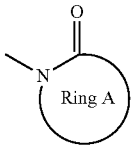

groups wherein the Ring A is a 4-8 membered ring optionally comprising one or two heteroatoms in addition to the Ring A nitrogen;

(iv) X$^1$ and X$^2$ are independently chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(v) each $\overline{\overline{---}}$ represents a single or double bond, provided that no more than one $\overline{\overline{---}}$ is a double bond;

(vi) each R$^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 halogens;

(vii) n is an integer chosen from 0, 1, 2, and 3; and (viii) Z$^1$, Z$^2$, and Z$^3$ are independently chosen from carbon, nitrogen, sulfur, and oxygen, wherein when Z$^1$, Z$^2$, and/or Z$^3$ are carbon or nitrogen, the valences of carbon and nitrogen are completed with hydrogen atoms, $C_1$-$C_8$ linear, branched, and cyclic alkyls, or cyano.

2. The compound of any one of embodiments 1, 14, or 16, a tautomer thereof, a pharmaceutically acceptable salt of the compound or the tautomer, or a deuterated derivative of the compound, the tautomer, or the salt, wherein R$^0$ is chosen from heteroaryl rings.

3. The compound of any one of embodiments 1, 14, or 16, a tautomer thereof, a pharmaceutically acceptable salt of the compound or the tautomer, or a deuterated derivative of the compound, the tautomer, or the salt, wherein R$^0$ is phenyl.

4. The compound of any one of embodiments 1-3, 14, or 16, a tautomer thereof, a pharmaceutically acceptable salt of the compound or the tautomer, or a deuterated derivative of the compound, the tautomer, or the salt, wherein R$^0$ is substituted with 1-2 substituents.

5. The compound of embodiment any one of embodiments 1-4, 14, or 16, a tautomer thereof, a pharmaceutically acceptable salt of the compound or the tautomer, or a deuterated derivative of the compound, the tautomer, or the salt, wherein the 1-2 substituents are independently chosen from halogens and $C_1$-$C_4$ alkyl groups.

6. The compound of any one of embodiments 1-5, 14, or 16, a tautomer thereof, a pharmaceutically acceptable salt of the compound or the tautomer, or a deuterated derivative of the compound, the tautomer, or the salt, wherein R$^0$ is substituted with a fluorine and/or a methyl group.

7. The compound of any one of embodiments 1, 14, or 16, a tautomer thereof, a pharmaceutically acceptable salt of the compound or the tautomer, or a deuterated derivative of the compound, the tautomer, or the salt, wherein R$^1$ is chosen from $C_1$-$C_3$ linear and branched alkyl groups and $C_4$-$C_6$ cyclic alkyl groups.

8. The compound of any one of embodiments 7, 14, or 16, a tautomer thereof, a pharmaceutically acceptable salt of the compound or the tautomer, or a deuterated derivative of the compound, the tautomer, or the salt, wherein R$^1$ is chosen from $C_6$ cyclic alkyl groups wherein 1 carbon atom is replaced by a heteroatom.

9. The compound of any one of embodiments 1-8, 14, or 16, a tautomer thereof, a pharmaceutically acceptable salt of the compound or the tautomer, or a deuterated derivative of the compound, the tautomer, or the salt, wherein R$^1$ is chosen from:

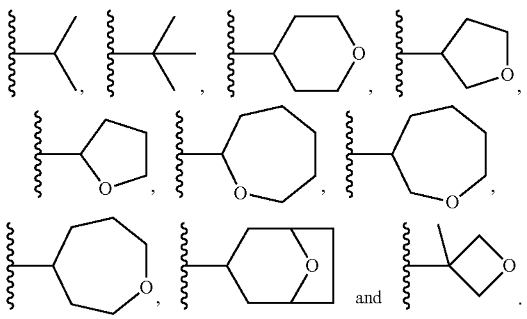

10. The compound of any one of embodiments 1, 14, or 16, a tautomer thereof, a pharmaceutically acceptable salt of the compound or the tautomer, or a deuterated derivative of the compound, the tautomer, or the salt, wherein at least one of Z$^1$, Z$^2$, and Z$^3$ is nitrogen.

11. The compound of embodiment 10, a tautomer thereof, a pharmaceutically acceptable salt of the compound or the tautomer, or a deuterated derivative of the compound, the tautomer, or the salt, wherein two of Z$^1$, Z$^2$, and Z$^3$ are nitrogen and the other is chosen from carbon and nitrogen.

12. The compound of embodiment 1, chosen from compounds of Formulae 1-6, 3-4, 3-5, 3-6, 4-3, 5-3, 6-4, 7-4, 8-4, 12-1, and 12-2:

1-6

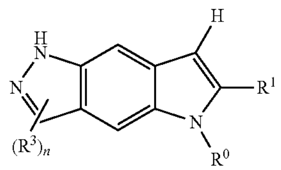

-continued 3-4

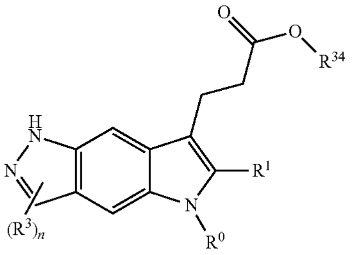

3-5

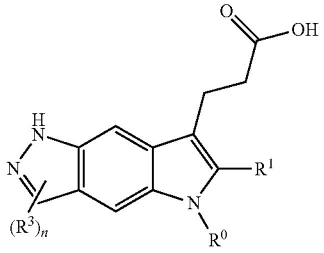

3-6

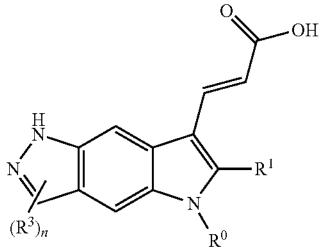

4-3

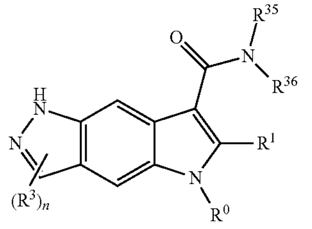

5-3

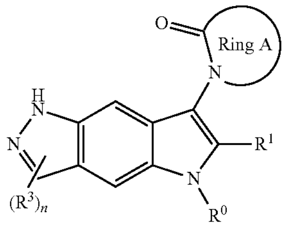

6-4

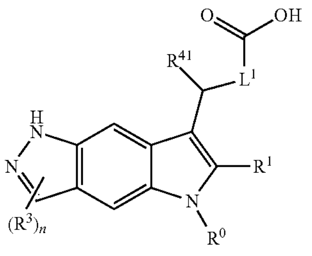

-continued 7-4

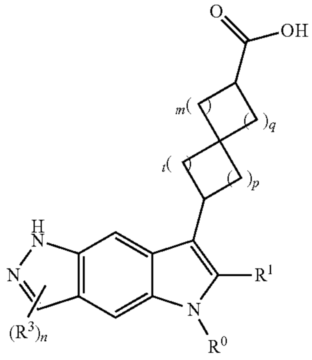

8-4

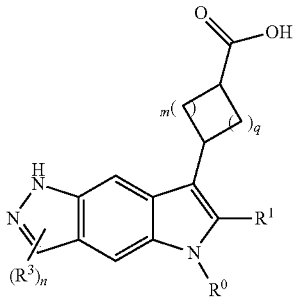

12-1

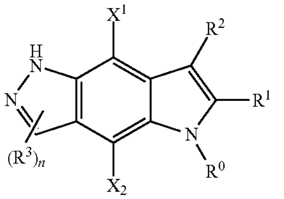

12-2

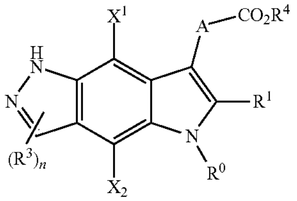

a tautomer thereof, a pharmaceutically acceptable salts of the compound or the tautomer, or a deuterated derivative of the compound, the tautomer, or the salt, wherein:

$R^0$, $R^1$, $R^2$, $R^3$, $R^4$, $X^1$, $X^2$, A, and n are defined for compounds of Formula (I), $R^{34}$ is selected from $C_1$-$C_6$ linear, branched, and cyclic alkyl groups;

$R^{35}$ and $R^{36}$ are selected from $C_1$-$C_6$ linear, branched, and cyclic alkyl groups; or $R^{35}$ and $R^{36}$, taken together with the N atom to which they are bound, form a 4 to 6 membered ring, optionally substituted with $C_1$-$C_6$ linear, branched, and cyclic alkyl groups;

$R^{41}$ is selected from H, $C_1$-$C_6$ linear, branched, and cyclic alkyl groups;

$L^1$ is chosen from:

$C_1$-$C_8$ linear, branched, and cyclic alkyl groups, $C_2$-$C_6$ linear, branched, and cyclic alkenyl groups, $C_3$-$C_5$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of $L^1$ are optionally substituted with 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, m is an integer chosen from 0-3, and q is an integer chosen from 0-3, provided that:

(i) if m is 0, then q is at least 1; and (ii) if q is 0, then m is at least 1;

and t is an integer chosen from 0-3, and p is an integer chosen from 0-3, provided that:

(i) if t is 0, then p is at least 2; and (ii) if p is 0, then t is at least 2.

13. A compound selected from:

1

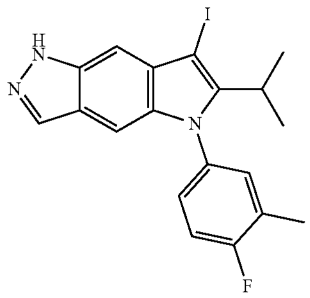

2

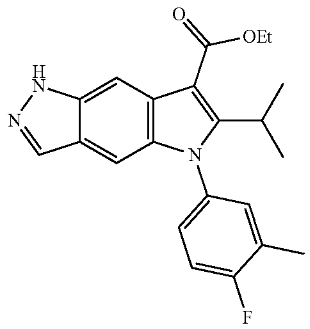

3

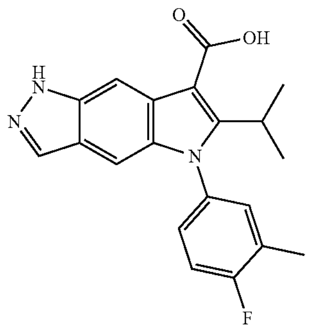

-continued

4

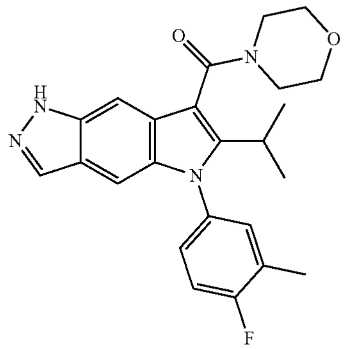

5

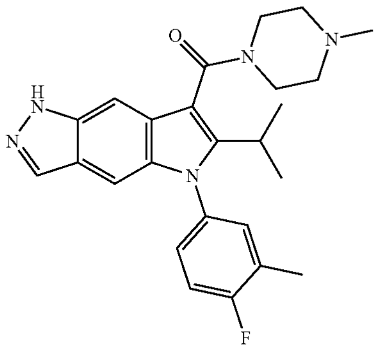

6

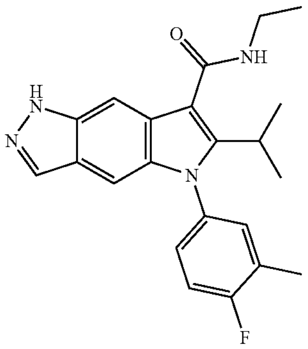

7

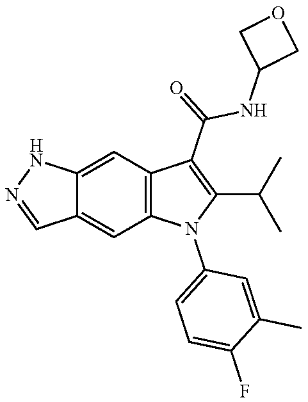

-continued
8
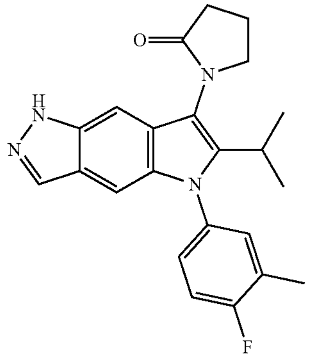
9
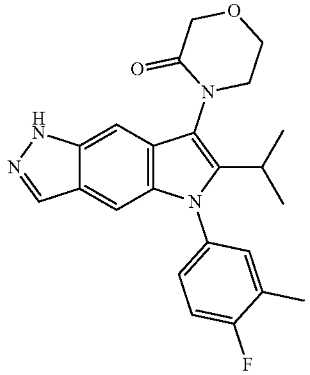
10
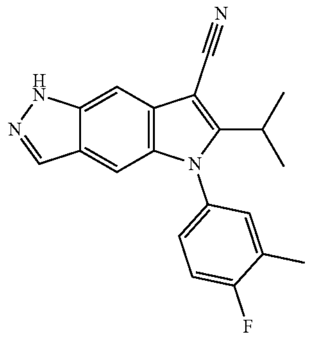
11
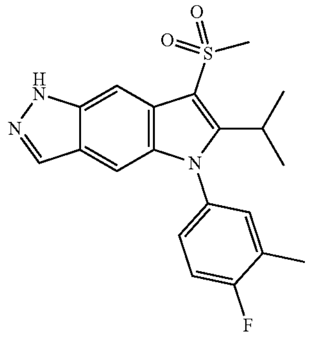
-continued
12
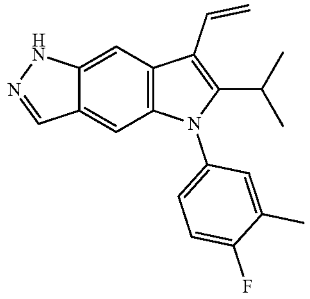
13
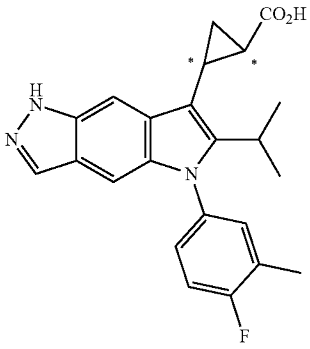
[TRANSEMAMT-1]
14
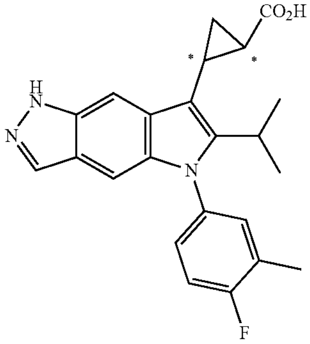
[TRANSEMAMT-2]
15
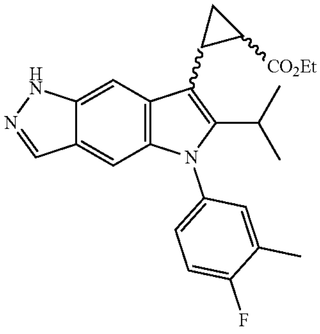

-continued
16
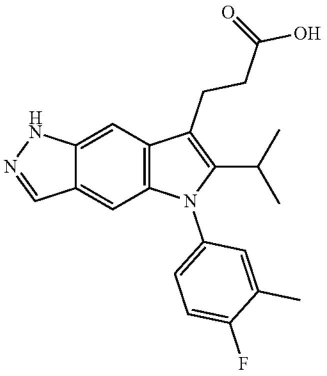
17
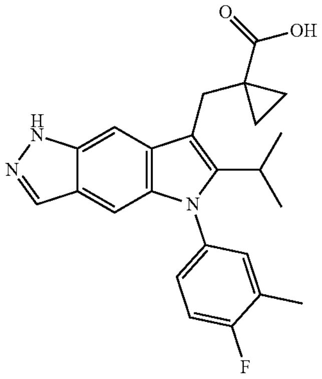
18
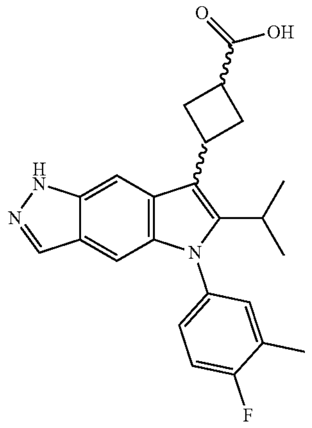
19
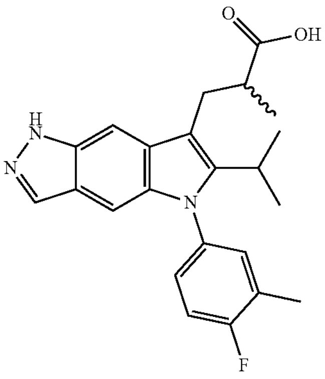
-continued
20
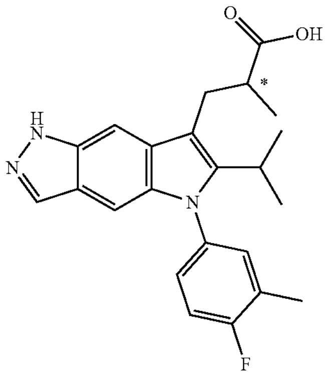
[ENANT-1]
21
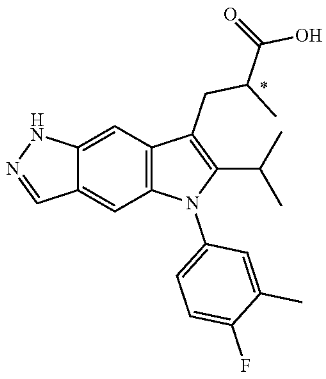
[ENANT-2]
22
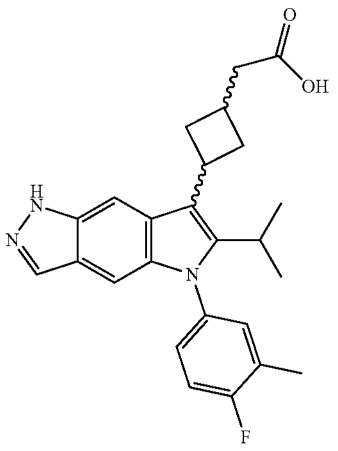

23
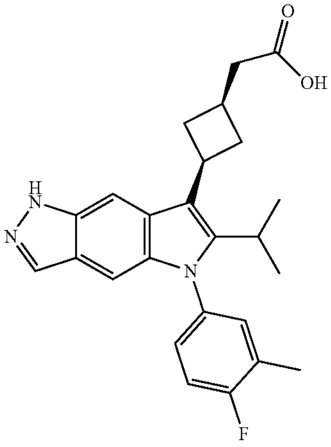
24
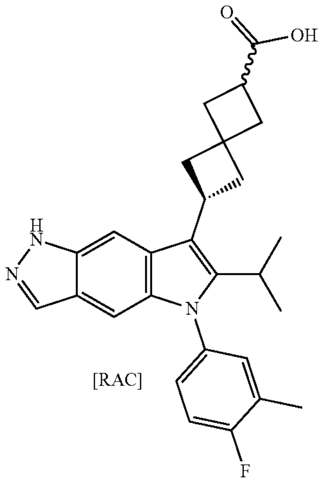
[RAC]
25
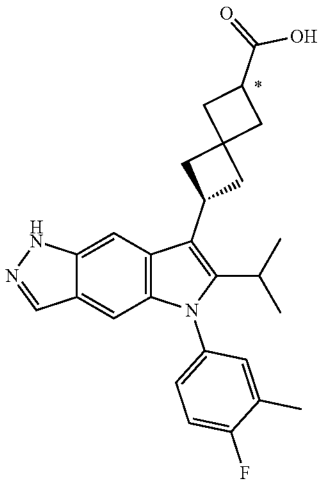
[ENANT-1]
26
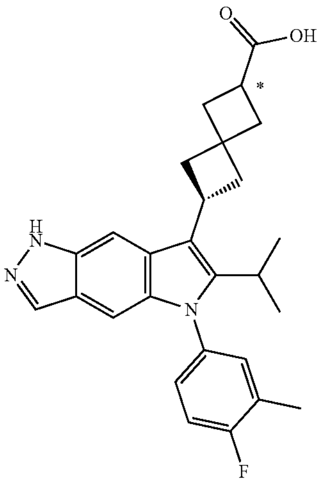
[ENANT-2]
27
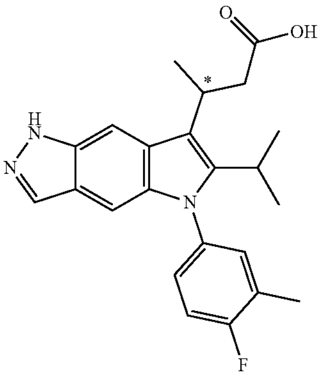
[ENANT-1]
28
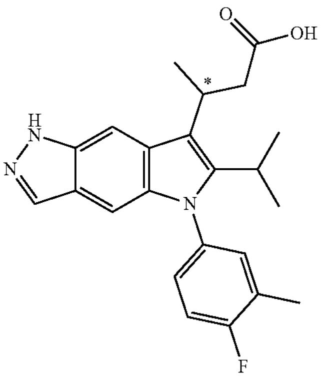
[ENANT-2]

-continued
29
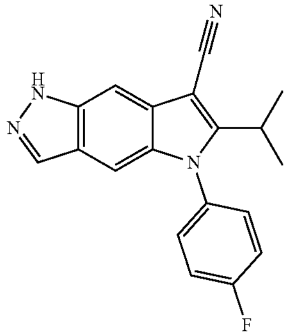
30
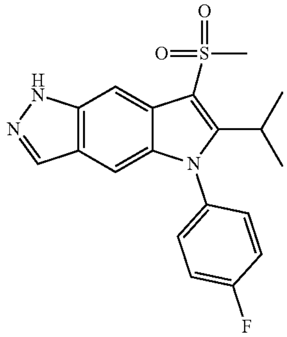
31
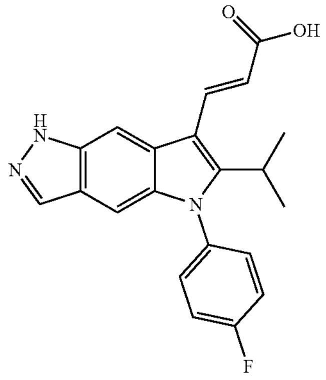
32
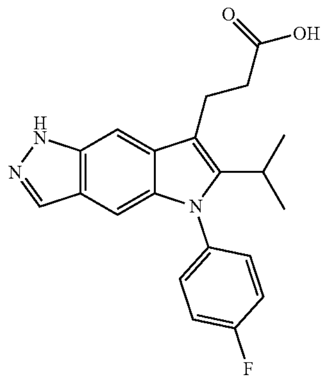
-continued
33
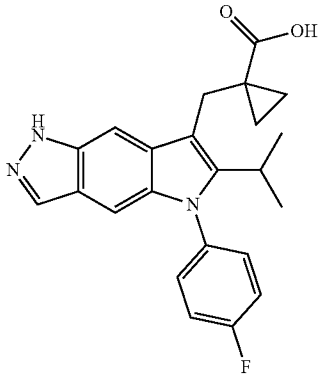
34
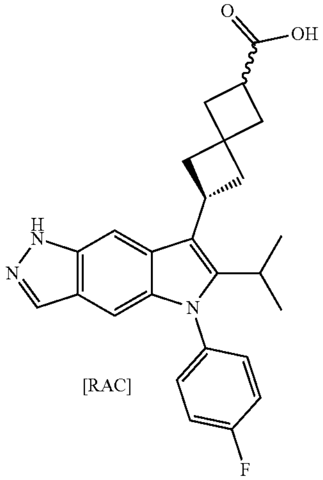
[RAC]
35
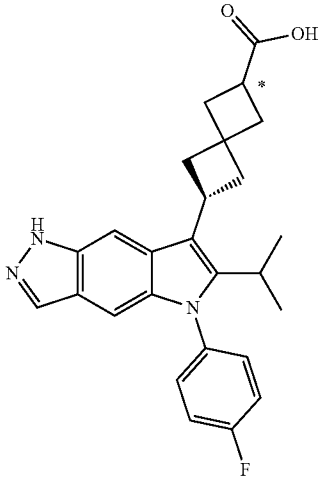
[ENANT-1]

-continued
36
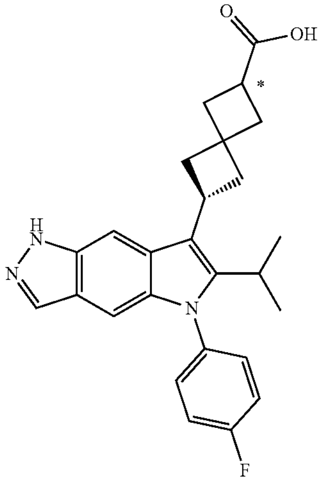
[ENANT-2]
37
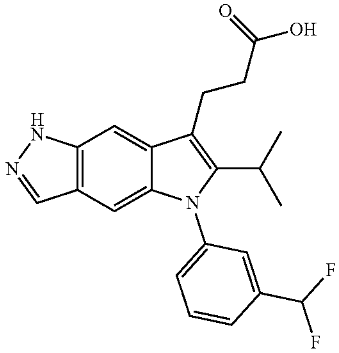
38
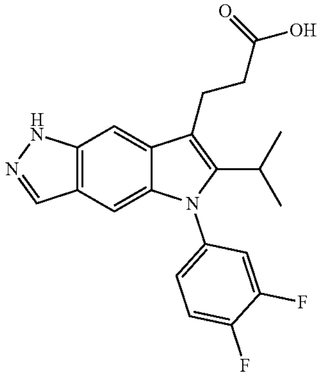
39
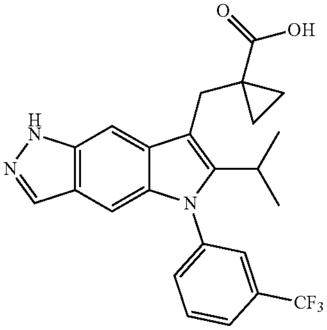
-continued
40
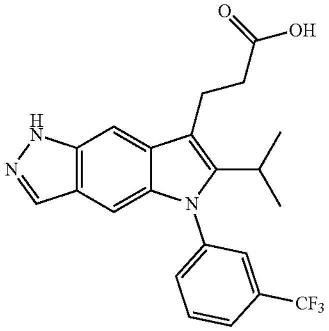
41
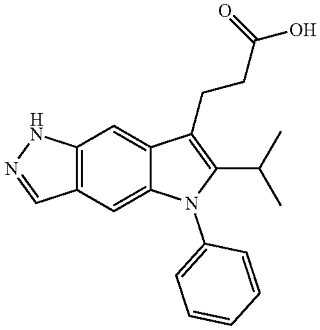
42
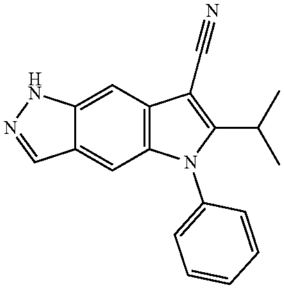
43
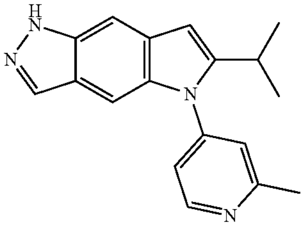
44
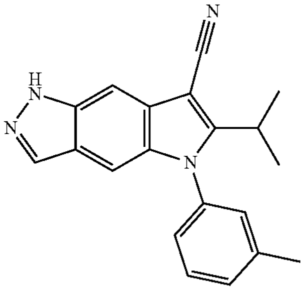

-continued
45
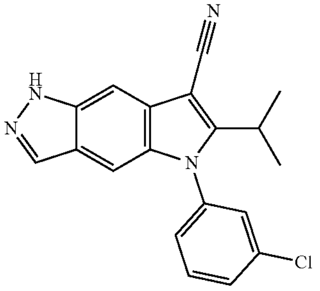
46
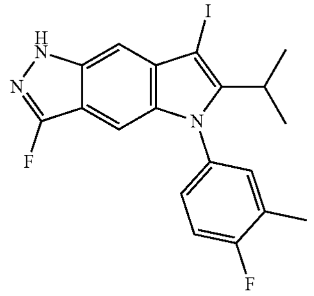
47
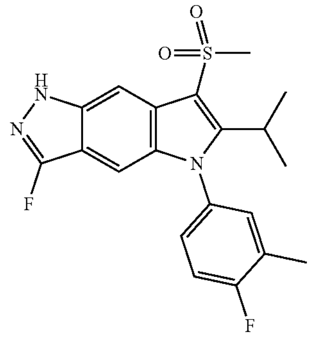
48
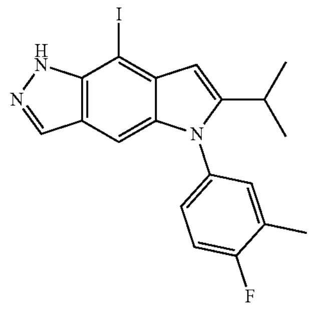
49
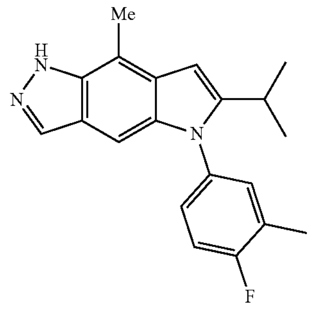
-continued
50
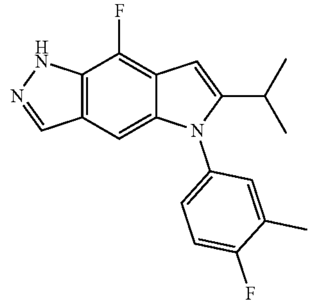
51
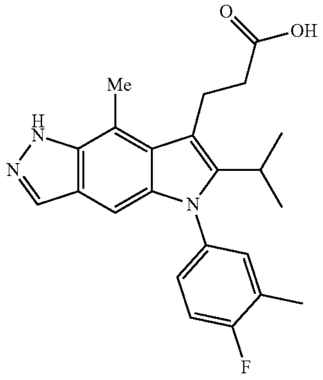
52
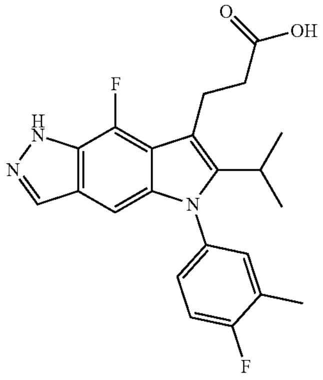
53
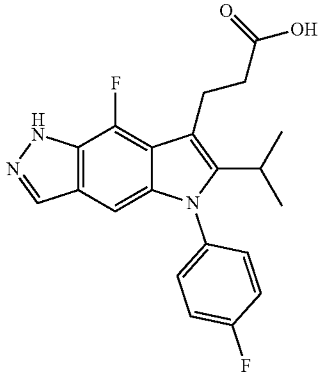

-continued
54
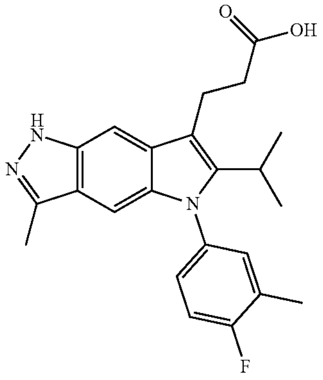
55
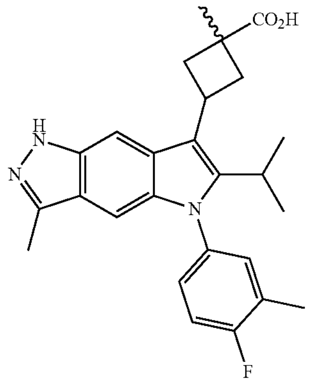
56
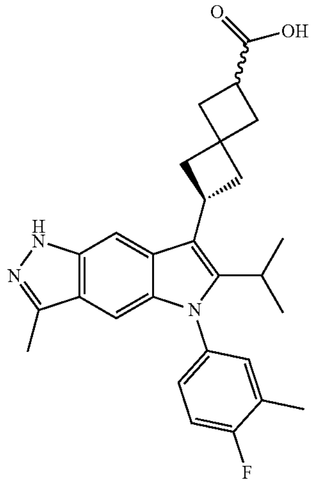
[Rac]
-continued
57
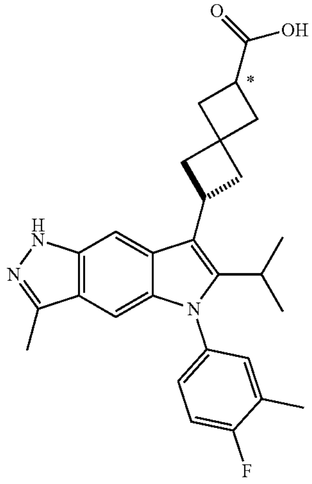
[ENANT-1]
58
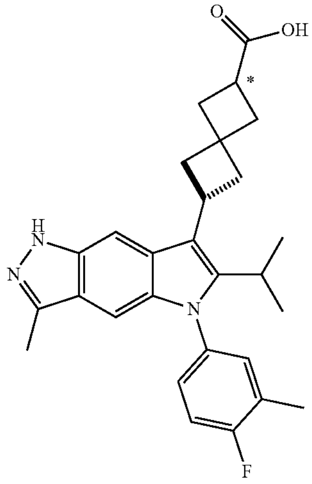
[ENANT-2]
59
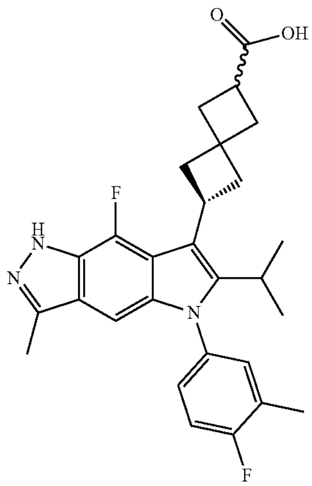
[Rac]

-continued
60
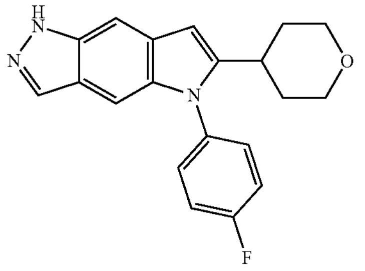
61
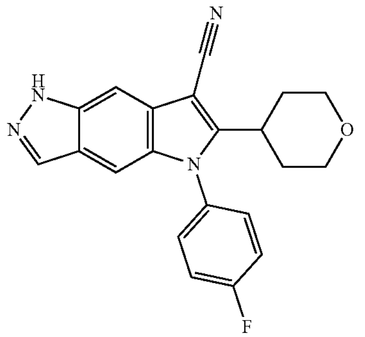
62
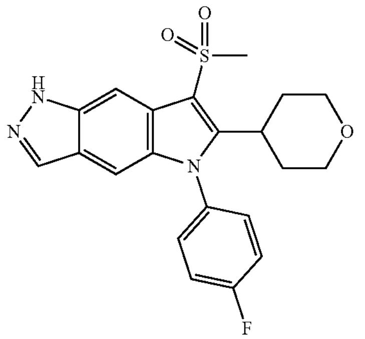
63
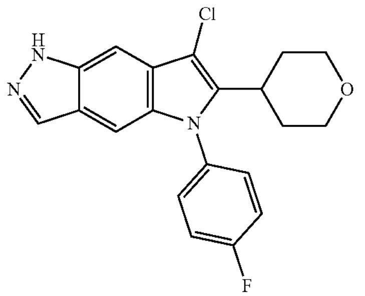
64
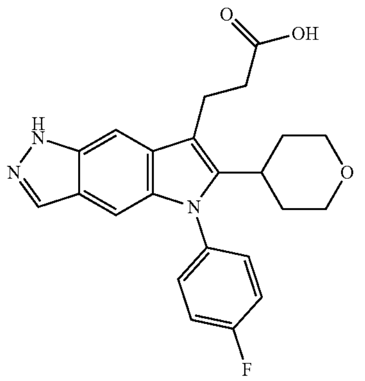
-continued
65
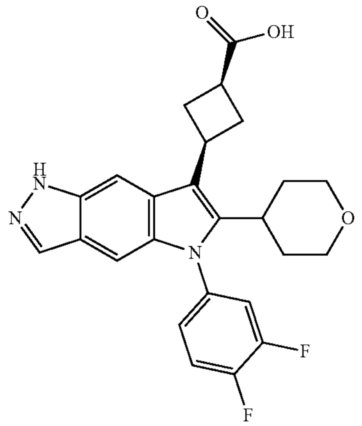
66
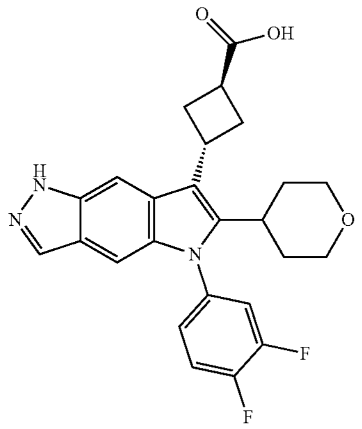
67
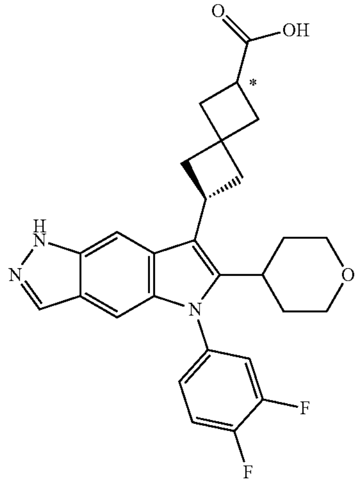
[ENANT-1]

-continued
68
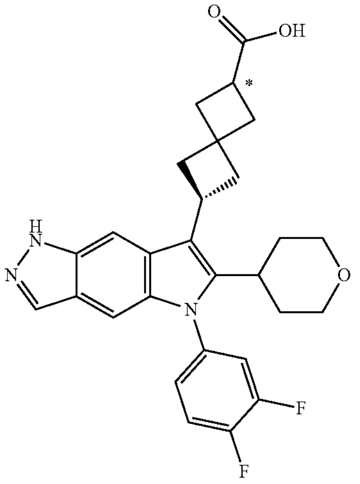
[ENANT-2]
69
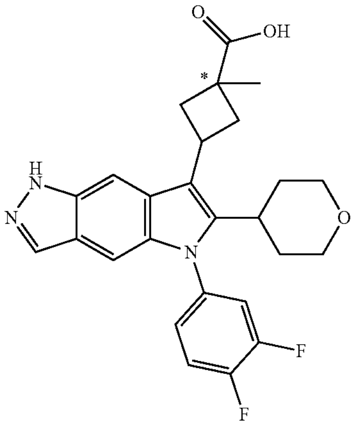
[Isomer-1]
70
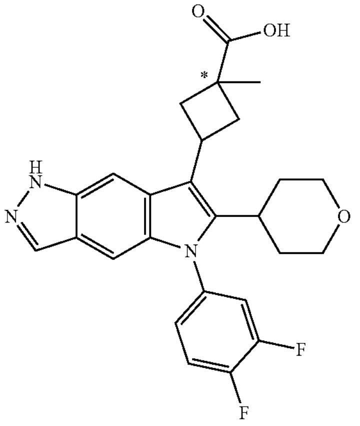
[Isomer-2]
-continued
71
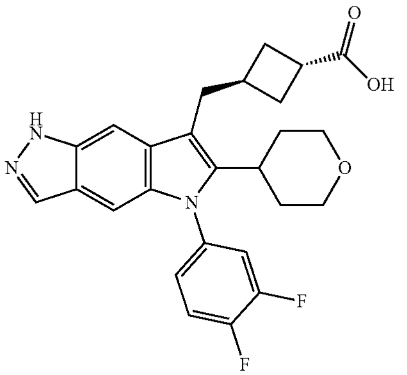
72
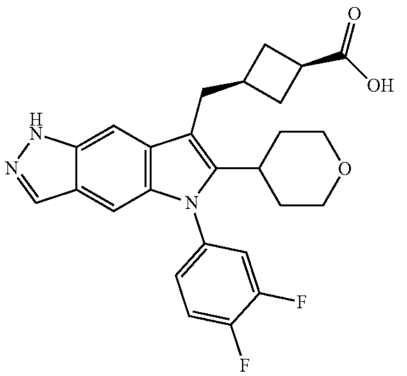
73
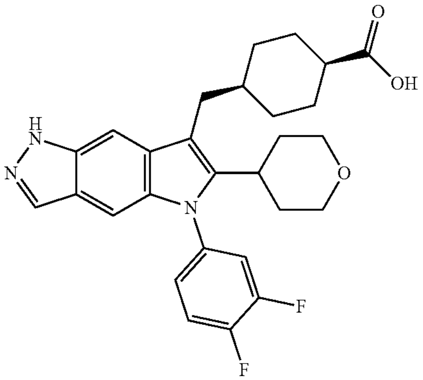
74
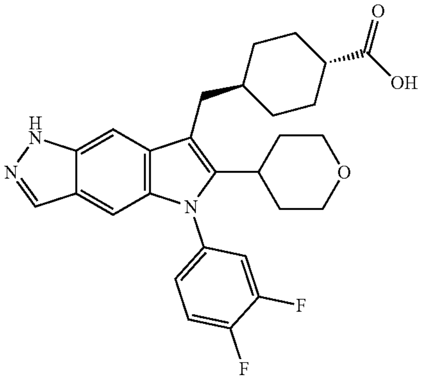

-continued
75
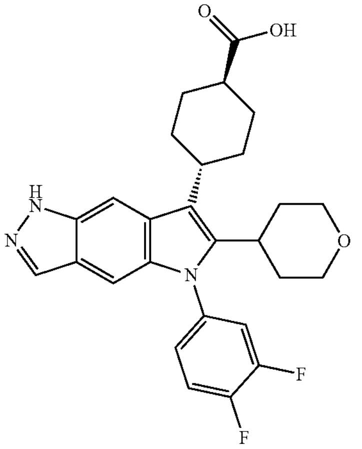
76
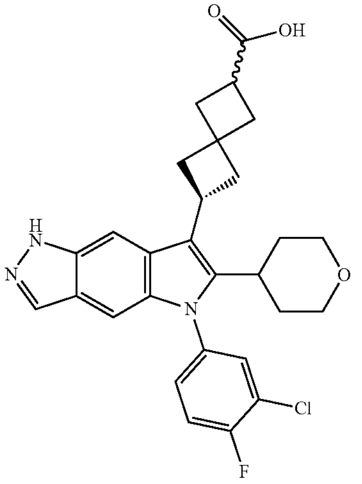
[RAC]
77
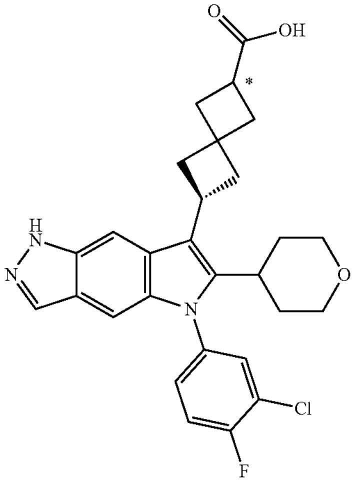
[ENANT-1]
78
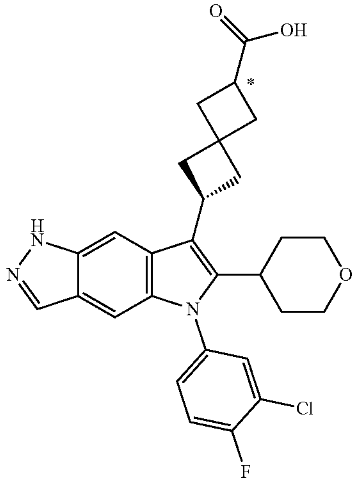
[ENANT-2]
79
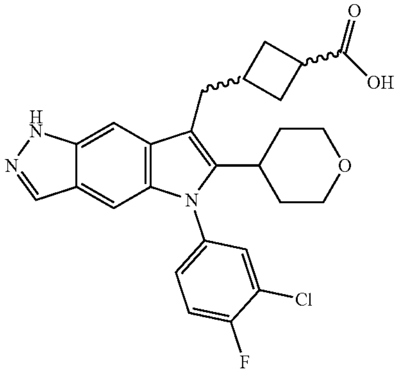
80
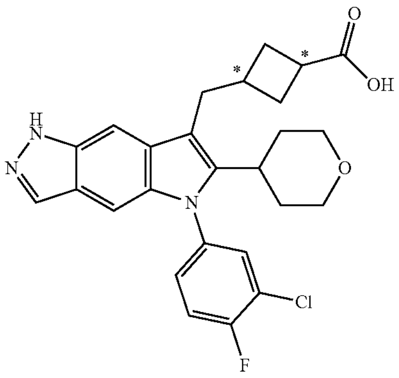
[Isomer-1]

-continued
81
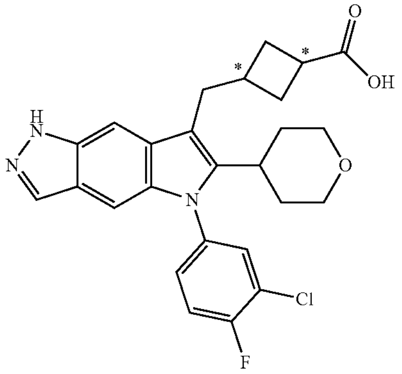
[Isomer-2]
82
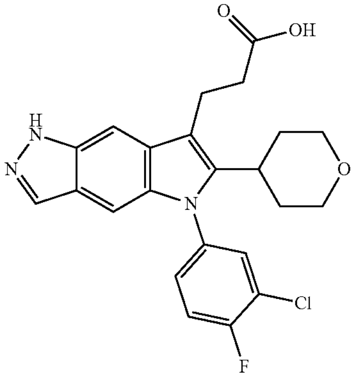
83
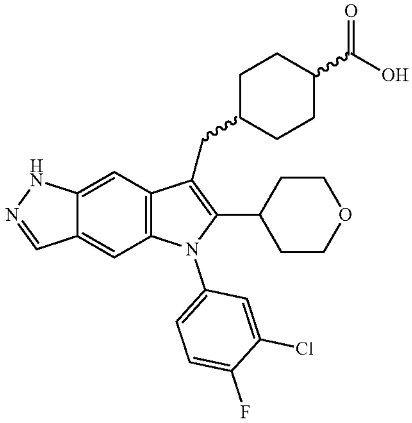
84
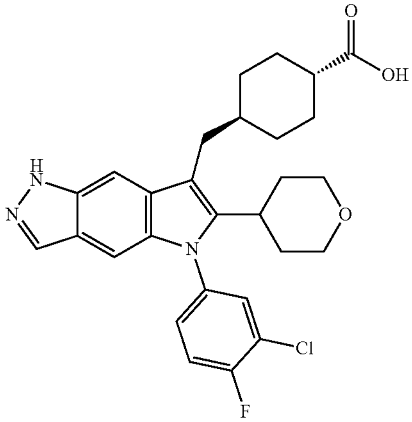
-continued
85
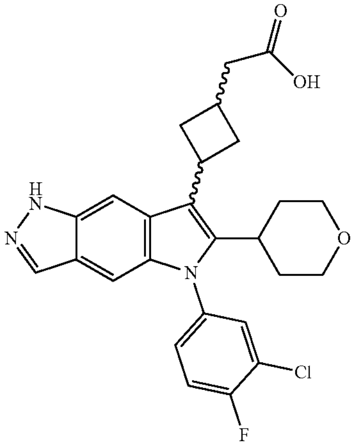
86
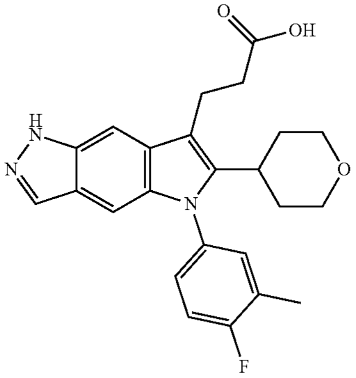
87
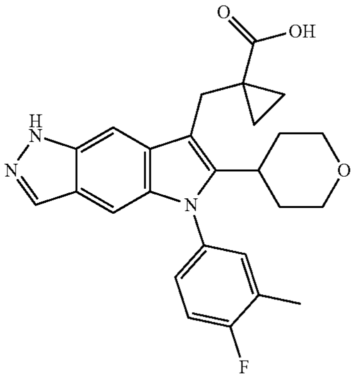
88
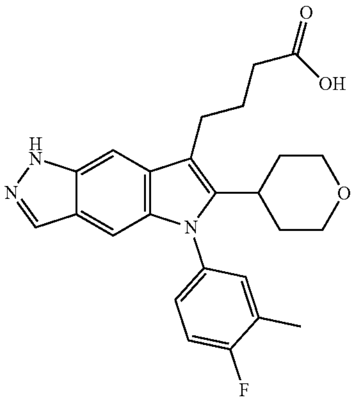

-continued
89
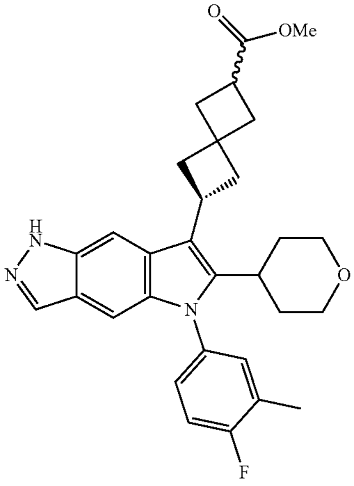
[RAC]
90
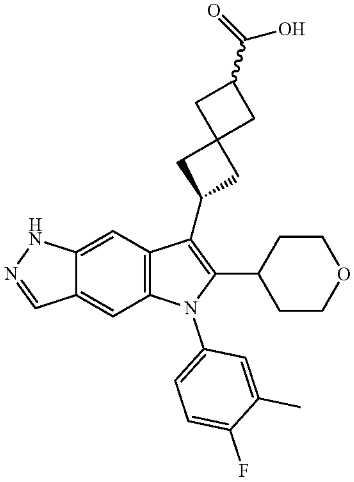
[RAC]
91
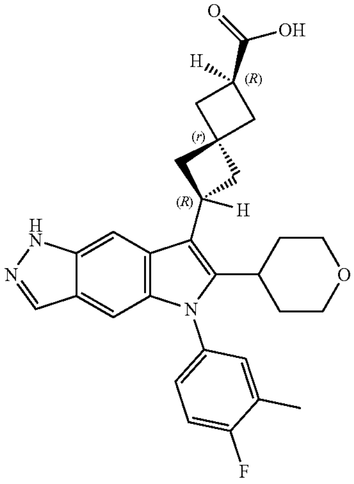
[ENANT-1]
-continued
92
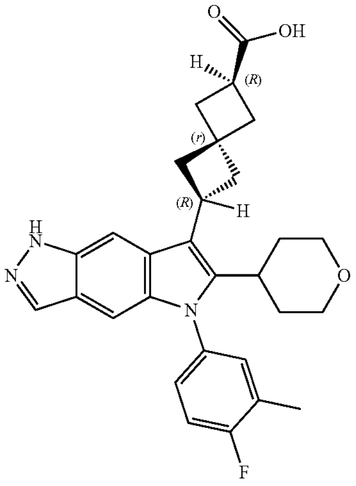
[ENANT-2]
93
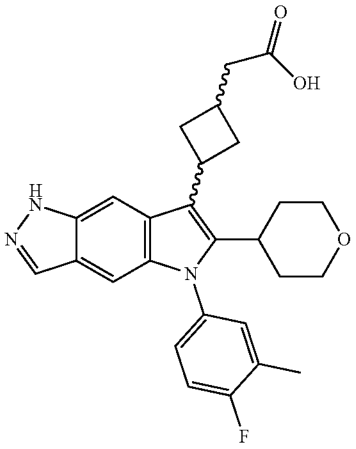
94
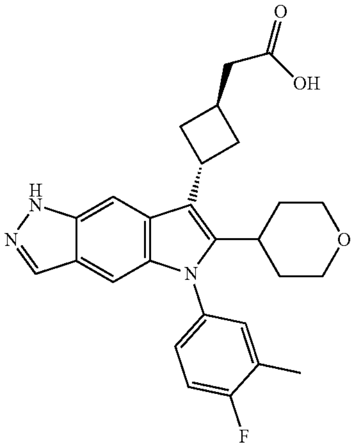

-continued
95
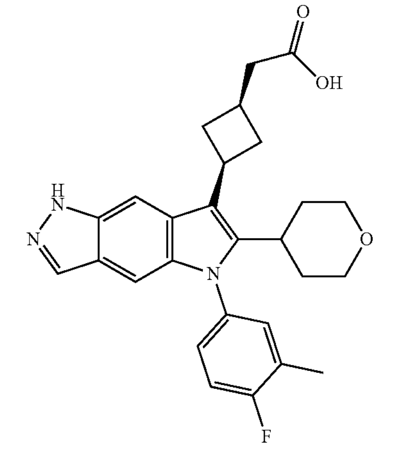
96
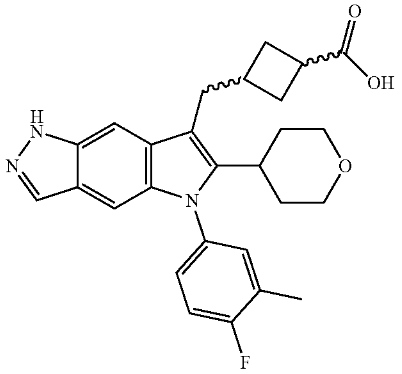
97
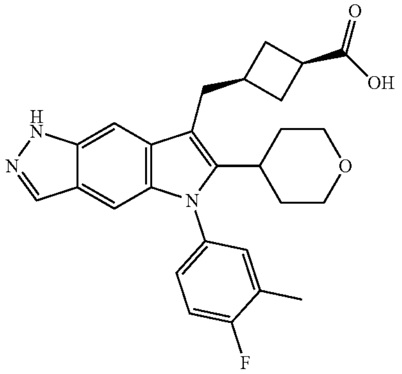
98
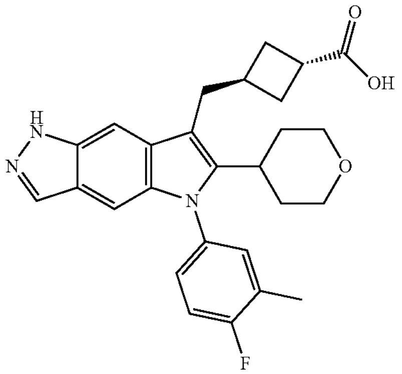
-continued
99
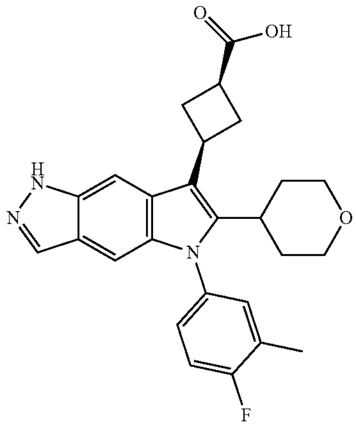
100
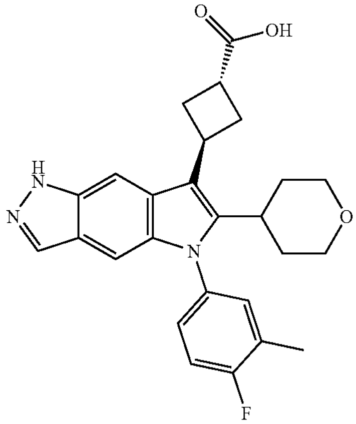
101
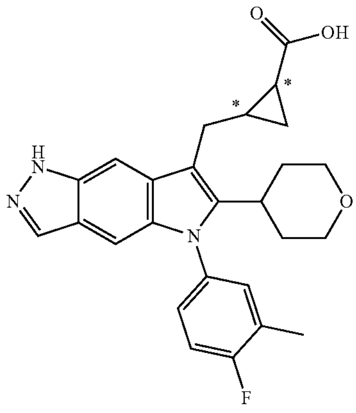
[TRANS-ENANT-1]

-continued
102
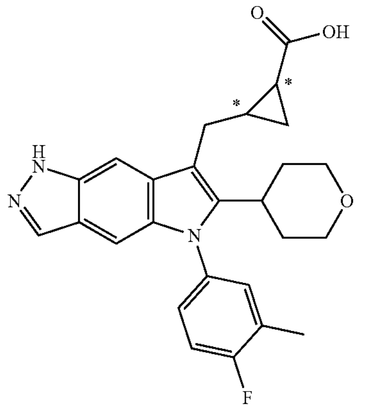
[TRANS-ENANT-2]
103
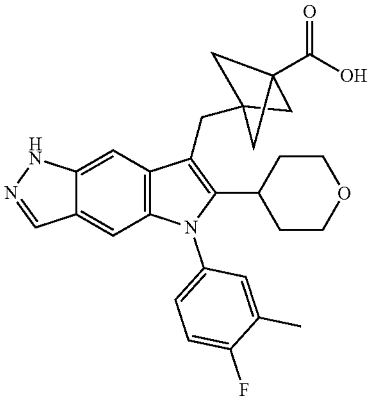
104
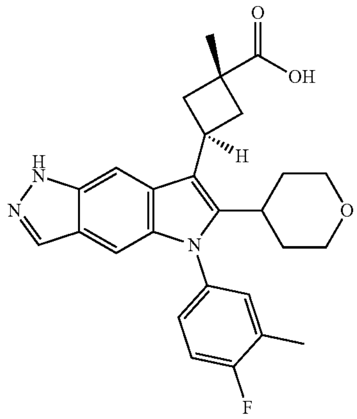
-continued
105
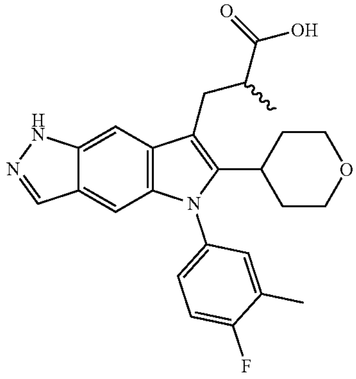
[Rac]
106
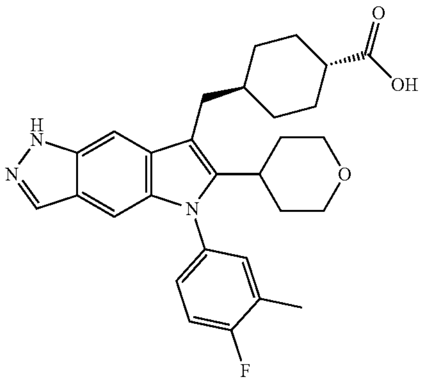
107
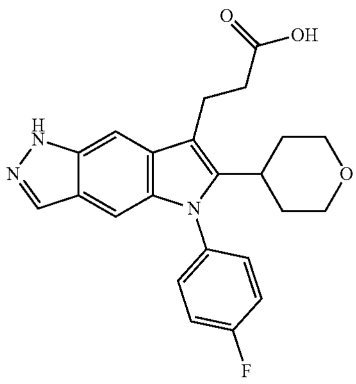

-continued
108
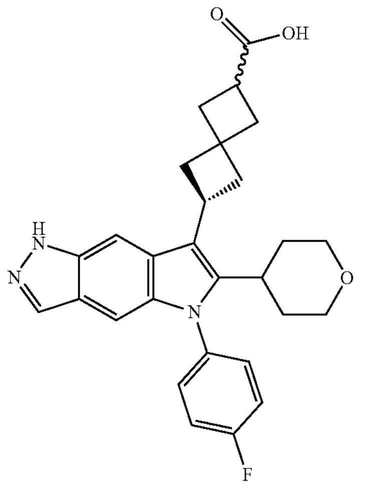
[RAC]
109
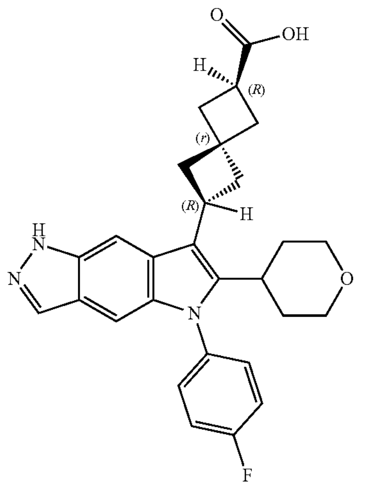
[ENANT-1]
110
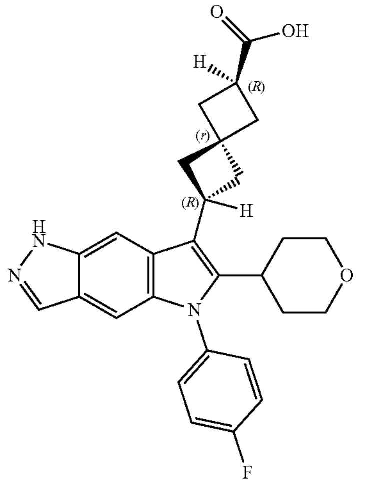
[ENANT-2]
-continued
111
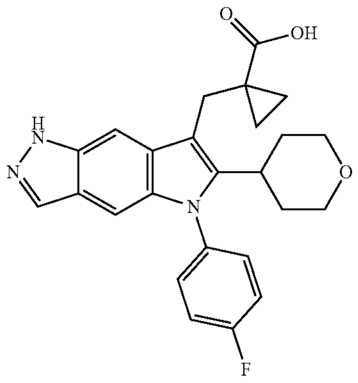
112
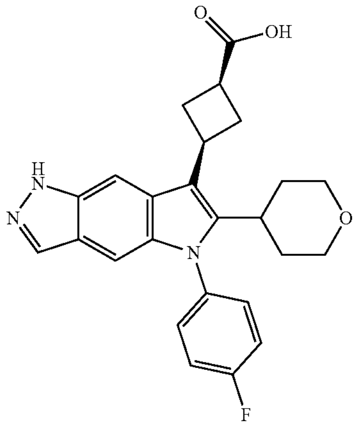
113
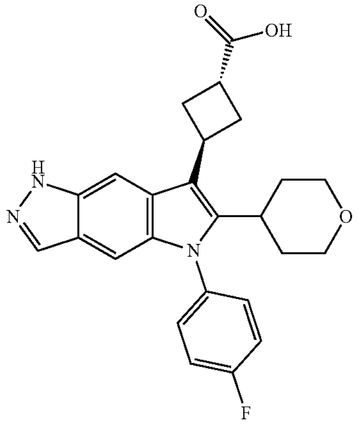

114
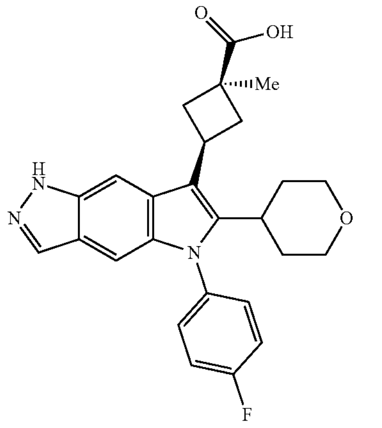
115
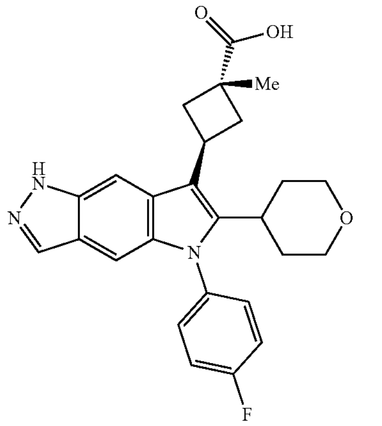
116
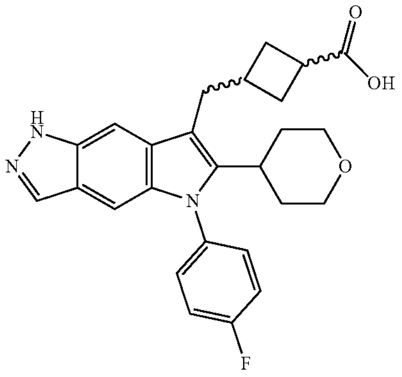
117
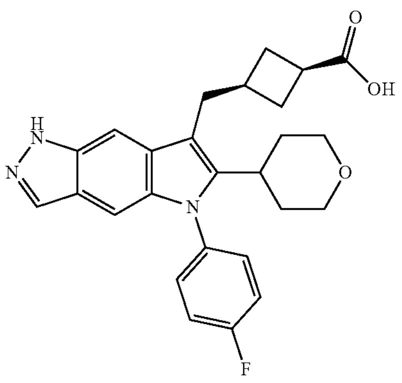
118
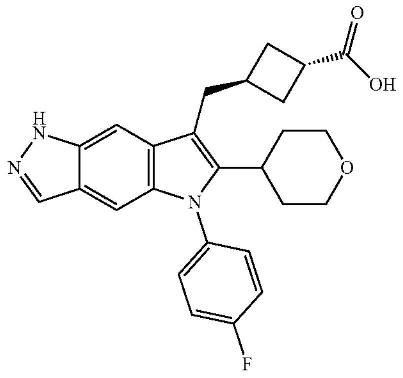
119
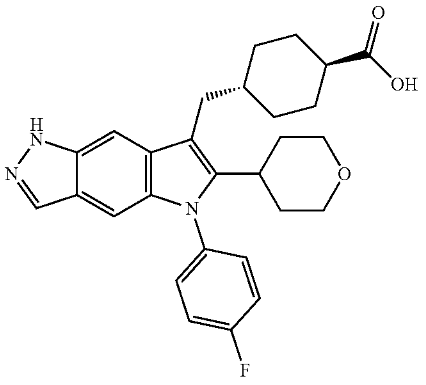
120
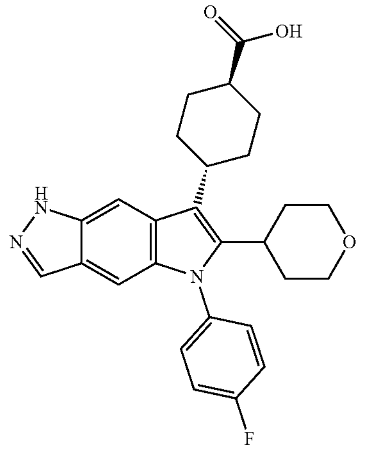
121
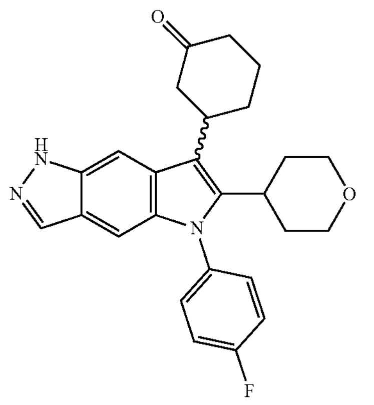
[RAC]

-continued
122
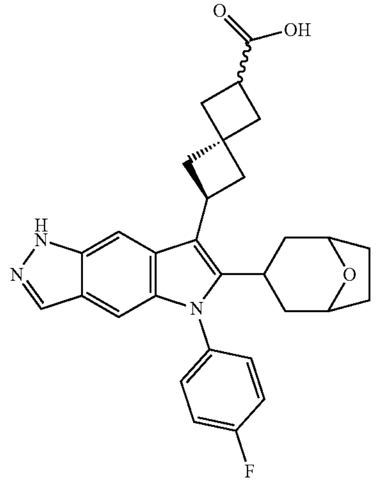
123
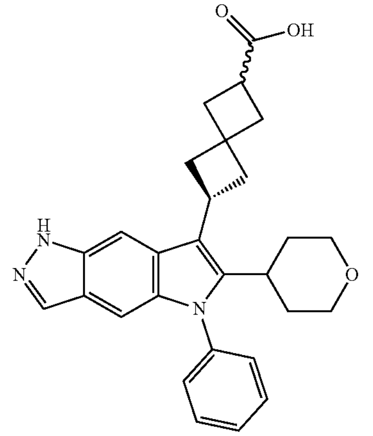
124
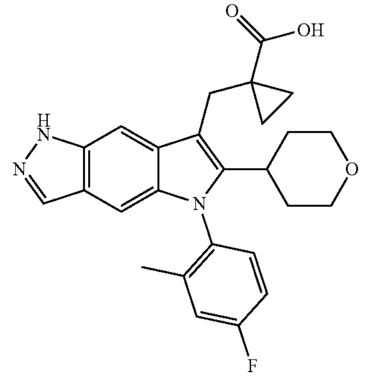
-continued
125
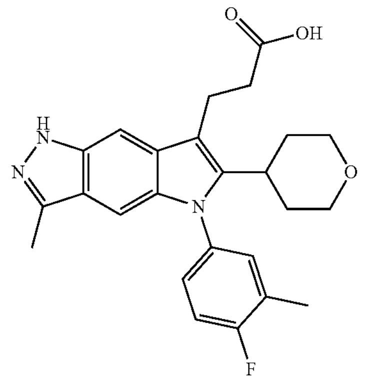
126
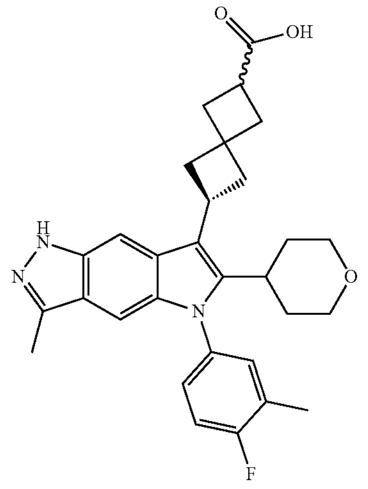
[Rac]
127
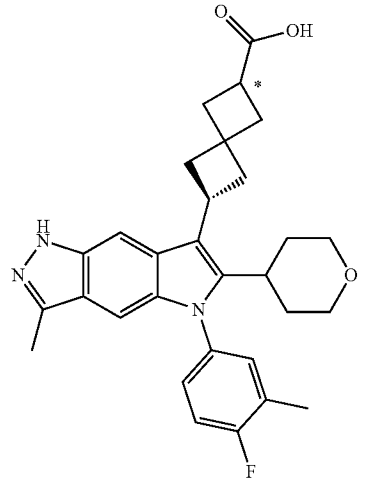
[ENANT-1]

-continued
128
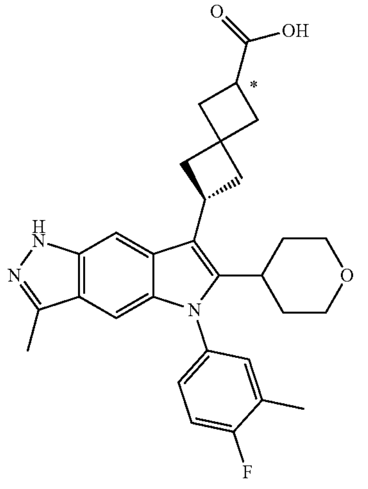
[ENANT-2]
129
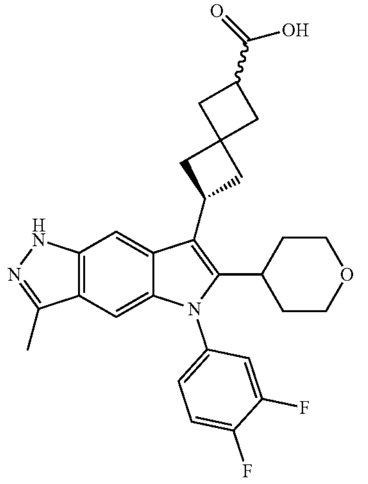
[RAC]
130
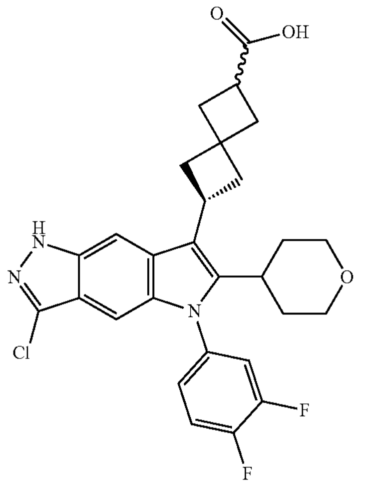
[RAC]
-continued
131
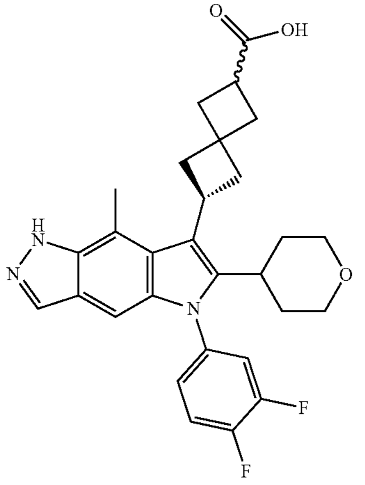
[RAC]
132
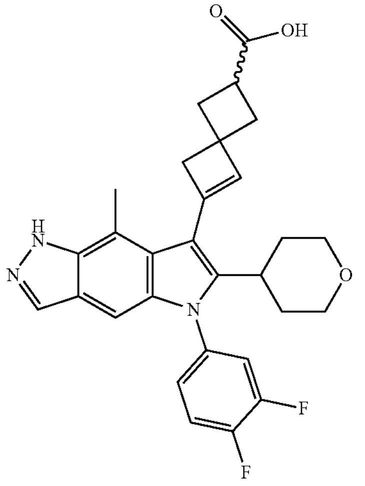
[RAC]
133
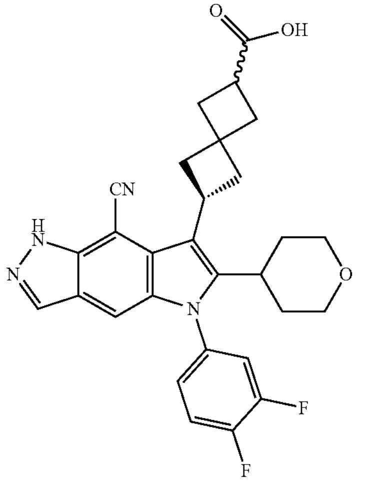
[RAC]

-continued
134
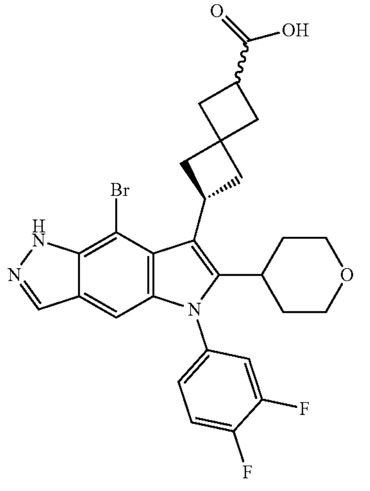
[RAC]
135
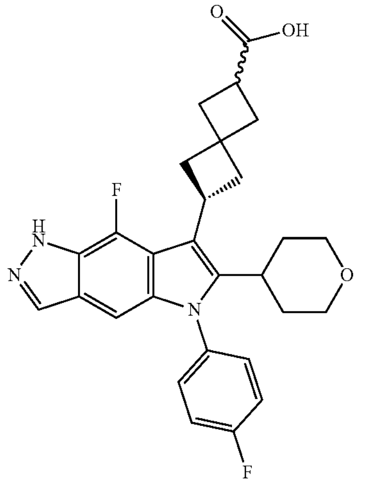
[RAC]
136
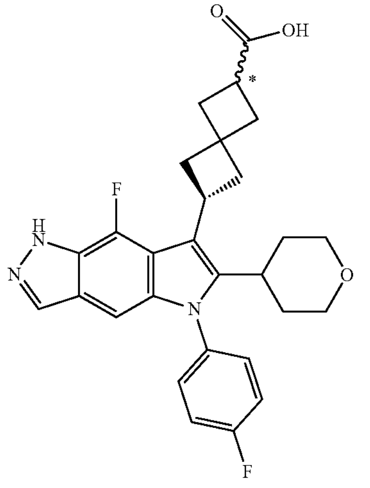
[ENANT-1]
-continued
137
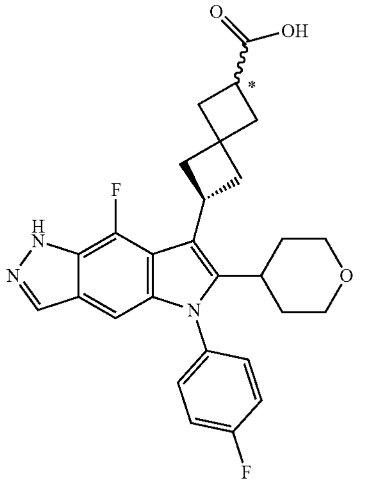
[ENANT-2]
138
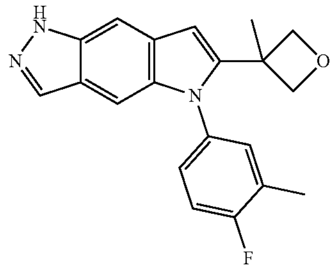
139
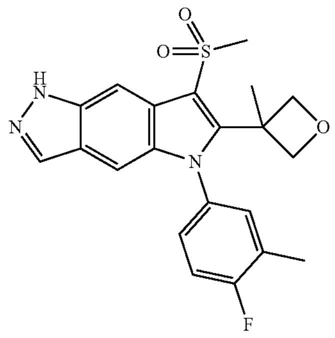
140
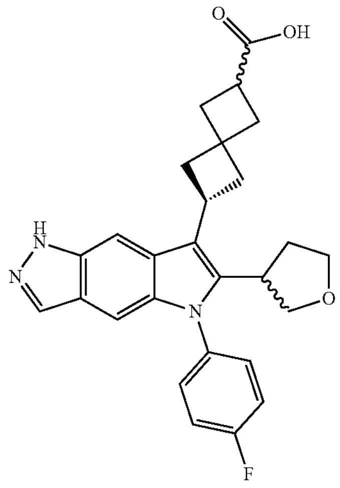

-continued
141
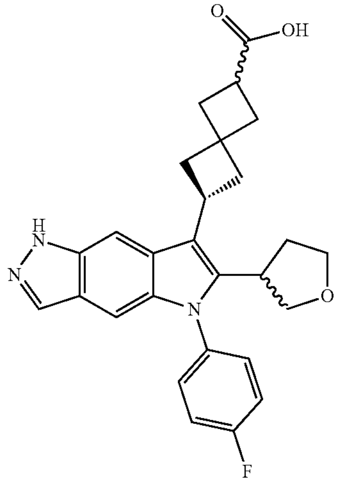
[DIAST MIX-1]
142
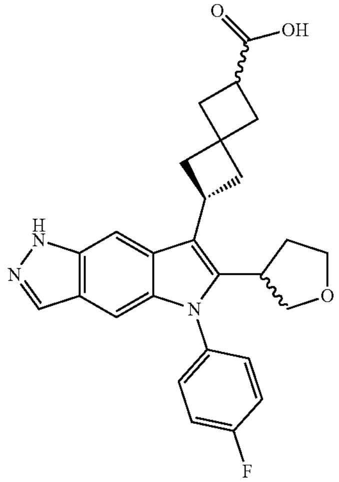
[DIAST MIX-1]
143
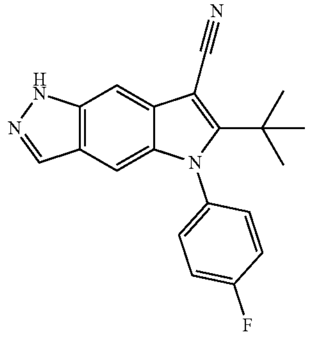
-continued
144
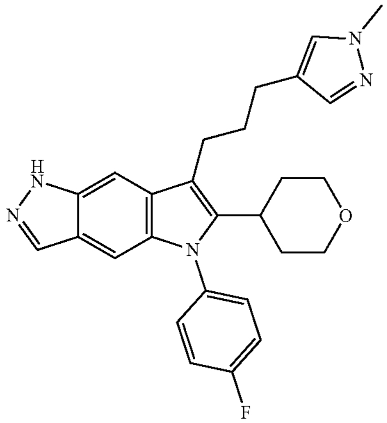
145
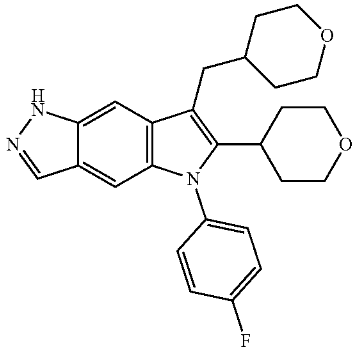
146
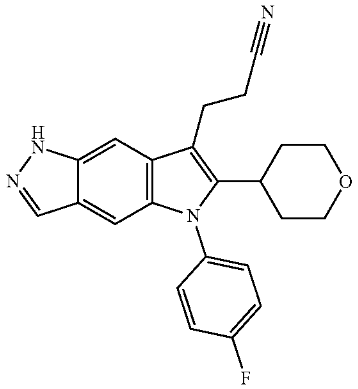
147
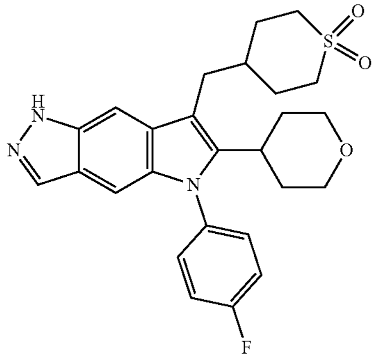

-continued
148
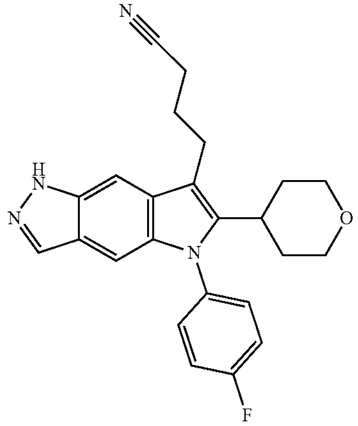
149
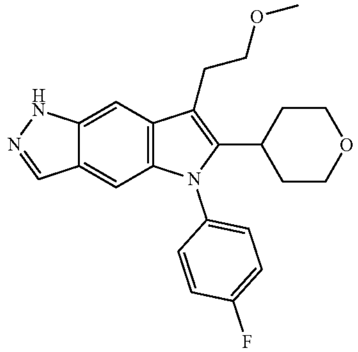
150
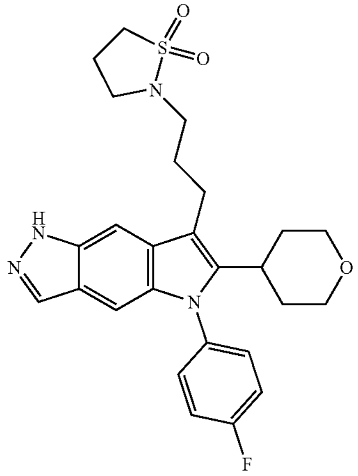
151
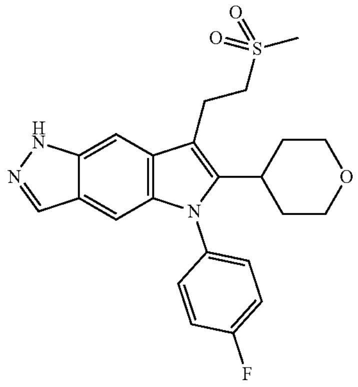
-continued
152
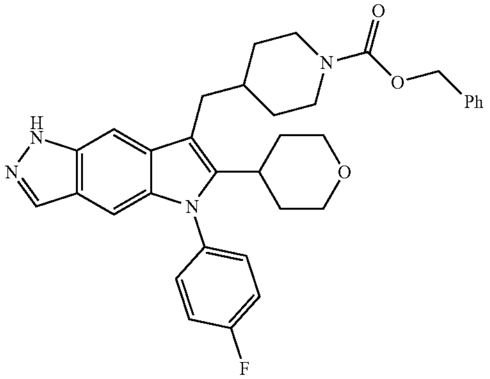
153
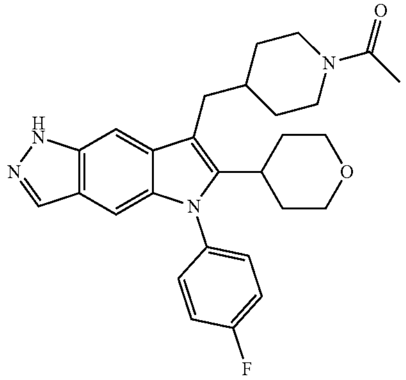
154
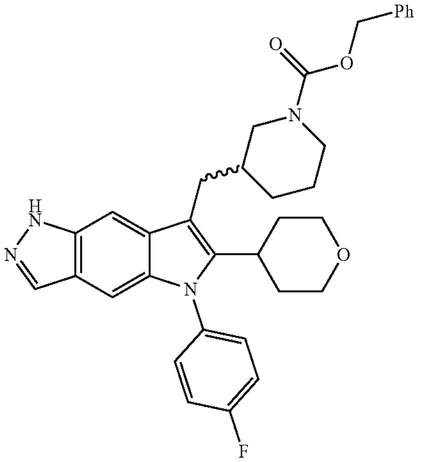

-continued
155
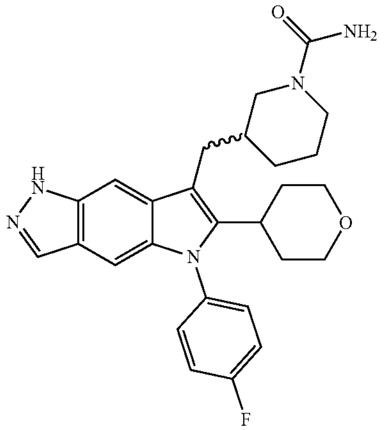
156
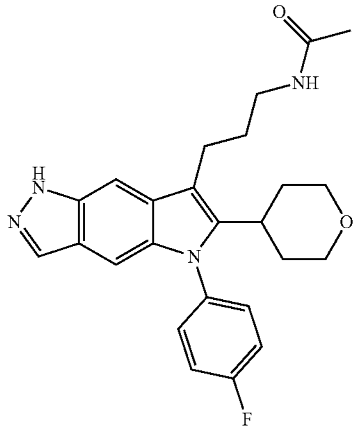
157
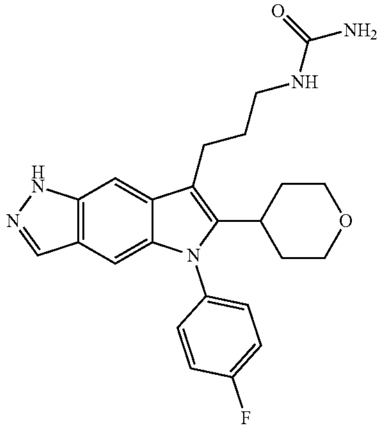
-continued
158
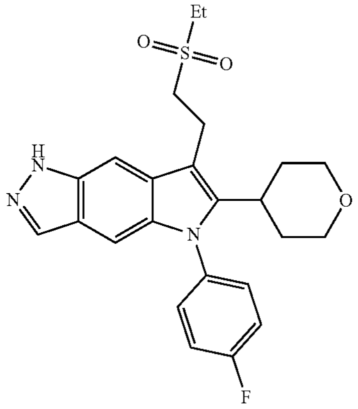
159
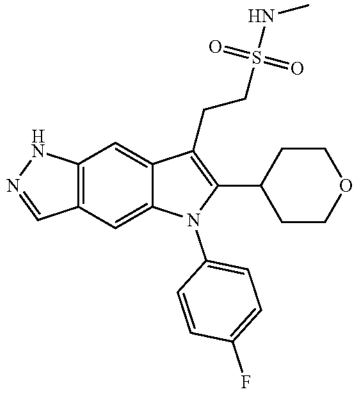
160
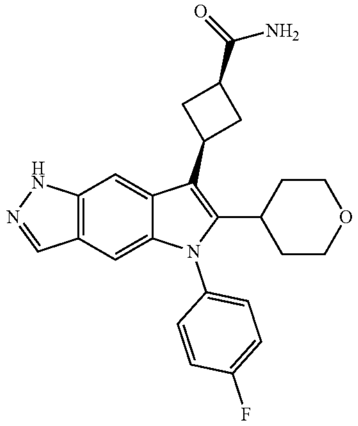
161
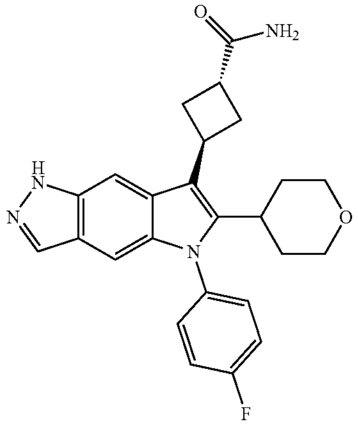

-continued
162
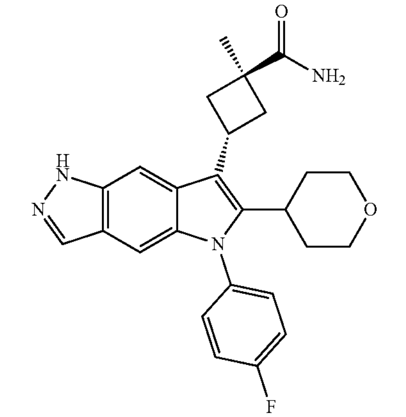
163
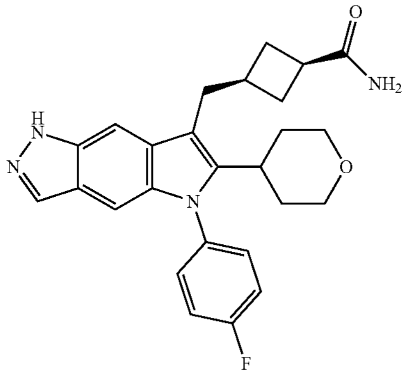
164
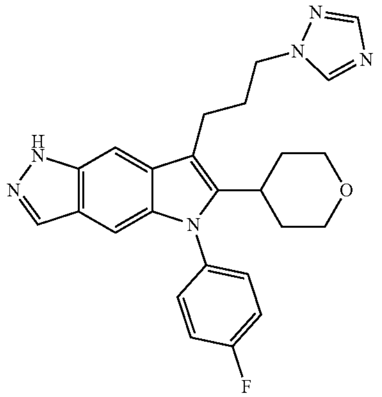
165
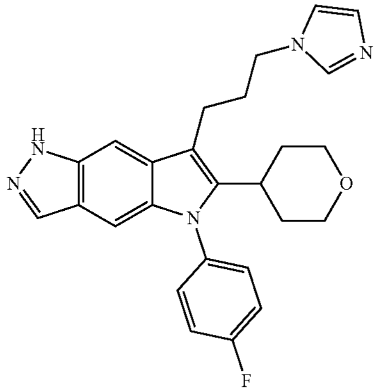
-continued
166
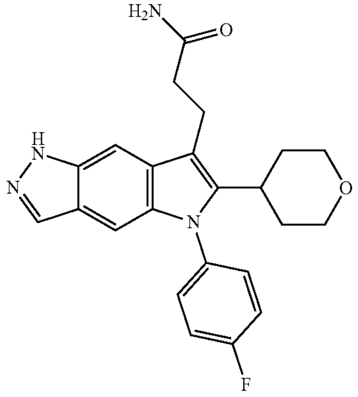
167
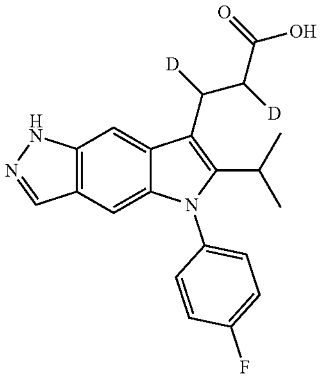
168
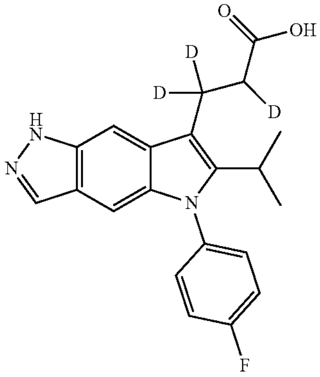
169
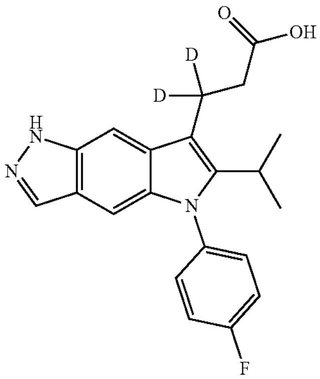

170
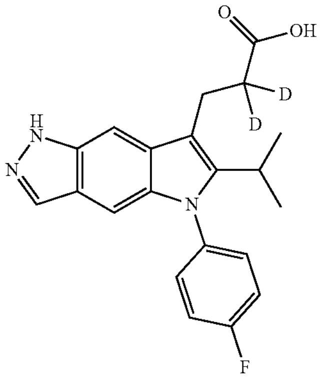
171
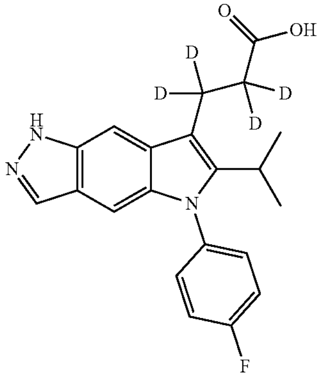
172
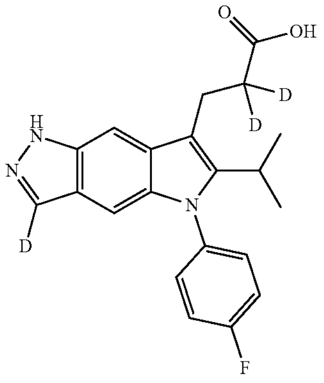
173
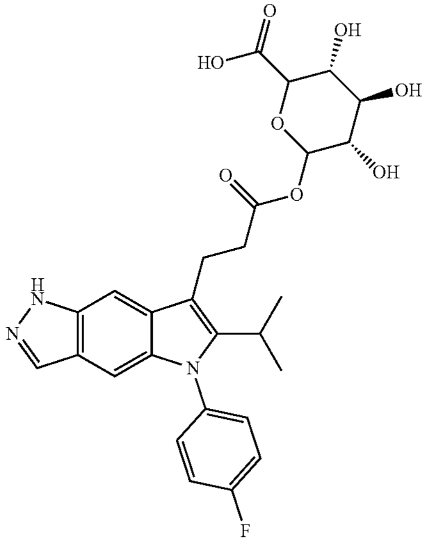
174
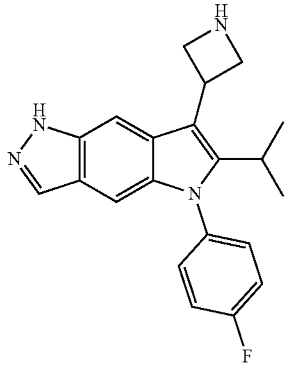
175
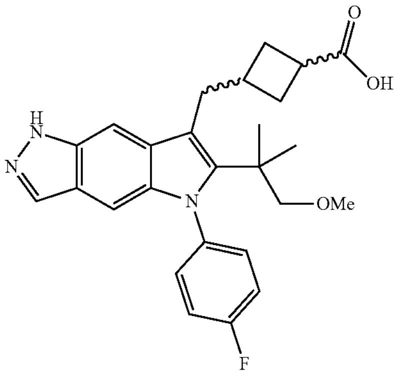

-continued
176
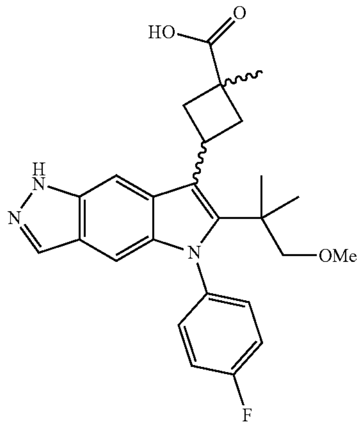
177
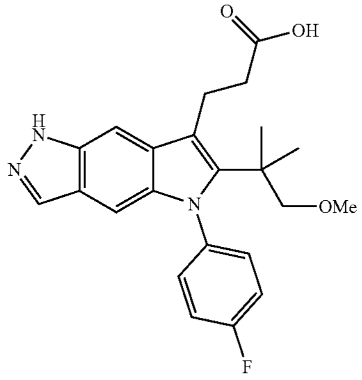
178
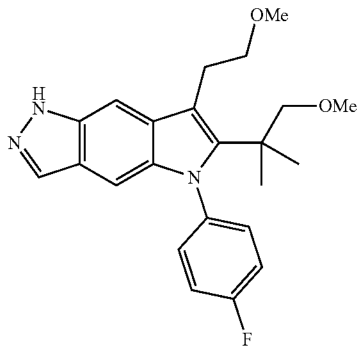
179
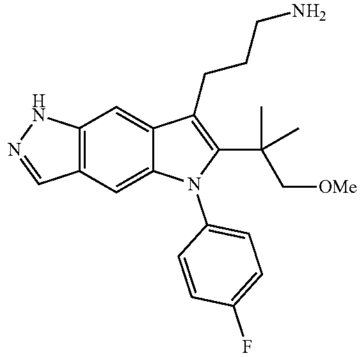
-continued
180
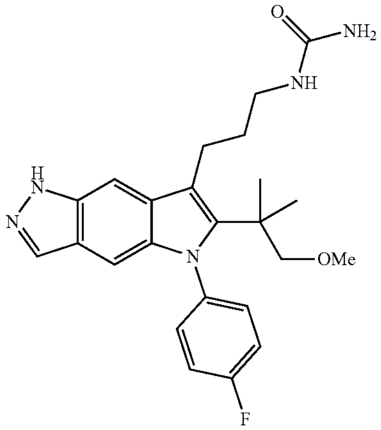
181
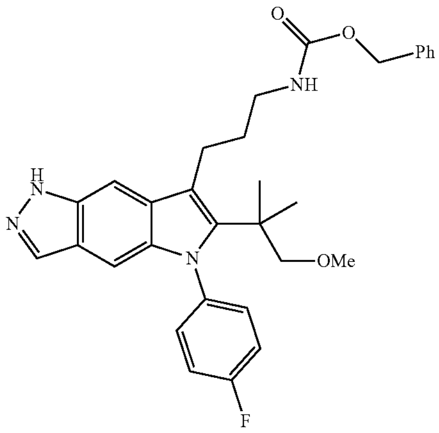
182
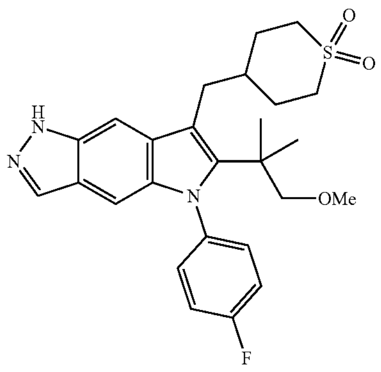
183
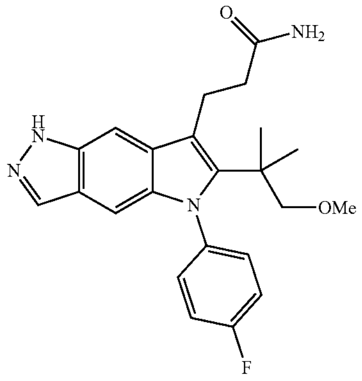

-continued
184
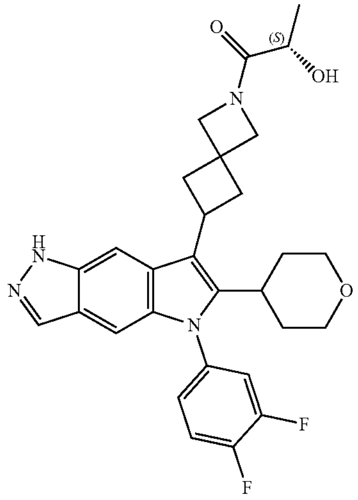
185
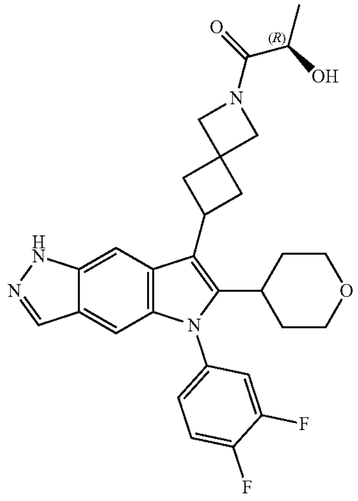
186
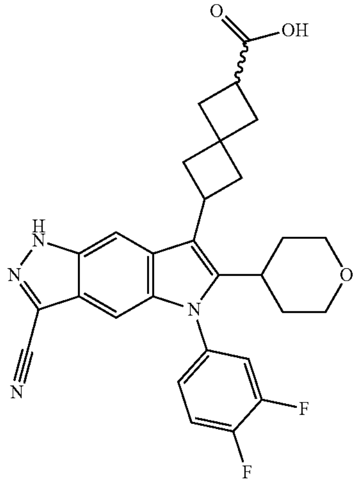
-continued
187
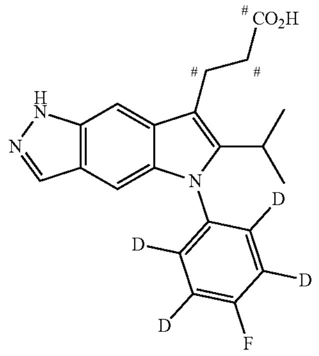
188
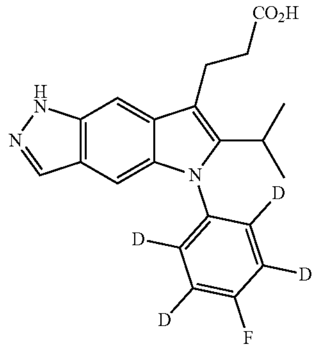
189
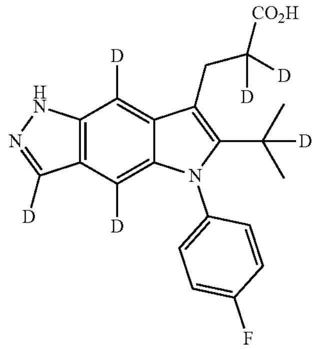
190
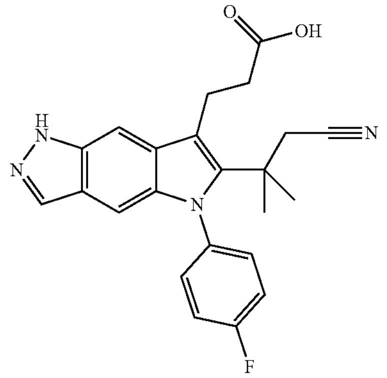

-continued
191
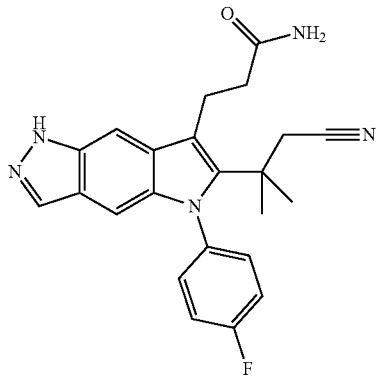
192
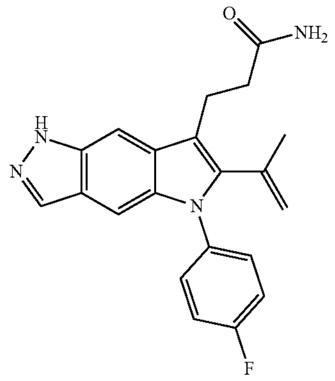
193
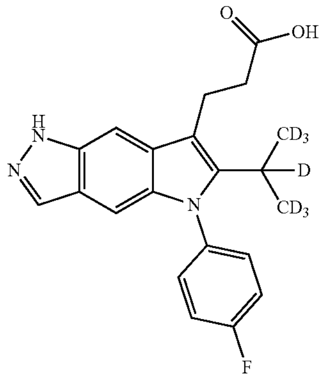
194
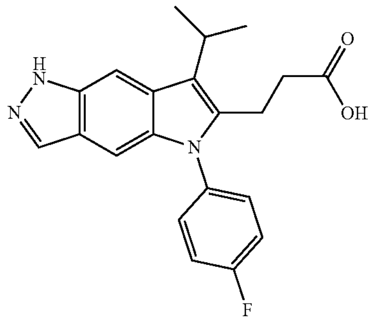
-continued
195
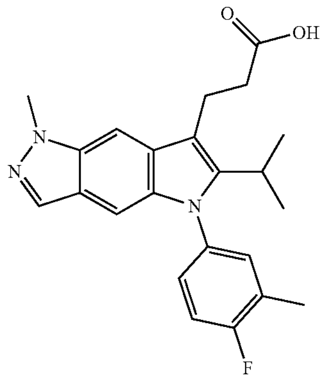
196
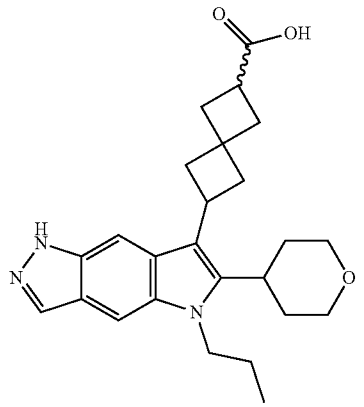
197
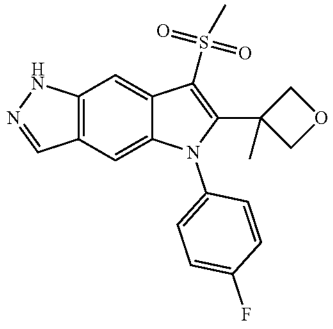
198
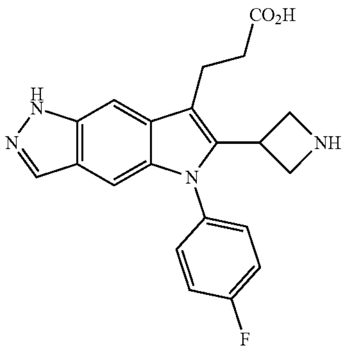

-continued
199
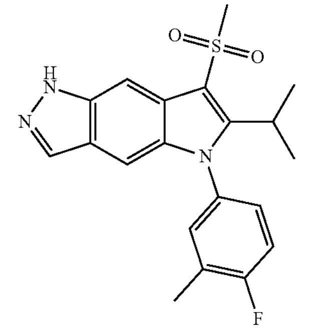
200
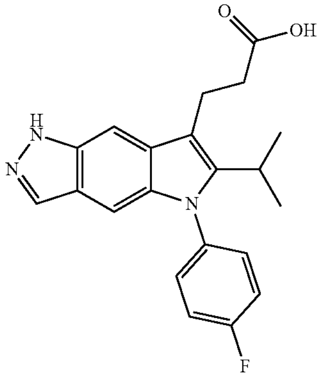
201
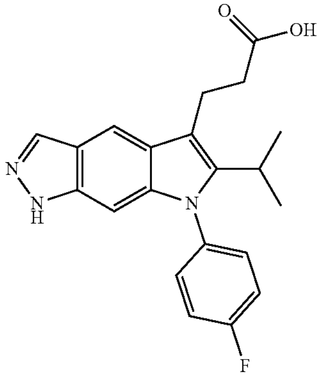
202
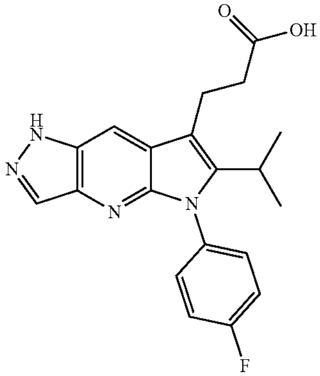
-continued
203
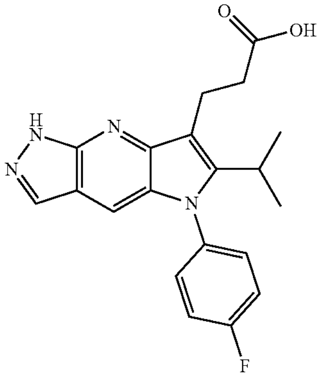
204
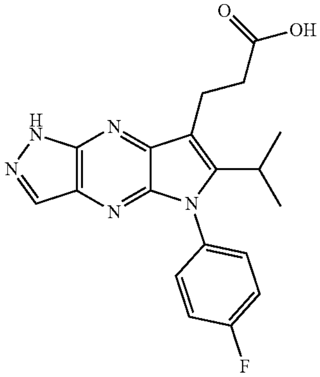
205
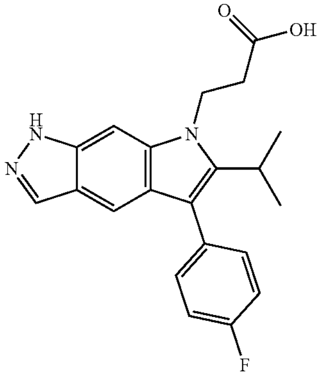
206
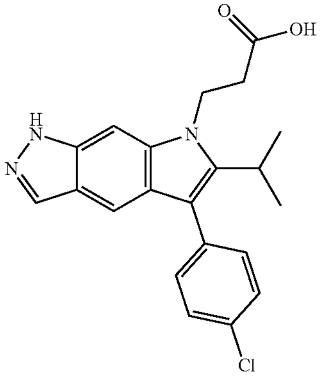

207
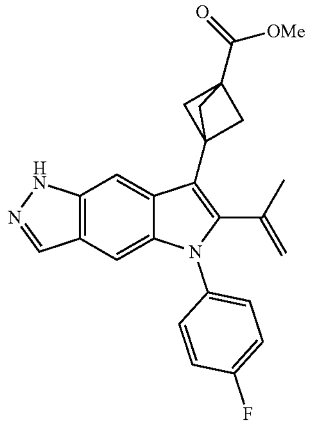
208
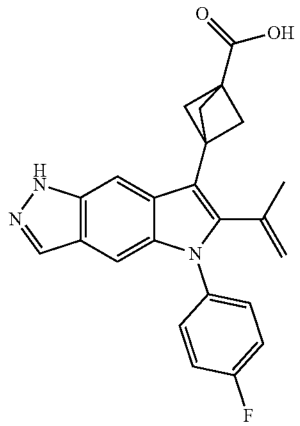
209
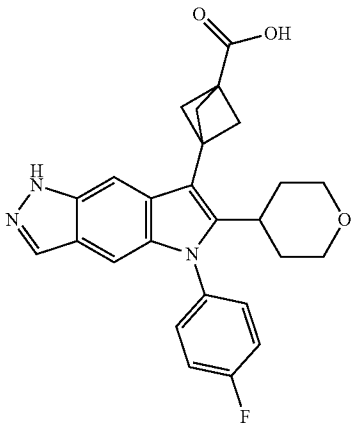
210
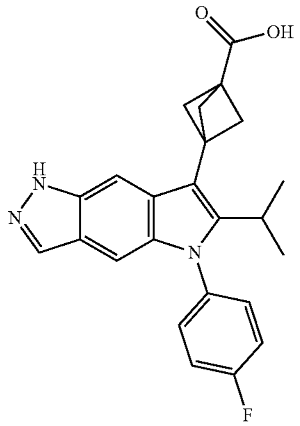
211
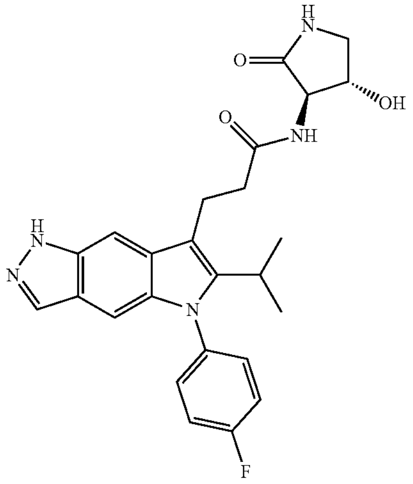
212
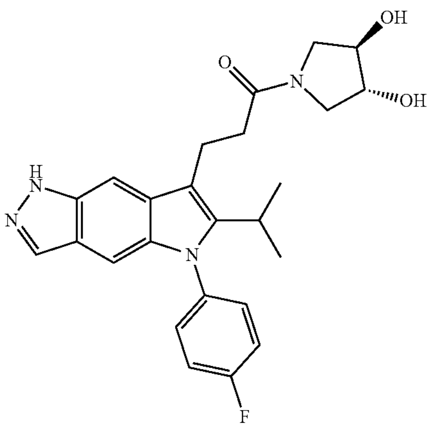

-continued

213

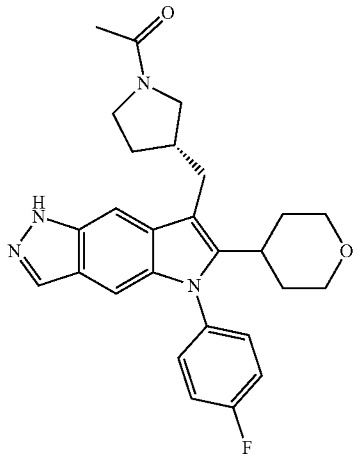

214

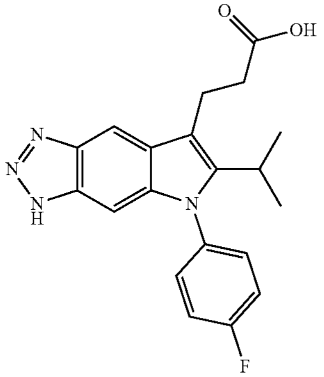

215

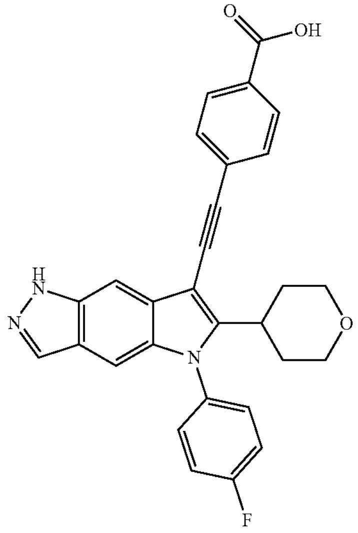

and tautomers thereof, pharmaceutically acceptable salts of the compounds and tautomers, and deuterated derivatives of the compounds, the tautomers, and the salts.

14. A compound of formula (II):

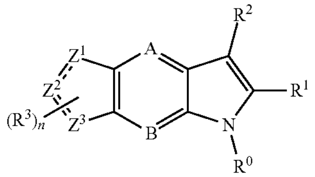

(II)

a tautomer thereof, a pharmaceutically acceptable salt of any of the foregoing, or a deuterated derivative of any of the foregoing;

wherein:

(i) A and B are each independently chosen from N and C—$X^1$ (ii) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy;

(iii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iv) $R^2$ is chosen from:

hydrogen, cyano, halogens, alkylamide groups, $C_1$-$C_8$ linear, branched, and cyclic alkyl groups optionally substituted with an oxo group, a $C_1$-$C_8$ linear, branched, and cyclic alkoxy group, a 5- or 6-membered heteroaryl group, a cyano group, an amino group, an aminoalkyl group,
an alkylamide group,
an alkylsulfonyl group,
an alkylsulfonamide group,
an alkylsulfoxide group,
a group

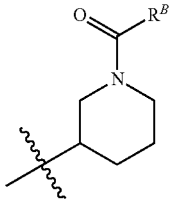

or

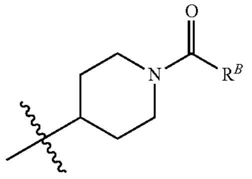

wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group, a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group.

a

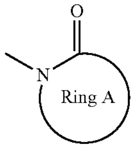

group wherein the Ring A is chosen from 4-8 membered rings optionally comprising one or two heteroatoms in addition to the Ring A nitrogen, and/or a carboxylic acid group esterified with a uronic acid, $C_2$-$C_6$ linear, branched, and cyclic alkenyl groups, $C_2$-$C_6$ linear, branched, and cyclic alkynyl groups, A-$CO_2R^4$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, A-$C(O)NH_2$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, $C(O)NR^6R^7$ wherein $R^6$ and $R^7$ are independently chosen from hydrogen, $C_1$-$C_8$ linear, branched, and cyclic alkyl groups, $C_2$-$C_6$ linear, branched, and cyclic alkenyl groups, 4- to 8-membered heterocycles optionally substituted by one or more substituents chosen from cyano, halogens, $C_1$-$C_8$ linear, branched, and cyclic alkyl groups, and $C_2$-$C_6$ linear, branched, and cyclic alkenyl groups, or $R^6$ and $R^7$ together with the nitrogen to which they are attached form a 4-8 membered ring optionally comprising one or two heteroatoms in addition to the nitrogen to which they are attached, and which ring is optionally substituted with a substituent chosen from halogens, cyano, hydroxy, and $C_1$-$C_6$ linear, branched, and cyclic alkyl groups, $SO_2R^5$ groups wherein $R^5$ is chosen from $C_1$-$C_8$ linear, branched, and cyclic alkyl groups, and $C_2$-$C_6$ linear, branched, and cyclic alkenyl groups, and

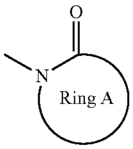

groups wherein the Ring A is a 4-8 membered ring optionally comprising one or two heteroatoms in addition to the Ring A nitrogen;

(v) $X^1$ is chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(vi) each ═══ represents a single or double bond, provided that no more than one ═══ is a double bond;

(vii) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 halogens;

(viii) n is an integer chosen from 0, 1, 2, and 3; and (ix) $Z^1$, $Z^2$, and $Z^3$ are independently chosen from carbon, nitrogen, sulfur, and oxygen, wherein when $Z^1$, $Z^2$, and/or $Z^3$ are carbon or nitrogen, the valences of carbon and nitrogen are completed with hydrogen atoms, $C_1$-$C_8$ linear, branched, and cyclic alkyls, or cyano.

15. The compound of embodiment 14, a tautomer thereof, a pharmaceutically acceptable salt of the compound or the tautomer, or a deuterated derivative of the compound, the tautomer, or the salt, wherein (i) $R^0$ is chosen from 5- to 10-membered aromatic rings optionally substituted with 1-4 $R^A$, wherein each $R^A$ is independently chosen from halogens;

(ii) $R^1$ is chosen from $C_1$-$C_8$ linear, branched, and cyclic alkyl groups;

(iii) $R^2$ is chosen from A-$CO_2R^4$ groups wherein A is chosen from $C_1$-$C_8$ linear, branched, and cyclic alkyl groups, and wherein $R^4$ is chosen from hydrogen and $C_1$-$C_8$ linear, branched, and cyclic alkyl groups;

(iv) $X^1$ is hydrogen; and (v) $Z^1$, $Z^2$, and $Z^3$ are independently chosen from carbon and nitrogen, and the valences of said carbon and said nitrogen are completed with hydrogen atoms.

16. A compound of formula (III):

(III)

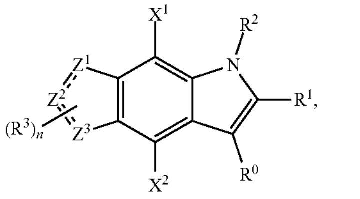

a tautomer thereof, a pharmaceutically acceptable salt of any of the foregoing, or a deuterated derivative of any of the foregoing;

wherein:

(i) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy;

(ii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iii) $R^2$ is chosen from:

hydrogen, cyano, halogens, alkylamide groups, $C_1$-$C_8$ linear, branched, and cyclic alkyl groups optionally substituted with an oxo group, a $C_1$-$C_8$ linear, branched, and cyclic alkoxy group, a 5- or 6-membered heteroaryl group, a cyano group, an amino group, an aminoalkyl group, an alkylamide group, an alkylsulfonyl group, an alkylsulfonamide group, an alkylsulfoxide group, a group

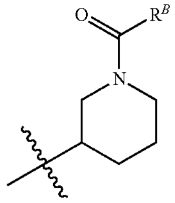

or

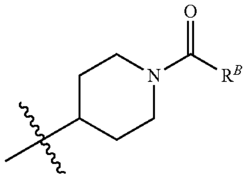

wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group, a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group.

a

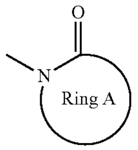

group wherein the Ring A is chosen from 4-8 membered rings optionally comprising one or two heteroatoms in addition to the Ring A nitrogen, and/or a carboxylic acid group esterified with a uronic acid, $C_2$-$C_6$ linear, branched, and cyclic alkenyl groups,
$C_2$-$C_6$ linear, branched, and cyclic alkynyl groups,
A-$CO_2R^4$ groups wherein A is optionally present and if present is chosen from
$C_1$-$C_8$ linear, branched, and cyclic alkyl and alkoxy groups,
$C_2$-$C_6$ linear, branched, and cyclic alkenyl groups,
$C_3$-$C_8$ cycloalkyl linked to $C_1$-$C_8$ linear or branched alkyl groups,
$C_1$-$C_8$ linear or branched alkyl linked to $C_3$-$C_8$ cycloalkyl groups,
$C_3$-$C_8$ cycloalkyl linked to $C_3$-$C_8$ cycloalkyl groups,
$C_1$-$C_8$ linear, branched, and cyclic alkyl linked to $C_3$-$C_8$ cycloalkyl linked to
a $C_1$-$C_8$ linear, branched, and cyclic alkyl groups,
wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and
wherein $R^4$ is chosen from hydrogen, $C_1$-$C_8$ linear, branched, and cyclic alkyl groups, and $C_2$-$C_6$ linear, branched, and cyclic alkenyl groups,
A-C(O)$NH_2$ groups wherein A is optionally present and if present is chosen from
$C_1$-$C_8$ linear, branched, and cyclic alkyl and alkoxy groups,
$C_2$-$C_6$ linear, branched, and cyclic alkenyl groups,
$C_3$-$C_8$ cycloalkyl linked to $C_1$-$C_8$ linear or branched alkyl groups,
$C_1$-$C_8$ linear or branched alkyl linked to $C_3$-$C_8$ cycloalkyl groups,
$C_3$-$C_8$ cycloalkyl linked to $C_3$-$C_8$ cycloalkyl groups,
$C_1$-$C_8$ linear, branched, and cyclic alkyl linked to $C_3$-$C_8$ cycloalkyl linked to
a $C_1$-$C_8$ linear, branched, and cyclic alkyl groups,
wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and
wherein $R^4$ is chosen from hydrogen, $C_1$-$C_8$ linear, branched, and cyclic alkyl groups, and $C_2$-$C_6$ linear, branched, and cyclic alkenyl groups,
C(O)$NR^6R^7$ wherein $R^6$ and $R^7$ are independently chosen from
hydrogen,
$C_1$-$C_8$ linear, branched, and cyclic alkyl groups,
$C_2$-$C_6$ linear, branched, and cyclic alkenyl groups,
4- to 8-membered heterocycles optionally substituted by one or more
substituents chosen from cyano, halogens,
$C_1$-$C_8$ linear, branched, and cyclic alkyl groups, and
$C_2$-$C_6$ linear, branched, and cyclic alkenyl groups,
or $R^6$ and $R^7$ together with the nitrogen to which they are attached form a 4-8 membered ring optionally comprising one or two heteroatoms in addition to the nitrogen to which they are attached, and which ring is optionally substituted with a substituent chosen from halogens, cyano, hydroxy, and $C_1$-$C_6$ linear, branched, and cyclic alkyl groups,
$SO_2R^5$ groups wherein $R^5$ is chosen from $C_1$-$C_8$ linear, branched, and cyclic alkyl groups, and $C_2$-$C_6$ linear, branched, and cyclic alkenyl groups, and

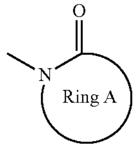

groups wherein the Ring A is a 4-8 membered ring optionally comprising one or two heteroatoms in addition to the Ring A nitrogen;

(iv) $X^1$ and $X^2$ are independently chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(v) each ═══ represents a single or double bond, provided that no more than one ═══ is a double bond;

(vi) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 halogens;

(vii) n is an integer chosen from 0, 1, 2, and 3; and (viii) $Z^1$, $Z^2$, and $Z^3$ are independently chosen from carbon, nitrogen, sulfur, and oxygen, wherein when $Z^1$, $Z^2$, and/or $Z^3$ are carbon or nitrogen, the valences of carbon and nitrogen are completed with hydrogen atoms, $C_1$-$C_8$ linear, branched, and cyclic alkyls, or cyano.

17. The compound of embodiment 16, a tautomer thereof, a pharmaceutically acceptable salt of the compound or the tautomer, or a deuterated derivative of the compound, the tautomer, or the salt, wherein (i) $R^0$ is chosen from 5- to 10-membered aromatic rings optionally substituted with 1-4 $R^A$, wherein each $R^A$ is independently chosen from halogens;

(ii) $R^1$ is chosen from $C_1$-$C_8$ linear, branched, and cyclic alkyl groups;

(iii) $R^2$ is chosen from A-$CO_2R^4$ groups wherein A is chosen from $C_1$-$C_8$ linear, branched, and cyclic alkyl groups, and wherein $R^4$ is chosen from hydrogen and $C_1$-$C_8$ linear, branched, and cyclic alkyl groups;

(iv) $X^1$ is hydrogen; and (v) $Z^1$, $Z^2$, and $Z^3$ are independently chosen from carbon and nitrogen, and the valences of said carbon and said nitrogen are completed with hydrogen atoms.

18. A compound of formula S3

S3

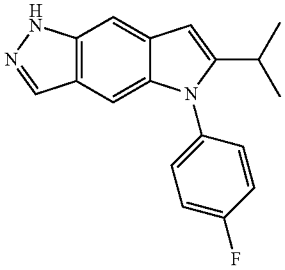

a tautomer thereof, a salt of any of the foregoing, or a deuterated derivative of any of the foregoing.

19. A compound of formula S6

S6

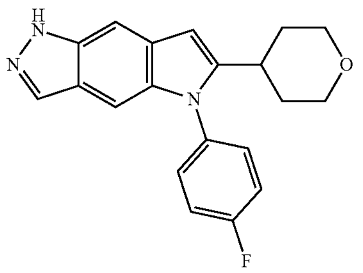

a tautomer thereof, a salt of any of the foregoing, or a deuterated derivative of any of the foregoing.

20. A compound of formula 32:

(Compound 32)

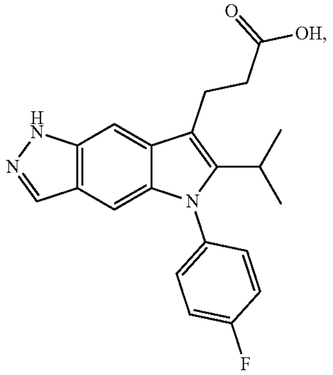

a tautomer thereof, a pharmaceutically acceptable salt of any of the foregoing, or a deuterated derivative of any of the foregoing.

21. A composition comprising at least one compound chosen from the compounds according to any one of embodiments 1-17 and 20, tautomers thereof, pharmaceutically acceptable salts of any of the foregoing, and deuterated derivatives of any of the foregoing.

22. Crystalline Form A of Compound 32:

(32)

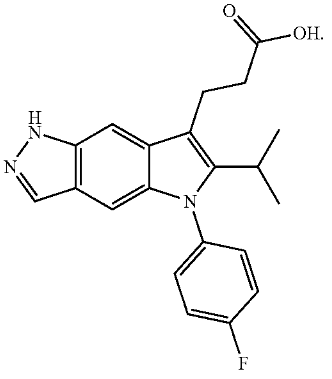

23. Crystalline Form A according to embodiment 22 in substantially pure form.

24. Crystalline Form A according to embodiment 22, characterized by an X-ray powder diffractogram substantially similar to that in FIG. 7.

25. Crystalline Form A according to embodiment 22, characterized by an X-ray powder diffractogram having a signal at at least two two-theta values chosen from 15.0±0.2, 15.4±0.2, 17.6±0.2, and 20.4±0.2.

26. Crystalline Form A according to embodiment 22, characterized by an X-ray powder diffractogram having a signal at at least three two-theta values chosen from 10.9±0.2, 15.0±0.2, 15.4±0.2, 17.6±0.2, 18.1±0.2, 18.6±0.2, and 20.4±0.2.

27. Crystalline Form A according to embodiment 22 having a single crystal unit cell characterized as follows:

| Crystal System<br>Space Group | Monoclinic<br>$P2_1/c$ |
|---|---|
| a (Å) | 9.3 ± 0.1 |
| b (Å) | 22.8 ± 0.1 |
| c (Å) | 8.6 ± 0.1 |
| α (°) | 90 ± 0.1 |
| β (°) | 94.7 ± 0.1 |
| γ (°) | 90 ± 0.1 |
| V ($Å^3$) | 1813.5 ± 0.2 |
| Z/Z' | 4/1 |

28. A composition comprising Crystalline Form A of Compound 32:

(32)

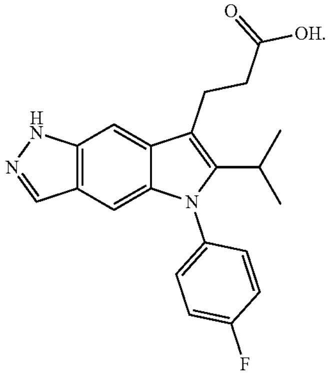

29. A composition comprising Compound 32:

(32)

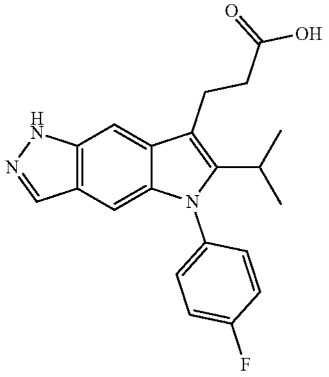

in substantially pure Crystalline Form A.

30. A composition comprising at least one active compound consisting essentially of Compound 32 in Crystalline Form A.

31. Crystalline Form A according to embodiment 22, characterized by a $^{13}C$ NMR spectrum having a signal at at least three ppm values chosen from 137.1±0.2, 131.4±0.2, 121.7±0.2, 107.6±0.2, and 98.8±0.2 ppm.

32. Crystalline Form A according to embodiment 22, characterized by a $^{19}F$ NMR spectrum having a signal at −109.8±0.2 ppm.

33. Crystalline Form B of Compound 32:

(32)

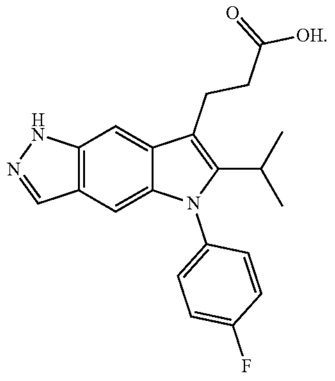

34. Crystalline Form B according to embodiment 33 in substantially pure form.

35. Crystalline Form B according to embodiment 33, characterized by an X-ray powder diffractogram substantially similar to that in FIG. 13.

36. Crystalline Form B according to embodiment 33, characterized by an X-ray powder diffractogram having a signal at at least two two-theta values chosen from 10.0±0.2, 11.3±0.2, 12.2±0.2, and 20.7±0.2.

37. Crystalline Form B according to embodiment 33, characterized by an X-ray powder diffractogram having a signal at at least three two-theta values chosen from 7.8±0.2, 10.0±0.2, 11.3±0.2, 12.2±0.2, 16.0±0.2, and 20.7±0.2.

38. A composition comprising Crystalline Form B of compound 32:

(32)

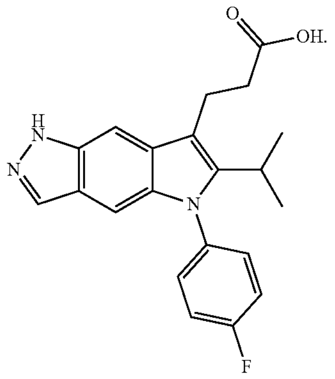

39. A composition comprising Compound 32:

(32)

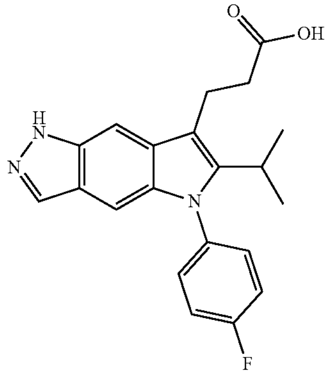

in substantially pure Crystalline Form B.

40. A composition comprising at least one active compound consisting essentially of Compound 32 in Crystalline Form B.

41. Crystalline Form B according to embodiment 33, characterized by a $^{13}C$ NMR spectrum having a signal at at least three ppm values chosen from 181.5±0.2, 162.1±0.2, 159.6±0.2, 145.6±0.2, 136.1±0.2, 130.1±0.2, 128.0±0.2, 122.6±0.2, 119.3±0.2, 117.2±0.2, 114.8±0.2, 113.3±0.2, 108.8±0.2, 101.8±0.2, 98.0±0.2, 95.8±0.2, 38.0±0.2, and 23.9±0.2 ppm.

42. Crystalline Form B according to embodiment 33, characterized by a $^{19}F$ NMR spectrum having a signal at −112.0±0.2 and/or −117.6±0.2 ppm.

43. Crystalline Form C of Compound 32:

(32)

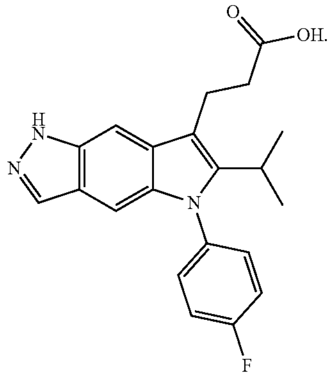

44. Crystalline Form C according to embodiment 43, in substantially pure form.

45. Crystalline Form C according to embodiment 43, characterized by an X-ray powder diffractogram substantially similar to that in FIG. 18.

46. Crystalline Form C according to embodiment 43, characterized by an X-ray powder diffractogram having a signal at at least two two-theta values chosen from 14.7±0.2, 14.9±0.2, and 17.0±0.2.

47. Crystalline Form C according to embodiment 43, characterized by an X-ray powder diffractogram having a signal at at least three two-theta values chosen from 13.1±0.2, 14.7±0.2, 14.9±0.2, 17.0±0.2, and 18.1±0.2.

48. A composition comprising Crystalline Form C of compound 32:

(32)

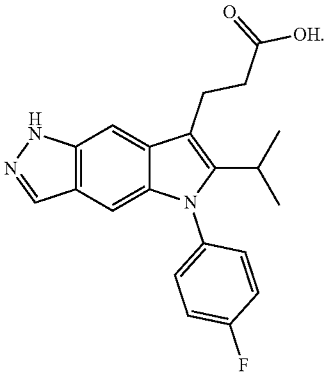

49. A composition comprising Compound 32:

(32)

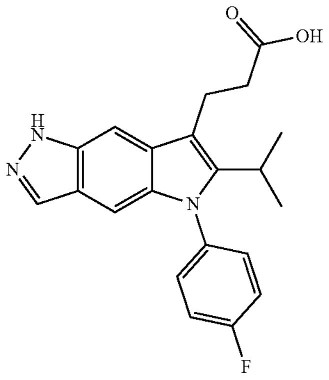

in substantially pure Crystalline Form C.

50. A composition comprising at least one active compound consisting essentially of Compound 32 in Crystalline Form C.

51. Crystalline Form C according to embodiment 43, characterized by a $^{13}C$ NMR spectrum having a signal at at least three ppm values chosen from 140.0±0.2, 137.5±0.2, 135.6±0.2, 133.7±0.2, 122.1±0.2, 121.4±0.2, 108.1±0.2, 99.2±0.2, 95.5±0.2, 22.7±0.2, and 20.6±0.2 ppm.

52. Crystalline Form C according to embodiment 43, characterized by a $^{19}F$ NMR spectrum having a signal at −109.3±0.2 and/or −112.4±0.2 ppm.

53. A composition comprising Crystalline Form A of Compound 32 and Crystalline Form C of Compound 32:

(32)

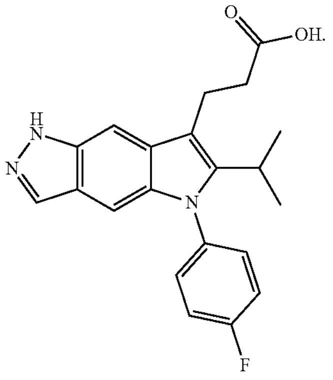

54. The composition according to embodiment 53, characterized by an X-ray powder diffractogram having a signal at at least three two-theta values chosen from 15.0±0.2, 15.4±0.2, 17.6±0.2, 18.0±0.2, and 20.3±0.2.

55. The composition comprising Crystalline Form A and Crystalline Form C according to embodiment 53, characterized by a $^{13}C$ NMR spectrum having a signal at at least three ppm values chosen from 140.1±0.2, 137.2±0.2, 131.5±0.2, 121.8±0.2, 107.7±0.2, and 98.9±0.2 ppm.

56. The composition comprising Crystalline Form A and Crystalline Form C according to embodiment 53, characterized by a $^{19}F$ NMR spectrum having a signal at −109.7±0.2 and/or −112.5±0.2 ppm.

57. Compound 32 monohydrochloride salt:

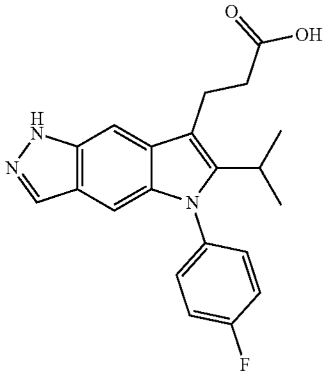

HCl.

58. Compound 32 monohydrochloride salt according to embodiment 57 having a single crystal unit cell characterized as follows:

| Crystal System<br>Space Group | Monoclinic<br>$P2_1/n$ |
|---|---|
| a (Å) | 12.2 ± 0.1 |
| b (Å) | 18.6 ± 0.1 |
| c (Å) | 18.0 ± 0.1 |
| α (°) | 90 ± 0.1 |
| β (°) | 102.0 ± 0.1 |
| γ (°) | 90 ± 0.1 |
| V ($Å^3$) | 3985 ± 0.2 |
| Z/Z' | 2/2 |

59. Compound 32 hemihydrochloride hemihydrate.

60. Compound 32 hemihydrochloride hemihydrate according to embodiment 59 having a single crystal unit cell characterized as follows:

| Crystal System | Triclinic |
|---|---|
| Space Group | P-1 |
| a (Å) | 10.4 ± 0.1 |
| b (Å) | 14.0 ± 0.1 |
| c (Å) | 14.3 ± 0.1 |
| α (°) | 102.2 ± 0.1 |
| β (°) | 91.7 ± 0.1 |
| γ (°) | 107.7 ± 0.1 |
| V (Å$^3$) | 1934 ± 0.2 |
| Z/Z' | 2/2 |

61. Amorphous Form of Compound 32:

(32)

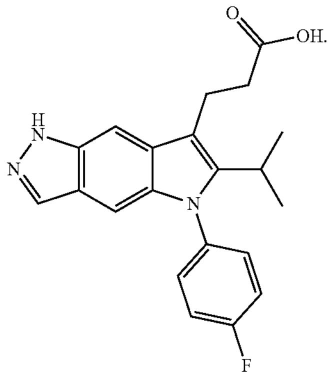

62. Amorphous Form according to embodiment 61, characterized by a $^{13}$C NMR spectrum having a signal at 146.5±0.2 and/or 120.6±0.2 ppm.

63. Amorphous Form according to embodiment 61, characterized by a $^{19}$F NMR spectrum having a signal at −113.3±0.2 ppm.

64. Compound 32 ethanol solvate:

(32)

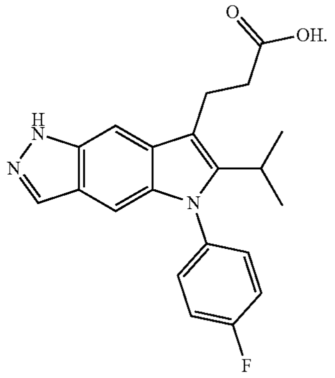

65. Compound 32 ethanol solvate according to embodiment 64, characterized by an X-ray powder diffractogram substantially similar to that in FIG. 24.

66. Compound 32 ethanol solvate according to embodiment 64, characterized by an X-ray powder diffractogram having a signal at at least three two-theta values chosen from 9.8±0.2, 11.3±0.2, 20.5±0.2, and 24.1±0.2.

67. Compound 32 ethanol solvate according to embodiment 64 having a single crystal unit cell characterized as follows:

| Crystal System | Triclinic |
|---|---|
| Space Group | P-1 |
| a (Å) | 92. ± 0.1 |
| b (Å) | 14.5 ± 0.1 |
| c (Å) | 15.5 ± 0.1 |
| α (°) | 73.6 ± 0.1 |
| β (°) | 75.7 ± 0.1 |
| γ (°) | 88.7 ± 0.1 |
| V (Å$^3$) | 1927 ± 0.2 |
| Z/Z' | 2/2 |

68. Compound 32 ethanol solvate according to embodiment 64, characterized by a $^{13}$C NMR spectrum having a signal at at least three ppm values chosen from 180.1±0.2, 175.2±0.2, 160.1±0.2, 132.3±0.2, 129.6±0.2, 114.1±0.2, 109.3±0.2, 100.2±0.2, 96.9±0.2, 58.2±0.2, 36.9±0.2, and 23.5±0.2 ppm.

69. Compound 32 ethanol solvate according to embodiment 64, characterized by a $^{19}$F NMR spectrum having a signal at −112.0±0.2 and/or −115.0±0.2 ppm.

70. A composition comprising Amorphous Form of Compound 32, Compound 32 monohydrochloride salt, Compound 32 hemihydrochloride hemihydrate, and/or Compound 32 ethanol solvate.

71. A method of treating alpha-1 antitrypsin deficiency comprising administering to a patient in need thereof a therapeutically effective amount of at least one compound according to any one of embodiments 1-17, 20, 22-27, 31-37, 41-47, 51, 52, and 57-69 or at least one composition according to any one of embodiments 21, 28, 29, 30, 38-40, 48-50, 53-56, and 70.

72. The method of embodiment 71, wherein the patient has a Z mutation in alpha-1 antitrypsin.

73. The method of embodiment 71, wherein the patient has an SZ mutation in alpha-1 antitrypsin.

74. The method of embodiment 71, wherein the patient is homozygous for Z-mutations in alpha-1 antitrypsin.

75. The method of embodiment 71, wherein said therapeutically effective amount of at least one compound according to any one of embodiments 1-17, 20, 22-27, 31-37, 41-47, 51, 52, and 57-69 or at least one composition according to any one of embodiments 21, 28, 29, 30, 38-40, 48-50, 53-56, and 70 is administered in combination with AAT augmentation therapy and/or AAT replacement therapy.

76. The method of any one of embodiments 71-75, comprising administering a therapeutically effective amount of Compound 32

32

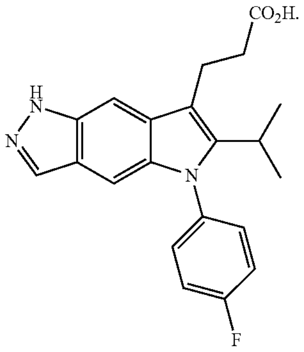

77. A method of modulating alpha-1 antitrypsin activity comprising the step of contacting said alpha-1-antitrypsin with a therapeutically effective amount of at least one compound according to any one of embodiments 1-17, 20, 22-27, 31-37, 41-47, 51, 52, and 57-69.

78. The method of embodiment 77, comprising administering a therapeutically effective amount of Compound 32

32

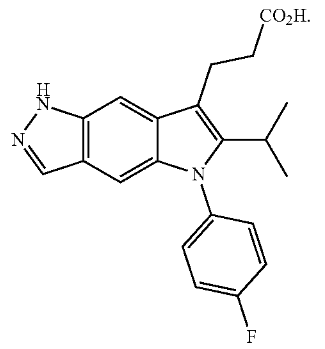

79. A method of preparing a compound of formula 1-3

I-3

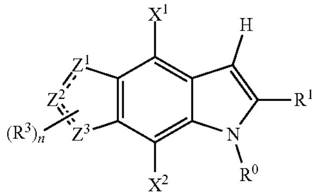

a salt thereof, or a deuterated derivative of any of the foregoing, comprising an internal alkyne amine coupling reaction in a compound of Formula I-4

I-4

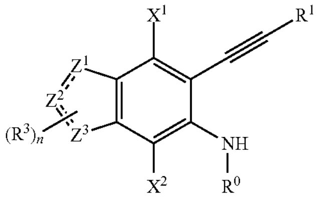

or a salt thereof, wherein, in the compounds of Formula 1-3 and compounds of Formula 1-4, (i) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents selected from halogens and methoxy;

(ii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iii) $X^1$ and $X^2$ are independently chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(v) each ═══ represents a single or double bond, provided that no more than one ═══ is a double bond;

(vi) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and alkoxy groups are optionally substituted with 1-4 halogens;

(vii) n is an integer chosen from 0, 1, 2, and 3; and (viii) $Z^1$, $Z^2$, and $Z^3$ are independently chosen from carbon, nitrogen, sulfur, and oxygen, wherein when $Z^1$, $Z^2$, and/or $Z^3$ are carbon or nitrogen, the valences of carbon and nitrogen are completed with hydrogen atoms, $C_1$-$C_8$ linear, branched, and cyclic alkyls, or cyano.

80. A method of preparing a compound of formula 32

32

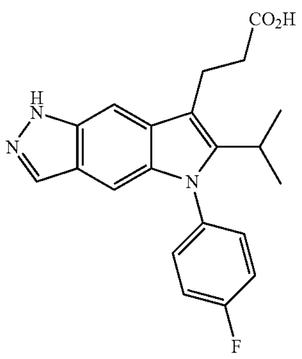

a pharmaceutically acceptable salt thereof, or a deuterated derivative of any of the foregoing, comprising reacting a compound of formula C4

C4

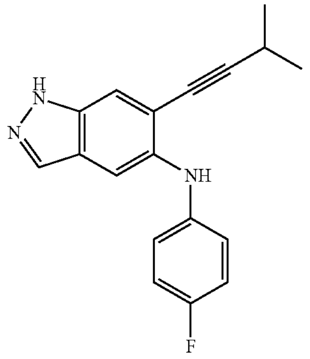

with at least one acid to produce a compound of formula S3

S3

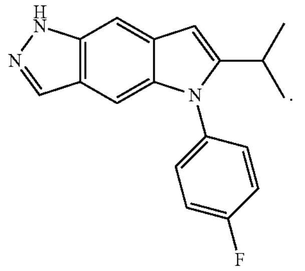

81. The method of embodiment 80, wherein the at least one acid is acetic acid.

82. The method of embodiment 80, further comprising reacting the compound of formula S3 with benzyl chloroformate in the presence of at least one base to produce a compound of formula S4

S4

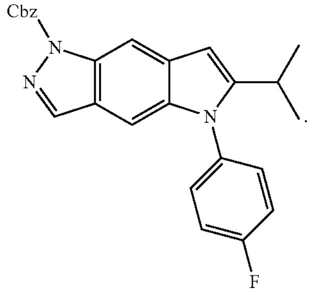

83. The method of embodiment 82, wherein the at least one base is chosen from potassium tert-butoxide, sodium tert-butoxide, sodium tert-amylate, and sodium methoxide.

84. The method of embodiment 83, further comprising reacting the compound of formula S4 with methyl-3,3-dimethoxypropionate in the presence of at least one acid to produce a compound of formula C35

C35

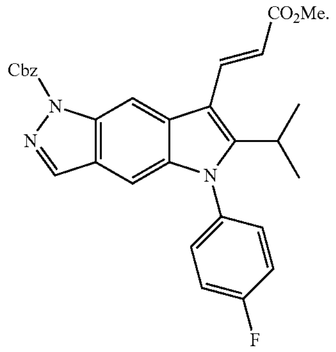

85. The method of embodiment 84, wherein the at least one acid is chosen from para-toluenesulfonic acid and para-toluenesulfonic acid hydrate.

86. The method of any one of embodiments 85 and 86, further comprising hydrogenating the compound of formula C35 to produce a compound of formula C36

C36

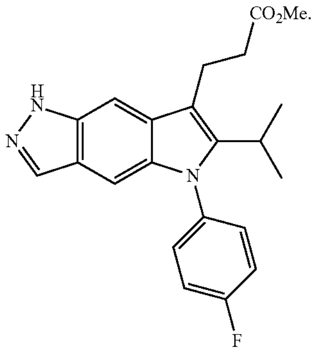

87. The method of embodiment 86, wherein the hydrogenation is performed using palladium on carbon and hydrogen gas.

88. The method of any one of embodiments 86 and 87, further comprising hydrolyzing the compound of formula C36 to produce the compound of formula 32.

89. The method of embodiment 88, wherein the hydrolysis comprises reacting the compound of formula C36 with at least one base and subsequent acidification with at least one acid.

90. The method of embodiment 88, wherein the hydrolysis comprises reacting the compound of formula C36 with at least one base chosen from potassium hydroxide, sodium hydroxide, lithium hydroxide, and sodium methoxide and subsequent acidification with at least one acid.

91. The method of embodiment 88, wherein the hydrolysis comprises reacting the compound of formula C36 with at least one base chosen from potassium hydroxide, sodium hydroxide, lithium hydroxide, and sodium methoxide and subsequent acidification with at least one acid chosen from acetic acid.

92. The method of embodiment 80, further comprising reacting a compound of formula C7

C7

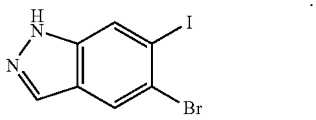

with 3-methyl-1-butyne in the presence of at least one coupling reagent and at least one base to produce a compound of formula C8

C8

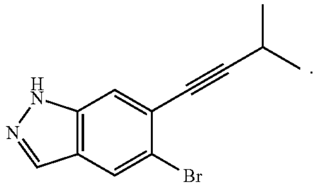

93. The method of embodiment 92, wherein the at least one coupling reagent is chosen from CuI and $Pd(PPh_3)_2Cl_2$.

94. The method of any one of embodiments 92 and 93, wherein the at least one base is chosen from triethylamine, diethylamine, diisopropylethylamine, and pyridine.

95. The method of any one of embodiments 92-94, further comprising reacting the compound of formula C8 with 4-fluoroaniline in the presence of a palladium catalyst and at least one base to produce the compound of formula C4.

96. The method of embodiment 95, wherein the at least one base is chosen from potassium tert-butoxide, sodium tert-butoxide, sodium tert-amylate, and sodium methoxide.

97. A method of preparing a compound of formula 32

32

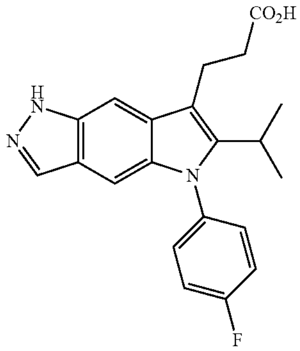

a pharmaceutically acceptable salt thereof, or a deuterated derivative of any of the foregoing, comprising:

(a) reacting a compound of formula C7

C7

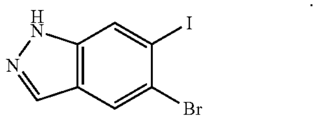

with 3-methyl-1-butyne in the presence of at least one coupling reagent and at least one base to produce a compound of formula C8

C8

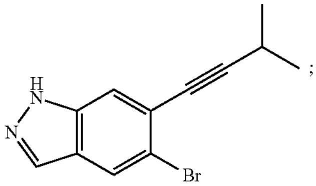

(b) reacting the compound of formula C8 with 4-fluoroaniline in the presence of a palladium catalyst and at least one base to produce a compound of formula C4

C4

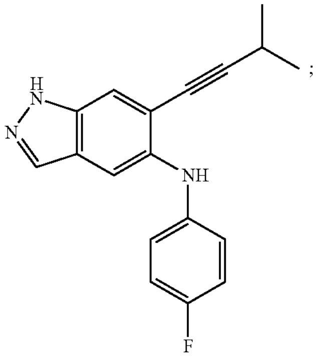

(c) reacting the compound of formula C4 with at least one acid to produce a compound of formula S3

S3

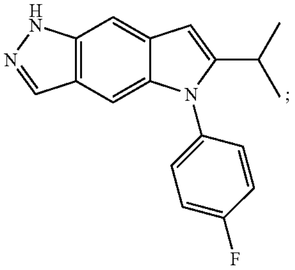

(d) reacting the compound of formula S3 with benzyl chloroformate in the presence of at least one base to produce a compound of formula S4

S4

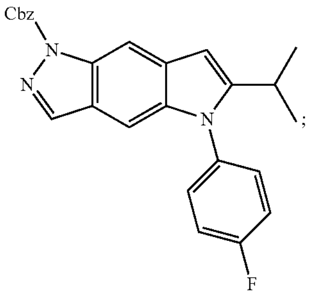

(e) reacting the compound of formula S4 with methyl-3, 3-dimethoxypropionate in the presence of at least one acid to produce a compound of formula C35

C35

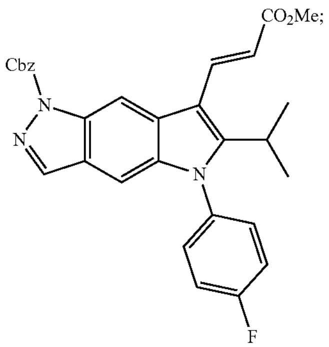

(f) hydrogenating the compound of formula C35 to produce a compound of formula C36

C36

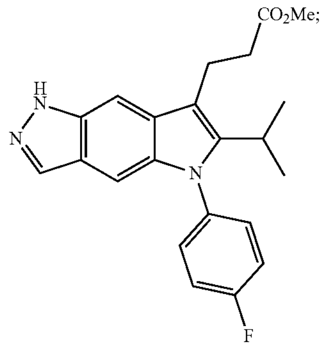

and (g) hydrolyzing the compound of formula C36 to produce the compound of formula 32.

98. The method of embodiment 97, wherein the at least one coupling reagent used in (a) is chosen from CuI and $Pd(PPh_3)_2Cl_2$.

99. The method of embodiment 97 or embodiment 98, wherein the at least one base in (a) is chosen from triethylamine, diethylamine, diisopropylethylamine, and pyridine.

100. The method of any one of embodiments 97-99, wherein the at least one base in (b) is chosen from potassium tert-butoxide, sodium tert-butoxide, sodium tert-amylate, and sodium methoxide.

101. The method of any one of embodiments 97-100, wherein the at least one acid in (c) is acetic acid.

102. The method of any one of embodiments 97-101, wherein the at least one base in (d) is chosen from potassium tert-butoxide, sodium tert-butoxide, sodium tert-amylate, and sodium methoxide.

103. The method of any one of embodiments 97-102, wherein the at least one acid in (e) is chosen from para-toluenesulfonic acid and para-toluenesulfonic acid hydrate.

104. The method of any one of embodiments 97-103, wherein the hydrogenation in (f) is performed using palladium on carbon and hydrogen gas.

105. The method of any one of embodiments 97-103, wherein the hydrolysis in (g) comprises reacting the compound of formula C36 with at least one base and subsequent acidification with at least one acid.

106. The method of any one of embodiments 97-103, wherein the hydrolysis in (g) comprises reacting the compound of formula C36 with at least one base chosen from potassium hydroxide, sodium hydroxide, lithium hydroxide, and sodium methoxide and subsequent acidification with at least one acid.

107. The method of any one of embodiments 97-103, wherein the hydrolysis in (g) comprises reacting the compound of formula C36 with at least one base chosen from potassium hydroxide, sodium hydroxide, lithium hydroxide, and sodium methoxide and subsequent acidification with at least one acid chosen from acetic acid.

108. A method of preparing a compound of formula S3

S3

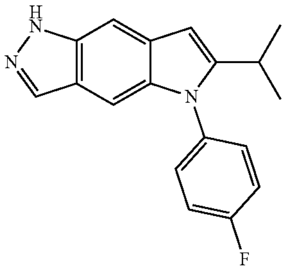

a salt thereof, or a deuterated derivative of any of the foregoing, comprising reacting a compound of formula C4

C4

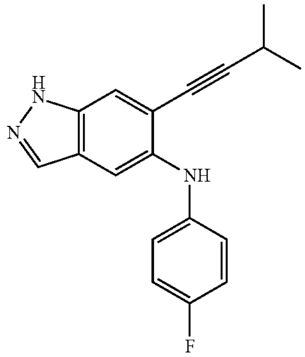

with at least one acid.

109. The method of embodiment 108, wherein the at least one acid is acetic acid.

110. The method of embodiment 108, wherein the compound of formula C4 is prepared by reacting a compound of formula C8

C8

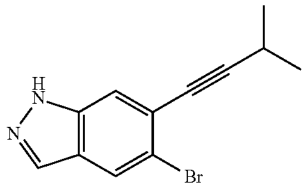

with 4-fluoroaniline in the presence of a palladium catalyst and at least one base.

111. The method of embodiment 108, wherein the at least one base is chosen from potassium tert-butoxide, sodium tert-butoxide, sodium tert-amylate, and sodium methoxide.

112. The method of embodiment 111, wherein the compound of formula C8 is prepared by reacting a compound of formula C7

C7

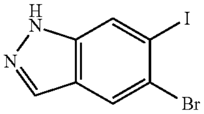

with 3-methyl-1-butyne in the presence of at least one coupling reagent and at least one base.

113. The method of embodiment 112, wherein the at least one coupling reagent is chosen from CuI and $Pd(PPh_3)_2Cl_2$.

114. The method of embodiment 112, wherein the at least one base is chosen from triethylamine, diethylamine, diisopropylethylamine, and pyridine.

115. A method of preparing a compound of formula S6

S6

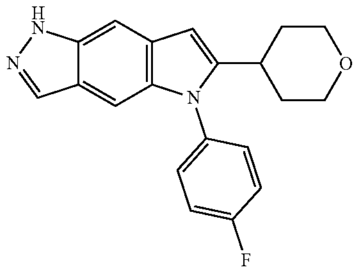

a salt thereof, or a deuterated derivative of any of the foregoing, comprising heating a solution comprising a compound of formula C15

C15

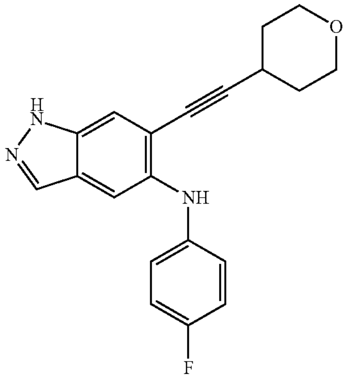

with at least one base.

116. The method of embodiment 115, further comprising reacting a compound of formula C14

C14

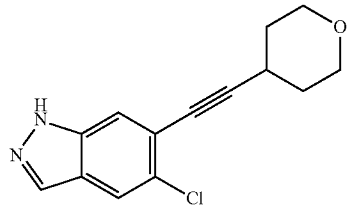

with 4-fluoroaniline, at least one base, and at least one palladium precatalyst to prepare the compound of formula S6.

117. The method of embodiment 115, wherein said at least one base is sodium t-butoxide.

118. The method of embodiment 115, wherein said at least one palladium precatalyst is BrettPhos Pd G4.

EXAMPLES

In order that the disclosure described herein may be more fully understood, the following examples are set forth. It should be understood that these examples are for illustrative purposes only and are not to be construed as limiting this disclosure in any manner

Example 1. Synthesis of Compounds

All the specific and generic compounds, the methods for making those compounds, and the intermediates disclosed for making those compounds, are considered to be part of the invention disclosed herein.

A. Synthesis of Starting Materials

Preparations of S1-S12 describe synthetic routes to intermediates used in the synthesis of compounds 1-215.

Preparation S1

5-(4-fluoro-3-methylphenyl)-6-isopropyl-1,5-dihydropyrrolo[2,3-f]indazole (S1)

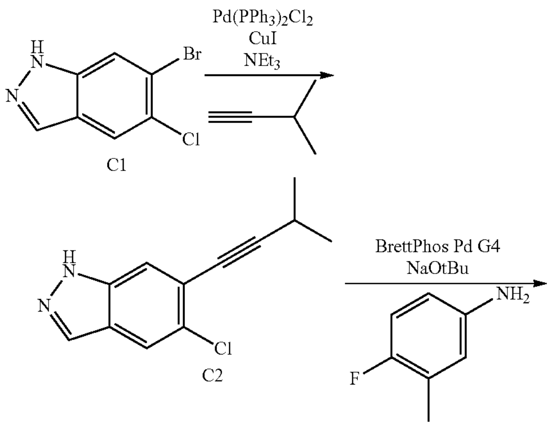

-continued

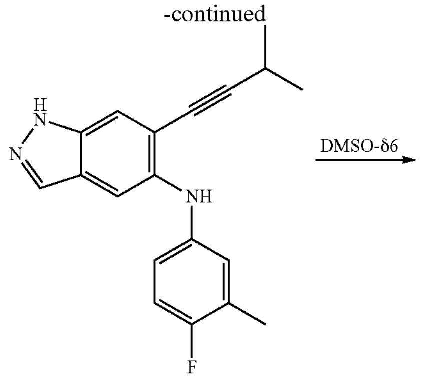

C3

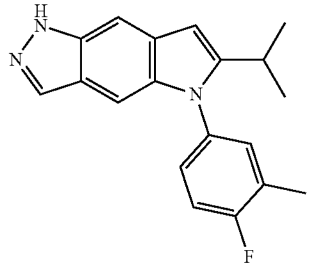

S1

Step 1. Synthesis of 5-chloro-6-(3-methylbut-1-yn-1-yl)-1H-indazole (C2)

$Pd(PPh_3)_2Cl_2$ (1.7 g, 2.4 mmol) was added to a nitrogen purged solution of 3-methylbut-1-yne (10.7 mL, 104.6 mmol), 6-bromo-5-chloro-1H-indazole C1 (10.4 g, 44.9 mmol) and CuI (497 mg, 2.6 mmol) in $Et_3N$ (100 mL) and 1,4-dioxane (100 mL). The solution was stirred at 90° C. overnight in a Parr bottle, whereupon Celite® and methanol were added, and the mixture concentrated in vacuo. Purification of the Celite® adsorbed mixture by silica gel chromatography (Gradient: 0-100% EtOAc in heptanes) afforded the product. Yield: 7.0 g, 71%. LCMS m/z 219.04 $[M+H]^+$. $^1H$ NMR (300 MHz, Chloroform-d) δ 10.17 (s, 1H), 8.02 (d, J=1.1 Hz, 1H), 7.80 (d, J=0.7 Hz, 1H), 7.62 (t, J=0.9 Hz, 1H), 2.88 (hept, J=6.9 Hz, 1H), 1.34 (d, J=6.9 Hz, 6H).

Step 2. Synthesis of N-(4-fluoro-3-methylphenyl)-6-(3-methylbut-1-yn-1-yl)-1H-indazol-5-amine (C3)

t-Butanol (45 mL) and 1,4-dioxane (15 mL) were added to a flask containing 4-fluoro-3-methyl-aniline (2.1 g, 16.8 mmol), 5-chloro-6-(3-methylbut-1-ynyl)-1H-indazole C2 (2.3 g, 10.5 mmol), sodium t-butoxide (3.9 g, 40.6 mmol), and BrettPhos Pd G4 catalyst (280 mg, 0.3 mmol). The mixture was degassed and stirred under Na at 100° C. overnight. The mixture was concentrated under reduced pressure, re-dissolved in dichloromethane, and washed with water. The organic layer was dried by passing through a phase separator and concentrated in vacuo. Silica gel chromatography (Gradient: 0-100% EtOAc in heptanes) afforded the product. Yield: 1.9 g, 58%. LCMS m/z 308.2 $[M+H]^+$. $^1H$ NMR (300 MHz, DMSO-d6) δ 12.93 (s, 1H), 7.92 (s, 1H), 7.52 (s, 1H), 7.40 (s, 1H), 7.16 (s, 1H), 7.02-6.91 (m, 1H), 6.87-6.71 (m, 2H), 2.75 (m, 1H), 2.15 (d, J=1.9 Hz, 3H), 1.11 (d, J=6.9 Hz, 6H).

Step 3. Synthesis of 5-(4-fluoro-3-methylphenyl)-6-isopropyl-1,5-dihydropyrrolo[2,3-f]indazole (S1)

A solution of N-(4-fluoro-3-methyl-phenyl)-6-(3-methyl-but-1-ynyl)-1H-indazol-5-amine C3 (254 mg, 0.83 mmol) in trideuterio(trideuteriomethylsulfinyl)methane (2.3 mL) was heated under microwave conditions at 150° C. for 30 min. The reaction mixture was poured into water (30 mL) and stirred for 4 hours. The resulting solid was filtered and dried under vacuum at 50° C. to afford the product. Yield: 143 mg, 53%. LCMS m/z 308.2 $[M+H]^+$. $^1H$ NMR (300 MHz, DMSO-d6) δ 12.58 (s, 1H), 7.96 (d, J=1.3 Hz, 1H), 7.53 (d, J=1.1 Hz, 1H), 7.45-7.27 (m, 3H), 7.16 (d, J=1.0 Hz, 1H), 6.46 (d, J=0.9 Hz, 1H), 3.03-2.83 (m, 1H), 2.34 (d, J=2.0 Hz, 3H), 1.18 (d, J=6.8 Hz, 6H).

Preparation S2 benzyl 5-(4-fluoro-3-methylphenyl)-6-isopropylpyrrolo[2,3-f]indazole-1(5H)-carboxylate (S2)

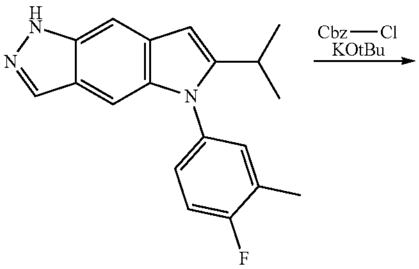

S1

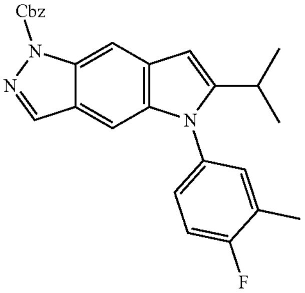

S2

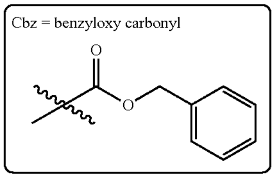

Step 1. benzyl 5-(4-fluoro-3-methylphenyl)-6-isopropylpyrrolo[2,3-f]indazole-1(5H)-carboxylate (S2)

To a suspension of 5-(4-fluoro-3-methyl-phenyl)-6-isopropyl-1H-pyrrolo[2,3-f]indazole S1 (1.3 g, 4.0 mmol) in THF (25 mL) at 0° C. (ice-water bath) was added KOtBu (605 mg, 5.4 mmol). After ~30 min, Cbz-Cl (1.8 mL of 3M, 5.4 mmol) was added and the mixture stirred for 30 min. An additional 400 μl of Cbz-Cl (3M solution) was added and the mixture stirred for a further 30 min. The reaction was quenched with water (18 mL), stirred for 15 min, then partitioned between EtOAc (25 mL) and water (10 mL). The organic layer was washed with brine (24 mL), dried ($MgSO_4$) and concentrated to dryness. MTBE (10 mL) was added to the residue, and the resulting suspension sonicated. The solid was filtered and further washed with MTBE, then dried under vacuum to yield the product as a yellow solid. Yield: 1.5 g, 83%. LCMS m/z 442.2 $[M+H]^+$. $^1H$ NMR (300 MHz, DMSO-d6) δ 8.36 (d, J=0.8 Hz, 1H), 8.28-8.21 (m, 1H), 7.59-7.51 (m, 2H), 7.51-7.31 (m, 7H), 6.64 (s, 1H), 5.52 (s, 2H), 2.95 (m, 1H), 2.34 (d, J=2.0 Hz, 3H), 1.20 (d, J=6.8 Hz, 6H).

Preparation S3

5-(4-fluorophenyl)-6-isopropyl-1,5-dihydropyrrolo[2,3-f]indazole (S3)

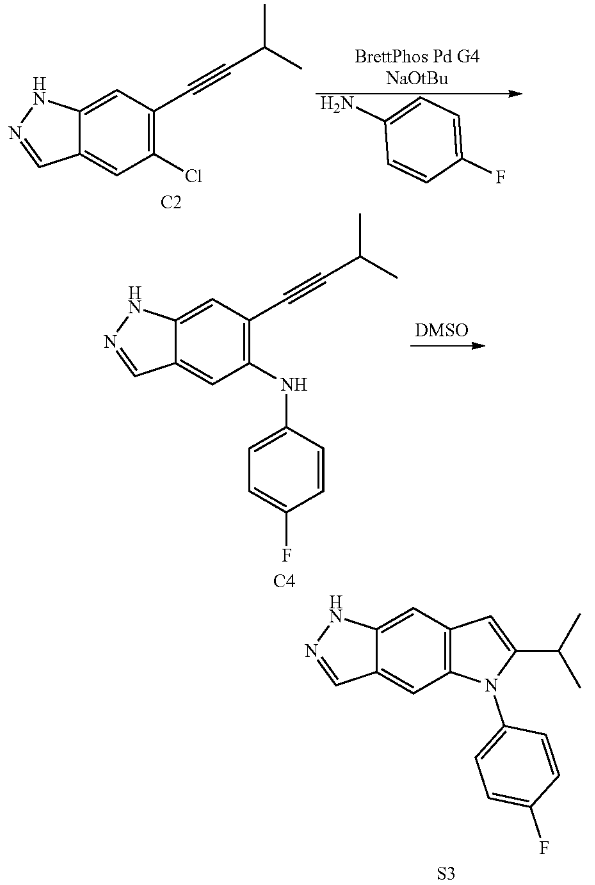

C2, C4, S3

Step 1. Synthesis of N-(4-fluorophenyl)-6-(3-methylbut-1-yn-1-yl)-1H-indazol-5-amine (C4)

t-Butanol (11 mL) was added to a vial containing 5-chloro-6-(3-methylbut-1-ynyl)-1H-indazole C2 (744 mg, 3.3 mmol), 4-fluoroaniline (600 mg, 5.4 mmol), sodium t-butoxide (1.3 g, 13.0 mmol), and BrettPhos Pd G4 catalyst (79 mg, 0.09 mmol). The mixture was degassed with nitrogen and stirred at 120° C. overnight. The mixture was diluted with dichloromethane (75 mL) and washed with 50% saturated sodium bicarbonate solution (mL40 mL). The organic layer was dried by passing through a phase separator. Celite® was added to the solution, and the mixture was concentrated to dryness under reduced pressure. Purification by silica gel chromatography (Gradient: 0-100% EtOAc in heptanes) afforded the product. Yield: 812 mg, 80%. LCMS m/z 294.3 $[M+H]^+$ confirmed the product C4 together with the cyclized S3 as a minor component (4.6:1). The crude mixture was progressed to step 2 without further purification.

Step 2. Synthesis of 5-(4-fluorophenyl)-6-isopropyl-1,5-dihydropyrrolo[2,3-f]indazole (S3)

A solution of N-(4-fluorophenyl)-6-(3-methylbut-1-ynyl)-1H-indazol-5-amine $C_4$ (812 mg, 2.7 mmol) in DMSO (3.5 mL) was heated in a sealed vial at 150° C. for 90 min. 50% saturated sodium bicarbonate (25 mL) was added and the resulting mixture was extracted with EtOAc (2×100 mL), dried over sodium sulfate, filtered and concentrated in vacuo to afford the product. Yield: 778 mg, 92%. LCMS m/z 294.3 $[M+H]^+$. $^1H$ NMR (300 MHz, DMSO-d6) δ 12.59 (s, 1H), 7.96 (d, J=1.0 Hz, 1H), 7.57-7.41 (m, 5H), 7.15 (t, J=1.0 Hz, 1H), 6.48 (d, J=0.8 Hz, 1H), 2.98-2.84 (m, 1H), 1.18 (d, J=6.8 Hz, 6H).

Preparation S4 benzyl 5-(4-fluorophenyl)-6-isopropylpyrrolo[2,3-f]indazole-1(5H)-carboxylate (S4)

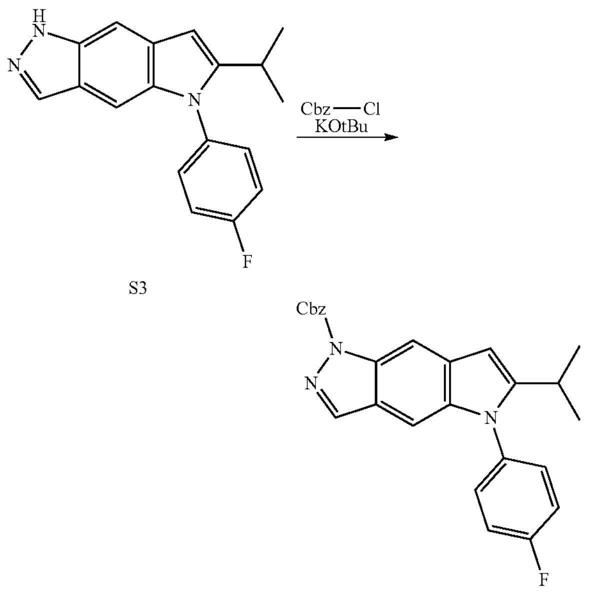

S3, S4

To a suspension of 5-(4-fluorophenyl)-6-isopropyl-1H-pyrrolo[2,3-f]indazole S3 (14.6 g, 49.1 mmol) in THF (288 mL) cooled to 1° C. on an ice-water bath, was added KOtBu (7.2 g, 64.2 mmol). After approx. 30 min, Cbz-Cl (21.5 mL of 3 M, 64.5 mmol) was added and the mixture stirred for an additional 1 h in a cooling bath. The reaction was quenched with water (300 mL), stirred for 5 min, then partitioned between EtOAc (400 mL) and water (100 mL). The organic layer was washed with brine (400 mL), dried over magnesium sulfate, and then concentrated in vacuo. The residue was treated with MTBE (40 mL) resulting in the formation of an orange/brown slurry. The slurry was poured into a filter funnel and the solid washed with MTBE until the material was a consistent pale yellow color. The solid was dried in a vacuum oven to afford the product. Yield: 17.04 g, 80%. LCMS m/z 428.25 $[M+H]^+$. $^1H$ NMR (300 MHz, DMSO-d6) δ 8.39-8.33 (m, 1H), 8.29-8.23 (m, 1H), 7.62-7.36 (m, 9H), 7.36-7.31 (m, 1H), 6.68-6.61 (m, 1H), 5.55-5.49 (m, 2H), 2.94 (m, 1H), 1.20 (dd, J=6.8, 1.7 Hz, 6H).

Alternative Preparations of S3 and S4

5-(4-fluorophenyl)-6-isopropyl-1,5-dihydropyrrolo[2,3-f]indazole (S3) & benzyl 5-(4-fluorophenyl)-6-isopropylpyrrolo[2,3-f]indazole-1(5H)-carboxylate (S4)

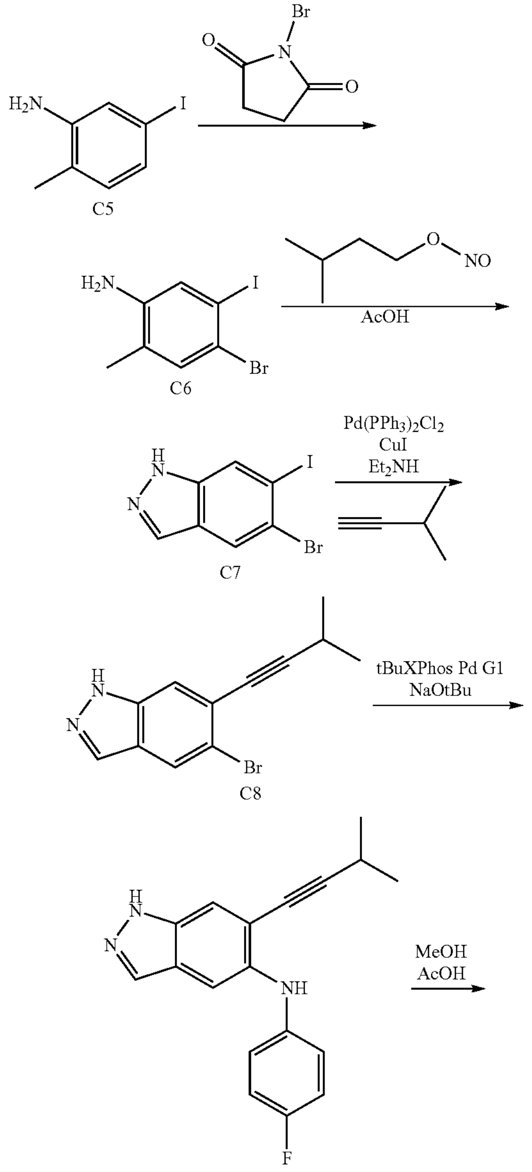

C5 C6 C7 C8 C4

-continued

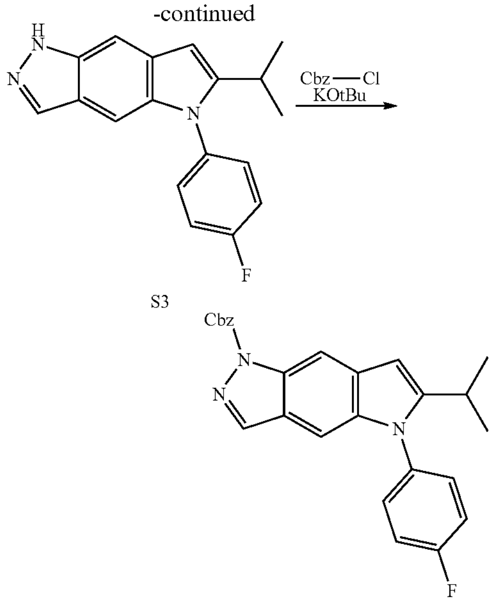

S3 S4

Step 1. Synthesis of 4-bromo-5-iodo-2-methylaniline (C6)

To a solution of 5-iodo-2-methylaniline $C_5$ (600 g, 2.6 mol) in DMF (3 L) at -6° C. was added N-bromosuccinimide (460 g, 2.58 mol) in 5 portions over ~45 min (maintaining the temperature between ~3 to −7° C.). The mixture was stirred at -5 to −8° C. for 55 min. The mixture was quenched by addition of 0.5M $Na_2S_2O_3$ (200 mL) then added to ice/water (4.8 kg) over 4 min. A slurry formed, and an exotherm to +10° C. was observed. The mixture was diluted with additional cold water (1 L), stirred for one hour at ~10° C., filtered and washed with water (1.5 L). The solids were dried at 45° C. under vacuum to afford the product as an off-white solid. Yield: 779 g, 97%. $^1H$ NMR (500 MHz, Chloroform-d) δ 7.25 (s, 1H), 7.14 (s, 1H), 3.60 (2H, s), 2.05 (3H, s).

Alternative Synthesis of 4-bromo-5-iodo-2-methylaniline (C6)

5-iodo-2-methyl-aniline (800 g, 1 eq) and DMF (3.2 L, 4 vol) were charged to a reactor. The mixture was stirred for 5 minutes and then cooled to −15° C. N-bromosuccinimide (623 g, 1.02 equiv) dissolved in DMF (800 ml, 1 vol) was added portion wise over 30 minutes. The resulting reaction mixture was stirred at −10° C. 60 minutes. Upon reaction completion, aqueous $Na_2S_2O3$ [0.5 M] (120 mL, 0.3 vol). Water (812.8 mL, 0.536 M, 8 vol) was charged to a second reactor and cooled to 3° C. The reaction solution was added to reactor containing water keeping temperature below 10° C. The quenched reaction was stirred for an hour at 10° C. The slurry was filtered and the reactor washed with water (1.6 L, 2 vol) and added to wet cake. The wet cake was rinsed with n-heptane (1.6 L, 2 vol). The wet cake was dried in vacuum oven at 45° C. with nitrogen bleed overnight to afford the product as a beige solid in 91% yield. $^1H$ NMR (400 MHz, $CDCl_3$) δ 7.25 (d, J=0.8 Hz, 1H), 7.15 (s, 1H), 3.60 (s, 2H), 2.08 (d, J=0.7 Hz, 3H) ppm.

Step 2. Synthesis of 5-bromo-6-iodo-1H-indazole (C7)

To a solution of C6 (791 g, 2.5 mol) in AcOH (4.2 L) at 44° C. was added isopentyl nitrite (333 g, 2.8 mol) over 1 h. The reaction was allowed to exotherm to 55° C., then held between 55-64° C. The mixture was stirred at 55° C. for 30 min, then cooled to 50° C. Ice-cold water (4.2 L) was added over 15 min while continuing to cool to 20° C. The slurry was stirred for 25 min at 20° C., filtered and washed with water (2 L). The crude orange solid was dried at 50° C. under vacuum. The solid was then triturated at room temperature in MeCN (2.25 L) for 30 minutes, filtered, and washed with MeCN (~750 mL) to afford the product as an orange solid. Yield: 679 g, 83%. $^1$H NMR (500 MHz, DMSO-d6) δ 13.25 (1H, s), 8.22 (1H, s), 8.20 (1H, s), 8.05 (1H, s).

Step 3. Synthesis of 5-bromo-6-(3-methylbut-1-yn-1-yl)-1H-indazole (C8)

A solution of $C_7$ (2738 g, 8.5 mol) in DMF (10 L) was de-oxygenated with 4× vacuum/nitrogen cycles. The mixture was cooled to 6° C. and then diethylamine (1.54 kg, 21.1 mol) and 3-methyl-1-butyne (652 g, 9.57 mol) were added. The mixture was transferred using nitrogen pressure to an inert 20-L autoclave containing copper (I) iodide (32 g, 168 mmol) and $PdCl_2(PPh_3)_2$ (115 g, 164 mmol). The autoclave was sealed, pressurized to 5 psi using nitrogen and then heated to 85° C. for 15 h. The pressure increased to 23 psi initially and then gradually decreased to 15 psi as the 3-methyl-1-butyne was consumed (the pressure stopped dropping after about 8 h, presumably indicating complete reaction). The mixture was cooled to 20° C. and then added to a mixture of 37% hydrochloric acid (1.5 kg, 14.9 mol), water (13.7 L) and MTBE (8.7 L) at 5° C. [exotherm to 26°]. The layers were separated, and the organic layer was washed with a mixture of water (8 L) and saturated brine (2 L), and then with saturated brine (3 L). The aqueous layers were sequentially re-extracted with MTBE (5 L then 3 L). The combined organics were dried over magnesium sulfate, filtered and concentrated to dryness in vacuo. The residue was triturated in dichloromethane (2 L) at 35° C., gradually diluted with hexane (2 L) and cooled to 20° C. The slurry was filtered, washed with 1:1 dichloromethane:hexane (1.5 L) and dried under vacuum at 40° C. to afford the product as a pale tan solid. Yield: 1492 g, 67%. $^1$H NMR (500 MHz, Chloroform-d) δ 10.6 (s, 1H), 8.01 (s, 1H), 7.98 (s, 1H), 2.85 (m, 1H), 1.32 (d, 9H).

Steps 4 and 5. Synthesis of $C_4$ and 5-(4-fluorophenyl)-6-isopropyl-1H-pyrrolo[2,3-f]indazole (S3)

To a 50 L glass reactor was added C8 (2973 g, 11.3 mol), 4-fluoroaniline (1419 g, 12.8 mol) and THF (29 L). The solution was vacuum purged with nitrogen (5×) and cooled to 3° C. Sodium t-butoxide (3473 g, 36 mol) was added in 1 kg portions over 20 minutes with a resulting heat rise to 16° C. The solution was vacuum purged with nitrogen (5×) and cooled to 11° C. tBuXPhos Pd G1 MTBE catalyst (200 g, 0.2 mol) was added in 3 portions over 1 hour. An exotherm to 33° C. over 2 h was observed. The contents were stirred overnight—cooling to room temperature. HPLC analysis indicated conversion to C4. The solution was diluted with hexanes (4 L) and cooled to 3° C. Acetic acid was added over 1 h (exotherm to 20° C.). Water (8 L) was added and the contents stirred, then settled. The lower layer was removed, and the upper layer concentrated by vacuum distillation to approx. 10 L. The solution was diluted with methanol (25 L) and heated overnight to about 55° C. The solution was concentrated by vacuum distillation to about 10 L and cooled to 16° C. The solids were collected by filtration and washed with cool methanol (4 L) and dried in a vacuum oven to provide the product S3 as a brown solid. Yield: 2.52 kg, 76% yield.

Step 6. Synthesis of benzyl 5-(4-fluorophenyl)-6-isopropylpyrrolo[2,3-f]indazole-1(5H)-carboxylate (S4)

A solution of S3 (132 g, 450 mmol) in THF (2 L) in a 5 L round-bottomed flask equipped with overhead stirrer was cooled to 12° C. KOtBu (70 g, 625 mmol, 1.4 eq) was added. The mixture warmed to 18° C. over 10 min, and was allowed to stir for a further 30 min Thick cotton-like needles resulted. An additional 200 mL of THF was added. Cbz-Cl (107 g, 90 mL 635 mmol) was added over 1 h, while cooling the flask in a water bath. The contents were maintained between 16° C. and 22° C. during and after the addition. The resulting slurry was diluted with MTBE (1 L) and washed with water (1 L). The organic layer was concentrated in vacuo to give a light yellow slurry. The material was slurried in methanol (0.5 L) and cooled overnight to about 0° C. The material was collected by filtration and washed with MeOH (0.2 L) followed by acetonitrile (0.1 L) then dried to afford the product as a light yellow solid. Yield: 145 g, 76% yield.

Preparation S5 benzyl 5-(4-fluoro-3-methylphenyl)-6-isopropyl-3-methylpyrrolo[2,3-f]indazole-1(5H)-carboxylate (S5)

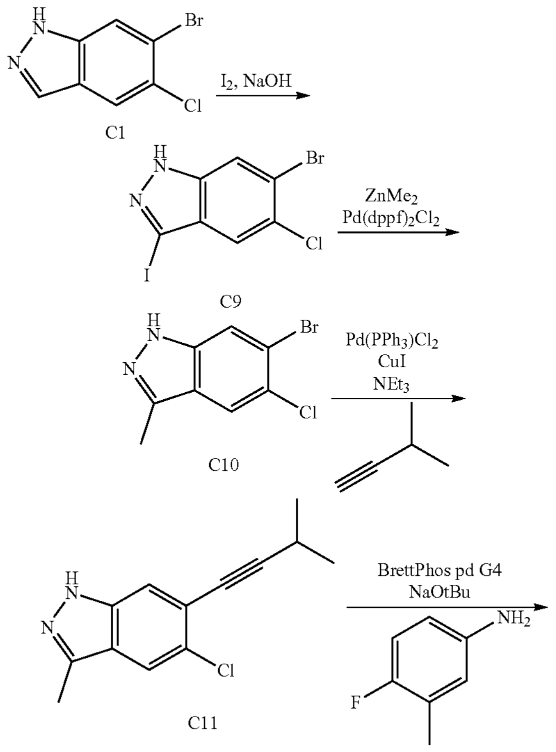

C1
C9
C10
C11

-continued

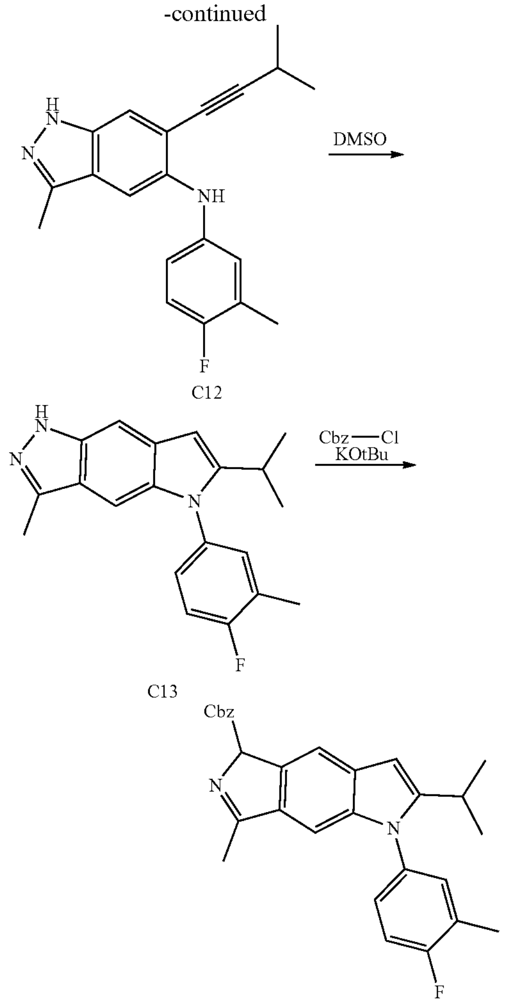

C12

C13

S5

Step 1. Synthesis of 6-bromo-5-chloro-3-iodo-1H-indazole (C9)

To a solution of 6-bromo-5-chloro-1H-indazole $C_1$ (22.2 g, 89.0 mmol) in DMF (220 mL) was added sodium hydroxide (5.2 g, 130.0 mmol) followed by portion wise addition of iodine (34 g, 134.0 mmol). The mixture was stirred at room temperature overnight, and then 1M aqueous sodium thiosulfate solution was added drop-wise until the dark color disappeared. The mixture was then poured onto ice, stirred for 1 h, and the solid filtered washing with water and toluene (5×) to afford the product. Yield: 34 g, $^1$H NMR (400 MHz, DMSO-d6) δ 13.78 (s, 1H), 8.07 (s, 1H), 7.70 (s, 1H).

Step 2. Synthesis of 6-bromo-5-chloro-3-methyl-1H-indazole (C10)

A solution of dimethylzinc (28 mL of 2M, 56.0 mmol) was added drop-wise to a solution of 6-bromo-5-chloro-3-iodo-1H-indazole C9 (20.5 g, 57.4 mmol) and $Pd(dppf)_2Cl_2$ (2.3 g, 2.8 mmol) in 1,4-dioxane (200 mL) cooled to 0° C. (ice bath). The mixture was heated at 90° C. for 3 h, then the reaction was quenched by adding of a few drops of MeOH. 1M HCl and dichloromethane were added, the organic phase was then separated on a phase separator, followed by concentration in vacuo. Purification by silica gel chromatography (Eluent: EtOAc in heptanes) provided the product. Yield: 10.5 g, 75%. $^1$H NMR (400 MHz, Methanol-d4) δ 7.91 (s, 1H), 7.84 (s, 1H), 2.52 (s, 3H).

Step 3. Synthesis of 5-chloro-3-methyl-6-(3-methylbut-1-ynyl)-1H-indazole (C11)

$Pd(PPh_3)_2Cl_2$ (815 mg, 1.2 mmol) was added to a $N_2$ purged solution of 3-methylbut-1-yne (3.3 g, 48.5 mmol), 6-bromo-5-chloro-3-methyl-1H-indazole C10 (5.4 g, 22.0 mmol) and CuI (248 mg, 1.3 mmol) in $Et_3N$ (55 mL) and 1,4-dioxane (55 mL). The solution was stirred at 90° C. overnight. The mixture was adsorbed directly onto silica and purified by silica gel chromatography (Eluent: EtOAc in Heptanes) to provide the product. Yield: 4.0 g, 79%. LCMS m/z 232.08 $[M+H]^+$. $^1$H NMR (400 MHz, DMSO-d6) δ 12.86 (s, 1H), 7.90 (s, 1H), 7.57 (s, 1H), 2.87 (h, J=6.9 Hz, 1H), 2.46 (d, J=1.2 Hz, 3H), 1.25 (dd, J=6.8, 1.2 Hz, 6H).

Step 4. Synthesis of N-(4-fluoro-3-methylphenyl)-3-methyl-6-(3-methylbut-1-yn-1-yl)-1H-indazol-5-amine (C12)

t-Butanol (37 mL) was added to a vial containing 5-chloro-3-methyl-6-(3-methylbut-1-ynyl)-1H-indazole C11 (2.6 g, 11.0 mmol), 4-fluoro-3-methyl-aniline (2.2 g, 17.6 mmol), sodium t-butoxide (4.4 g, 45.8 mmol) and BrettPhos Pd G4 catalyst (281 mg, 0.3 mmol). The mixture was degassed with nitrogen and heated overnight at 120° C. Water and dichloromethane were added. The organic phase was separated on a phase separator and concentrated in vacuo. Purification by silica gel chromatography (Eluent: EtOAc in Heptanes) provided the product. Yield 2.7 g, 77%. LCMS m/z 322.3 $[M+H]^+$ confirmed formation of the product $Cl_2$ as a mixture with cyclized product C13. The mixture was progressed to the next reaction without further purification.

Step 5. Synthesis of 5-(4-fluoro-3-methyl-phenyl)-6-isopropyl-1H-pyrrolo[2,3-f]indazole (C13)

The mixture of C12 and C13 from step 4 (2.7 g) was dissolved in DMSO (13 mL) and heated under microwave conditions at 150° C. for 30 min Complete by LCMS. Water and EtOAc were added. The aqueous layer was extracted with EtOAc, and the organic layers were combined, dried with sodium sulfate, and concentrated in vacuo. Purification by silica gel chromatography (Eluent: EtOAc in Heptanes) provided the product C13. Yield: 2.2 g, 83%. LCMS m/z 322.2 $[M+H]^+$. $^1$H NMR (400 MHz, DMSO-d6) δ 12.13 (s, 1H), 7.45 (s, 1H), 7.40 (dd, J=10.7, 7.3 Hz, 2H), 7.33 (t, J=4.0 Hz, 1H), 7.03 (s, 1H), 6.44 (s, 1H), 2.90 (m, J=6.8 Hz, 1H), 2.40 (s, 3H), 2.34 (d, J=1.9 Hz, 3H), 1.16 (d, J=10.7 Hz, 6H).

Step 6. Synthesis of benzyl 5-(4-fluoro-3-methylphenyl)-6-isopropyl-3-methylpyrrolo[2,3-f]indazole-1(5H)-carboxylate (S5)

KOtBu (565 mg, 5.4 mmol) was added to a solution of 5-(4-fluoro-3-methyl-phenyl)-6-isopropyl-1H-pyrrolo[2,3-f]indazole $C_{13}$ (1.2 g, 4.0 mmol) in THF (30 mL). Cbz-Cl (640 μL, 4.5 mmol) was added and the reaction stirred for 1 h at room temperature then poured over onto ice. The mixture was extracted with dichloromethane and the combined organic layers were dried over magnesium sulfate and concentrated in vacuo to afford a light golden-yellow solid. The solid was triturated with heptanes and the mixture filtered and dried in vacuo to afford the product as a light golden yellow solid. Yield: 1.52 g, 87%. $^1$H NMR (300 MHz, Chloroform-d) δ 8.35 (s, 1H), 8.11 (d, J=0.8 Hz, 1H), 7.63-7.51 (m, 2H), 7.47-7.30 (m, 3H), 7.24-7.12 (m, 4H), 6.52 (s, 1H), 5.56 (s, 2H), 2.94 (m, J=6.8 Hz, 1H), 2.37 (d, J=2.0 Hz, 3H), 1.24 (dd, J=6.9, 2.8 Hz, 6H) ppm.

Preparation S6

5-(4-fluorophenyl)-6-(tetrahydro-2H-pyran-4-yl)-1,5-dihydropyrrolo[2,3-f]indazole (S6)

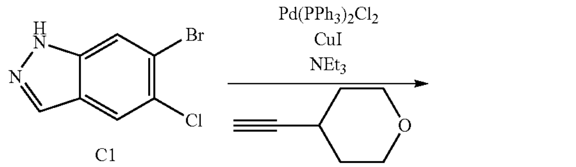

C1

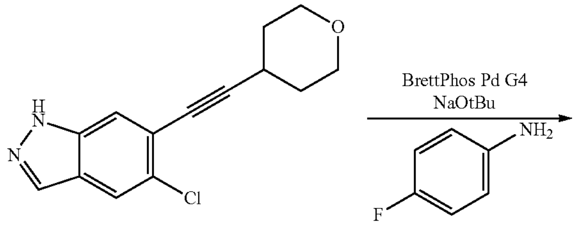

C14

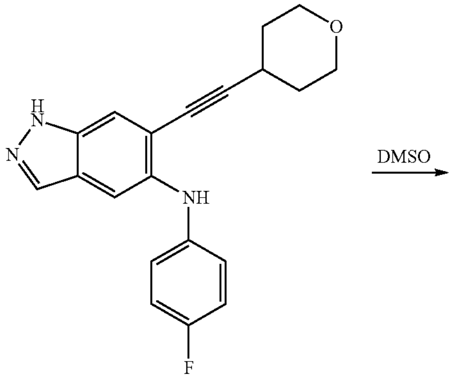

C15

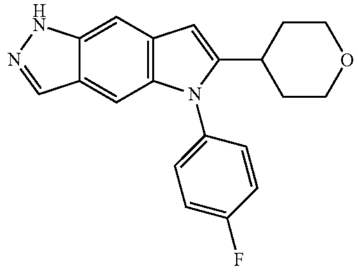

S6 (Compound 60)

Step 1. Synthesis of 5-chloro-6-(2-tetrahydropyran-4-ylethynyl)-1H-indazole (C14)

$Pd(PPh_3)_2Cl_2$ (176 mg, 0.25 mmol) was added to a nitrogen purged solution of 4-ethynyltetrahydropyran (1.1 g, 9.5 mmol), 6-bromo-5-chloro-1H-indazole C1 (1.1 g, 4.7 mmol) and CuI (53 mg, 0.3 mmol) in $Et_3N$ (10 mL) and 1,4-dioxane (10 mL). The solution was stirred at 110° C. for 30 min Methanol and Celite® were added, and the mixture concentrated in vacuo to adsorb the crude mixture onto Celite®. Silica gel chromatography (Gradient: 0-100% EtOAc in heptanes) afforded the product. Yield: 814 mg, 64%. LCMS m/z 261.2 [M+1]$^+$. $^1$H NMR (300 MHz, DMSO-d6) δ 13.31 (s, 1H), 8.07 (t, J=1.3 Hz, 1H), 8.00-7.92 (m, 1H), 7.71 (t, J=0.8 Hz, 1H), 3.84 (ddd, J=11.5, 5.8, 3.6 Hz, 2H), 3.50 (ddd, J=11.4, 8.3, 3.0 Hz, 2H), 3.00 (tt, J=8.4, 4.1 Hz, 1H), 1.94-1.82 (m, 2H), 1.65 (dtd, J=12.4, 8.4, 3.6 Hz, 2H).

Step 2. Synthesis N-(4-fluorophenyl)-6-(2-tetrahydropyran-4-ylethynyl)-1H-indazol-5-amine (C15)

t-Butanol (12 mL) was added to a nitrogen purged vial containing 5-chloro-6-(2-tetrahydropyran-4-ylethynyl)-1H-indazole C14 (814 mg, 3.015 mmol), 4-fluoroaniline (550 mg, 5.0 mmol), sodium t-butoxide (1.2 g, 12.5 mmol), and BrettPhos Pd G4 (75 mg, 0.08). The solution was degassed with nitrogen and stirred at 120° C. overnight. The reaction mixture was diluted with dichloromethane (75 mL) and washed with a 50% saturated aqueous sodium bicarbonate solution (40 mL). The organic phase was passed through a phase separator, Celite® was added, and the solvent was removed by concentration in vacuo. Purification of the Celite®-adsorbed mixture by silica gel chromatography (Gradient: 0-100% EtOAc in heptanes) yielded the product C15. Yield: 696 mg, 66%. LCMS m/z calc. 336.2 [M+1]$^+$ confirmed the product C15 as well as the presence of the cyclized compound S6 as the minor component (2:1). The mixture was progressed to step 3 to complete the conversion to the cyclized product S6.

Step 3. Synthesis of 5-(4-fluorophenyl)-6-(tetrahydro-2H-pyran-4-yl)-1,5-dihydropyrrolo[2,3-f]indazole (S6)

A solution of N-(4-fluorophenyl)-6-(2-tetrahydropyran-4-ylethynyl)-1H-indazol-5-amine $C_{15}$ (696 mg, 2.0 mmol) in DMSO (3 mL) was heated at 150° C. for 90 min A 50% saturated aqueous sodium bicarbonate solution (25 mL) was added and the mixture washed with EtOAc (2×100 mL), dried over sodium sulfate and concentrated in vacuo to yield the product. Yield: 638 mg, 89%. LCMS m/z 336.2 [M+1]$^+$. $^1$H NMR (300 MHz, DMSO-d6) δ 12.61 (s, 1H), 8.00-7.93 (m, 1H), 7.59-7.42 (m, 5H), 7.18-7.15 (m, 1H), 6.51 (t, J=0.8 Hz, 1H), 3.91-3.81 (m, 2H), 3.30-3.18 (m, 2H), 2.90-2.79 (m, 1H), 1.74-1.63 (m, 4H).

Preparation S7 benzyl 5-(4-fluorophenyl)-6-(tetrahydro-2H-pyran-4-yl)pyrrolo[2,3-f]indazole-1(5H)-carboxylate (S7)

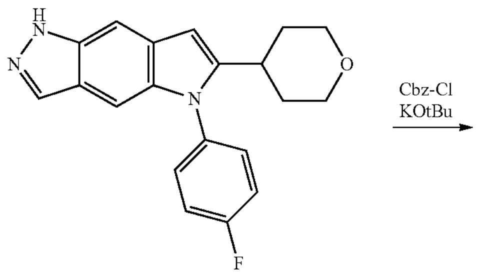

S6
(compound 60)

-continued

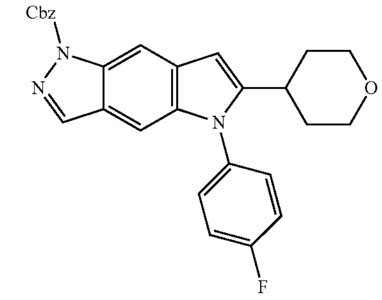

S7

KOtBu (1.3 g, 11.9 mmol) was added to a solution of 5-(4-fluorophenyl)-6-tetrahydropyran-4-yl-1H-pyrrolo[2,3-f]indazole S6 (2.0 g, 6.0 mmol) in THF (50 mL) at 0° C. under Na. After 2 h, Cbz-Cl (3.6 mL of 3 M, 10.8 mmol) was added and the mixture stirred at 0° C. for 1 h. Aqueous sodium bicarbonate solution was added and the mixture was extracted with EtOAc (3×). The organic phase was dried over $MgSO_4$ and concentrated in vacuo. Purification was performed by silica gel chromatography (Gradient: 0-50% EtOAc in heptanes), then by combining clean fractions and concentrating in vacuo. The residue was then suspended in a minimal amount of MTBE and the solid product collected by filtration to yield the product as an off white solid. Yield: 2.2 g, 79%. LCMS m/z 470.2 $[M+1]^+$. $^1H$ NMR (300 MHz, Chloroform-d) δ 8.40 (s, 1H), 8.14 (d, J=0.9 Hz, 1H), 7.59 (dd, J=7.9, 1.7 Hz, 2H), 7.47-7.30 (m, 7H), 7.22 (t, J=0.9 Hz, 1H), 6.58 (d, J=0.8 Hz, 1H), 5.59 (s, 2H), 4.01 (dd, J=11.5, 4.0 Hz, 2H), 3.37 (td, J=11.7, 2.3 Hz, 2H), 2.84 (tt, J=11.5, 4.1 Hz, 1H), 1.96-1.71 (m, 4H).

Preparation S8 and Preparation S9

5-(4-fluoro-3-methylphenyl)-6-(tetrahydro-2H-pyran-4-yl)-1,5-dihydropyrrolo[2,3-f]indazole (S8) and benzyl 5-(4-fluoro-3-methylphenyl)-6-(tetrahydro-2H-pyran-4-yl)pyrrolo[2,3-f]indazole-1(5H)-carboxylate (S9)

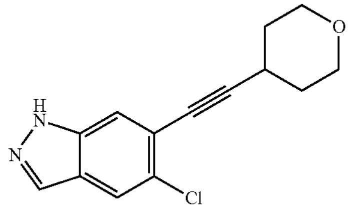

C14

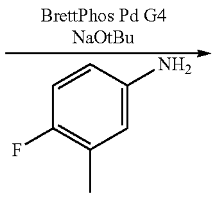

-continued

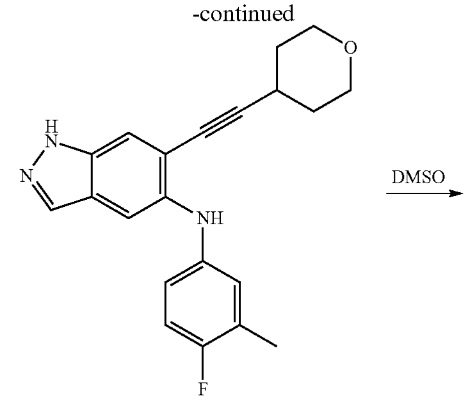

C16

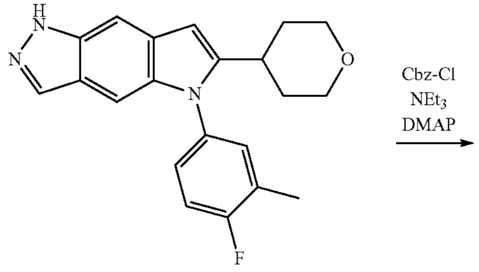

S8

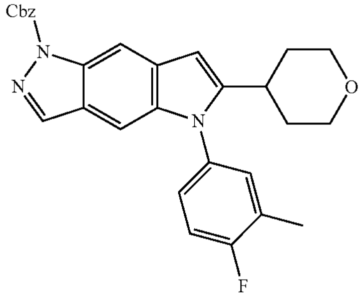

S9

Step 1. Synthesis of N-(4-fluoro-3-methyl-phenyl)-6-(2-tetrahydropyran-4-ylethynyl)-1H-indazol-5-amine; 5-(4-fluoro-3-methyl-phenyl)-6-tetrahydropyran-4-yl-1H-pyrrolo[2,3-f]indazole (C16)

t-Butanol (58 mL) was added to a vial containing 5-chloro-6-(2-tetrahydropyran-4-ylethynyl)-1H-indazole C14 (4 g, 14.8 mmol), 4-fluoro-3-methyl-aniline (2.8 g, 22.3 mmol), sodium t-butoxide (4.3 g, 44.4 mmol), and BrettPhos Pd G4 (682 mg, 0.7 mmol). The solution was degassed with nitrogen and heated at 120° C. overnight. An additional one equivalent of NaOtBu, 0.05 equivalents of BrettPhos Pd G4, and 0.3 equivalents of 4-fluoro-3-methyl-aniline were added and the mixture heated at 110° C. for an additional three days. A further 1 g of NaOtBu, 500 mg of BrettPhos Pd G4, and 600 mg of 4-fluoro-3-methyl-aniline were added and the mixture heated overnight at 110° C., which resulted in consumption of C14. The reaction mixture was concentrated in vacuo and the residue was diluted with dichloromethane (300 mL). The mixture was washed with 50% saturated sodium bicarbonate solution (200 mL). The organic layer was passed through a phase separator and concentrated under reduced pressure. Silica gel chromatography (Gradient: 0-100% EtOAc in heptanes) afforded the product C16.

Yield: 2.3 g, 42%. LCMS m/z 350.25 [M+1]$^+$ confirmed the product C16 as well as the cyclized product S8 (1:1). The mixture was progressed to step 2 to complete the conversion to S8.

Step 2. Synthesis of 5-(4-fluoro-3-methylphenyl)-6-(tetrahydro-2H-pyran-4-yl)-1,5-dihydropyrrolo[2,3-f]indazole (S8)

A solution of N-(4-fluoro-3-methyl-phenyl)-6-(2-tetrahydropyran-4-ylethynyl)-1H-indazol-5-amine and 5-(4-fluoro-3-methyl-phenyl)-6-tetrahydropyran-4-yl-1H-pyrrolo[2,3-f]indazole C16 (2.3 g, 6.2 mmol) was dissolved in DMSO (9.4 mL) was heated at 150° C. for 90 min. A 50% saturated aqueous sodium bicarbonate solution (50 mL) was added and the mixture washed with EtOAc (2×100 mL), dried over sodium sulfate, and concentrated in vacuo to yield the product. Yield: 2.1 g, 98%. $^1$H NMR (300 MHz, DMSO-d6) δ 12.60 (s, 1H), 7.97 (t, J=1.3 Hz, 1H), 7.55 (t, J=1.1 Hz, 1H), 7.48-7.26 (m, 3H), 7.22-7.14 (m, 1H), 6.49 (s, 1H), 3.93-3.79 (m, 2H), 3.25 (td, J=11.2, 3.8 Hz, 2H), 2.92-2.78 (m, 1H), 2.34 (d, J=2.0 Hz, 3H), 1.78-1.60 (m, 4H).

Step 3. Synthesis of benzyl 5-(4-fluoro-3-methylphenyl)-6-(tetrahydro-2H-pyran-4-yl)pyrrolo[2,3-f]indazole-1(5H)-carboxylate (S9)

KOtBu (2.3 g, 20.7 mmol) was added to a solution of 5-(4-fluoro-3-methyl-phenyl)-6-tetrahydropyran-4-yl-1H-pyrrolo[2,3-f]indazole S8 (2.3 g, 6.5 mmol) in THF (50 mL) at 0° C. After 15 min, the ice bath was removed and the mixture was warmed to room temperature. After 45 min, the reaction mixture was cooled to 0° C. with an ice bath, and Cbz-Cl (5.4 mL of 3 M, 16.20 mmol) was added. The mixture was stirred overnight, then poured into an aqueous sodium bicarbonate solution (200 mL). The mixture was extracted with EtOAc (3×) and dichloromethane (1×). The combined organic phases were dried over magnesium sulfate and concentrated in vacuo. Purification by silica gel chromatography (Gradient: 0-50% EtOAc in heptanes) afforded the product as a white solid. Yield: 2.6 g, 84%. LCMS m/z 484.2 [M+H]$^+$. $^1$H NMR (300 MHz, Chloroform-d) δ 8.30 (s, 1H), 8.05 (d, J=0.8 Hz, 1H), 7.55-7.44 (m, 2H), 7.41-7.24 (m, 3H), 7.15-7.04 (m, 4H), 6.47 (d, J=0.8 Hz, 1H), 5.49 (s, 2H), 3.92 (ddd, J=11.8, 4.4, 1.9 Hz, 2H), 3.29 (td, J=11.7, 2.6 Hz, 2H), 2.75 (tt, J=11.3, 4.1 Hz, 1H), 2.31 (d, J=1.9 Hz, 3H), 1.87-1.61 (m, 4H).

Preparation S10 benzyl 5-(3,4-difluorophenyl)-6-(tetrahydro-2H-pyran-4-yl)pyrrolo[2,3-f]indazole-1(5H)-carboxylate (S10)

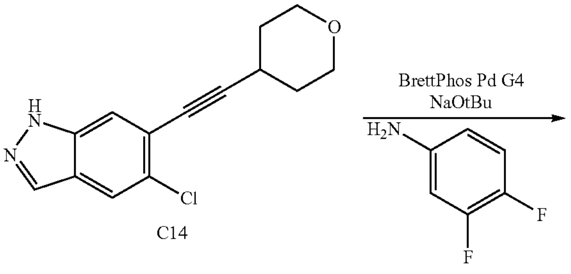

C14

-continued

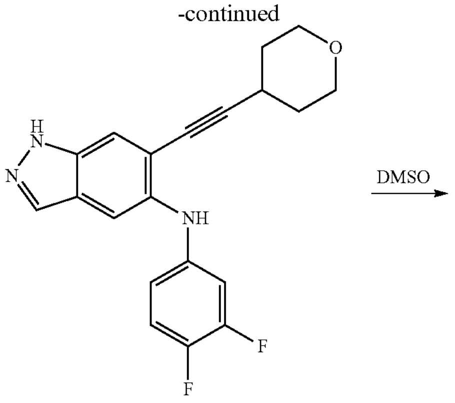

C17

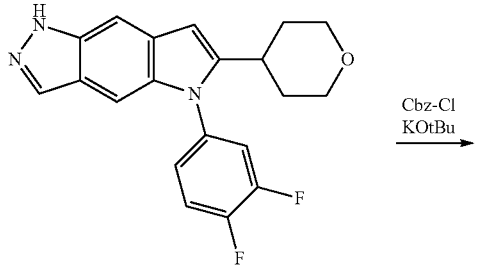

C18

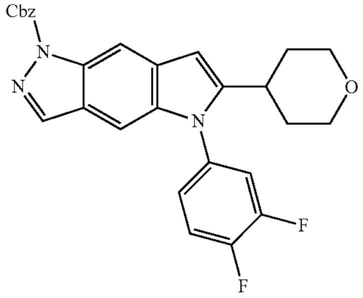

S10

Step 1. Synthesis of N-(3,4-difluorophenyl)-6-((tetrahydro-2H-pyran-4-yl)ethynyl)-1H-indazol-5-amine (C17)

C17 was prepared from C14 and using 3,4-difluoroaniline using the method described for C4 in preparation S3. Purification on silica gel (Gradient: 0-40% EtOAc in heptanes) yielded the product C17. Yield: 3.5 g, 65%. LCMS m/z 354.2 [M+H]$^+$ confirmed the product was present as a mixture with ring closed product C18 (4:6). The mixture was advanced to step 2 to complete the conversion to cyclized product.

Step 2. Synthesis of 5-(3,4-difluorophenyl)-6-(tetrahydro-2H-pyran-4-yl)-1,5-dihydropyrrolo[2,3-f]indazole (C18)

C18 was prepared from C17 (product mixture with C18 from step 1) using the method described for synthesis of S3 from C4. The product was purified by silica gel chromatography to afford the product C18 as a pale yellow solid. Yield: 2.5 g, 85%. LCMS m/z 354.2 [M+H]$^+$. $^1$H NMR (400 MHz, Chloroform-d) δ 10.32 (s, 1H), 8.08 (d, J=1.0 Hz, 1H), 7.59 (t, J=1.1 Hz, 1H), 7.40 (dt, J=9.9, 8.6 Hz, 1H), 7.31-7.22 (m, 2H), 7.18 (dddd, J=8.3, 4.0, 2.5, 1.6 Hz, 1H), 6.50 (d, J=0.9 Hz, 1H), 4.02 (ddd, J=11.6, 4.3, 1.7 Hz, 2H), 3.40 (td, J=11.8, 2.3 Hz, 2H), 2.83 (tt, J=11.5, 3.9 Hz, 1H), 1.87 (dtd, J=13.4, 11.7, 4.3 Hz, 2H), 1.77 (dq, J=13.2, 2.1 Hz, 2H).

Step 3. Synthesis of benzyl 5-(3,4-difluorophenyl)-6-(tetrahydro-2H-pyran-4-yl)pyrrolo[2,3-f]indazole-1(5H)-carboxylate (S10)

S10 was prepared from C18 according to the method described for preparation of S5 from C13. Purification by column chromatography on silica gel (Gradient: 0-5% of EtOAc in dichloromethane) afforded the product S10 as pale yellow solid. Yield: 2.9 g, 87%. LCMS m/z 488.22 $[M+1]^+$. $^1H$ NMR (400 MHz, Chloroform-d) δ 8.41 (s, 1H), 8.16 (d, J=0.9 Hz, 1H), 7.65-7.52 (m, 2H), 7.48-7.35 (m, 4H), 7.32-7.27 (m, 1H), 7.26 (t, J=1.0 Hz, 1H), 7.22-7.15 (m, 1H), 6.59 (d, J=0.9 Hz, 1H), 5.59 (s, 2H), 4.09-3.97 (m, 2H), 3.40 (td, J=11.8, 2.1 Hz, 2H), 2.85 (tt, J=11.6, 3.9 Hz, 1H), 1.97-1.82 (m, 2H), 1.82-1.72 (m, 2H).

Preparation S11 benzyl 5-(3-chloro-4-fluorophenyl)-6-(tetrahydro-2H-pyran-4-yl)pyrrolo[2,3-f]indazole-1(5H)-carboxylate (S11)

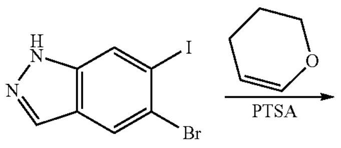

C7

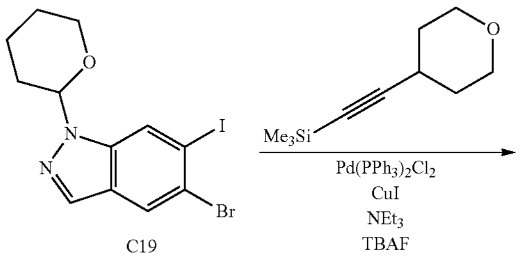

C19

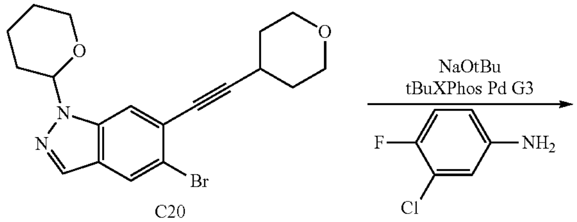

C20

-continued

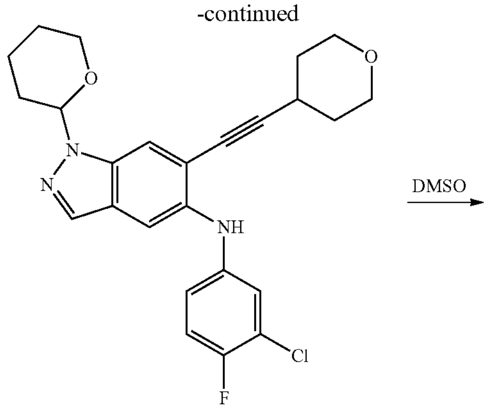

C21

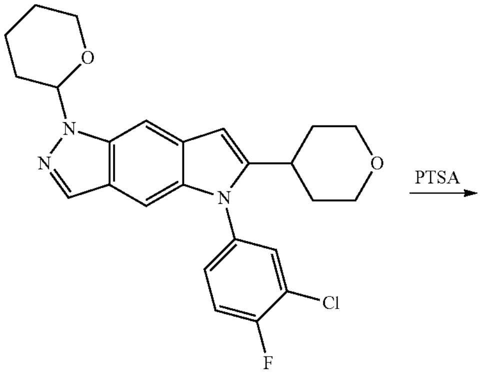

C22

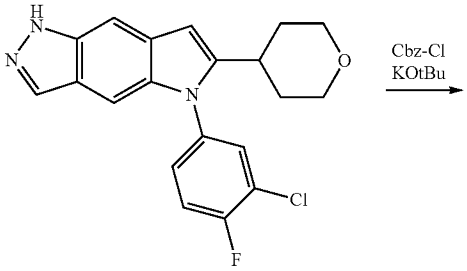

C23

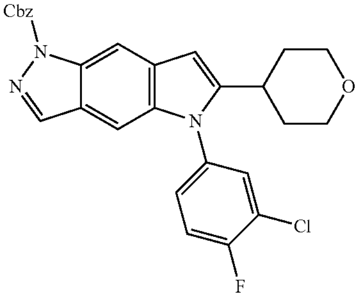

S11

Step 1. Synthesis of 5-bromo-6-iodo-1-tetrahydropyran-2-yl-indazole (C19)

3,4-dihydro-2H-pyran (6.6 mL, 72.3 mmol) and 4-methylbenzenesulfonic acid hydrate (460 mg, 2.5 mmol) were added to a solution of 5-bromo-6-iodo-1H-indazole C7 (7.8 g, 24.2 mmol) in dichloromethane (150 mL). After stirring at room temperature for 1 h, the mixture was washed with saturated sodium bicarbonate solution and the organic layer concentrated in vacuo. Purification by silica gel chromatography (Gradient: 0-50% EtOAc in heptanes) yielded the product as a yellow solid. Yield: 7.4 g, 75%. $^1$H NMR (300 MHz, Chloroform-d) δ 8.23 (d, J=0.9 Hz, 1H), 8.04 (d, J=0.5 Hz, 1H), 7.94 (d, J=1.0 Hz, 1H), 5.67 (dd, J=9.2, 2.7 Hz, 1H), 4.03 (d, J=11.1 Hz, 1H), 3.77 (ddd, J=11.5, 9.6, 3.5 Hz, 1H), 2.60-2.41 (m, 1H), 2.26-2.01 (m, 2H), 1.89-1.62 (m, 3H).

Step 2. Synthesis of 5-bromo-1-tetrahydropyran-2-yl-6-(2-tetrahydropyran-4-ylethynyl)indazole (C20)

A 5 L 3-neck flask equipped with mechanical stirrer was charged with 5-bromo-6-iodo-1-tetrahydropyran-2-yl-indazole C19 (80.5 g, 197.8 mmol), $Et_3N$ (640 mL), and 1,4-dioxane (640 mL). Trimethyl(2-tetrahydropyran-4-ylethynyl)silane (46 g, 239.7 mmol), water (7.1 mL, 394.1 mmol), copper (I) iodide (3.7 g, 19.43 mmol), and $PdCl_2(PPh3)_2$ (6.4 g, 9.118 mmol) was added to the resulting solution. Tetrabutylammonium fluoride (240 mL of 1 M, 240.0 mmol) (1 M in THF) was added over the course of 5 min via an addition funnel and the reaction allowed to stir for 18 h. The mixture was filtered, and the collected solid was washed with EtOAc (100 mL), and then discarded. The combined filtrate was concentrated and the residue partitioned between EtOAc and water (700 mL each). The organic layer was separated, washed with sat aq. ammonium chloride, then saturated aqueous sodium bicarbonate (2×700 mL), water (500 mL), and finally brine (500 mL). The combined water and brine wash layers were extracted with dichloromethane (300 mL), and then all organic layers combined, dried over magnesium sulfate and concentrated in vacuo. The residual dark brown solid was refluxed in MTBE (300 mL) for 5 min, cooled to 0° C. then filtered off, washing with MTBE (100 mL) to give the product as pale orange crystals. Yield: 59.5 g, 77%. LCMS m/z 389.11 [M+1]$^+$. $^1$H NMR (300 MHz, Chloroform-d) δ 7.96 (d, J=0.6 Hz, 1H), 7.95 (d, J=0.9 Hz, 1H), 7.74 (s, 1H), 5.69 (dd, J=9.2, 2.7 Hz, 1H), 4.04 (ddd, J=11.6, 6.4, 3.5 Hz, 3H), 3.77 (ddd, J=11.5, 9.7, 3.3 Hz, 1H), 3.64 (ddd, J=11.3, 7.7, 3.2 Hz, 2H), 3.00 (tt, J=8.0, 4.2 Hz, 1H), 2.53 (dtd, J=11.3, 9.1, 5.1 Hz, 1H), 2.28-1.94 (m, 3H), 1.94-1.62 (m, 4H).

Step 3 and Step 4. Synthesis of 5-(3-chloro-4-fluoro-phenyl)-1-tetrahydropyran-2-yl-6-tetrahydropyran-4-yl-pyrrolo[2,3-f]indazole (C22) via C21

To a solution of 5-bromo-1-tetrahydropyran-2-yl-6-(2-tetrahydropyran-4-ylethynyl)indazole C22 (3.0 g, 7.8 mmol) in xylene (75 mL) was added 3-chloro-4-fluoro-aniline (1.0 g, 7.0 mmol), NaOtBu (2.4 g, 24.2 mmol) and tBuXPhos Pd G3 (510 mg, 0.6 mmol) and the mixture stirred at room temperature for 3 h. The reaction was quenched with addition of silica and purified by silica gel chromatography (Gradient: 10-50% EtOAc in dichloromethane) to afford C21 (3.0 g, 94%) as confirmed by LCMS m/z 454.52 [M+1]$^+$. This crude product C21 was heated in DMSO (30 mL) at 100° C. for 40 min. The mixture was diluted with 50% brine and extracted with dichloromethane (3×100 mL). The combined organic layers were dried over magnesium sulfate and concentrated in vacuo to afford the product C22. Yield: 2.90 g, 91%. LCMS m/z 454.51 [M+H]$^+$. $^1$H NMR (400 MHz, Chloroform-d) δ 8.00 (d, J=0.9 Hz, 1H), 7.69 (t, J=1.0 Hz, 1H), 7.48 (dd, J=6.5, 2.5 Hz, 1H), 7.37 (t, J=8.5 Hz, 1H), 7.33-7.28 (m, 2H), 7.22 (t, J=0.9 Hz, 1H), 6.51 (t, J=0.8 Hz, 1H), 5.78 (dd, J=9.3, 2.7 Hz, 1H), 4.03 (t, J=12.9 Hz, 4H), 3.87-3.72 (m, 1H), 3.39 (dd, J=12.9, 10.7 Hz, 2H), 2.80 (td, J=11.1, 10.6, 5.7 Hz, 1H), 2.23-2.01 (m, 2H), 1.93-1.73 (m, 9H).

Step 5. Synthesis of 5-(3-chloro-4-fluoro-phenyl)-6-tetrahydropyran-4-yl-1H-pyrrolo[2,3-f]indazole (C23)

To a suspension of 5-(3-chloro-4-fluoro-phenyl)-1-tetrahydropyran-2-yl-6-tetrahydropyran-4-yl-pyrrolo[2,3-f]indazole C22 (2.9 g, 6.4 mmol) in a mixture of methanol (40 mL), EtOAc (40 mL) and water (20 mL) was added 4-methylbenzenesulfonic acid hydrate (6.0 g, 31.5 mmol). The mixture was heated at 70° C. for 1 h and the reaction mixture was then concentrated in vacuo. The residue was suspended in EtOAc and resulting precipitate was filtered and dried to give a tan solid. The crude product was dissolved in dichloromethane, washed with saturated sodium bicarbonate, and then concentrated in vacuo to afford the product which was used without further purification. Yield: 1.95 g, 75%. LCMS m/z 370.39 [M+1]$^+$.

Step 6. Synthesis of benzyl 5-(3-chloro-4-fluoro-phenyl)-6-(tetrahydro-2H-pyran-4-yl)pyrrolo[2,3-f]indazole-1(5H)-carboxylate (S11)

KOtBu (1.1 g, 9.8 mmol) was added to a solution of 5-(3-chloro-4-fluoro-phenyl)-6-tetrahydropyran-4-yl-1H-pyrrolo[2,3-f]indazole C23 (2.0 g, 4.8 mmol) in THF (100 mL) at 0° C. After 10 min, Cbz-Cl (4.8 mL of 3 M, 14.4 mmol) was added and the reaction warmed to room temperature and stirred for 3 h. Aqueous saturated ammonium chloride solution and dichloromethane were added. The organic phase was separated on a phase separator and purification performed by silica gel chromatography (Gradient: EtOAc in dichloromethane) to afford the product. Yield: 2.10 g, 78%. LCMS 504.3 [M+1]$^+$. $^1$H NMR (400 MHz, Chloroform-d) δ 8.38 (s, 1H), 8.13 (d, J=0.9 Hz, 1H), 7.65-7.51 (m, 2H), 7.47 (dd, J=6.4, 2.5 Hz, 1H), 7.46-7.34 (m, 4H), 7.33-7.25 (m, 2H), 6.56 (t, J=0.8 Hz, 1H), 5.56 (s, 2H), 4.00 (d, J=11.4 Hz, 2H), 3.38 (t, J=11.7 Hz, 2H), 2.80 (tt, J=11.5, 3.8 Hz, 1H), 1.95-1.66 (m, 4H).

Preparation S12 benzyl 5-(4-fluoro-3-methylphenyl)-3-methyl-6-(tetrahydro-2H-pyran-4-yl)pyrrolo[2,3-f]indazole-1(5H)-carboxylate (S12)

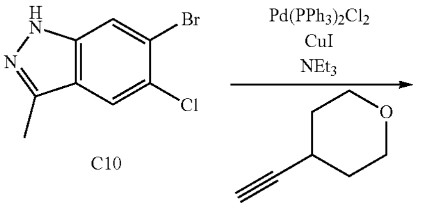

C10

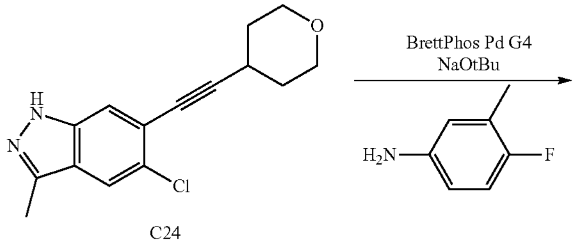

C24

-continued

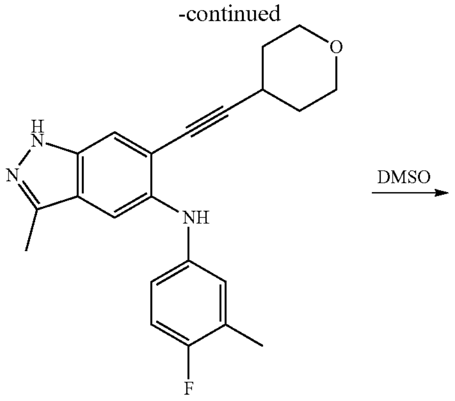

C25

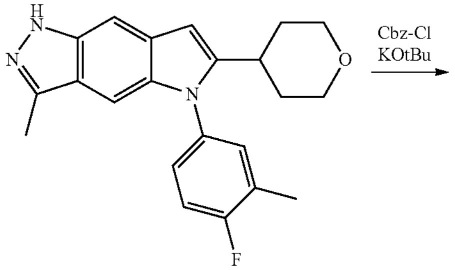

C26

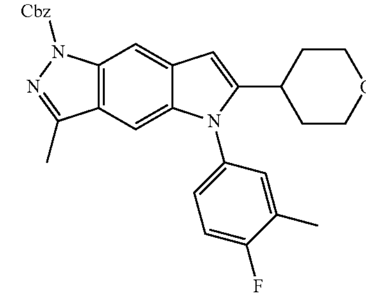

S12

Step 1. Synthesis of 5-chloro-3-methyl-6-(3-methylbut-1-ynyl)-1H-indazole (C24)

$Pd(PPh_3)_2Cl_2$ (525 mg, 0.75 mmol) was added to a nitrogen purged solution of 3-methylbut-1-yne (3.2 mL, 31.3 mmol), 6-bromo-5-chloro-3-methyl-1H-indazole (3.5 g, 14.2 mmol) and CuI (160 mg, 0.8 mmol) in $Et_3N$ (35 mL) and 1,4-dioxane (35 mL). The solution was stirred at 90° C. for 18 h. The mixture was then adsorbed directly onto silica gel and purified by silica gel chromatography (Eluent: EtOAc in heptanes) to yield the product. Yield: 2.7 g, 82%. LCMS m/z 233.15 $[M+1]^+$. $^1H$ NMR (400 MHz, DMSO-d6) δ 12.85 (s, 1H), 7.90 (s, 1H), 7.57 (s, 1H), 2.87 (m, J=6.9 Hz, 1H), 1.25 (dd, J=6.9, 1.5 Hz, 7H).

Step 2. Synthesis of N-(4-fluoro-3-methylphenyl)-3-methyl-6-((tetrahydro-2H-pyran-4-yl)ethynyl)-1H-indazol-5-amine (C25)

5-chloro-3-methyl-6-(3-methylbut-1-ynyl)-1H-indazole (2.6 g, 11.0 mmol), 4-fluoro-3-methyl-aniline (2.2 g, 17.58 mmol) and sodium t-butoxide (4.4 g, 45.8 mmol) were placed in a reaction vial under nitrogen. t-Butanol (37 mL) and BrettPhos Pd G4 (281 mg, 0.31 mmol) was added and the mixture was degassed with nitrogen. The mixture was then heated at 120° C. overnight. Water and dichloromethane were added, and the phases were separated on a phase separator. The combined organic layers were concentrated in vacuo and purified by silica gel chromatography (Eluent: EtOAc in Heptanes) to yield the product C25 together with the cyclized product C26 as a mixture. Yield: 2.7 g, 77%. LCMS m/z 322.3 $[M+1]^+$. The mixture of C25 and C26 was advanced to step 3 without further to complete the conversion to C26.

Step 3. Synthesis of 5-(4-fluoro-3-methylphenyl)-3-methyl-6-(tetrahydro-2H-pyran-4-yl)-1,5-dihydropyrrolo[2,3-f]indazole (C26)

A mixture of C25 and C26 (290 mg, 0.8 mmol) from step 2 was dissolved in DMSO (1.2 mL) and heated at 150° C. for 90 min. A 50% saturated solution of sodium bicarbonate (50 mL) was added to the reaction mixture. The mixture was then extracted with EtOAc (2×) and the combined organic layers were dried over sodium sulfate. Purification by silica gel chromatography (Eluent: EtOAc in heptanes) afforded the product C26. Yield: 247 mg, 77%. LCMS m/z 364.3 [M+H]+. $^1H$ NMR (400 MHz, DMSO-d6) δ 12.15 (s, 1H), 7.53-7.30 (m, 4H), 7.04 (s, 1H), 6.47 (s, 1H), 3.85 (d, J=10.5 Hz, 2H), 3.25 (dt, J=13.2, 6.5 Hz, 2H), 2.82 (tt, J=10.2, 4.9 Hz, 1H), 2.40 (s, 3H), 2.34 (d, J=1.8 Hz, 3H), 1.76-1.63 (m, 4H).

Step 4. Synthesis of benzyl 5-(4-fluoro-3-methylphenyl)-3-methyl-6-(tetrahydro-2H-pyran-4-yl)pyrrolo[2,3-f]indazole-1(5H)-carboxylate (S12)

KOtBu (775 mg, 6.9 mmol) was added to a solution of 5-(4-fluoro-3-methyl-phenyl)-3-methyl-6-tetrahydropyran-4-yl-1H-pyrrolo[2,3-f]indazole C26 (1.9 g, 5.3 mmol) in THF (45 mL) at 0° C. After 5 min, Cbz-Cl (2 mL of 3 M, 6.0 mmol) was added and the mixture stirred at 0° C. for 1 h. Aqueous saturated ammonium chloride and dichloromethane were added, and the organic phase was isolated on a phase separator. Purification by silica gel chromatography (Eluent: EtOAc in dichloromethane) provided the product. Yield: 1.20 g, 45%. LCMS m/z 498.3 $[M+H]^+$. $^1H$ NMR (400 MHz, Acetone-d6) δ 8.33 (s, 1H), 7.60 (d, J=7.5 Hz, 2H), 7.50-7.31 (m, 7H), 7.27 (s, 1H), 6.65 (s, 1H), 5.53 (s, 2H), 3.89 (d, J=11.6 Hz, 2H), 3.38-3.11 (m, 3H), 3.01-2.85 (m, 1H), 2.45 (s, 3H), 2.38 (d, J=2.0 Hz, 3H), 1.78 (s, 4H).

B. Synthesis of Compounds 1-215

All the specific and generic compounds, and the intermediates disclosed for making those compounds, are considered to be part of the invention disclosed herein.

Compound 1

5-(4-fluoro-3-methyl-phenyl)-7-iodo-6-isopropyl-1H-pyrrolo[2,3-f]indazole (I)

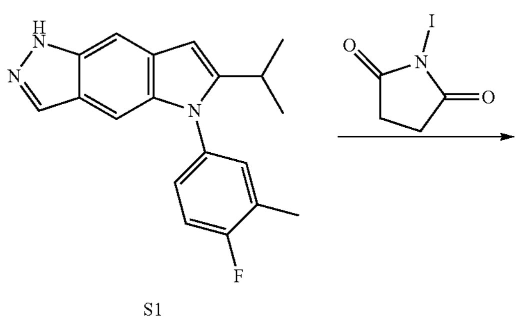

S1

-continued

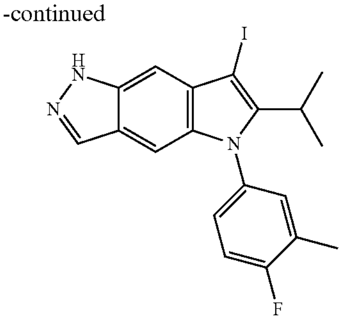

1

Dichloroethane (12.6 mL) was added to a mixture of 1-iodopyrrolidine-2,5-dione (285 mg, 1.3 mmol) and 5-(4-fluoro-3-methyl-phenyl)-6-isopropyl-1H-pyrrolo[2,3-f]indazole S1 (420 mg, 1.3 mmol). The reaction was stirred at for 30 min, then adsorbed onto Celite® by addition of Celite® to the mixture, then concentration in vacuo. Purification by silica gel chromatography (Gradient: 0-50% EtOAc in heptanes) yielded the product. Yield: 194.6 mg, 34%. LCMS m/z 434.09 $[M+1]^+$. $^1H$ NMR (300 MHz, DMSO-d6) δ 12.73 (s, 1H), 8.02 (t, J=1.3 Hz, 1H), 7.48-7.29 (m, 4H), 7.09 (t, J=0.8 Hz, 1H), 3.04 (m, J=7.1 Hz, 1H), 2.33 (d, J=2.0 Hz, 3H), 1.34 (dd, J=7.1, 1.3 Hz, 6H).

Compound 2 and Compound 3 ethyl 5-(4-fluoro-3-methyl-phenyl)-6-isopropyl-1H-pyrrolo[2,3-f]indazole-7-carboxylate (2) and 5-(4-fluoro-3-methyl-phenyl)-6-isopropyl-1H-pyrrolo[2,3-f]indazole-7-carboxylic Acid (3)

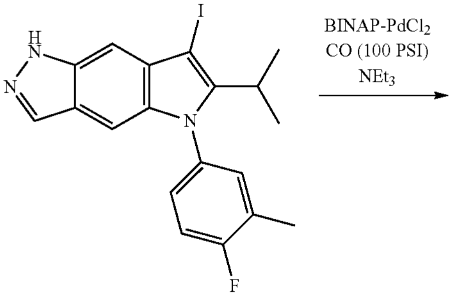

1

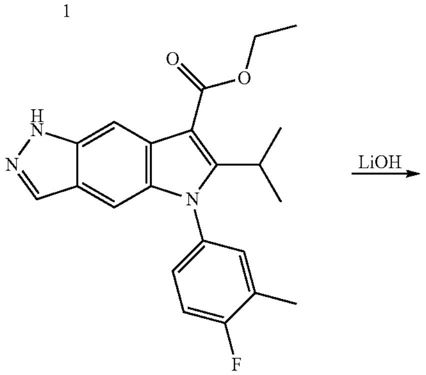

2

-continued

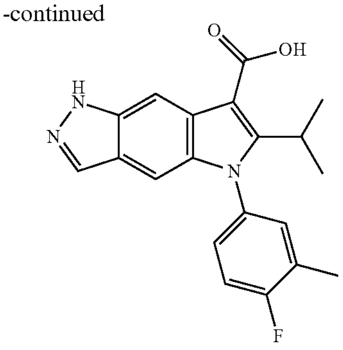

3

Step 1. Synthesis of ethyl 5-(4-fluoro-3-methyl-phenyl)-6-isopropyl-1H-pyrrolo[2,3-f]indazole-7-carboxylate (2)

5-(4-fluoro-3-methyl-phenyl)-7-iodo-6-isopropyl-1H-pyrrolo[2,3-f]indazole 1 (87 mg, 0.2 mmol) and dichloro [(R)-(+)-2,2'-bis(diphenylphosphino)-1,1'-binaphthyl]palladium(II) (approx. 15.9 mg, 0.02 mmol) were weighed in high pressure reactor vessel. The vessel was placed under an inert atmosphere by applying vacuum then purging with nitrogen (×3). Degassed ethanol and $NEt_3$ (approximately 40 mg, 55 μL, 0.4 mmol) were added. The mixture was then placed under an atmosphere 100 psi carbon monoxide and heated at 100° C. overnight. The mixture was concentrated in vacuo, diluted with dichloromethane, and washed with 50% saturated sodium bicarbonate. The organic phase was isolated by passing through a phase separator and then concentrated in vacuo. Silica gel chromatography (Gradient: 0-100% EtOAc in heptanes) yielded the product. Yield: 45.5 mg, 58%. LCMS m/z 380.26 $[M+1]^+$. $^1H$ NMR (300 MHz, DMSO-d6) δ 12.78 (s, 1H), 8.13 (t, J=1.1 Hz, 1H), 8.01 (t, J=1.3 Hz, 1H), 7.53-7.31 (m, 3H), 7.06 (t, J=0.8 Hz, 1H), 4.39 (q, J=7.1 Hz, 2H), 3.53-3.41 (m, 1H), 2.35 (d, J=2.0 Hz, 3H), 1.44 (t, J=7.1 Hz, 3H), 1.32 (d, J=7.1 Hz, 6H).

Step 2. Synthesis of 5-(4-fluoro-3-methyl-phenyl)-6-isopropyl-1H-pyrrolo[2,3-f]indazole-7-carboxylic Acid (3)

An aqueous solution of LiOH (4.26 mL of 2 M, 8.5 mmol) was added to a solution of ethyl 5-(4-fluoro-3-methyl-phenyl)-6-isopropyl-1H-pyrrolo[2,3-f]indazole-7-carboxylate 2 (324 mg, 0.9 mmol) in THF (6 mL) and methanol (2 mL). The reaction was stirred at 70-80° C. for ~40 hours. The reaction mixture was concentrated in vacuo, then diluted with dichloromethane and washed with water. 6M HCl was added dropwise to the aqueous layer until a precipitate formed. The aqueous layer was then extracted with dichloromethane. These combined dichloromethane layers were purified by chromatography on a reverse phase column (C18 column. Gradient: 10-100% acetonitrile in water with 0.1% TFA). 10% saturated sodium bicarbonate was added to the combined product fractions, and the mixture was extracted with dichloromethane. The dichloromethane layer was then dried and concentrated to give the product. Yield: 131.7 mg, 43%. LCMS m/z 352.14 $[M+1]^+$. $^1H$ NMR (400 MHz, DMSO-d6) δ 12.71 (s, 1H), 12.32 (s, 1H), 8.17 (t, J=1.1 Hz, 1H), 7.99 (d, J=1.1 Hz, 1H), 7.47 (dd, J=6.8, 2.5 Hz, 1H), 7.43 (t, J=8.9 Hz, 1H), 7.36 (ddd, J=8.3, 4.6, 2.6 Hz, 1H), 7.02 (d, J=1.2 Hz, 1H), 3.55 (m, J=7.1 Hz, 1H), 2.35 (d, J=1.9 Hz, 3H), 1.31 (d, J=7.1 Hz, 6H).

Compound 4

[5-(4-fluoro-3-methyl-phenyl)-6-isopropyl-1H-pyrrolo[2,3-f]indazol-7-yl]-morpholino-methanone (4)

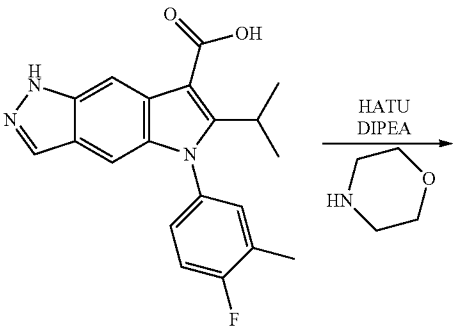

3

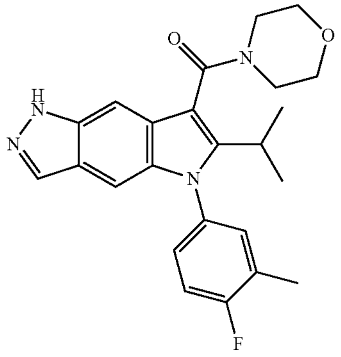

4

To a solution of 5-(4-fluoro-3-methyl-phenyl)-6-isopropyl-1H-pyrrolo[2,3-f]indazole-7-carboxylic acid 3 (40 mg, 0.1 mmol) in DMF (1.5 mL) was added N-ethyl-N-isopropyl-propan-2-amine (30 μL, 0.2 mmol) followed by HATU reagent (47 mg, 0.1 mmol) and morpholine (20 μL, 0.2 mmol). The mixture was stirred at room temperature overnight, and then concentrated to dryness. The mixture was purified on a by reverse phase chromatography (C18 column; Gradient: 10-100% acetonitrile in water with 0.1% TFA). Yield: 31.7 mg, 63%. LCMS m/z 421.22 $[M+1]^+$. $^1H$ NMR (300 MHz, DMSO-d6) δ 12.63 (s, 1H), 8.00 (t, J=1.3 Hz, 1H), 7.55-7.30 (m, 4H), 7.18-7.10 (m, 1H), 3.63 (d, J=24.7 Hz, 8H), 2.91 (m, J=6.9 Hz, 1H), 2.34 (d, J=2.0 Hz, 3H), 1.27 (d, J=6.9 Hz, 6H). LCMS m/z 421.2 $[M+1]^+$.

Compound 5

[5-(4-fluoro-3-methyl-phenyl)-6-isopropyl-1H-pyrrolo[2,3-f]indazol-7-yl]-(4-methylpiperazin-1-yl) methanone (5)

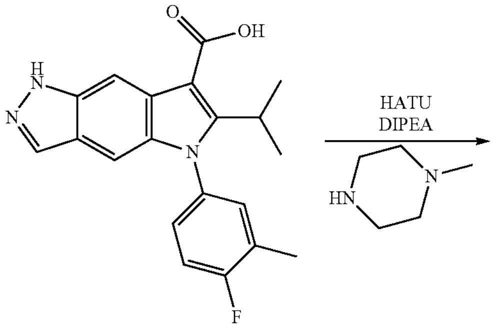

3

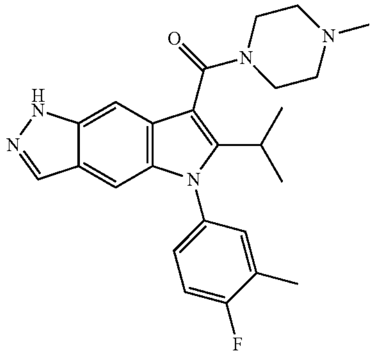

5

Compound 5 was prepared from compound 3 and N-methyl piperazine using the method described for compound 4 to afford the product. Yield: 16.0 mg, 26%. LCMS m/z 434.3 $[M+H]^+$. $^1H$ NMR (300 MHz, DMSO-d6) δ 12.65 (s, 1H), 8.14 (s, 2H), 8.00 (d, J=1.0 Hz, 1H), 7.51-7.43 (m, 1H), 7.43-7.31 (m, 3H), 7.12 (d, J=1.1 Hz, 1H), 3.50-3.1 (m, 8 h) (obscured by water), 2.90 (m, J=6.9 Hz, 1H), 2.34 (d, J=2.0 Hz, 3H), 2.23 (s, 3H), 1.26 (d, J=7.0 Hz, 6H).

Compound 6

N-ethyl-5-(4-fluoro-3-methyl-phenyl)-6-isopropyl-1H-pyrrolo[2,3-f]indazole-7-carboxamide (6)

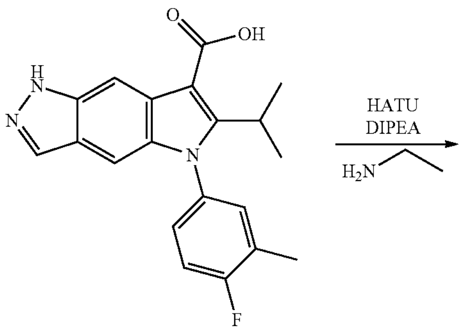

3

-continued

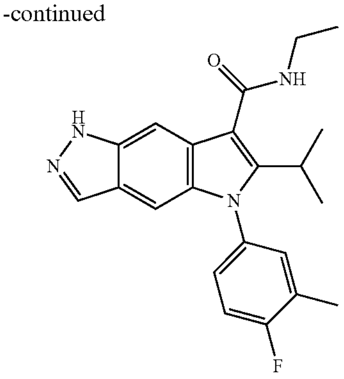

6

Compound 6 was prepared from compound 3 and ethylamine hydrochloride salt using the method described for compound 4 to afford the product. Yield: 14 mg, 51%. LCMS m/z 379.2 $[M+H]^+$. $^1H$ NMR (300 MHz, DMSO-d6) δ 12.69 (s, 1H), 8.09 (t, J=5.7 Hz, 1H), 7.99 (t, J=1.3 Hz, 1H), 7.62 (t, J=1.1 Hz, 1H), 7.46-7.36 (m, 2H), 7.32-7.24 (m, 1H), 7.06 (t, J=0.8 Hz, 1H), 3.43-3.35 (m, 2H), 3.10 (m, J=7.1 Hz, 1H), 2.35 (d, J=1.9 Hz, 3H), 1.29 (d, J=7.1 Hz, 6H), 1.21 (t, J=7.1 Hz, 3H).

Compound 7

5-(4-fluoro-3-methyl-phenyl)-6-isopropyl-N-(oxetan-3-yl)-1H-pyrrolo[2,3-f]indazole-7-carboxamide (7)

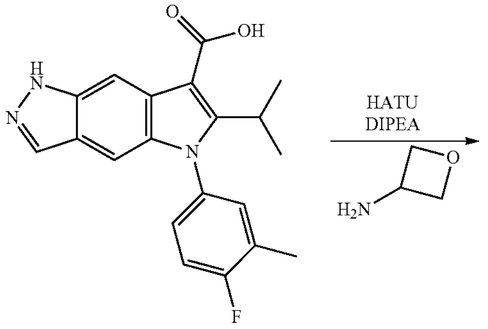

3

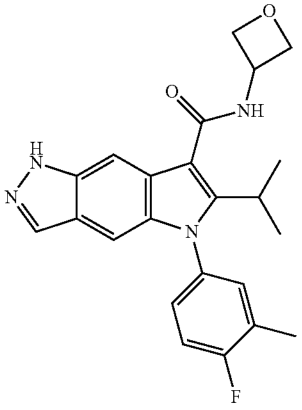

7

Compound 7 was prepared using the method described for compound 4, from compound 3 and oxetan-3-amine to afford the product. Yield: 15.4 mg, 53%. LCMS 407.3 $[M+1]^+$. $^1H$ NMR (300 MHz, DMSO-d6) δ 12.71 (s, 1H), 8.86 (d, J=6.2 Hz, 1H), 8.00 (t, J=1.3 Hz, 1H), 7.72-7.65 (m, 1H), 7.47-7.36 (m, 2H), 7.33-7.24 (m, 1H), 7.08 (t, J=0.8 Hz, 1H), 5.09 (h, J=6.9 Hz, 1H), 4.85 (dd, J=7.5, 6.1 Hz, 2H), 4.66 (t, J=6.4 Hz, 2H), 3.10 (m, J=7.0 Hz, 1H), 2.35 (d, J=1.9 Hz, 3H), 1.28 (d, J=7.1 Hz, 6H).

Compound 8

1-[5-(4-fluoro-3-methyl-phenyl)-6-isopropyl-1H-pyrrolo[2,3-f]indazol-7-yl]pyrrolidin-2-one (8)

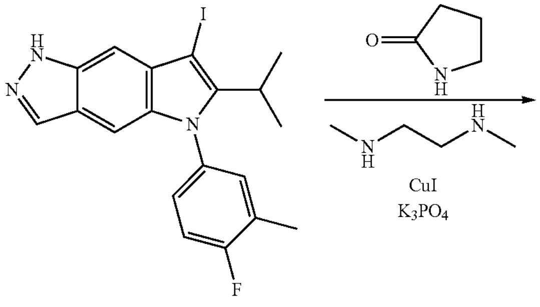

1

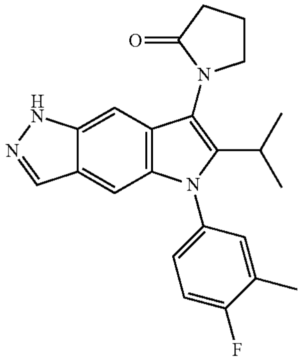

8

CuI (24 mg, 0.13 mmol) and N,N'-dimethylethane-1,2-diamine (72 μL, 0.7 mmol) in 1,4-dioxane (1.6 mL) were heated under microwave conditions at 100° C. for 5 min 5-(4-fluoro-3-methyl-phenyl)-7-iodo-6-isopropyl-1H-pyrrolo[2,3-f]indazole 1 (55 mg, 0.13 mmol), pyrrolidin-2-one (48 μL, 0.6 mmol) and $K_3PO_4$ (67 mg, 0.3 mmol) were added, and the mixture was heated at 100° C. for 3 days. The mixture was diluted with dichloromethane and washed with water. The organic layer was passed through a phase separator and concentrated in vacuo. The product mixture was purified by silica gel chromatography (Gradient: 0-10% methanol in dichloromethane), and then subjected to reverse phase chromatography (Column: Biotage C18 snap cartridge; Gradient: 20-100% acetonitrile in water with trifluoroacetic acid modifier). The eluting product fractions were concentrated in vacuo, diluted with dichloromethane, and washed with 50% saturated sodium bicarbonate solution. The organic layer was passed through a phase separator, then concentrated in vacuo to yield the product. Yield: 10.1 mg, 20%. LCMS m/z 391.2 [M+H]+ $^1H$ NMR (300 MHz, DMSO-d6) δ 12.65 (s, 1H), 8.00 (t, J=1.3 Hz, 1H), 7.51-7.35

(m, 3H), 7.33 (t, J=1.1 Hz, 1H), 7.18-7.07 (m, 1H), 4.03-3.81 (m, 1H), 3.68-3.54 (m, 1H), 2.90 (m, J=7.0 Hz, 1H), 2.66-2.54 (m, 2H), 2.34 (s, 3H), 2.30-2.13 (m, 2H), 1.28-1.11 (m, 6H).

Compound 9

4-[5-(4-fluoro-3-methyl-phenyl)-6-isopropyl-1H-pyrrolo[2,3-f]indazol-7-yl]morpholin-3-one (9)

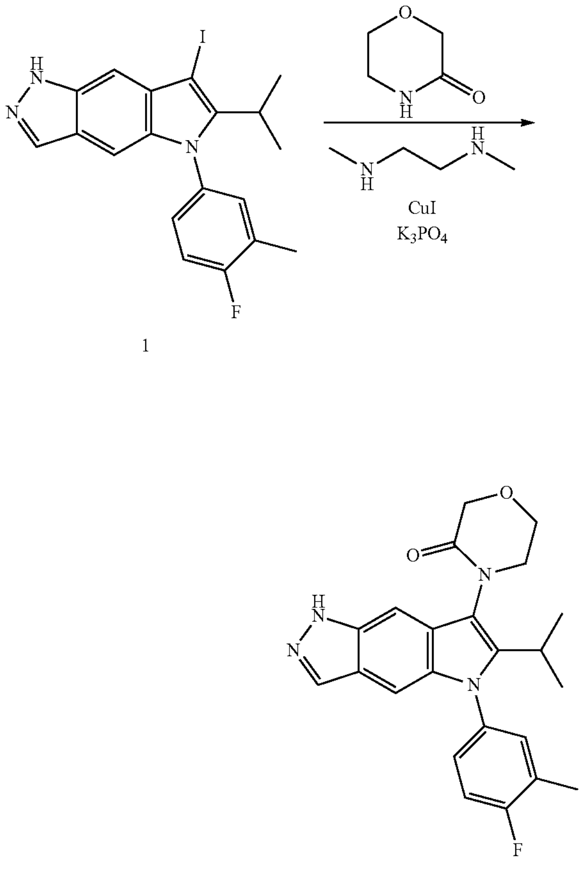

1

9

Compound 9 was prepared using the method described for example 8. Reaction of compound 1 with morpholin-3-one, followed by purification by reverse phase chromatography (Column: Biotage C18 snap cartridge; Gradient: 20-100% acetonitrile in water with trifluoroacetic acid modifier) followed by silica gel chromatography (Gradient: 0-10% methanol in dichloromethane) afforded the product. Yield: 4.1 mg, 4%. LCMS m/z 407.22 $[M+1]^+$. $^1$H NMR (300 MHz, Chloroform-d) δ 10.14 (s, 1H), 7.92 (dd, J=3.1, 1.0 Hz, 1H), 7.48-7.39 (m, 1H), 7.27-7.11 (m, 3H), 7.02 (dd, J=4.5, 1.2 Hz, 1H), 4.62-4.43 (m, 2H), 4.21-4.14 (m, 2H), 3.96 (dt, J=12.3, 5.1 Hz, 1H), 3.80-3.70 (m, 1H), 3.03 (m, J=7.1 Hz, 1H), 2.39 (dd, J=9.3, 2.0 Hz, 3H), 1.37-1.28 (m, 6H).

Compound 10

5-(4-fluoro-3-methyl-phenyl)-6-isopropyl-1H-pyrrolo[2,3-f]indazole-7-carbonitrile (10)

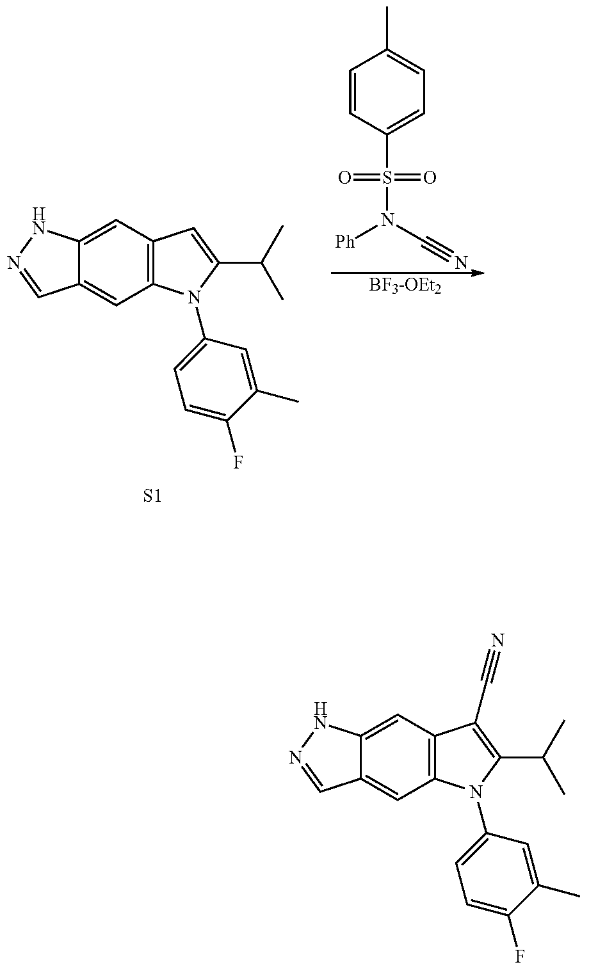

S1

10

Anhydrous 1,2-dichloroethane (2 mL) was added to a mixture of 5-(4-fluoro-3-methyl-phenyl)-6-isopropyl-1H-pyrrolo[2,3-f]indazole S1 (143 mg, 0.4 mmol) and N-cyano-4-methyl-N-phenyl-benzenesulfonamide (250 mg, 0.9 mmol) under nitrogen atmosphere. Boron trifluoride diethyl etherate (215 µL of 46.5% w/v, 0.7 mmol) was added and the mixture was heated at 120° C. for 24 h. The reaction was diluted with dichloromethane (10 mL) and washed with saturated sodium bicarbonate solution. The organic layer was passed through a phase separator and concentrated in vacuo. Purification by silica gel chromatography (Gradient: 0-100% EtOAc in heptanes) yielded the product. Yield: 77.2 mg, 53%. LCMS m/z 333.1 $[M+1]^+$. $^1$H NMR (300 MHz, Chloroform-d) δ 10.07 (s, 1H), 8.13-8.05 (m, 1H), 7.80-7.71 (m, 1H), 7.28-7.14 (m, 4H), 3.04 (hept, J=7.1 Hz, 1H), 2.42 (d, J=2.0 Hz, 3H), 1.50 (dd, J=7.0, 4.6 Hz, 6H).

Compound 11

5-(4-fluoro-3-methyl-phenyl)-6-isopropyl-7-methylsulfonyl-1H-pyrrolo[2,3-f]indazole (11)

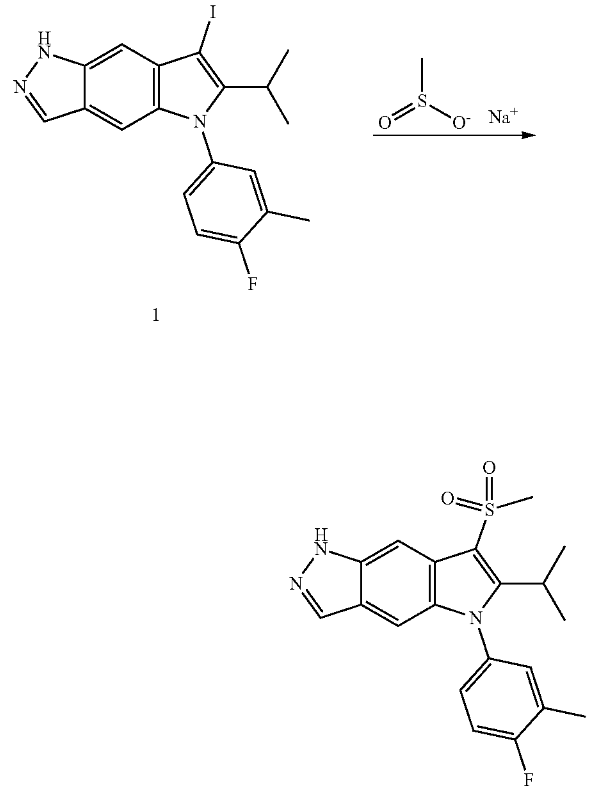

1

11

NMP (2 mL) was added to a mixture of 5-(4-fluoro-3-methyl-phenyl)-7-iodo-6-isopropyl-1H-pyrrolo[2,3-f]indazole 1 (40 mg, 0.09 mmol), sodium methanesulfinate (43 mg, 0.4 mmol), and CuI (82 mg, 0.4 mmol) under nitrogen. The resulting slurry was heated at 125° C. for 3 h. Upon cooling to room temperature, the mixture was filtered. The filter cake was washed with DMSO (1 mL). The solution was passed through a reversed phase column (C18 Aq 50 g column; Gradient: acetonitrile in water with a TFA modifier) and the product concentrated in vacuo. The residue was then diluted with dichloromethane, washed with saturated sodium bicarbonate solution and passed through a phase separator. The isolated organic phase was concentrated in vacuo the purified by chromatography on silica gel (Gradient: 0-100% EtOAc in heptanes). Yield: 15 mg, 43%. LCMS m/z 386.1 $[M+1]^+$. $^1H$ NMR (300 MHz, Chloroform-d) δ 9.84 (s, 1H), 7.99 (t, J=1.1 Hz, 1H), 7.87 (d, J=1.1 Hz, 1H), 7.09-6.98 (m, 3H), 6.92 (d, J=1.1 Hz, 1H), 3.77-3.58 (m, 1H), 3.05 (s, 3H), 2.23 (d, J=2.0 Hz, 3H), 1.17 (d, J=7.2 Hz, 6H).

Compound 12

5-(4-fluoro-3-methyl-phenyl)-6-isopropyl-7-vinyl-1H-pyrrolo[2,3-f]indazole (12)

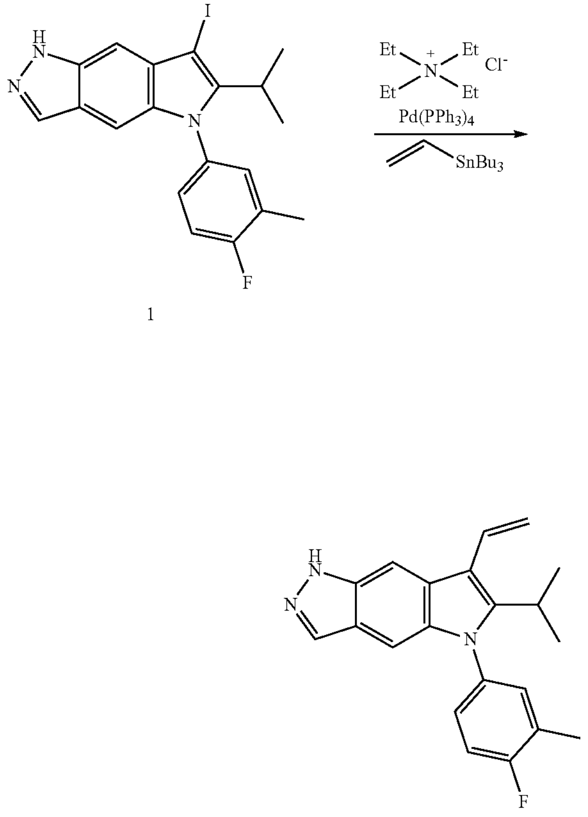

1

12

A microwave vial was charged with 5-(4-fluoro-3-methyl-phenyl)-7-iodo-6-isopropyl-1H-pyrrolo[2,3-f]indazole (134 mg, 0.3 mmol), tributyl(vinyl)stannane (135.0 μL, 0.5 mmol), tetraethylammonium chloride (75 mg, 0.5 mmol), and $Pd(PPh_3)_4$ (16 mg, 0.01 mmol). The vial was sealed, evacuated, and back filled with nitrogen. DMF (3 mL) was added, and the mixture was heated at 80° C. for 1 h. The reaction was quenched with 30% KF solution (2 mL) and stirred for 2 h. The crude mixture was filtered through a pad of Celite®, diluted with dichloromethane, washed with brine and concentrated in vacuo. Purification by silica gel chromatography (Gradient: 0-30% EtOAc in heptane) yielded the product as a pale yellow solid. Yield: 50.0 mg, 37%. LCMS m/z 334.7 $[M+1]^+$. $^1H$ NMR (400 MHz, Chloroform-d) δ 7.90 (d, J=1.1 Hz, 1H), 7.78 (t, J=1.1 Hz, 1H), 7.11-7.00 (m, 4H), 7.00-6.98 (m, 2H), 5.61 (dd, J=17.8, 1.7 Hz, 1H), 5.21 (dd, J=11.5, 1.6 Hz, 1H), 2.96 (hept, J=7.2 Hz, 1H), 2.24 (d, J=2.0 Hz, 3H), 1.22 (dd, J=7.2, 2.5 Hz, 6H).

Compound 13 and Compound 14

2-[5-(4-fluoro-3-methyl-phenyl)-6-isopropyl-1H-pyrrolo[2,3-f]indazol-7-yl]cyclopropanecarboxylic acid, [TRANS-ENANT-1] (13) and 2-[5-(4-fluoro-3-methyl-phenyl)-6-isopropyl-1H-pyrrolo[2,3-f]indazol-7-yl]cyclopropanecarboxylic acid, TRANS-[ENANT-2] (14)

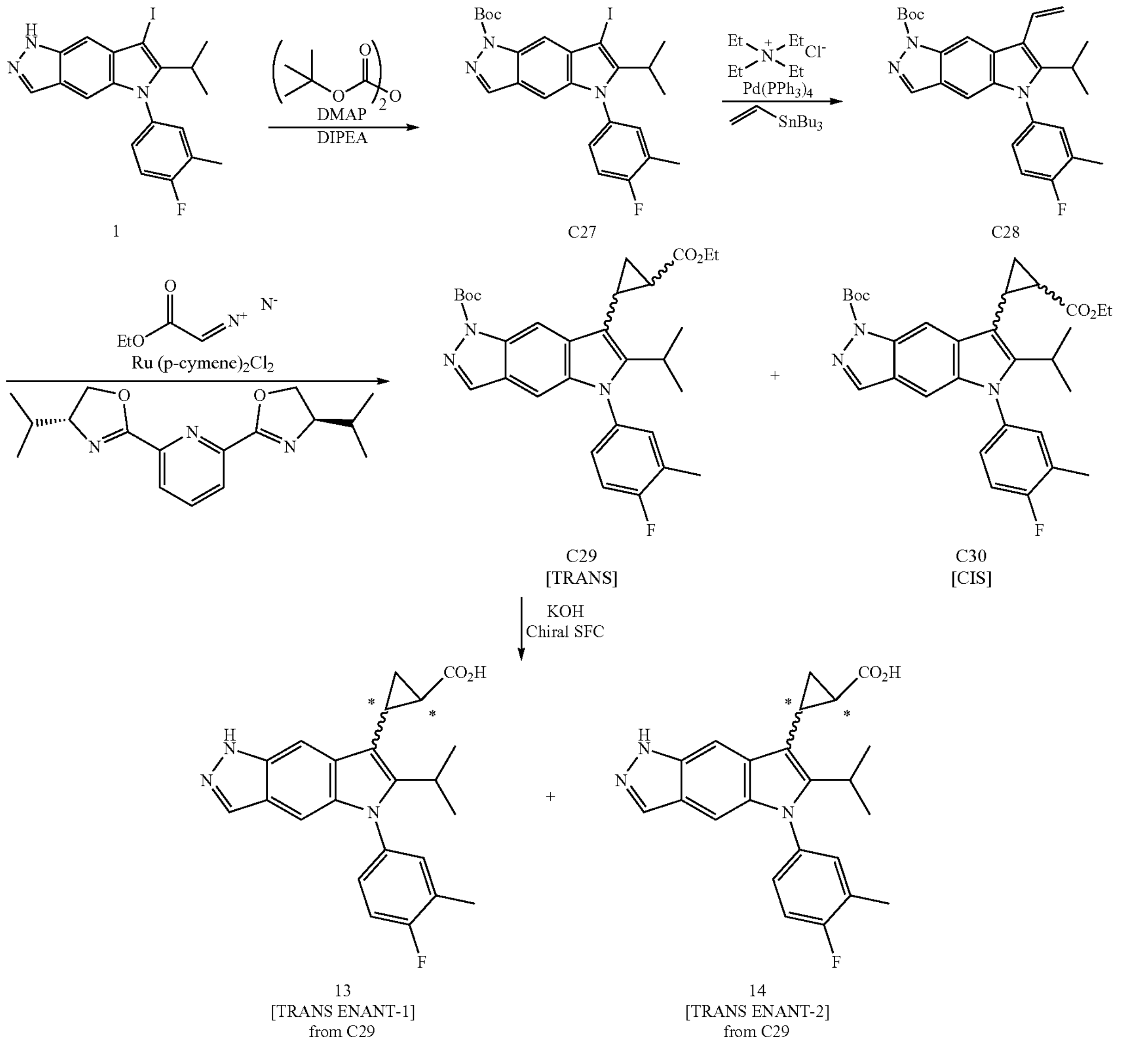

1
C27
C28
C29 [TRANS]
C30 [CIS]
13 [TRANS ENANT-1] from C29
14 [TRANS ENANT-2] from C29

Step 1. Synthesis of tert-butyl 5-(4-fluoro-3-methyl-phenyl)-7-iodo-6-isopropyl-pyrrolo[2,3-f]indazole-1-carboxylate (C27)

To a solution of 5-(4-fluoro-3-methyl-phenyl)-7-iodo-6-isopropyl-1H-pyrrolo[2,3-f]indazole 1 (1.2 g, 2.9 mmol) in dichloromethane (30 mL) was added t-butoxycarbonyl t-butyl carbonate (940 mg, 4.3 mmol), DIPEA (1.2 mL, 6.9 mmol) and N,N'-dimethylpyridin-4-amine (80 mg, 0.7 mmol). The mixture was allowed to stir at 25° C. for 16 h then purified by silica gel chromatography (Gradient: 0-40% EtOAc in heptanes) to afford the product. The product mixture was obtained as a mixture of major and minor regioisomers, with each presumed to have the Boc group on a different nitrogen atom of the pyrazole ring. The mixture of major and minor isomers was advanced to the next step as a mixture. Yield: 240 mg, 97%. LCMS m/z $[M+H]^+$ 533.6. $^1H$ NMR (400 MHz, Chloroform-d) Minor δ 8.39 (d, J=1.2 Hz, 1H), 7.52 (t, J=1.3 Hz, 1H), 7.02-6.87 (m, 3H), 6.62 (d, J=1.3 Hz, 1H), 2.14 (dd, J=4.9, 2.0 Hz, 3H), 1.50 (s, 9H), 1.15 (ddd, J=10.3, 7.2, 3.4 Hz, 6H). Major: δ 7.99 (s, 1H), 7.90 (d, J=0.9 Hz, 1H), 7.02-6.87 (m, 3H), 6.62 (d, J=1.3 Hz, 1H), 2.93 (m, J=7.2 Hz, 1H), 2.14 (dd, J=4.9, 2.0 Hz, 3H), 1.56 (s, 9H), 1.15 (ddd, J=10.3, 7.2, 3.4 Hz, 6H).

Step 2. Synthesis of tert-butyl 5-(4-fluoro-3-methyl-phenyl)-6-isopropyl-7-vinyl-pyrrolo[2,3-f]indazole-1-carboxylate (C28)

A flask containing tert-butyl 5-(4-fluoro-3-methyl-phenyl)-7-iodo-6-isopropyl-pyrrolo[2,3-f]indazole-1-carboxylate C27 (1.4 g, 2.6 mmol), tributyl(vinyl)stannane (1.2 mL, 4.1 mmol), tetraethylammonium chloride (880 mg, 5.3 mmol), and $Pd(PPh_3)_4$ (145 mg, 0.13 mmol) was purged with nitrogen. DMF (50 mL) was added and the mixture heated at 80° C. for 5 h. A solution of 30% KF solution (30 mL) was added and the reaction stirred for a further 2 h. The crude mixture was filtered through Celite®, diluted with EtOAc, washed with brine and concentrated in vacuo. The product was purified by silica gel chromatography (Gradient: 0-40% EtOAc in heptanes) to afford the product as a pale yellow solid. Yield: 1.0 g, 90%. $^1H$ NMR (400 MHz, Chloroform-d) δ 8.67 (s, 1H), 8.13 (s, 1H), 7.25-7.14 (m, 3H), 7.12 (d, J=3.4 Hz, 2H), 5.94-5.75 (m, 1H), 5.42 (dd, J=11.5, 1.4 Hz, 1H), 3.13 (m, J=7.2 Hz, 1H), 2.40 (d, J=1.9 Hz, 3H), 1.79 (s, 9H), 1.37 (dd, J=7.2, 2.6 Hz, 6H).

Step 3. Synthesis of Diastereoisomeric Mixture of tert-butyl 7-(2-(ethoxycarbonyl)cyclopropyl)-5-(4-fluoro-3-methylphenyl)-6-isopropylpyrrolo[2,3-f]indazole-1(5H)-carboxylate, [Trans](C29) and tert-butyl 7-(2-(ethoxycarbonyl)cyclopropyl)-5-(4-fluoro-3-methylphenyl)-6-isopropylpyrrolo[2,3-f]indazole-1(5H)-carboxylate, [CIS](C30)

Ethyl 2-diazoacetate (1.3 mL, 12.4 mmol) was added to a solution of [2,6-bis[(4R)-4-isopropyl-4,5-dihydrooxazol-2-yl]-1-pyridyl]-dichloro-vinyl-ruthenium (48 mg, 0.10 mmol) tert-butyl 5-(4-fluoro-3-methyl-phenyl)-6-isopropyl-7-vinyl-pyrrolo[2,3-f]indazole-1-carboxylate C28 (400 mg, 0.9 mmol) in THF (13 mL) at 55° C. over 60 min. The mixture was allowed to stir at 55° C. for 16 h. Purification by silica gel chromatography (Gradient: 0-50% EtOAc in heptanes) afforded the products C29 and C30.

C29 is the trans isomer and is presumed to be composed of a mixture of the two possible trans stereoisomers: tert-butyl 7-[(1S,2S)-2-ethoxycarbonylcyclopropyl]-5-(4-fluoro-3-methyl-phenyl)-6-isopropyl-pyrrolo[2,3-f]indazole-1-carboxylate and tert-butyl 7-[(1R,2R)-2-ethoxycarbonylcyclopropyl]-5-(4-fluoro-3-methyl-phenyl)-6-isopropyl-pyrrolo[2,3-f]indazole-1-carboxylate. The enantiomeric ratio (ER) could not be determined at this stage, but was estimated based on chiral chromatographic analysis of enantiomers during step 4 in the synthesis of 13 and 14. Absolute stereochemistry of the major trans enantiomer in C29 is presumed to be (S,S) configuration based on nature of the chiral ligand used in the cyclopropanation step. See Organic Process Research & Development 2008, 12, 168-177. C30 is the cis isomer.

C29 tert-butyl 7-(2-(ethoxycarbonyl)cyclopropyl)-5-(4-fluoro-3-methylphenyl)-6-isopropylpyrrolo[2,3-f]indazole-1(5H)-carboxylate, [Trans]. Yield: 100 mg, 21%. $^1H$ NMR (400 MHz, Chloroform-d) δ 8.40 (s, 1H), 8.07 (d, J=0.8 Hz, 1H), 7.22-7.08 (m, 3H), 7.03 (d, J=1.0 Hz, 1H), 4.38-4.14 (m, 2H), 3.26-3.08 (m, 1H), 2.69-2.51 (m, 1H), 2.35 (d, J=1.9 Hz, 3H), 2.14-2.02 (m, 1H), 1.76 (s, 9H), 1.58 (dtt, J=10.8, 4.5, 2.3 Hz, 1H), 1.38 (td, J=7.1, 1.6 Hz, 3H), 1.31 (ddt, J=7.2, 5.1, 2.6 Hz, 6H).

C30 tert-butyl 7-(2-(ethoxycarbonyecyclopropyl)-5-(4-fluoro-3-methylphenyl)-6-isopropylpyrrolo[2,3-f]indazole-1(5H)-carboxylate, [CIS] (120 mg, 25%)$^1H$ NMR (400 MHz, Chloroform-d) δ 8.40 (s, 1H), 8.06 (d, J=0.9 Hz, 1H), 7.22-7.05 (m, 3H), 6.97 (t, J=1.1 Hz, 1H), 3.96-3.63 (m, 2H), 3.43-3.24 (m, 1H), 2.53 (q, J=8.3 Hz, 1H), 2.35 (d, J=2.0 Hz, 3H), 2.28 (q, J=7.8 Hz, 1H), 1.78 (s, 9H), 1.68-1.57 (m, 1H), 1.35-1.24 (m, 3H), 1.20 (dd, J=7.2, 1.4 Hz, 3H), 0.95 (t, J=7.1 Hz, 3H).

Step 4. 2-[5-(4-fluoro-3-methyl-phenyl)-6-isopropyl-1H-pyrrolo[2,3-f]indazol-7-yl]cyclopropanecarboxylic acid, [TRANS-ENANT-1] (13) and 2-[5-(4-fluoro-3-methyl-phenyl)-6-isopropyl-1H-pyrrolo[2,3-f]indazol-7-yl]cyclopropanecarboxylic acid, TRANS-[ENANT-2] (14)

KOH (400 µL of 1.5 M, 0.6 mmol) was added to a solution of C29 (60 mg, 0.1 mmol) and in methanol (5 mL). The mixture was heated at 120° C. under microwave conditions for 30 min. The reaction was neutralized with 0.6 mL of 1M HCl and concentrated in vacuo. The mixture of enantiomers 13 (presumed (15, 25)-2-[5-(4-fluoro-3-methyl-phenyl)-6-isopropyl-1H-pyrrolo[2,3-f]indazol-7-yl]cyclopropanecarboxylic acid) and 14 (presumed (1R,2R)-2-[5-(4-fluoro-3-methyl-phenyl)-6-isopropyl-1H-pyrrolo[2,3-f]indazol-7-yl]cyclopropanecarboxylic acid) were purified by silica gel chromatography (Gradient: 0-100% EtOAc in heptanes) to afford the mixture of enantiomers as a brown solid. Yield: 12.2 mg, 25%. LCMS m/z 392.3 $[M+H]^+$. $^1H$ NMR (400 MHz, Chloroform-d) δ 8.01 (d, J=1.0 Hz, 1H), 7.74 (d, J=1.2 Hz, 1H), 7.22-7.11 (m, 3H), 7.07 (d, J=1.1 Hz, 1H), 3.37-3.09 (m, 1H), 2.71 (ddd, J=9.0, 6.8, 4.2 Hz, 1H), 2.36 (d, J=1.7 Hz, 3H), 2.17 (dt, J=8.3, 4.2 Hz, 1H), 1.86 (dt, J=9.0, 4.5 Hz, 1H), 1.53 (dq, J=7.5, 3.5 Hz, 1H), 1.33 (ddd, J=16.7, 7.2, 4.9 Hz, 6H).

Analysis of the mixture by chiral supercritical fluid chromatography revealed the component enantiomers were present in a 62:38 ratio by area. Analytical Method: [Column: Daicel Chiralpak AD-H, 4.6×100 mm; Mobile Phase: 20% methanol (containing 5 mM ammonia) in carbon dioxide; Flow rate 1 mL/min].

The mixture of enantiomers was separated into their component enantiomers of compound 13 and compound 14 by chiral supercritical fluid chromatography. [Column: Daicel Chiralpak AD-H, 20×250 mm; Eluent: 20% methanol (containing 5 mM ammonia) in carbon dioxide; Flow rate 75 mL/min]. The first eluting peak was compound 14. Yield: 9.1 mg. $^1H$ NMR (400 MHz, Methanol-d4) δ 7.92 (d, J=1.0 Hz, 1H), 7.66 (t, J=1.1 Hz, 1H), 7.32-7.14 (m, 3H), 7.01 (d, J=1.1 Hz, 1H), 3.23 (m, J=7.2 Hz, 1H), 2.52 (t, J=9.9 Hz, 1H), 2.36 (d, J=1.9 Hz, 3H), 2.00 (s, 1H), 1.67 (dt, J=8.9, 4.4 Hz, 1H), 1.49 (d, J=8.9 Hz, 1H), 1.33 (ddd, J=12.5, 7.2, 2.7 Hz, 6H). LCMS m/z 392.6 $[M+H]^+$.

The second eluting peak was compound 13. Yield: 19.6 mg. $^1H$ NMR (400 MHz, Methanol-d4) δ 7.92 (d, J=1.0 Hz, 1H), 7.66 (t, J=1.1 Hz, 1H), 7.32-7.14 (m, 3H), 7.01 (d, J=1.1 Hz, 1H), 3.23 (m, J=7.2 Hz, 1H), 2.52 (t, J=9.9 Hz, 1H), 2.36 (d, J=1.9 Hz, 3H), 2.00 (s, 1H), 1.67 (dt, J=8.9, 4.4 Hz, 1H), 1.49 (d, J=8.9 Hz, 1H), 1.33 (ddd, J=12.5, 7.2, 2.7 Hz, 6H). LCMS m/z 391.7 $[M+H]^+$.

Compound 15 ethyl (1R,2S)-2-[5-(4-fluoro-3-methyl-phenyl)-6-isopropyl-1H-pyrrolo[2,3-f]indazol-7-yl]cyclopropanecarboxylate (15)

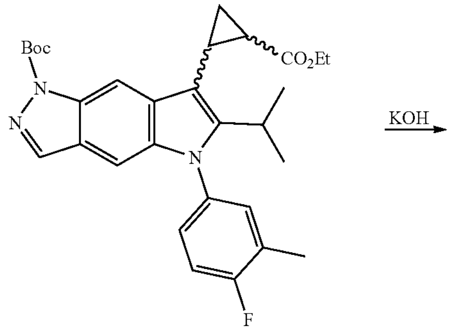

C30
[CIS]

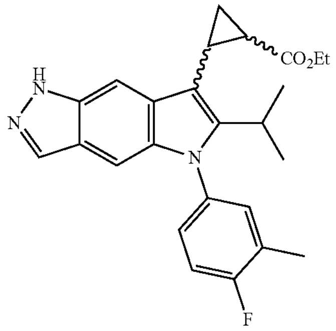

15
[CIS]

To a solution of tert-butyl 7-[(1S,2R)-2-ethoxycarbonylcyclopropyl]-5-(4-fluoro-3-methyl-phenyl)-6-isopropyl-pyrrolo[2,3-f]indazole-1-carboxylate C30 (60 mg, 0.1 mmol) in MeOH (5 mL) was added potassium hydroxide (350 µL of 1 M, 0.4 mmol) and the mixture was heated under microwave conditions at 120° C. for 40 min. [Note: the ethyl ester was not subject to hydrolysis under these conditions]. The solvent was evaporated in vacuo and silica gel chromatography (Gradient: 0-100% EtOAc in heptanes) afforded the product. Yield: 38 mg, 74%. LCMS m/z 420.3 $[M+1]^+$. $^1$H NMR (400 MHz, Chloroform-d) δ 9.96 (s, 1H), 8.02-7.92 (m, 1H), 7.74-7.59 (m, 1H), 7.22-7.10 (m, 3H), 6.98 (q, J=1.2 Hz, 1H), 3.83-3.65 (m, 2H), 3.32 (pd, J=7.2, 5.1 Hz, 1H), 2.55 (td, J=8.7, 7.7 Hz, 1H), 2.35 (dd, J=2.0, 1.1 Hz, 3H), 2.23 (td, J=8.2, 5.3 Hz, 1H), 1.87 (dt, J=7.7, 4.9 Hz, 1H), 1.60 (ddd, J=8.9, 8.0, 4.4 Hz, 1H), 1.31 (dd, J=7.2, 3.5 Hz, 3H), 1.20 (dd, J=7.2, 1.5 Hz, 3H), 0.83 (ddd, J=7.2, 6.5, 4.6 Hz, 3H).

Compound 16

3-[5-(4-fluoro-3-methyl-phenyl)-6-isopropyl-1H-pyrrolo[2,3-f]indazol-7-yl]propanoic Acid (16)

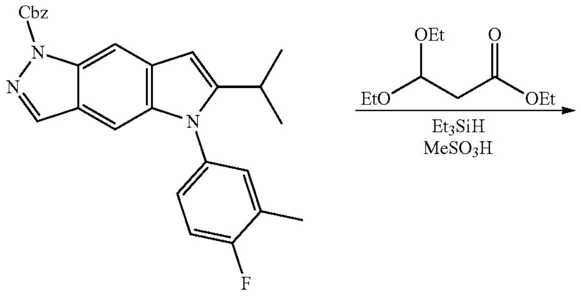

S2

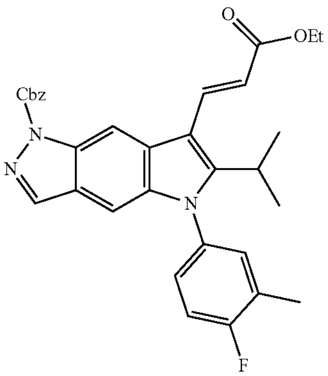

C31

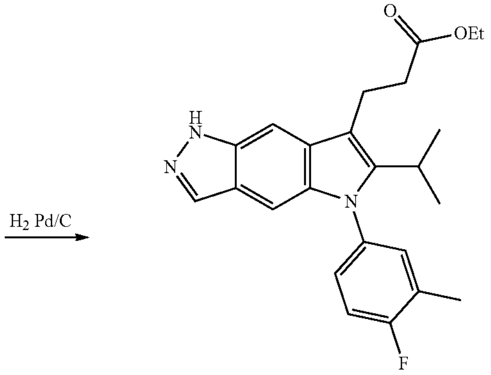

C32

-continued

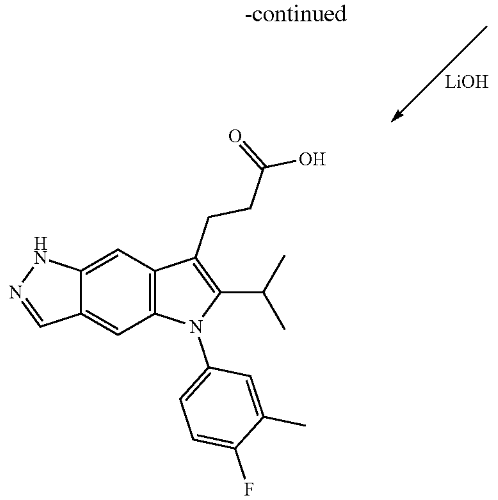

16

Step 1. Synthesis of benzyl 7-[(E)-3-ethoxy-3-oxo-prop-1-enyl]-5-(4-fluoro-3-methyl-phenyl)-6-isopropyl-pyrrolo[2,3-f]indazole-1-carboxylate (C31)

To a mixture of benzyl 5-(4-fluoro-3-methyl-phenyl)-6-isopropyl-pyrrolo[2,3-f]indazole-1-carboxylate S2 (2.8 g, 6.1 mmol) and methanesulfonic acid (600 μL, 9.2 mmol) in dichloromethane (8 mL) was added ethyl 3,3-diethoxypropanoate (6 mL, 30.6 mmol) followed by triethylsilane (2.9 mL, 18.2 mmol). The mixture was stirred at room temperature for 1 h, heated at 50° C. overnight, and then for an additional 3 days. Addition of Celite®, concentration in vacuo, followed by silica gel chromatography (0-100% EtOAc in heptanes) afforded the product. Yield: 1.5 g, 44%. LCMS m/z 540.3 [M+1]+. 1H NMR (300 MHz, DMSO-d6) δ 8.58 (d, J=1.0 Hz, 1H), 8.42 (d, J=0.7 Hz, 1H), 8.23 (s, 1H), 8.17 (s, 1H), 7.61-7.51 (m, 3H), 7.49-7.39 (m, 5H), 7.33 (d, J=0.9 Hz, 1H), 6.41 (s, 1H), 6.36 (s, 1H), 5.55 (s, 2H), 4.25 (q, J=7.1 Hz, 2H), 3.22-3.10 (m, 1H), 2.40-2.30 (m, 3H), 1.44-1.34 (m, 6H), 1.31 (d, J=7.1 Hz, 3H).

Step 2. Synthesis of ethyl 3-[5-(4-fluoro-3-methyl-phenyl)-6-isopropyl-1H-pyrrolo[2,3-f]indazol-7-yl] propanoate (C32)

A solution of benzyl 7-[(E)-3-ethoxy-3-oxo-prop-1-enyl]-5-(4-fluoro-3-methyl-phenyl)-6-isopropyl-pyrrolo[2,3-f]indazole-1-carboxylate C31 (2.1 g, 3.8 mmol) in EtOAc (180 mL) was purged with nitrogen. 10% Palladium on carbon (wet, Degussa) (805 mg, 0.4 mmol) was added and the hydrogen balloon was applied to the reaction. The reaction was stirred overnight at room temperature. The mixture was then filtered through Celite®, washing with EtOAc, and the filtrate concentrated in vacuo. Silica gel chromatography (0-100% EtOAc in heptanes) afforded product (1.31 g). However, $^{1}$H NMR analysis showed the presence of some unreduced alkene. This mixture was retreated under the hydrogenation conditions described, using a mixture of EtOAc (90 mL) and methanol (90 mL) as the solvent. Silica gel chromatography (Gradient: 0-40% EtOAc in dichloromethane) afforded the product. Yield: 1.02 g, 66%. LCMS m/z 408.3 $[M+H]^+$. $^{1}$H NMR (300 MHz, DMSO-d6) δ 12.66-12.54 (m, 1H), 7.95 (t, J=1.3 Hz, 1H), 7.47 (t, J=1.1 Hz, 1H), 7.43-7.31 (m, 2H), 7.31-7.20 (m, 1H), 7.01 (t, J=0.8 Hz, 1H), 4.11 (q, J=7.1 Hz, 2H), 3.15 (dd, J=9.5, 6.5 Hz, 2H), 3.01 (m, J=7.1 Hz, 1H), 2.65 (dd, J=9.4, 6.5 Hz, 2H), 2.32 (d, J=2.0 Hz, 3H), 1.34-1.23 (m, 6H), 1.20 (t, J=7.1 Hz, 3H).

Step 3. Synthesis of 3-[5-(4-fluoro-3-methyl-phenyl)-6-isopropyl-1H-pyrrolo[2,3-f]indazol-7-yl]propanoic acid (16)

A solution of LiOH (582 mg, 12.2 mmol) in water (4.2 mL) was added to a solution of ethyl 3-[5-(4-fluoro-3-methyl-phenyl)-6-isopropyl-1H-pyrrolo[2,3-f]indazol-7-yl] propanoate C32 (1.0 g, 2.4 mmol) in THF (13 mL) and methanol (25 mL). The reaction was stirred at room temperature for 120 min and then concentrated to dryness. The mixture was diluted with dichloromethane (100 mL) and washed with HCl (2.4 mL of 6 M, 14.4 mmol) in 50 mL of water. Solid sodium chloride was added to the water layer and extracted with dichloromethane (3×). Combined organic layers were concentrated in vacuo. Purification was performed using reverse-phase chromatography [Column: 275 g C18 cartridge; Gradient: 10-100% acetonitrile in water with an ammonium formate modifier]. Pooled desired fractions and concentrated to dryness under reduced pressure to afford the product. Yield: 764 mg, 79%. LCMS m/z 380.1 $[M+1]^+$. $^{1}$H NMR (300 MHz, DMSO-d6) δ 12.60 (s, 1H), 7.95 (d, J=0.9 Hz, 1H), 7.48 (t, J=1.1 Hz, 1H), 7.42-7.32 (m, 2H), 7.30-7.21 (m, 1H), 7.01 (d, J=1.1 Hz, 1H), 3.17-3.07 (m, 2H), 3.01 (m, J=7.1 Hz, 1H), 2.61-2.53 (m, 2H), 2.32 (d, J=1.9 Hz, 3H), 1.32-1.21 (m, 6H).

Compound 17

1-[[5-(4-fluoro-3-methyl-phenyl)-6-isopropyl-1H-pyrrolo[2,3-f]indazol-7-yl]methyl]cyclopropanecarboxylic Acid (17)

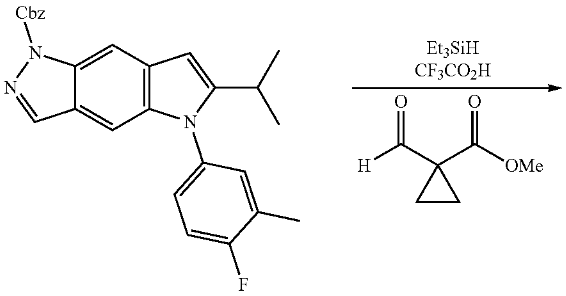

S2

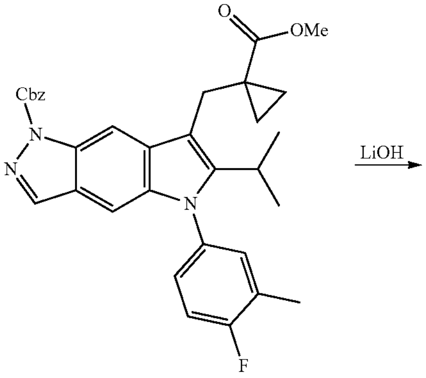

C33

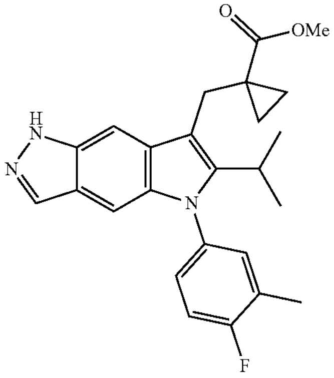

17

Step 1. Synthesis of solution benzyl 5-(4-fluoro-3-methyl-phenyl)-6-isopropyl-7-[(1-methoxycarbonylcyclopropyl)methyl]pyrrolo[2,3-f]indazole-1-carboxylate (C33)

To a solution of benzyl 5-(4-fluoro-3-methyl-phenyl)-6-isopropyl-pyrrolo[2,3-f]indazole-1-carboxylate S2 (3.7 g, 8.1 mmol) in dichloromethane (46 mL) was added methyl 1-formylcyclopropanecarboxylate (3.1 g, 24.4 mmol) followed by trifluoroacetic acid (3.8 mL, 49.3 mmol). Triethylsilane (3.9 mL, 24.4 mmol) was then added and the reaction was stirred at 50° C. in a sealed vessel overnight. An additional equivalent of methyl 1-formylcyclopropanecarboxylate was added and the mixture stirred at 50° C. for 6 h. The reaction was diluted with dichloromethane and washed with saturated aqueous $NaHCO_3$. The organic layer was passed through a phase separator and concentrated to dryness in vacuo. Silica gel chromatography (Gradient: 0-30% EtOAc in dichloromethane) afforded the product (as confirmed by LCMS) was advanced to the next step. Yield: 4.1 g, 90%. LCMS 554.25 $[M+1]^+$.

Step 2. Synthesis of –[[5-(4-fluoro-3-methyl-phenyl)-6-isopropyl-1H-pyrrolo[2,3-f]indazol-7-yl]methyl]cyclopropanecarboxylic Acid (17)

Aqueous LiOH solution (28.5 mL of 2 M, 57 mmol) was added to a solution benzyl 5-(4-fluoro-3-methyl-phenyl)-6-isopropyl-7-[(1-methoxycarbonylcyclopropyl)methyl]pyrrolo[2,3-f]indazole-1-carboxylate C33 (4.1 g, 90%) was diluted with THF (50 mL) and methanol (100 mL). The reaction was stirred at 50° C. overnight then concentrated in vacuo. A solution of 1M HCl was added to adjust the pH to between pH 4-5. The mixture was then washed with EtOAc (2×200 mL). The combined organic layers were dried over sodium sulfate, filtered, and the mixture concentrated to dryness in vacuo with Celite®. Purification by silica gel chromatography (Gradient: 0-10% methanol in dichloromethane) afforded the product as a foam. The product was dissolved in EtOAc and concentrated to dryness in vacuo, which also yielded the product in foam form. Minimal methanol was added, and the product solution was added dropwise into water. The resulting precipitate was filtered, washed with water, and dried under vacuum (2 h at 50° C.). The product was then diluted in EtOAc again and concentrated in vacuo (×3). Drying under vacuum overnight afforded the product as a white powder. Yield: 1.8 g, 53%. LCMS m/z 406.2 $[M+1]^+$. $^1H$ NMR (300 MHz, DMSO-d6) δ 12.56 (s, 1H), 12.29 (s, 1H), 7.94 (d, J=0.9 Hz, 1H), 7.45 (d, J=1.1 Hz, 1H), 7.43-7.33 (m, 2H), 7.33-7.22 (m, 1H), 6.95 (d, J=1.0 Hz, 1H), 3.44 (s, 2H), 3.12 (m, J=7.1 Hz, 1H), 2.32 (d, J=1.9 Hz, 3H), 1.18 (dd, J=7.2, 1.9 Hz, 6H), 1.04 (q, J=3.6 Hz, 2H), 0.66 (q, J=3.8 Hz, 2H).

Compounds 18-28

Compounds 18-28 (see Table 2) were prepared in from intermediate S2 using the appropriate aldehyde or ketone reagent, and using the methods as described for compound 16 or compound 33 (below). Modifications to this method are noted in Table 2 and accompanying footnotes. In some examples, methanesulfonic acid is used instead of trifluoroacetic acid in step 1. In some examples, an alternative base such as KOH or NaOH is used in step 2.

TABLE 2

| Method of preparation, structure and physicochemical data for Compounds 18-28 | | | | |
|---|---|---|---|---|
| Compound | Aldehyde or ketone reagent | Product | Method | $^1$H NMR; LCMS m/z $[M + H]^+$; Structure Comment |
| 18 | 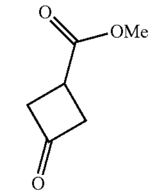 | 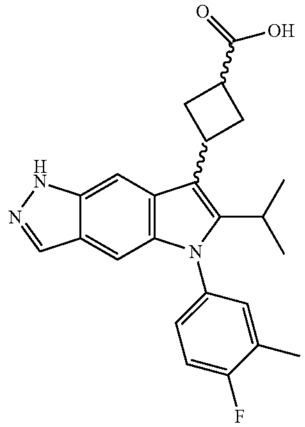 [SMILES: Cc1cc(-n2c(C(C)C)c(C3CC(C(=O)O)C3)c3cc4[nH]ncc4cc32)ccc1F] | Compound 33[1] | $^1$H NMR (400 MHz, DMSO-d6) δ 12.54 (s, 1H), 12.31 (s, 1H), 7.98 (d, J = 16.6 Hz, 1H), 7.85 (s, 1H), 7.36 (d, J = 8.4 Hz, 2H), 7.26 (d, J = 4.9 Hz, 1H), 7.03 (d, J = 4.8 Hz, 1H), 4.22 (m, J = 9.4 Hz, 1H), 3.17 (d, J = 4.1 Hz, 2H), 3.11-2.83 (m, 3H), 2.32 (s, 3H), 1.24 (d, J = 7.1 Hz, 6H); 406.2; Cis and trans mixture. |
| 19 | 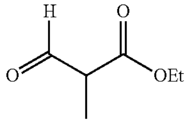 | 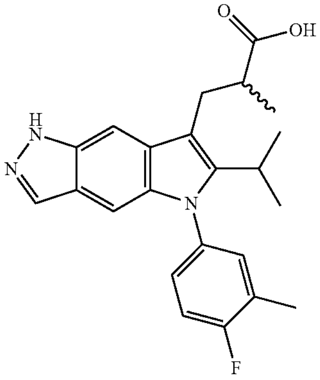 [Rac] | Compound 33 | $^1$H NMR (300 MHz, DMSO-d6) δ 12.58 (s, 1H), 12.23 (s, 1H), 7.94 (d, J = 0.9 Hz, 1H), 7.50 (t, J = 1.1 Hz, 1H), 7.41-7.32 (m, 2H), 7.31-7.22 (m, 1H), 6.95 (d, J = 1.0 Hz, 1H), 3.28-3.08 (m, 2H), 2.91-2.76 (m, 2H), 2.32 (d, J = 1.9 Hz, 3H), 1.25-1.17 (m, 6H), 1.15 (d, J = 6.4 Hz, 3H); 394.2; racemic mixture |
| 20 | | 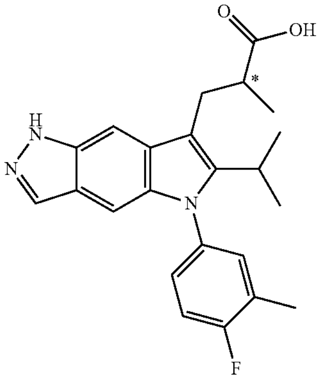 [ENANT-1] | chiral SFC from Compound 19[2] | $^1$H NMR (300 MHz, DMSO-d6) δ 12.59 (s, 1H), 7.93 (d, J = 1.0 Hz, 1H), 7.52 (d, J = 1.1 Hz, 1H), 7.41-7.31 (m, 2H), 7.31-7.22 (m, 1H), 6.94 (d, J = 1.0 Hz, 1H), 3.26-3.09 (m, 2H), 2.88-2.71 (m, 2H), 2.32 (d, J = 1.9 Hz, 3H), 1.25-1.15 (m, 6H), 1.12 (d, J = 6.5 Hz, 3H); 394.2; Single enantiomer. |

TABLE 2-continued

Method of preparation, structure and physicochemical data for Compounds 18-28

| Compound | Aldehyde or ketone reagent | Product | Method | $^1$H NMR; LCMS m/z [M + H]$^+$; Structure Comment |
|---|---|---|---|---|
| 21 | | 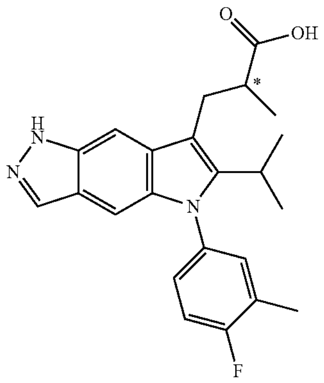 [ENANT-2] | chiral SFC from Compound 19[2] | $^1$H NMR (300 MHz, DMSO-d6) δ 12.59 (s, 1H), 7.93 (d, J = 0.9 Hz, 1H), 7.51 (d, J = 1.4 Hz, 1H), 7.43-7.31 (m, 2H), 7.31-7.22 (m, 1H), 6.94 (d, J = 1.0 Hz, 1H), 3.27-3.09 (m, 2H), 2.88-2.69 (m, 2H), 2.32 (d, J = 1.9 Hz, 3H), 1.26-1.15 (m, 5H), 1.11 (d, J = 6.5 Hz, 3H); 394.2; Single enantiomer. |
| 22 | 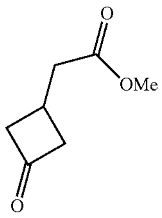 | 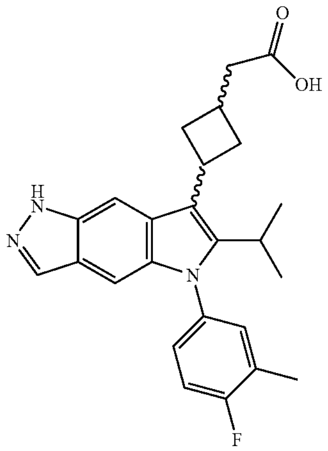 [SMILES: Cc1cc(-n2c(C(C)C)c(C3CC(CC(=O)O)C3)c3cc4[nH]ncc4cc32)ccc1F] | Compound 33 | $^1$H NMR (300 MHz, DMSO-d6) δ 12.51 (s, 1H), 12.14 (s, 1H), 7.99-7.90 (m, 1H), 7.90-7.80 (m, 1H), 7.41-7.30 (m, 2H), 7.30-7.20 (m, 1H), 7.05-6.96 (m, 1H), 3.84 (q, J = 9.0 Hz, 1H), 3.03-2.87 (m, 2H), 2.75-2.55 (m, 3H), 2.47-2.40 (m, 3H), 2.32 (d, J = 1.9 Hz, 3H), 1.25 (dd, J = 7.3, 3.5 Hz, 5H). 420.3; cis and trans mixture. |
| 23 | | 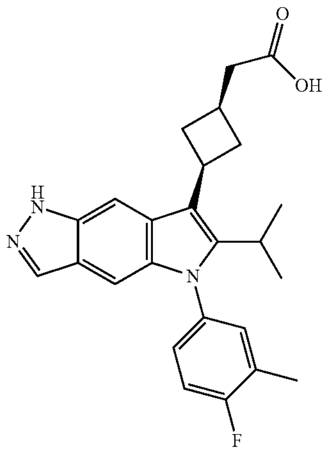 [SMILES: Cc1cc(-n2c(C(C)C)c([C@H]3C[C@@H](CC(=O)O)C3)c3cc4[nH]ncc4cc32)ccc1F] | chiral SFC from Compound 22[3] | $^1$H NMR (300 MHz, DMSO-d6) δ 12.50 (s, 1H), 12.13 (s, 1H), 7.94 (s, 1H), 7.85 (t, J = 1.2 Hz, 1H), 7.43-7.31 (m, 2H), 7.31-7.19 (m, 1H), 7.00 (d, J = 1.0 Hz, 1H), 3.85 (m, J = 9.3 Hz, 1H), 2.96 (m, J = 7.2 Hz, 1H), 2.75-2.55 (m, 3H), 2.48-2.36 (m, 4H), 2.32 (d, J = 2.0 Hz, 3H), 1.25 (d, J = 7.2 Hz, 6H). 420.2; cis isomer. |

TABLE 2-continued

Method of preparation, structure and physicochemical data for Compounds 18-28

| Compound | Aldehyde or ketone reagent | Product | Method | $^{1}$H NMR; LCMS m/z [M + H]$^{+}$; Structure Comment |
|---|---|---|---|---|
| 24 | 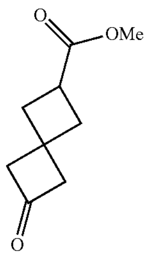 [SMILES: COC(=O)C1CC2(CC(=O)C2)C1] | 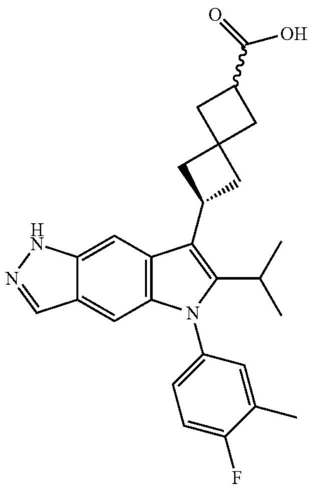 [Rac] | Compound 33 | $^{1}$H NMR (300 MHz, DMSO-d6) δ 12.54 (s, 1H), 12.08 (s, 1H), 7.93 (s, 1H), 7.70 (s, 1H), 7.41-7.29 (m, 2H), 7.29-7.20 (m, 1H), 7.00 (d, J = 1.0 Hz, 1H), 3.93-3.78 (m, 1H), 3.13-2.89 (m, 2H), 2.84-2.67 (m, 2H), 2.47-2.25 (m, 9H), 1.23 (dd, J = 7.2, 1.9 Hz, 6H).; 446.3; Racemic. |
| 25 | | 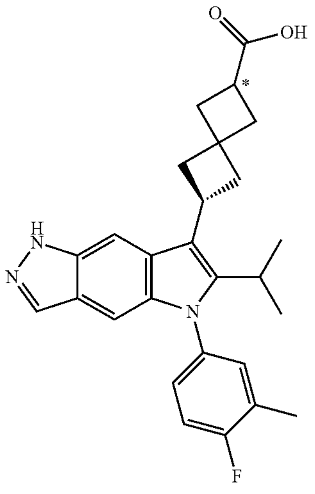 [ENANT-1] | chiral SFC from Compound 24[4] | $^{1}$H NMR (400 MHz, DMSO-d6) δ 12.55 (s, 1H), 12.11 (s, 1H), 7.93 (d, J = 0.9 Hz, 1H), 7.70 (t, J = 1.2 Hz, 1H), 7.40-7.31 (m, 2H), 7.28-7.21 (m, 1H), 7.00 (d, J = 1.0 Hz, 1H), 3.89-3.75 (m, 1H), 3.05 (m, J = 8.4 Hz, 1H), 2.95 (m, J = 7.2 Hz, 1H), 2.82-2.68 (m, 2H), 2.49-2.43 (m, 2H), 2.42-2.22 (m, 7H), 1.23 (dd, J = 7.2, 2.5 Hz, 6H).; 446.3; Single enantiomer. |

TABLE 2-continued

Method of preparation, structure and physicochemical data for Compounds 18-28

| Compound | Aldehyde or ketone reagent | Product | Method | $^{1}$H NMR; LCMS m/z $[M + H]^+$; Structure Comment |
|---|---|---|---|---|
| 26 | | 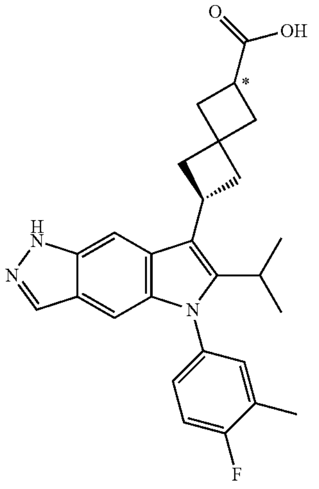 [ENANT-2] | chiral SFC from Compound 24[4] | $^{1}$H NMR (300 MHz, DMSO-d6) δ 12.54 (s, 1H), 12.10 (s, 1H), 7.93 (d, J = 0.9 Hz, 1H), 7.75-7.65 (m, 1H), 7.42-7.30 (m, 2H), 7.30-7.18 (m, 1H), 7.00 (d, J = 1.0 Hz, 1H), 3.85 (m, J = 9.4 Hz, 1H), 3.14-2.87 (m, 2H), 2.84-2.67 (m, 2H), 2.48-2.42 (m, 2H), 2.41-2.24 (m, 7H), 1.23 (dd, J = 7.2, 1.9 Hz, 6H).; 446.3; Single enantiomer. |
| 27 | 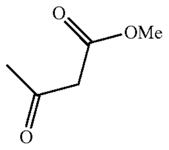 | 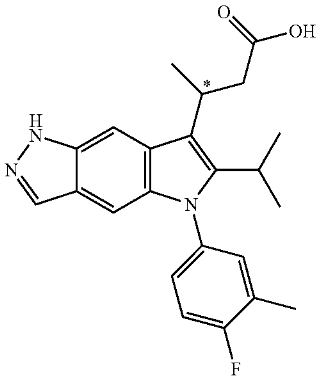 [ENANT-1] | Compound 16[5] | $^{1}$H NMR (300 MHz, DMSO-d6) δ 12.55 (s, 1H), 7.95 (s, 1H), 7.64-7.52 (m, 1H), 7.43-7.31 (m, 2H), 7.31-7.18 (m, 1H), 7.07-6.97 (m, 1H), 3.85-3.67 (m, 1H), 3.09-2.84 (m, 2H), 2.72 (ddd, J = 15.0, 6.0, 2.5 Hz, 1H), 2.32 (d, J = 1.9 Hz, 3H), 1.48 (d, J = 6.9 Hz, 3H), 1.28 (dd, J = 7.2, 5.4 Hz, 6H).; 394.2; Single enantiomer. |
| 28 | 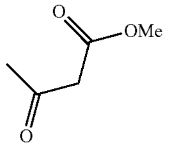 | 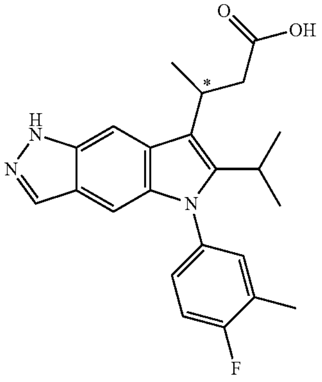 [ENANT-2] | Compound 16[5] | $^{1}$H NMR (300 MHz, DMSO-d6) δ 12.53 (s, 2H), 7.95 (s, 1H), 7.59 (s, 1H), 7.43-7.30 (m, 2H), 7.30-7.18 (m, 1H), 7.06-6.98 (m, 1H), 3.75 (m, J = 7.0 Hz, 1H), 3.08-2.85 (m, 2H), 2.79-2.65 (m, 1H), 2.32 (d, J = 1.9 Hz, 3H), 1.48 (d, J = 6.9 Hz, 3H), 1.28 (dd, J = 7.2, 5.4 Hz, 6H).; 394.1; Single enantiomer. |

Table 2 Footnotes:

[1]NaOH used as base in step 2.

[2]Compound 19 (racemic mixture) was separated into component enantiomers by chiral supercritical fluid chromatography (SFC) to give compounds 20 and 21. Conditions: Column: Daicel Chiralpak AD-H IC column, 10 x 250 mm, Mobile Phase 30% IPA (containing 5 mM Ammonia), 70 % $CO_2$. Compound 20 was the first eluting peak. Compound 21 was the second eluting peak.

[3]Preparation Method: IC, 20 x 250 mm, Mobile phase: 20% EtOH (containing 5 mM Ammonia) 80% $CO_2$ Flow: 75 mL/min.

[4]Compound 24 (racemic mixture) was separated into component enantiomers by chiral supercritical chromatography to give compounds 25 and 26. Conditions Column: Daicel Chiralpak AD-H IC column, 10 x 250 mm, Mobile Phase 30% Ethanol (containing 5 mM Ammonia), 70 % $CO_2$. Compound 25 was the first eluting peak (Retention time: 0.95 min). Compound 26 was the second eluting peak (Retention time: 1.1 min).

TABLE 2-continued

| Method of preparation, structure and physicochemical data for Compounds 18-28 | | | | |
|---|---|---|---|---|
| Compound | Aldehyde or ketone reagent | Product | Method | $^1$H NMR; LCMS m/z [M + H]$^+$; Structure Comment |

[5]Compounds 27 and 28 were prepared by separation of the racemic mixture using chiral SFC. Conditions. Column: preparative IC column, 10 × 250 mm, Mobile Phase 40% Methanol (containing 5 mM Ammonia), 70 % $CO_2$. Compound 27 was the first eluting peak. Compound 28 was the second eluting peak.

Compound 29

5-(4-fluorophenyl)-6-isopropyl-1H-pyrrolo[2,3-f]indazole-7-carbonitrile

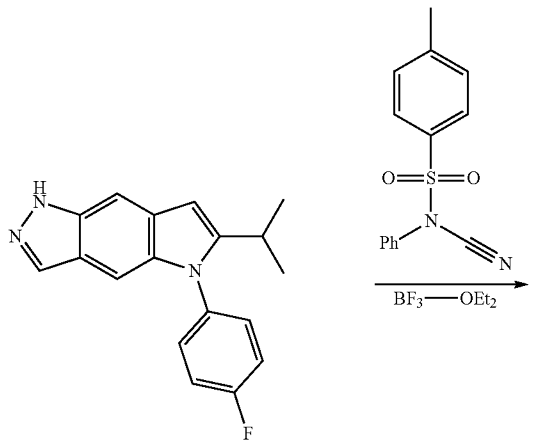

S3

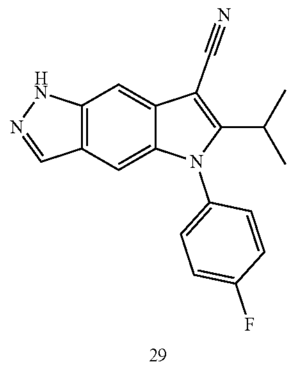

29

Compound 29 was prepared from S3 using the method described for compound 10. Purification by chromatography on silica gel (0-100% ethyl acetate in heptane) afforded the product. Yield: 19.1 mg, 15%. LCMS m/z 319.1 [M+H]$^+$. $^1$H NMR (300 MHz, DMSO-d6) δ 12.91 (s, 1H), 8.13-8.05 (m, 1H), 7.71-7.63 (m, 2H), 7.60 (t, J=1.1 Hz, 1H), 7.58-7.48 (m, 2H), 7.29 (d, J=1.1 Hz, 1H), 2.96 (h, J=6.9 Hz, 1H), 1.40 (d, J=7.0 Hz, 6H).

Compound 30

5-(4-fluorophenyl)-6-isopropyl-7-methylsulfonyl-1H-pyrrolo[2,3-f]indazole

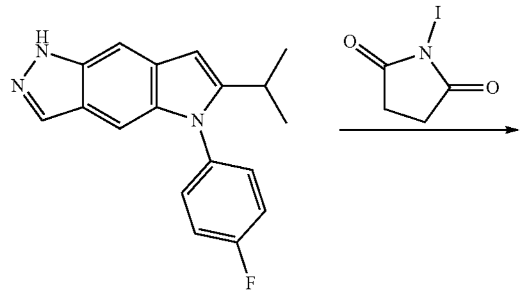

S3

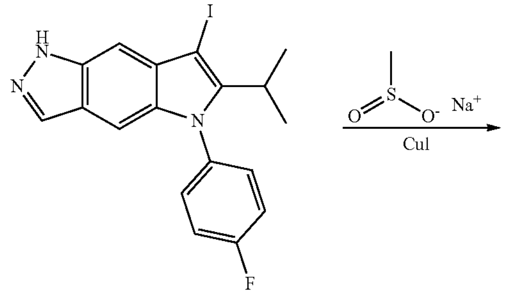

C34

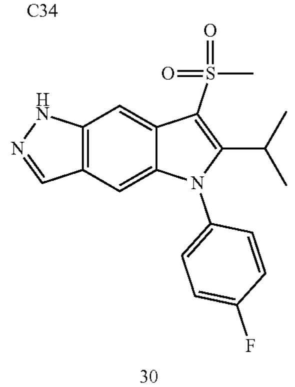

30

Step 1. Synthesis of 5-(4-fluorophenyl)-7-iodo-6-isopropyl-1H-pyrrolo[2,3-f]indazole (C34)

C34 was prepared as described for compound 1. In this case, purification was carried out by chromatography on silica gel (Gradient: 0-100% EtOAc in heptanes) to afford the product. Yield: 712 mg, 74%. LCMS m/z 420.2 [M+H]$^+$. $^1$H NMR (400 MHz, DMSO-d6) δ 12.78-12.69 (m, 1H), 8.02 (t, J=1.3 Hz, 1H), 7.57-7.43 (m, 4H), 7.34 (t, J=1.1 Hz, 1H), 7.08 (t, J=0.8 Hz, 1H), 3.04 (m, J=7.2 Hz, 1H), 1.33 (d, J=7.2 Hz, 6H).

Step 2. Synthesis of 5-(4-fluorophenyl)-6-isopropyl-7-methylsulfonyl-1H-pyrrolo[2,3-f]indazole (30)

Compound 30 was prepared from C34 as described for compound 11. In this case, purification was carried out by chromatography on Si-amine column cartridge (Gradient: 0-100% EtOAc in heptanes followed by 0-10% methanol in dichloromethane). Yield: 18.1 mg, 20%. LCMS m/z 372.2 $[M+H]^+$. $^1H$ NMR (300 MHz, DMSO-d6) δ 12.88 (s, 1H), 8.05 (t, J=1.3 Hz, 1H), 8.00 (t, J=1.1 Hz, 1H), 7.71-7.60 (m, 2H), 7.58-7.48 (m, 2H), 7.08 (t, J=0.8 Hz, 1H), 3.83-3.66 (m, 1H), 3.25 (s, 3H), 1.26 (d, J=7.2 Hz, 6H).

Compound 31

(E)-3-[5-(4-fluorophenyl)-6-isopropyl-1H-pyrrolo[2,3-f]indazol-7-yl]prop-2-enoic Acid

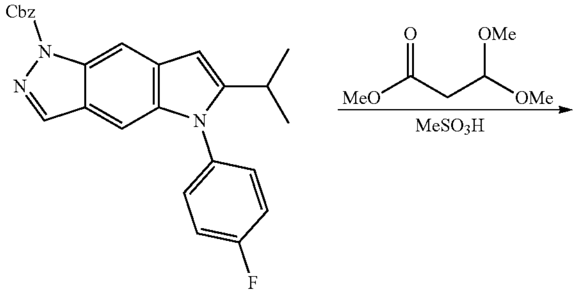

S4

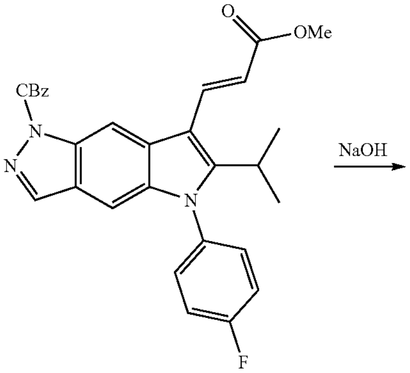

C35

-continued

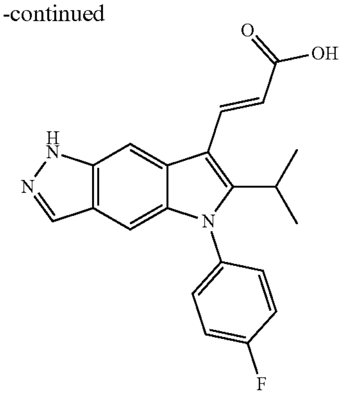

31

Step 1. Synthesis of benzyl 5-(4-fluorophenyl)-6-isopropyl-7-[(E)-3-methoxy-3-oxo-prop-1-enyl] pyrrolo[2,3-f]indazole-1-carboxylate (C35)

To a solution of S4 (452 mg, 1.0 mmol) in toluene (2 mL) and chloroform (2 mL) was added methyl 3,3-dimethoxypropanoate (178 μL, 1.3 mmol), and then methanesulfonic acid (102 μL, 1.6 mmol). The mixture was stirred at room temperature for 2 h, and the temperature was increased to 50° C. and stirred overnight. The mixture was washed with a solution of saturated sodium bicarbonate, and the organic phase isolated on a phase separator. The organic phase was concentrated in vacuo, then purified by silica gel chromatography (Gradient: 0-5% EtOAc in dichloromethane) to afford the product. Yield: 338 mg, 63%. LCMS m/z 512.3 $[M+H]^+$. $^1H$ NMR (300 MHz, DMSO-d6) δ 8.58 (s, 1H), 8.45-8.37 (m, 1H), 8.19 (d, J=15.9 Hz, 1H), 7.69-7.36 (m, 9H), 7.32 (d, J=0.8 Hz, 1H), 6.39 (d, J=15.9 Hz, 1H), 5.55 (s, 2H), 3.78 (s, 3H), 3.16 (m, J=7.2 Hz, 1H), 1.35 (d, J=7.2 Hz, 6H).

Step 2. Synthesis of (E)-3-[5-(4-fluorophenyl)-6-isopropyl-1H-pyrrolo[2,3-f]indazol-7-yl]prop-2-enoic Acid (31)

To a solution of benzyl 5-(4-fluorophenyl)-6-isopropyl-7-[(E)-3-methoxy-3-oxo-prop-1-enyl]pyrrolo[2,3-f]indazole-1-carboxylate C35 (360 mg, 0.7 mmol) in THF (3.4 mL) was added a solution of sodium hydroxide (1.8 mL of 2 M, 3.6 mmol) in water (1.7 mL). MeOH (5.9 mL) was added, and the mixture was stirred for 3 h at room temperature. The reaction was poured into 1M HCl and extracted with EtOAc. The combined organic extracts were dried over sodium sulfate and concentrated in vacuo. Silica gel chromatography (0-10% methanol in dichloromethane) afforded the product. Yield: 67.2 mg, 26%. LCMS m/z 364.1 $[M+H]^+$. $^1H$ NMR (300 MHz, DMSO-d6) δ 12.76 (s, 1H), 12.07 (s, 1H), 8.14 (d, J=15.8 Hz, 1H), 8.04 (d, J=0.9 Hz, 1H), 7.88 (t, J=1.1 Hz, 1H), 7.65-7.45 (m, 4H), 7.11 (d, J=1.0 Hz, 1H), 6.36 (d, J=15.8 Hz, 1H), 3.22-3.02 (m, 1H), 1.34 (d, J=7.2 Hz, 6H.

Compound 32

3-[5-(4-fluorophenyl)-6-isopropyl-1H-pyrrolo[2,3-f]indazol-7-yl]propanoic Acid

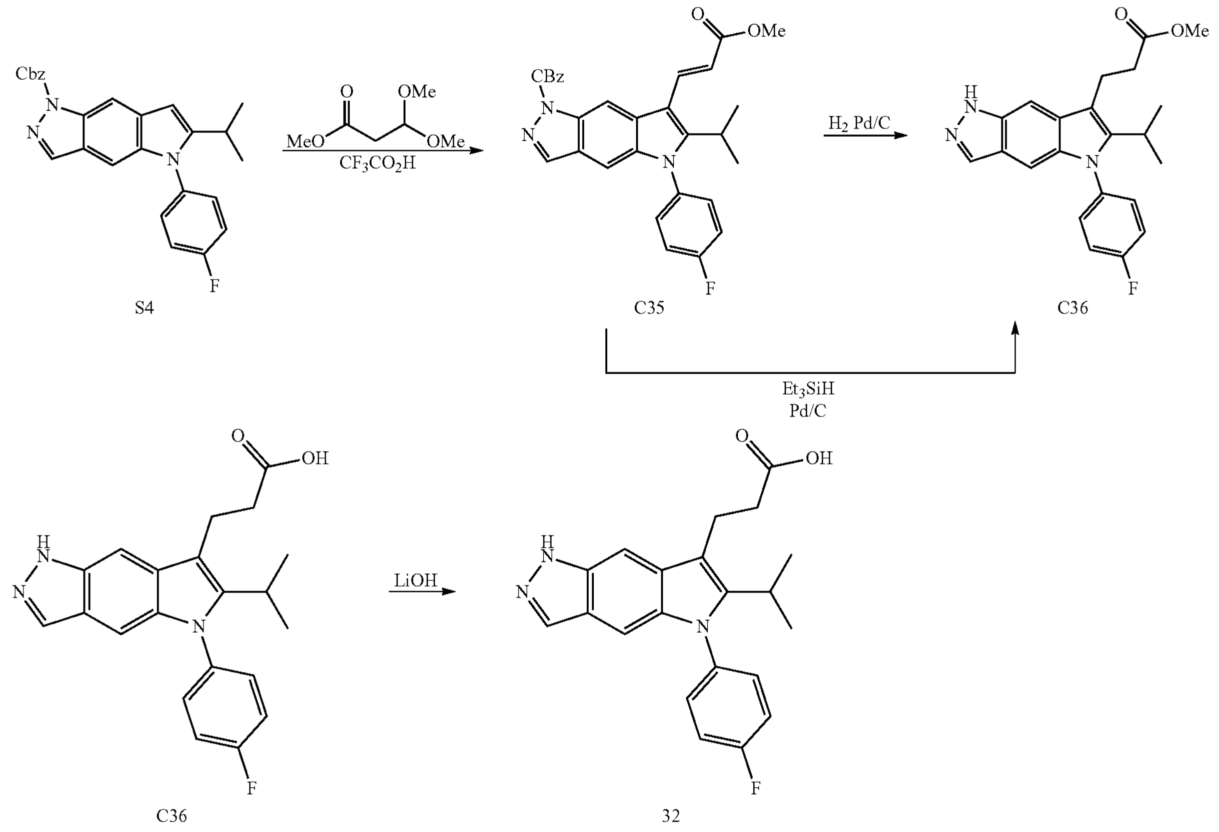

Step 1. Synthesis of benzyl 5-(4-fluorophenyl)-6-isopropyl-7-[(E)-3-methoxy-3-oxo-prop-1-enyl]pyrrolo[2,3-f]indazole-1-carboxylate (C35)

To a solution of benzyl 5-(4-fluorophenyl)-6-isopropyl-pyrrolo[2,3-f]indazole-1-carboxylate (122 g, 282 mmol) dissolved in dichloromethane (1 L) was added methyl 3,3-dimethoxypropanoate (42 mL, 296 mmol) and trifluoroacetic acid (140 mL, 1.8 mol). The reaction was stirred overnight at 50° C. An additional 0.1 equivalents of methyl 3,3-dimethoxypropanoate were then added and the mixture stirred for an additional 6 h at 50° C. The reaction mixture was concentrated to an oil, and then diluted with dichloromethane. The mixture was washed with saturated aqueous sodium bicarbonate. The organic layer was dried over sodium sulfate, filtered, and concentrated in vacuo to afford the product as yellow oil, which was progressed to the next step without further purification. Yield: 140 g, 81%. LCMS m/z 512.3 [M+H]$^+$.

Step 2. Synthesis of methyl 3-[5-(4-fluorophenyl)-6-isopropyl-1H-pyrrolo[2,3-f]indazol-7-yl]propanoate (C36)

A solution of benzyl 5-(4-fluorophenyl)-6-isopropyl-7-[(E)-3-methoxy-3-oxo-prop-1-enyl]pyrrolo[2,3-f]indazole-1-carboxylate C35 (140 g) in methanol (1.5 L) and EtOAc (1.5 L) was divided equally into 3 batches. A slurry of 10% Palladium on carbon (18 g, 16.9 mmol) in EtOAc was added to each batch. The mixtures were degassed (by evacuation) and then placed under an atmosphere of hydrogen gas using a hydrogen balloon (2 balloons per reaction). After 4 h, the hydrogen balloons were replenished, and the mixtures stirred at room temperature overnight. Hydrogen balloons were replenished again, and the reactions stirred for a further overnight period. The mixtures were purged with nitrogen, and then filtered through Celite®, washing with methanol and EtOAc. The combined organic filtrate was concentrated in vacuo. Dilution with EtOAc resulted in the formation of a precipitate, which was filtered off and dried at 40° C. under vacuum to afford the product. Yield: 79 g, 72%. LCMS m/z 380.2 [M+H]$^+$.

Alternative Synthesis of methyl 3-[5-(4-fluorophenyl)-6-isopropyl-1H-pyrrolo[2,3-f]indazol-7-yl]propanoate (C36)

To a solution of benzyl 5-(4-fluorophenyl)-6-isopropyl-7-[(E)-3-methoxy-3-oxo-prop-1-enyl]pyrrolo[2,3-f]indazole-1-carboxylate C35 (49.2 g, 96.1 mmol) in EtOH (1 L) in a 2 L three-necked round-bottomed flask equipped with a magnetic stirbar, dropping funnel, and reflux condenser was added 10% Pd on carbon (10 g, 9.397 mmol) catalyst. Triethylsilane (155 mL, 970.4 mmol) was then added dropwise at room temperature. The reaction was stirred at room temperature for 1 h. The reaction was filtered over a Celite® plug. The celite plug was washed with EtOH and the filtrate was evaporated in vacuo to afford a slightly yellow oil. The oil was dissolved in dichloromethane and filtered over a plug of silica gel. The plug was eluted with dichloromethane to elute residual silyl by-products, and then 50% EtOAc in dichloromethane to elute the product. The filtrate was evaporated in vacuo to afford the product as a white solid (30.9 g, 85%). $^1$H NMR (400 MHz, Chloroform-d) δ 9.93 (s, 1H), 8.04 (d, J=1.3 Hz, 1H), 7.55 (t, J=1.1 Hz, 1H), 7.39-7.33 (m, 2H), 7.31-7.26 (m, 2H), 7.13 (t, J=0.8 Hz, 1H), 3.77 (s, 3H), 3.37-3.21 (m, 2H), 3.09 (m, J=7.2 Hz, 1H), 2.87-2.64 (m, 2H), 1.33 (d, J=7.2 Hz, 6H). $^{19}$F NMR (376 MHz, Chloroform-d) 6-112.83.

Step 3. Synthesis of 3-[5-(4-fluorophenyl)-6-isopropyl-1H-pyrrolo[2,3-f]indazol-7-yl]propanoic acid (32)

An aqueous solution of LiOH (183 mL of 2.5 M, 458 mmol) was added to a solution of C36 (35.8 g, 91.4 mmol) in THF (336 mL) and methanol (336 mL). The reaction was stirred at room temperature for 1 h. The mixture was the concentrated in vacuo reducing the volume to ~400 mL. 1M NaOH (400 mL) was added and the aqueous layer washed with dichloromethane (2×500 mL). The aqueous layer was then acidified to ~pH 3-4 by the addition of 6M HCl solution, then extracted with EtOAc (2×800 mL). The EtOAc layers were combined and dried over sodium sulfate, and concentrated in vacuo. Purification in 4 batches by silica gel chromatography (Gradient: 0-10% methanol in dichloromethane) then concentration in vacuo gave the product as a foam. Addition of minimal EtOAc resulted in the formation of a precipitate which was filtered and dried under vacuum to afford the product as an off-white solid. Yield: 40.2 g, 66%. LCMS m/z 366.2 [M+H]$^+$. $^1$H NMR (300 MHz, DMSO-d6) δ 12.57 (s, 1H), 12.22 (s, 1H), 7.94 (d, J=1.0 Hz, 1H), 7.52-7.39 (m, 5H), 7.00 (d, J=1.1 Hz, 1H), 3.13 (dd, J=9.5, 6.6 Hz, 2H), 3.02 (m, J=7.2 Hz, 1H), 2.63-2.53 (m, 2H), 1.25 (d, J=7.2 Hz, 6H).

Alternative Preparation for 3-[5-(4-fluorophenyl)-6-isopropyl-1H-pyrrolo[2,3-f]indazol-7-yl]propanoic Acid (32)

To a slurry of C36 (1237 g, 3.3 mol) in methanol (5 L) at 27° C. was added a mixture of 45% KOH (760 mL, 8.9 mol) in water (2.7 L) over 1 min [exotherm to 40° C.]. The mixture was heated to 46-49° C. for 3 h. The mixture was then cooled to 14° C., and then treated with acetic acid (560 mL, 9.8 mol) over 3 min. The resulting slurry was diluted with water (1.4 L) and then stirred at −20° C. overnight before filtering. The solids were washed with water (2 L) and dried under vacuum oven at 50° C. to afford the product as an off-white solid. (1173 g, 3.2 mol, 98%).

Compound 33

1-[[5-(4-fluorophenyl)-6-isopropyl-1H-pyrrolo[2,3-f]indazol-7-yl]methyl]cyclopropanecarboxylic Acid

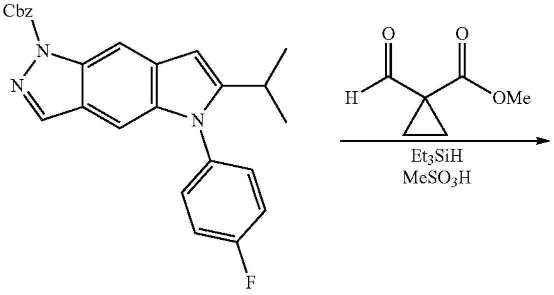

S4

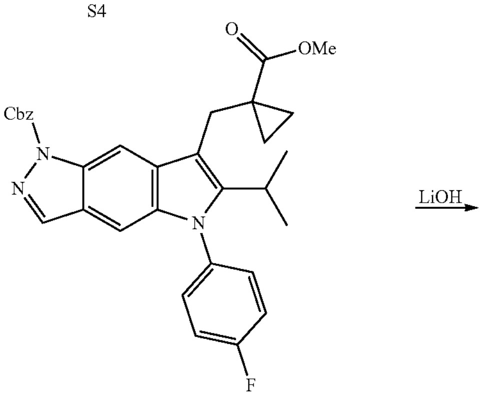

C37

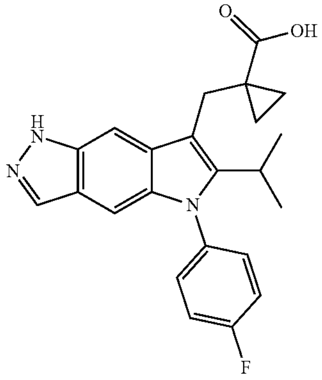

33

Step 1. Synthesis of benzyl 5-(4-fluorophenyl)-6-isopropyl-7-((1-(methoxycarbonyl)cyclopropyl)methyl)pyrrolo[2,3-f]indazole-1(5H)-carboxylate (C37)

To a solution of S4 (325 mg, 0.7 mmol) in dichloromethane (950 μL) was added methanesulfonic acid (73 μL, 1.1 mmol) followed by methyl 1-formylcyclopropanecarboxylate (233 mg, 1.8 mmol) and triethylsilane (360 μL, 2.3 mmol). The mixture was heated at 50° C. overnight. The reaction mixture was partitioned between dichloromethane and aqueous sat. sodium bicarbonate solution and stirred for 5 minutes. The organic phase was separated, passed through a phase separator, and concentrated in vacuo. The residue was purified by silica gel chromatography (Gradient: 0-50%

EtOAc in heptanes) to afford the product. LCMS 540.4 [M+1]$^+$. 104 mg, 26%. $^1$H NMR (300 MHz, DMSO-d6) δ 8.34 (d, J=0.8 Hz, 1H), 8.15 (s, 1H), 7.60-7.51 (m, 4H), 7.49-7.38 (m, 5H), 7.13 (d, J=0.9 Hz, 1H), 5.51 (s, 2H), 3.69 (s, 3H), 3.22-3.09 (m, 1H), 1.17 (d, J=7.2 Hz, 6H), 1.05 (q, J=3.9 Hz, 2H), 0.68 (q, J=4.0 Hz, 2H).

Step 2. Synthesis of 1-[[5-(4-fluorophenyl)-6-isopropyl-1H-pyrrolo[2,3-f]indazol-7-yl]methyl]cyclopropanecarboxylic Acid (33)

Compound 33 was prepared from C37 using the method described for compound 17. Yield: 50.6 mg, 66%. LCMS m/z 392.2 [M+H]$^+$. $^1$H NMR (300 MHz, DMSO-d6) δ 12.58 (s, 1H), 12.31 (s, 1H), 7.94 (d, J=1.0 Hz, 1H), 7.53-7.39 (m, 5H), 6.93 (d, J=1.1 Hz, 1H), 3.44 (s, 2H), 3.13 (m, J=7.1 Hz, 1H), 1.20-1.12 (m, 6H), 1.04 (q, J=3.6 Hz, 2H), 0.67 (q, J=3.8 Hz, 2H).

Compound 34, Compound 35, and Compound 36

6-[5-(4-fluorophenyl)-6-isopropyl-1H-pyrrolo[2,3-f]indazol-7-yl]spiro[3.3]heptane-2-carboxylic acid (34), 6-[5-(4-fluorophenyl)-6-isopropyl-1H-pyrrolo[2,3-f]indazol-7-yl]spiro[3.3]heptane-2-carboxylic acid, [ENANT-1] (35) 6-[5-(4-fluorophenyl)-6-isopropyl-1H-pyrrolo[2,3-f]indazol-7-yl]spiro[3.3]heptane-2-carboxylic acid, [ENANT-2] (36)

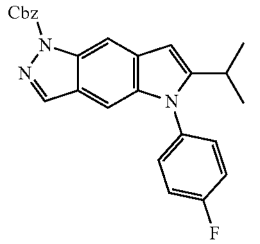

S4

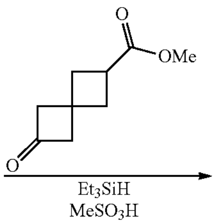

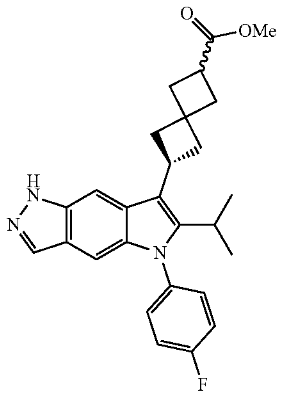

C38

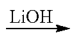

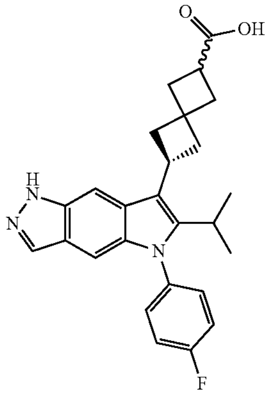

[RAC]
34

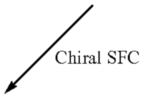

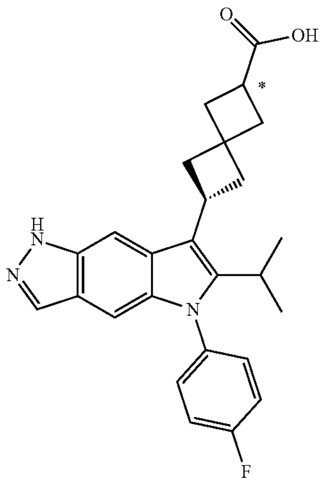

[ENANT-1]
35

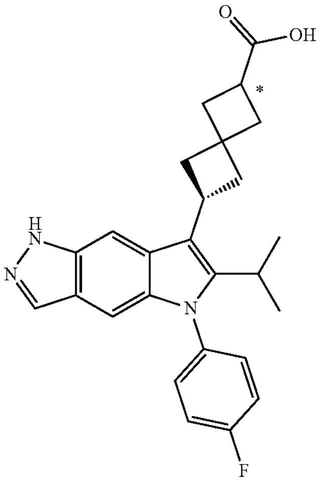

[ENANT-2]
36

Steps 1 and 2. Synthesis of 6-[5-(4-fluorophenyl)-6-isopropyl-1H-pyrrolo[2,3-f]indazol-7-yl]spiro[3.3]heptane-2-carboxylic Acid (34)

Compound 34 was prepared in two steps from S4 using the same method described for compound 33. 34 was obtained as a racemic mixture of 6-[5-(4-fluorophenyl)-6-isopropyl-1H-pyrrolo[2,3-f]indazol-7-yl]spiro[3.3]heptane-2-carboxylic acid. Yield: 246 mg, 77%. LCMS m/z 432.54 $[M+1]^+$. $^1H$ NMR (400 MHz, DMSO-d6) δ 12.56 (s, 1H), 12.09 (s, 1H), 7.94 (s, 1H), 7.71 (s, 1H), 7.53-7.25 (m, 4H), 7.00 (s, 1H), 3.85 (m, J=9.3 Hz, 1H), 3.00 (dp, J=37.6, 7.8, 7.2 Hz, 2H), 2.76 (dt, J=21.4, 10.5 Hz, 2H), 2.37 (dd, J=16.8, 8.4 Hz, 4H), 1.23 (dd, J=7.2, 2.4 Hz, 6H).

Step 3. Preparation of 6-[5-(4-fluorophenyl)-6-isopropyl-1H-pyrrolo[2,3-f]indazol-7-yl]spiro[3.3]heptane-2-carboxylic acid, [ENANT-1] (35), and 6-[5-(4-fluorophenyl)-6-isopropyl-1H-pyrrolo[2,3-f]indazol-7-yl]spiro[3.3]heptane-2-carboxylic acid, [ENANT-2] (36)

Separation of compound 34 into its constituent enantiomers compound 35 and compound 36 was carried out via supercritical fluid chromatography [Column: Daicel Chiralpak AD-H IC column, 20×250 mm; Mobile phase: 40% EtOH (containing 5 mM Ammonia) in 60% carbon dioxide; flow rate 80 mL/min].

The first eluting enantiomer was 35 [ENANT-1]. Yield: 26.8 mg, 22%. LCMS m/z 432.3 $[M+H]^+$.

The second eluting enantiomer was 36 [ENANT-2] Yield: 20.7 mg, 17%. LCMS m/z 432.3.

Compound 37

3-[5-[3-(difluoromethyl)phenyl]-6-isopropyl-1H-pyrrolo[2,3-f]indazol-7-yl]propanoic Acid (37)

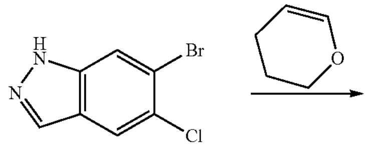

C1

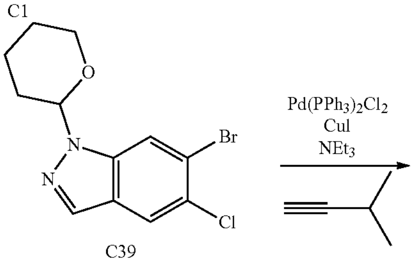

C39

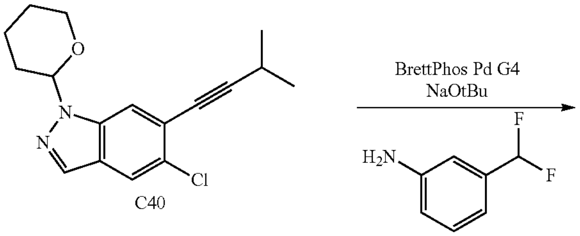

C40

-continued

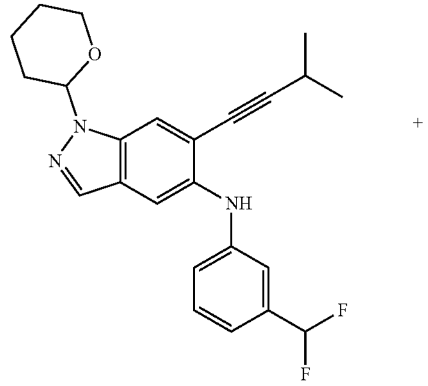

C41

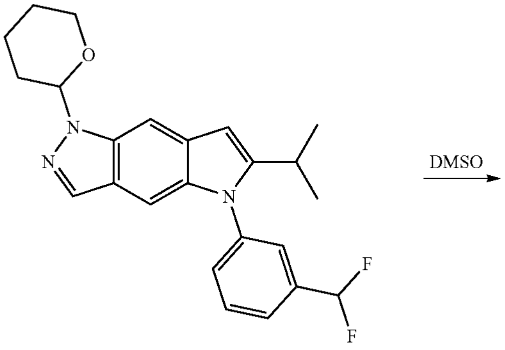

C42

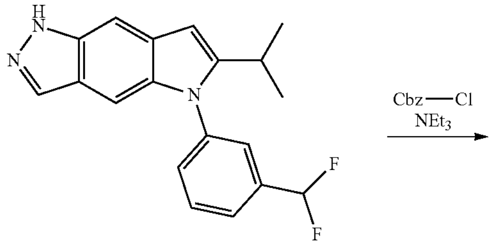

C43

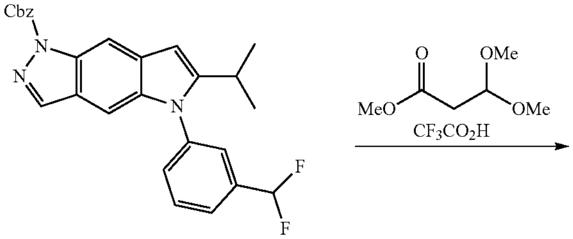

C44

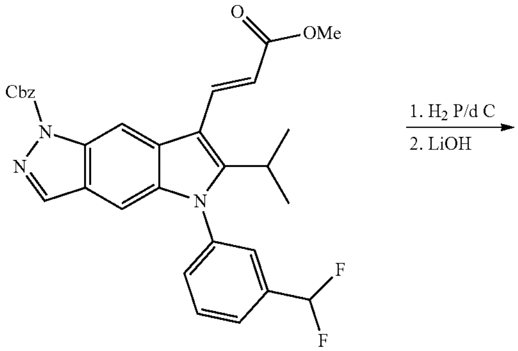

C45

-continued

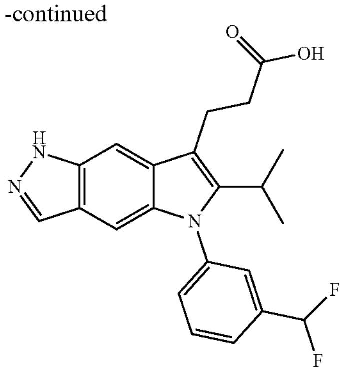

37

Steps 1-5. Synthesis of benzyl 5-(3-(difluoromethyl)phenyl)-6-isopropylpyrrolo[2,3-f]indazole-1(5H)-carboxylate (C44)

Compound C44 was prepared from C1 using the method described for preparation of S11. BrettPhos Pd G4 was used as the catalyst in step 3, to obtain a mixture of C41 and C42. The THP protecting group was removed in the cyclization step 4.

Step 6. Synthesis of benzyl (E)-5-(3-(difluoromethyl)phenyl)-6-isopropyl-7-(3-methoxy-3-oxoprop-1-en-1-yl)pyrrolo[2,3-f]indazole-1(5H)-carboxylate (C45)

C45 was prepared as described for compound 32. LCMS m/z 544.3 [M+H]$^+$.

Step 7 and 8. Synthesis of 3-[5-[3-(difluoromethyl)phenyl]-6-isopropyl-1H-pyrrolo[2,3-f]indazol-7-yl]propanoic Acid (37)

Compound 37 was prepared in two steps from C45 using the method as described for compound 32. Yield: 17 mg, 22% (over 2 steps). LCMS m/z 398.2 [M+H]$^+$. $^1$H NMR (400 MHz, DMSO-d6) δ 12.64 (s, 1H), 12.32 (s, 1H), 7.96 (d, J=1.0 Hz, 1H), 7.81-7.73 (m, 2H), 7.65-7.57 (m, 2H), 7.51 (t, J=1.1 Hz, 1H), 7.30-7.00 (m, 2H), 3.19-3.10 (m, 2H), 3.01 (m, J=7.2 Hz, 1H), 2.62-2.56 (m, 2H), 1.26 (d, J=7.1 Hz, 6H).

Compound 38

3-[5-(3,4-difluorophenyl)-6-isopropyl-1H-pyrrolo[2,3-f]indazol-7-yl]propanoic Acid (38)

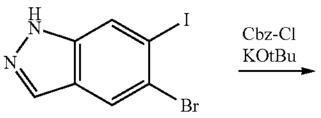

C7

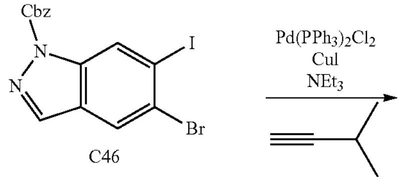

C46

-continued

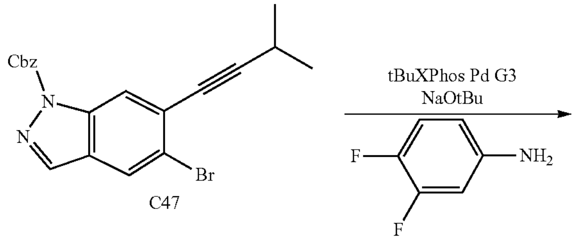

C47

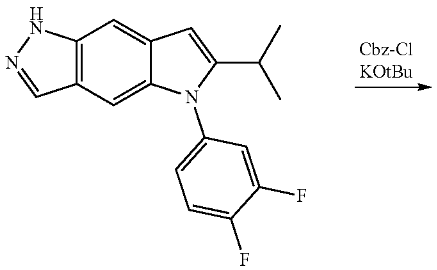

C48

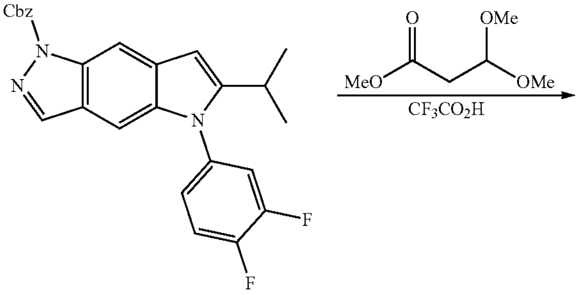

C49

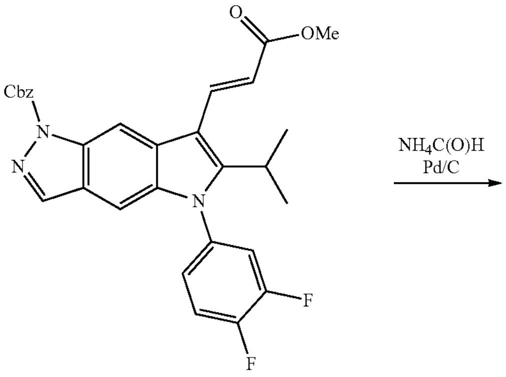

C50

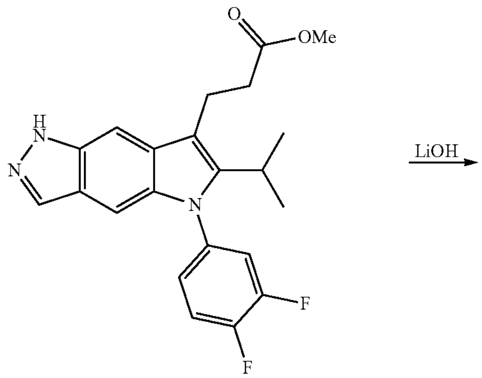

C51

-continued

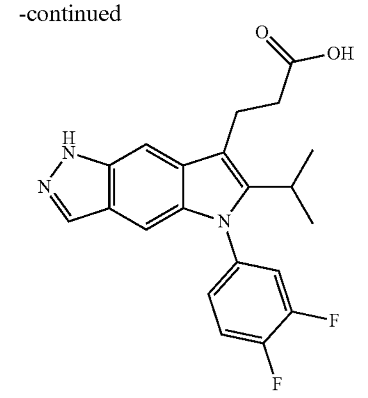

38

Step 1. Synthesis of benzyl 5-bromo-6-iodo-1H-indazole-1-carboxylate (C46)

Compound C46 was prepared from C7 and CBz-C1 using the method described in preparation S4.

Step 2 and 3. Synthesis of benzyl 5-bromo-6-(3-methylbut-1-yn-1-yl)-1H-indazole-1-carboxylate (C48)

Compound C48 was prepared in two steps from C46 using the method described in preparation S1. In this case tBuXPhos Pd G3 was used as the catalyst in step 2.

Step 4. Synthesis of benzyl (E)-5-(3,4-difluorophenyl)-6-isopropyl-7-(3-methoxy-3-oxoprop-1-en-1-yl) pyrrolo[2, 3-f]indazole-1(5H)-carboxylate (C50)

Compound C50 was prepared as described for compound 17 (trifluoroacetic acid and triethylsilane) using 1,2-dichloroethane as the solvent. The product was advanced to the next step without further purification. Yield: 124 mg, 45%. LCMS m/z 530.4 $[M+H]^+$.

Step 5. Synthesis of methyl 3-(5-(3,4-difluorophenyl)-6-isopropyl-1,5-dihydropyrrolo[2,3-f]indazol-7-yl)propanoate (C51)

To a solution of C50 (114 mg, 0.3 mmol) in MeOH (3 mL) was added palladium on carbon (46 mg of 5% w/w, 0.02 mmol) and ammonium formate (160 mg, 2.5 mmol). The mixture was heated at 50° C. for 2 h. The mixture was cooled to room temperature and stirred for an additional 12 h. Purification by chromatography on silica gel (Gradient: 0-50% EtOAc in heptanes) afforded the product. Yield: 38 mg, 42%. LCMS m/z 400.5 $[M+H]^+$. $^1H$ NMR (400 MHz, Chloroform-d) δ 8.21 (d, J=13.2 Hz, 1H), 8.07 (d, J=1.1 Hz, 1H), 7.63-7.45 (m, 2H), 7.16-6.99 (m, 1H), 6.83-6.61 (m, 2H), 4.59 (d, J=13.1 Hz, 1H), 3.67 (s, 3H), 2.42 (t, J=8.2 Hz, 2H), 1.49 (dt, J=13.1, 6.6 Hz, 1H), 0.81 (d, J=6.5 Hz, 6H).

Step 6. Synthesis of 3-[5-(3,4-difluorophenyl)-6-isopropyl-1H-pyrrolo[2,3-f]indazol-7-yl]propanoic Acid (38)

Preparation of 38 from C51 was achieved using the hydrolysis method described for compound 16. Yield: 26 mg, 59%. LCMS m/z 384.4 $[M+H]^+$. $^1H$ NMR (400 MHz, Chloroform-d) δ 7.94 (d, J=1.0 Hz, 1H), 7.85 (t, J=1.1 Hz, 1H), 7.34 (dt, J=9.9, 8.7 Hz, 1H), 7.20 (ddd, J=10.4, 7.0, 2.5 Hz, 1H), 7.11 (dddd, J=8.3, 4.0, 2.5, 1.6 Hz, 1H), 7.07 (d, J=1.1 Hz, 1H), 3.36 (t, J=7.3 Hz, 2H), 3.08 (hept, J=7.2 Hz, 1H), 2.81 (t, J=7.2 Hz, 2H), 1.33 (d, J=7.2 Hz, 6H).

Compound 39

1-[[6-isopropyl-5-[3-(trifluoromethyl)phenyl]-1H-pyrrolo[2,3-f]indazol-7-yl]methyl]cyclopropanecarboxylic Acid (39)

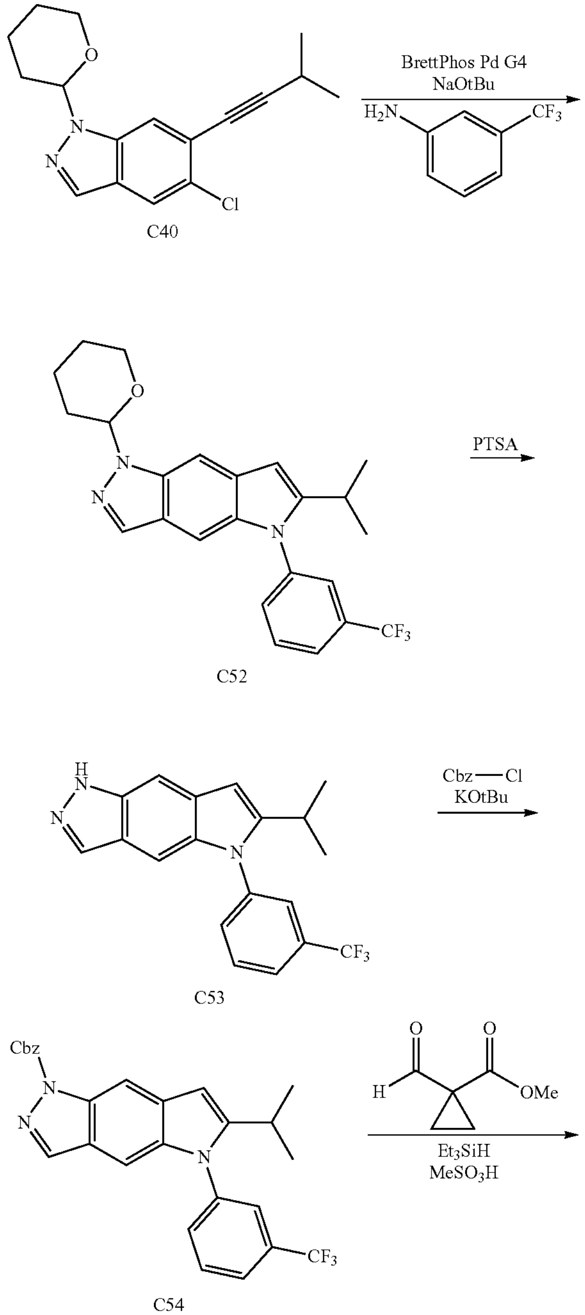

C40

C52

C53

C54

-continued

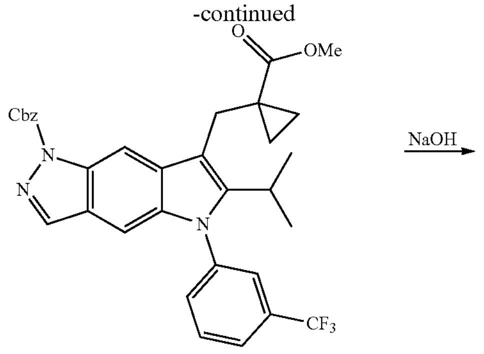

C55

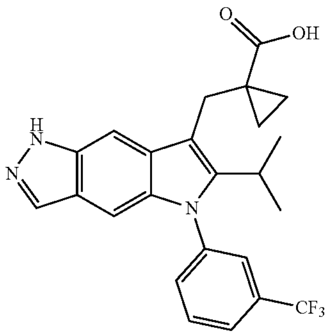

39

Steps 1-3. Preparation of benzyl 6-isopropyl-5-(3-(trifluoromethyl)phenyl)pyrrolo[2,3-f]indazole-1(5H)-carboxylate (C54)

Compound C54 was prepared as described for preparation of S11. LCMS m/z 478.2 $[M+H]^+$. $^1H$ NMR (300 MHz, DMSO-d6) δ 8.37 (d, J=0.8 Hz, 1H), 8.29-8.25 (m, 1H), 7.99-7.84 (m, 4H), 7.59-7.52 (m, 2H), 7.49-7.34 (m, 4H), 6.73-6.67 (m, 1H), 5.52 (s, 2H), 2.94 (m, J=6.8 Hz, 1H), 1.19 (d, J=6.8 Hz, 6H).

Steps 4-5. Preparation of 1-[[6-isopropyl-5-[3-(trifluoromethyl)phenyl]-1H-pyrrolo[2,3-f]indazol-7-yl]methyl]cyclopropanecarboxylic Acid (39)

Compound 39 was prepared from C54 and methyl 1-formylcyclopropanecarboxylate using the methods described for compound 33. In this case, sodium hydroxide was used as the base in the ester hydrolysis step. LCMS m/z 442.2 $[M+H]^+$ $^1H$ NMR (300 MHz, DMSO-d6) δ 12.62 (s, 1H), 12.30 (s, 1H), 7.99-7.90 (m, 2H), 7.90-7.74 (m, 3H), 7.49 (t, J=1.1 Hz, 1H), 6.96 (d, J=1.1 Hz, 1H), 3.45 (s, 2H), 3.12 (m, J=7.2 Hz, 1H), 1.16 (d, J=7.1 Hz, 6H), 1.05 (d, J=3.6 Hz, 2H), 0.70 (d, J=3.7 Hz, 2H).

Compound 40

3-[6-isopropyl-5-[3-(trifluoromethyl)phenyl]-1H-pyrrolo[2,3-f]indazol-7-yl]propanoic Acid (40)

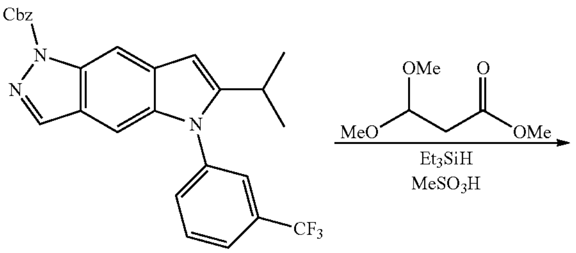

C54

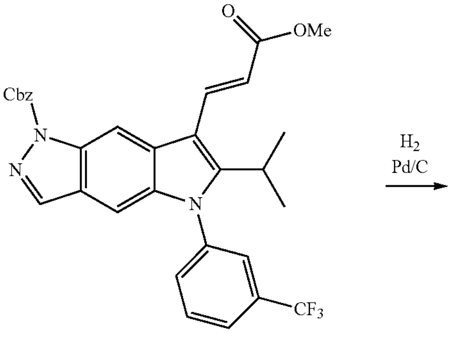

C56

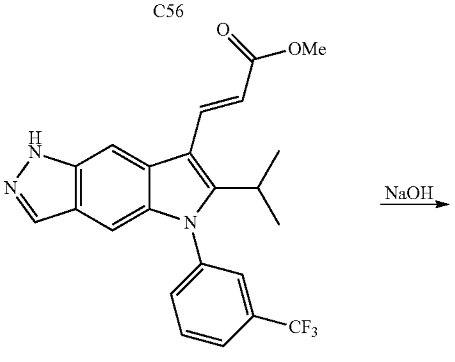

C57

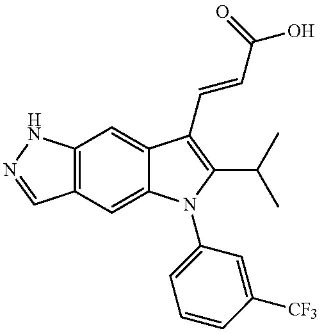

40

Compound 40 was prepared using a similar method to that described for compound 16. In this case, sodium hydroxide was used instead of lithium hydroxide in the final ester hydrolysis step. LCMS m/z 416.2 $[M+H]^+$. $^1H$ NMR (300 MHz, DMSO-d6) δ 12.64 (s, 1H), 12.27 (s, 1H), 7.99-7.72

(m, 5H), 7.52 (t, J=1.1 Hz, 1H), 7.05 (d, J=1.1 Hz, 1H), 3.20-3.09 (m, 2H), 3.00 (m, J=7.1 Hz, 1H), 2.63-2.55 (m, 2H), 1.26 (d, J=7.1 Hz, 6H).

Compound 41

3-(6-isopropyl-5-phenyl-1H-pyrrolo[2,3-f]indazol-7-yl)propanoic Acid (41)

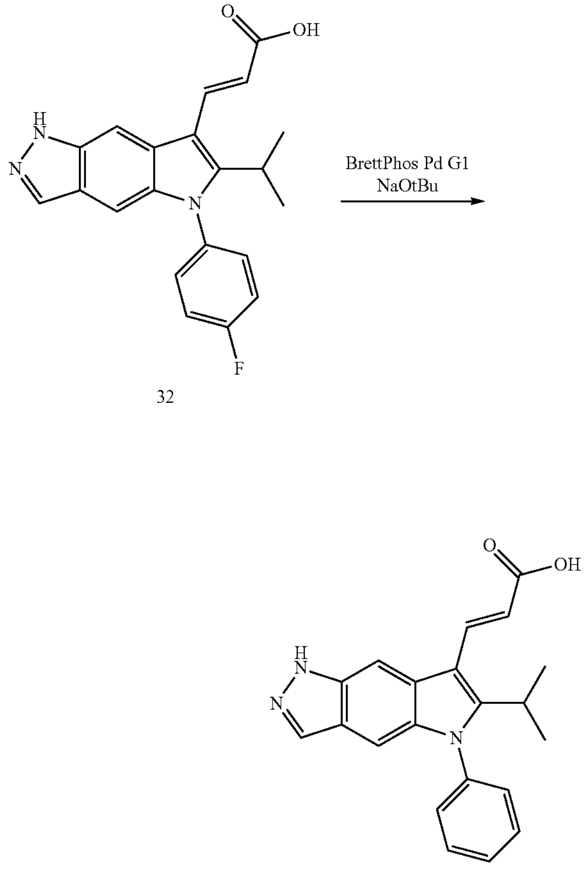

32

41

Isopropyl alcohol (3 mL) was added to a nitrogen purged vial containing sodium t-butoxide (80 mg, 0.8 mmol), BrettPhos palladacycle Gen 1 (60 mg, 0.08 mmol), and 3-[5-(4-fluorophenyl)-6-isopropyl-1H-pyrrolo[2,3-f]indazol-7-yl] propanoic acid 32 (100 mg, 0.3 mmol). The mixture was heated under microwave conditions at 150° C. for 210 min. The mixture was then diluted with EtOAc and washed with 50% saturated sodium bicarbonate. The organic layer was dried over sodium sulfate and concentrated to dryness. Purification by silica gel chromatography (Gradient: 0-10% methanol in dichloromethane), followed by stirring the product with MP-TMT scavenger resin afforded the product as a light yellow oil Yield: 43.5 mg, 45%. LCMS m/z 348.1 $[M+H]^+$. $^1H$ NMR (300 MHz, DMSO-d6) δ 12.59 (s, 1H), 12.24 (s, 1H), 7.95 (d, J=0.9 Hz, 1H), 7.66-7.51 (m, 3H), 7.50-7.47 (m, 1H), 7.43-7.37 (m, 2H), 7.02 (d, J=1.1 Hz, 1H), 3.19-3.08 (m, 2H), 3.07-2.96 (m, 1H), 2.64-2.54 (m, 2H), 1.26 (d, J=7.2 Hz, 6H).

Compound 42

6-isopropyl-5-phenyl-1H-pyrrolo[2,3-f]indazole-7-carbonitrile (42)

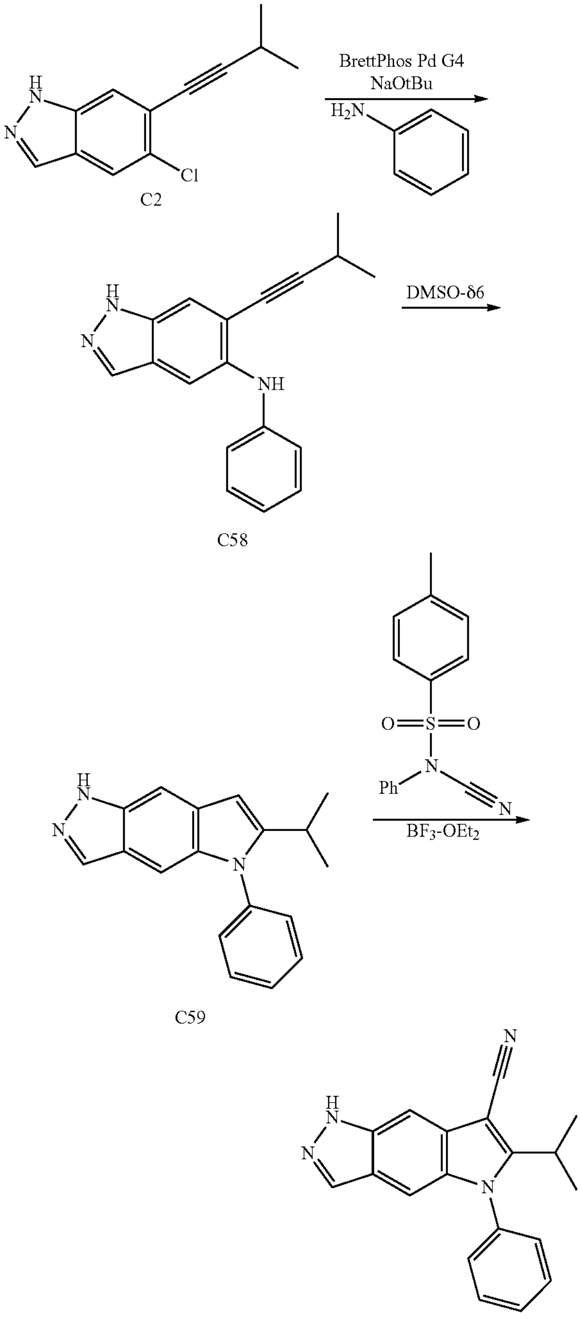

C2

C58

C59

42

Step 1-2. Synthesis of 6-isopropyl-5-phenyl-1,5-dihydropyrrolo[2,3-f]indazole (C59)

Compound C59 was prepared from C2 as described in preparation S1. LCMS 276.2 $[M+H]^+$. $^1H$ NMR (300 MHz, DMSO-d6) δ 12.58 (s, 1H), 7.96 (t, J=1.3 Hz, 1H), 7.67-7.61

(m, 2H), 7.57-7.51 (m, 2H), 7.50-7.44 (m, 2H), 7.17 (s, 1H), 6.48 (d, J=0.8 Hz, 1H), 2.96 (m, J=6.8 Hz, 1H), 1.17 (d, J=6.8 Hz, 6H).

Step 3. Synthesis of 6-isopropyl-5-phenyl-1H-pyrrolo[2,3-f]indazole-7-carbonitrile (42)

Compound 42 was prepared from C59 using the method described for Compound 10. 24 mg, 23%. LCMS m/z 301.1 [M+H]$^+$. $^1$H NMR (300 MHz, DMSO-d6) δ 12.90 (s, 1H), 8.13-8.06 (m, 1H), 7.77-7.53 (m, 6H), 7.34-7.26 (m, 1H), 3.07-2.90 (m, 1H), 1.39 (dd, J=6.9, 3.5 Hz, 6H).

Compound 43

6-isopropyl-5-(2-methyl-4-pyridyl)-1H-pyrrolo[2,3-f]indazole (43)

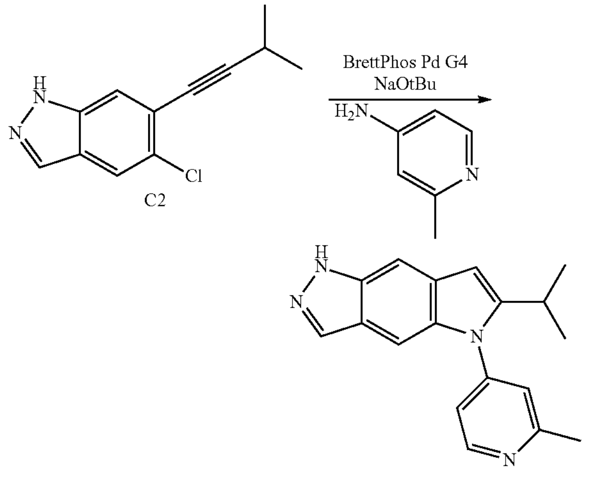

C2

43

Compound 43 was prepared from C2 using the method described for S1 in preparation S1. In this case, a separate cyclization step was not required as the intermediate product of the Buchwald coupling cyclized spontaneously in the reaction. Yield: 377 mg, 53%. LCMS m/z 291.2 [M+H]$^+$. $^1$H NMR (300 MHz, DMSO-d6) δ 12.65 (s, 1H), 8.67 (dd, J=5.3, 0.7 Hz, 1H), 7.99 (t, J=1.3 Hz, 1H), 7.57 (t, J=1.1 Hz, 1H), 7.46 (d, J=2.0 Hz, 1H), 7.43-7.31 (m, 2H), 6.56 (d, J=0.9 Hz, 1H), 3.11 (m, J=6.8 Hz, 1H), 2.60 (s, 3H), 1.18 (d, J=6.8 Hz, 6H).

Compound 44

6-isopropyl-5-(m-tolyl)-1H-pyrrolo[2,3-f]indazole-7-carbonitrile (44)

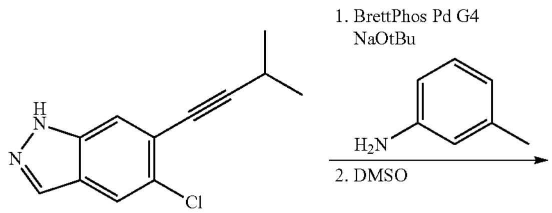

C2

-continued

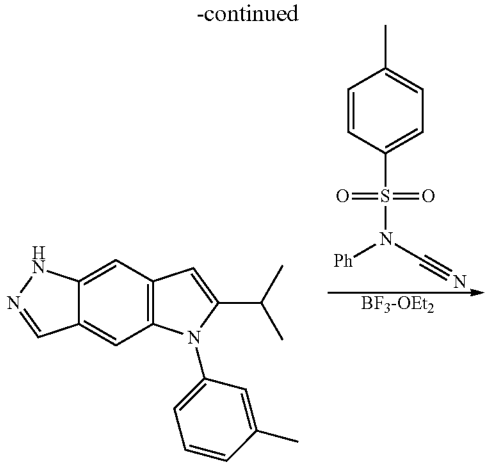

C60

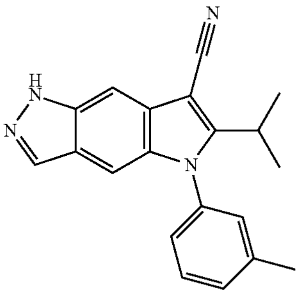

44

Step 1. Synthesis of 6-isopropyl-5-(m-tolyl)-1H-pyrrolo[2,3-f]indazole (C60)

Compound C60 was prepared from C2 in two steps using the method described for preparation of S1. Yield: 470 mg, 64%. LCMS m/z 290.2.2 [M+H]$^+$. $^1$H NMR (300 MHz, DMSO-d6) δ 12.57 (s, 1H), 7.95 (t, J=1.3 Hz, 1H), 7.53 (t, J=1.2 Hz, 1H), 7.50 (d, J=7.6 Hz, 1H), 7.35 (d, J=7.7 Hz, 1H), 7.29-7.22 (m, 2H), 7.18-7.15 (m, 1H), 6.47 (d, J=0.9 Hz, 1H), 2.96 (m, J=6.7 Hz, 1H), 2.42 (s, 3H), 1.18 (d, J=6.8 Hz, 6H).

Step 2. Synthesis of 6-isopropyl-5-(m-tolyl)-1H-pyrrolo[2,3-f]indazole-7-carbonitrile (44)

Compound 44 was prepared from compound C60 using the method described for compound 10. Yield: 34.3 mg, 27%. LCMS m/z 315.2 [M+H]$^+$. $^1$H NMR (300 MHz, DMSO-d6) δ 12.89 (s, 1H), 8.09 (t, J=1.3 Hz, 1H), 7.60 (t, J=1.1 Hz, 1H), 7.56 (d, J=7.7 Hz, 1H), 7.49-7.44 (m, 1H), 7.40-7.37 (m, 1H), 7.37-7.31 (m, 1H), 7.30-7.26 (m, 1H), 2.98 (m, J=6.9 Hz, 1H), 2.44 (s, 3H), 1.40 (dd, J=7.0, 3.1 Hz, 6H).

Compound 45

5-(3-chlorophenyl)-6-isopropyl-1H-pyrrolo[2,3-f]indazole-7-carbonitrile (45)

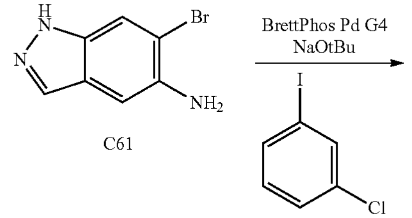

C61

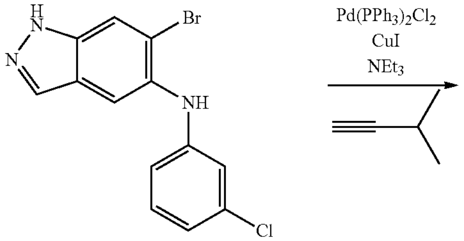

C62

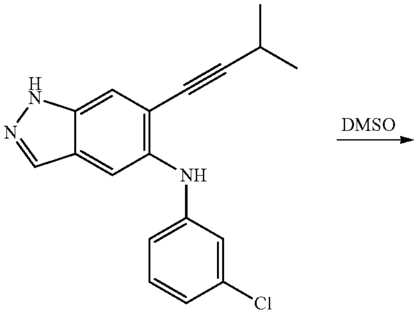

C63

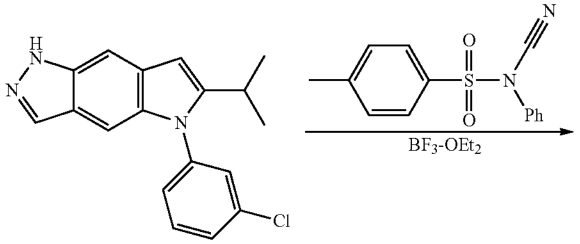

C64

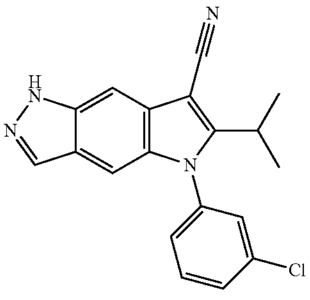

45

Step 1. Synthesis of 6-bromo-N-(3-chlorophenyl)-1H-indazol-5-amine (C62)

Compound C62 was prepared from C61 and 1-chloro-3-iodo-benzene using the method described for the preparation of C3 in Preparation S1. Yield: 89 mg, 12%. LCMS m/z 322.1 $[M+H]^+$. $^1$H NMR (300 MHz, DMSO-d6) δ 13.16 (s, 1H), 8.06 (t, J=1.3 Hz, 1H), 7.93 (t, J=1.3 Hz, 2H), 7.73 (s, 1H), 7.17-7.04 (m, 1H), 6.72-6.65 (m, 1H), 6.66-6.57 (m, 2H).

Steps 2 and 3. Synthesis of 5-(3-chlorophenyl)-6-isopropyl-1H-pyrrolo[2,3-f]indazole (C64)

Compound C64 was prepared using the method used for compound S1 in preparation S1. Yield: 33 mg, 41%. LCMS m/z 310.2 $[M+H]^+$. $^1$H NMR (300 MHz, Chloroform-d) δ 9.86 (s, 1H), 8.06 (s, 1H), 7.60-7.55 (m, 1H), 7.55-7.47 (m, 2H), 7.44 (td, J=1.9, 0.6 Hz, 1H), 7.34 (dt, J=7.0, 2.0 Hz, 1H), 7.31 (t, J=1.0 Hz, 1H), 6.50 (t, J=0.8 Hz, 1H), 3.12-2.88 (m, 1H), 1.29-1.20 (m, 6H).

Step 4. Synthesis of 5-(3-chlorophenyl)-6-isopropyl-1H-pyrrolo[2,3-f]indazole-7-carbonitrile (45)

Compound 45 was prepared using from compound C64 using the method described for compound 10. Yield: 12.0 mg, 23%. LCMS m/z $[M+H]^+$ 335.2. $^1$H NMR (300 MHz, DMSO-d6) δ 12.92 (s, 1H), 8.10 (t, J=1.3 Hz, 1H), 7.84-7.79 (m, 1H), 7.79-7.67 (m, 2H), 7.62-7.54 (m, 2H), 7.33 (d, J=0.9 Hz, 1H), 2.96 (m, J=7.0 Hz, 1H), 1.40 (t, J=7.2 Hz, 6H).

Compound 46 and Compound 47

3-fluoro-5-(4-fluoro-3-methyl-phenyl)-7-iodo-6-isopropyl-1H-pyrrolo[2,3-f]indazole (46) and 3-fluoro-5-(4-fluoro-3-methyl-phenyl)-6-isopropyl-7-methylsulfonyl-1H-pyrrolo[2,3-f]indazole (47)

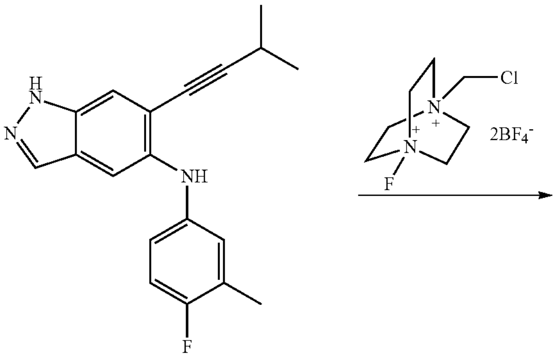

C3

-continued

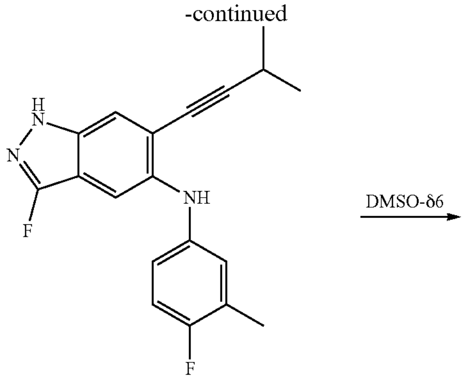

C65

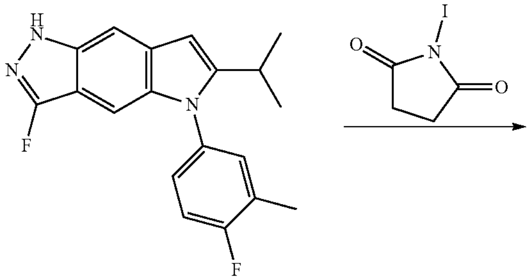

C66

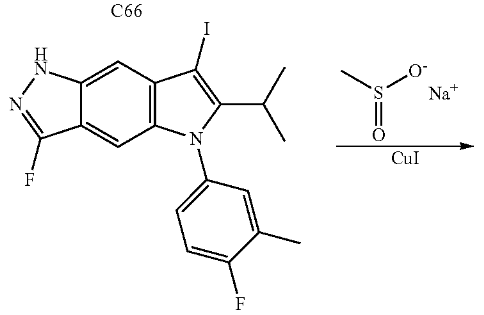

46

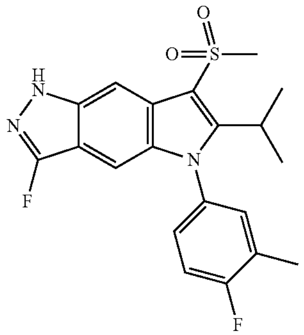

47

Step 1. Synthesis of 3-fluoro-N-(4-fluoro-3-methyl-phenyl)-6-(3-methylbut-1-ynyl)-1H-indazol-5-amine (C65)

To a solution of C3 (606 mg, 1.9 mmol) in MeCN (50 mL) was added acetic acid (123 μL, 2.2 mmol) and 1-(chloromethyl)-4-fluoro-1,4-diazoniabicyclo[2.2.2]octane ditetrafluoroborate (793 mg, 2.2 mmol). The reaction was stirred at room temperature for 40 min. The mixture was diluted with dichloromethane (150 mL) and washed with water. The combined organic layers were passed through a phase separator, and then concentrated in vacuo. Purification by silica gel chromatography (Gradient: 0-100% EtOAc in heptanes) afforded the product. Yield: 228.5 mg, 36%. LCMS m/z 326.1 $[M+H]^{+1}$H NMR (300 MHz, DMSO-d6) δ 13.40 (s, 1H), 8.16 (d, J=1.0 Hz, 1H), 7.43 (d, J=1.0 Hz, 1H), 7.28 (s, 1H), 6.86 (t, J=9.0 Hz, 1H), 6.41 (t, J=7.3 Hz, 2H), 2.64 (m, J=6.8 Hz, 1H), 2.10 (d, J=1.9 Hz, 3H), 1.00 (d, J=6.8 Hz, 6H).

Step 2. Synthesis of 3-fluoro-5-(4-fluoro-3-methyl-phenyl)-6-isopropyl-1H-pyrrolo[2,3-f]indazole (C66)

Compound C66 was prepared as described for C3 in preparation S1. Yield: 187 mg, 85%. LCMS m/z 326.2 $[M+H]^+$ $^1$H NMR (300 MHz, DMSO-d6) δ 12.85 (s, 1H), 8.04 (t, J=1.3 Hz, 1H), 7.48-7.26 (m, 4H), 6.51 (dd, J=2.3, 0.7 Hz, 1H), 2.80 (m, J=6.8 Hz, 1H), 2.31 (d, J=2.0 Hz, 3H), 1.17 (dd, J=6.7, 4.9 Hz, 6H).

Step 3. Synthesis of 3-fluoro-5-(4-fluoro-3-methyl-phenyl)-7-iodo-6-isopropyl-1H-pyrrolo[2,3-f]indazole (46)

Compound 46 was prepared from compound C66 using the method described for compound 1. Yield: 61.5 mg, 25%. LCMS m/z 452.1 $[M+H]^+$ $^1$H NMR (300 MHz, DMSO-d6) δ 13.00 (s, 1H), 8.10 (dd, J=1.6, 1.1 Hz, 1H), 7.49 (dd, J=6.9, 2.6 Hz, 1H), 7.44-7.36 (m, 1H), 7.32 (t, J=8.9 Hz, 1H), 7.19 (d, J=1.0 Hz, 1H), 2.94 (m, J=7.1 Hz, 1H), 2.31 (d, J=2.0 Hz, 3H), 1.33 (dd, J=7.2, 2.6 Hz, 6H).

Step 4. Synthesis of 3-fluoro-5-(4-fluoro-3-methyl-phenyl)-6-isopropyl-7-methylsulfonyl-1H-pyrrolo[2,3-f]indazole (47)

Compound 47 was prepared from compound 46 using the method described for compound 11. Yield: 10.3 mg, 24%. LCMS m/z 404.2 $[M+H]^+$. $^1$H NMR (300 MHz, Chloroform-d) δ 10.11 (s, 1H), 8.13 (d, J=1.1 Hz, 1H), 7.97 (d, J=1.1 Hz, 1H), 7.30 (d, J=3.5 Hz, 1H), 7.26 (dd, J=4.6, 2.7 Hz, 1H), 7.20 (t, J=8.6 Hz, 1H), 3.83-3.63 (m, 1H), 3.23 (s, 3H), 2.40 (d, J=2.0 Hz, 3H), 1.36 (dd, J=7.2, 1.1 Hz, 6H).

Compound 48 and Compound 49

5-(4-fluoro-3-methyl-phenyl)-8-iodo-6-isopropyl-1H-pyrrolo[2,3-f]indazole (48) and 5-(4-fluoro-3-methyl-phenyl)-6-isopropyl-8-methyl-1H-pyrrolo[2,3-f]indazole (49)

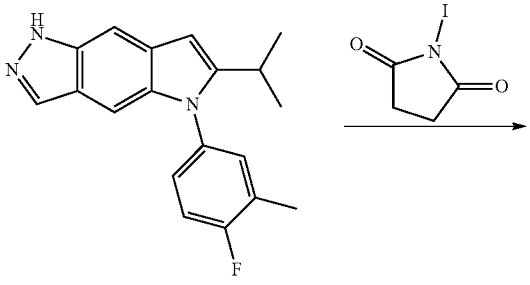

#S1

-continued

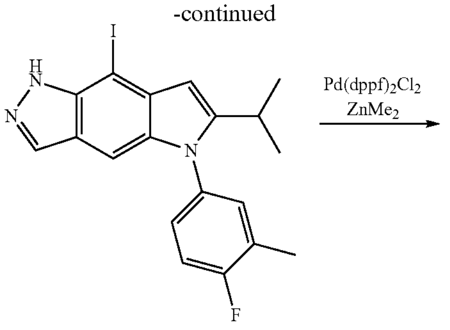

48

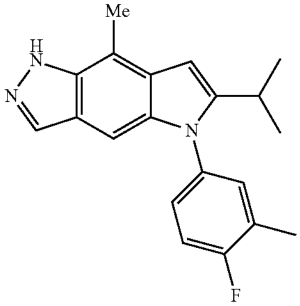

49

Step 1. Synthesis of 5-(4-fluoro-3-methyl-phenyl)-8-iodo-6-isopropyl-1H-pyrrolo[2,3-f]indazole (48)

1-iodopyrrolidine-2,5-dione (880 mg, 3.9 mmol) was added portion-wise to a solution of 5-(4-fluoro-3-methyl-phenyl)-6-isopropyl-1H-pyrrolo[2,3-f]indazole S1 (1.3 g, 4.0 mmol) in dichloromethane (35 mL). The reaction mixture was stirred for 2 days at room temperature. The reaction was quenched with 1M sodium thiosulfate, and then water and dichloromethane were added. The organic phase was isolated using a phase separator and then concentrated in vacuo. Purification by silica gel chromatography (Eluent: EtOAc in heptanes) afforded the product. Yield: 921 mg, 53%. $^1$H NMR (400 MHz, DMSO-d6) δ 12.73 (s, 1H), 8.15 (d, J=1.5 Hz, 1H), 7.48-7.31 (m, 3H), 7.17 (s, 1H), 6.30 (s, 1H), 2.92 (m, J=6.8 Hz, 1H), 2.34 (d, J=2.0 Hz, 3H), 1.20 (d, J=6.7 Hz, 6H).

Step 2. Synthesis of 5-(4-fluoro-3-methyl-phenyl)-6-isopropyl-8-methyl-1H-pyrrolo[2, 3-f]indazole (49)

Compound 49 was prepared using the method described for C10 in preparation S5. Yield: 29 mg, 50%. LCMS m/z 322.5 [M+H]$^+$. $^1$H NMR (400 MHz, DMSO-d6) δ 12.65 (s, 1H), 7.94 (s, 1H), 7.38 (dd, J=10.8, 7.1 Hz, 2H), 7.29 (dt, J=8.1, 3.8 Hz, 1H), 6.97 (s, 1H), 6.49 (s, 1H), 2.92 (m, J=6.7 Hz, 1H), 2.68 (s, 3H), 2.33 (d, J=1.9 Hz, 3H), 1.19 (d, J=6.8 Hz, 6H).

Compound 50

8-fluoro-5-(4-fluoro-3-methyl-phenyl)-6-isopropyl-1H-pyrrolo[2,3-f]indazole (50)

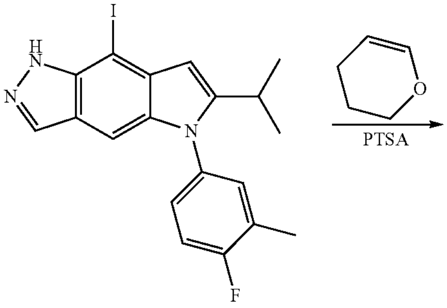

48

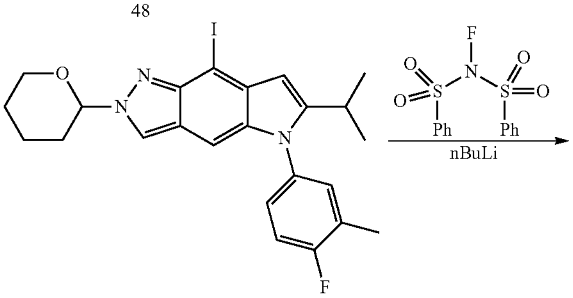

C67

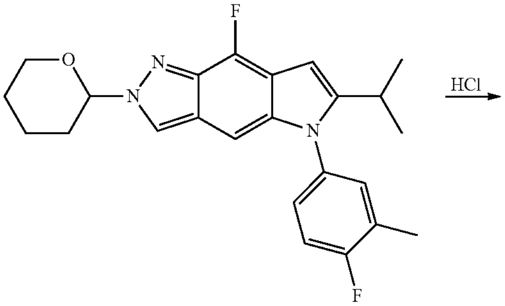

C68

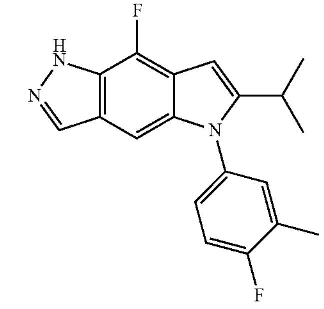

50

Step 1. Synthesis of 5-(4-fluoro-3-methyl-phenyl)-8-iodo-6-isopropyl-2-tetrahydropyran-2-yl-pyrrolo[2,3-f]indazole (C67)

3,4-dihydro-2H-pyran (178 μL, 2.0 mmol) and 4-methylbenzenesulfonic acid (Pyridine) (16 μL, 0.07 mmol) were added to a solution of 5-(4-fluoro-3-methyl-phenyl)-8-iodo-6-isopropyl-1H-pyrrolo[2,3-f]indazole 48 (278 mg, 0.6 mmol) in dichloromethane (4 mL). The reaction was stirred at room temperature for 48 h, and then saturated aqueous sodium bicarbonate and dichloromethane were added. The organic phase was isolated on a phase separator and the mixture concentrated in vacuo. Purification by silica gel chromatography (Eluent: EtOAc in heptanes) afforded the product as a single isomer. Yield: 243 mg, 73%. LCMS m/z 518.3 [M+H]+ $^1$H NMR (400 MHz, DMSO-d6) δ 8.60 (s, 1H), 7.52-7.19 (m, 3H), 7.06 (s, 1H), 6.24 (s, 1H), 5.76 (dd, J=9.7, 2.6 Hz, 1H), 4.06-3.92 (m, 1H), 3.74 (td, J=11.1, 4.5 Hz, 1H), 2.86 (h, J=6.8 Hz, 1H), 2.33 (d, J=1.8 Hz, 3H), 2.23-1.90 (m, 3H), 1.85-1.66 (m, 1H), 1.61 (tt, J=9.1, 3.9 Hz, 2H), 1.22-1.12 (m, 7H).

Step 2. Synthesis of 8-fluoro-5-(4-fluoro-3-methyl-phenyl)-6-isopropyl-2-tetrahydropyran-2-yl-pyrrolo[2,3-f]indazole (C68)

To solution of compound C67 5-(4-fluoro-3-methyl-phenyl)-8-iodo-6-isopropyl-2-tetrahydropyran-2-yl-pyrrolo[2,3-f]indazole (710 mg, 1.4 mmol) in THF (14 mL) and cooled to −78° C. was added n-butyl lithium solution (~548.8 μL of 2.5 M, 1.4 mmol) After 5 min, a solution of N-(benzenesulfonyl)-N-fluoro-benzenesulfonamide (approximately 433 mg, 1.4 mmol) in THF (9 mL) was added. After 5 min, aqueous saturated $NH_4Cl$ was added, and the mixture warmed to room temperature. Water and dichloromethane were added, and the phases were separated on a phase separator. Purification by silica gel chromatography (Eluent: EtOAc in heptanes) afforded the product which used directly in the next step. Yield: 157 mg, 28%. LCMS m/z $[M+H]^+$ 410.3.

Step 3. Synthesis of 8-fluoro-5-(4-fluoro-3-methyl-phenyl)-6-isopropyl-1H-pyrrolo[2,3-f]indazole (50)

To a solution of compound C68 8-fluoro-5-(4-fluoro-3-methyl-phenyl)-6-isopropyl-2-tetrahydropyran-2-yl-pyrrolo[2,3-f]indazole (17 mg, 0.04 mmol) in EtOH (1 mL) was added HCl (200 μL of 1 M, 0.2 mmol). After stirring at room temperature for 30 min, saturated aqueous sodium bicarbonate and dichloromethane were added. The phases were separated on a phase separated and the organic layer was concentrated in vacuo. Purification by silica gel chromatography (Eluent: EtOAc in heptanes) afforded the product. Yield: 4 mg, 28%. LCMS m/z 326.2 $[M+H]^+$. $^1$H NMR (400 MHz, Methanol-d4) δ 8.00 (d, J=3.2 Hz, 1H), 7.37-7.17 (m, 3H), 7.01 (s, 1H), 6.53 (s, 1H), 2.96 (m, J=6.8 Hz, 1H), 2.37 (d, J=2.0 Hz, 3H), 1.25 (d, J=6.8 Hz, 6H).

Compound 51

3-[5-(4-fluoro-3-methyl-phenyl)-6-isopropyl-8-methyl-1H-pyrrolo[2,3-f]indazol-7-yl]propanoic acid (51)

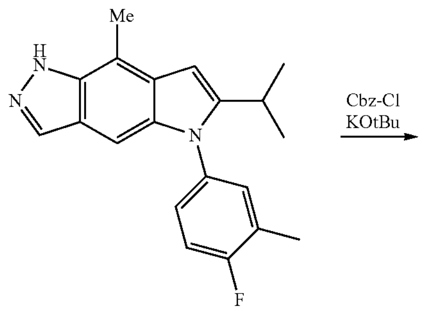

49

-continued

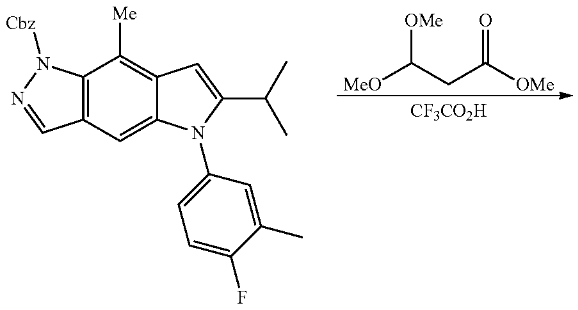

C69

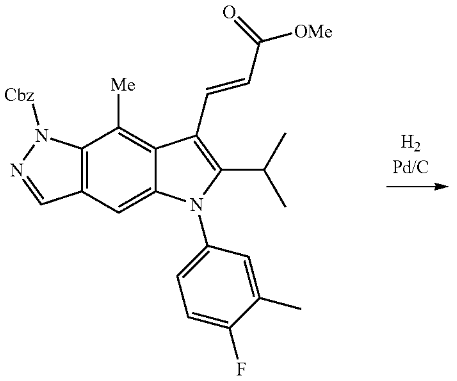

C70

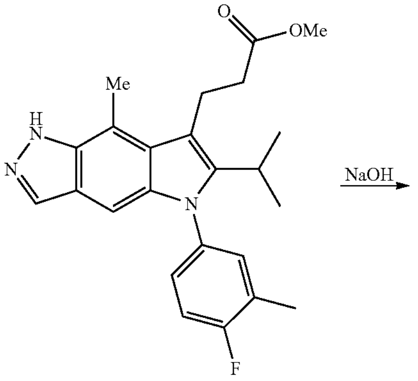

C71

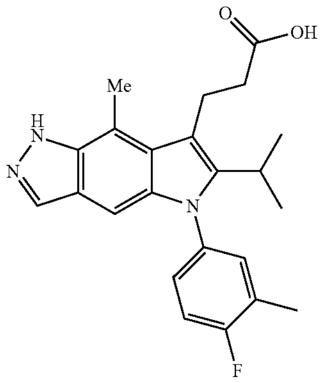

51

Step 1. Synthesis of 5-(4-fluoro-3-methyl-phenyl)-6-isopropyl-8-methyl-pyrrolo[2,3-f]indazole-1-carboxylate (C69)

Compound C69 was prepared from compound 49 as described for compound S2 in Preparation S2. Yield: 200 mg, 78%. LCMS m/z 456.3 [M+H]$^+$.

Steps 2-4. Synthesis of 3-[5-(4-fluoro-3-methyl-phenyl)-6-isopropyl-8-methyl-1H-pyrrolo[2,3-f]indazol-7-yl]propanoic Acid (51)

Compound 51 was prepared in three steps from compound C69 according to the method of preparing compound 32. In this case, sodium hydroxide was used in place of lithium hydroxide in the final hydrolysis step. Yield: 77.7 mg, 79%. LCMS m/z 394.2 [M+H]$^+$. $^1$H NMR (400 MHz, DMSO-d6) δ 12.61 (s, 1H), 12.28 (s, 1H), 7.91 (s, 1H), 7.42-7.27 (m, 2H), 7.22 (dt, J=7.9, 3.6 Hz, 1H), 6.76 (s, 1H), 3.30-3.12 (m, 2H), 3.05 (m, J=7.2 Hz, 1H), 2.60-2.53 (m, 2H), 2.32 (d, J=1.8 Hz, 3H), 1.23 (d, J=7.1 Hz, 6H).

Compound 52

3-[8-fluoro-5-(4-fluoro-3-methyl-phenyl)-6-isopropyl-1H-pyrrolo[2,3-f]indazol-7-yl]propanoic Acid (52)

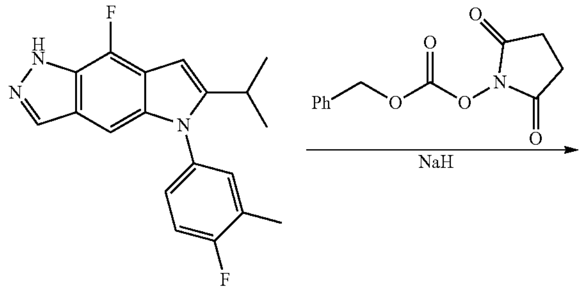

50

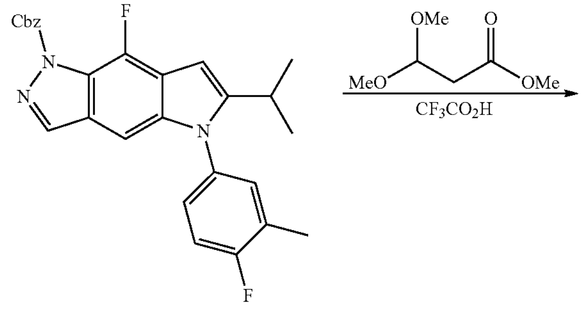

C72

-continued

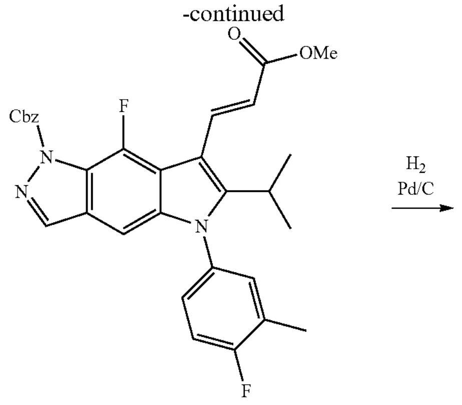

C73

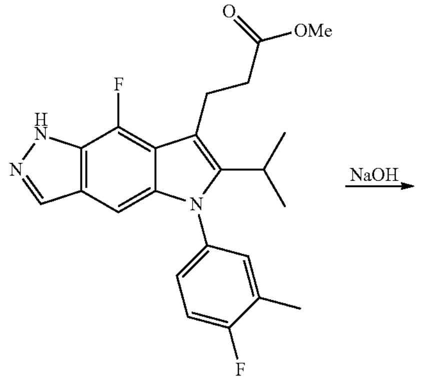

C74

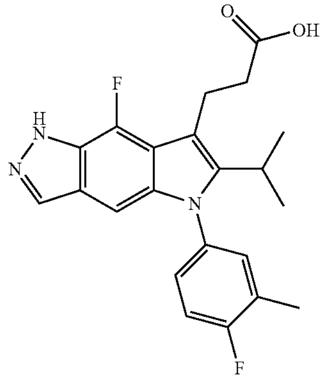

52

Step 1. Synthesis of benzyl 8-fluoro-5-(4-fluoro-3-methyl-phenyl)-6-isopropyl-pyrrolo[2,3-f]indazole-1-carboxylate (C72)

Sodium hydride (21 mg, 0.5 mmol) was added to a solution of 8-fluoro-5-(4-fluoro-3-methyl-phenyl)-6-isopropyl-1H-pyrrolo[2,3-f]indazole 50 (167 mg, 0.3 mmol) in THF (1.4 mL) and stirred for 30 min. Benzyl (2,5-dioxopyrrolidin-1-yl) carbonate (250 mg, 1.0 mmol) was added, and the reaction allowed to stir for 2 h. The reaction was concentrated in vacuo, then purified by silica gel chromatography (Eluent: EtOAc in Heptanes) to afford the product. Yield: 125 mg, 82%. LCMS m/z 460.3 [M+H]$^+$.

Steps 2-4. Synthesis of 3-[8-fluoro-5-(4-fluoro-3-methyl-phenyl)-6-isopropyl-1H-pyrrolo[2,3-f]indazol-7-yl]propanoic Acid (52)

Compound 52 was prepared from C72 in three steps according to the method outlined for the preparation of compound 32. In this case, sodium hydroxide was used in place of lithium hydroxide in the final hydrolysis step. Yield: 73.5 mg, 72%. LCMS m/z 398.0 $[M+H]^+$. $^1H$ NMR (400 MHz, Methanol-d4) δ 7.97 (d, J=3.2 Hz, 1H), 7.30-7.23 (m, 2H), 7.21 (t, J=4.0 Hz, 1H), 6.85 (s, 1H), 3.09 (q, J=7.2 Hz, 1H), 2.78-2.61 (m, 2H), 2.36 (d, J=1.9 Hz, 3H), 1.31 (dd, J=7.1, 1.7 Hz, 6H).

Compound 53

3-[8-fluoro-5-(4-fluorophenyl)-6-isopropyl-1H-pyrrolo[2,3-f]indazol-7-yl]propanoic Acid (53)

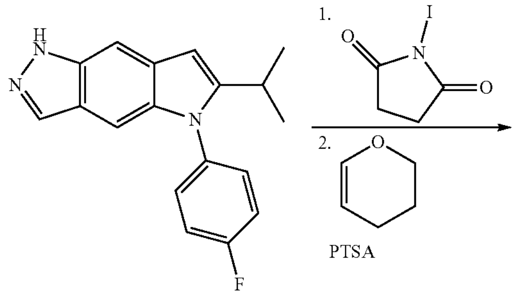

S3

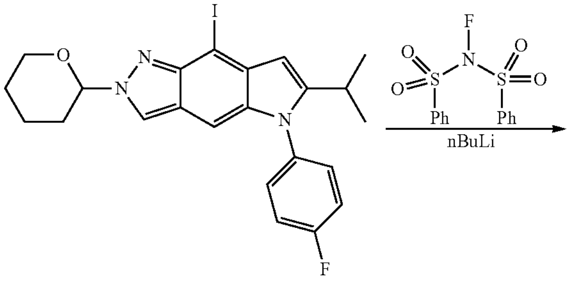

C75

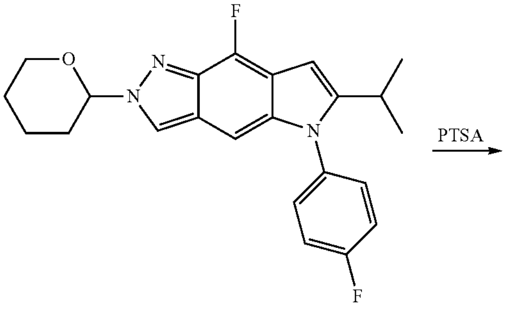

C76

-continued

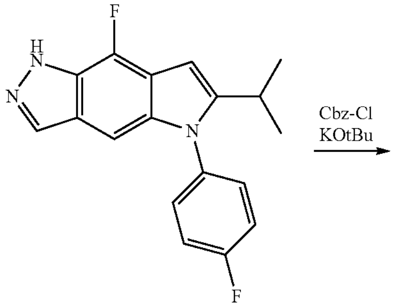

C77

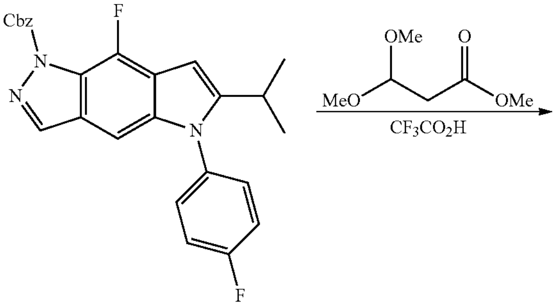

C78

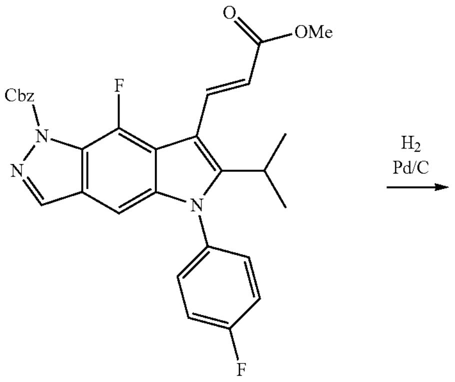

C79

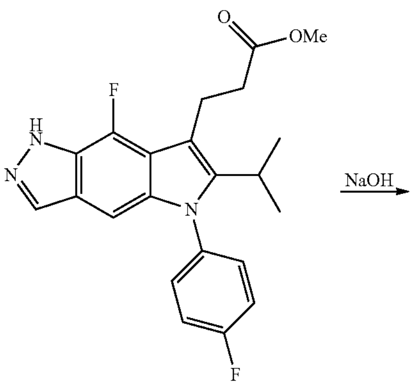

C80

-continued

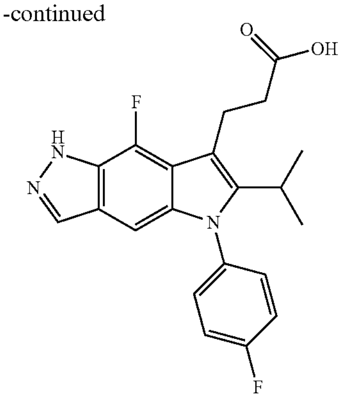

53

Step 1. Synthesis of 5-(4-fluorophenyl)-8-iodo-6-isopropyl-2-tetrahydropyran-2-yl-pyrrolo[2,3-f]indazole (C75)

Compound C75 was prepared from S3 using the method described for the preparation of compound 48. Yield: 1.6 g, 76%. LCMS m/z 504.2 $[M+H]^+$. 1H NMR (400 MHz, DMSO) δ 8.60 (s, 1H), 7.55 (dd, J=8.4, 4.9 Hz, 2H), 7.47 (t, J=8.4 Hz, 2H), 7.05 (s, 1H), 6.26 (s, 1H), 5.85-5.69 (m, 1H), 4.11-3.89 (m, 1H), 3.89-3.61 (m, 1H), 2.86 (hept, J=6.6 Hz, 1H), 2.22-1.88 (m, 3H), 1.81-1.50 (m, 3H), 1.19 (dd, J=7.0, 3.5 Hz, 7H).

Steps 2-3. Synthesis of 8-fluoro-5-(4-fluorophenyl)-6-isopropyl-1H-pyrrolo[2,3-f]indazole (C77)

Compound C77 was prepared in two steps from C75 using the methods described for compound 50. Yield: 349 mg, 68%. LCMS m/z 311.1 $[M+H]^+$.

Step 4. Synthesis of benzyl 8-fluoro-5-(4-fluorophenyl)-6-isopropyl-pyrrolo[2,3-f]indazole-1-carboxylate (C78)

Compound C78 was prepared from compound C77 using the method described in Preparation S2. Yield: 380 mg, 98%. LCMS m/z 446.2 $[M+H]^+$. $^1H$ NMR (400 MHz, DMSO-d6) δ 8.42 (s, 1H), 7.66-7.35 (m, 9H), 7.21 (s, 1H), 6.70 (s, 1H), 5.49 (s, 2H), 2.93 (q, J=7.0 Hz, 1H), 1.20 (d, J=6.8 Hz, 6H).

Step 5-7. 3-[8-fluoro-5-(4-fluorophenyl)-6-isopropyl-M-pyrrolo[2,3-f]indazol-7-yl]propanoic Acid (53)

Compound 53 was prepared in three steps from compound C78 using the method described for compound 32. In this case, sodium hydroxide was used in place of lithium hydroxide in the final step. Yield: 118.3 mg, 76%. LCMS m/z 384.2 $[M+H]^+$. $^1H$ NMR (400 MHz, DMSO) δ 13.07 (s, 1H), 12.31 (s, 1H), 8.03 (d, J=3.3 Hz, 1H), 7.55-7.32 (m, 4H), 6.83 (s, 1H), 3.24-3.12 (m, 3H), 3.00 (h, J=7.2 Hz, 1H), 2.60 (t, J=8.0 Hz, 2H), 1.25 (d, J=7.1 Hz, 6H).

Compound 54

3-[5-(4-fluoro-3-methyl-phenyl)-6-isopropyl-3-methyl-1H-pyrrolo[2,3-f]indazol-7-yl]propanoic Acid (54)

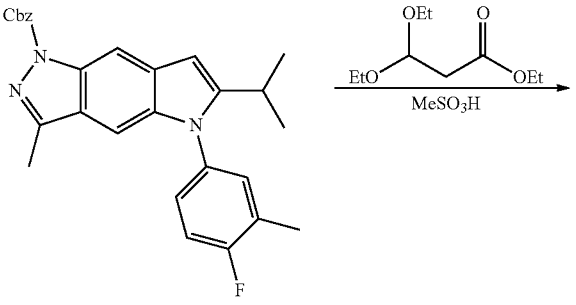

S5

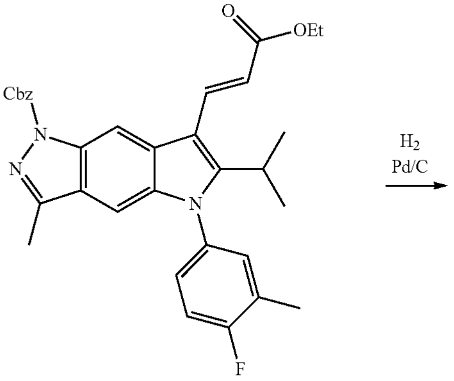

C81

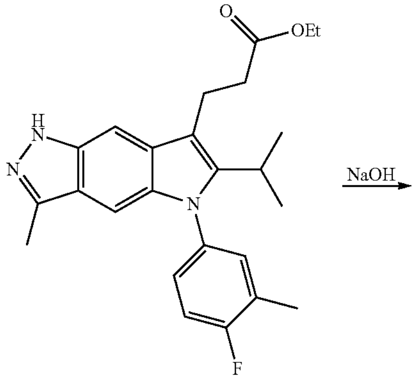

C82

-continued

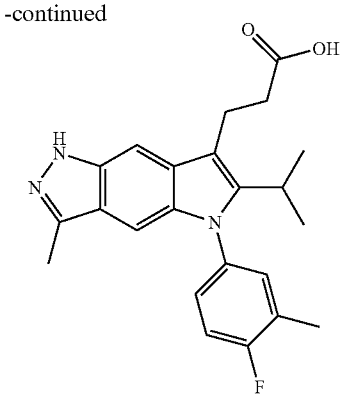

54

Compound 54 was prepared in three steps from S5 using the method described for compound 32. In this case, methanesulfonic acid was used instead of trifluoroacetic acid in step 1 (as described for the synthesis of C35 in preparation of compound 31). Yield: 19.8 mg, 85%. LCMS m/z 394.4 $[M+H]^+$. $^1H$ NMR (400 MHz, DMSO-d6) δ 12.18 (d, J=27.5 Hz, 2H), 7.45-7.32 (m, 3H), 7.26 (dt, J=8.3, 3.4 Hz, 1H), 6.89 (s, 1H), 3.11 (t, J=8.1 Hz, 2H), 2.98 (m, J=7.2 Hz, 1H), 2.61-2.53 (m, 1H), 2.39 (s, 3H), 2.33 (s, 3H), 1.25 (t, J=6.4 Hz, 6H).

Compound 55

3-[5-(4-fluoro-3-methyl-phenyl)-6-isopropyl-3-methyl-1H-pyrrolo[2,3-f]indazol-7-yl]-1-methyl-cyclobutanecarboxylic Acid (55)

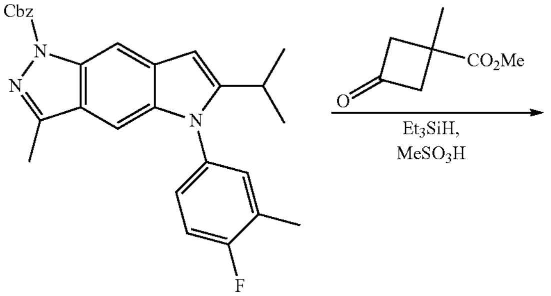

S5

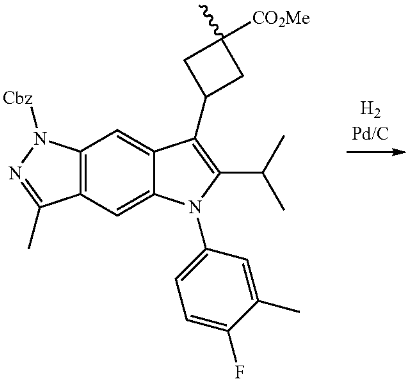

C83

-continued

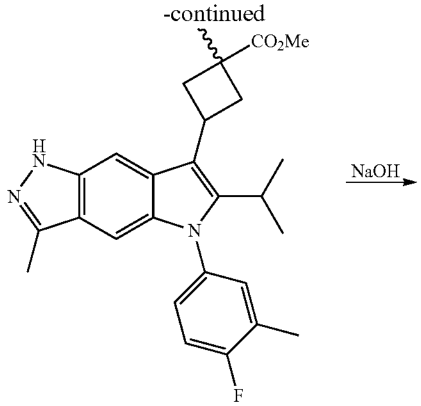

C84

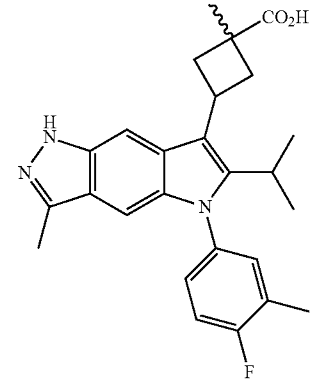

55

Step 1. Synthesis of benzyl 5-(4-fluoro-3-methyl-phenyl)-6-isopropyl-7-(3-methoxycarbonyl-3-methyl-cyclobutyl)-3-methyl-pyrrolo[2,3-f]indazole-1-carboxylate (C83)

Compound C83 was prepared from S5 using the same method used for preparation of C37 as described in the preparation of compound 33. The product was used directly in the next step. Yield: 271 mg, 96%. LCMS 582.3 $[M+H]^+$.

Steps 2 and 3. 3-[5-(4-fluoro-3-methyl-phenyl)-6-isopropyl-3-methyl-1H-pyrrolo[2,3-f]indazol-7-yl]-1-methyl-cyclobutanecarboxylic Acid (55)

Compound 55 was prepared in two steps from C83 using the same method used for compound 32. In this case, the removal of the Cbz protecting group is the only transformation occurring in the hydrogenation step. Sodium hydroxide was used in place of lithium hydroxide for the final hydrolysis step. The product was obtained as a 5:1 mixture of cis/trans isomers. LCMS m/z 434.3 $[M+H]^+$. $^1H$ NMR (400 MHz, DMSO-d6) δ 12.26 (s, 1H), 7.76 (s, 1H), 7.44-7.32 (m, 2H), 7.32-7.16 (m, 1H), 6.90 (d, J=7.3 Hz, 1H), 4.17-3.79 (m, 1H), 2.91 (m, J=7.0 Hz, 1H), 2.70 (d, J=9.8 Hz, 3H), 2.39 (s, 3H), 2.32 (d, J=1.8 Hz, 3H), 1.58 (d, J=7.4 Hz, 3H), 1.23 (dd, J=7.1, 4.2 Hz, 6H).

Compound 56, Compound 57, and Compound 58
6-[5-(4-fluoro-3-methyl-phenyl)-6-isopropyl-3-methyl-1H-pyrrolo[2,3-f]indazol-7-yl]spiro[3.3]heptane-2-carboxylic acid (56), 6-[5-(4-fluoro-3-methyl-phenyl)-6-isopropyl-3-methyl-1H-pyrrolo[2,3-f]indazol-7-yl]spiro[3.3]heptane-2-carboxylic acid, [ENANT-1] (57), 6-[5-(4-fluoro-3-methyl-phenyl)-6-isopropyl-3-methyl-1H-pyrrolo[2,3-f]indazol-7-yl]spiro[3.3]heptane-2-carboxylic acid, [ENANT-2] (58)
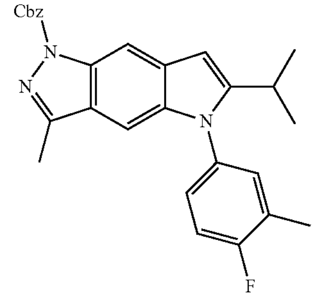
S5
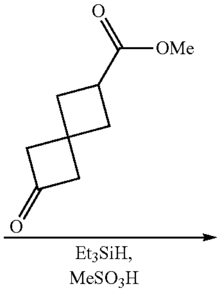
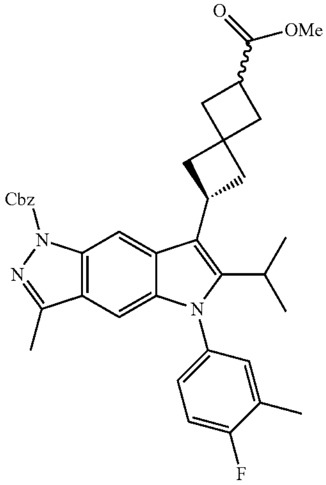
C85
-continued
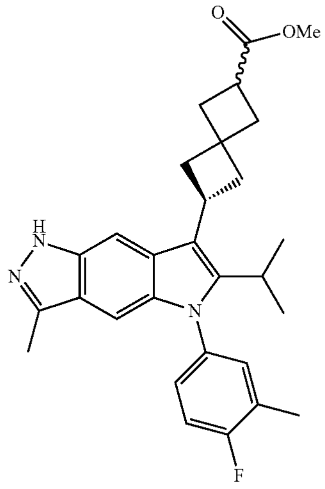
C86
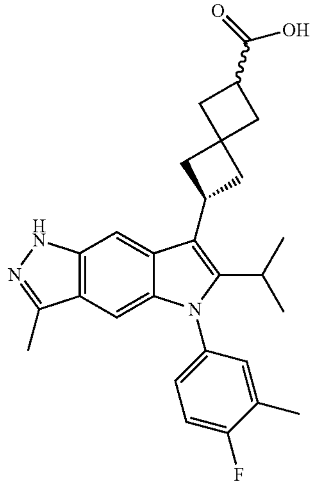
56
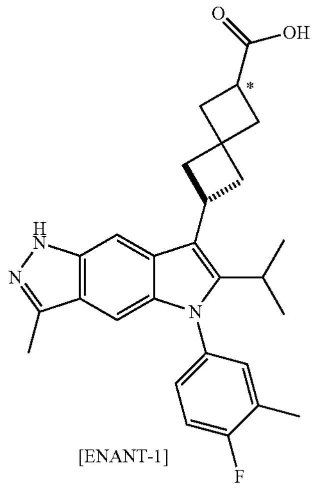
[ENANT-1]
57
+

-continued

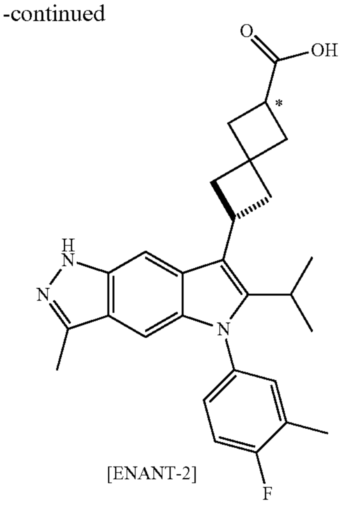

[ENANT-2]

58

Step 1. Synthesis of 6-[5-(4-fluoro-3-methyl-phenyl)-6-isopropyl-3-methyl-1H-pyrrolo[2,3-f]indazol-7-yl]spiro[3.3]heptane-2-carboxylic Acid (56)

Compound 56 was prepared in three steps from S5 using the method described for synthesis of compound 34. In this case, the Cbz protecting group was removed by an additional hydrogenation step after the reductive coupling step. In the final step, the ester hydrolysis was performed using sodium hydroxide instead of lithium hydroxide. The product was obtained as a racemic mixture. Yield: 520.6 mg. LCMS m/z 460.3 $[M+H]^+$. $^1H$ NMR (400 MHz, DMSO-d6) δ 12.07 (d, J=19.7 Hz, 3H), 7.62 (s, 1H), 7.43-7.30 (m, 2H), 7.25 (s, 1H), 6.88 (s, 1H), 3.84 (q, J=9.2 Hz, 1H), 3.03 (q, J=8.5 Hz, 1H), 2.91 (q, J=7.2 Hz, 1H), 2.75 (dt, J=21.5, 10.3 Hz, 2H), 2.42-2.19 (m, 10H), 1.29-1.16 (m, 6H).

Step 2. Preparation of 6-[5-(4-fluoro-3-methyl-phenyl)-6-isopropyl-3-methyl-1H-pyrrolo[2,3-f]indazol-7-yl]spiro[3.3]heptane-2-carboxylic acid, [ENANT-1] (57) and 6-[5-(4-fluoro-3-methyl-phenyl)-6-isopropyl-3-methyl-1H-pyrrolo[2,3-f]indazol-7-yl]spiro[3.3]heptane-2-carboxylic acid, [ENANT-2] (58)

Racemic mixture 56 (500 mg, 1.1 mmol) was separated into constituent enantiomers by chiral SFC separation. Column: Phenomenex Cellulose-2, 20×250 mm Mobile phase: 40% MeOH (5 mM Ammonia), 60% $CO_2$. Flow: 75 mL/min.

Compound (57) was the first eluting enantiomer [ENANT-1]: 6-[5-(4-fluoro-3-methyl-phenyl)-6-isopropyl-3-methyl-1H-pyrrolo[2,3-f]indazol-7-yl]spiro[3.3]heptane-2-carboxylic acid. Yield: 178.8 mg, 68%. LCMS m/z 460.3 $[M+H]^+$. $^1H$ NMR (400 MHz, DMSO-d6) δ 12.11 (s, 1H), 7.62 (s, 1H), 7.36 (q, J=7.2, 5.3 Hz, 2H), 7.26 (s, 1H), 6.88 (s, 1H), 3.85 (m, J=9.1 Hz, 1H), 3.03 (m, J=8.5 Hz, 1H), 2.92 (m, J=7.4 Hz, 1H), 2.75 (dt, J=21.9, 10.8 Hz, 2H), 2.35 (d, J=23.9 Hz, 9H), 1.23 (dt, J=6.6, 3.0 Hz, 6H).

Compound (58) was the second eluting enantiomer [ENANT-2]: 6-[5-(4-fluoro-3-methyl-phenyl)-6-isopropyl-3-methyl-1H-pyrrolo[2,3-f]indazol-7-yl]spiro[3.3]heptane-2-carboxylic acid Yield: 198 mg, 76%. LCMS m/z 460.3 $[M+H]^+$. $^1H$ NMR (400 MHz, DMSO-d6) δ 12.11 (s, 1H), 7.62 (s, 1H), 7.36 (q, J=7.2, 5.3 Hz, 2H), 7.26 (s, 1H), 6.88 (s, 1H), 3.85 (m, J=9.1 Hz, 1H), 3.03 (m, J=8.5 Hz, 1H), 2.92 (m, J=7.4 Hz, 1H), 2.75 (dt, J=21.9, 10.8 Hz, 2H), 2.35 (d, J=23.9 Hz, 9H), 1.23 (dt, J=6.6, 3.0 Hz, 6H).

Compound 59

6-[8-fluoro-5-(4-fluoro-3-methyl-phenyl)-6-isopropyl-3-methyl-1H-pyrrolo[2,3-f]indazol-7-yl]spiro[3.3]heptane-2-carboxylic Acid (59)

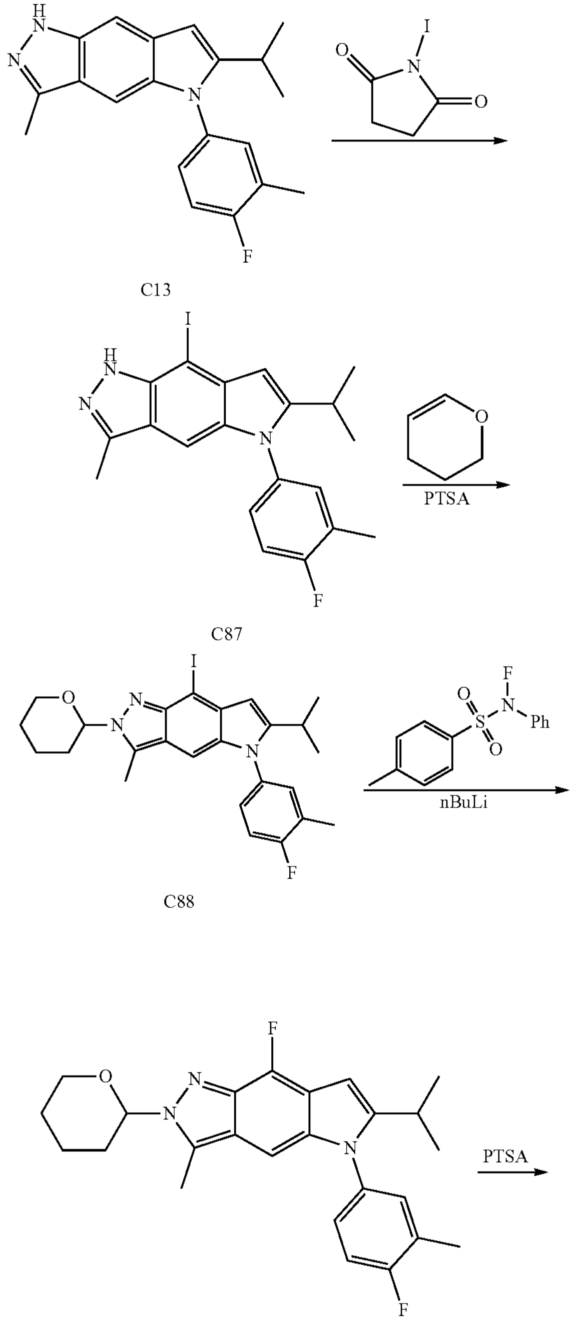

C13

C87

C88

C88

-continued

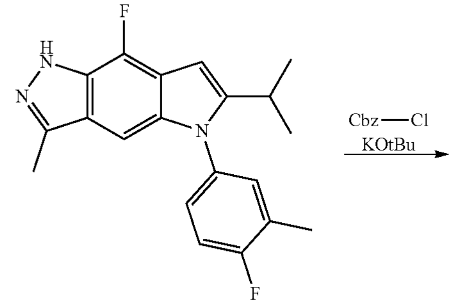

C89

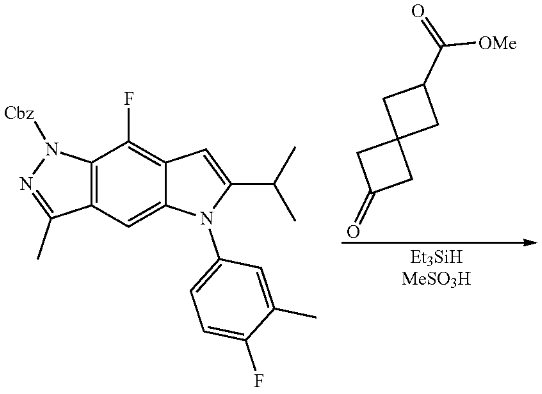

C90

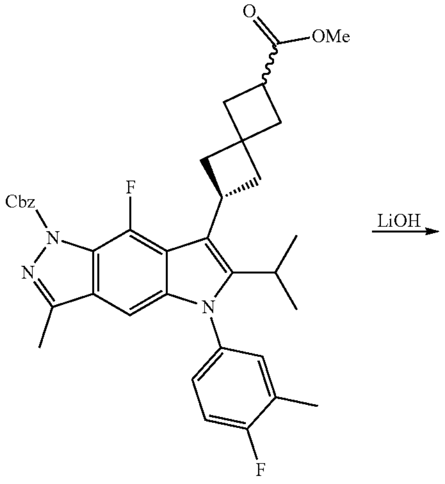

C91

-continued

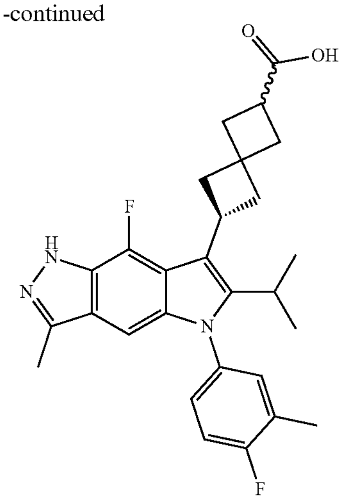

59

Compound 59 was prepared in 7 steps from compound C13. Intermediate C90 was prepared using the methods described for compound 53. Compound C90 was then converted into compound 59 in two steps as described for compound 34. Purification by reversed phase chromatography (Column: C18; Gradient: Acetonitrile in water with 0.1% TFA) afforded compound 59 as a racemic mixture. Yield: 5.8 mg, 26%. LCMS m/z 478.3 $[M+H]^+$. $^1H$ NMR (400 MHz, Methanol-d4) δ 7.26 (q, J=8.0, 7.2 Hz, 2H), 7.19 (d, J=4.4 Hz, 1H), 6.80 (s, 1H), 4.05-3.89 (m, 1H), 3.16-2.92 (m, 2H), 2.66 (dt, J=30.5, 10.9 Hz, 2H), 2.57-2.43 (m, 6H), 2.36 (s, 6H), 1.31 (dt, J=7.2, 2.6 Hz, 6H).

Compound 60

5-(4-fluorophenyl)-6-tetrahydropyran-4-yl-1H-pyrrolo[2,3-f]indazole (60)

See Preparation for S6

Compound 61

5-(4-fluorophenyl)-6-tetrahydropyran-4-yl-1H-pyrrolo[2,3-f]indazole-7-carbonitrile (61)

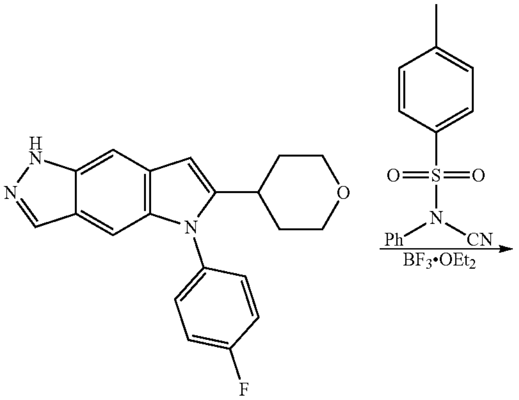

60 (S6)

-continued

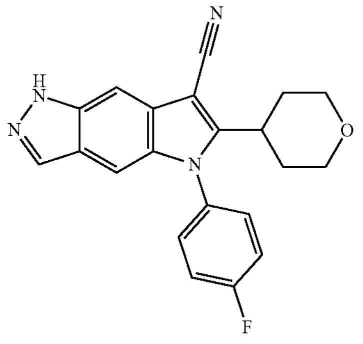

61

Compound 61 was prepared from compound 60 (also “S6”) using the method described for compound 10. Yield: 5.7 mg, 3%. LCMS m/z 361.2 $[M+H]^+$. $^1H$ NMR (300 MHz, DMSO-d6) δ 12.93 (s, 1H), 8.10 (t, J=1.2 Hz, 1H), 7.71-7.64 (m, 2H), 7.62 (t, J=1.1 Hz, 1H), 7.54 (t, J=8.7 Hz, 2H), 7.30 (d, J=1.1 Hz, 1H), 3.92 (dd, J=11.5, 4.0 Hz, 2H), 3.23 (t, J=11.3 Hz, 2H), 2.92-2.80 (m, 1H), 2.11 (qd, J=12.5, 4.3 Hz, 2H), 1.82 (d, J=11.2 Hz, 2H).

Compound 62

5-(4-fluorophenyl)-7-methylsulfonyl-6-tetrahydropyran-4-yl-1H-pyrrolo[2,3-f]indazole (62)

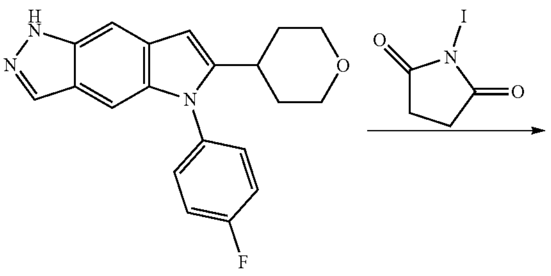

60 (S6)

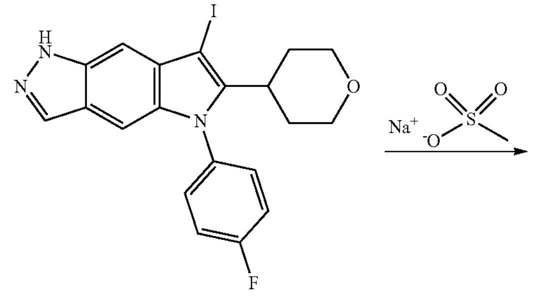

C92

-continued

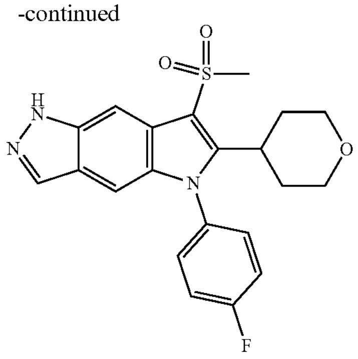

62

Step 1. Synthesis of 5-(4-fluorophenyl)-3,7-diiodo-6-tetrahydropyran-4-yl-1H-pyrrolo[2,3-f]indazole (C92)

Compound C92 was prepared from S6 using the method described for compound 1. The desired product was obtained as an inseparable mixture with the starting material (2:1 ratio of C92 to S6). The mixture was carried onto the next step without further attempts at purification.

Step 2. Synthesis of 5-(4-fluorophenyl)-7-methylsulfonyl-6-tetrahydropyran-4-yl-1H-pyrrolo[2,3-f]indazole (62)

Compound 62 was prepared from C92 using the method described for compound 11. Purification on a Si-amine column (Gradient: 0-10% Methanol in dichloromethane) afforded the product. Yield: 14.7 mg, 18%. LCMS m/z 414.3 $[M+H]^+$. $^1H$ NMR (300 MHz, DMSO-d6) δ 12.89 (s, 1H), 8.06 (t, J=1.1 Hz, 1H), 8.01 (t, J=1.1 Hz, 1H), 7.71-7.62 (m, 2H), 7.55 (t, J=8.7 Hz, 2H), 7.08 (d, J=1.1 Hz, 1H), 3.83 (dd, J=11.3, 3.9 Hz, 2H), 3.77-3.64 (m, 1H), 3.28 (s, 3H), 3.24 (t, J=11.2 Hz, 2H), 1.99-1.82 (m, 2H), 1.69 (d, J=12.2 Hz, 2H).

Compound 63

7-chloro-5-(4-fluorophenyl)-6-tetrahydropyran-4-yl-1H-pyrrolo[2,3-f]indazole (63)

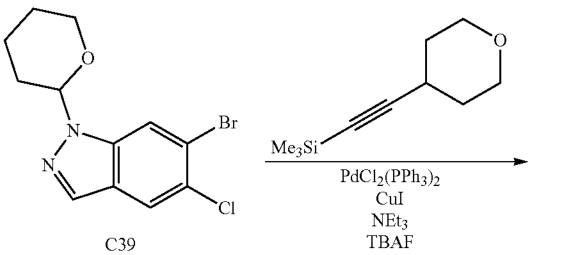

C39

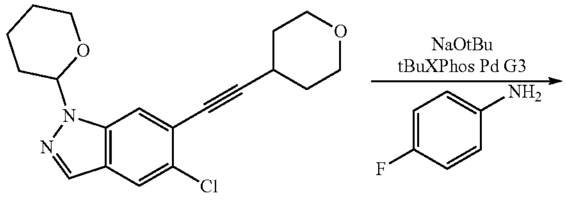

C93

-continued

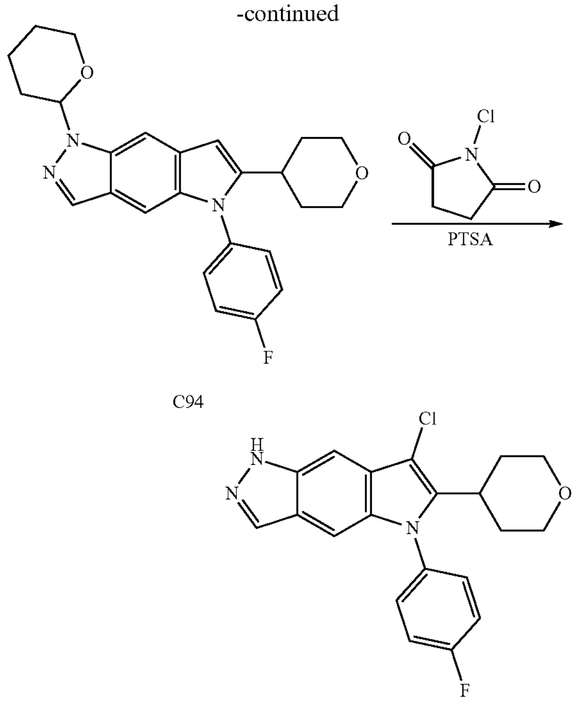

C94

63

Steps 1 and 2. Synthesis of 5-(4-fluorophenyl)-1-tetrahydropyran-2-yl-6-tetrahydropyran-4-yl-pyrrolo [2,3-f] (C94)

Compound C94 was prepared in two steps from C39 using the method outlined in preparation S11 for the synthesis of C21 from C19. In this case, 4-fluoroaniline is used as the reagent in the amination step. Yield: 8.74 g LCMS m/z 420.2 $[M+H]^+$. $^1$H NMR (300 MHz, Chloroform-d) δ 7.90 (d, J=0.9 Hz, 1H), 7.60 (t, J=1.0 Hz, 1H), 7.35-7.23 (m, 2H), 7.24-7.14 (m, 2H), 7.12 (t, J=1.0 Hz, 1H), 6.42 (t, J=0.8 Hz, 1H), 5.69 (dd, J=9.2, 2.6 Hz, 1H), 4.01-3.80 (m, 3H), 3.77-3.64 (m, 1H), 3.40-3.22 (m, 2H), 2.83-2.65 (m, 1H), 2.64-2.45 (m, 1H), 2.18-1.98 (m, 2H), 1.92-1.54 (m, 7H).

Step 3. Synthesis of 7-chloro-5-(4-fluorophenyl)-6-tetrahydropyran-4-yl-1H-pyrrolo[2,3-f]indazole (63)

To a solution of 5-(4-fluorophenyl)-1-tetrahydropyran-2-yl-6-tetrahydropyran-4-yl-pyrrolo[2,3-f]indazole C94 (61 mg, 0.14 mmol) in dichloromethane (2 mL) was added N-chlorosuccinimide (22 mg, 0.2 mmol) at room temperature. After 30 min, the mixture was treated with 4-methylbenzenesulfonic acid monohydrate (50 mg, 0.3 mmol), methanol (1 mL) and water (0.1 mL) at 50° C. for 1 h. The mixture was evaporated, and the residue was partitioned in dichloromethane and aqueous sodium bicarbonate. Upon extraction with additional dichloromethane, the organic phase was evaporated and the residue was purified by chromatography on silica gel (Gradient: 0-60% EtOAc in heptanes). The product was suspended in MTBE and filtered to afford the product as a white solid. 16.5 mg. LCMS m/z 370.1 $[M+H]^+$. $^1$H NMR (300 MHz, Chloroform-d) δ 9.95 (s, 1H), 8.07 (s, 1H), 7.63 (s, 1H), 7.34 (ddd, J=9.4, 6.6, 4.5 Hz, 4H), 7.20 (d, J=1.1 Hz, 1H), 4.05 (dd, J=11.6, 4.4 Hz, 2H), 3.49-3.21 (m, 2H), 3.02-2.77 (m, 1H), 2.47 (qd, J=12.6, 4.5 Hz, 2H), 1.65 (d, J=13.6 Hz, 2H).

Compound 64

3-[5-(3,4-difluorophenyl)-6-tetrahydropyran-4-yl-1H-pyrrolo[2,3-f]indazol-7-yl]propanoic Acid (64)

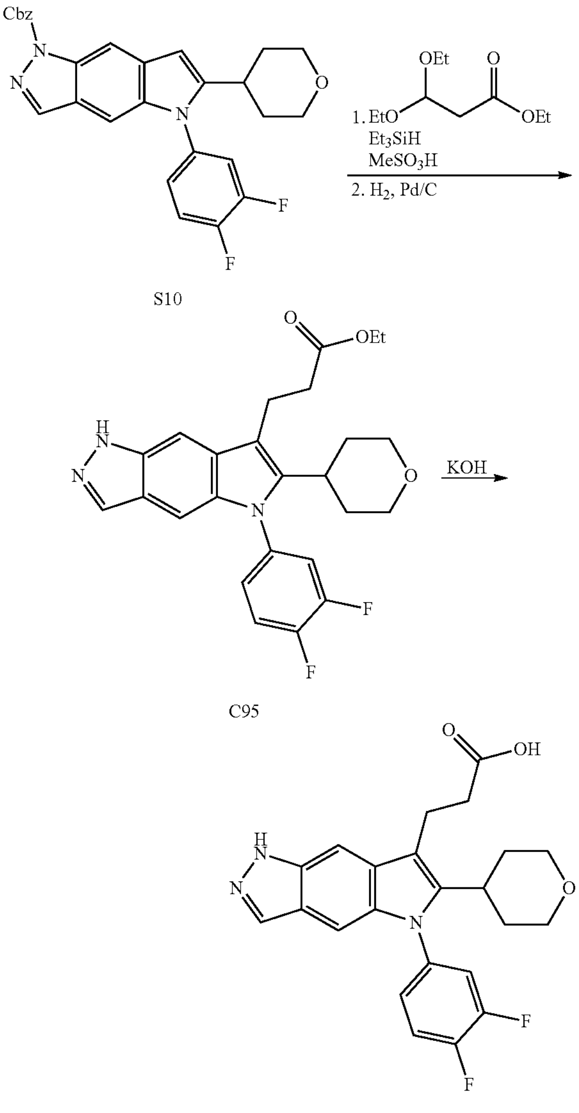

S10

C95

64

Step 1 and 2. Synthesis of ethyl 3-[5-(3,4-difluorophenyl)-6-tetrahydropyran-4-yl-1H-pyrrolo[2,3-f]indazol-7-yl]propanoate (C95)

To a solution of S10 in $CHCl_3$ (1.2 mL) and toluene (1.2 mL) was added ethyl 3,3-diethoxypropanoate (470 mg, 2.5 mmol), triethylsilane (395 µL, 2.5 mmol) and methanesulfonic acid (160 µL, 2.5 mmol). The mixture was heated at 50° C. for 2 days. The mixture was partitioned between dichloromethane and an aqueous saturated $NaHCO_3$ solution. The organic phase was collected, filtered through a phase separator, and concentrated in vacuo. The product obtained was a mixture of benzyl difluorophenyl)-7-(3-ethoxy-3-oxo-propyl)-6-tetrahydropyran-4-yl-pyrrolo[2,3-f]indazole-1-carboxylate. LCMS 588.2 $[M+H]^+$ and the unsaturated product and benzyl 5-(3,4-difluorophenyl)-7-[(E)-3-ethoxy-3-oxo-prop-1-enyl]-6-tetrahydropyran-4-yl-pyrrolo[2,3-f]indazole-1-carboxylate. LCMS 586.3 $[M+H]^+$. The mixture was progressed to the next step without further purification.

The product mixture from step 1 (480 mg) was dissolved in ethanol (10 mL) and the solution purged with nitrogen. 10% Pd on carbon catalyst (45 mg, 0.04 mmol) was added and the solution was stirred for 28 h under a pressure of hydrogen gas. The mixture was filtered through a pad of silica gel and the filtrate concentrated in vacuo. Purification by flash chromatography (Gradient 0-50% EtOAc in dichloromethane) on silica gel afforded the product as a yellow solid. Yield: 300 mg, 81%. LCMS m/z 454.3 $[M+H]^+$.

Step 3. Synthesis of 3-[5-(3,4-difluorophenyl)-6-tetrahydropyran-4-yl-1H-pyrrolo[2,3-f]indazol-7-yl] propanoic Acid (64)

Potassium hydroxide was added to a solution of ethyl 3-[5-(3,4-difluorophenyl)-6-tetrahydropyran-4-yl-1H-pyrrolo[2,3-f]indazol-7-yl]propanoate (300 mg) in water (500 µL) and ethanol (4.5 mL). The reaction was allowed to stir at room temperature for 21 h. Water and 1M HCl were added. The mixture was extracted with $CHCl_3$: IPA (3:1). The combined organic phases were dried over sodium sulfate and concentrated in vacuo. Purification by reversed phase chromatography (Column: C18; 0-5% of EtOAc in dichloromethane) afforded the product. Yield: 170 mg, 47%. LCMS m/z 426.2 $[M+H]^+$. $^1H$ NMR (400 MHz, Methanol-d4) δ 8.10 (s, 1H), 7.62 (s, 1H), 7.53 (q, J=9.2 Hz, 1H), 7.42 (m, 1H), 7.24 (m, 1H), 7.16 (s, 1H), 3.97 (dd, J=11.6, 4.2 Hz, 3H), 3.37 (t, J=11.6 Hz, 3H), 3.26 (m, 2H), 3.03 (t, J=12.2 Hz, 1H), 2.75-2.66 (m, 2H), 2.04 (m, 2H), 1.75 (d, J=12.0 Hz, 2H).

Compounds 65-74

Compounds 65 to 74 (see Table 3) were prepared in two steps from intermediate S10 using the method described for compound 33 with the appropriate aldehyde or ketone reagent. Chiral SFC was using to separate mixtures of isomers or stereoisomers.

TABLE 3

Method of preparation, structure and physicochemical data for Compounds 65-74

| Compound | Aldehyde or ketone | Product | Method | $^1H$ NMR; LCMS m/z $[M + H]^+$; Structure Comment |
|---|---|---|---|---|
| 65 | 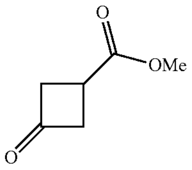 | 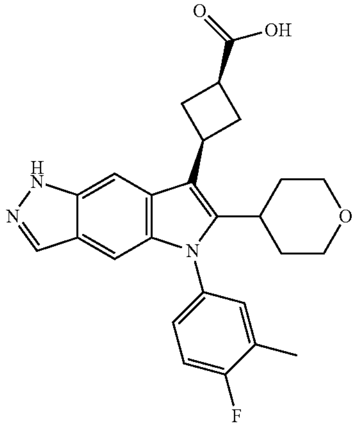 [CIS] | Compound 33[1] | $^1H$ NMR (400 MHz, DMSO-d6) δ 12.87 (s, 1H), 8.24 (s, 1H), 7.97 (s, 1H), 7.75-7.63 (m, 2H), 7.38-7.28 (m, 1H), 7.11 (s, 1H), 4.06-3.94 (m, 1H), 3.92-3.83 (m, 2H), 3.28-3.12 (m, 3H), 3.05-2.93 (m, 2H), 2.88-2.76 (m, 1H), 2.50 (overlap, 2H), 2.01-1.87 (m, 2H), 1.74-1.62 (m, 2H).; 452.5; Cis isomer. |
| 66 | 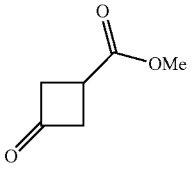 | 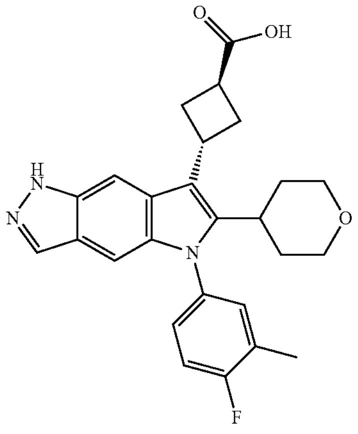 [TRANS] | Compound 33[1] | $^1H$ NMR (400 MHz, DMSO-d6) δ 12.63 (s, 1H), 7.98 (s, 1H), 7.90 (s, 1H), 7.75-7.62 (m, 2H), 7.35-7.27 (m, 1H), 7.13 (s, 1H), 4.30-4.16 (m, 1H), 3.96-3.82 (m, 2H), 3.37-3.27 (m, 1H), 3.26-3.15 (m, 2H), 3.05-2.92 (m, 2H), 2.85-2.72 (m, 1H), 2.50 (overlap, 1H,), 2.37-2.27 (m, 1H), 1.96-1.81 (m, 2H), 1.75-1.61 (m, 2H).; 452.6; trans isomer. |

TABLE 3-continued

| Method of preparation, structure and physicochemical data for Compounds 65-74 | | | | |
|---|---|---|---|---|
| Compound | Aldehyde or ketone | Product | Method | $^{1}$H NMR; LCMS m/z $[M + H]^+$; Structure Comment |
| 67 | 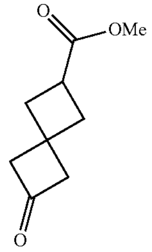 [SMILES: COC(=O)C1CC2(CC(=O)C2)C1] | 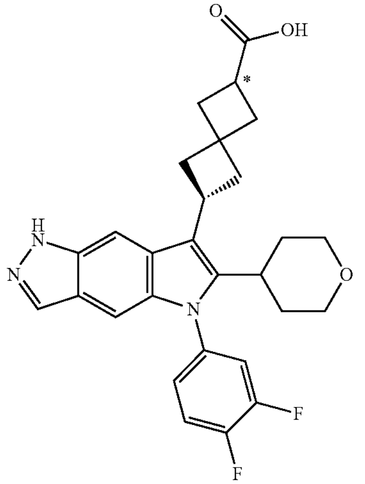 [ENANT-1] | Compound 33[2] | $^{1}$H NMR (400 MHz, Methanol-d4) δ 7.96 (s, 1H), 7.83 (s, 1H), 7.52 (q, J = 9.2 Hz, 1H), 7.42-7.34 (m, 1H), 7.23-7.16 (m, 1H), 7.13 (s, 1H), 4.07-3.91 (m, 3H), 3.39-3.33 (m, 2H), 3.19-3.09 (m, 1H), 3.01-2.79 (m, 3H), 2.64-2.35 (m, 6H), 2.14-1.99 (m, 2H), 1.70 (d, J = 12.7 Hz, 2H). 492.5; Single enantiomer. |
| 68 | 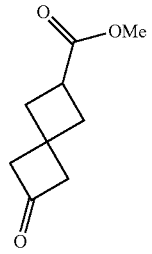 [SMILES: COC(=O)C1CC2(CC(=O)C2)C1] | 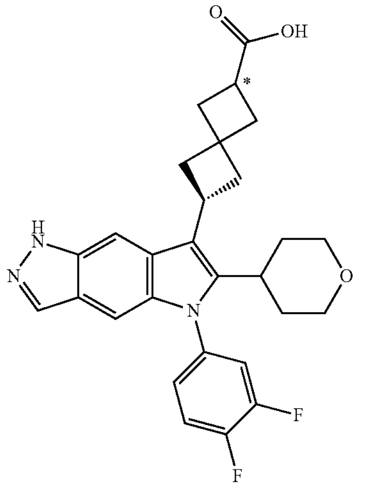 [ENANT-2] | Compound 33[2] | $^{1}$H NMR (400 MHz, Methanol-d4) δ 7.96 (s, 1H), 7.83 (s, 1H), 7.52 (q, J = 9.2 Hz, 1H), 7.42-7.34 (m, 1H), 7.23-7.16 (m, 1H), 7.13 (s, 1H), 4.07-3.91 (m, 3H), 3.39-3.33 (m, 2H), 3.19-3.09 (m, 1H), 3.01-2.79 (m, 3H), 2.64-2.35 (m, 6H), 2.14-1.99 (m, 2H), 1.70 (d, J = 12.7 Hz, 2H).; 492.5; Single enantiomer. |
| 69 | 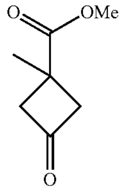 | 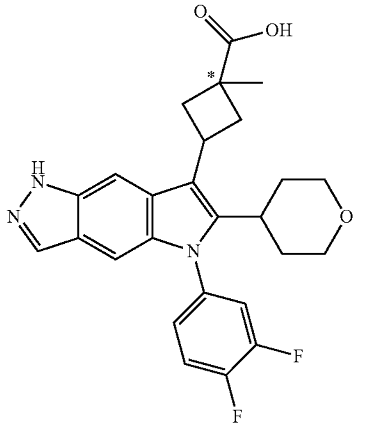 [Isomer-1] | Compound 33[3,4] | No $^{1}$H NMR; 466.6; Single isomer |

TABLE 3-continued

Method of preparation, structure and physicochemical data for Compounds 65-74

| Compound | Aldehyde or ketone | Product | Method | $^1$H NMR; LCMS m/z $[M + H]^+$; Structure Comment |
|---|---|---|---|---|
| 70 | 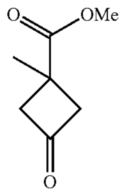 | 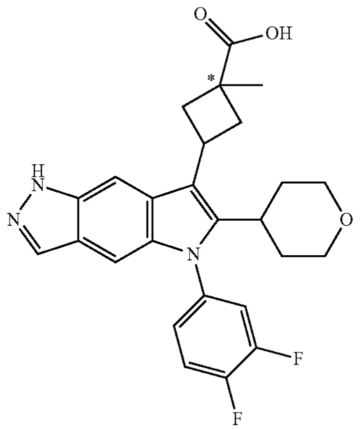 [Isomer-2] | Compound 33[3,4] | $^1$H NMR (400 MHz, DMSO-d6) δ 12.61 (s, 1H), 7.97 (s, 1H), 7.89 (s, 1H), 7.75-7.62 (m, 2H), 7.36-7.27 (m, 1H), 7.13 (s, 1H), 4.09 (m, J = 9.6 Hz, 1H), 3.89 (dd, J = 11.3, 4.1 Hz, 2H), 3.27-3.15 (m, 2H), 2.84-2.65 (m, 5H), 1.89 (qd, J = 12.7, 4.5 Hz, 2H), 1.73-1.66 (m, 2H), 1.61 (s, 3H).; 466.5; Single isomer. |
| 71 | 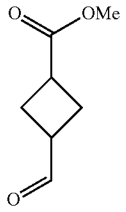 | 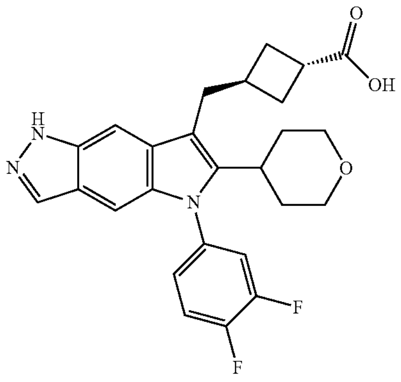 [SMILES: O=C(O)[C@H]1C[C@H](Cc2c(C3CCOCC3)n(-c3ccc(F)c(F)c3)c3cc4cn[nH]c4cc23)C1] | Compound 33[5,6] | $^1$H NMR (400 MHz, DMSO-d6) δ 12.63 (s, 1H), 7.95 (s, 1H), 7.69 (m), 7.56 (s, 1H), 7.34 (m), 7.03 (s, 1H), 3.86 (d, J = 11.1 Hz, 2H), 3.33-3.12 (m, 3H), 3.02 (m, 3H), 2.74 (m, 1H), 2.25 (m, 2H), 2.07 (m, 2H), 1.82 (m, 2H), 1.67 (d, J = 12.7 Hz, 2H).; 466.3; Trans isomer. |
| 72 | 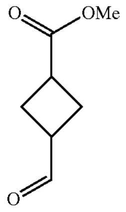 | 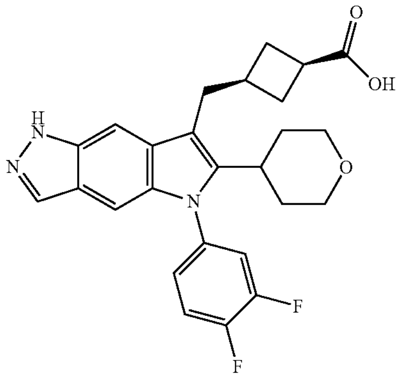 | Compound 33[5,6] | $^1$H NMR (400 MHz, DMSO-d6) δ 12.63 (s, 1H), 7.96 (d, J = 1.0 Hz, 1H), 7.77-7.62 (m, 2H), 7.53 (m), 7.36-7.25 (m, 1H), 7.04 (d, J = 1.1 Hz, 1H), 3.86 (dd, J = 11.4, 3.9 Hz, 2H), 3.25 (t, J = 11.7 Hz, 2H), 3.02-2.81 (m, 4H), 2.57 (m, J = 8.0 Hz, 1H), 2.25 (m, 2H), 2.03 (m, 2H), 1.83 (q, J = 12.3 Hz, 2H), 1.67 (d, J = 12.9 Hz, 2H).; 466.3; Cis isomer. |

TABLE 3-continued

Method of preparation, structure and physicochemical data for Compounds 65-74

| Compound | Aldehyde or ketone | Product | Method | $^1$H NMR; LCMS m/z $[M + H]^+$; Structure Comment |
|---|---|---|---|---|
| 73 | 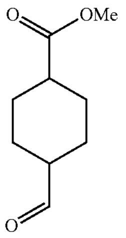 [SMILES: COC(=O)C1CCC(C=O)CC1] | 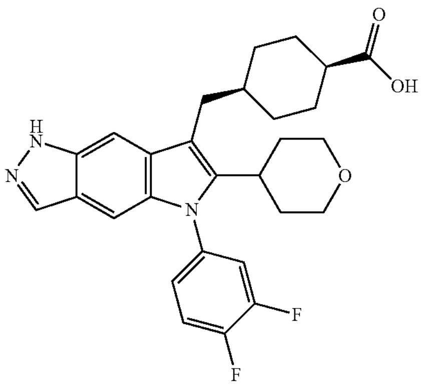 [SMILES: O=C(O)[C@H]1CC[C@@H](Cc2c(C3CCOCC3)n(-c3ccc(F)c(F)c3)c3cc4cn[nH]c4cc23)CC1] | Compound 33[5,7] | $^1$H NMR (400 MHz, Methanol-d4) δ 7.95 (s, 1H), 7.56-7.47 (m, 2H), 7.41 (ddd, J = 10.5, 7.2, 2.6 Hz, 1H), 7.23 (d, J = 8.6 Hz, 1H), 7.04 (d, J = 1.1 Hz, 1H), 3.94 (d, J = 11.0 Hz, 2H), 3.37 (t, J = 11.7 Hz, 2H), 3.11-3.01 (m, 1H), 2.84 (d, J = 7.3 Hz, 2H), 2.57 (m, 1H), 2.12 (d, J = 13.1 Hz, 2H), 2.05-1.87 (m, 3H), 1.70 (d, J = 13.2 Hz, 4H), 1.55 (t, J = 12.5 Hz, 2H), 1.44 (q, J = 11.3, 10.0 Hz, 2H).; 494.6; Cis isomer. |
| 74 | 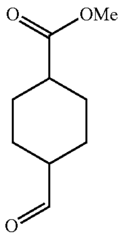 | 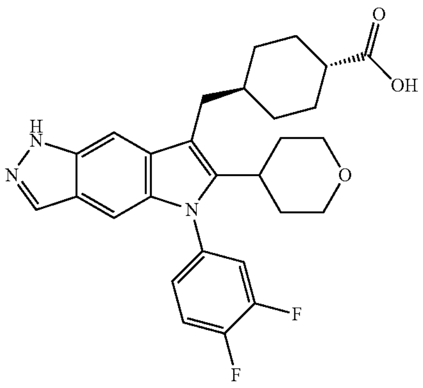 | Compound 33[5,7] | $^1$H NMR (400 MHz, Methanol-d4) δ 7.96 (d, J = 1.0 Hz, 1H), 7.59-7.47 (m, 2H), 7.42 (ddd, J = 11.0, 7.2, 2.5 Hz, 1H), 7.24 (ddt, J = 8.3, 4.1, 2.1 Hz, 1H), 7.07 (d, J = 1.1 Hz, 1H), 3.94 (dd, J = 11.7, 5.1 Hz, 2H), 3.37 (t, J = 11.6 Hz, 2H), 3.06 (tt, J = 12.4, 3.4 Hz, 1H), 2.84 (d, J = 7.2 Hz, 2H), 2.29 (tt, J = 12.1, 3.5 Hz, 1H), 2.00 (d, J = 12.9 Hz, 3H), 1.92 (d, J = 13.5 Hz, 2H), 1.85-1.75 (m, 1H), 1.72 (d, J = 12.6 Hz, 2H), 1.46-1.14 (m, 5H).; 494.6; Trans isomer. |

Table 3 Footnotes:

[1]Mixture of cis/trans isomers was separated by purification by Chiral SFC. Prep method: Daicel Chiralpak AD-H IC column, 20 x 250 mm, Mobile phase: 30% MeOH (containing 5 mM Ammonia) 70% $CO_2$ Flow: 75 mL/min.

[2]Racemic mixture was separated into its component enantiomers 67 and 68 by chiral SFC. Prep method: Daicel Chiralpak AD-H IC column, 20 x 250 mm, Mobile phase: 30% MeOH (5 mM Ammonia) 70% $CO_2$ Flow: 80 mL/min. Compound 67 was the first eluting enantiomer. Compound 68 was the second eluting enantiomer.

[3]NaOH used as base in step 2.

[4]Compounds 69 and 70 were separated from the mixture by chiral SFC. Prep Method: Daicel Chiralpak AD-H IC column, 20 x 250 mm, Mobile phase: 40% MeOH (containing 5 mM Ammonia) 60% $CO_2$ Flow: 75 mL/min. Compound 69 was the first eluting peak and compound 70 was the second eluting peak.

[5]KOH used as the base in step 2.

[6]Prep method: Daicel Chiralpak AD-H IC column, 20 x 250 mm, Mobile phase: 40% EtOH (5 mM Ammonia) 60% $CO_2$ Flow: 75 mL/min. Compound 72 was the first eluting peak and compound 71 was the second eluting peak.

[7]Compound 73 and 74 were separated from the mixture by chiral SFC. Prep method: Daicel Chiralpak AD-H IC column, 20 x 250 mm, Mobile phase: 30% MeOH (5 mM Ammonia) 70% $CO_2$ Flow: 75 mL/min. Compound 73 was the first eluting peak and compound 74 was the second eluting peak.

Compound 75

(1r,4r)-4-(5-(3,4-difluorophenyl)-6-(tetrahydro-2H-pyran-4-yl)-1,5-dihydropyrrolo[2,3-f]indazol-7-yl) cyclohexane-1-carboxylic Acid (75)

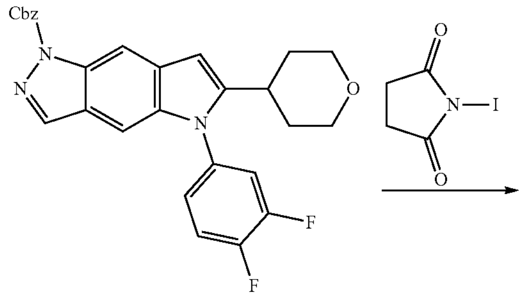

S10

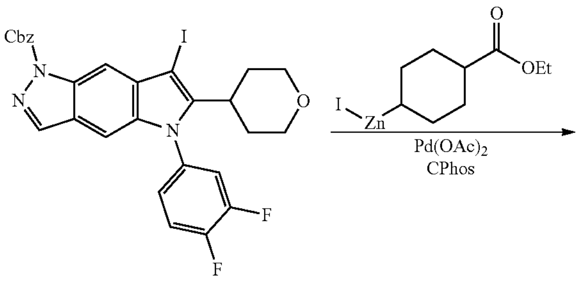

S96

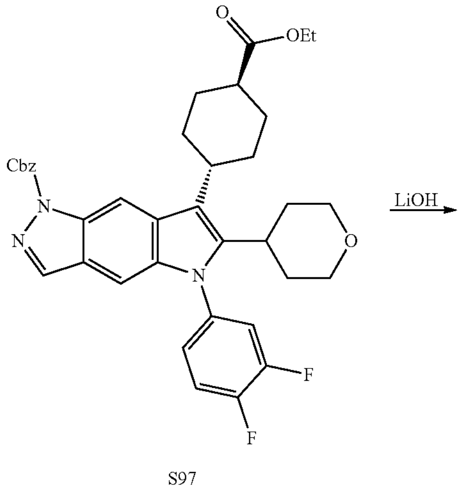

S97

-continued

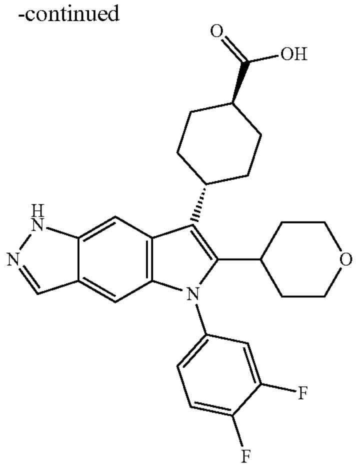

[TRANS]
75

Step 1. Preparation of benzyl 5-(3,4-difluorophenyl)-7-iodo-6-tetrahydropyran-4-yl-pyrrolo[2,3-f] indazole-1-carboxylate (C96)

To a solution of compound S10 (1.0 g, 2.1 mmol) was in dichloromethane (10.3 mL) was added 1-iodopyrrolidine-2,5-dione (490 mg, 2.1 mmol). The mixture was allowed to stir at room temperature for 1 day. The mixture was concentrated in vacuo and the residue purified by chromatography on silica gel (Gradient: 0-100% EtOAc in dichloromethane) to afford the product. Yield: 1.2 g, 97%. LCMS m/z 614.4 $[M+H]^+$. $^1H$ NMR (400 MHz, Chloroform-d) δ 8.29 (s, 1H), 8.15 (d, J=0.9 Hz, 1H), 7.64-7.57 (m, 2H), 7.47-7.35 (m, 4H), 7.21 (ddd, J=9.9, 6.9, 2.5 Hz, 1H), 7.14-7.11 (m, 1H), 7.10 (d, J=1.0 Hz, 1H), 5.59 (s, 2H), 4.04 (dd, J=11.5, 4.4 Hz, 2H), 3.42-3.32 (m, 2H), 3.02 (tt, J=12.4, 3.6 Hz, 1H), 2.43 (qdd, J=12.5, 7.5, 4.5 Hz, 2H), 1.64-1.57 (m, 2H).

Preparation of Organo Zinc Reagent:

Zn (214 mg, 3.3 mmol) was placed under nitrogen, and THF (2.1 mL) followed by 1,2-dibromoethane (2 μL, 0.02 mmol) was added. The mixture was warmed with a heat gun then ethyl 4-iodocyclohexanecarboxylate (300 mg, 1.1 mmol) (cis/trans mixture) was added. The mixture was allowed to stir at room temperature for 4 h. Thin layer chromatography indicated consumption of the iodide to give (4-ethoxycarbonylcyclohexyl)-iodo-zinc.

Step 2. Synthesis of benzyl 5-(3,4-difluorophenyl)-7-(4-ethoxycarbonylcyclohexyl)-6-tetrahydropyran-4-yl-pyrrolo[2,3-f]indazole-1-carboxylate (C97)

Benzyl 5-(3,4-difluorophenyl)-7-iodo-6-tetrahydropyran-4-yl-pyrrolo[2,3-f]indazole-1-carboxylate (108 mg, 0.17 mmol), $Pd(OAc)_2$ (3.7 mg, 0.02 mmol), and CPhos ligand (11 mg, 0.03 mmol) were placed in a vial under nitrogen. THF (400 μL) was added and the mixture cooled in an ice bath. (4-ethoxycarbonylcyclohexyl)-iodo-zinc (650 μL of 0.4 M, 0.26 mmol) was added dropwise and the reaction warmed to room temperature. An additional spatula tip of $Pd(OAc)_2$ was added and the mixture allowed to stir for 30 min Purification by reverse phase chromatography (column: C18 column; Gradient: MeCN in water with 0.1% TFA) afforded the product. Yield: 29 mg, 27%. LCMS m/z 642.4 $[M+H]^+$.

Step 3. 4-[5-(3,4-difluorophenyl)-6-tetrahydropyran-4-yl-1H-pyrrolo[2,3-f]indazol-7-yl]cyclohexanecarboxylic Acid (75)

Compound 75 was prepared from C97 using the method described in step 3 for the preparation of compound 16 to afford the product as exclusively one regioisomer. The product was assumed to be the trans isomer based on literature studies using this reagent. *See Org. Lett.* 2014, 16, 924. Yield: 3.6 mg, 16%. LCMS m/z 480.3 $[M+H]^+$. $^{1}$H NMR (400 MHz, DMSO-$d_6$) δ 12.54 (s, 1H), 12.13 (s, 1H), 7.96 (s, 1H), 7.77-7.65 (m, 2H), 7.31 (s, 1H), 7.11 (s, 1H), 3.90 (d, J=10.6 Hz, 3H), 3.23 (s, 2H), 3.07 (s, 1H), 2.81 (s, 1H), 2.21 (d, J=13.1 Hz, 2H), 2.10 (d, J=15.1 Hz, 2H), 2.05-1.48 (m, 6H).

Compounds 76-85

Compounds 76-85 (see Table 4) were prepared in two steps from intermediate S11 and the appropriate ketone, aldehyde or enol ether, using the method described for compound 33. Modifications to this method are noted in the table and accompanying footnotes. Chiral SFC was using to separate mixtures of isomers or stereoisomers. In some preparations, an alternative base such as KOH or NaOH is used in step 2.

TABLE 4

Method of preparation, structure and physicochemical data for Compounds 76-85

| Compound | Aldehyde, ketone or enol ether | Product | Method | $^{1}$H NMR; LCMS m/z $[M + H]^+$; Structure Comment |
|---|---|---|---|---|
| 76 | 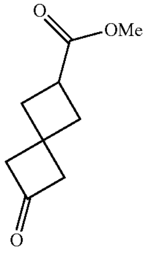 | 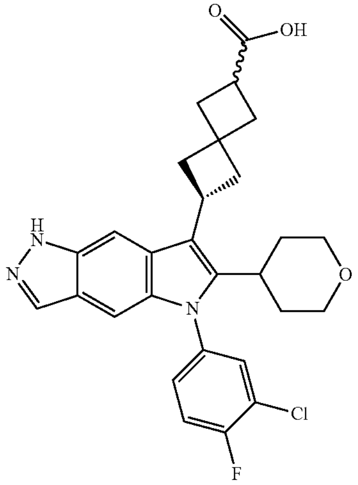 [RAC] | Compound 33 | No NMR; 508.5; Racemic mixture |
| 77 | | 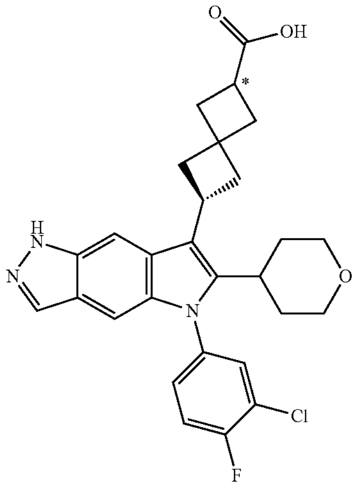 [ENANT-1] | Chiral SFC from compound 76[1] | $^{1}$H NMR (400 MHz, Chloroform-d) δ 8.04 (d, J = 1.0 Hz, 1H), 7.87 (t, J = 1.1 Hz, 1H), 7.46-7.33 (m, 2H), 7.23 (ddt, J = 8.8,4.6, 2.4 Hz, 1H), 7.15 (d, J = 1.0 Hz, 1H), 4.07 (dd, J = 11.5, 4.1 Hz, 2H), 3.97 (q, J = 9.3 Hz, 2H), 3.42-3.31 (m, 2H), 2.99-2.80 (m, 3H), 2.75-2.42 (m, 6H), 2.18-2.03 (m, 2H), 1.74-1.61 (m, 2H); 508.5; Single enantiomer. |

TABLE 4-continued

Method of preparation, structure and physicochemical data for Compounds 76-85

| Compound | Aldehyde, ketone or enol ether | Product | Method | $^{1}$H NMR; LCMS m/z $[M + H]^+$; Structure Comment |
|---|---|---|---|---|
| 78 | | 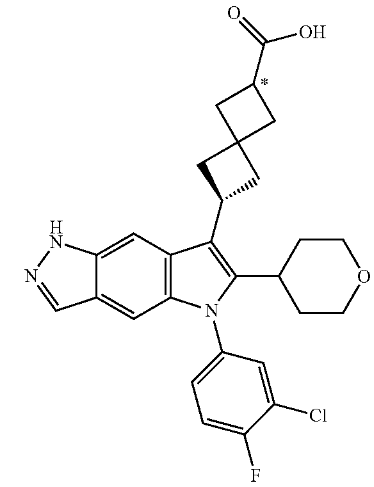 [ENANT-2] | Chiral SFC from compound 76[1] | $^{1}$H NMR (400 MHz, Chloroform-d) δ 8.04 (d, J = 1.0 Hz, 1H), 7.87 (t, J = 1.1 Hz, 1H), 7.46-7.33 (m, 2H), 7.23 (ddt, J = 8.8, 4.6, 2.4 Hz, 1H), 7.15 (d, J = 1.0 Hz, 1H), 4.07 (dd, J = 11.5, 4.1 Hz, 2H), 3.97 (q, J = 9.3 Hz, 2H), 3.42-3.31 (m, 2H), 2.99-2.80 (m, 3H), 2.75-2.42 (m, 6H), 2.18-2.03 (m, 2H), 1.74-1.61 (m, 2H).; 508.5. Single enantiomer. |
| 79 | 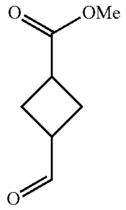 | 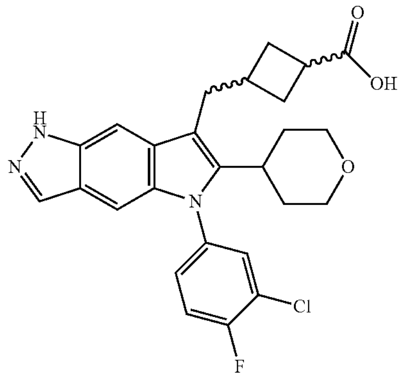 [SMILES: O=C(O)C1CC(Cc2c(C3CCOCC3)n(-c3ccc(F)c(Cl)c3)c3cc4cn[nH]c4cc23)C1] | compound 33[2] | $^{1}$H NMR (400 MHz, DMSO) δ 12.62 (s, 1H), 12.16 (s, 1H), 7.96 (s, 1H), 7.87-7.73 (m, 1H), 7.66 (t, J = 8.9 Hz, 1H), 7.59-7.39 (m, 2H), 7.02 (d, J = 4.7 Hz, 1H), 3.86 (d, J = 10.8 Hz, 2H), 3.26 (t, J = 11.5 Hz, 2H), 3.08-2.82 (m, 4H), 2.24 (q, J = 8.9 Hz, 2H), 2.05 (dq, J = 20.2, 9.9 Hz, 2H), 1.81 (q, J = 12.7 Hz, 2H), 1.67 (d, J = 12.5 Hz, 2H). 482.2; Cis and Trans mixture. |
| 80 | | 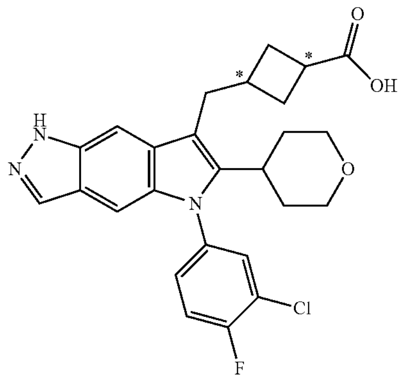 [Isomer-1] | Chiral SFC from compound 79[3] | $^{1}$H NMR (400 MHz, DMSO-d6) δ 12.63 (s, 1H), 7.96 (s, 1H), 7.79 (dd, J = 6.4, 2.3 Hz, 1H), 7.66 (t, J = 8.9 Hz, 1H), 7.50 (d, J = 22.4 Hz, 2H), 7.02 (s, 1H), 3.86 (d, J = 11.3 Hz, 1H), 3.26 (t, J = 11.6 Hz, 1H), 2.89 (dd, J = 41.6, 8.0 Hz, 4H), 2.23 (d, J = 9.5 Hz, 2H), 2.02 (q, J = 10.0 Hz, 2H), 1.81 (d, J = 12.7 Hz, 2H), 1.67 (d, J = 13.1 Hz, 2H).; 482.2; Single isomer. |

TABLE 4-continued

| Method of preparation, structure and physicochemical data for Compounds 76-85 | | | | |
|---|---|---|---|---|
| Compound | Aldehyde, ketone or enol ether | Product | Method | $^1$H NMR; LCMS m/z $[M + H]^+$; Structure Comment |
| 81 | | 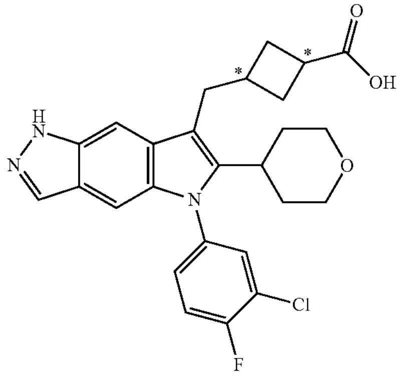 [Isomer-2] | Chiral SFC from compound 79[3] | $^1$H NMR (400 MHz, DMSO) δ 12.65 (d, J = 4.1 Hz, 1H), 7.95 (s, 1H), 7.89-7.75 (m, 1H), 7.66 (t, J = 8.9 Hz, 1H), 7.56 (s, 1H), 7.49 (t, J = 6.0 Hz, 1H), 7.01 (s, 1H), 4.13-3.70 (m, 4H), 3.19-2.87 (m, 5H), 2.72 (s, 1H), 2.22 (q, J = 8.8, 7.1 Hz, 2H), 2.03 (q, J = 9.9, 9.0 Hz, 2H), 1.80 (q, J = 11.8 Hz, 2H), 1.67 (d, J = 12.7 Hz, 2H).; 482.2; Single isomer. |
| 82 | 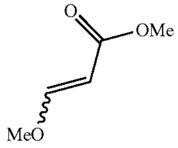 | 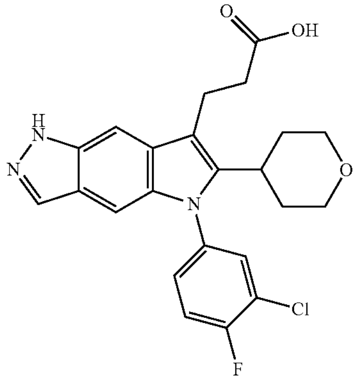 | compound 33[2,] | $^1$H NMR (400 MHz, DMSO-d6) δ 12.65 (s, 1H), 12.24 (s, 1H), 7.97 (s, 1H), 7.80 (dd, J = 6.7, 2.6 Hz, 1H), 7.67 (t, J = 8.9 Hz, 1H), 7.52 (s, 1H), 7.47 (ddd, J = 8.7, 4.4, 2.6 Hz, 1H), 3.88 (d, J = 11.2 Hz, 2H), 3.24 (t, J = 11.5 Hz, 2H), 3.20-3.10 (m, 2H), 2.89 (t, J = 12.3 Hz, 1H), 2.59 (s, 1H), 1.87 (q, J = 10.2 Hz, 2H), 1.73 (s, 1H).; 442.2. |
| 83 | 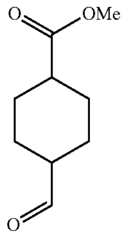 [SMILES: COC(=O)C1CCC(C=O)CC1] | 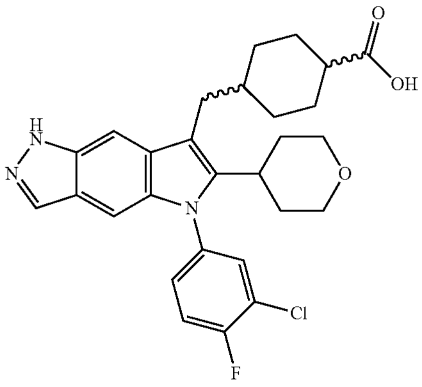 [SMILES: O=C(O)C1CCC(Cc2c(C3CCOCC3)n(-c3ccc(F)c(Cl)c3)c3cc4cn[nH]c4cc23)CC1] | compound 33[4] | No NMR; 510.3; cis and trans mixture |

TABLE 4-continued

| Method of preparation, structure and physicochemical data for Compounds 76-85 | | | | |
|---|---|---|---|---|
| Compound | Aldehyde, ketone or enol ether | Product | Method | $^1H$ NMR; LCMS m/z $[M + H]^+$; Structure Comment |
| 84 | | 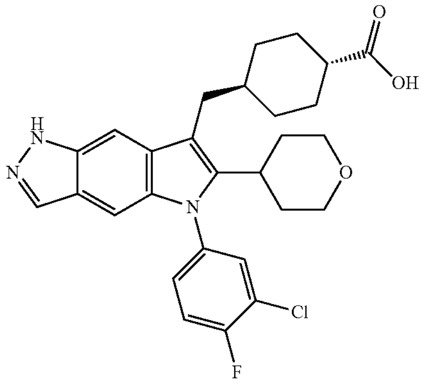 | Chiral SFC from compound 83[5] | $^1H$ NMR (400 MHz, Chloroform-d) δ 7.99 (s, 1H), 7.55 (s, 1H), 7.43 (dd, J = 6.5, 2.5 Hz, 1H), 7.34 (t, J = 8.5 Hz, 1H), 7.27-7.21 (m, 2H), 7.05 (d, J = 0.9 Hz, 1H), 4.00 (dd, J = 11.1, 4.0 Hz, 2H), 3.85-3.67 (m, 3H), 3.43-3.21 (m, 2H), 2.94 (tt, J = 12.6, 3.5 Hz, 1H), 2.80 (d, J = 7.1 Hz, 2H), 2.33 (td, J = 9.9, 8.9, 5.4 Hz, 1H), 2.14-1.75 (m, 4H), 1.66 (d, J = 13.4 Hz, 2H), 1.52-1.29 (m, 2H), 1.26-1.08 (m, 2H).; 510.5; Trans isomer. |
| 85 | 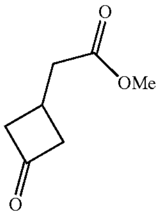 | 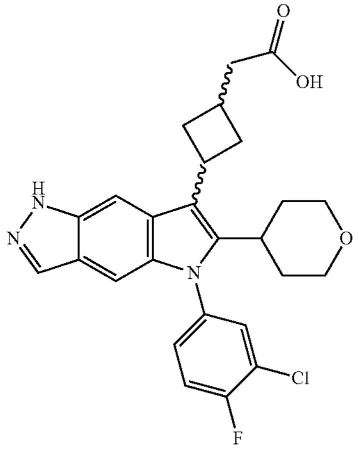 [SMILES: O=C(O)CC1CC(c2c(C3CCOCC3)n(-c3ccc(F)c(Cl)c3)c3cc4cn[nH]c4cc23)C1] | compound 33 | $^1H$ NMR (400 MHz, Chloroform-d) δ 8.02 (s, 1H), 7.97 (d, J = 0.9 Hz, 1H), 7.37-7.24 (m, 2H), 7.19-7.10 (m, 2H), 7.05 (d, J = 1.0 Hz, 1H), 3.96 (dd, J = 3.85 (q, J = 9.2 Hz, 1H), 3.27 (td, J = 11.9, 5.7 Hz, 2H), 2.86-2.61 (m, 6H), 2.53-2.36 (m, 2H), 2.06 (q, J = 12.9, 12.5 Hz, 2H), 1.58 (d, J = 13.1 Hz, 2H).; 482.5. Cis/Trans mixture. |

Table 4 Footnotes:

[1]Compound 76 was separated into its component enantiomers by chiral SFC to give compound 77 (first eluting peak) and compound 78 (second eluting peak) Method: Daicel Chiralpak AD-H IC column, 20 x 250 mm, Mobile phase: 40% EtOH (5 mM Ammonia) 60% $CO_2$ Flow: 75 mL/min.

[2]NaOH used in step 2.

[3]Compounds80 and 81 were obtained by chiral SFC separation of a mixture of the two compounds obtained in compound 79. Method: Daicel Chiralpak AD-H IC column, 10 x 250 mm, Mobile phase: 40% EtOH (5 mM Ammonia) 60% CO2 Flow: 15 mL/min

[4]Product was obtained as a trans/cis (7:1) mixture. Trans was presumed to be the major isomer as the aldehyde reagent used had the trans regiochemistry.

[5]Compound 84 was prepared by purification of compound 83 by chiral SFC. Method: Daicel Chiralpak AD-H IC column, 20 x 250 mm, Mobile phase: 40% IPA (5 mM Ammonia) 60% $CO_2$ Flow: 75 mL/min.

Compounds 86-108

Compounds 86-108 (see Table 5) were prepared in two or three steps from intermediate S9 and the appropriate ketone, aldehyde, enol ether, or acetal, using the method described for compounds 17, 32, or 33. Modifications to these methods are noted in Table 5 and accompanying footnotes. Chiral SFC was using to separate mixtures of isomers or stereoisomers. In some preparations, an alternative base such as KOH or NaOH is used in step 2.

TABLE 5

Method of preparation, structure and physicochemical data for Compounds 86-106

| Compound | Aldehyde, ketone, enol ether or acetal | Product | Method | $^1H$ NMR; LCMS m/z $[M + H]^+$; Structure Comment |
|---|---|---|---|---|
| 86 | 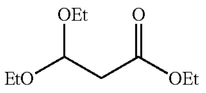 | 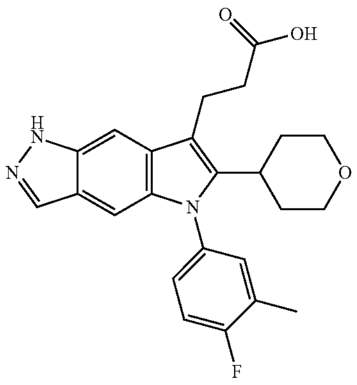 [SMILES: Cc1cc(-n2c(C3CCOCC3)c(CCC(=O)O)c3cc4[nH]ncc4cc32)ccc1F] | Compound 32 | $^1H$ NMR (300 MHz, DMSO-d6) δ 12.61 (s, 1H), 12.30 (s, 1H), 7.96 (d, J = 1.0 Hz, 1H), 7.50 (t, J = 1.1 Hz, 1H), 7.44-7.32 (m, 2H), 7.32-7.21 (m, 1H), 7.02 (d, J = 1.1 Hz, 1H), 3.87 (d, J = 9.6 Hz, 2H), 3.24-3.11 (m, 4H), 2.91 (t, J = 11.5 Hz, 1H), 2.63-2.54 (m, 2H), 2.33 (d, J = 1.9 Hz, 3H), 1.98-1.80 (m, 2H), 1.75-1.61 (m, 2H).; 422.3 |
| 87 | 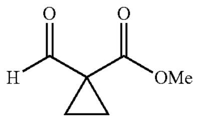 | 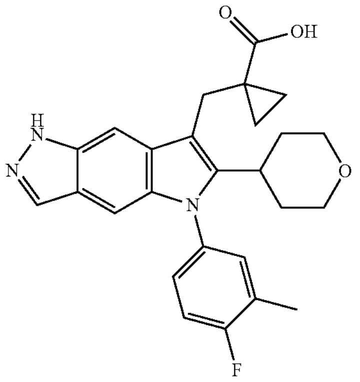 [SMILES: Cc1cc(-n2c(C3CCOCC3)c(CC3(C(=O)O)CC3)c3cc4[nH]ncc4cc32)ccc1F] | Compound 17 | $^1H$ NMR (300 MHz, DMSO-d6) δ 12.59 (s, 1H), 12.32 (s, 1H), 7.95 (d, J = 0.9 Hz, 1H), 7.47 (t, J = 1.1 Hz, 1H), 7.42-7.33 (m, 2H), 7.32-7.25 (m, 1H), 6.95 (d, J = 1.1 Hz, 1H), 3.89-3.78 (m, 2H), 3.23 (t, J = 11.3 Hz, 2H), 3.03 (t, J = 12.3 Hz, 1H), 2.33 (d, J = 1.9 Hz, 3H), 1.89-1.69 (m, 2H), 1.62 (d, J = 12.1 Hz, 2H), 1.04 (q, J = 3.6 Hz, 2H), 0.67 (q, J = 3.8 Hz, 2H).; 448.4 |
| 88 | 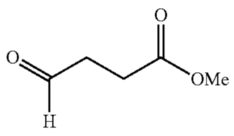 | 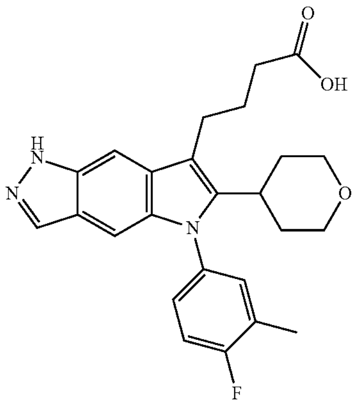 [SMILES: Cc1cc(-n2c(C3CCOCC3)c(CCCC(=O)O)c3cc4[nH]ncc4cc32)ccc1F] | Compound 33 | $^1H$ NMR (300 MHz, DMSO-d6) δ 12.62 (s, 1H), 12.17 (s, 1H), 7.95 (d, J = 1.0 Hz, 1H), 7.55 (t, J = 1.1 Hz, 1H), 7.42-7.33 (m, 2H), 7.31-7.23 (m, 1H), 7.01 (d, J = 1.1 Hz, 1H), 3.92-3.80 (m, 2H), 3.21 (t, J = 11.6 Hz, 2H), 2.95-2.80 (m, 3H), 2.43 (t, J = 7.0 Hz, 2H), 2.33 (d, J = 1.9 Hz, 3H), 1.97-1.81 (m, 4H), 1.67 (d, J = 13.1 Hz, 2H).; 436.4 |

TABLE 5-continued

Method of preparation, structure and physicochemical data for Compounds 86-106

| Compound | Aldehyde, ketone, enol ether or acetal | Product | Method | $^{1}$H NMR; LCMS m/z $[M + H]^+$; Structure Comment |
|---|---|---|---|---|
| 89 | 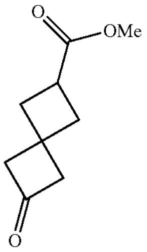 [SMILES: COC(=O)C1CC2(CC(=O)C2)C1] | 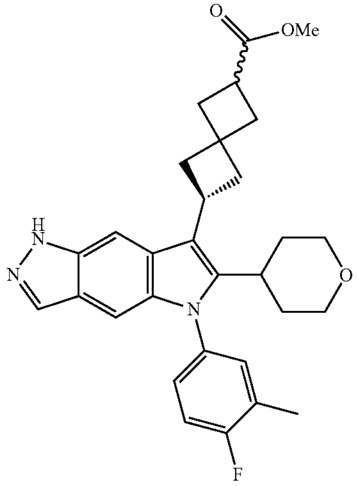 [Rac] | Compound 33 (step 1 only) | $^{1}$H NMR (300 MHz, Chloroform-d) δ 9.75 (s, 1H), 7.92 (d, J = 1.0 Hz, 1H), 7.69 (t, J = 1.1 Hz, 1H), 7.15-6.96 (m, 4H), 3.98-3.79 (m, 3H), 3.65 (s, 3H), 3.36-3.17 (m, 2H), 3.08 (m, J = 8.4 Hz, 1H), 2.92-2.66 (m, 3H), 2.56-2.30 (m, 6H), 2.28 (d, J = 1.8 Hz, 3H), 2.10-1.90 (m, 1H), 1.56 (d, J = 13.5 Hz, 2H).; 502.3. racemic |
| 90 | 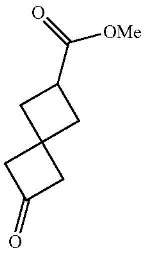 [SMILES: COC(=O)C1CC2(CC(=O)C2)C1] | 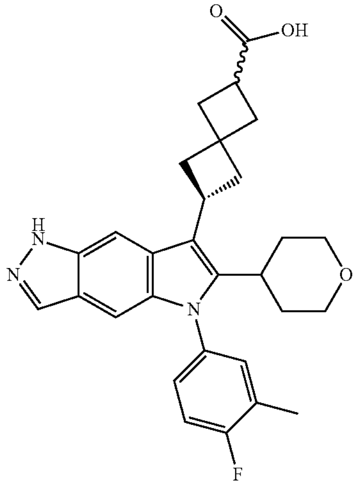 [Rac] | Compound 33 | $^{1}$H NMR (400 MHz, DMSO-d6) δ 12.58 (s, 1H), 12.10 (s, 1H), 7.94 (d, J = 0.9 Hz, 1H), 7.72 (d, J = 1.1 Hz, 1H), 7.43-7.31 (m, 2H), 7.31-7.18 (m, 1H), 7.02 (d, J = 1.0 Hz, 1H), 3.89 (dd, J = 16.7, 9.0 Hz, 3H), 3.34 (m, 1H), 3.25-3.13 (m, 2H), 3.06 (m, J = 8.4 Hz, 1H), 2.90-2.62 (m, 3H), 2.44-2.24 (m, 7H), 1.89 (q, J = 5.6, 4.7 Hz, 2H), 1.65 (m, 2H).; 488.3; racemic |
| 91 | 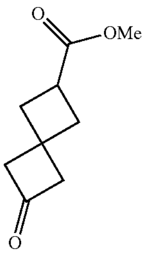 [SMILES: COC(=O)C1CC2(CC(=O)C2)C1] | 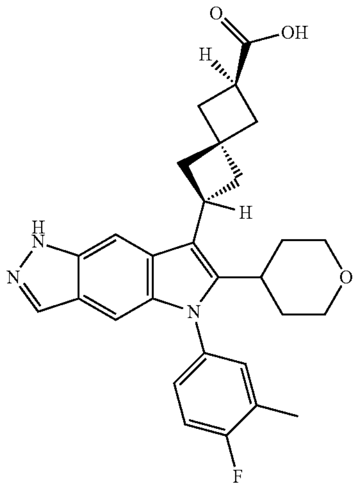 | Chiral SFC from compound 90[1,2] | $^{1}$H NMR (300 MHz, DMSO-d6) δ 12.55 (s, 1H), 12.13 (s, 1H), 7.95 (t, J = 1.5 Hz, 1H), 7.72 (d, J = 1.1 Hz, 1H), 7.49-7.30 (m, 2H), 7.25 (dt, J = 8.2, 4.0 Hz, 1H), 7.02 (d, J = 1.0 Hz, 1H), 4.06-3.72 (m, 3H), 3.20 (t, J = 11.7 Hz, 2H), 3.06 (m, J = 8.5 Hz, 1H), 2.87-2.68 (m, 3H), 2.52 (m, 2H), 2.46-2.33 (m, 4H), 2.32 (d, J = 1.9 Hz, 3H), 2.02-1.77 (m, 2H), 1.63 (br. d, J = 12.9 Hz, 2H).; 488.2; Single enantiomer. |

TABLE 5-continued

Method of preparation, structure and physicochemical data for Compounds 86-106

| Compound | Aldehyde, ketone, enol ether or acetal | Product | Method | $^{1}$H NMR; LCMS m/z $[M + H]^+$; Structure Comment |
|---|---|---|---|---|
| 92 | 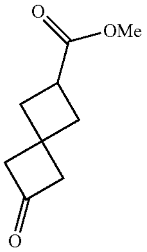 [SMILES: COC(=O)C1CC2(CC(=O)C2)C1] | 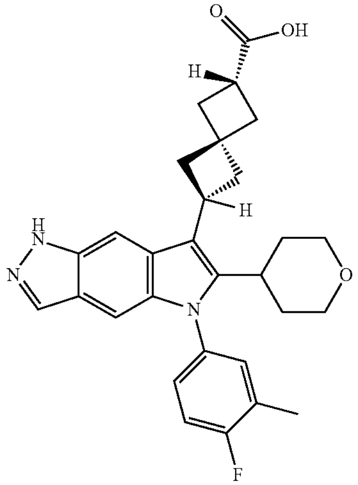 | Chiral SFC from compound 90[1,2] | $^{1}$H NMR (300 MHz, DMSO-d6) δ 12.57 (s, 1H), 12.14 (s, 1H), 7.94 (d, J = 0.9 Hz, 1H), 7.72 (d, J = 1.1 Hz, 1H), 7.50-7.30 (m, 2H), 7.31-7.17 (m, 1H), 7.02 (d, J = 1.0 Hz, 1H), 4.06-3.71 (m, 3H), 3.27-3.12 (m, 2H), 3.06 (m, J = 8.4 Hz, 1H), 2.94-2.66 (m, 3H), 2.52 (m, 2H), 2.45-2.33 (m, 4H), 2.32 (d, J = 1.9 Hz, 3H), 1.89 (d, J = 13.4 Hz, 2H), 1.63 (d, J = 13.1 Hz, 2H). 488.3; Single enantiomer. |
| 93 | 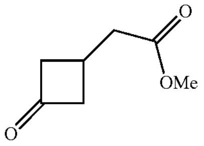 | 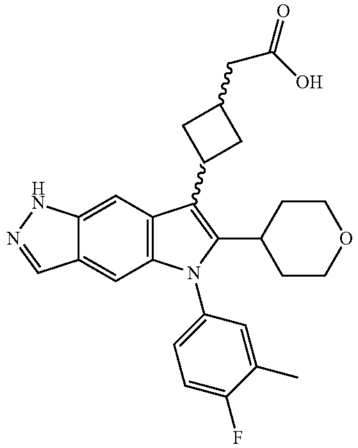 [SMILES: Cc1cc(-n2c(C3CCOCC3)c(C3CC(CC(=O)O)C3)c3cc4[nH]ncc4cc32)ccc1F] | Compound 33 | $^{1}$H NMR (300 MHz, Chloroform-d) δ 9.61 (br. s, 2H), 8.09 (s, 1H), 8.03 (d, J = 0.9 Hz, 1H), 7.25-6.98 (m, 4H), 4.11-3.80 (m, 3H), 3.35 (td, J = 11.9, 2.0 Hz, 2H), 2.93-2.67 (m, 6H), 2.58 (dtd, J = 13.6, 7.0, 3.8 Hz, 2H), 2.38 (d, J = 1.9 Hz, 3H), 2.25-2.05 (m, 2H), 1.76-1.56 (m, 2H).; 462.2; Cis and trans mixture. |
| 94 | 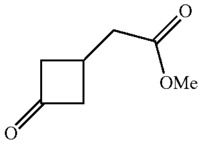 | 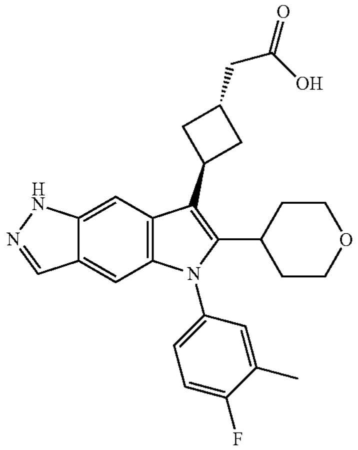 [SMILES: Cc1cc(-n2c(C3CCOCC3)c([C@H]3C[C@H](CC(=O)O)C3)c3cc4[nH]ncc4cc32)ccc1F] | Chiral SFC from compound 93[3] | $^{1}$H NMR (300 MHz, DMSO-d6) δ 12.72 (s, 1H), 7.97 (s, 1H), 7.95 (s, 1H), 7.46-7.14 (m, 3H), 7.02 (s, 1H), 3.87 (dd, J = 10.9, 3.6 Hz, 3H), 3.28-3.12 (m, 2H), 2.84 (td, J = 10.5, 8.6, 6.2 Hz, 1H), 2.78-2.67 (m, 1H), 2.61 (d, J = 7.2 Hz, 2H), 2.5 (m, 2H), 2.32 (d, J = 2.0 Hz, 4H), 2.02-1.80 (m, 2H), 1.64 (d, J = 13.0 Hz, 2H).; 462.3; Trans isomer. |

TABLE 5-continued

Method of preparation, structure and physicochemical data for Compounds 86-106

| Compound | Aldehyde, ketone, enol ether or acetal | Product | Method | $^1$H NMR; LCMS m/z $[M + H]^+$; Structure Comment |
|---|---|---|---|---|
| 95 | 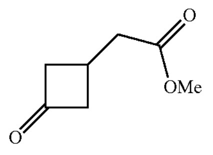 | 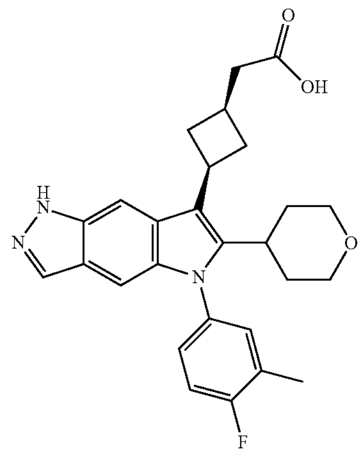 [SMILES: Cc1cc(-n2c(C3CCOCC3)c([C@H]3C[C@@H](CC(=O)O)C3)c3cc4[nH]ncc4cc32)ccc1F] | Chiral SFC from compound 93[3] | $^1$H NMR (300 MHz, DMSO-d6) δ 7.96 (s, 1H), 7.89 (s, 1H), 7.37 (td, J = 7.7, 6.6, 4.2 Hz, 2H), 7.26 (ddd, J = 8.3, 4.7, 2.5 Hz, 1H), 7.04 (d, J = 0.9 Hz, 1H), 4.20 (d, J = 9.5 Hz, 1H), 3.87 (dd, J = 11.5, 3.9 Hz, 2H), 3.32-3.05 (m, 2H), 2.87 (d, J = 27.7 Hz, 4H), 2.69 (d, J = 5.7 Hz, 2H), 2.32 (s, 3H), 2.14 (t, J = 9.0 Hz, 2H), 1.90 (d, J = 12.5 Hz, 2H), 1.62 (d, J = 13.0 Hz, 2H).; 462.3; Cis isomer. |
| 96 | 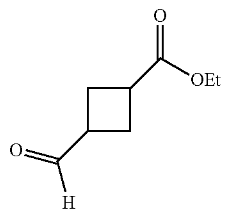 [SMILES: CCOC(=O)C1CC(C=O)C1] | 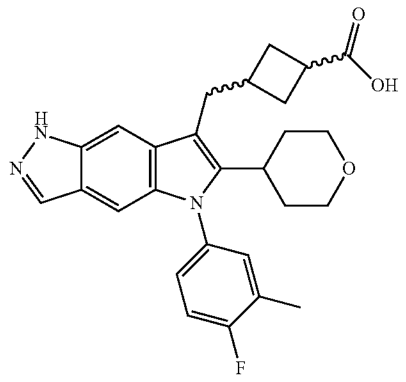 [SMILES: Cc1cc(-n2c(C3CCOCC3)c(CC3CC(C(=O)O)C3)c3cc4[nH]ncc4cc32)ccc1F] | Compound 33 | $^1$H NMR (400 MHz, DMSO-d6) δ 12.58 (s, 1H), 12.06 (s, 1H), 7.97-7.91 (m, 1H), 7.52 (dt, J = 9.7, 1.1 Hz, 1H), 7.42-7.34 (m, 2H), 7.32-7.23 (m, 1H), 6.95 (dd, J = 4.5, 1.1 Hz, 1H), 3.85 (d, J = 11.2 Hz, 2H), 3.29-3.14 (m, 3H), 3.06-2.93 (m, 3H), 2.86 (q, J = 8.8 Hz, 1H), 2.36-2.30 (m, 3H), 2.29-2.20 (m, 2H), 2.12-2.00 (m, 2H), 1.91-1.74 (m, 2H), 1.64 (d, J = 13.0 Hz, 2H).; 462.1; Cis and trans mixture. |
| 97 | 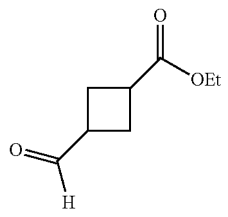 [SMILES: CCOC(=O)C1CC(C=O)C1] | 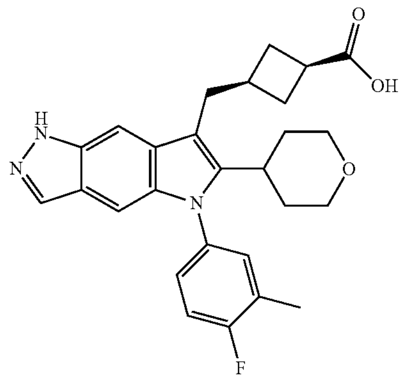 [SMILES: Cc1cc(-n2c(C3CCOCC3)c(C[C@H]3C[C@@H](C(=O)O)C3)c3cc4[nH]ncc4cc32)ccc1F] | Chiral SFC from compound 96[4] | $^1$H NMR (400 MHz, DMSO-d6) δ 12.59 (s, 1H), 12.18 (s, 1H), 7.94 (d, J = 0.9 Hz, 1H), 7.51 (t, J = 1.1 Hz, 1H), 7.42-7.32 (m, 2H), 7.31-7.22 (m, 1H), 6.96 (d, J = 1.1 Hz, 1H), 3.85 (d, J = 9.3 Hz, 2H), 3.28-3.18 (m, 2H), 3.03-2.91 (m, 3H), 2.87 (m, J = 8.9 Hz, 1H), 2.62-2.52 (m, 1H), 2.33 (d, J = 1.9 Hz, 3H), 2.29-2.19 (m, 2H), 2.02 (q, J = 9.9 Hz, 2H), 1.92-1.76 (m, 2H), 1.64 (d, J = 12.7 Hz, 2H).; 462.3; Cis isomer. |

TABLE 5-continued

Method of preparation, structure and physicochemical data for Compounds 86-106

| Compound | Aldehyde, ketone, enol ether or acetal | Product | Method | $^1$H NMR; LCMS m/z [M + H]$^+$; Structure Comment |
|---|---|---|---|---|
| 98 | 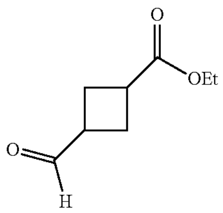 [SMILES: CCOC(=O)C1CC(C=O)C1] | 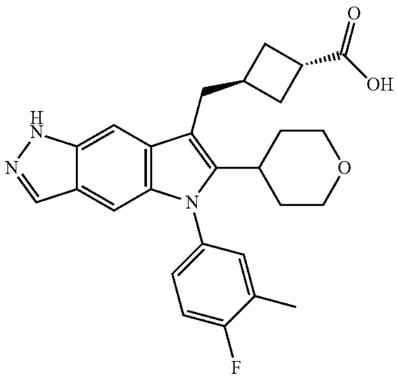 [SMILES: Cc1cc(-n2c(C3CCOCC3)c(C[C@H]3C[C@H](C(=O)O)C3)c3cc4[nH]ncc4cc32)ccc1F] | Chiral SFC from compound 96[4] | $^1$H NMR (400 MHz, DMSO-d6) δ 12.64 (s, 1H), 7.94 (d, J = 1.0 Hz, 1H), 7.56 (d, J = 1.2 Hz, 1H), 7.43-7.32 (m, 2H), 7.31-7.22 (m, 1H), 6.94 (d, J = 1.1 Hz, 1H), 3.89-3.80 (m, 2H), 3.30-3.20 (m, 2H), 3.15 (td, J = 8.8, 4.4 Hz, 1H), 3.06-2.94 (m, 3H), 2.79-2.65 (m, 1H), 2.33 (d, J = 1.9 Hz, 3H), 2.28-2.18 (m, 2H), 2.11-1.97 (m, 2H), 1.91-1.73 (m, 2H), 1.64 (d, J = 12.8 Hz, 2H).; 462.2; Trans isomer. |
| 99 | 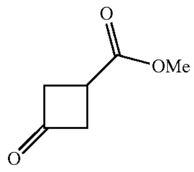 | 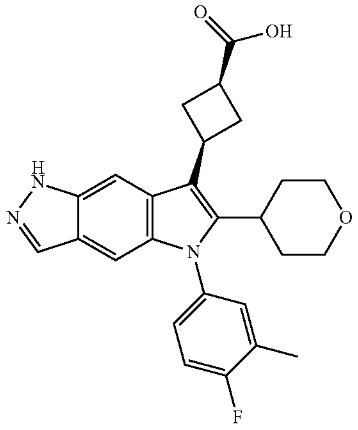 | Compound 33[5] | $^1$H NMR (300 MHz, DMSO-d6) δ 12.76 (s, 1H), 8.06 (s, 1H), 7.96 (d, J = 0.9 Hz, 1H), 7.44-7.31 (m, 2H), 7.31-7.22 (m, 1H), 7.04 (d, J = 1.0 Hz, 1H), 4.06-3.95 (m, 1H), 3.88 (d, J = 9.2 Hz, 2H), 3.30-3.13 (m, 5H), 3.02-2.79 (m, 3H), 2.32 (d, J = 1.9 Hz, 3H), 2.02-1.87 (m, 2H), 1.65 (d, J = 13.1 Hz, 2H). ; 448.3; Cis isomer. |
| 100 | 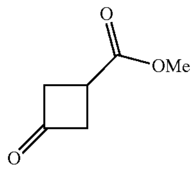 | 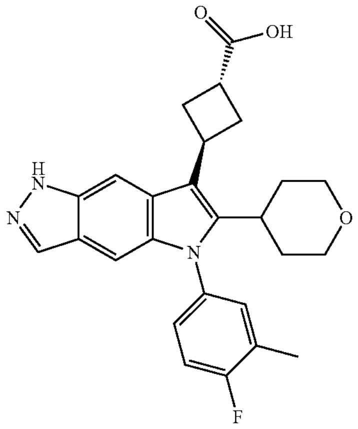 [SMILES: Cc1cc(-n2c(C3CCOCC3)c([C@H]3C[C@H](C(=O)O)C3)c3cc4[nH]ncc4cc32)ccc1F] | Compound 33[5] | $^1$H NMR (300 MHz, DMSO-d6) δ 12.58 (s, 1H), 7.96 (d, J = 0.9 Hz, 1H), 7.88 (t, J = 1.2 Hz, 1H), 7.41-7.33 (m, 2H), 7.29-7.22 (m, 1H), 7.05 (d, J = 1.0 Hz, 1H), 4.30-4.17 (m, 1H), 3.88 (d, J = 9.3 Hz, 2H), 3.24-3.14 (m, 3H), 3.05-2.92 (m, 2H), 2.86-2.74 (m, 1H), 2.59 (d, J = 9.7 Hz, 2H), 2.32 (d, J = 2.0 Hz, 3H), 1.99-1.79 (m, 2H), 1.64 (d, J = 13.0 Hz, 2H).; 448.5; Trans isomer. |

TABLE 5-continued

Method of preparation, structure and physicochemical data for Compounds 86-106

| Compound | Aldehyde, ketone, enol ether or acetal | Product | Method | $^1$H NMR; LCMS m/z $[M + H]^+$; Structure Comment |
|---|---|---|---|---|
| 101 | 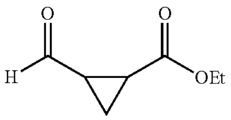 | 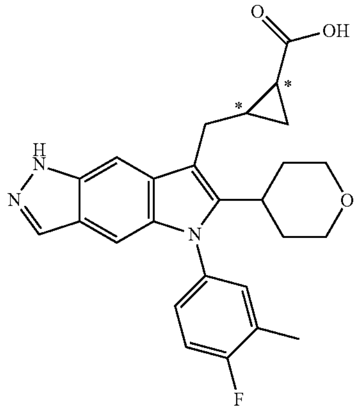 [TRANS-ENANT-1] | Compound 33[6,7] | $^1$H NMR (400 MHz, DMSO-d6) δ 12.62 (s, 1H), 7.96 (s, 1H), 7.55 (s, 1H), 7.44-7.34 (m, 2H), 7.32-7.26 (m, 1H), 6.99 (s, 1H), 4.64-4.54 (m, 2H), 3.85 (d, J = 8.9 Hz, 2H), 3.27-3.20 (m, 1H), 2.98 (m, 2H), 2.33 (s, 3H), 1.92-1.79 (m, 2H), 1.60 (m, 4H), 1.09-0.93 (m, 2H).; 448.5.Trans isomer. |
| 102 | 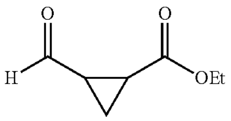 | 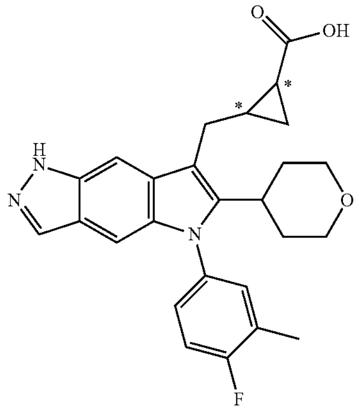 [TRANS-ENANT-2] | Compound 33[6,7] | $^1$H NMR (400 MHz, DMSO-d6) δ 12.62 (s, 1H), 7.96 (s, 1H), 7.55 (s, 1H), 7.44-7.34 (m, 2H), 7.32-7.26 (m, 1H), 6.99 (s, 1H), 4.64-4.54 (m, 2H), 3.85 (d, J = 8.9 Hz, 2H), 3.27-3.20 (m, 1H), 2.98 (m, 2H), 2.33 (s, 3H), 1.92-1.79 (m, 2H), 1.60 (m, 4H), 1.09-0.93 (m, 2H).; 448.5; Trans isomer. |
| 103 | 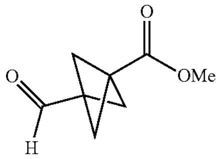 [SMILES: COC(=O)C12CC(C=O)(C1)C2] | 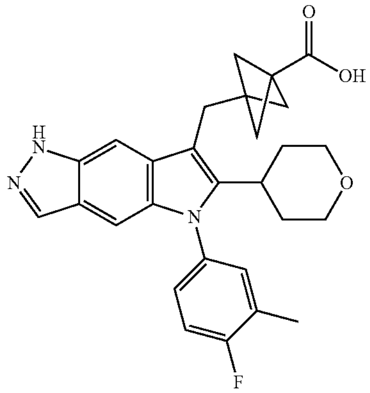 [SMILES: Cc1cc(-n2c(C3CCOCC3)c(CC34CC(C(=O)O)(C3)C4)c3cc4[nH]ncc4cc32)ccc1F] | Compound 33 | $^1$H NMR (400 MHz, Chloroform-d) δ 7.98 (d, J = 1.0 Hz, 1H), 7.48 (t, J = 1.1 Hz, 1H), 7.24-7.10 (m, 4H), 3.99 (dd, J = 11.5, 4.1 Hz, 2H), 3.32 (t, J = 11.6 Hz, 2H), 3.17 (s, 2H), 2.94-2.79 (m, 1H), 2.37 (d, J = 1.9 Hz, 3H), 2.05 (m, 8H), 1.65 (d, J = 13.0 Hz, 2H).; 474.6. |

TABLE 5-continued

Method of preparation, structure and physicochemical data for Compounds 86-106

| Compound | Aldehyde, ketone, enol ether or acetal | Product | Method | $^1H$ NMR; LCMS m/z $[M + H]^+$; Structure Comment |
|---|---|---|---|---|
| 104 | 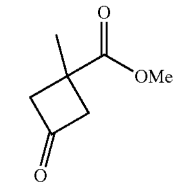 | 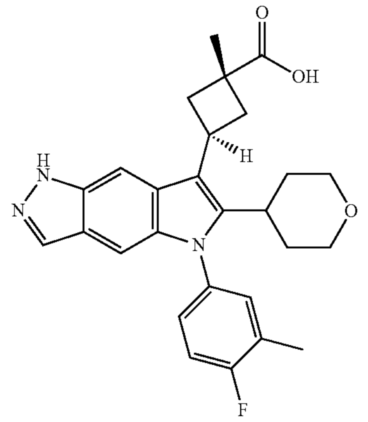 [SMILES: Cc1cc(-n2c(C3CCOCC3)c([C@H]3C[C@](C)(C(=O)O)C3)c3cc4[nH]ncc4cc32)ccc1F] | Compound 33[6,8] | $^1H$ NMR (300 MHz, Chloroform-d) δ 8.05 (d, J = 0.9 Hz, 1H), 7.94 (d, J = 1.1 Hz, 1H), 7.25-7.10 (m, 4H), 4.34-4.19 (m, 1H), 4.05 (dd, J = 11.5, 4.1 Hz, 2H), 3.36 (t, J = 11.6 Hz, 2H), 3.07-2.96 (m, 2H), 2.96-2.82 (m, 3H), 2.39 (d, J = 1.9 Hz, 3H), 2.21-2.08 (m, 2H), 1.78 (s, 3H), 1.67 (d, J = 13.2 Hz, 2H). ; 462.3. Single enantiomer. |
| 105 | 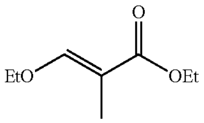 | 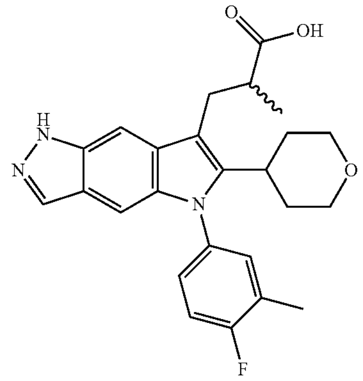 [Rac] | Compound 33 | $^1H$ NMR (300 MHz, DMSO-d6) δ 12.57 (s, 1H), 12.20 (s, 1H), 7.94 (d, J = 1.0 Hz, 1H), 7.51 (t, J = 1.1 Hz, 1H), 7.38 (t, J = 8.9 Hz, 2H), 7.26 (dt, J = 8.0, 4.0 Hz, 1H), 6.94 (d, J = 1.0 Hz, 1H), 3.83 (d, J = 11.1 Hz, 2H), 3.32-3.12 (m, 3H), 3.13-2.98 (m, 1H), 2.86 (ddd, J = 26.0, 14.0, 7.5 Hz, 2H), 2.33 (d, J = 1.9 Hz, 3H), 1.83 (m, 2H), 1.63 (d, J = 12.9 Hz, 2H), 1.17 (d, J = 6.5 Hz, 3H).; 436.2; Racemic. |
| 106 | 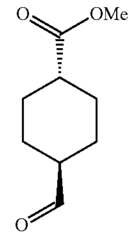 [SMILES: COC(=O)[C@H]1CC[C@H](C=O)CC1] | 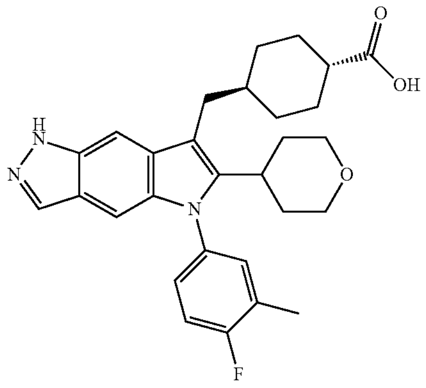 [SMILES: Cc1cc(-n2c(C3CCOCC3)c(C[C@H]3CC[C@H](C(=O)O)CC3)c3cc4[nH]ncc4cc32)ccc1F] | Compound 33 | $^1H$ NMR (400 MHz, DMSO-d6) δ 12.56 (s, 1H), 11.98 (s, 1H), 7.94 (d, J = 1.0 Hz, 1H), 7.47 (t, J = 1.1 Hz, 1H), 7.41-7.34 (m, 2H), 7.31-7.25 (m, 1H), 6.95 (d, J = 1.0 Hz, 1H), 3.84 (d, J = 9.4 Hz, 2H), 3.27-3.19 (m, 2H), 2.98 (t, J = 12.4 Hz, 1H), 2.76 (d, J = 7.0 Hz, 2H), 2.33 (d, J = 1.9 Hz, 3H), 2.24-2.15 (m, 1H), 1.94-1.75 (m, 6H), 1.73-1.58 (m, 3H), 1.32-1.10 (m, 4H).; 490.2; Single enantiomer. |

Table 5 Footnotes:

[1]Compounds 91 and 92 were prepared by separation of compound 90 into its component enantiomers by chiral SFC. Prep method: Daicel Chiralpak AD-H IC column, 20 x 250 mm, Mobile phase: 40% MeOH (5 mM Ammonia) 60% $CO_2$ Flow: 80 mL/min. Compound 91 was the first eluting peak [optical rotation: $[\alpha]_D$ in MeOH: 1.87]. Compound 92 was the second eluting peak [optical rotation: $[\alpha]_D$ in MeOH: -1.75].

[2]Absolute stereochemistry for compounds 91 and 92 was established by obtaining a single crystal extra structure for compound 91. Compound 91 was confirmed as (2R,4r,6R)-6-(5-(4-fluoro-3-methylphenyl)-6-(tetrahydro-2H-pyran-4-yl)-1,5-dihydropyrrolo[2,3-f]indazol-7-yl)spiro[3.3]heptane-2-carboxylic acid. Compound 92 was confirmed as (2S,4s,6S)-6-(5-(4-fluoro-3-methylphenyl)-6-(tetrahydro-2H-pyran-4-yl)-1,5-dihydropyrrolo[2,3-f]indazol-7-yl)spiro[3.3]heptane-2-carboxylic acid.

[3]Prepared from compound 93 by separation into constituent isomers by chiral SFC. Prep method: Daicel Chiralpak AD-H IC column, 20 x 250 mm, Mobile phase: 30% MeOH (5 mM Ammonia) 70% $CO_2$ Flow: 80 mL/min Compound 94 was obtained as the first eluting peak and compound 95 was the second eluting peak.

[4]Compound 97 and 98 were obtained by chiral separation into its constituent regioisomers. Prep method: Daicel Chiralpak AD-H IC column, 20 x 250 mm, Mobile phase: 40% EtOH (5 mM Ammonia) 60% $CO_2$ Flow: 80 mL/min. Compound 97 was the first eluting peak and was confirmed as having cis regiochemistry by NMR NOE experiments. Compound 98 was the second eluting peak.

[5]Compound 99 and 100 were obtained by separation of the racemic mixture. Prep method: Daicel Chiralpak AD-H IC column, 20 x 250 mm, Mobile phase: 40% EtOH (5 mM Ammonia) 60% $CO_2$.

[6]NaOH was used in step 2.

[7]Compound 101 and 102 (both trans enantiomers) were obtained by separation of the racemic mixture by chiral SFC. Prep method: Daicel Chiralpak AD-H IC column, 20 x 250 mm, Mobile phase: 40% IPA (5 mM Ammonia) 60% $CO_2$. Flow: 75 mL/min.

[8]Single crystal x-ray structure confirmed stereochemistry.

Compounds 107-121

Compounds 107-121 (see Table 6) were prepared in two or three steps from intermediate S7 and the appropriate ketone, aldehyde, or acetal, using the method described for compounds 16 or 33. In cases whereby modifications or alternatives to these methods have been used, explanations are noted in the table and accompanying footnotes. Chiral SFC was using to separate mixtures of isomers or stereoisomers. In some preparations, an alternative base such as KOH or NaOH is used in step 2.

TABLE 6

Method of preparation, structure and physicochemical data for Compounds 107-121

| Compound | Aldehyde, ketone, other reagent | Product | Method | $^1$H NMR; LCMS m/z [M + H]$^+$; Structure Comment |
|---|---|---|---|---|
| 107 | 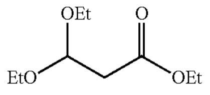 [SMILES: CCOC(=O)CC(OCC)OCC] | 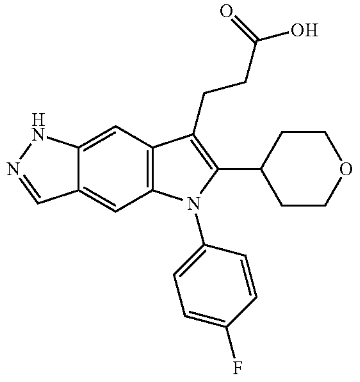 [SMILES: O=C(O)CCc1c(C2CCOCC2)n(-c2ccc(F)cc2)c2cc3cn[nH]c3cc12] | compound 16[1] | $^1$H NMR (400 MHz, DMSO-d6) δ 12.63 (s, 1H), 12.29 (s, 1H), 7.96 (s, 1H), 7.59-7.37 (m, 4H), 7.02 (s, 1H), 3.86 (dd, J = 10.8, 4.0 Hz, 2H), 3.28-3.05 (m, 3H), 2.91 (t, J = 12.5 Hz, 1H), 2.59 (t, J = 8.0 Hz, 2H), 1.87 (q, J = 11.7, 11.1 Hz, 2H), 1.68 (d, J = 13.2 Hz, 2H).; 408.3. |
| 108 | 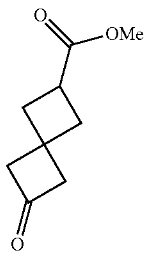 [SMILES: COC(=O)C1CC2(CC(=O)C2)C1] | 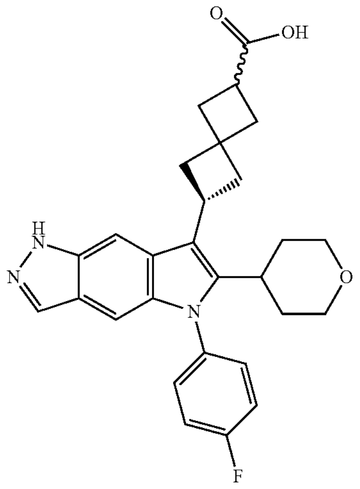 [RAC] | compound 33 | $^1$H NMR (300 MHz, Chloroform-d) δ 8.07-7.96 (m, 1H), 7.84 (s, 1H), 7.28 (m, 4H), 7.12 (d, J = 1.1 Hz, 1H), 4.07-3.88 (m, 3H), 3.40-3.18 (m, 3H), 2.91 (t, J = 11.2 Hz, 3H), 2.70-2.39 (m, 2H), 2.09 (q, J = 12.1 Hz, 2H), 1.65 (d, J = 13.1 Hz, 2H).; 474.2; Racemic. |

TABLE 6-continued

Method of preparation, structure and physicochemical data for Compounds 107-121

| Compound | Aldehyde, ketone, other reagent | Product | Method | $^1H$ NMR; LCMS m/z $[M + H]^+$; Structure Comment |
|---|---|---|---|---|
| 109 | | 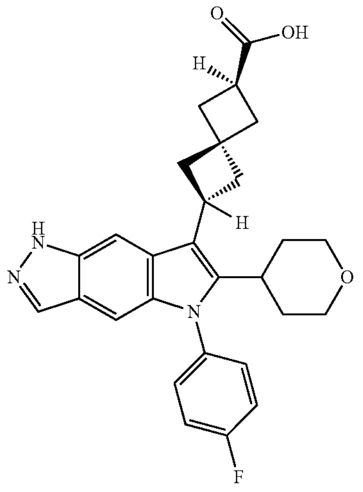 [ENANT-1] | Chiral SFC from compound $108^{2,3}$ | $^1H$ NMR (300 MHz, DMSO-d6) δ 12.59 (s, 1H), 7.94 (d, J = 0.9 Hz, 1H), 7.73 (d, J = 1.1 Hz, 1H), 7.52-7.34 (m, 4H), 7.01 (d, J = 1.0 Hz, 1H), 3.96-3.75 (m, 3H), 3.24-3.11 (m, 2H), 3.11-2.93 (m, 2H), 2.89-2.65 (m, 3H), 2.44-2.18 (m, 5H), 1.96-1.76 (m, 2H), 1.63 (d, J = 12.8 Hz, 2H). 474.3. Single enantiomer. |
| 110 | | 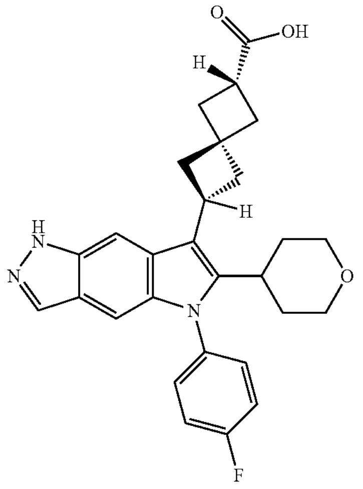 [ENANT-2] | Chiral SFC from compound $108^{2,3}$ | $^1H$ NMR (300 MHz, DMSO-d6) δ 12.57 (s, 1H), 12.10 (s, 1H), 7.94 (d, J = 0.9 Hz, 1H), 7.73 (d, J = 1.1 Hz, 1H), 7.55-7.30 (m, 4H), 7.01 (d, J = 1.0 Hz, 1H), 4.14-3.70 (m, 3H), 3.29-3.12 (m, 2H), 3.06 (m, J = 8.4 Hz, 1H), 2.88-2.64 (m, 3H), 2.5 (m, 2H), 2.43-2.26 (m, 4H), 2.00-1.73 (m, 2H), 1.77-1.48 (m, 2H).; 474.3; Single enantiomer. |
| 111 | 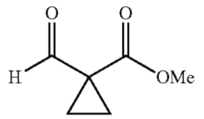 | 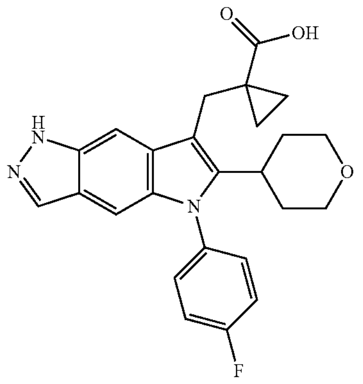 [SMILES: O=C(O)C1(Cc2c(C3CCOCC3)n(-c3ccc(F)cc3)c3cc4cn[nH]c4cc23)CC1] | compound 33 | $^1H$ NMR (400 MHz, DMSO-d6) δ 12.45 (br. 2H), 7.95 (s, 1H), 7.58-7.31 (m, 5H), 6.94 (s, 1H), 3.82 (dd, J = 11.3, 4.1 Hz, 2H), 3.47 (s, 2H), 3.29-3.09 (m, 3H), 3.03 (t, J = 11.8 Hz, 1H), 1.86-1.44 (m, 4H), 1.05 (t, J = 3.5 Hz, 2H), 0.69 (q, J = 3.9 Hz, 2H).; 433.2. |

TABLE 6-continued

| Method of preparation, structure and physicochemical data for Compounds 107-121 | | | | |
|---|---|---|---|---|
| Compound | Aldehyde, ketone, other reagent | Product | Method | $^1H$ NMR; LCMS m/z $[M + H]^+$; Structure Comment |
| 112 | 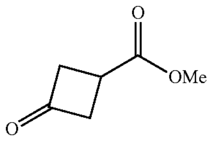 | 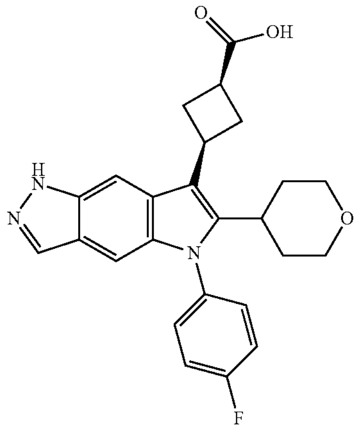 [SMILES: O=C(O)[C@H]1C[C@@H](c2c(C3CCOCC3)n(-c3ccc(F)cc3)c3cc4cn[nH]c4cc32)C1] | compound 33[4] | $^1H$ NMR (400 MHz, DMSO-d6) δ 12.81 (s, 1H), 8.16 (s, 1H), 7.96 (d, J = 0.9 Hz, 1H), 7.57-7.34 (m, 4H), 7.03 (d, J = 1.0 Hz, 1H), 3.99 (m, J = 9.5 Hz, 1H), 3.88 (dd, J = 11.2, 4.2 Hz, 2H), 3.3 (m, 1H), 3.23-3.07 (m, 4H), 2.97 (q, J = 10.3 Hz, 2H), 2.88-2.74 (m, 1H), 1.94 (qd, J = 12.6, 4.5 Hz, 2H), 1.65 (d, J = 12.9 Hz, 2H).; 434.2; Cis isomer. |
| 113 | 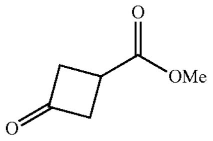 | 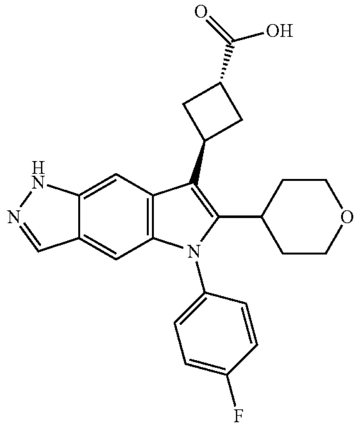 [TRANS] | compound 33[4] | $^1H$ NMR (400 MHz, DMSO-d6) δ 12.60 (s, 1H), 7.96 (d, J = 0.9 Hz, 1H), 7.89 (d, J = 1.2 Hz, 1H), 7.56-7.33 (m, 4H), 7.05 (d, J = 1.0 Hz, 1H), 4.23 (m, J = 9.4 Hz, 1H), 3.87 (dd, J = 11.1, 4.1 Hz, 2H), 3.31 (t, J = 9.6 Hz, 1H), 3.18 (t, J = 11.6 Hz, 2H), 2.98 (dt, J = 11.6, 9.4 Hz, 2H), 2.77 (t, J = 10.3 Hz, 1H), 2.65-2.52 (m, 2H), 1.88 (tq, J = 12.4, 5.9, 4.4 Hz, 2H), 1.64 (d, J = 12.7 Hz, 2H).; 434.2; Trans isomer. |
| 114 | 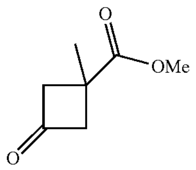 | 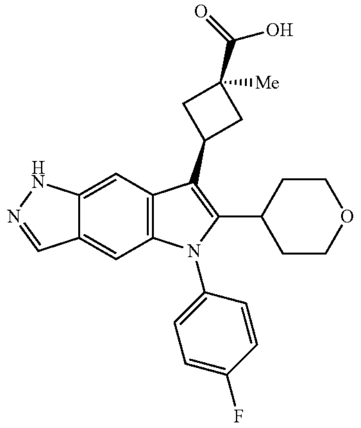 [SMILES: C[C@]1(C(=O)O)C[C@@H](c2c(C3CCOCC3)n(-c3ccc(F)cc3)c3cc4cn[nH]c4cc32)C1] | compound 33[5] | $^1H$ NMR (400 MHz, DMSO-d6) δ 12.84 (s, 1H), 8.22 (s, 1H), 7.96 (d, J = 0.9 Hz, 1H), 7.57-7.36 (m, 4H), 7.01 (d, J = 1.0 Hz, 1H), 4.10 (m, J = 9.3 Hz, 1H), 3.88 (dd, J = 11.1, 4.1 Hz, 2H), 3.28-3.10 (m, 4H), 2.96-2.80 (m, 1H), 2.14 (dd, J = 11.2, 8.4 Hz, 2H), 1.98-1.78 (m, 2H), 1.74-1.63 (m, 2H), 1.59 (s, 3H).; 448.2; Single isomer. |

TABLE 6-continued

Method of preparation, structure and physicochemical data for Compounds 107-121

| Compound | Aldehyde, ketone, other reagent | Product | Method | $^1$H NMR; LCMS m/z [M + H]$^+$; Structure Comment |
|---|---|---|---|---|
| 115 | 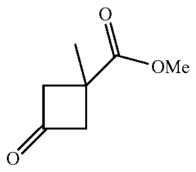 | 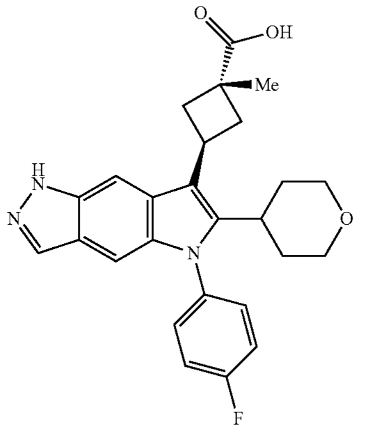 [SMILES: C[C@]1(C(=O)O)C[C@H](c2c(C3CCOCC3)n(-c3ccc(F)cc3)c3cc4cn[nH]c4cc32)C1] | compound 33[5] | $^1$H NMR (400 MHz, DMSO-d6) δ 12.59 (s, 1H), 7.96 (d, J = 0.9 Hz, 1H), 7.88 (d, J = 1.2 Hz, 1H), 7.55-7.31 (m, 4H), 7.04 (d, J = 1.0 Hz, 1H), 4.07 (m, J = 9.8 Hz, 1H), 3.88 (dd, J = 11.3, 4.0 Hz, 2H), 3.24-3.02 (m, 2H), 2.73 (m, 5H), 1.88 (qd, J = 12.5, 4.4 Hz, 2H), 1.74-1.60 (m, 2H), 1.60 (s, 3H).; 448.2. Single isomer. |
| 116 | 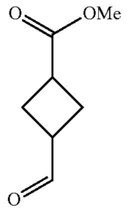 | 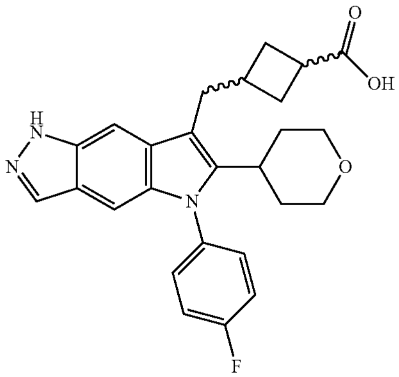 [SMILES: O=C(O)C1CC(Cc2c(C3CCOCC3)n(-c3ccc(F)cc3)c3cc4cn[nH]c4cc23)C1] | compound 33 | $^1$H NMR (300 MHz, DMSO-d6) δ 12.56 (s, 1H), 12.01 (s, 1H), 7.94 (d, J = 0.9 Hz, 1H), 7.71-7.24 (m, 5H), 6.94 (dd, J = 2.9, 1.1 Hz, 1H), 3.85 (d, J = 11.2 Hz, 2H), 3.28-3.12 (m, 3H), 3.09-2.67 (m, 3H), 2.55 (d, J = 19.0 Hz, 2H), 2.34-2.15 (m, 2H), 2.13-1.90 (m, 1H), 1.82 (q, J = 12.6 Hz, 2H), 1.64 (d, J = 12.7 Hz, 2H).; 448.3; Racemic. |
| 117 | 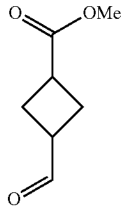 | 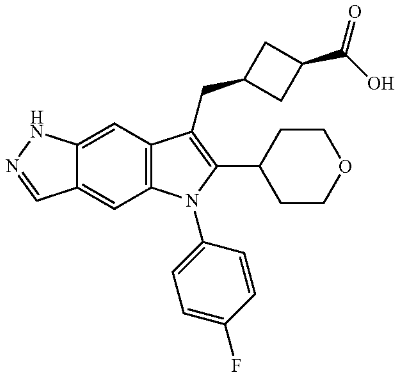 [SMILES: O=C(O)[C@H]1C[C@@H](Cc2c(C3CCOCC3)n(-c3ccc(F)cc3)c3cc4cn[nH]c4cc23)C1] | Chiral SFC from compound 116[6] | $^1$H NMR (300 MHz, Chloroform-d) δ 7.95 (s, 1H), 7.61 (s, 1H), 7.35-7.17 (m, 4H), 7.04 (d, J = 1.0 Hz, 1H), 3.99 (dd, J = 11.4, 4.0 Hz, 2H), 3.46-3.27 (m, 3H), 3.10-2.86 (m, 4H), 2.66 (m, J = 8.1 Hz, 1H), 2.44-2.28 (m, 2H), 2.17 (dt, J = 11.8, 9.2 Hz, 2H), 2.09-1.88 (m, 1H), 1.68 (d, J = 12.9 Hz, 2H).; 448.2. Cis isomer. |

TABLE 6-continued

Method of preparation, structure and physicochemical data for Compounds 107-121

| Compound | Aldehyde, ketone, other reagent | Product | Method | $^1$H NMR; LCMS m/z $[M + H]^+$; Structure Comment |
|---|---|---|---|---|
| 118 | 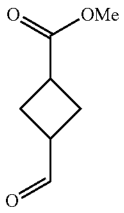 | 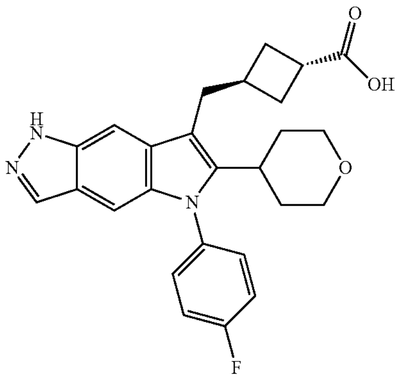 [SMILES: O=C(O)[C@H]1C[C@H](Cc2c(C3CCOCC3)n(-c3ccc(F)cc3)c3cc4cn[nH]c4cc23)C1] | Chiral SFC from compound 116[6] | $^1$H NMR (300 MHz, Chloroform-d) δ 7.95 (s, 1H), 7.57 (d, J = 1.1 Hz, 1H), 7.34-7.20 (m, 4H), 7.03 (d, J = 1.0 Hz, 1H), 3.99 (dd, J = 11.6, 4.1 Hz, 2H), 3.43-3.29 (m, 4H), 3.22 (dq, J = 9.5, 4.9, 4.2 Hz, 1H), 3.12-2.83 (m, 4H), 2.43 (dt, J = 13.5, 7.7 Hz, 2H), 2.28-2.09 (m, 1H), 2.01 (q d, J = 12.9, 4.3 Hz, 2H), 1.68 (d, J = 12.9 Hz, 2H).; 448.2; Trans isomer. |
| 119 | 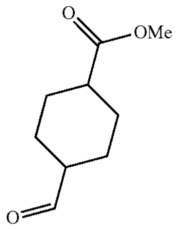 [SMILES: COC(=O)C1CCC(C=O)CC1] | 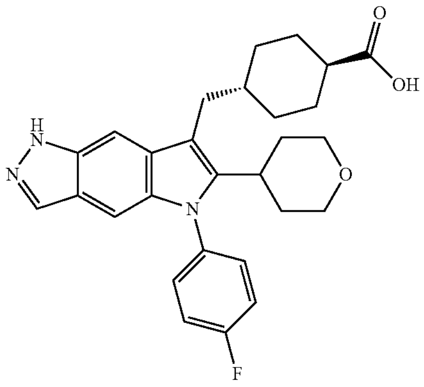 [SMILES: O=C(O)[C@H]1CC[C@H](Cc2c(C3CCOCC3)n(-c3ccc(F)cc3)c3cc4cn[nH]c4cc23)CC1] | compound 33 | $^1$H NMR (300 MHz, DMSO-d6) δ 12.56 (s, 1H), 12.00 (s, 1H), 7.94 (d, J = 0.9 Hz, 1H), 7.56-7.37 (m, 5H), 6.94 (d, J = 1.0 Hz, 1H), 3.92-3.74 (m, 2H), 3.22 (t, J = 11.4 Hz, 2H), 2.98 (t, J = 12.3 Hz, 1H), 2.76 (d, J = 7.0 Hz, 2H), 2.26-2.10 (m, 1H), 1.95-1.54 (m, 9H), 1.34-1.17 (m, 4H).; 476.3; Trans isomer. |
| 120 | See footnote 7 | 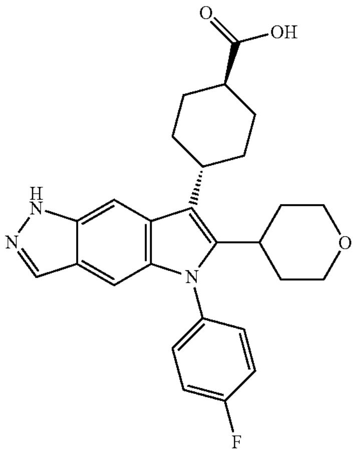 [SMILES: O=C(O)[C@H]1CC[C@H](c2c(C3CCOCC3)n(-c3ccc(F)cc3)c3cc4cn[nH]c4cc32)CC1] | compound 75[7] | $^1$H NMR (400 MHz, DMSO-d6) δ 12.51 (s, 1H), 7.94 (s, 1H), 7.71 (s, 1H), 7.46 (d, J = 8.4 Hz, 4H), 7.03 (s, 1H), 3.89 (d, J = 12.0 Hz, 3H), 3.20 (t, J = 11.5 Hz, 2H), 3.07 (s, 1H), 2.82 (t, J = 12.8 Hz, 1H), 2.22 (d, J = 13.1 Hz, 2H), 2.10 (d, J = 12.9 Hz, 2H), 2.02-1.77 (m, 5H), 1.75-1.42 (m, 5H).; 462.3; Trans isomer. |

TABLE 6-continued

Method of preparation, structure and physicochemical data for Compounds 107-121

| Compound | Aldehyde, ketone, other reagent | Product | Method | $^1$H NMR; LCMS m/z [M + H]$^+$; Structure Comment |
|---|---|---|---|---|
| 121 | 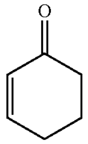 | 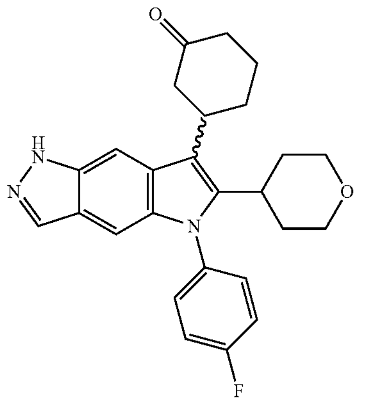 [RAC] | See footnote 8 | $^1$H NMR (400 MHz, DMSO-d6) δ 12.59 (s, 1H), 7.97 (s, 1H), 7.87 (s, 1H), 7.47 (td, J = 5.3, 4.7, 3.1 Hz, 4H), 7.05 (s, 1H), 3.86 (d, J = 10.7 Hz, 2H), 3.52 (t, J = 13.0 Hz, 1H), 3.19 (t, J = 11.4 Hz, 2H), 2.89-2.60 (m, 2H), 2.32 (dd, J = 13.6, 6.2 Hz, 2H), 2.16 (d, J = 11.6 Hz, 1H), 1.86 (dt, J = 23.5, 12.5 Hz, 6H), 1.67 (d, J = 13.0 Hz, 2H).; 432.4; Racemic. |

Table 6 Footnotes:

[1]NaOH used as base in step 3.

[2]Racemic compound 108 was separated into its constituent enantiomers by chiral SFC to give compound 109 and compound 110. Prep method: Daicel Chiralpak AD-H IC column, 20 x 250 mm, Mobile phase: 40% IPA (5 mM Ammonia) 60% $CO_2$. Flow: 75 mL/min. Compound 109 was the first eluting peak [optical rotation $[\alpha]_D$ in MeOH: 0.97] and compound 110 was the second eluting peak. [optical rotation $[\alpha]_D$ in MeOH: −1.13].

[3]Absolute stereochemistry for compounds 109 and 110 was established by obtaining a single crystal x-ray structure for compound 109. See Table 7 for X-ray structural data. Compound 109 was confirmed as (2R,4r,6R)-6-(5-(4-fluorophenyl)-6-(tetrahydro-2H-pyran-4-yl)-1,5-dihydropyrrolo[2,3-f]indazol-7-yl)spiro[3.3]heptane-2-carboxylic acid. The enantiomer compound 110 was confirmed as the (2S,4s,6S)-6-(5-(4-fluorophenyl)-6-(tetrahydro-2H-pyran-4-yl)-1,5-dihydropyrrolo[2,3-f]indazol-7-yl)spiro[3.3]heptane-2-carboxylic acid.

[4]Compounds 112 and 113 were separated from a mixture of the constituent isomers using chiral SFC. Prep method: Daicel Chiralpak AD-H IC column, 20 x 250 mm, Mobile phase: 20% EtOH (containing 5 mM Ammonia) 80% $CO_2$. Flow: 80 mL/min.

[5]A mixture of isomers were separated into the constituents using chiral SFC to give compound 114 (first eluting peak) and compound 115 (second eluting peak). Prep method: Daicel Chiralpak AD-H IC column, 20 x 250 mm, Mobile phase: 20% EtOH (5 mM Ammonia) 80% $CO_2$. Flow: 80 mL/min Relative structural assignments was based on NMR NOE experiments.

[6]Compounds 117 and 118 were obtained from separation of the mixture compound 116 into constituent isomers using chiral SFC. Prep method: Daicel Chiralpak AD-H IC column, 20 x 250 mm, Mobile phase: 20% EtOH (containing 5 mM Ammonia) 80% $CO_2$. Flow: 80 mL/min.

[7]Zinc reagent used, as for compound 75.

[8]Step 1: bismuth triflate (110 mg, 0.18 mmol) was added to a stirred suspension of benzyl 5-(4-fluorophenyl)-6-tetrahydropyran-4-yl-pyrrolo[2,3-f]indazole-1-carboxylate S7 (435 mg, 0.93 mmol) and cyclohex-2-en-1-one (230 μL, 2.4 mmol) in acetonitrile (7 mL) and MeOH (700 μL) and the mixture was allowed to stir at 50° C. for 30 min. The mixture was diluted with dichloromethane (30 mL) and washed with saturated $NaHCO_3$, dried and concentrated to afford benzyl 5-(4-fluorophenyl)-7-(3-oxocyclohexyl)-6-tetrahydropyran-4-yl-pyrrolo[2,3-f]indazole-1-carboxylate (Yield: 360 mg, 63%). Step 2: To a solution of benzyl 5-(4-fluorophenyl)-7-(3-oxocyclohexyl)-6-tetrahydropyran-4-yl-pyrrolo[2,3-f]indazole-1-carboxylate (240 mg, 0.4 mmol) in MeOH (5 mL) and dichloromethane (2 mL) was added potassium carbonate (220 mg, 1.6 mmol) and the mixture was stirred for 20 min. The mixture was filtered, concentrated. The residue was diluted with dichloromethane, washed with water and filtered through phase separator, and dried to afford 3-[5-(4-fluorophenyl)-6-tetrahydropyran-4-yl-1H-pyrrolo[2,3-f]indazol-7-yl]cyclohexanone (Yield: 160 mg, 91%).

Compound 122

6-[5-(4-fluorophenyl)-6-(8-oxabicyclo[3.2.1]octan-3-yl)-1H-pyrrolo[2,3-f]indazol-7-yl]spiro[3.3]heptane-2-carboxylic Acid (122)

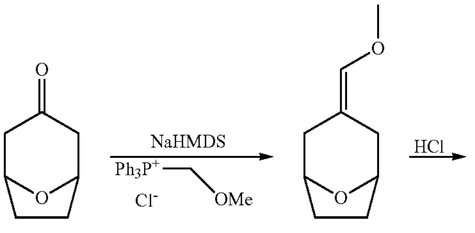

C98 C99

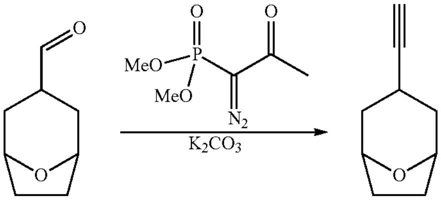

C100 C101

-continued

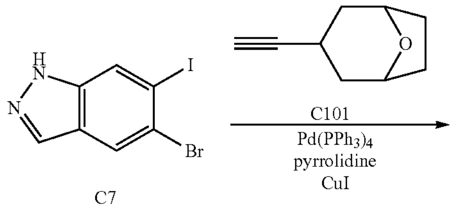

C7

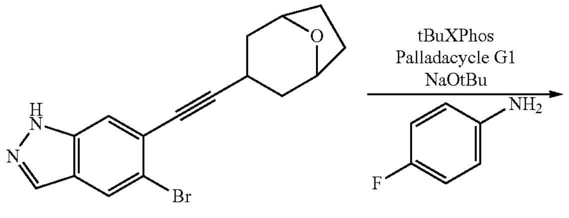

C102

-continued

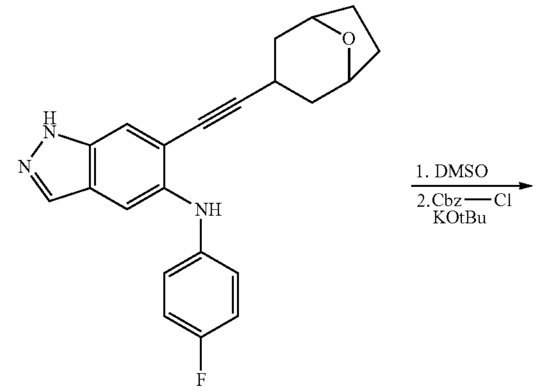

C103

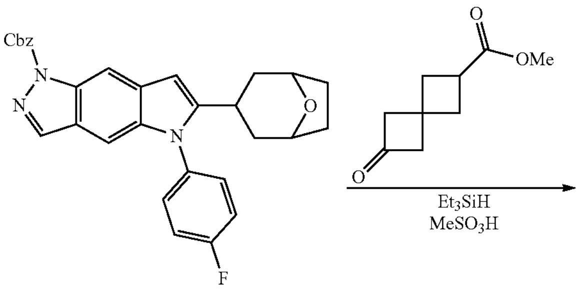

C104

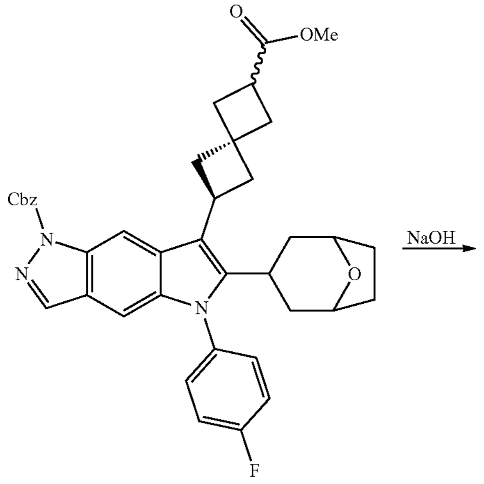

C105

-continued

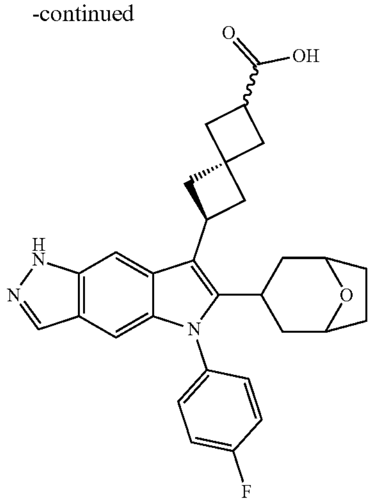

122

Step 1. Synthesis of 3-(methoxymethylene)-8-oxabicyclo[3.2.1]octane (C99)

To a suspension of methoxymethyl(triphenyl)phosphonium chloride (2.9 g, 8.6 mmol) in THF (50 mL) at −40° C. was added [bis(trimethylsilyl)amino]sodium (6.4 mL of 2 M, 12.8 mmol) dropwise. The mixture was stirred at −40° C. for 30 min, and 8-oxabicyclo[3.2.1]octan-3-one (1 g, 7.9 mmol) in 10 mL THF was added at −40° C. The reaction was warmed to room temperature and stirred overnight. The reaction was then quenched with aqueous saturated $NH_4Cl$ (50 mL). The mixture was filtered and the solid washed with EtOAc. The filtrate was further extracted with EtOAc (3×50 mL). The combined organic phases were dried over sodium sulfate and concentrated in vacuo. Silica gel chromatography (Gradient: 0-25% EtOAc in heptanes) afforded the product. Yield: 594 mg, 49%. $^1H$ NMR (400 MHz, Chloroform-d) δ 5.90-5.64 (m, 1H), 4.30 (m, J=4.5 Hz, 2H), 3.43 (d, J=1.3 Hz, 3H), 2.31 (d, J=14.0 Hz, 2H), 2.14-1.95 (m, 1H), 1.74 (m, J=4.1 Hz, 2H), 1.62 (d, J=13.9 Hz, 1H), 1.58-1.45 (m, 2H).

Step 2. Synthesis of 8-oxabicyclo[3.2.1]octane-3-carbaldehyde (C100)

To a solution of 3-(methoxymethylene)-8-oxabicyclo[3.2.1]octane C99 (6.9 g, 50 mmol) in acetonitrile (50 mL) was added HCl (25 mL of 2 M, 50 mmol). The reaction mixture was stirred at room temperature for 90 min, and then a solution of aqueous saturated sodium bicarbonate (100 mL) was added. The mixture was extracted with dichloromethane (3×50 mL). The combined organic phases were dried over sodium sulfate and concentrated in vacuo. Purification by silica gel chromatography (Gradient: 0-40% EtOAc in heptanes) afforded the product as a pale clear yellow liquid. The product was determined to be a ca. 3:1 ratio of exo:endo isomers, as determined by NMR spectroscopy. Yield 4.8 g, 76%.

Step 3. Synthesis of 3-ethynyl-8-oxabicyclo[3.2.1]octane (C101)

Potassium carbonate (3.1 g, 22.1 mmol) was added portion wise to a solution of 8-oxabicyclo[3.2.1]octane-3-carbaldehyde C100 (1.9 g, 13.8 mmol) and methanol (170 mL). The mixture was allowed to stir for 5 min 1-diazo-1-dimethoxyphosphoryl-propan-2-one (4.4 g, 22.6 mmol) was then added dropwise. And the mixture allowed to stir overnight at room temperature. The mixture was concentrated in vacuo and EtOAc (250 mL) was added. This solution was washed with an aqueous saturated sodium bicarbonate solution, and water (2×250 mL). The organic phase was dried over sodium sulfate, filtered, and concentrated in vacuo to afford the product as a light yellow liquid. This material was used without further purification in the subsequent reaction. Yield: 1.6 g, 85%. $^{1}$H NMR (400 MHz, Chloroform-d) δ 4.46-4.36 (m, 2H), 2.82-2.68 (m, 1H), 2.12-2.04 (m, 2H), 1.99 (dd, J=8.9, 4.5 Hz, 2H), 1.88 (td, J=12.7, 3.2 Hz, 2H), 1.77-1.68 (m, 4H).

Step 4-9. Synthesis of 6-[5-(4-fluorophenyl)-6-(8-oxabicyclo[3.2.1]octan-3-yl)-1H-pyrrolo[2,3-f]indazol-7-yl]spiro[3.3]heptane-2-carboxylic Acid (122)

Compound 122 was synthesized from C101 and C7 using the methods described in preparation S1, S2, and compound 34 respectively. In the Sonagashira reaction of step 4, pyrrolidine is used as the base. In the final hydrolysis step, sodium hydroxide is used. Purification by reverse phase chromatography (C18 column; 10-100% acetonitrile in water containing 0.1% TFA) afforded the product as a light yellow solid (trifluoroacetate salt) as a mixture of steroisomers. Yield: 6.8 mg, 32%. LCMS m/z 500.4 [M+H]$^{+}$. $^{1}$H NMR (400 MHz, Methanol-d4) δ 8.07 (s, 1H), 7.86 (s, 1H), 7.39 (d, J=6.6 Hz, 4H), 7.18 (s, 1H), 4.49-4.40 (m, 2H), 4.04 (m, J=9.4 Hz, 1H), 3.24-3.09 (m, 2H), 3.03-2.84 (m, 2H), 2.71-2.47 (m, 5H), 2.46-2.38 (m, 1H), 2.23 (t, J=13.2 Hz, 2H), 1.95-1.87 (m, 2H), 1.59 (dd, J=13.7, 4.9 Hz, 2H), 1.53-1.44 (m, 2H).

Compound 123

6-(5-phenyl-6-tetrahydropyran-4-yl-1H-pyrrolo[2,3-f]indazol-7-yl)spiro[3.3]heptane-2-carboxylic Acid (123)

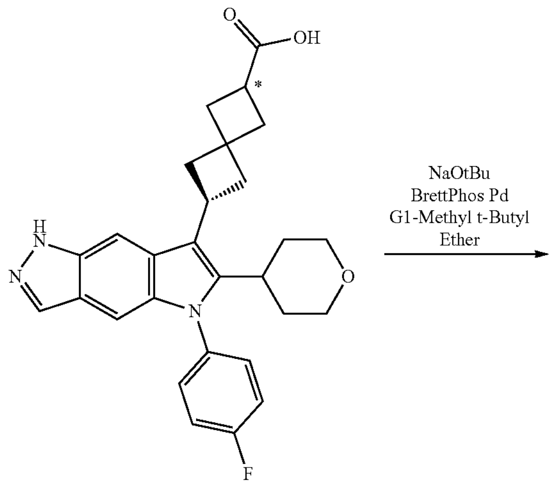

109
[ENANT-1]

-continued

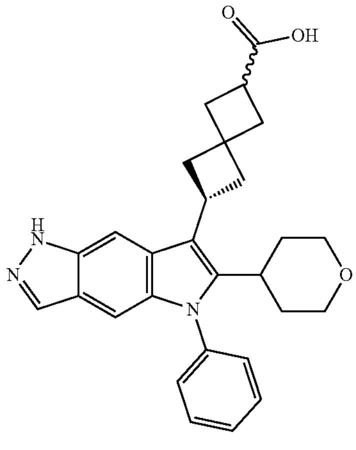

123

Compound 123 was prepared using the method described for compound 41. Compound 123 is presumed to be of unknown stereochemistry. Compound 109 which was used in preparation of compound 123 is a single enantiomer; however, enantiomeric purity of the product compound 123 was not tested following this transformation. Yield: 14.3 mg, 18%. LCMS m/z 456.3 [M+H]$^{+}$. $^{1}$H NMR (300 MHz, DMSO-d6) δ 12.57 (s, 1H), 12.11 (s, 1H), 7.97-7.90 (m, 1H), 7.75-7.70 (m, 1H), 7.67-7.52 (m, 3H), 7.43-7.36 (m, 2H), 7.02 (d, J=1.0 Hz, 1H), 3.95-3.80 (m, 3H), 3.17 (t, J=11.5 Hz, 2H), 3.10-2.98 (m, 1H), 2.90-2.69 (m, 4H), 2.44-2.29 (m, 5H), 1.96-1.80 (m, 2H), 1.63 (d, J=12.9 Hz, 2H).

Compound 124

1-[[5-(4-fluoro-2-methyl-phenyl)-6-tetrahydropyran-4-yl-1H-pyrrolo[2,3-f]indazol-7-yl]methyl]cyclopropanecarboxylic Acid (124)

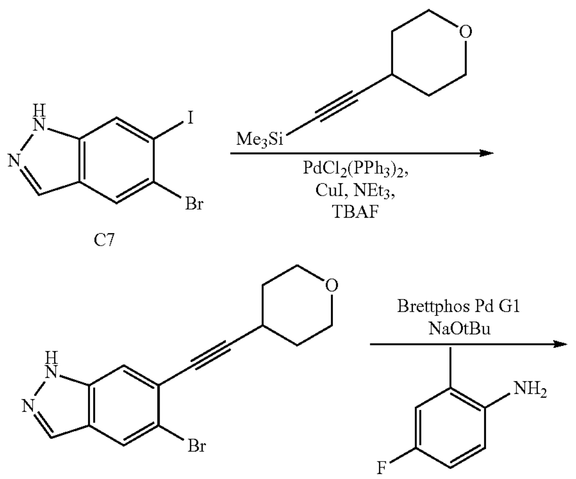

C7

C106

-continued

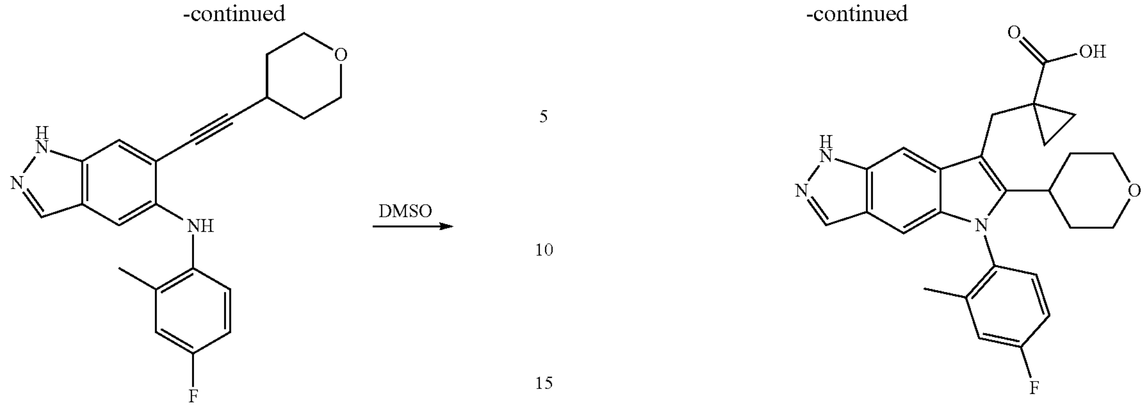

C107

124

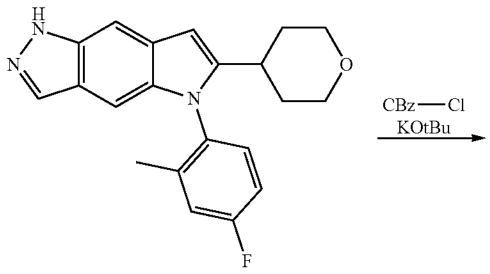

C108

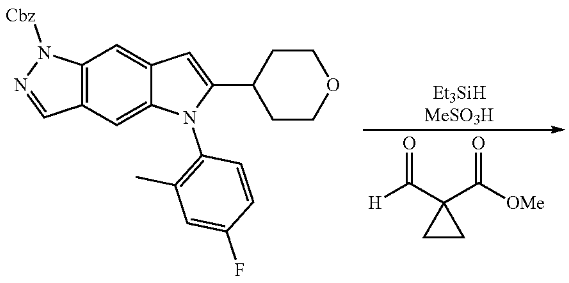

C109

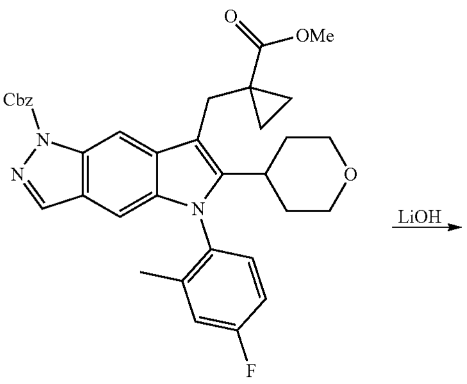

C110

Step 1. Synthesis of 5-bromo-6-(2-tetrahydropyran-4-ylethynyl)-1H-indazole (C106)

Compound C106 was prepared using the method described in step 2 of preparation S11. Yield: 77 g, 68%. LCMS m/z 305.3 [M+H]$^+$. $^1$H NMR (300 MHz, Chloroform-d) δ 10.40 (s, 1H), 8.02 (dd, J=3.5, 0.9 Hz, 2H), 7.65 (t, J=0.9 Hz, 1H), 4.04 (ddd, J=11.6, 6.5, 3.5 Hz, 2H), 3.65 (ddd, J=11.3, 7.7, 3.2 Hz, 2H), 3.00 (tt, J=8.0, 4.2 Hz, 1H), 2.06-1.92 (m, 2H), 1.85 (dtd, J=13.4, 7.7, 3.5 Hz, 2H).

Steps 2-5. Synthesis of 1-[[5-(4-fluoro-2-methyl-phenyl)-6-tetrahydropyran-4-yl-1H-pyrrolo[2,3-f]indazol-7-yl]methyl]cyclopropanecarboxylic Acid (124)

Compound C109 was prepared from C7 as described in Preparations S1 and S2. Compound 124 was then prepared from C109 using the methods described for compound 33. Yield: 16.9 mg, 43%. LCMS m/z 448.3 [M+H]$^+$. $^1$H NMR (300 MHz, DMSO-d6) δ 12.61 (s, 1H), 12.33 (s, 1H), 7.93 (d, J=0.9 Hz, 1H), 7.52-7.42 (m, 2H), 7.38 (dd, J=9.6, 3.0 Hz, 1H), 7.28 (td, J=8.5, 3.1 Hz, 1H), 6.79 (d, J=1.0 Hz, 1H), 3.81 (t, J=12.4 Hz, 2H), 3.46 (s, 2H), 3.17 (s, 2H), 2.96 (t, J=12.4 Hz, 1H), 1.93-1.81 (m, 1H), 1.74 (s, 3H), 1.66-1.45 (m, 3H), 1.08-0.99 (m, 2H), 0.70-0.57 (m, 2H).

Compound 125

3-[5-(4-fluoro-3-methyl-phenyl)-3-methyl-6-tetrahydropyran-4-yl-1H-pyrrolo[2,3-f]indazol-7-yl]propanoic Acid (125)

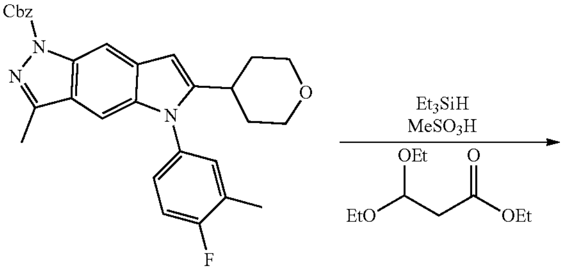

S12

-continued

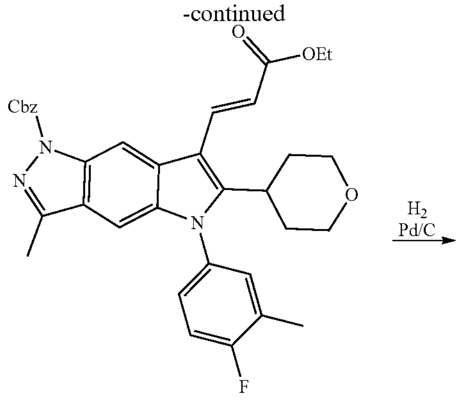

C111

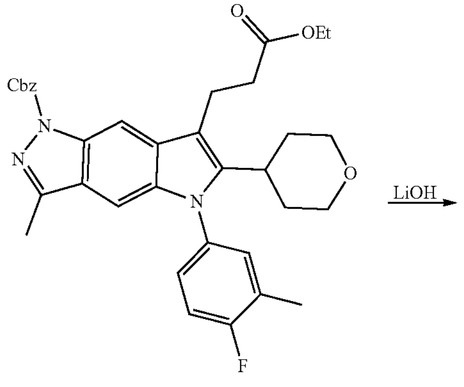

C112

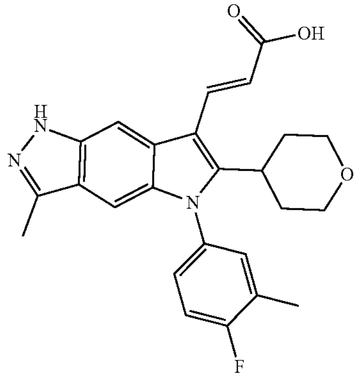

125

Compound 125 was prepared from S12 using the method described for compound 16. In this case, sodium hydroxide was used as the based in the final hydrolysis step. Yield: 24.9 mg, 49%. LCMS m/z 436.3 $[M+H]^+$. $^1H$ NMR (400 MHz, DMSO-d6) δ 12.17 (s, 2H), 7.42 (d, J=4.2 Hz, 1H), 7.37 (dd, J=9.1, 4.2 Hz, 2H), 7.27 (dt, J=8.1, 3.3 Hz, 1H), 6.90 (s, 1H), 3.87 (dd, J=11.3, 3.9 Hz, 2H), 3.27-3.01 (m, 4H), 2.88 (t, J=12.4 Hz, 1H), 2.58 (t, J=8.0 Hz, 2H), 2.39 (s, 3H), 2.34 (s, 3H), 1.89 (tt, J=16.7, 8.3 Hz, 2H), 1.68 (d, J=12.9 Hz, 2H).

Compounds 126-128

6-[5-(4-fluoro-3-methyl-phenyl)-3-methyl-6-tetrahydropyran-4-yl-1H-pyrrolo[2,3-f]indazol-7-yl]spiro[3.3]heptane-2-carboxylic acid (126), 6-[5-(4-fluoro-3-methyl-phenyl)-3-methyl-6-tetrahydropyran-4-yl-1H-pyrrolo[2,3-f]indazol-7-yl]spiro[3.3]heptane-2-carboxylic acid, [ENANT-1] (127), and 6-[5-(4-fluoro-3-methyl-phenyl)-3-methyl-6-tetrahydropyran-4-yl-1H-pyrrolo[2,3-f]indazol-7-yl]spiro[3.3]heptane-2-carboxylic acid, [ENANT-2](128)

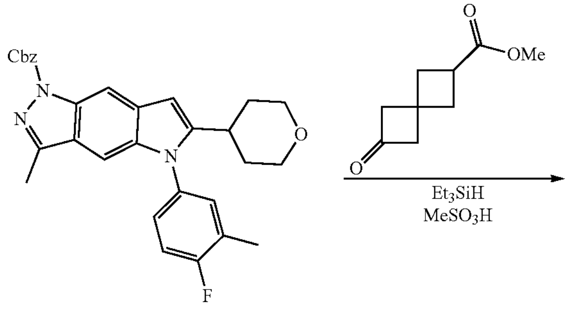

S12

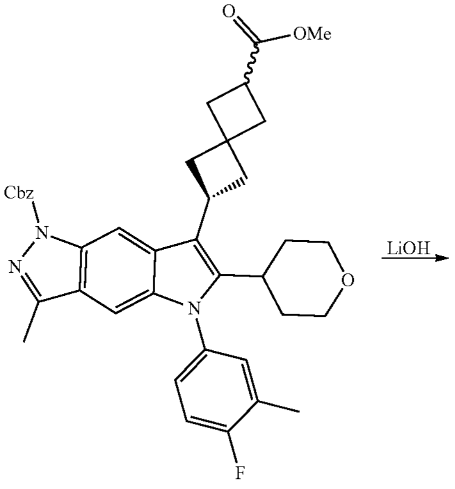

C113

-continued

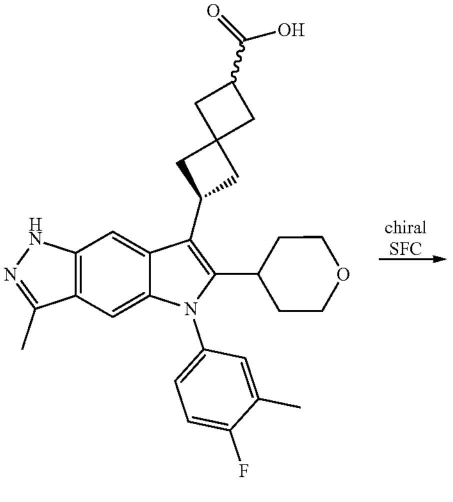

126

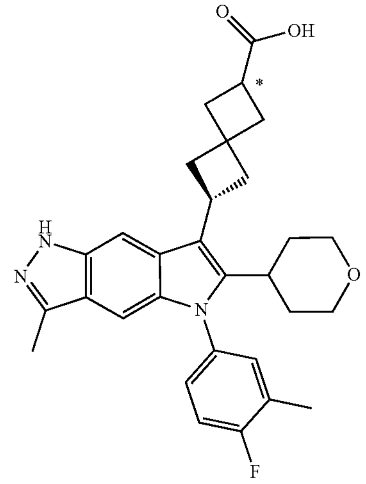

+

[ENANT-1]
127

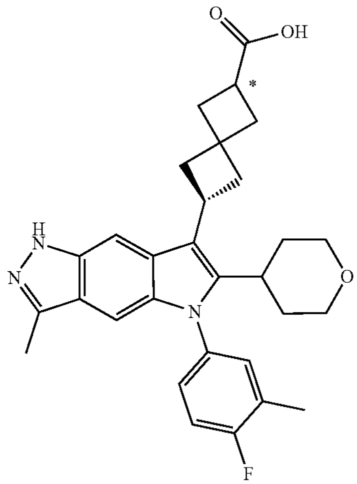

[ENANT-2]
128

Step 1. Synthesis of 6-[5-(4-fluoro-3-methyl-phenyl)-3-methyl-6-tetrahydropyran-4-yl-1H-pyrrolo[2,3-f]indazol-7-yl]spiro[3.3]heptane-2-carboxylic acid (126)

Racemic compound 126 was prepared as described for compound 34. Yield: 458 mg, 74%. LCMS 502.4 $[M+H]^+$. $^1H$ NMR (400 MHz, DMSO-d6) δ 12.09 (d, J=27.0 Hz, 1H), 7.64 (s, 1H), 7.44-7.30 (m, 2H), 6.90 (s, 1H), 3.89 (dd, J=14.8, 9.8 Hz, 3H), 3.19 (t, J=11.6 Hz, 2H), 3.12-2.94 (m, 1H), 2.76 (dt, J=24.3, 10.6 Hz, 3H), 2.43-2.25 (m, 10H), 1.86 (s, 2H), 1.63 (d, J=13.0 Hz, 1H).

Step 2. Preparation of 6-[5-(4-fluoro-3-methyl-phenyl)-3-methyl-6-tetrahydropyran-4-yl-1H-pyrrolo[2,3-f]indazol-7-yl]spiro[3.3]heptane-2-carboxylic acid, [ENANT-1] (127) and 6-[5-(4-fluoro-3-methyl-phenyl)-3-methyl-6-tetrahydropyran-4-yl-1H-pyrrolo[2,3-f]indazol-7-yl]spiro[3.3]heptane-2-carboxylic acid, [ENANT-2](128)

Racemic mixture 126 (400 mg, 0.8 mmol) was separated into constituent enantiomers by chiral SFC separation. Column: Phenomenex Cellulose-2, 20×250 mm Mobile phase: 40% MeOH (5 mM Ammonia), 60% $CO_2$. Flow: 75 mL/min. Compound (127) [ENANT-1] was the first eluting enantiomer. Yield: 151.0 mg, 76%. LCMS m/z 502.3 $[M+H]^+$. $^1H$ NMR (400 MHz, DMSO-d6) δ 12.13 (s, 1H), 7.64 (s, 1H), 7.43-7.31 (m, 2H), 7.26 (d, J=6.7 Hz, 1H), 6.90 (s, 1H), 4.03-3.77 (m, 3H), 3.26-3.12 (m, 2H), 3.03 (m, J=8.3 Hz, 1H), 2.76 (dt, J=25.4, 10.6 Hz, 3H), 2.44-2.26 (m, 10H), 1.88 (d, J=11.4 Hz, 2H), 1.76-1.46 (m, 2H).

Compound (128) was the second eluting enantiomer. Yield: 160 mg, 80%. LCMS m/z 502.4 $[M+H]^+$. $^1H$ NMR (400 MHz, DMSO-d6) δ 12.13 (s, 1H), 7.64 (s, 1H), 7.37 (q, J=7.3, 5.8 Hz, 2H), 7.27 (s, 1H), 6.90 (s, 1H), 3.96-3.74 (m, 3H), 3.25-3.12 (m, 2H), 3.05 (m, J=8.4 Hz, 1H), 2.76 (dt, J=24.8, 10.6 Hz, 3H), 2.44-2.25 (m, 10H), 1.97-1.75 (m, 2H), 1.63 (d, J=12.3 Hz, 2H).

Compound 129

6-[5-(3,4-difluorophenyl)-3-methyl-6-tetrahydropyran-4-yl-1H-pyrrolo[2,3-f]indazol-7-yl]spiro[3.3]heptane-2-carboxylic Acid (129)

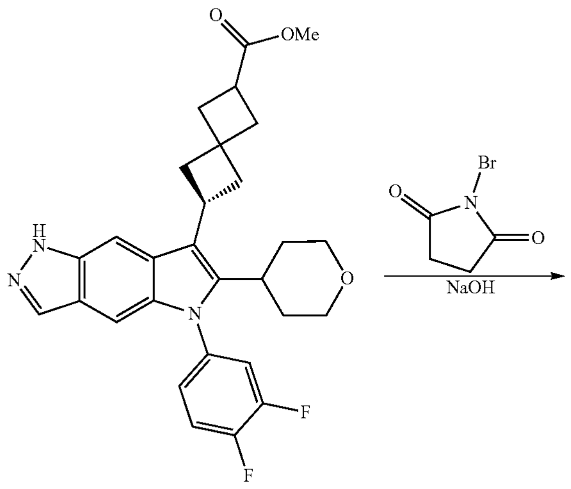

[RAC]
C114

-continued

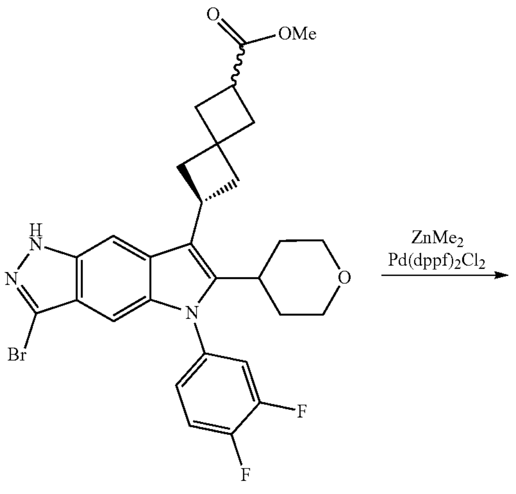

C115

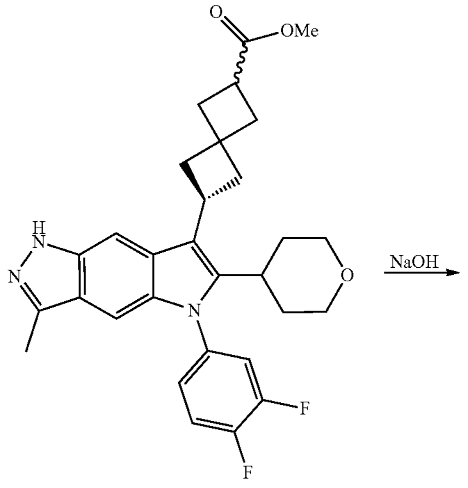

C116

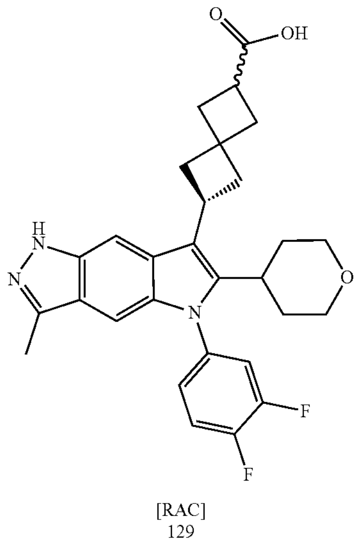

[RAC]
129

Step 1. Synthesis of methyl 6-[3-bromo-5-(3,4-difluorophenyl)-6-tetrahydropyran-4-yl-1H-pyrrolo[2,3-f]indazol-7-yl]spiro[3.3]heptane-2-carboxylate (C115)

A solution of NaOH (26 mg, 0.63 mmol) was added to a solution of methyl 6-[5-(3,4-difluorophenyl)-6-tetrahydropyran-4-yl-1H-pyrrolo[2,3-f]indazol-7-yl]spiro[3.3]heptane-2-carboxylate (300 mg, 0.6 mmol) in DMF (2 mL), and the reaction was stirred at 0° C. for 10 min. A solution of N-bromosuccinimide (111 mg, 0.62 mmol) in DMF (2 mL) was added, and the reaction was stirred at 0° C. for 10 min. The mixture was quenched with a saturated solution of $NH_4Cl$ and diluted with was diluted with additional dichloromethane. The phases were separated, and the aqueous phase was extracted with further dichloromethane. The combined organic layers were dried over sodium sulfate and concentrated in vacuo. Purification by silica gel chromatography (Gradient: 0-100% EtOAc in dichloromethane) afforded the product. Yield: 251 mg, 64%. LCMS m/z 502.3 $[M+H]^+$. $^1H$ NMR (400 MHz, Chloroform-d) δ 11.11 (s, 1H), 7.78 (d, J=0.8 Hz, 1H), 7.43-7.32 (m, 1H), 7.20-7.04 (m, 2H), 6.94-6.89 (m, 1H), 4.05-3.84 (m, 3H), 3.69 (s, 3H), 3.31 (td, J=11.7, 5.5 Hz, 2H), 3.19-3.05 (m, 1H), 2.85-2.75 (m, 3H), 2.56-2.32 (m, 6H), 2.12-1.97 (m, 2H), 1.66-1.58 (m, 2H).

Step 2. methyl 6-[5-(3,4-difluorophenyl)-3-methyl-6-tetrahydropyran-4-yl-1H-pyrrolo[2,3-f]indazol-7-yl]spiro[3.3]heptane-2-carboxylate (C116)

Compound C116 was prepared from C115 as for compound C10 in Preparation S5. Yield: 24 mg, 69%. LCMS m/z 520.5 $[M+1]^+$.

Step 3. 6-[5-(3,4-difluorophenyl)-3-methyl-6-tetrahydropyran-4-yl-1H-pyrrolo[2,3-f]indazol-7-yl]spiro[3.3]heptane-2-carboxylic Acid (129)

Compound 129 was prepared from C116 using sodium hydroxide to affect ester hydrolysis as described for compound 56. 9.8 mg, 41%. LCMS m/z 506.3 $[M+1]^+$. $^1H$ NMR (400 MHz, DMSO-d6) δ 12.19 (s, 1H), 7.74-7.62 (m, 3H), 7.34-7.27 (m, 1H), 7.00 (s, 1H), 3.95-3.81 (m, 3H), 3.29-3.15 (m, 2H), 3.11-2.99 (m, 1H), 2.85-2.67 (m, 3H), 2.55-2.45 (m, 2H, overlap DMSO), 2.42-2.30 (m, 7H), 1.96-1.79 (m, 2H), 1.74-1.58 (m, 2H).

Compound 130

6-[3-chloro-5-(3,4-difluorophenyl)-6-tetrahydropyran-4-yl-1H-pyrrolo[2,3-f]indazol-7-yl]spiro[3.3]heptane-2-carboxylic Acid (130)

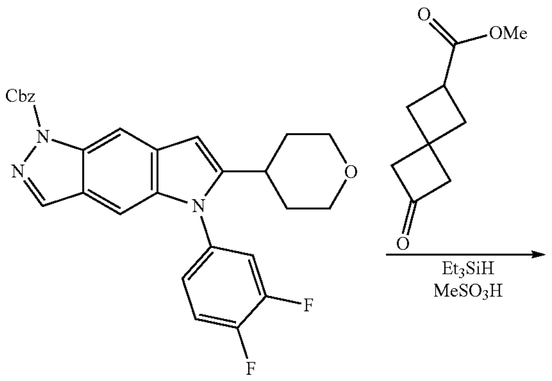

S10

-continued

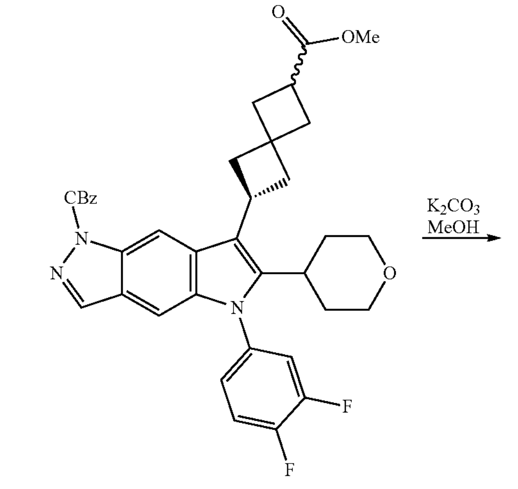

C117

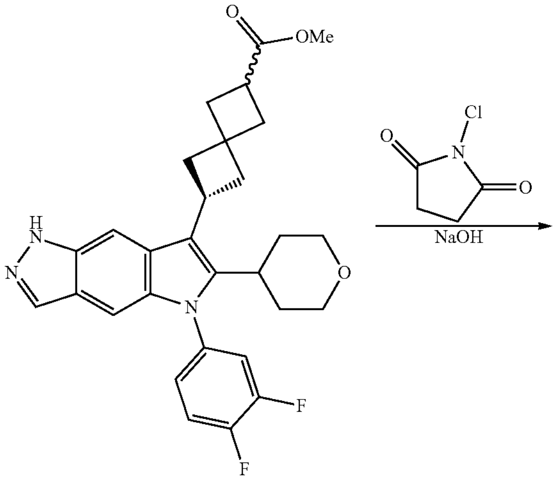

C118

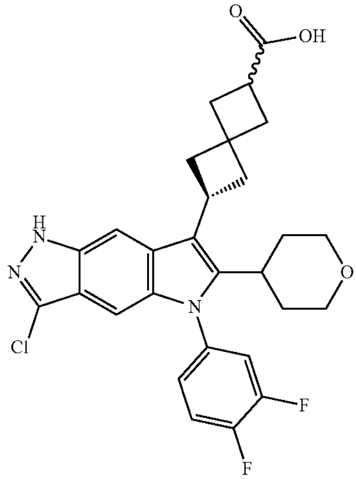

[RAC]
130

Step 1. Synthesis of benzyl 5-(3,4-difluorophenyl)-7-(2-methoxycarbonylspiro[3.3]heptan-6-yl)-6-tetrahydropyran-4-yl-pyrrolo[2,3-f]indazole-1-carboxylate (C117)

Compound C117 was prepared from S10 using the reductive coupling method as described for compound 34. Yield: 990 mg, 81%. LCMS m/z 640.5 $[M+1]^+$.

Step 2. 6-[5-(3,4-difluorophenyl)-6-tetrahydropyran-4-yl-1H-pyrrolo[2,3-f]indazol-7-yl]spiro[3.3]heptane-2-carboxylate (C118)

To a solution of benzyl 5-(3,4-difluorophenyl)-7-(2-methoxycarbonylspiro[3.3]heptan-6-yl)-6-tetrahydropyran-4-yl-pyrrolo[2,3-f]indazole-1-carboxylate C117 (4.3 g, 5.9 mmol) in methanol (19.3 mL) and dichloromethane (19.3 mL) was added potassium carbonate (1.2 g, 8.8 mmol). The reaction was stirred for 5 min at room temperature, diluted with an excess of dichloromethane and quenched with HCl (2.0 mL of 6 M, 12 mmol). The phases were separated, and the aqueous phase was extracted with dichloromethane (×2). The combined organic layers were dried over sodium sulfate and concentrated in vacuo. Purification by silica gel chromatography (Gradient: 0-100% EtOAc in dichloromethane. Yield: 2.7 g, 87%. LCMS 506.5 $[M+1]^+$. $^1H$ NMR (400 MHz, Chloroform-d) δ 9.85 (s, 1H), 8.01 (d, J=1.0 Hz, 1H), 7.77 (t, J=1.1 Hz, 1H), 7.41-7.31 (m, 1H), 7.20-7.14 (m, 1H), 7.12 (d, J=1.1 Hz, 1H), 7.10-7.05 (m, 1H), 4.02 (dd, J=11.6, 4.2 Hz, 2H), 3.94 (m, J=9.3 Hz, 1H), 3.72 (s, 3H), 3.38-3.27 (m, 2H), 3.15 (m, J=8.5 Hz, 1H), 2.93-2.78 (m, 3H), 2.58-2.48 (m, 4H), 2.47-2.37 (m, 2H), 2.13-2.01 (m, 2H), 1.64 (d, J=13.4 Hz, 2H).

Step 3. Synthesis of 6-[3-chloro-5-(3,4-difluorophenyl)-6-tetrahydropyran-4-yl-1H-pyrrolo[2,3-f]indazol-7-yl]spiro[3.3]heptane-2-carboxylic Acid (130)

To a solution of methyl 6-[5-(3,4-difluorophenyl)-6-tetrahydropyran-4-yl-1H-pyrrolo[2,3-f]indazol-7-yl]spiro[3.3]heptane-2-carboxylate C118 (30 mg, 0.06 mmol) in DMF (212 μL) was added NaOH (4 mg, 0.1 mmol). The reaction was stirred at 0° C. for 10 min and a solution of N-chlorosuccinimide (9 mg, 0.07 mmol) in DMF (212 μL) was added. The reaction was stirred at 0° C. for 10 min, then quenched with MeOH (212 μL), THF (212 μL) and NaOH (178 μL of 2 M, 0.4 mmol). The reaction was warmed to room temperature and stirred overnight. The mixture was quenched with HCl (69 μL of 6 M, 0.4 mmol) and was diluted with an excess of dichloromethane. The phases were separated, and the aqueous phase was extracted twice with dichloromethane. The combined organic layers were dried over sodium sulfate and concentrated in vacuo. Purification by chromatography afforded the product. Yield: 4.2 mg, 13%. LCMS 526.4 $[M+H]^+$. $^1H$ NMR (400 MHz, DMSO-d6) δ 12.83 (s, 1H), 12.11 (s, 1H), 7.78-7.63 (m, 3H), 7.38-7.30 (m, 1H), 6.89 (s, 1H), 3.95-3.81 (m, 4H), 3.28-3.16 (m, 2H), 3.11-2.98 (m, 1H), 2.86-2.64 (m, 4H), 2.43-2.30 (m, 4H), 1.94-1.79 (m, 2H), 1.72-1.60 (m, 2H).

Compound 131 and Compound 132
6-[5-(3,4-difluorophenyl)-8-methyl-6-tetrahydropyran-4-yl-1H-pyrrolo[2,3-f]indazol-7-yl]spiro[3.3]heptane-2-carboxylic acid (131) and 2-[5-(3,4-difluorophenyl)-8-methyl-6-tetrahydropyran-4-yl-1H-pyrrolo[2,3-f]indazol-7-yl]spiro[3.3]hept-2-ene-6-carboxylic Acid (132)
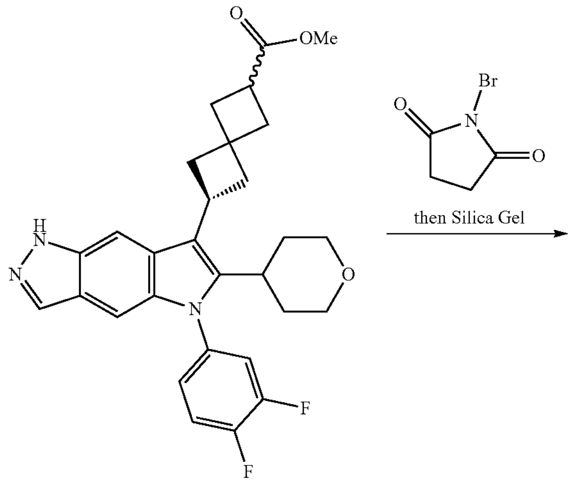
C118
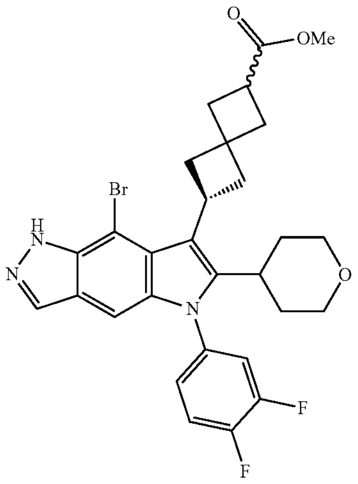
C119
+
-continued
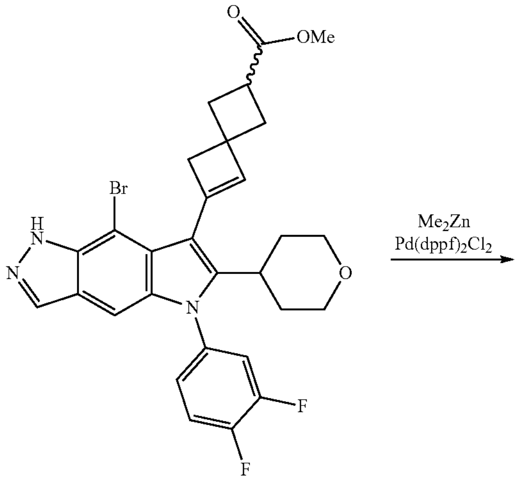
C120
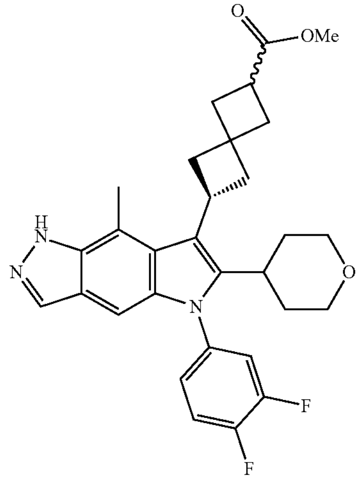
C121
+
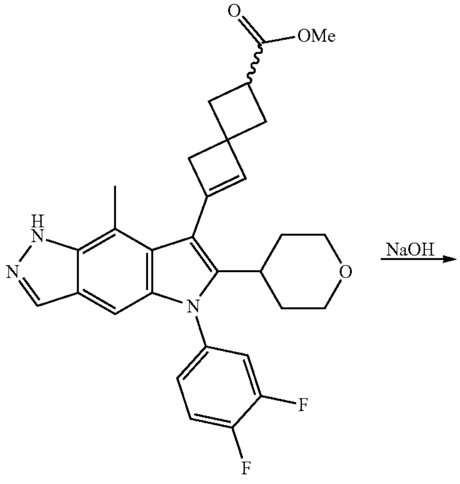
C122

-continued

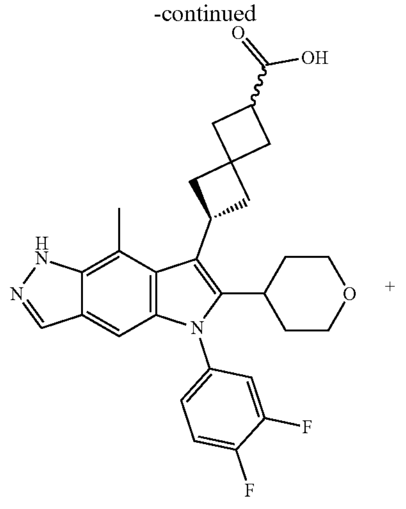

[RAC]
131

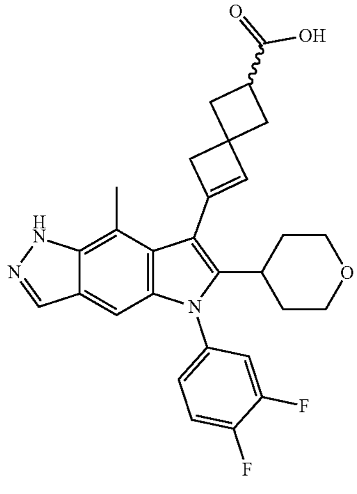

[RAC]
132

Step 1. Synthesis of methyl 6-[8-bromo-5-(3,4-difluorophenyl)-6-tetrahydropyran-4-yl-1H-pyrrolo[2,3-f]indazol-7-yl]spiro[3.3]heptane-2-carboxylate (C119) and methyl 2-[8-bromo-5-(3,4-difluorophenyl)-6-tetrahydropyran-4-yl-1H-pyrrolo[2,3-f]indazol-7-yl]spiro[3.3]hept-2-ene-6-carboxylate (C120)

N-bromosuccinimide (58 mg, 0.3 mmol) was added to a solution of methyl 6-[5-(3,4-difluorophenyl)-6-tetrahydropyran-4-yl-1H-pyrrolo[2,3-f]indazol-7-yl]spiro[3.3]heptane-2-carboxylate C118 (158 mg, 0.3 mmol) in dichloromethane (1 mL). An additional portion of N-bromosuccimide (28 mg, 0.16 mmol) was added. The reaction mixture was purified directly by silica gel chromatography (Gradient: 0-100% EtOAc in dichloromethane) giving to afford a 2:1 inseparable mixture of C119. Yield: 30 mg, 13%. LCMS m/z 584.2 $[M+H]^+$, and C120 Yield: 8 mg, 4%. LCMS m/z 583.0 $[M+H]^+$. Note: C118 racemic and is prepared as described for compounds 67 and 68 in Table 3.

Step 2. Synthesis of methyl 6-[5-(3,4-difluorophenyl)-8-methyl-6-tetrahydropyran-4-yl-1H-pyrrolo[2,3-f]indazol-7-yl]spiro[3.3]heptane-2-carboxylate (C121) and methyl 2-[5-(3,4-difluorophenyl)-8-methyl-6-tetrahydropyran-4-yl-1H-pyrrolo[2,3-f]indazol-7-yl]spiro[3.3]hept-2-ene-6-carboxylate (C122)

The inseparable mixture of compound C119 and compound 120 was converted into a mixture of C121 and C122 using the method described for preparation of compound 49. Purification by silica gel chromatography (Gradient: 0-100% dichloromethane in EtOAc) gave a 1.5:1 inseparable mixture of C121 Yield: 13 mg, 36%. LCMS m/z 520.5 $[M+1]^+$ and C122. Yield: 7 mg, 21%. LCMS m/z 518.0 $[M+1]^+$.

Step 3. Synthesis of 6-[5-(3,4-difluorophenyl)-8-methyl-6-tetrahydropyran-4-yl-M-pyrrolo[2,3-f]indazol-7-yl]spiro[3.3]heptane-2-carboxylic acid (131) and 2-[5-(3,4-difluorophenyl)-8-methyl-6-tetrahydropyran-4-yl-1H-pyrrolo[2,3-f]indazol-7-yl]spiro[3.3]hept-2-ene-6-carboxylic Acid (132)

Compounds 131 and 132 were prepared from hydrolysis of the mixture of C119 and C120 using sodium hydroxide as described for previous examples (e.g., compound 56). The products were separated using reverse-phase chromatography (Column: C18 Waters Sunfire column, 30×150 mm, 5 micron, Mobile Phase: acetonitrile in water with 0.1% TFA modifier) to afford compound 131. Yield: 6.2 mg, 31%. LCMS m/z 506.5 $[M+H]^+$. $^1$H NMR (400 MHz, DMSO-d6) δ 12.64 (s, 1H), 7.90 (s, 1H), 7.74-7.63 (m, 2H), 7.33-7.27 (m, 1H), 6.70 (s, 1H), 4.27-4.14 (m, 1H), 3.91-3.81 (m, 3H), 3.30-3.22 (m, 2H), 3.11-2.96 (m, 1H), 2.88 (s, 3H), 2.72-2.63 (m, 1H), 2.50-2.23 (m, 7H), 1.79-1.59 (m, 4H).

Compound 132: Yield: 3.7 mg, 19%. LCMS m/z 504.5 $[M+H]^+$. $^1$H NMR (400 MHz, DMSO-d6) δ 12.70 (s, 1H), 12.04 (s, 1H), 7.95 (s, 1H), 7.77-7.50 (m, 2H), 7.24 (s, 1H), 7.11 (s, 1H), 5.98 (s, 1H), 4.14 (s, 2H), 4.01-3.78 (m, 1H), 3.52 (s, 2H), 3.02-2.92 (m, 1H), 2.84 (s, 3H), 2.60-2.55 (m, 1H), 2.46-1.84 (m, 9H).

Example 133 and Example 134
6-[8-cyano-5-(3,4-difluorophenyl)-6-tetrahydropyran-4-yl-1H-pyrrolo[2,3-f]indazol-7-yl]spiro[3.3]heptane-2-carboxylic acid (133) and 6-[8-bromo-5-(3,4-difluorophenyl)-6-tetrahydropyran-4-yl-1H-pyrrolo[2,3-f]indazol-7-yl]spiro[3.3]heptane-2-carboxylic Acid (134)
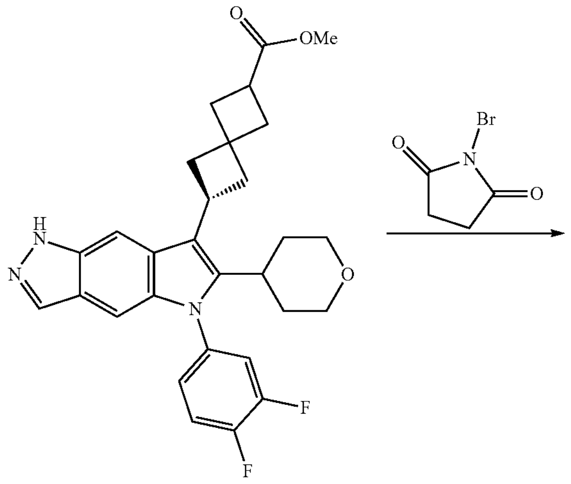
C118
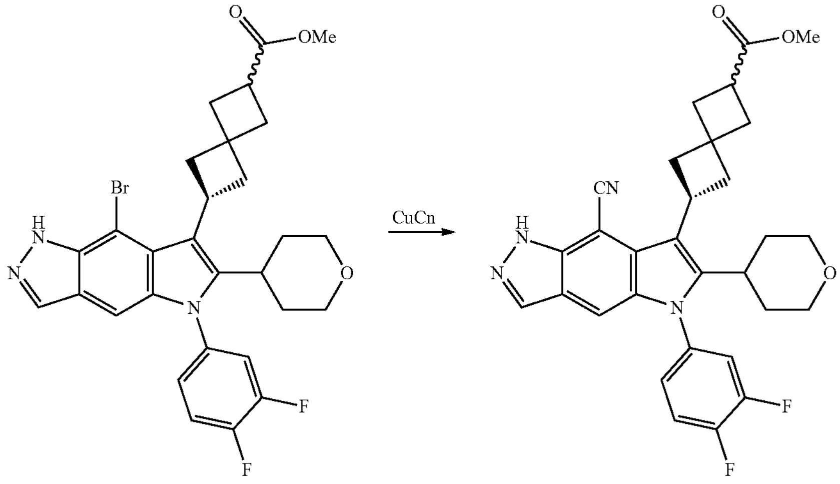
C119 C123
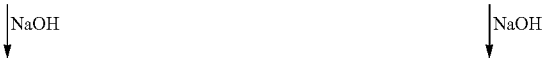

-continued

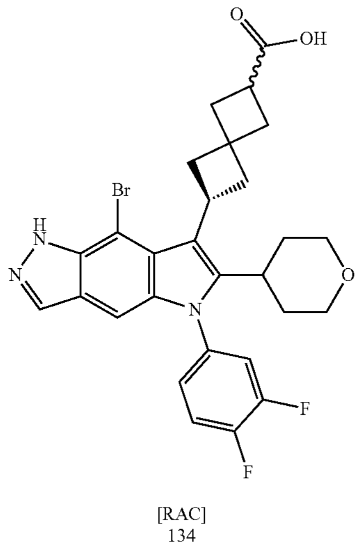

[RAC]
134

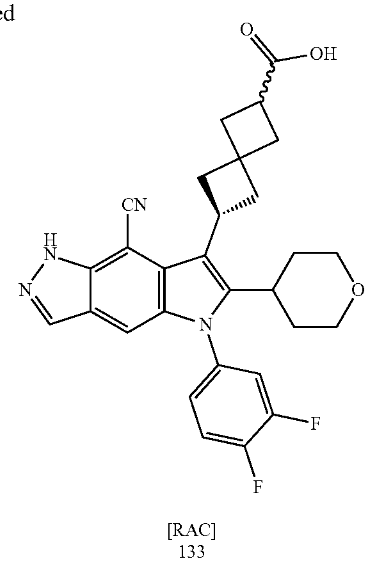

[RAC]
133

Step 1. Synthesis of methyl 6-[8-bromo-5-(3,4-difluorophenyl)-6-tetrahydropyran-4-yl-1H-pyrrolo[2,3-f]indazol-7-yl]spiro[3.3]heptane-2-carboxylate (C119)

To a solution of methyl 6-[5-(3,4-difluorophenyl)-6-tetrahydropyran-4-yl-1H-pyrrolo[2,3-f]indazol-7-yl]spiro[3.3]heptane-2-carboxylate C118 (971 mg, 1.8 mmol) in dichloromethane (12 mL) was added a solution of N-bromosuccinimide (354 mg, 1.9 mmol) in dichloromethane (12 mL). The reaction was stirred at 0° C. for 10 min, and then quenched with a saturated solution of $NH_4Cl$. The mixture was diluted with additional dichloromethane. The phases were separated and the aqueous phase was extracted with dichloromethane (×2). The combined organic layers were dried over sodium sulfate, filtered and concentrated in vacuo. Purification by silica gel cartridge (Gradient: 0-100% EtOAc in dichloromethane) afforded the product. Yield: 340 mg, 20%. LCMS m/z 584.5 $[M+H]^+$. $^1H$ NMR (400 MHz, Chloroform-d) δ 9.99 (s, 1H), 8.05 (s, 1H), 7.44-7.32 (m, 1H), 7.22-7.13 (m, 1H), 7.13-7.07 (m, 1H), 6.91 (s, 1H), 4.66-4.54 (m, 1H), 4.04-3.96 (m, 2H), 3.71 (s, 3H), 3.42-3.31 (m, 3H), 3.14 (m, 1H), 2.73-2.61 (m, 3H), 2.60-2.32 (m, 5H), 2.00-1.90 (m, 2H), 1.71-1.63 (m, 2H).

Step 2. methyl 6-[8-cyano-5-(3,4-difluorophenyl)-6-tetrahydropyran-4-yl-1H-pyrrolo[2,3-f]indazol-7-yl]spiro[3.3]heptane-2-carboxylate (C123)

To a nitrogen purged vial containing methyl 6-[8-bromo-5-(3,4-difluorophenyl)-6-tetrahydropyran-4-yl-1H-pyrrolo[2,3-f]indazol-7-yl]spiro[3.3]heptane-2-carboxylate (27 mg, 0.03 mmol) and cyanocopper (5 mg, 0.06 mmol) was added NMP (581 μL). The reaction was heated in the microwave at 200° C. for 1 h. The reaction was diluted with dichloromethane and quenched with water. The phases were separated, and the aqueous phase was extracted with dichloromethane (×2). The combined organic layers were dried over sodium sulfate, filtered and concentrated in vacuo. The crude product C123 was used directly in the next step without further purification. Yield: 14 mg, 85%. LCMS m/z 531.6 $[M+H]^+$.

Step 3. Synthesis of 6-[8-cyano-5-(3,4-difluorophenyl)-6-tetrahydropyran-4-yl-1H-pyrrolo[2,3-f]indazol-7-yl]spiro[3.3]heptane-2-carboxylic Acid (133)

To a solution of C132 (15 mg, 0.03 mmol) in THF (354 μL) and methanol (179 μL) was added a solution of sodium hydroxide (30 μL of 1 M, 0.03 mmol). The reaction was stirred at room temperature for 3 h. The reaction was quenched with HCl (33 μL of 6 M, 0.2 mmol) and diluted with an excess of dichloromethane. The phases were separated and the aqueous phase was extracted dichloromethane (×2). The combined organic layers were dried over sodium sulfate, and concentrated in vacuo. Purification afforded 6-[8-cyano-5-(3,4-difluorophenyl)-6-tetrahydropyran-4-yl-1H-pyrrolo[2,3-f]indazol-7-yl]spiro[3.3]heptane-2-carboxylic acid containing 0.5 of TFA. Yield: 4.2 mg, 26% $^1H$ NMR (400 MHz, Methanol-d4) δ 8.11 (s, 0.5H), 8.02 (s, 0.5H), 7.85 (s, 0.5H), 7.63-7.46 (m, 2H), 7.44 (s, 0.5H), 7.42-7.36 (m, 0.5H), 7.30-7.24 (m, 0.5H), 7.23-7.18 (m, 0.5H), 7.15 (s, 0.5H), 4.30-4.18 (m, 0.5H), 3.99 (d, J=11.6 Hz, 2.5H), 3.43-3.35 (m, 1H), 3.16-3.08 (m, 2H), 2.98-2.80 (m, 3H), 2.68-2.34 (m, 6H), 2.13-1.96 (m, 2H), 1.79-1.66 (m, 2H). LCMS m/z 517.6 $[M+H]^+$. NMR shows a 1:1 population of partially protonated product.

Synthesis of 6-[8-bromo-5-(3,4-difluorophenyl)-6-tetrahydropyran-4-yl-1H-pyrrolo[2,3-f]indazol-7-yl]spiro[3.3]heptane-2-carboxylic Acid (134)

Compound 134 was prepared from C132 as described for preparation of compound 133. 6-[8-bromo-5-(3,4-difluorophenyl)-6-tetrahydropyran-4-yl-1H-pyrrolo[2,3-f]indazol-7-yl]spiro[3.3]heptane-2-carboxylic acid Yield: 11.8 mg, 47%. LCMS m/z 570.4 $[M+H]^+$. $^1H$ NMR (400 MHz, Methanol-d4) δ 8.04 (s, 1H), 7.55 (q, J=9.3 Hz, 1H), 7.48-7.41 (m, 1H), 7.29-7.22 (m, 1H), 6.99 (s, 1H), 4.72-4.60 (m, 1H), 4.01-3.92 (m, 2H), 3.40 (t, J=11.9 Hz, 3H), 3.18-3.07 (m, 1H), 2.82-2.64 (m, 3H), 2.62-2.45 (m, 3H), 2.39 (d, J=8.5 Hz, 2H), 2.02-1.88 (m, 2H), 1.80-1.69 (m, 2H). LCMS m/z 570.4 $[M+H]^+$.

Compound 135, Compound 136, and Compound 137
6-[8-fluoro-5-(4-fluorophenyl)-6-tetrahydropyran-4-yl-1H-pyrrolo[2,3-f]indazol-7-yl]spiro[3.3]heptane-2-carboxylic acid (135), 6-[8-fluoro-5-(4-fluorophenyl)-6-tetrahydropyran-4-yl-1H-pyrrolo[2,3-f]indazol-7-yl]spiro[3.3]heptane-2-carboxylic acid, [ENANT-1] (136), and 6-[8-fluoro-5-(4-fluorophenyl)-6-tetrahydropyran-4-yl-1H-pyrrolo[2,3-f]indazol-7-yl]spiro[3.3]heptane-2-carboxylic acid, [ENANT-2](137)
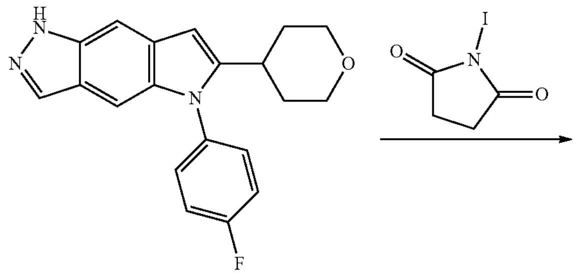
S6
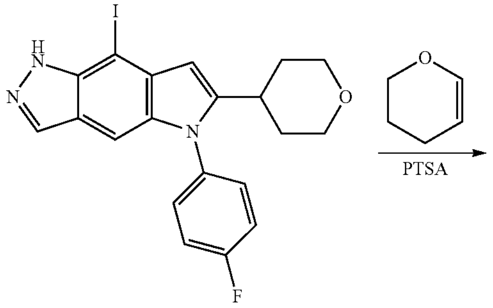
C124
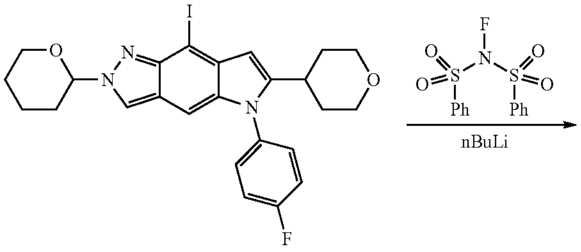
C125
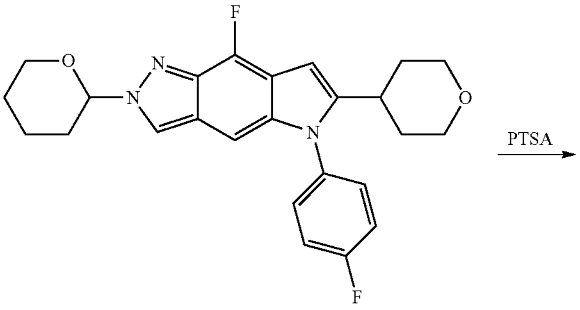
C126
-continued
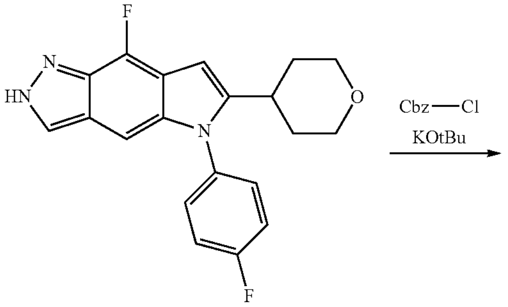
C127
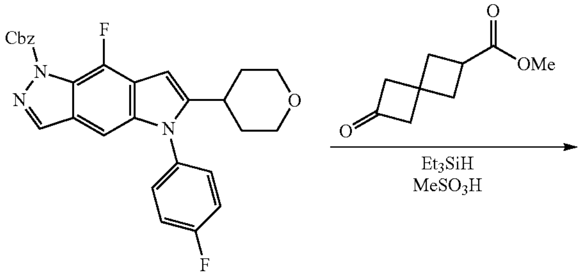
C128
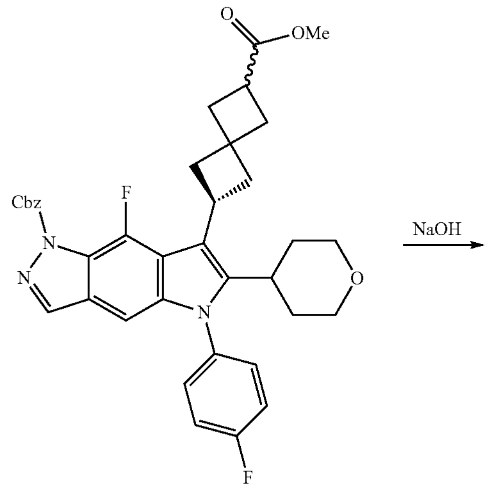
C129
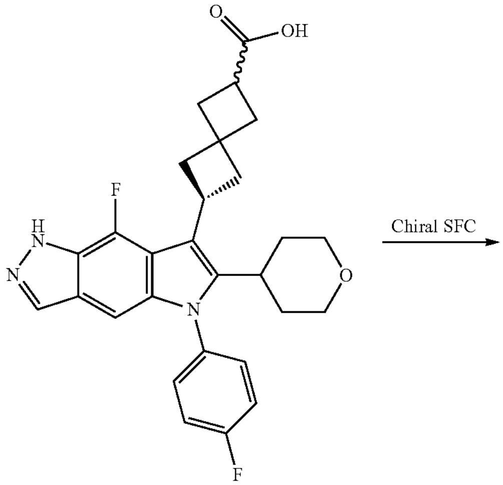
135

-continued

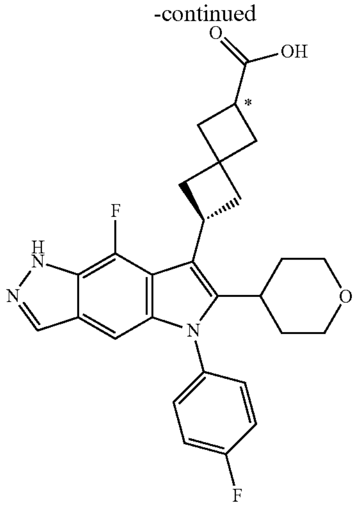

+

[ENANT-1]
136

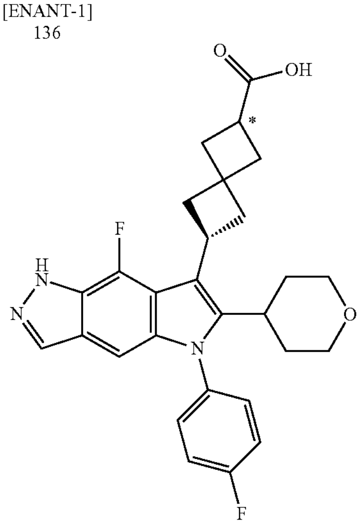

[ENANT-2]
137

Steps 1-5. Synthesis of benzyl 8-fluoro-5-(4-fluorophenyl)-6-tetrahydropyran-4-yl-pyrrolo[2,3-f]indazole-1-carboxylate (C129)

Compound C128 was prepared in five steps from compound S6 using methods described for compound 48 (for step 1) and compound 53 (for steps 2-5). Yield: 53 mg. LCMS m/z 488.2 $[M+H]^+$. $^1H$ NMR (400 MHz, Chloroform-d) δ 8.13 (s, 1H), 7.60 (d, J=7.2 Hz, 2H), 7.39 (ddd, J=22.9, 14.7, 4.1 Hz, 6H), 7.03 (s, 1H), 6.70 (s, 1H), 5.58 (s, 2H), 4.02 (d, J=11.1 Hz, 2H), 3.37 (t, J=11.7 Hz, 2H), 2.83 (s, 1H), 1.98-1.82 (m, 2H), 1.77 (d, J=13.4 Hz, 2H).

Steps 6-7. Synthesis of 6-[8-fluoro-5-(4-fluorophenyl)-6-tetrahydropyran-4-yl-1H-pyrrolo[2,3-f]indazol-7-yl]spiro[3.3]heptane-2-carboxylic Acid (135)

Compound 135 was prepared in two steps from C128 using the same method described for compound 34 to afford racemic 6-[8-fluoro-5-(4-fluorophenyl)-6-tetrahydropyran-4-yl-1H-pyrrolo[2,3-f]indazol-7-yl]spiro[3.3]heptane-2-carboxylic acid. Yield: 138.5 mg. LCMS m/z 492.4 $[M+H]^+$. $^1H$ NMR (400 MHz, DMSO) δ 13.10 (s, 1H), 12.07 (s, 1H), 8.04 (d, J=3.2 Hz, 1H), 7.60-7.32 (m, 4H), 6.84 (s, 1H), 4.10-3.71 (m, 3H), 3.19 (t, J=11.5 Hz, 2H), 3.02 (m, J=8.3 Hz, 1H), 2.80 (dq, J=12.6, 6.4, 4.5 Hz, 1H), 2.45-2.15 (m, 4H), 1.92 (ddt, J=19.4, 13.7, 7.5 Hz, 2H), 1.65 (d, J=12.8 Hz, 2H).

Step 8. Preparation of 6-[8-fluoro-5-(4-fluorophenyl)-6-tetrahydropyran-4-yl-1H-pyrrolo[2,3-f]indazol-7-yl]spiro[3.3]heptane-2-carboxylic acid, [ENANT-1] (136) and 6-[8-fluoro-5-(4-fluorophenyl)-6-tetrahydropyran-4-yl-1H-pyrrolo[2,3-f]indazol-7-yl]spiro[3.3]heptane-2-carboxylic acid [ENANT-2] (137)

Racemic compound 135 was separated into its enantiomers by chiral SFC separation. Column: Phenomenex Cellulose-2, 20×250 mm Mobile phase: 40% MeOH (5 mM Ammonia), 60% $CO_2$. Flow: 75 mL/min.

Compound 136 [ENANT-1] was the first eluting enantiomer. Yield: 63.2 mg. $^1H$ NMR (400 MHz, DMSO-d6) δ 13.23-12.59 (m, 1H), 8.04 (d, J=3.2 Hz, 1H), 7.47 (m, J=8.7 Hz, 4H), 6.84 (s, 1H), 4.11-3.74 (m, 3H), 3.23-3.09 (m, 2H), 2.99 (m, J=8.4 Hz, 1H), 2.80 (t, J=12.7 Hz, 1H), 2.42-2.18 (m, 4H), 1.91 (dt, J=18.9, 8.6 Hz, 2H), 1.65 (d, J=13.0 Hz, 2H). LCMS m/z 492.4 $[M+H]^+$.

Compound 137 [ENANT-2] was the second eluting enantiomer. Yield: 58.9 mg. $^1H$ NMR (300 MHz, DMSO-d6) δ 13.06 (s, 1H), 8.03 (d, J=3.5 Hz, 1H), 7.47 (td, J=5.7, 5.2, 3.1 Hz, 4H), 6.83 (s, 1H), 4.11-3.70 (m, 3H), 3.26-3.13 (m, 2H), 2.99 (m, J=8.1 Hz, 1H), 2.81 (t, J=12.2 Hz, 1H), 2.44-2.17 (m, 2H), 1.91 (q, J=12.7, 11.5 Hz, 2H), 1.64 (d, J=12.8 Hz, 2H). LCMS m/z 492.46 $[M+H]^+$.

Compound 138 and Compound 139

5-(4-fluoro-3-methyl-phenyl)-6-(3-methyloxetan-3-yl)-1H-pyrrolo[2,3-f]indazole (138) and 5-(4-fluoro-3-methyl-phenyl)-6-(3-methyloxetan-3-yl)-7-methylsulfonyl-1H-pyrrolo[2,3-f]indazole (139)

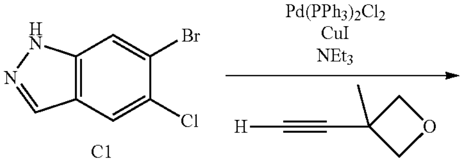

C1

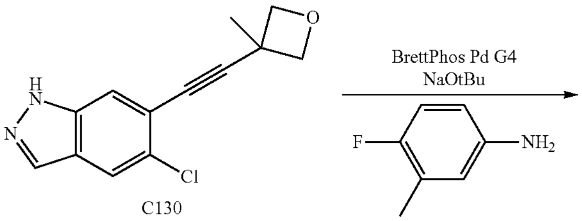

C130

-continued

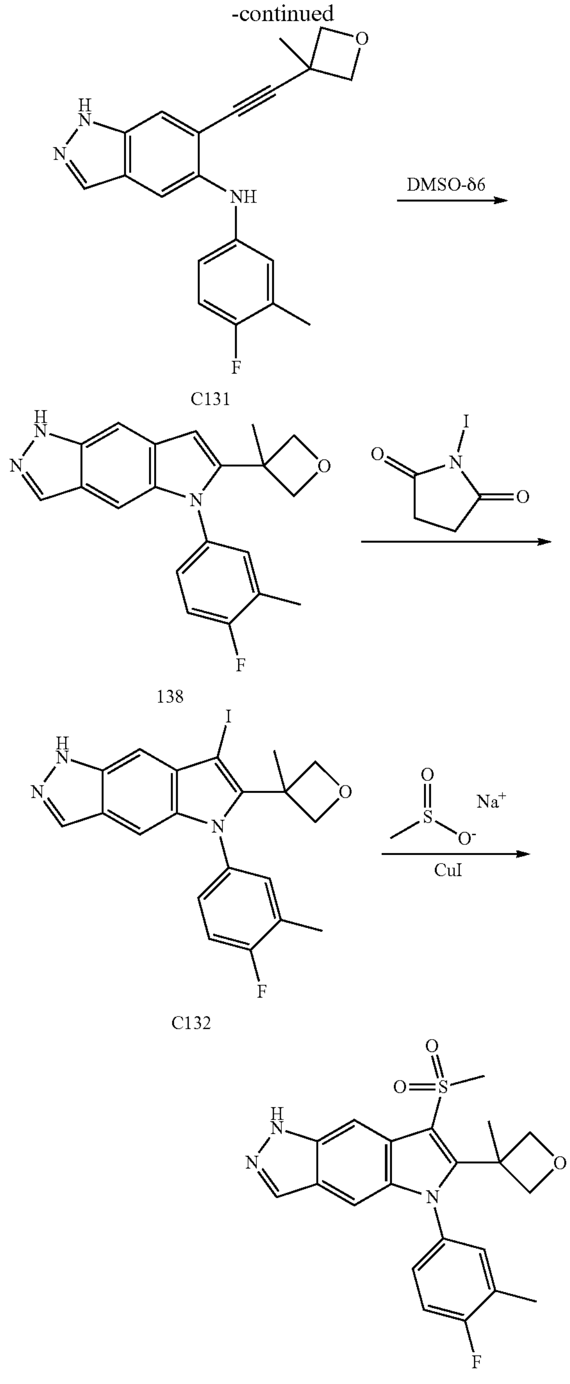

C131

138

C132

139

Steps 1-3. Synthesis of 5-(4-fluoro-3-methyl-phenyl)-6-(3-methyloxetan-3-yl)-1H-pyrrolo[2,3-f]indazole (138)

Compound 138 was prepared from C1 in three steps using a method analogous to that described for in Preparation S1. Yield: 167 mg. LCMS m/z 336.2 $[M+H]^+$. $^1H$ NMR (300 MHz, DMSO-d6) δ 12.63 (s, 1H), 7.97 (t, J=1.3 Hz, 1H), 7.57 (t, J=1.1 Hz, 1H), 7.47-7.22 (m, 3H), 7.07 (s, 1H), 6.50 (d, J=0.8 Hz, 1H), 5.03 (d, J=5.6 Hz, 2H), 4.15 (d, J=5.5 Hz, 2H), 2.31 (d, J=2.0 Hz, 3H), 1.53 (s, 3H).

Steps 4-6. Synthesis of 5-(4-fluoro-3-methyl-phenyl)-6-(3-methyloxetan-3-yl)-7-methylsulfonyl-1H-pyrrolo[2,3-f]indazole (139)

Compound 138 was converted to 139 in two steps using the methods described for compound 1 and Compound 11. Yield: 19.8 mg. LCMS m/z 414.2 $[M+1]^+$. $^1H$ NMR (300 MHz, DMSO-d6) δ 12.92 (s, 1H), 8.08 (t, J=1.2 Hz, 1H), 7.89 (t, J=1.1 Hz, 1H), 7.56 (d, J=31.2 Hz, 2H), 7.42 (t, J=8.9 Hz, 1H), 7.20 (d, J=0.8 Hz, 1H), 4.86 (s, 2H), 3.32-3.28 (m, 5H), 2.34 (d, J=1.8 Hz, 3H), 1.99 (s, 3H).

Compound 140, Compound 141, and Compound 142

6-[5-(4-fluorophenyl)-6-tetrahydrofuran-3-yl-1H-pyrrolo[2,3-f]indazol-7-yl]spiro[3.3]heptane-2-carboxylic acid (140), 6-[5-(4-fluorophenyl)-6-tetrahydrofuran-3-yl-1H-pyrrolo[2,3-f]indazol-7-yl]spiro[3.3]heptane-2-carboxylic acid (141), and 6-[5-(4-fluorophenyl)-6-tetrahydrofuran-3-yl-1H-pyrrolo[2,3-f]indazol-7-yl]spiro[3.3]heptane-2-carboxylic Acid (142)

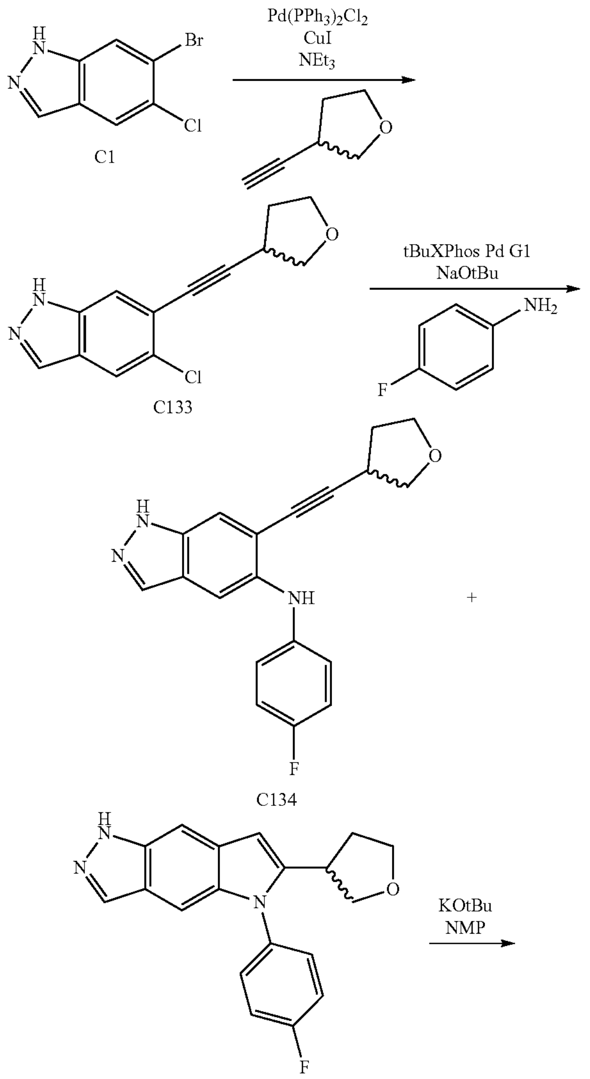

C1

C133

C134

+

C135

-continued

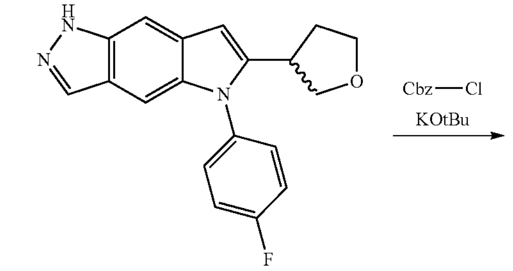

C135

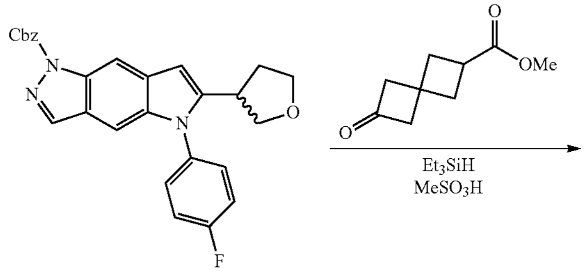

C136

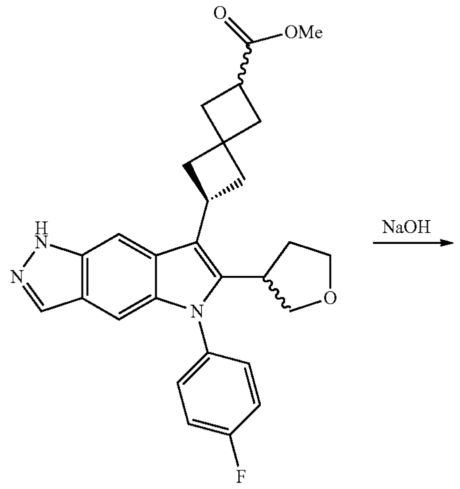

C137

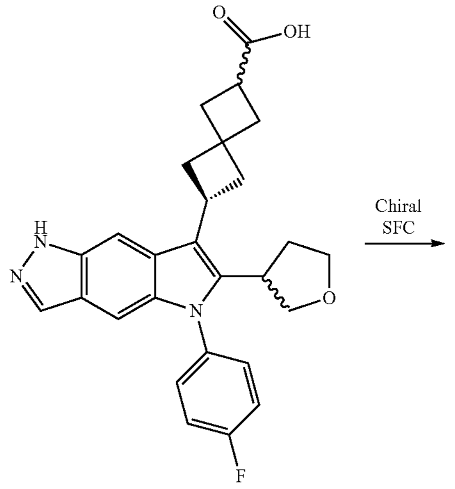

140

-continued

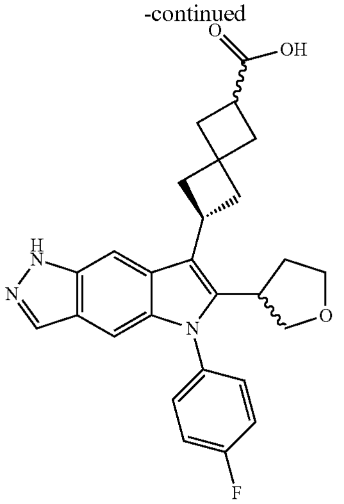

+

[DIAST MIX-1]
141

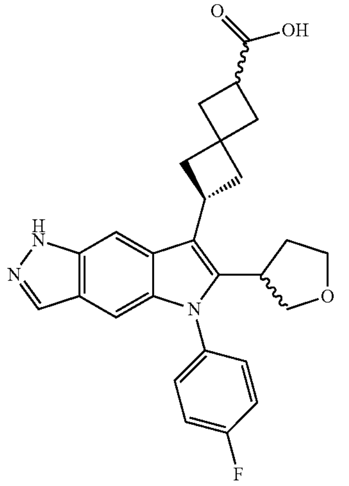

[DIAST MIX-2]
142

Steps 1-4. benzyl 5-(4-fluorophenyl)-6-tetrahydrofuran-3-yl-pyrrolo[2,3-f]indazole-1-carboxylate (C136)

Compound C136 was prepared from C1 using the methods described in Preparation S1 and S2. In this case, NMP solvent and base KOtBu was used in the cyclization of C134 into C135. LCMS m/z 456.3 $[M+H]^+$. $^1H$ NMR (400 MHz, Chloroform-d) δ 8.40 (s, 1H), 8.15 (s, 1H), 7.60 (d, J=7.3 Hz, 2H), 7.47-7.30 (m, 6H), 7.24 (s, 1H), 6.63 (s, 1H), 5.59 (s, 2H), 4.05 (td, J=8.2, 5.1 Hz, 1H), 3.97 (t, J=7.9 Hz, 1H), 3.88 (q, J=7.7 Hz, 1H), 3.81 (t, J=7.8 Hz, 1H), 3.40 (m, J=7.7 Hz, 1H), 2.30-2.06 (m, 2H).

Steps 5-6. Synthesis of 6-[5-(4-fluorophenyl)-6-tetrahydrofuran-3-yl-1H-pyrrolo[2,3-f]indazol-7-yl]spiro[3.3]heptane-2-carboxylic Acid (140)

Compound 140 was prepared from C136 in two steps as described for Compound 34. LCMS m/z 460.3 $[M+H]^+$. $^1H$ NMR (400 MHz, Methanol-d4) δ 8.07 (s, 1H), 7.89 (s, 1H), 7.48-7.33 (m, 4H), 7.20 (s, 1H), 4.17-4.05 (m, 1H), 4.04-3.87 (m, 3H), 3.83-3.69 (m, 1H), 3.42 (t, J=8.6 Hz, 1H), 3.23-3.10 (m, 1H), 3.03-2.86 (m, 2H), 2.64-2.45 (m, 5H), 2.43-2.26 (m, 2H), 2.24-2.08 (m, 1H).

Step 7. Preparation of 6-[5-(4-fluorophenyl)-6-tetrahydrofuran-3-yl-1H-pyrrolo[2,3-f]indazol-7-yl]spiro[3.3]heptane-2-carboxylic acid (141) and 6-[5-(4-fluorophenyl)-6-tetrahydrofuran-3-yl-1H-pyrrolo[2,3-f]indazol-7-yl]spiro[3.3]heptane-2-carboxylic Acid (142)

Compound 140 (30 mg, 0.07 mmol) is a mixture containing up to four possible diastereomers. C140 was separated by chiral SFC into two mixtures which may each be composed of a sets of two disastereomers. Column: Phenomenex Cellulose-2, 20×250 mm Mobile phase: 40% MeOH (5 mM Ammonia), 60% $CO_2$. Flow: 75 mL/min. The relative and absolute stereochemistry of these pairs is unknown.

The first eluting peak was compound 141 [DIAST MIX-1]. 9.3 mg, 27%. LCMS m/z 460.36 $[M+H]^+$. $^1$H NMR (400 MHz, Methanol-d4) δ 7.96 (s, 1H), 7.89 (s, 1H), 7.42-7.32 (m, 4H), 7.15 (s, 1H), 4.08 (td, J=8.4, 3.4 Hz, 1H), 4.01-3.87 (m, 3H), 3.75 (q, J=8.4 Hz, 1H), 3.40 (m, J=9.6, 9.2 Hz, 1H), 3.17-3.03 (m, 1H), 2.92 (dtd, J=26.0, 12.1, 11.3, 4.0 Hz, 2H), 2.58-2.40 (m, 5H), 2.40-2.24 (m, 2H), 2.15 (tt, J=13.1, 8.4 Hz, 1H).

The second eluting peak was compound 142 [DIAST MIX-2]. 9.5 mg, 27%. LCMS m/z 459.95 $[M+H]^+$. $^1$H NMR (400 MHz, Methanol-d4) δ 7.98 (s, 1H), 7.88 (s, 1H), 7.43-7.32 (m, 5H), 7.15 (s, 1H), 4.08 (td, J=8.4, 3.4 Hz, 1H), 4.01-3.86 (m, 3H), 3.75 (q, J=8.7 Hz, 1H), 3.45-3.36 (m, 1H), 3.16-3.04 (m, 1H), 2.92 (dtd, J=26.2, 11.8, 11.2, 3.8 Hz, 2H), 2.58-2.42 (m, 5H), 2.39-2.24 (m, 2H), 2.22-2.10 (m, 1H).

Compound 143

6-tert-butyl-5-(4-fluorophenyl)-1H-pyrrolo[2,3-f]indazole-7-carbonitrile (143)

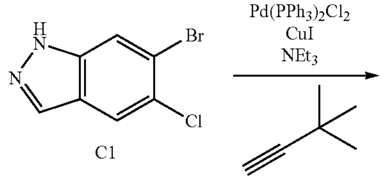

C1

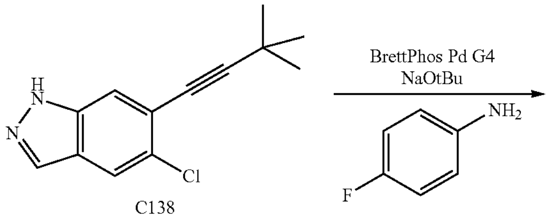

C138

-continued

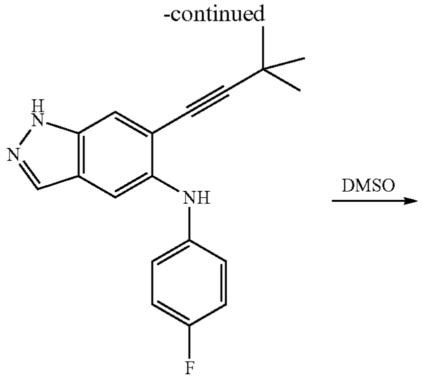

C139

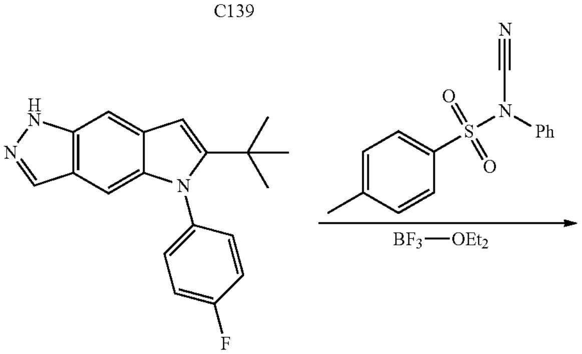

C140

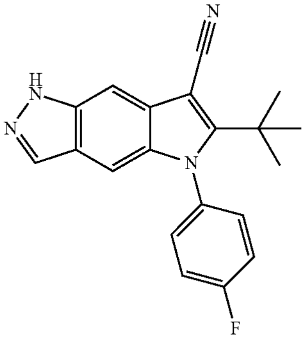

143

Step 1. Synthesis of 5-chloro-6-(3,3-dimethylbut-1-ynyl)-1H-indazole (C138)

$Pd(PPh_3)_2Cl_2$ (174 mg, 0.25 mmol) was added to a nitrogen purged solution of 3,3-dimethylbut-1-yne (1.4 mL, 11.7 mmol), 6-bromo-5-chloro-1H-indazole C1 (1.1 g, 4.6 mmol) and CuI (53 mg, 0.28 mmol) in $Et_3N$ (10 mL) and 1,4-dioxane (10 mL). The solution was stirred at 110° C. for 30 min Celite® and methanol were added and the mixture concentrated in vacuo. Silica gel chromatography (Gradient: 0-100% EtOAc in heptanes) afforded the product. Yield: 811 mg, 72%. LCMS m/z 233.2 $[M+H]^+$. $^1$H NMR (300 MHz, DMSO-d6) δ 13.29 (s, 1H), 8.06 (dd, J=1.6, 1.1 Hz, 1H), 7.97-7.91 (m, 1H), 7.65 (t, J=0.9 Hz, 1H), 1.33 (s, 9H).

Step 2. Synthesis of 6-(3,3-dimethylbut-1-ynyl)-N-(4-fluorophenyl)-1H-indazol-5-amine (C139)

Compound C139 was prepared from 5-chloro-6-(3,3-dimethylbut-1-ynyl)-1H-indazole C138 using the method described in preparation S1. Yield: 861 mg, 82%. LCMS m/z 308.22 [M+H]$^+$. $^1$H NMR (300 MHz, DMSO-d6) δ 12.97 (s, 1H), 7.99-7.91 (m, 1H), 7.51 (t, J=0.9 Hz, 1H), 7.44 (s, 1H), 7.31 (s, 1H), 7.07-6.94 (m, 2H), 6.89-6.76 (m, 2H), 1.15 (s, 9H).

Step 3. Synthesis of 6-tert-butyl-5-(4-fluorophenyl)-1H-pyrrolo[2,3-f]indazole (C140)

A solution of 6-(3,3-dimethylbut-1-ynyl)-N-(4-fluorophenyl)-1H-indazol-5-amine C139 (858 mg, 2.8 mmol) was dissolved in DMSO (4 mL) and the mixture heated under microwave conditions at 150° C. for 5 h. The mixture was diluted with EtOAc (75 mL) and washed with 50% saturated sodium bicarbonate. The organic layer was passed through a phase separator containing sodium sulfate, and then concentrated to in vacuo to afford the product, which was used in the subsequent step without further purification. Yield: 861 mg, 100%. LCMS 308.25 [M+H]$^+$. $^1$H NMR (300 MHz, DMSO-d6) δ 12.57 (s, 1H), 7.94-7.90 (m, 1H), 7.54-7.38 (m, 5H), 6.76 (s, 1H), 6.49 (d, J=0.8 Hz, 1H), 1.24 (s, 9H).

Step 4. 6-tert-butyl-5-(4-fluorophenyl)-1H-pyrrolo[2,3-f]indazole-7-carbonitrile (143)

Compound C140 was converted into compound 143 using the method described for compound 10. Yield: 4.2 mg, 4%. LCMS m/z 333.2 [M+H]$^+$. $^1$H NMR (300 MHz, DMSO-d6) δ 12.89 (s, 1H), 8.07 (t, J=1.3 Hz, 1H), 7.69-7.62 (m, 2H), 7.57 (t, J=1.1 Hz, 1H), 7.54-7.46 (m, 2H), 6.97 (t, J=0.9 Hz, 1H), 1.39 (s, 9H).

Compound 108 (Alternative Preparation)

Alternative Preparation of 6-(5-(4-fluorophenyl)-6-(tetrahydro-2H-pyran-4-yl)-1,5-dihydropyrrolo[2,3-f]indazol-7-yl)spiro[3.3]heptane-2-carboxylic Acid (108)

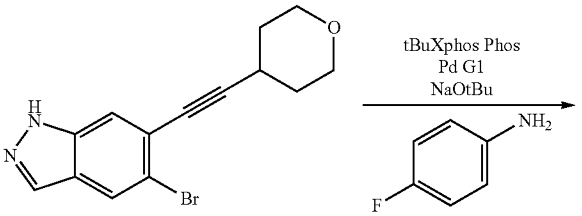

C106

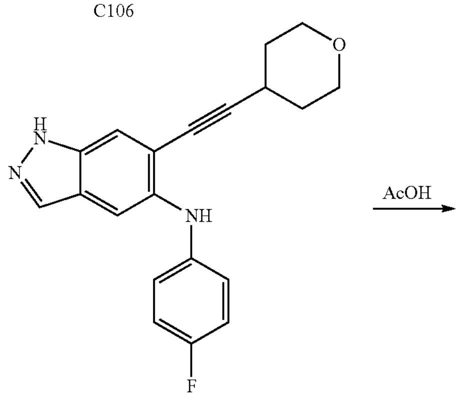

C15

-continued

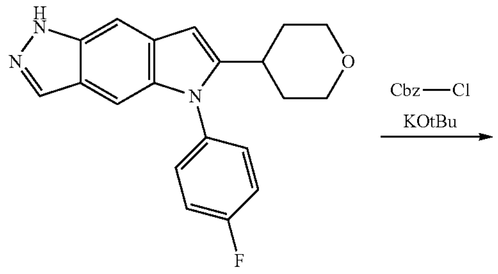

S6

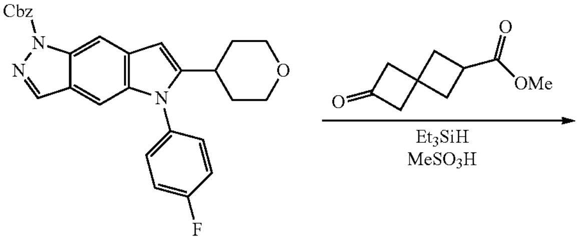

S7

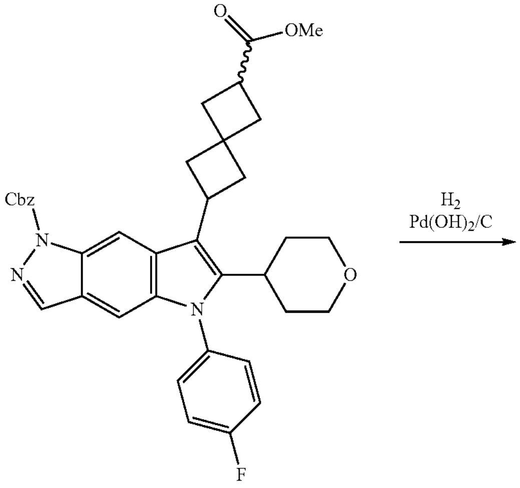

C141

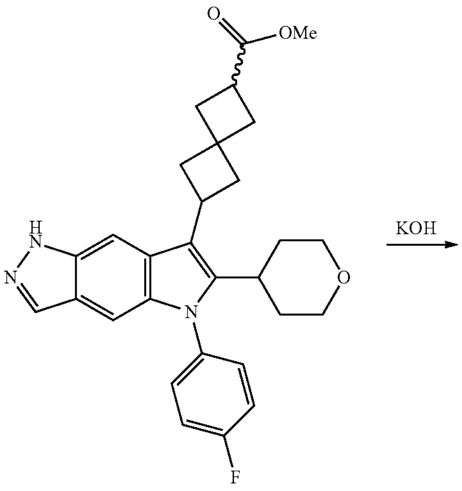

C142

-continued

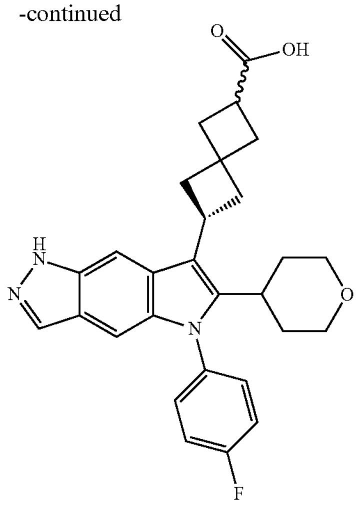

108

Step 1 and 2. Synthesis of 5-(4-fluorophenyl)-6-(tetrahydro-2H-pyran-4-yl)-1,5-dihydropyrrolo[2,3-f]indazole (S6)

5-bromo-6-(2-tetrahydropyran-4-ylethynyl)-1H-indazole C106 (255 g, 0.84 mol), 4-Fluoroaniline (114 g, 1.0 mol) and THF 2.5 L) were added to a 5 L flask. The stirred slurry was vacuum purged with nitrogen (5×). NaOtBu (248 g, 2.6 mol) was then added in portions over 30 min, while the flask was contained in a water bath. An exotherm to 31° C. was noted. tBuXPhos Pd G1 MTBE adduct catalyst (18 g, 2.5%, 0.03 mol) was added, and an exotherm to 38° C. in 30 min was observed. The reaction was stirred overnight, cooling to room temperature. The slurry was diluted with 1 L MTBE and transferred into a 6 L sep. funnel containing 1 L water and 250 g acetic acid (5 eq) pH=7. The organic layer was separated, concentrated to an oil, and diluted with methanol (500 mL). The solution was heated at 50° C. overnight, then cooled to room temperature. An additional portion of MeOH (100 mL) was added and the reaction heated for a further 12 h. HPLC showed 3% step 4. The slurry was concentrated in vacuo, dissolved in 10% ethyl acetate in methylene chloride, and purified by silica gel chromatography (Column: silica gel (3 kg); Gradient: 10% EtOAc in dichloromethane). The product was concentrated in vacuo, and the resulting solids triturated with 200 mL MTBE at room temperature. Filtration of the solid, and washing with cool MTBE afforded the product as a red brown solid (containing approx. 1 eq acetic acid). Yield: 85%

Step 3. Synthesis of benzyl 5-(4-fluorophenyl)-6-(tetrahydro-2H-pyran-4-yl)pyrrolo[2,3-f]indazole-1(5H)-carboxylate (S7)

S7 was prepared from S6 as described above in preparation S7.

Step 4. Synthesis of benzyl 5-(4-fluorophenyl)-7-(6-(methoxycarbonyl)spiro[3.3]heptan-2-yl)-6-(tetrahydro-2H-pyran-4-yl)pyrrolo[2,3-f]indazole-1(5H)-carboxylate (C141)

To a solution of benzyl 5-(4-fluorophenyl)-6-(tetrahydro-2H-pyran-4-yl)pyrrolo[2,3-f]indazole-1(5H)-carboxylate S7 (200.5 g, 427 mmol) in chloroform (560 mL) and toluene (560 mL) at 23° C. was added in order methanesulfonic acid (42 mL, 647 mmol), methyl 6-oxospiro[3.3]heptane-2-carboxylate (93.7 g, 557 mmol) and triethylsilane (210 mL, 1.31 mol). The mixture was heated to 60° C. for 18 h. Additional methyl 6-oxospiro[3.3]heptane-2-carboxylate (12.7 g, 76 mmol) and triethylsilane (20 mL, 125 mmol) was added. The mixture was heated at 60° C. for a further 4 h [HPLC 92% completion]. Then additional methanesulfonic acid (6 mL, 92 mmol) was added, and the reaction heated at 60° C. for 19 h [HPLC 97% completion]. The mixture was cooled to room temperature then slowly added to sodium bicarbonate (125 g, 1.5 mol) in water (1 L) [gas evolved], rinsing in with dichloromethane (250 mL). The layers were mixed well and then separated. The aqueous layer was re-extracted with dichloromethane (150 mL). The combined organic layers were dried over $MgSO_4$, then filtered and evaporated. The residue was triturated in MTBE (750 mL) at 45° C. for 25 min, then cooled to room temperature overnight. The slurry was filtered (slow), washed with MTBE (150 mL) and dried to afford the product as a yellow solid. Yield: 218 g, 351 mmol, 82%.

Step 5. Synthesis of methyl 6-(5-(4-fluorophenyl)-6-(tetrahydro-2H-pyran-4-yl)-1,5-dihydropyrrolo[2,3-f]indazol-7-yl)spiro[3.3]heptane-2-carboxylate (C142)

A solution of benzyl 5-(4-fluorophenyl)-7-(6-(methoxycarbonyl)spiro[3.3]heptan-2-yl)-6-(tetrahydro-2H-pyran-4-yl)pyrrolo[2,3-f]indazole-1(5H)-carboxylate C141 (218 g, 351 mmol) in dichloromethane (800 mL) and MeOH (200 mL) was subjected to hydrogenation conditions of 20 psi hydrogen and 20% $Pd(OH)_2/C$ (~50% water, 7 g, 5 mmol) catalyst at 20-28° C. for 3 h. The mixture was filtered through a pad of Solkafloc, washing with 80:20 $CH_2Cl_2$:MeOH (250 mL). The filtrate was evaporated and azeotroped with methanol (100 mL). The residue was triturated in methanol (525 mL) at 50° C., cooled to 10° C., filtered [slow], washed with cooled methanol (200 mL) and dried to afford a grey solid (161 g). This material was dissolved in 5:95 MeOH:$CH_2Cl_2$ (2.8 L), stirred with magnesol (33 g) and silica (23 g) for 2 h. The mixture was then filtered through a pad of magnesol (32 g, top) and silica (32 g, bottom), washing with 5:95 MeOH: $CH_2Cl_2$ (500 mL) The filtrate was evaporated, triturated in MTBE (500 mL) at 50° C., cooled to 20° C. Filtration followed by washing with MTBE, then drying afforded the product as a pale grey solid Yield: 152.5 g, 313 mmol, 89%.

Step 6. Synthesis of 6-(5-(4-fluorophenyl)-6-(tetrahydro-2H-pyran-4-yl)-1,5-dihydropyrrolo[2,3-f]indazol-7-yl)spiro[3.3]heptane-2-carboxylic Acid (108)

To a slurry of methyl 6-(5-(4-fluorophenyl)-6-(tetrahydro-2H-pyran-4-yl)-1,5-dihydropyrrolo[2,3-f]indazol-7-yl)spiro[3.3]heptane-2-carboxylate (152 g, 312 mmol) in methanol (500 mL) was added a mixture of 45% KOH (75 mL, 0.88 mol) in water (250 mL). The mixture was heated to 50° C. for 21 h. The mixture was cooled to 25° C., stirred with Celite® (5 g) for 30 min, then filtered through a pad of Celite® (15 g), washing with 1:1 water:methanol (100 mL). The filtrate was cooled to 17° C. and treated with acetic acid (56 mL, 0.98 mol). The resulting slurry was diluted with water (250 mL) and then stirred at ~20° C. for 65 min before filtering. The solids were washed with water (250 mL) and dried in a vacuum oven at 45° C. to afford the product as a white solid. Yield: 140.6 g, 297 mmol, 95%.

Single Crystal X-Ray Structural Determination of Compound 109

Crystals of compound 109 were grown by slow evaporation of a 5 mg/mL solution in dichloromethane and methanol. X-ray diffraction data were acquired at 100K on a Bruker diffractometer equipped with Cu K radiation (1=1.5478) and a CPAD detector. The structure was solved and refined using the SHELX program suite (Sheldrick, G. M., Acta Cryst., (2008) A64, 112-122.) The absolute structure was determined to be correctly assigned by anomalous dispersion with a refined flack parameter of 0.11(5). Further Bijvoet analysis was conducted using PLATON producing Bayesian Statistics consistent with the correct assignment of absolute structure, P2(true)=1.000 P3(true)=1.000 P3(rac-twin)=0.2*$10^{-12}$ P3(false)=0.2*$10^{-85}$. (Spek, A. L., Acta Cryst., (2009) D65, 148-155). Crystallographic data are summarized in Table 7.

TABLE 7

| Crystal data and structure refinement for Compound 109 | | |
|---|---|---|
| Empirical formula | $C_{56}H_{56}F_2N_6O_6$ | |
| Formula weight | 947.06 | |
| Temperature | 100(2) K | |
| Wavelength | 1.54178 Å | |
| Crystal system | Triclinic | |
| Space group | P1 | |
| Unit cell dimensions | a = 13.0131(3) Å | α = 94.6870(10)°. |
| | b = 13.3927(3) Å | β = 97.2570(10)°. |
| | c = 16.2347(4) Å | γ = 102.3450(10)°. |
| Volume | 2724.52(11) $Å^3$ | |
| Z | 2 | |
| Density (calculated) | 1.154 $Mg/m^3$ | |
| Goodness-of-fit on $F^2$ | 1.030 | |
| Final R indices [I > 2sigma(I)] | R1 = 0.0493, wR2 = 0.1325 | |
| R indices (all data) | R1 = 0.0555, wR2 = 0.1411 | |
| Absolute structure parameter | 0.11(5) | |

Compound 144-151

Compounds 144-151 (Table 7) were prepared from S7 and the corresponding aldehyde or acetal by reductive alkylation, followed by Cbz removal, as described for preparation of compound 16 or 33. In these examples, $MePh_2SiH$ and $MeSO_3H$ were used in the reductive alkylation step. The Cbz group was removed with Pd/C and ammonium formate.

TABLE 7

Method of Preparation, structure and physicochemical data for compound 144-151

| Compound | Aldehyde or acetal | Product | $^1$HNMR; LC m/z [M + H]$^+$. structure comment |
|---|---|---|---|
| 144[1] | 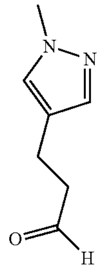 | 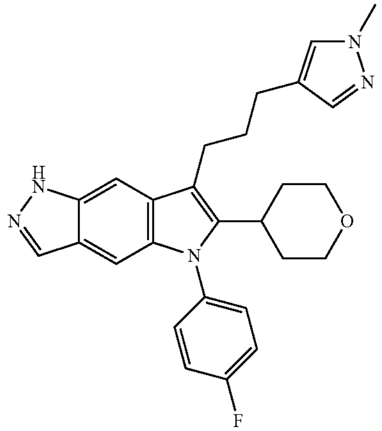 [SMILES: Cn1cc(CCCc2c(C3CCOCC3)n(-c3ccc(F)cc3)c3cc4cn[nH]c4cc23)cn1] | $^1$H NMR (400 MHz, DMSO-$d_6$) δ 12.60 (s, 1H), 7.95 (s, 1H), 7.53 (s, 1H), 7.49-7.40 (m, 5H), 7.31 (s, 1H), 7.01 (s, 1H), 3.88-3.81 (m, 2H), 3.79 (s, 3H), 3.17 (t, J = 11.5 Hz, 2H), 2.90 (t, J = 8.2 Hz, 2H), 2.82 (m, 1H), 2.60 (t, J = 7.4 Hz, 2H), 1.91 (m, 2H), 1.82 (qd, J = 12.9, 6.4 Hz, 2H), 1.64 (d, J = 12.9 Hz, 2H). LCMS m/z 458.18 [M + H]$^+$. |
| 145[1] | 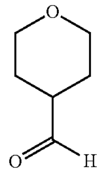 | 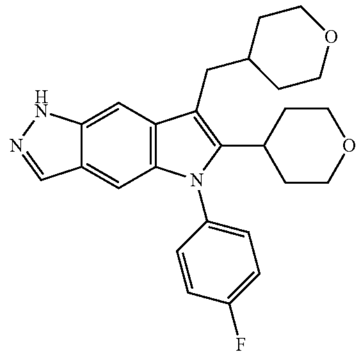 [SMILES: Fc1ccc(-n2c(C3CCOCC3)c(CC3CCOCC3)c3cc4[nH]ncc4cc32)cc1] | $^1$H NMR (400 MHz, Methanol-$d_4$) δ 8.08 (d, J = 1.0 Hz, 1H), 7.60 (d, J = 1.1 Hz, 1H), 7.44-7.29 (m, 4H), 7.05 (d, J = 1.2 Hz, 1H), 3.93 (m, 4H), 3.43-3.32 (m, 4H), 3.07 (tt, J = 12.4, 3.5 Hz, 1H), 2.88 (d, J = 7.3 Hz, 2H), 2.15-1.89 (m, 3H), 1.69 (m, 4H), 1.58-1.41 (m, 2H). LCMS m/z 434.15 [M + H]$^+$. |

TABLE 7-continued

Method of Preparation, structure and physicochemical data for compound 144-151

| Compound | Aldehyde or acetal | Product | $^1$HNMR; LC m/z [M + H]+. structure comment |
|---|---|---|---|
| 146[1] | 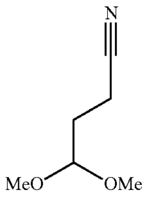 | 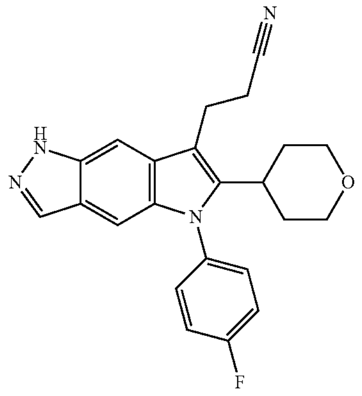 [SMILES: N#CCCc1c(C2CCOCC2)n(-c2ccc(F)cc2)c2cc3cn[nH]c3cc12] | $^1$H NMR (400 MHz, DMSO-$d_6$) δ 12.69 (s, 1H), 7.97 (s, 1H), 7.62 (s, 1H), 7.47 (m, 4H), 7.00 (s, 1H), 3.85 (dd, J = 11.4, 3.9 Hz, 2H), 3.24 (m, 4H), 3.00 (m, 1H), 2.87 (t, J = 7.2 Hz, 2H), 1.82 (m, 2H), 1.70 (d, J = 12.8 Hz, 2H). LCMS m/z 389.23 $[M + H]^+$. |
| 147[1] | 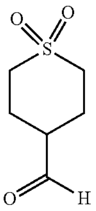 | 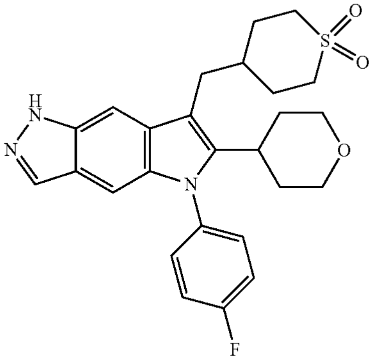 [SMILES: O=S1(=O)CCC(Cc2c(C3CCOCC3)n(-c3ccc(F)cc3)c3cc4cn[nH]c4cc23)CC1] | $^1$H NMR (400 MHz, Methanol-$d_4$) δ 8.14 (d, J = 1.0 Hz, 1H), 7.63 (t, J = 1.1 Hz, 1H), 7.46-7.29 (m, 4H), 7.09 (d, J = 1.1 Hz, 1H), 3.93 (dd, J = 11.5, 4.2 Hz, 2H), 3.36 (m, 2H), 3.17-3.06 (m, 3H), 3.06-2.98 (m, 2H), 2.96 (d, J = 7.0 Hz, 2H), 2.25-2.07 (m, 3H), 2.05-1.87 (m, 4H), 1.71 (d, J = 12.9 Hz, 2H). LCMS m/z 482.11 $[M + H]^+$. |
| 148[1] | 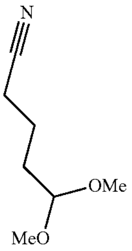 | 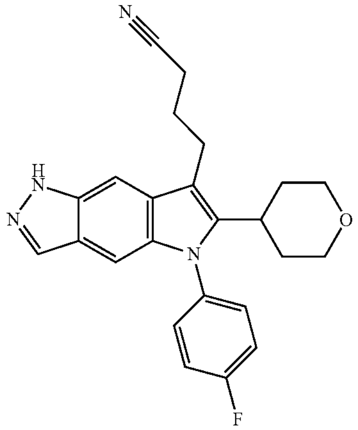 [SMILES: N#CCCCc1c(C2CCOCC2)n(-c2ccc(F)cc2)c2cc3cn[nH]c3cc12] | $^1$H NMR (400 MHz, Methanol-$d_4$) δ 8.06 (s, 1H), 7.59 (d, J = 1.2 Hz, 1H), 7.45-7.29 (m, 5H), 7.08 (d, J = 1.0 Hz, 1H), 3.95 (dd, J = 11.6, 4.2 Hz, 2H), 3.39-3.31 (m, 2H), 3.17-3.05 (m, 2H), 3.01 (tt, J = 12.5, 3.6 Hz, 1H), 2.61 (t, J = 6.9 Hz, 2H), 2.13-1.96 (m, 4H), 1.78-1.67 (m, 2H). LCMS m/z 403.23 $[M + H]^+$. |
| 149[1] | 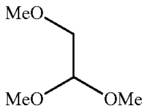 | 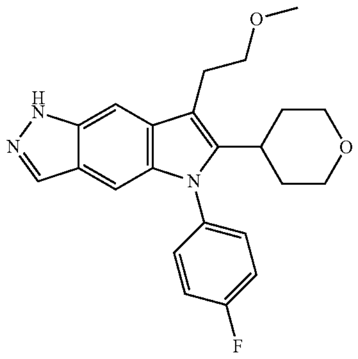 [SMILES: COCCc1c(C2CCOCC2)n(-c2ccc(F)cc2)c2cc3cn[nH]c3cc12] | $^1$H NMR (400 MHz, DMSO-$d_6$) δ 12.62 (s, 1H), 7.96 (s, 1H), 7.52 (s, 1H), 7.51-7.40 (m, 4H), 7.01 (s, 1H), 3.86 (dd, J = 11.4, 4.0 Hz, 2H), 3.61 (t, J = 7.4 Hz, 2H), 3.33 (s, 3H), 3.21 (t, J = 11.7 Hz, 2H), 3.14 (t, J = 7.4 Hz, 2H), 2.90 (t, J = 12.4 Hz, 1H), 1.97-1.80 (m, 2H), 1.67 (d, J = 12.8 Hz, 2H). LCMS m/z 394.2 $[M + H]^+$. |

TABLE 7-continued

| Method of Preparation, structure and physicochemical data for compound 144-151 | | | |
|---|---|---|---|
| Compound | Aldehyde or acetal | Product | $^1$HNMR; LC m/z $[M + H]^+$. structure comment |
| 150[1] | 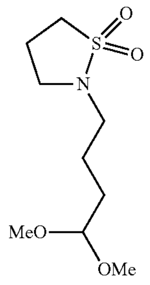 [SMILES: COC(CCCN1CCCS1(=O)=O)OC] | 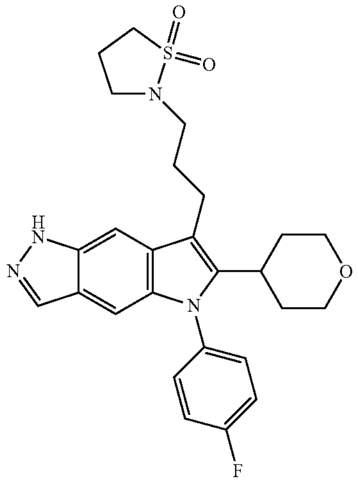 [SMILES: O=S1(=O)CCCN1CCCc1c(C2CCOCC2)n(-c2ccc(F)cc2)c2cc3cn[nH]c3cc12] | $^1H$ NMR (400 MHz, DMSO-$d_6$) δ 12.64 (s, 1H), 7.96 (s, 1H), 7.53 (s, 1H), 7.51-7.41 (m, 4H), 7.01 (s, 1H), 3.86 (dd, J = 11.3, 4.0 Hz, 2H), 3.29-3.17 (m, 6H), 3.09 (t, J = 6.9 Hz, 2H), 2.91 (m, 3H), 2.27 (p, J = 6.9 Hz, 2H), 1.89 (m, 4H), 1.67 (d, J = 12.9 Hz, 2H). LCMS m/z 497.15 $[M + H]^+$. |
| 151[1] | 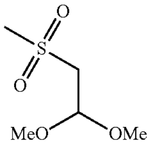 | 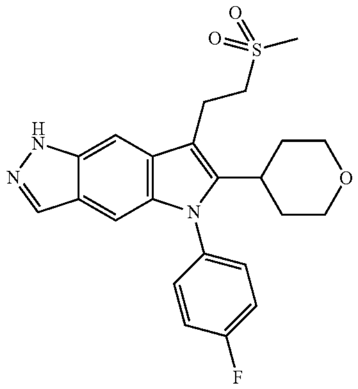 [SMILES: CS(=O)(=O)CCc1c(C2CCOCC2)n(-c2ccc(F)cc2)c2cc3cn[nH]c3cc12] | $^1H$ NMR (400 MHz, Methanol-$d_4$) δ 8.00 (d, J = 1.0 Hz, 1H), 7.62 (t, J = 1.1 Hz, 1H), 7.52-7.29 (m, 4H), 7.11 (d, J = 1.2 Hz, 1H), 3.97 (dd, J = 11.6, 4.2 Hz, 2H), 3.49 (m, 4H), 3.40-3.31 (m, 2H), 3.07 (s, 3H), 3.00 (tt, J = 12.6, 3.6 Hz, 1H), 2.14-1.97 (m, 2H), 1.76 (d, J = 12.2 Hz, 2H). LCMS m/z 442.16 $[M + H]^+$. |

[1]Purification by reversed-phase HPLC. Method: C18 Waters Sunfire column (30 × 150 mm, 5 micron). Gradient: MeCN in $H_2O$ with 0.1% trifluoroacetic acid

Compound 152 and 153

Benzyl 4-[[5-(4-fluorophenyl)-6-tetrahydropyran-4-yl-1H-pyrrolo[2,3-f]indazol-7-yl]methyl]piperidine-1-carboxylate (152) and 1-[4-[[5-(4-fluorophenyl)-6-tetrahydropyran-4-yl-1H-pyrrolo[2,3-f]indazol-7-yl]methyl]-1-piperidyl]ethanone (153)

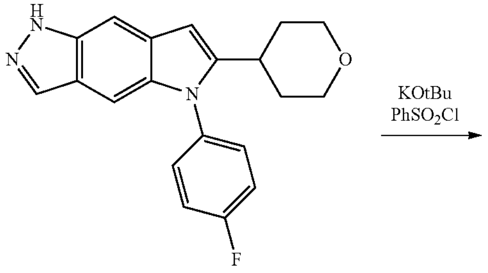

S6

-continued

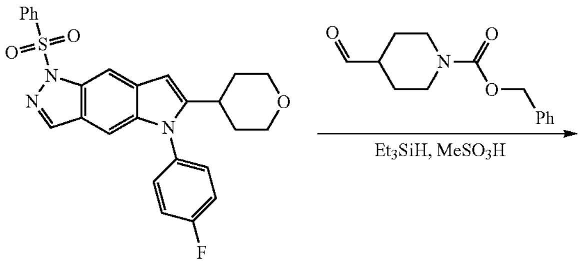

C143

-continued

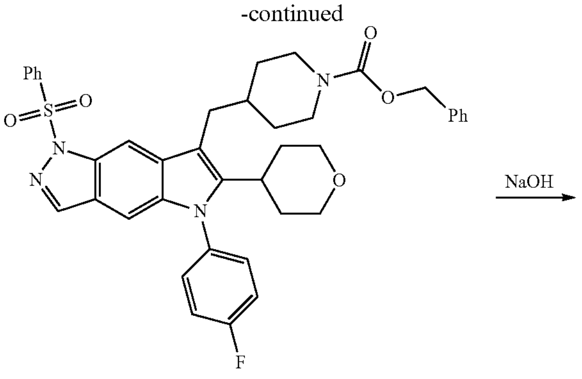

C144

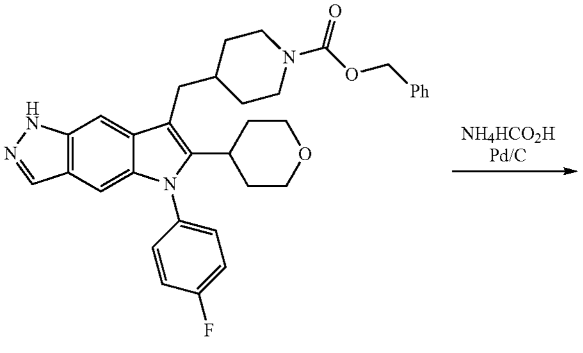

152

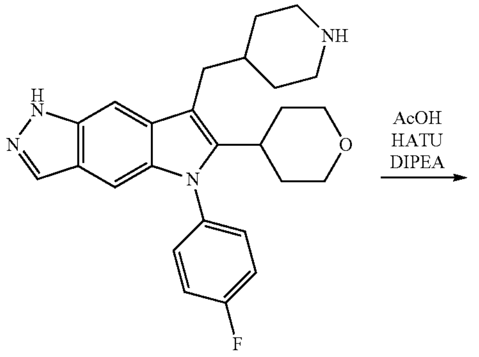

C145

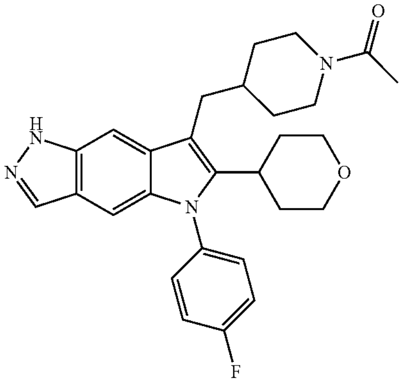

153

Step 1. Synthesis of 1-(benzenesulfonyl)-5-(4-fluorophenyl)-6-tetrahydropyran-4-yl-pyrrolo[2,3-f]indazole (C143)

To a solution of 5-(4-fluorophenyl)-6-tetrahydropyran-4-yl-1H-pyrrolo[2,3-f]indazole S6 (10 g, 29.8 mmol) in THF (120 mL) at 0° C. was added KOtBu (4.2 g, 37.3 mmol) and the mixture stirred for 10 min. Benzene sulfonyl chloride (4.4 mL, 34.5 mmol) was added, and the mixture stirred for 1 h at 0° C., then for an additional 1 h at room temperature. The mixture was concentrated in vacuo, and then saturated $NH_4Cl$ and $CH_2Cl_2$ were added. The organic layer was separated, and dried. Purification by silica gel chromatography (Gradient: 0-60% $CH_2Cl_2$ in EtOAc) afforded the product as a white solid, containing around 5% of S6 (11.8 g, 83%). $^1$H NMR (300 MHz, Chloroform-d) δ 8.38 (t, J=1.0 Hz, 1H), 8.14 (d, J=0.9 Hz, 1H), 8.04-7.93 (m, 2H), 7.57-7.47 (m, 1H), 7.46-7.38 (m, 2H), 7.38-7.30 (m, 3H), 7.15 (t, J=0.9 Hz, 1H), 6.62 (d, J=0.8 Hz, 1H), 4.08-3.94 (m, 2H), 3.37 (td, J=11.8, 2.3 Hz, 2H), 2.82 (ddt, J=11.5, 8.0, 3.9 Hz, 1H), 1.98-1.70 (m, 5H). LCMS m/z 476.2 [M+H]$^+$.

Step 2. Synthesis of benzyl 4-[[1-(benzenesulfonyl)-5-(4-fluorophenyl)-6-tetrahydropyran-4-yl-pyrrolo[2,3-f]indazol-7-yl]methyl]piperidine-1-carboxylate (C144)

Benzyl 4-[[1-(benzenesulfonyl)-5-(4-fluorophenyl)-6-tetrahydropyran-4-yl-pyrrolo[2,3-f]indazol-7-yl]methyl]piperidine-1-carboxylate was prepared from C143 and benzyl 4-formylpiperidine-1-carboxylate using the reductive coupling method described for the preparation of compound 33. Purification by reversed-phase chromatography (Column: C18. Gradient: 0-100% MeCN in water with 0.2% formic acid) afforded the product. Benzyl 4-[[1-(benzenesulfonyl)-5-(4-fluorophenyl)-6-tetrahydropyran-4-yl-pyrrolo[2,3-f]indazol-7-yl]methyl]piperidine-1-carboxylate (168.1 mg, 77%). $^1$H NMR (400 MHz, DMSO-$d_6$) δ 8.45 (s, 1H), 8.12 (s, 1H), 7.83 (d, J=7.9 Hz, 2H), 7.61 (t, J=7.6 Hz, 1H), 7.47 (dt, J=21.7, 7.9 Hz, 6H), 7.40-7.27 (m, 5H), 7.07 (s, 1H), 5.10 (s, 2H), 4.09 (d, J=13.0 Hz, 2H), 3.89-3.80 (m, 2H), 3.24 (t, J=11.7 Hz, 2H), 3.03 (t, J=12.6 Hz, 1H), 2.91-2.65 (m, 4H), 1.91-1.58 (m, 7H), 1.39-1.26 (m, 2H). LCMS m/z 707.03 [M+H]$^+$.

Step 3. Synthesis of benzyl 4-[[5-(4-fluorophenyl)-6-tetrahydropyran-4-yl-1H-pyrrolo[2,3-f]indazol-7-yl]methyl]piperidine-1-carboxylate (152)

A vial was charged with benzyl 4-[[1-(benzenesulfonyl)-5-(4-fluorophenyl)-6-tetrahydropyran-4-yl-pyrrolo[2,3-f]indazol-7-yl]methyl]piperidine-1-carboxylate C144 (160 mg, 0.23 mmol) and dissolved in THF (3.2 mL) and MeOH (1.6 mL). NaOH (1.36 mL of 1 M, 1.4 mmol) was added, and the reaction was heated to 50° C. for 90 minutes. The solvent was evaporated, and the residue was suspended in water (5 mL). HCl (1.36 mL of 1 M, 1.4 mmol) was added to neutralize the reaction. Purification by reversed-phase HPLC (Method: C18 Waters Sunfire column (30×150 mm, 5 micron). Gradient: 10-100% MeCN in $H_2O$ with 0.2% formic acid) afforded the product as a white solid. Benzyl 4-[[5-(4-fluorophenyl)-6-tetrahydropyran-4-yl-1H-pyrrolo[2,3-f]indazol-7-yl]methyl]piperidine-1-carboxylate (96.6 mg, 65%). $^1$H NMR (300 MHz, DMSO-d6) δ 12.57 (s, 1H), 7.94 (d, J=1.4 Hz, 1H), 7.51 (s, 1H), 7.49-7.44 (m, 4H), 7.40-7.31 (m, 5H), 6.94 (s, 1H), 5.07 (s, 2H), 4.04 (d, J=13.2 Hz, 2H), 3.83 (d, J=10.2 Hz, 2H), 3.23 (t, J=11.3 Hz, 2H), 3.07-2.93 (m, 1H), 2.81 (d, J=7.1 Hz, 4H), 1.81-1.57 (m, 7H), 1.35-1.27 (m, 2H). LCMS m/z 567.16 [M+H]$^+$.

Step 4. Synthesis of 5-(4-fluorophenyl)-7-(4-piperidylmethyl)-6-tetrahydropyran-4-yl-1H-pyrrolo[2,3-f]indazole (C145)

A 20 mL scintillation vial was charged with benzyl 4-[[5-(4-fluorophenyl)-6-tetrahydropyran-4-yl-1H-pyrrolo

[2,3-f]indazol-7-yl]methyl]piperidine-1-carboxylate (90 mg, 0.14 mmol), palladium on carbon (64 mg, 0.60 mmol), and ammonium formate (120 mg, 1.90 mmol). MeOH (2 mL) was added, and the vial was sealed and heated to 60° C. for 20 minutes. The reaction mixture was passed through a plug of Celite®, and the filter was washed with excess MeOH. Purification by reversed-phase chromatography (Column: C18. Gradient: 10-100% MeCN in water with 0.2% formic acid) afforded the product. The desired product was obtained as an off-white solid. 5-(4-fluorophenyl)-7-(4-piperidylmethyl)-6-tetrahydropyran-4-yl-1H-pyrrolo[2,3-f] indazole (52.5 mg, 85%). $^{1}$H NMR (400 MHz, DMSO-d6) δ 12.65 (s, 1H), 8.37 (s, 1H), 7.95 (s, 1H), 7.51-7.43 (m, 5H), 6.95 (s, 1H), 3.89-3.79 (m, 2H), 3.28-3.16 (m, 4H), 2.99 (t, J=12.6 Hz, 1H), 2.82 (d, J=7.0 Hz, 2H), 2.73 (t, J=12.5 Hz, 2H), 2.02-1.89 (m, 1H), 1.87-1.74 (m, 4H), 1.64 (d, J=12.8 Hz, 2H), 1.54-1.38 (m, 2H). LCMS m/z 433.16 [M+H]$^{+}$.

Step 5. Synthesis of 1-[4-[[5-(4-fluorophenyl)-6-tetrahydropyran-4-yl-1H-pyrrolo[2,3-f]indazol-7-yl]methyl]-1-piperidyl]ethanone (153)

A 1 dram vial was charged with 5-(4-fluorophenyl)-7-(4-piperidylmethyl)-6-tetrahydropyran-4-yl-1H-pyrrolo[2,3-f] indazole C145 (8 mg, 0.02 mmol), and dissolved in DMF (350 μL). AcOH (1.1 μL, 0.02 mmol) and DIPEA (3.4 μL, 0.02 mmol) were added, and the solution was cooled to 0° C. HATU (8 mg, 0.02 mmol) was added, and the reaction was allowed to stir at 0° C. for 20 minutes. The reaction mixture was purified by SFC to afford the product. 1-[4-[[5-(4-fluorophenyl)-6-tetrahydropyran-4-yl-1H-pyrrolo[2,3-f] indazol-7-yl]methyl]-1-piperidyl]ethanone (2.0 mg, 22%). LCMS m/z 475.14 [M+H]$^{+}$.

Compound 154 benzyl 3-[[5-(4-fluorophenyl)-6-tetrahydropyran-4-yl-M-pyrrolo[2,3-f]indazol-7-yl]methyl]piperidine-1-carboxylate (154)

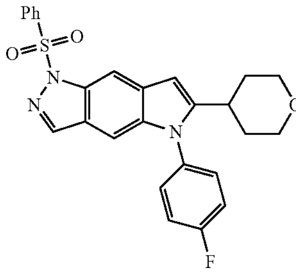

C143

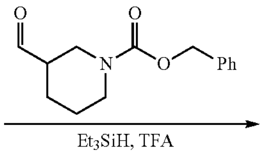

-continued

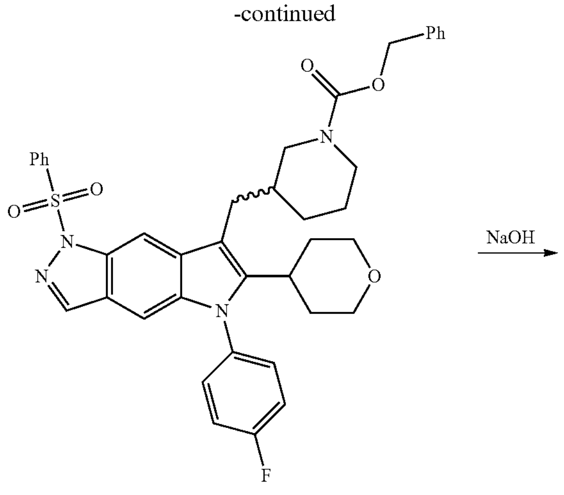

C146

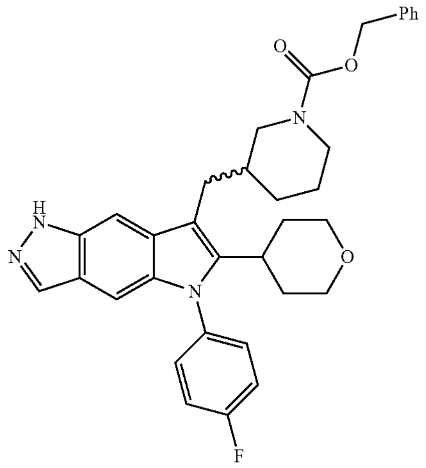

154

Compound 154 was prepared by reductive coupling of (C143) with benzyl 3-formylpiperidine-1-carboxylate, then hydrolysis with NaOH to remove the phenyl sulfonyl group using the method as described for the preparation of compound 152. $^{1}$H NMR (400 MHz, DMSO-$d_6$) δ 12.60 (s, 1H), 7.96 (s, 1H), 7.54-7.04 (m, 10H), 6.95 (s, 1H), 5.09-4.86 (m, 2H), 4.06-3.94 (m, 2H), 3.86-3.71 (m, 2H), 3.29-3.14 (m, 2H), 3.07-2.94 (m, 1H), 2.87-2.62 (m, 4H), 1.96-1.48 (m, 7H), 1.40-1.28 (m, 2H). LCMS m/z 567.21 [M+H]$^{+}$.

Compound 155

3-[[5-(4-fluorophenyl)-6-tetrahydropyran-4-yl-1H-pyrrolo[2,3-f]indazol-7-yl]methyl]piperidine-1-carboxamide (155)

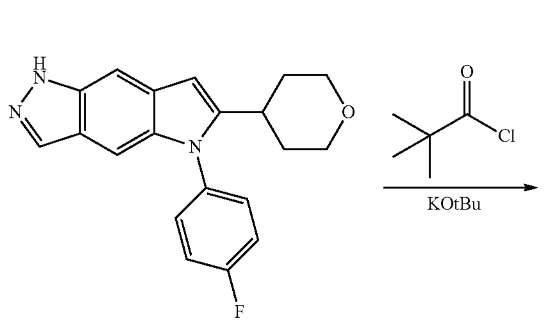

S6

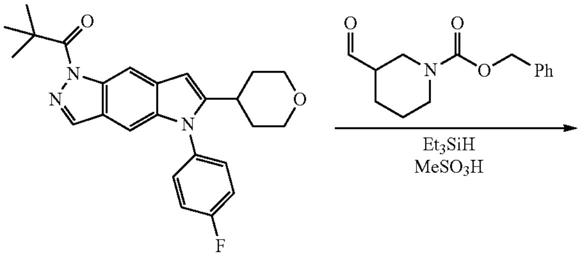

C147

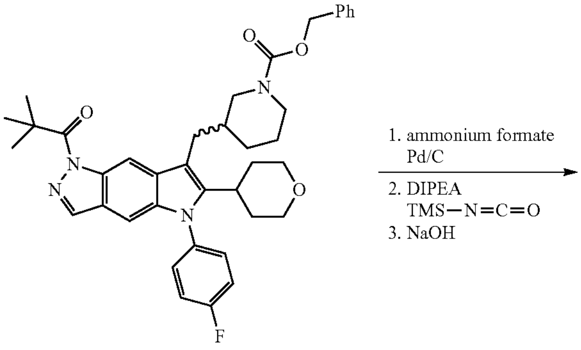

C148

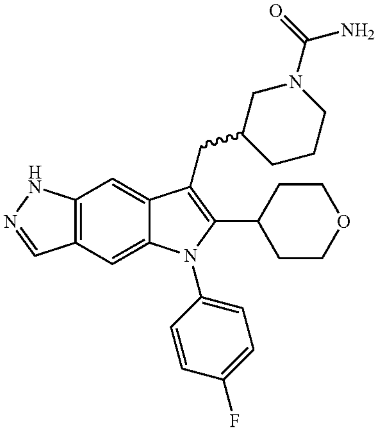

155

Step 1. Synthesis of 1-[5-(4-fluorophenyl)-6-tetrahydropyran-4-yl-pyrrolo[2,3-f]indazol-1-yl]-2,2-dimethyl-propan-1-one (C147)

To a vial containing 5-(4-fluorophenyl)-6-tetrahydropyran-4-yl-1H-pyrrolo[2,3-f]indazole S6 (10 g, 29.8 mmol) was added THF (320 mL) and the mixture was cooled to 0° C. in an ice bath. KOtBu (7.39 g, 65.9 mmol) was added and the mixture was allowed to stir for five minutes. 2,2-dimethylpropanoyl chloride (14.5 mL, 117.9 mmol) was added dropwise, giving a yellow/brown solution and the mixture allowed to stir at 0° C. for 1 hour. Water (200 mL) and dichloromethane (250 mL) were added and the mixture was extracted with additional dichloromethane (2×50 mL). The organic phase was dried over $Na_2SO_4$, and the solvent removed. Purification by silica gel chromatography (Gradient: 0-5% EtOAc in heptane) yielded the product. 1-[5-(4-fluorophenyl)-6-tetrahydropyran-4-yl-pyrrolo[2,3-f]indazol-1-yl]-2,2-dimethyl-propan-1-one (10.7 g, 83%). $^1H$ NMR (400 MHz, Chloroform-d) δ 8.69 (s, 1H), 8.07 (s, 1H), 7.39 (dd, J=8.4, 4.9 Hz, 2H), 7.32 (d, J=8.3 Hz, 2H), 7.21 (s, 1H), 6.59 (s, 1H), 4.01 (dd, J=12.0, 4.1 Hz, 2H), 3.37 (t, J=11.7 Hz, 2H), 2.89-2.80 (m, 1H), 1.89 (qd, J=12.2, 4.1 Hz, 2H), 1.78 (d, J=13.0 Hz, 2H), 1.61 (d, J=1.3 Hz, 9H). LCMS m/z 420.34 $[M+H]^+$.

Step 2. Synthesis of benzyl 3-[[1-(2,2-dimethylpropanoyl)-5-(4-fluorophenyl)-6-tetrahydropyran-4-yl-pyrrolo[2,3-f]indazol-7-yl]methyl]piperidine-1-carboxylate (C148)

A 20 mL scintillation vial was charged with 1-[5-(4-fluorophenyl)-6-tetrahydropyran-4-yl-pyrrolo[2,3-f]indazol-1-yl]-2,2-dimethyl-propan-1-one C147 (260 mg, 0.61 mmol) and benzyl 3-formylpiperidine-1-carboxylate (641 mg, 2.6 mmol). Dichloromethane (3 mL) followed by $Et_3SiH$ (360 μL, 2.3 mmol) and methanesulfonic acid (73 μL, 1.13 mmol) were added. The vial was sealed and placed in a 50° C. heating block, and heated overnight. The mixture was washed with sat. $NaHCO_3$, and passed through a phase separator to collect the organic phase. Purification by reversed-phase chromatography (Column: C18. Gradient: 0-100% MeCN in water with 0.2% formic acid) afforded the product. Benzyl 3-[[1-(2,2-dimethylpropanoyl)-5-(4-fluorophenyl)-6-tetrahydropyran-4-yl-pyrrolo[2,3-f]indazol-7-yl]methyl]piperidine-1-carboxylate (363.8 mg, 90%). LCMS m/z 651.18 $[M+H]^+$.

Step 3. Synthesis of 1-[5-(4-fluorophenyl)-7-(3-piperidylmethyl)-6-tetrahydropyran-4-yl-pyrrolo[2,3-f]indazol-1-yl]-2,2-dimethyl-propan-1-one A 20 mL scintillation vial was charged with benzyl 3-[[1-(2,2-dimethylpropanoyl)-5-(4-fluorophenyl)-6-tetrahydropyran-4-yl-pyrrolo[2,3-f]indazol-7-yl]methyl]piperidine-1-carboxylate C148 (363 mg, 0.55 mmol), palladium on carbon (340 mg, 3.2 mmol), and ammonium formate (430 mg, 6.82 mmol). MeOH (5 mL) was added, and the vial was sealed and heated to 60° C. for 10 minutes. The reaction mixture was passed through a plug of Celite®, and the filter washed with excess MeOH. The solvent was evaporated and the crude material was taken up in minimal DMSO and purified by reverse phase chromatography using a gradient of 10-100% acetonitrile in water with 0.2% formic acid on a 15.5 g gold C18 column. The desired product was obtained as a white solid. 1-[5-(4-fluorophenyl)-7-(3-piperidylmethyl)-6-tetrahydropyran-4-yl-pyrrolo[2,3-f]indazol-1-yl]-2, 2-dimethyl-propan-1-one (215.4 mg, 76%). $^1H$ NMR (400 MHz, DMSO-d6) δ 8.50 (s, 1H), 8.37 (s, 1H), 8.30 (s, 1H), 7.59-7.44 (m, 4H), 7.14 (s, 1H), 3.89-3.78 (m, 2H), 3.26 (t, J=11.5 Hz, 2H), 3.21-3.00 (m, 4H), 2.88-2.81 (m, 2H), 2.78-2.63 (m, 2H), 2.15-2.02 (m, 1H), 1.86-1.72 (m, 4H), 1.68-1.59 (m, 2H), 1.52 (s, 9H), 1.41-1.29 (m, 1H). LCMS m/z 517.17 $[M+H]^+$.

Step 4 & 5. Synthesis of 3-[[5-(4-fluorophenyl)-6-tetrahydropyran-4-yl-1H-pyrrolo[2,3-f]indazol-7-yl]methyl]piperidine-1-carboxamide (155)

A vial was charged with 1-[5-(4-fluorophenyl)-7-(3-piperidylmethyl)-6-tetrahydropyran-4-yl-pyrrolo[2,3-f]indazol-1-yl]-2,2-dimethyl-propan-1-one (11 mg, 0.021 mmol) and dissolved in dichloromethane (500 μL). DIPEA (4.1 μL, 0.02354 mmol) and isocyanato(trimethyl)silane (3.2 μL, 0.024 mmol) were added, and the reaction was stirred at room temperature for 1 hour. The solvent was evaporated, and the residue was dissolved in THF (240 μL) and MeOH (120 μL). NaOH (126 μL of 1 M, 0.13 mmol) was added and the reaction was heated to 50° C. for 30 minutes. The solvent was evaporated, and residue was suspended in HCl (126 μL of 1 M, 0.13 mmol). The crude material was taken up in minimal DMSO and purified by reverse phase chromatography using a gradient of 10-100% acetonitrile in water with 0.2% formic acid modifier on a 15.5 g gold C18 column. The desired product was obtained as an off-white solid. 3-[[5-(4-fluorophenyl)-6-tetrahydropyran-4-yl-1H-pyrrolo[2,3-f]indazol-7-yl]methyl]piperidine-1-carboxamide (5.5 mg, 49%). LCMS m/z 476.13 $[M+H]^+$.

Compound 156 and Compound 157

N-[3-[5-(4-fluorophenyl)-6-tetrahydropyran-4-yl-1H-pyrrolo[2,3-f]indazol-7-yl]propyl]acetamide (156) and 3-[5-(4-fluorophenyl)-6-tetrahydropyran-4-yl-1H-pyrrolo[2,3-f]indazol-7-yl]propylurea (157)

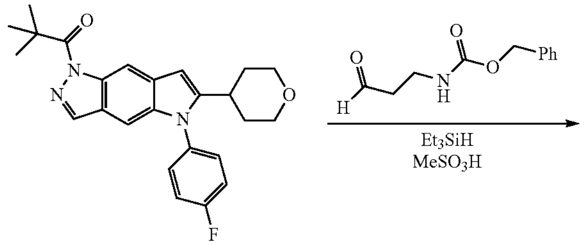

C147

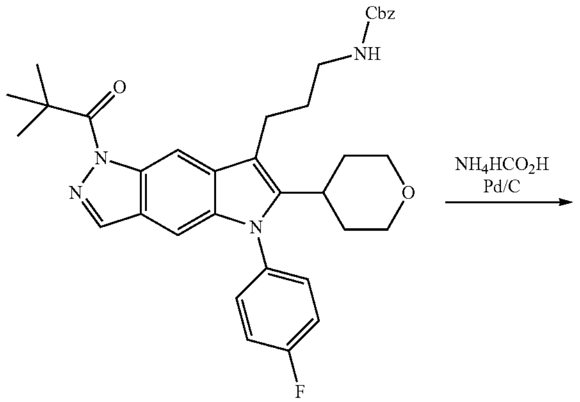

C149

-continued

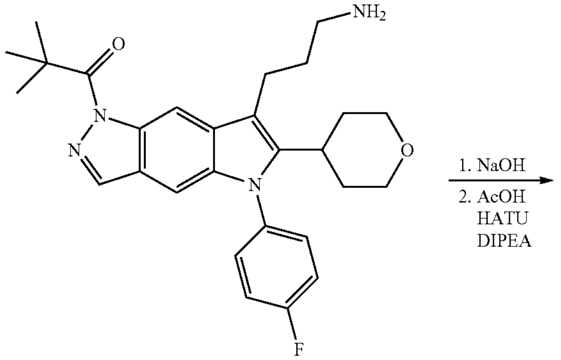

C150

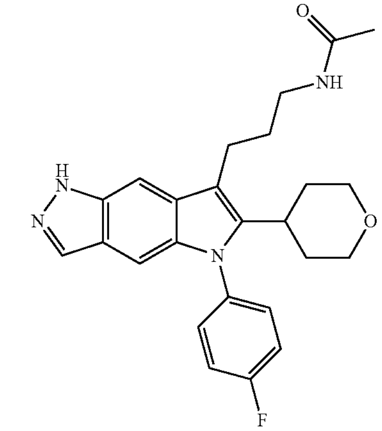

156

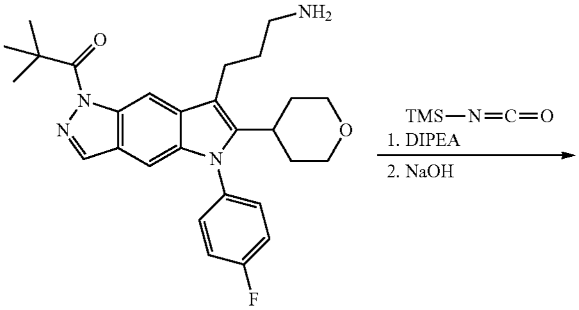

C150

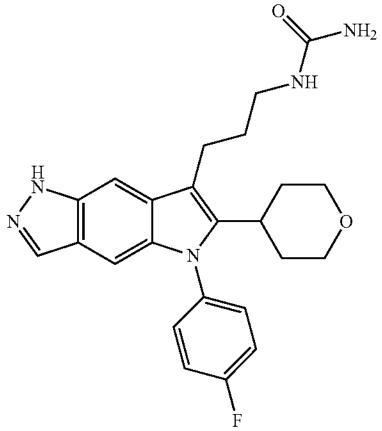

157

Step 1. Synthesis of benzyl N-[3-[1-(2,2-dimethylpropanoyl)-5-(4-fluorophenyl)-6-tetrahydropyran-4-yl-pyrrolo[2,3-f]indazol-7-yl]propyl]carbamate (C149)

A 1 dram vial was charged with 1-[5-(4-fluorophenyl)-6-tetrahydropyran-4-yl-pyrrolo[2,3-f]indazol-1-yl]-2,2-dimethyl-propan-1-one C147 (147 mg, 0.34 mmol) and benzyl N-(3-oxopropyl)carbamate (290 mg, 1.4 mmol). Dichloromethane (1.5 mL) was added, followed by $Et_3SiH$ (190 μL, 1.2 mmol) and methanesulfonic acid (50 μL, 0.77 mmol). The vial was sealed and allowed to stir at room temperature for 15 minutes. The reaction mixture was washed with sat. $NaHCO_3$, and the mixture was passed through a phase separator to collect the organic phase. The solvent was evaporated and the crude material was dissolved in minimal DMSO and purified by reverse phase chromatography (C18 column. Gradient: 10-100% acetonitrile in water with 0.2% formic acid) to afford the product. benzyl N-[3-[1-(2,2-dimethylpropanoyl)-5-(4-fluorophenyl)-6-tetrahydropyran-4-yl-pyrrolo[2,3-f]indazol-7-yl]propyl]carbamate (101.0 mg, 44%)$^1$H NMR (400 MHz, DMSO-$d_6$) δ 8.49 (s, 1H), 8.38 (s, 1H), 7.56-7.45 (m, 5H), 7.40-7.26 (m, 5H), 7.19 (s, 1H), 5.05 (s, 2H), 3.90-3.81 (m, 2H), 3.28-3.14 (m, 4H), 2.98-2.84 (m, 3H), 1.96-1.78 (m, 4H), 1.72-1.64 (m, 2H), 1.51 (s, 9H). LCMS m/z 611.17 $[M+H]^+$.

Step 2. Synthesis of 1-[7-(3-aminopropyl)-5-(4-fluorophenyl)-6-tetrahydropyran-4-yl-pyrrolo[2,3-f]indazol-1-yl]-2,2-dimethyl-propan-1-one (C150)

A 20 mL vial was charged with benzyl N-[3-[1-(2,2-dimethylpropanoyl)-5-(4-fluorophenyl)-6-tetrahydropyran-4-yl-pyrrolo[2,3-f]indazol-7-yl]propyl]carbamate C149 (100 mg, 0.16 mmol), palladium (122 mg, 1.15 mmol), and ammonium formate (123 mg, 1.95 mmol). MeOH (4 mL) was added, and the vial was sealed and heated to 60° C. for 10 minutes. The reaction mixture was passed through a plug of Celite®, and the filter washed with excess MeOH. The solvent was evaporated and the crude material was taken up in minimal DMSO and purified by reverse phase chromatography (Gradient: 10-100% acetonitrile in water with 0.2% formic acid). 1-[7-(3-aminopropyl)-5-(4-fluorophenyl)-6-tetrahydropyran-4-yl-pyrrolo[2,3-f]indazol-1-yl]-2,2-dimethyl-propan-1-one (52.9 mg, 67%). $^1$H NMR (400 MHz, DMSO-d6) δ 8.52 (s, 1H), 8.42-8.34 (m, 1H), 7.58-7.42 (m, 4H), 7.20 (s, 1H), 3.92-3.81 (m, 2H), 3.24 (t, J=11.5 Hz, 2H), 3.05-2.87 (m, 5H), 1.99-1.82 (m, 4H), 1.68 (d, J=12.5 Hz, 2H), 1.52 (s, 9H). LCMS m/z 477.16 $[M+H]^+$.

Step 3. Synthesis of N-[3-[5-(4-fluorophenyl)-6-tetrahydropyran-4-yl-1H-pyrrolo[2,3-f]indazol-7-yl]propyl]acetamide (156)

A vial was charged with 1-[7-(3-aminopropyl)-5-(4-fluorophenyl)-6-tetrahydropyran-4-yl-pyrrolo[2,3-f]indazol-1-yl]-2,2-dimethyl-propan-1-one C150 (6 mg, 0.013 mmol), and dissolved in DMF (300 μL). AcOH (1 μL, 0.018 mmol) and DIPEA (2.4 μL, 0.014 mmol) were added, and the solution was cooled to 0° C. HATU (6 mg, 0.016 mmol) was added, and the reaction was allowed to stir at 0° C. for 30 minutes. NaOH (75 μL of 1 M, 0.08 mmol) was added directly to the reaction mixture, which was heated to 50° C. Purification by reversed-phase chromatography (Column: C18. Gradient: 0-100% MeCN in water with 0.2% formic acid) afforded the product. N-[3-[5-(4-fluorophenyl)-6-tetrahydropyran-4-yl-1H-pyrrolo[2,3-f]indazol-7-yl]propyl]acetamide (3.0 mg, 54%). $^1$H NMR (400 MHz, Methanol-d4) δ 8.24-8.10 (m, 1H), 7.94 (s, 1H), 7.55 (d, J=3.6 Hz, 1H), 7.41-7.30 (m, 4H), 7.06 (s, 1H), 4.00-3.91 (m, 2H), 3.42-3.31 (m, 4H), 3.02-2.89 (m, 3H), 2.12-1.88 (m, 7H), 1.71 (d, J=13.2 Hz, 2H). LCMS m/z 435.14 $[M+H]^+$.

Step 4. Synthesis of 3-[5-(4-fluorophenyl)-6-tetrahydropyran-4-yl-1H-pyrrolo[2,3-f]indazol-7-yl]propylurea (157)

A vial was charged with 1-[7-(3-aminopropyl)-5-(4-fluorophenyl)-6-tetrahydropyran-4-yl-pyrrolo[2,3-f]indazol-1-yl]-2,2-dimethyl-propan-1-one C150 (7.4 mg, 0.015 mmol) and dissolved in dichloromethane (300 μL). DIPEA (3 μL, 0.017 mmol) and isocyanato(trimethyl)silane (2.3 μL, 0.02 mmol) were added, and the reaction was stirred at room temperature overnight. The solvent was evaporated, and the residue was dissolved in THF (160 μL), MeOH (80 μL), and NaOH (92 μL of 1 M, 0.09 mmol) was added. The reaction was heated to 50° C. for 30 minutes. The solvent was evaporated, and the residue was suspended in HCl (92 μL of 1 M, 0.09 mmol). Purification by reversed-phase chromatography (Column: C18. Gradient: 0-100% MeCN in water with 0.2% formic acid) afforded the product. 3-[5-(4-fluorophenyl)-6-tetrahydropyran-4-yl-1H-pyrrolo[2,3-f]indazol-7-yl]propylurea (4.0 mg, 57%). $^1$H NMR (400 MHz, Methanol-$d_4$) δ 8.27-8.10 (m, 1H), 7.94 (s, 1H), 7.55 (d, J=3.6 Hz, 1H), 7.42-7.29 (m, 4H), 7.06 (s, 1H), 4.00-3.90 (m, 2H), 3.38-3.34 (m, 2H), 3.03-2.86 (m, 3H), 2.15-1.88 (m, 6H), 1.71 (d, J=13.2 Hz, 2H). LCMS m/z 435.99 $[M+H]^+$.

Compound 158

7-(2-ethylsulfonylethyl)-5-(4-fluorophenyl)-6-tetrahydropyran-4-yl-1H-pyrrolo[2,3-f]indazole (158)

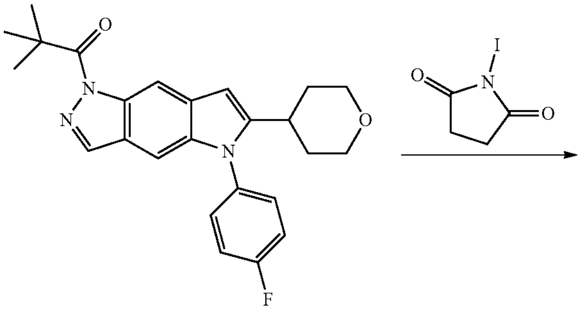

C147

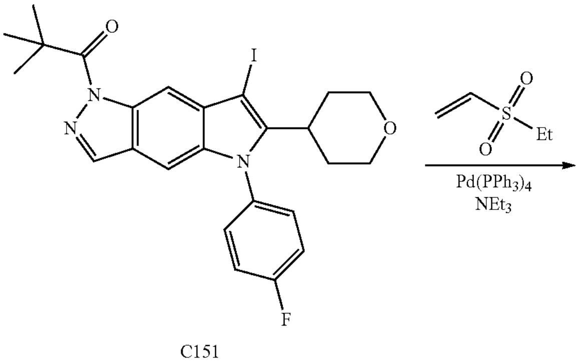

C151

-continued

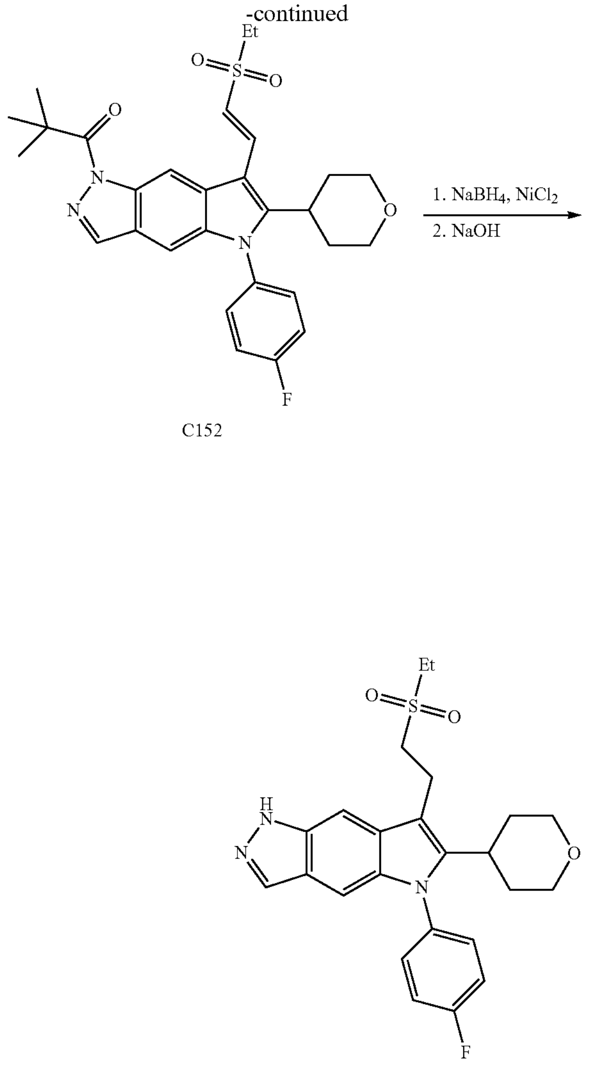

C152

158

Step 1. Synthesis of 1-[5-(4-fluorophenyl)-7-iodo-6-tetrahydropyran-4-yl-pyrrolo[2,3-f]indazol-1-yl]-2,2-dimethyl-propan-1-one (C151)

1-[5-(4-fluorophenyl)-7-iodo-6-tetrahydropyran-4-yl-pyrrolo[2,3-f]indazol-1-yl]-2,2-dimethyl-propan-1-one C147 was prepared from 1-[5-(4-fluorophenyl)-6-tetrahydropyran-4-yl-pyrrolo[2,3-f]indazol-1-yl]-2,2-dimethyl-propan-1-one (10.67 g, 25.4 mmol) according to the method described for the preparation of compound 1. Purification by silica gel chromatography (Gradient: 0-5% EtOAc in heptane), trituration with heptane afforded a brown solid containing succinimide Water (250 mL) was added and the mixture was stirred vigorously for 30 minutes. The mixture was filtered washing the solid with excess water. The solid was dissolved in dichloromethane (250 mL) and washed with water (250 mL). The phases were separated with a phase separator and the organic phase was concentrated to afford the product. 1-[5-(4-fluorophenyl)-7-iodo-6-tetrahydropyran-4-yl-pyrrolo[2,3-f]indazol-1-yl]-2,2-dimethyl-propan-1-one (11.744 g, 84%). $^1$H NMR (400 MHz, Chloroform-d) δ 8.63 (s, 1H), 8.08 (s, 1H), 7.37-7.30 (m, 4H), 7.08 (s, 1H), 4.04 (dd, J=11.7, 4.2 Hz, 2H), 3.38 (t, J=11.8 Hz, 2H), 3.07 (t, J=12.6 Hz, 1H), 2.43 (qd, J=12.5, 4.3 Hz, 2H), 1.62 (s, 9H). LCMS m/z 546.33 $[M+H]^+$.

Step 2. Synthesis of 1-[7-[(E)-2-ethylsulfonylvinyl]-5-(4-fluorophenyl)-6-tetrahydropyran-4-yl-pyrrolo[2,3-f]indazol-1-yl]-2,2-dimethyl-propan-1-one (C152)

1-[5-(4-fluorophenyl)-7-iodo-6-tetrahydropyran-4-yl-pyrrolo[2,3-f]indazol-1-yl]-2,2-dimethyl-propan-1-one C151 (100 mg, 0.17 mmol) and $Pd(PPh_3)_4$ (20 mg, 0.017 mmol) were suspended in N,N-dimethylformamide (1600 μL). Then, 1-vinylsulfonylethane (40 μL, 0.38 mmol) and $Et_3N$ (90 μL, 0.65 mmol) were added. The reaction was heated in the microwave at 120° C. μW for 20 minutes. Water and dichloromethane were added. The mixture was extracted with dichloromethane (3×). The organic phases were passed through a phase separator, combined and concentrated in vacuo. Purification by reversed-phase chromatography (Column: C18. Gradient: 0-70% MeCN in water with 0.1% formic acid) afforded the product. 1-[7-[(E)-2-ethylsulfonylvinyl]-5-(4-fluorophenyl)-6-tetrahydropyran-4-yl-pyrrolo[2,3-f]indazol-1-yl]-2,2-dimethyl-propan-1-one (63.0 mg, 65%). LCMS m/z 538.09 $[M+H]^+$.

Step 3. Synthesis of 7-(2-ethylsulfonylethyl)-5-(4-fluorophenyl)-6-tetrahydropyran-4-yl-1H-pyrrolo[2,3-f]indazole (158)

Part A.

To a suspension of $NiCl_2$ (32.54 mg, 0.25 mmol) in MeOH (2 mL), $NaBH_4$ (9.5 mg, 0.25 mmol) was added while in an ice bath. The mixture was stirred for 15 minutes and a suspension of 1-[7-[(E)-2-ethylsulfonylvinyl]-5-(4-fluorophenyl)-6-tetrahydropyran-4-yl-pyrrolo[2,3-f]indazol-1-yl]-2,2-dimethyl-propan-1-one C152 (45 mg, 0.08 mmol) in MeOH (1 mL) was added slowly. The mixture was stirred for 30 minutes. An additional amount of sodium borohydride (9.5 mg, 0.25 mmol) was added and the mixture was stirred for 30 minutes more. The reaction was quenched with water, filtered and concentrated. Water and dichloromethane were added. The mixture was extracted with dichloromethane (3×). The organic phases were passed through a phase separator, combined and concentrated in vacuo.

The crude was used as is in the next step. 1-[7-(2-ethylsulfonylethyl)-5-(4-fluorophenyl)-6-tetrahydropyran-4-yl-pyrrolo[2,3-f]indazol-1-yl]-2,2-dimethyl-propan-1-one LCMS m/z 540.16 $[M+H]^+$.

Part B.

The crude from part A was suspended in EtOH (0.75 mL). Then, an aqueous solution of NaOH (250 μL of 1 M, 0.25 mmol) was added and the reaction was heated at 50° C. for 2 hours. Water and dichloromethane were added. The mixture was extracted with dichloromethane (3×). The organic phases were passed through a phase separator, combined and concentrated in vacuo. A white solid was obtained, 7-(2-ethylsulfonylethyl)-5-(4-fluorophenyl)-6-tetrahydropyran- 4-yl-1H-pyrrolo[2,3-f]indazole (5.2 mg, 13%). $^1$H NMR (400 MHz, Methanol-$d_4$) δ 7.96 (s, 1H), 7.60 (t, J=1.1 Hz, 1H), 7.50-7.25 (m, 4H), 7.10 (d, J=1.1 Hz, 1H), 3.97 (dd, J=11.5, 4.2 Hz, 2H), 3.52-3.40 (m, 4H), 3.38-3.32 (m, 2H), 3.19 (q, J=7.4 Hz, 2H), 3.06-2.94 (m, 1H), 2.13-1.99 (m, 2H), 1.76 (d, J=13.1 Hz, 2H), 1.39 (t, J=7.5 Hz, 3H). LCMS m/z 456.06 $[M+H]^+$.

Compound 159

2-[5-(4-fluorophenyl)-6-tetrahydropyran-4-yl-1H-pyrrolo[2,3-f]indazol-7-yl]-N-methyl-ethanesulfonamide (159)

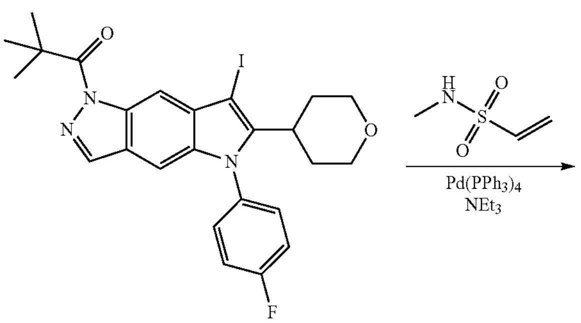

C151

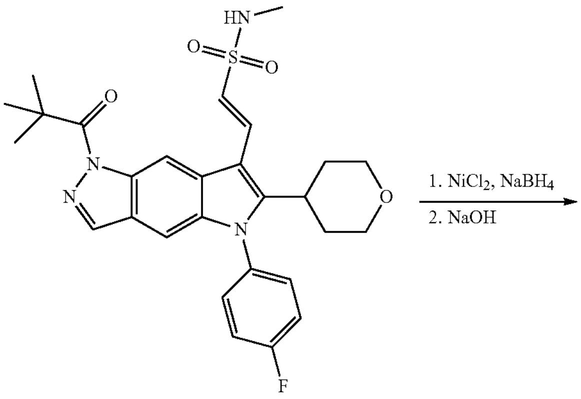

C153

-continued

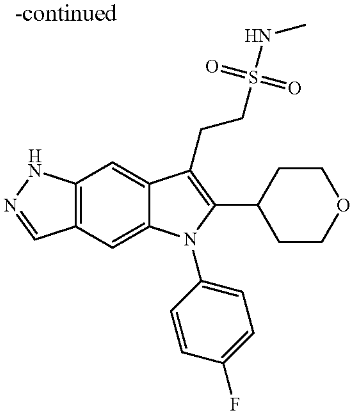

159

Compound 159 was prepared from 1-[5-(4-fluorophenyl)-7-iodo-6-tetrahydropyran-4-yl-pyrrolo[2,3-f]indazol-1-yl]-2,2-dimethyl-propan-1-one using the method described for the preparation of 158. Purification by reversed-phase HPLC. Method: C18 Waters Sunfire column (30×150 mm, 5 micron). Gradient: MeCN in $H_2O$ with 0.1% trifluoroacetic acid. The product was then triturated with a mixture of heptane:dichloromethane (8:2) to afford the product. 2-[5-(4-fluorophenyl)-6-tetrahydropyran-4-yl-1H-pyrrolo[2,3-f]indazol-7-yl]-N-methyl-ethanesulfonamide (6.1 mg, 11%). $^1$H NMR (400 MHz, Methanol-$d_4$) δ 7.96 (d, J=1.0 Hz, 1H), 7.57 (t, J=1.1 Hz, 1H), 7.44-7.32 (m, 4H), 7.11 (d, J=1.1 Hz, 1H), 3.97 (dd, J=11.7, 4.1 Hz, 2H), 3.45-3.32 (m, 6H), 3.03-2.89 (m, 1H), 2.82 (s, 3H), 2.07 (qd, J=12.6, 4.4 Hz, 2H), 1.77 (d, J=13.2 Hz, 2H). LCMS m/z 457.1 $[M+H]^+$.

Compounds 160-163

Compounds 160-163 (Table 8) were prepared from the corresponding acids by HATU coupling with ammonia using the standard primary amide method described.

Standard Primary Amide Formation Procedure:

Carboxylic acid (5 mg) and HATU were suspended in DMF (0.3 mL), then DIPEA was added followed by an aqueous solution of $NH_3$. The reaction was stirred for 30 minutes. Water and dichloromethane were added. The mixture was extracted with dichloromethane (3×). The organic phases were passed through a phase separator, combined and concentrated. Purification by reversed-phase HPLC. Method: C18 Waters Sunfire column (30×150 mm, 5 micron). Gradient: MeCN in $H_2O$ with 0.2% formic acid.

TABLE 8

| Method of Preparation, structure and physicochemical data for compound 160-163 | | | |
|---|---|---|---|
| Compound | Acid Starting Material | Product | $^{1}$HNMR; LC m/z $[M + H]^+$. structure comment |
| 160 | From 112 | 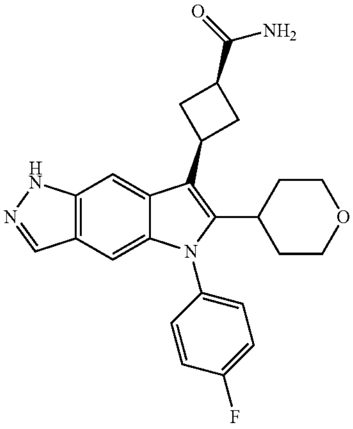 [SMILES: NC(=O)[C@H]1C[C@@H](c2c(C3CCOCC3)n(-c3ccc(F)cc3)c3cc4cn[nH]c4cc32)C1] | $^{1}$H NMR (400 MHz, DMSO-$d_6$) δ 12.77 (s, 1H), 8.28 (s, 1H), 7.95 (s, 1H), 7.53-7.42 (m, 4H), 7.40 (s, 1H), 7.02 (s, 1H), 6.94-6.72 (m, 1H), 3.96 (q, J = 9.3 Hz, 1H), 3.88 (dd, J = 11.5, 4.0 Hz, 2H), 3.21 (t, J = 11.8 Hz, 2H), 3.11 (p, J = 8.8 Hz, 1H), 2.96 (m, 2H), 2.84 (m, 1H), 2.44-2.32 (m, 2H), 1.95 (m, 2H), 1.65 (d, J = 12.8 Hz, 2H). LCMS m/z 433.34 $[M + H]^+$. |
| 161 | From 113 | 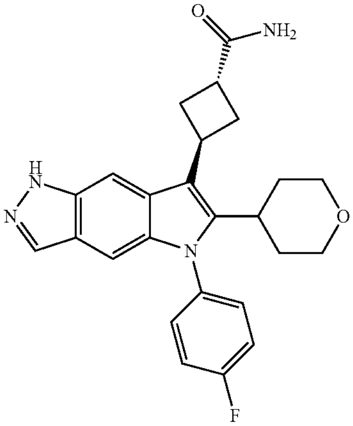 [SMILES: NC(=O)[C@H]1C[C@H](c2c(C3CCOCC3)n(-c3ccc(F)cc3)c3cc4cn[nH]c4cc32)C1] | $^{1}$H NMR (400 MHz, DMSO-$d_6$) δ 12.63 (s, 1H), 7.97 (s, 1H), 7.87 (s, 1H), 7.46 (m, 4H), 7.39 (s, 1H), 7.05 (s, 1H), 6.89 (s, 1H), 4.23 (m, 1H), 3.88 (d, J = 10.8 Hz, 2H), 3.25 (m, 1H), 3.19 (t, J = 11.6 Hz, 2H), 2.93 (q, J = 10.2 Hz, 2H), 2.78 (m, 1H), 1.89 (q, J = 12.7, 12.2 Hz, 2H), 1.64 (d, J = 13.0 Hz, 2H). $CH_2$ from cyclobutyl overlaps with DMSO peak. LCMS m/z 433.39 $[M + H]^+$. |
| 162 | From 114 | 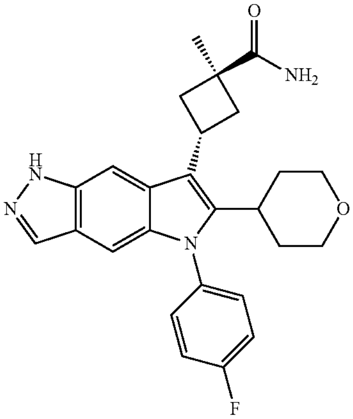 [SMILES: C[C@]1(C(N)=O)C[C@H](c2c(C3CCOCC3)n(-c3ccc(F)cc3)c3cc4cn[nH]c4cc32)C1] | $^{1}$H NMR (400 MHz, DMSO-$d_6$) δ 12.59 (s, 1H), 7.96 (s, 1H), 7.87 (s, 1H), 7.46 (m, 4H), 7.41 (s, 1H), 7.03 (s, 1H), 6.98 (s, 1H), 3.96-3.78 (m, 3H), 3.18 (t, J = 11.6 Hz, 2H), 2.86-2.73 (m, 3H), 2.63 (t, J = 11.0 Hz, 2H), 1.85 (m, 2H), 1.70-1.61 (m, 2H), 1.59 (s, 3H). LCMS m/z 447.38 $[M + H]^+$. |

TABLE 8-continued

| Method of Preparation, structure and physicochemical data for compound 160-163 | | | |
|---|---|---|---|
| Compound | Acid Starting Material | Product | $^1$HNMR; LC m/z $[M + H]^+$. structure comment |
| 163 | From 117 | 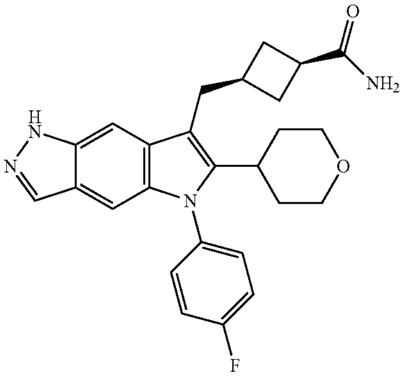 [SMILES: NC(=O)[C@H]1C[C@@H](Cc2c(C3CCOCC3)n(-c3ccc(F)cc3)c3cc4cn[nH]c4cc23)C1] | $^1$H NMR (400 MHz, DMSO-$d_6$) δ 12.61 (s, 1H), 7.95 (s, 1H), 7.54 (s, 1H), 7.46 (m, 4H), 7.19 (s, 1H), 6.96 (s, 1H), 6.72 (s, 1H), 3.85 (dd, J = 10.8, 3.8 Hz, 2H), 3.24 (t, J = 11.5 Hz, 2H), 3.07-2.88 (m, 3H), 2.83-2.70 (m, 1H), 2.15 (q, J = 8.8, 8.1 Hz, 2H), 2.07-1.92 (m, 2H), 1.83 (q, J = 12.1, 11.4 Hz, 2H), 1.65 (d, J = 12.8 Hz, 2H). A cyclobutyl CH overlaps with water peak. LCMS m/z 447.38 $[M + H]^+$. |

Compound 164-165

Compound 164-165 (Table 9) were prepared from S7 and the corresponding acetal as described for preparation of compound 16 or 33. In these examples, $MePh_2SiH$ and $MeSO_3H$ were used in the reductive coupling. The Cbz group was removed by transfer hydrogenation with Pd/C and ammonium formate.

TABLE 9

| Method of Preparation, structure and physicochemical data for compound 164-165 | | | |
|---|---|---|---|
| Compound | Aldehyde or acetal | Product | $^1$HNMR; LC m/z $[M + H]^+$. structure comment |
| 164 | 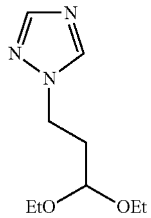 [SMILES: CCOC(CCn1cncn1)OCC] | 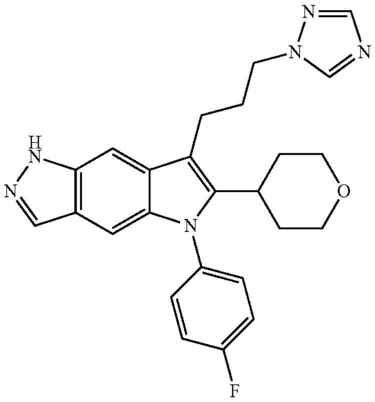 [SMILES: Fc1ccc(-n2c(C3CCOCC3)c(CCCn3cncn3)c3cc4[nH]ncc4cc32)cc1] | $^1$H NMR (400 MHz, Methanol-$d_4$) δ 8.55 (s, 1H), 8.08 (s, 1H), 7.93 (d, J = 1.0 Hz, 1H), 7.46 (t, J = 1.1 Hz, 1H), 7.40-7.29 (m, 4H), 7.05 (d, J = 1.1 Hz, 1H), 4.44 (t, J = 6.6 Hz, 2H), 3.97-3.86 (m, 2H), 3.27 (m, 2H), 2.97-2.89 (m, 3H), 2.38-2.25 (m, 2H), 1.93 (qd, J = 12.7, 4.4 Hz, 2H), 1.70-1.62 (m, 2H). LCMS m/z 445.31 $[M + H]^+$. |
| 165 | 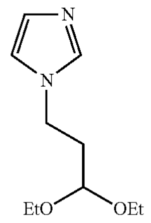 [SMILES: CCOC(CCn1ccnc1)OCC] | 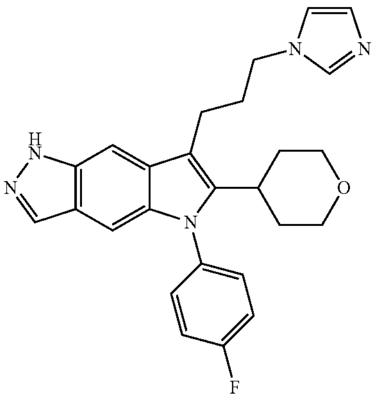 [SMILES: Fc1ccc(-n2c(C3CCOCC3)c(CCCn3ccnc3)c3cc4[nH]ncc4cc32)cc1] | $^1$H NMR (400 MHz, Methanol-$d_4$) δ 8.28 (s, 1H), 8.23 (m, 1H), 7.93 (d, J = 1.0 Hz, 1H), 7.44 (m, 2H), 7.37-7.29 (m, 4H), 7.26 (m, 1H), 7.05 (d, J = 1.1 Hz, 1H), 4.31 (t, J = 6.8 Hz, 2H), 3.98-3.86 (m, 2H), 3.25 (td, J = 11.8, 1.9 Hz, 2H), 3.01-2.79 (m, 3H), 2.32-2.18 (m, 2H), 1.90 (qd, J = 12.7, 4.4 Hz, 2H), 1.73-1.57 (m, 2H). LCMS m/z 444.32 $[M + H]^+$ |

Compound 166

3-[5-(4-fluorophenyl)-6-tetrahydropyran-4-yl-1H-pyrrolo[2,3-f]indazol-7-yl]propanamide (166)

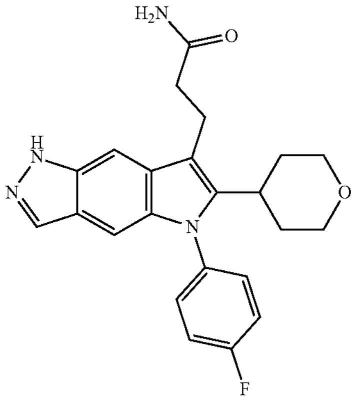 [SMILES: NC(=O)CCc1c(C2CCOCC2)n(-c2ccc(F)cc2)c2cc3cn[nH]c3cc12]

Compound 166 was prepared from compound 107 by HATU coupling according to the standard primary amide formation procedure described for the preparation of compounds 160-163.

$^1H$ NMR (400 MHz, DMSO-$d_6$) δ 12.65 (s, 1H), 7.96 (s, 1H), 7.55 (s, 1H), 7.46 (m, 5H), 7.02 (s, 1H), 6.87 (s, 1H), 3.94-3.82 (m, 2H), 3.22 (t, J=11.6 Hz, 3H), 3.11 (dd, J=10.0, 6.5 Hz, 2H), 2.89 (m, 1H), 2.48-2.39 (m, 2H), 2.00-1.78 (m, 2H), 1.67 (d, J=12.9 Hz, 2H). LCMS m/z 407.33 $[M+H]^+$.

Compound 167

2,3-dideuterio-3-[5-(4-fluorophenyl)-6-isopropyl-1H-pyrrolo[2,3-f]indazol-7-yl]propanoic Acid (167)

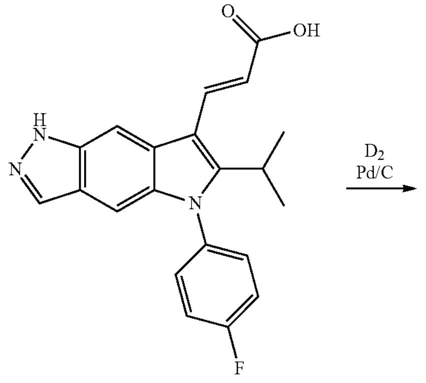

31

-continued

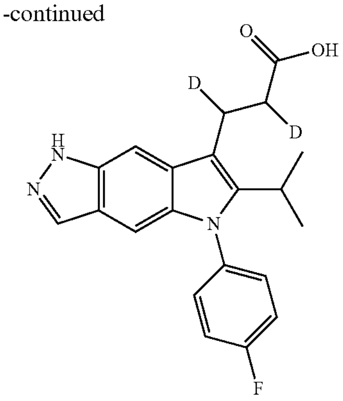

167

Step 1. Synthesis of 2,3-dideuterio-3-[5-(4-fluorophenyl)-6-isopropyl-1H-pyrrolo[2,3-f]indazol-7-yl] propanoic Acid (167)

Compound 31 (30 mg, 0.083 mmol) was added to a round bottle flask, into which Pd on carbon (9 mg, 0.008 mmol) was added under $N_2$, followed by adding EtOAc (5 mL) and Methanol-$d_4$ (4 mL). A three way adaptor with one side connected to a balloon of $D_2$ was added onto the round bottle, and exhausted the system with vacuum and refill with $D_2$, repeated three times and the mixture was stirred under $D_2$ balloon at room temperature for 4 h. The catalyst was filtered off through a pad of Celite® and washed with EtOAc and methanol. The filtrate was concentrated under reduced pressure. Purification by reversed-phase HPLC. Method: C18 Waters Sunfire column (30×150 mm, 5 micron). Gradient: MeCN in $H_2O$ with 0.2% formic acid. 2,3-dideuterio-3-[5-(4-fluorophenyl)-6-isopropyl-1H-pyrrolo[2,3-f]indazol-7-yl]propanoic acid (15.1 mg, 48%). $^1H$ NMR (300 MHz, DMSO-$d_6$) δ 12.60 (s, 1H), 12.43 (s, 1H), 7.95 (d, J=1.0 Hz, 1H), 7.53-7.37 (m, 5H), 7.01 (d, J=1.1 Hz, 1H), 3.10 (d, J=5.6 Hz, 1H), 3.01 (p, J=7.1 Hz, 1H), 2.54 (d, J=5.5 Hz, 1H), 1.25 (d, J=7.2 Hz, 6H). LCMS m/z 368.12 $[M+H]^+$.

Compound 168 and 169
2,3,3-trideuterio-3-[5-(4-fluorophenyl)-6-isopropyl-1H-pyrrolo[2,3-f]indazol-7-yl]propanoic acid (168) and 3,3-dideuterio-3-[5-(4-fluorophenyl)-6-isopropyl-1H-pyrrolo[2,3-f]indazol-7-yl]propanoic Acid (169)
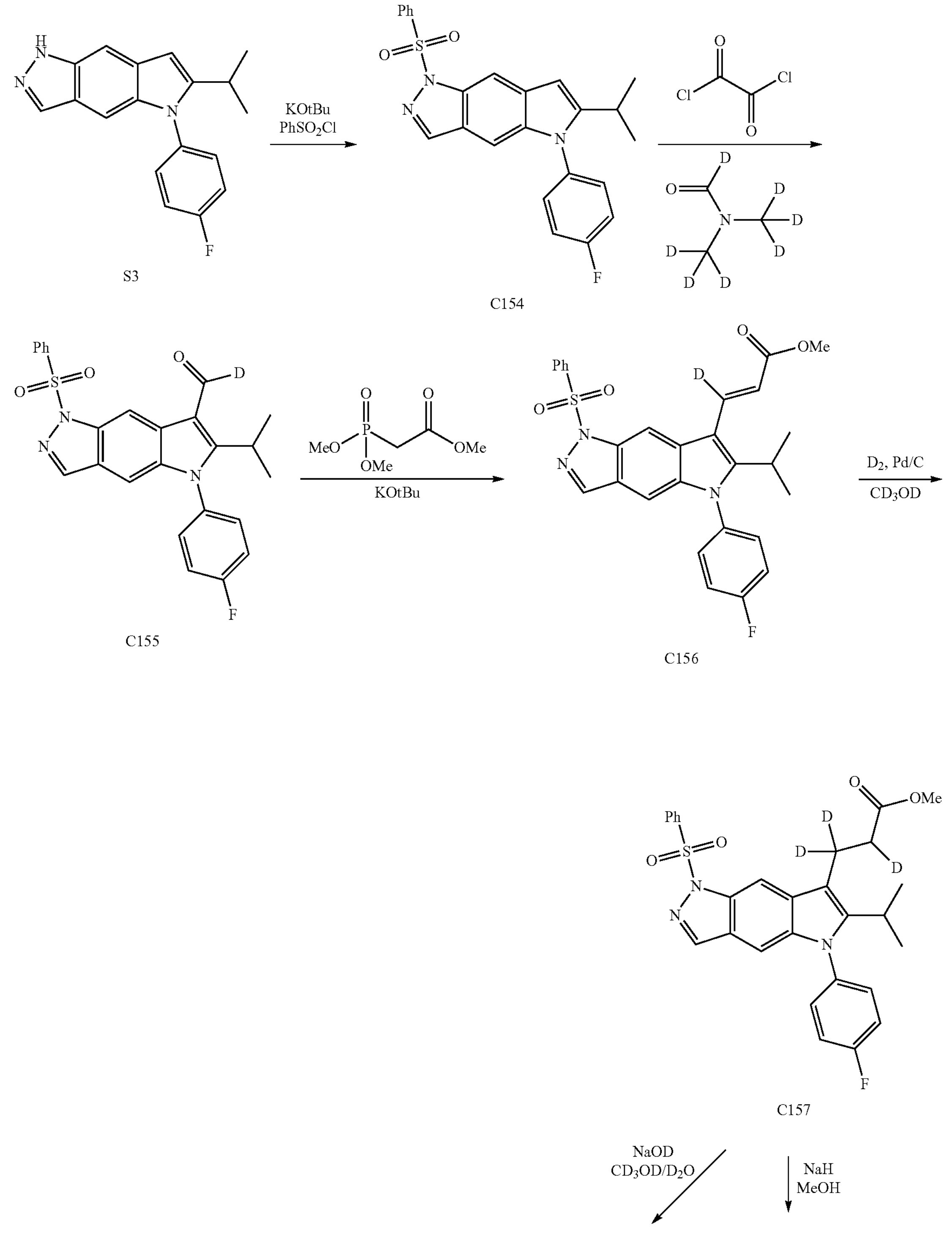
S3
C154
C155
C156
C157

-continued

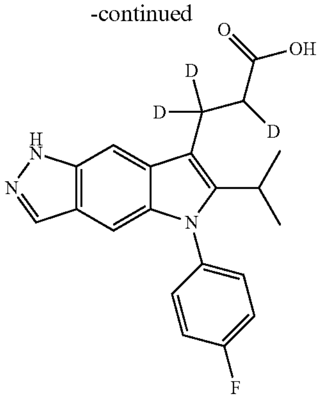

168

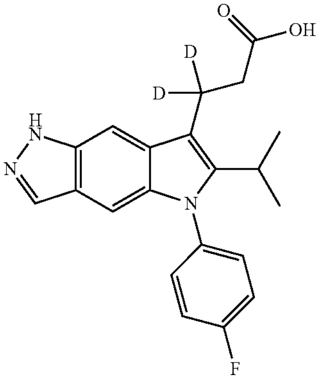

169

Step 1. Synthesis of [1-(benzenesulfonyl)-5-(4-fluorophenyl)-6-isopropyl-pyrrolo[2,3-f]indazol-7-yl]-deuterio-methanone (C155)

1-deuterio-N,N-bis(trideuteriomethyl)formamide (2.22 mL, 28.53 mmol) was added to a stirred solution of $(COCl)_2$ (2.22 mL of 2 M, 4.440 mmol) at 0° C. The white suspension was stirred at 0° C. for 10 minutes. A solution of 1-(benzenesulfonyl)-5-(4-fluorophenyl)-6-isopropyl-pyrrolo[2,3-f]indazole C154 (1 g, 2.30 mmol) in dichloromethane (10 mL) was added dropwise. The suspension slowly dissolved to form a red solution and the solution was stirred at room temperature for 30 minutes, then for an additional 1 hour. The amber solution was basified with sat. $NaHCO_3$(50 mL), and diluted with dichloromethane (100 mL). The organic layer was separated, dried over $Na_2SO_4$, and the solvent was removed under reduced pressure. The crude product was slurried into 10 mL of MTBE and filtered. The filter cake was dried under high vacuum overnight to give [1-(benzenesulfonyl)-5-(4-fluorophenyl)-6-isopropyl-pyrrolo[2,3-f]indazol-7-yl]-deuterio-methanone (926 mg, 86%). $^1H$ NMR (300 MHz, DMSO-$d_6$) δ 9.01 (t, J=1.0 Hz, 1H), 8.51 (d, J=0.9 Hz, 1H), 7.90-7.78 (m, 2H), 7.74-7.62 (m, 3H), 7.62-7.47 (m, 4H), 7.29 (d, J=1.0 Hz, 1H), 3.20 (p, J=7.2 Hz, 1H), 1.43 (d, J=7.2 Hz, 6H). LCMS m/z 463.17 $[M+H]^+$.

Step 2. Synthesis of methyl (E)-3-[1-(benzenesulfonyl)-5-(4-fluorophenyl)-6-isopropyl-pyrrolo[2,3-f]indazol-7-yl]-3-deuterio-prop-2-enoate (C156)

At 0° C., KOtBu (3.91 mL of 1 M, 3.910 mmol) was added to a solution of methyl 2-dimethoxyphosphorylacetate (717 μL, 4.43 mmol) in THF (12 mL) and the solution was stirred at room temperature for 30 minutes. The solution turned white and the reaction mixture was cooled on an ice bath. A solution of [1-(benzenesulfonyl)-5-(4-fluorophenyl)-6-isopropyl-pyrrolo[2,3-f]indazol-7-yl]-deuterio-methanone C155 (926 mg, 1.97 mmol) in THF (12 mL) was added dropwise. The reaction mixture was heated at 70° C. for 18 h, and cooled to room temperature. The solvent was evaporated under reduced pressure and the residue slurried in water (50 mL). The aqueous layer was extracted with EtOAc (2×50 mL) and the organic phase was dried over $Na_2SO_4$, filtered and evaporated. The crude was slurried into MeCN, filtered and dried in the vacuum oven over the weekend to give methyl (E)-3-[1-(benzenesulfonyl)-5-(4-fluorophenyl)-6-isopropyl-pyrrolo[2,3-f]indazol-7-yl]-3-deuterio-prop-2-enoate (594 mg, 57%). $^1H$ NMR (300 MHz, DMSO-d6) δ 8.50 (s, 2H), 7.91-7.80 (m, 2H), 7.71-7.44 (m, 7H), 7.27 (d, J=0.8 Hz, 1H), 6.48 (s, 1H), 3.80 (s, 3H), 3.21-3.09 (m, 1H), 1.35 (d, J=7.2 Hz, 6H). LCMS 519.2 $[M+H]^+$.

Step 3. Synthesis of methyl 3-[1-(benzenesulfonyl)-5-(4-fluorophenyl)-6-isopropyl-pyrrolo[2,3-f]indazol-7-yl]-2,3,3-trideuterio-propanoate (C157)

10% Pd/C (128 mg, 0.12 mmol) was added under nitrogen to a round bottom flask. The Pd/C was wet with ethyl acetate and a solution of methyl (E)-3-[1-(benzenesulfonyl)-5-(4-fluorophenyl)-6-isopropyl-pyrrolo[2,3-f]indazol-7-yl]-3-deuterio-prop-2-enoate C156 (594 mg, 1.13 mmol) in EtOAc (11 mL) and trideuterio(deuteriooxy)methane (11 mL) was added. A three way adaptor with one side connected with a balloon of deuterium was added onto the flask. The system was evacuated and refilled with $D_2$. The cycle was repeated three times and the mixture was stirred under $D_2$ balloon at room temperature for 4 hours. The catalyst was filtered off over a pad of Celite®, washing with EtOAc and methanol. The filtrate was concentrated to afford the product. Methyl 3-[1-(benzenesulfonyl)-5-(4-fluorophenyl)-6-isopropyl-pyrrolo[2,3-f]indazol-7-yl]-2,3,3-trideuterio-propanoate (550 mg, 91%). $^1H$ NMR (300 MHz, DMSO-d6) δ 8.43 (d, J=0.9 Hz, 1H), 8.16 (t, J=1.0 Hz, 1H), 7.91-7.84 (m, 2H), 7.68-7.61 (m, 1H), 7.56-7.39 (m, 6H), 7.13 (d, J=1.0 Hz, 1H), 3.68 (s, 3H), 3.04 (p, J=7.2 Hz, 1H), 2.69 (s, 1H), 1.25 (d, J=7.1 Hz, 6H). LCMS m/z 523.25 $[M+H]^+$.

Step 4. Synthesis of 2,3,3-trideuterio-3-[5-(4-fluorophenyl)-6-isopropyl-1H-pyrrolo[2,3-f]indazol-7-yl]propanoic Acid (168)

3-[1-(benzenesulfonyl)-5-(4-fluorophenyl)-6-isopropyl-pyrrolo[2,3-f]indazol-7-yl]-2,3,3-trideuterio-propanoate C157 (70 mg, 0.13 mmol) was dissolved in trideuterio (deuteriooxy)methane (1.5 mL) and THF (1.5 mL). D20 (0.5 mL) and [$^2$H]O (Sodium salt) (135 μL of 40% w/v, 1.317 mmol) was added and the mixture was stirred for 2 hours at 65° C. The mixture was cooled to room temperature and concentrated to dryness under reduced pressure. $D_2O$ (1 mL) and 2 mL of DMSO-d6 were added. Purification by reversed-phase chromatography (Column: C18. Gradient: 10-100% MeCN in water with 0.1% trifluoacetic acid) afforded the product. 2,3,3-trideuterio-3-[5-(4-fluorophenyl)-6-isopropyl-1H-pyrrolo[2,3-f]indazol-7-yl]propanoic acid (Trifluoroacetic acetate salt) (35.3 mg, 61%). $^1H$ NMR (300 MHz, DMSO-$d_6$) δ 12.61 (s, 2H), 7.95 (d, J=1.0 Hz, 1H), 7.52-7.40 (m, 5H), 7.01 (d, J=1.1 Hz, 1H), 3.01 (p, J=7.2 Hz, 1H), 2.55 (s, 1H), 1.25 (d, J=7.2 Hz, 6H). LCMS m/z 369.2 $[M+H]^+$.

Step 5. Synthesis of 3,3-dideuterio-3-[5-(4-fluorophenyl)-6-isopropyl-1H-pyrrolo[2,3-f]indazol-7-yl]propanoic Acid (169)

Methyl 3-[1-(benzenesulfonyl)-5-(4-fluorophenyl)-6-isopropyl-pyrrolo[2,3-f]indazol-7-yl]-2,3,3-trideuterio-propanoate C157 (59 mg, 0.11 mmol) and a stir bar were added to a 30 ml vial followed by methanol (3.3 mL). Sodium hydride (28 mg, 0.70 mmol) was added and the reaction was flushed the vial with nitrogen and sealed. The reaction was heated at 70° C. overnight, then concentrated to dryness. Purification by reversed-phase chromatography (Column: C18. Gradient: 10-100% MeCN in water with 0.1% TFA) afforded the product. 3,3-dideuterio-3-[5-(4-fluorophenyl)-6-isopropyl-1H-pyrrolo[2,3-f]indazol-7-yl]propanoic acid (Trifluoroacetic Acid (0.5)) (13.0 mg, 27%). $^1H$ NMR (300 MHz, DMSO-$d_6$) δ 12.45 (s, 2H), 7.95 (d, J=1.0 Hz, 1H), 7.52-7.38 (m, 5H), 7.01 (d, J=1.1 Hz, 1H), 3.01 (p, J=7.1 Hz, 1H), 2.57 (s, 2H), 1.25 (d, J=7.1 Hz, 6H). LCMS m/z 368.21 $[M+H]^+$.

Compound 170

2,2-dideuterio-3-[5-(4-fluorophenyl)-6-isopropyl-1H-pyrrolo[2,3-f]indazol-7-yl]propanoic Acid (170)

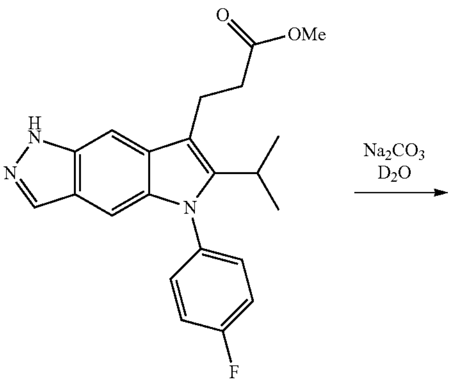

C36

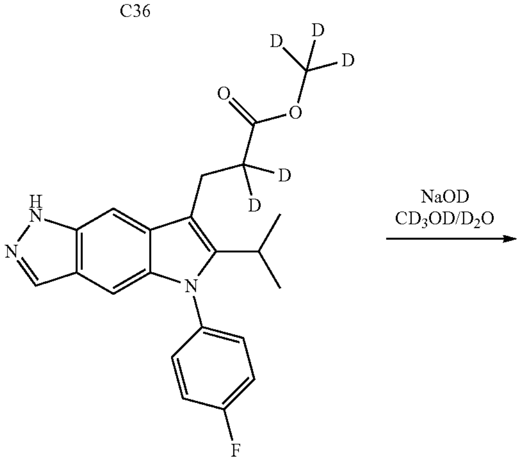

C158

-continued

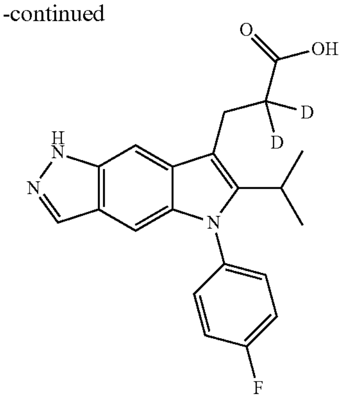

170

Step 1. Synthesis of trideuteriomethyl 2,2-dideuterio-3-[5-(4-fluorophenyl)-6-isopropyl-1H-pyrrolo[2,3-f]indazol-7-yl]propanoate (C158)

Methyl 3-[5-(4-fluorophenyl)-6-isopropyl-1H-pyrrolo[2,3-f]indazol-7-yl]propanoate C36 (22.9 mg, 0.06 mmol) and $Na_2CO_3$ (30 mg, 0.28 mmol) were weighed into a 4 ml vial and a stir bar was added. Added trideuterio(deuteriooxy)methane (1.5 mL) and flushed with nitrogen. The reaction vial was sealed and heated overnight at 70° C. The mixture was concentrated in vacuo then diluted with dichloromethane (24 mL) and washed with $D_2O$ (10 mL). The saponified by-product stayed in the water layer leaving the product in the organic layer. The organic layer was passed through a phase separator and concentrated to dryness to give trideuteriomethyl 2,2-dideuterio-3-[5-(4-fluorophenyl)-6-isopropyl-1H-pyrrolo[2,3-f]indazol-7-yl]propanoate (15.6 mg, 66%). $^1H$ NMR (300 MHz, DMSO-$d_6$) δ 12.61 (s, 1H), 7.95 (d, J=1.3 Hz, 1H), 7.51-7.39 (m, 5H), 7.01 (s, 1H), 3.15 (s, 2H), 3.01 (p, J=7.1 Hz, 1H), 1.25 (d, J=7.2 Hz, 6H). LCMS m/z 382.43 $[M+H]^+$.

Step 2. Synthesis of 2,2-dideuterio-3-[5-(4-fluorophenyl)-6-isopropyl-1H-pyrrolo[2,3-f]indazol-7-yl]propanoic Acid (170)

Trideuteriomethyl 2,2-dideuterio-3-[5-(4-fluorophenyl)-6-isopropyl-1H-pyrrolo[2,3-f]indazol-7-yl]propanoate C158 (15 mg, 0.04 mmol) was dissolved in methanol (750 μL) and THF (750 μL). Aqueous $[^2H]O$ (Sodium salt) (40 μL of 40% w/v, 0.4 mmol) was added and stirred over 1 hour at 50° C. The mixture was cooled to room temperature and concentrated to dryness under reduced pressure. $D_2O$ (1 mL) and 2 mL of DMSO-$d_6$ was added. Purification by reversed-phase HPLC. Method: C18 Waters Sunfire column (30×150 mm, 5 micron). Gradient: 20-100% MeCN in $H_2O$ with 0.2% formic acid. 2,2-dideuterio-3-[5-(4-fluorophenyl)-6-isopropyl-1H-pyrrolo[2,3-f]indazol-7-yl]propanoic acid (8.3 mg, 54%). $^1H$ NMR (300 MHz, Methanol-$d_4$) δ 7.93 (d, J=1.0 Hz, 1H), 7.56 (t, J=1.1 Hz, 1H), 7.43-7.28 (m, 4H), 7.04 (d, J=1.1 Hz, 1H), 3.23 (s, 2H), 3.09 (h, J=7.2 Hz, 1H), 1.32 (d, J=7.2 Hz, 6H). LCMS m/z 368.12 $[M+H]^+$.

Compound 171
2,2,3,3-tetradeuterio-3-[5-(4-fluorophenyl)-6-isopropyl-1H-pyrrolo[2,3-f]indazol-7-yl]propanoic Acid (171)
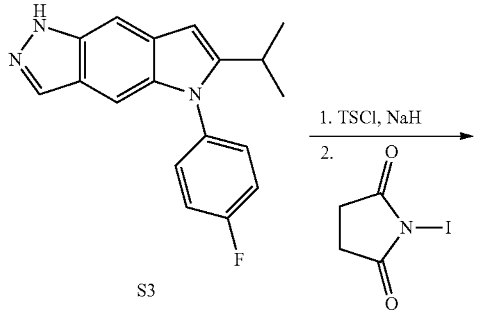
S3
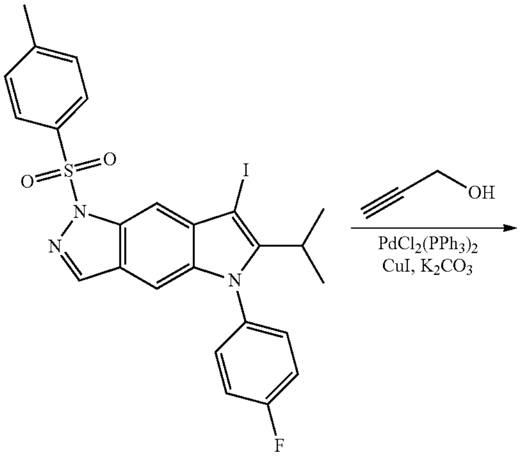
C159
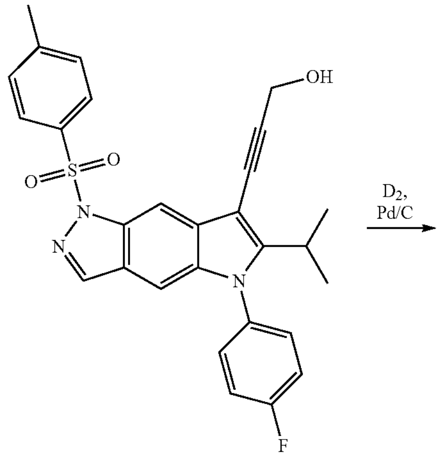
C160
-continued
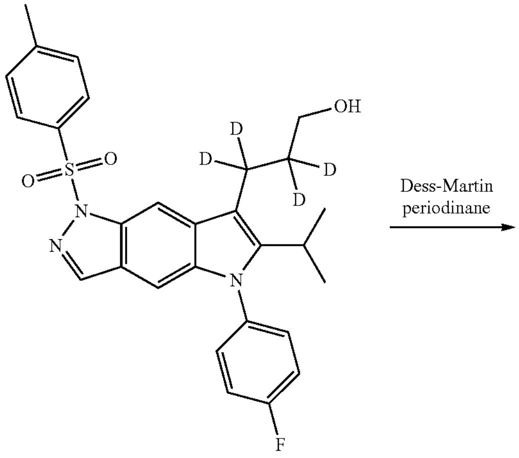
C161
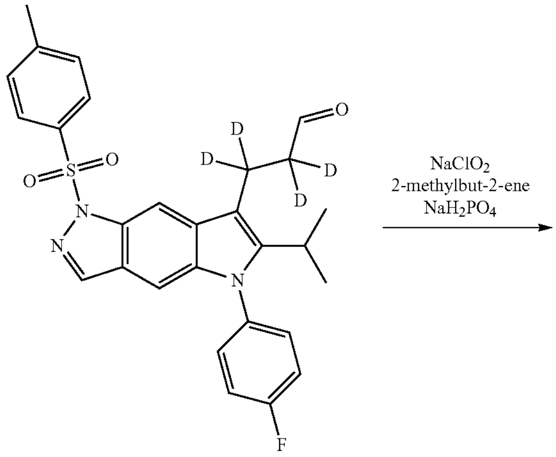
C162
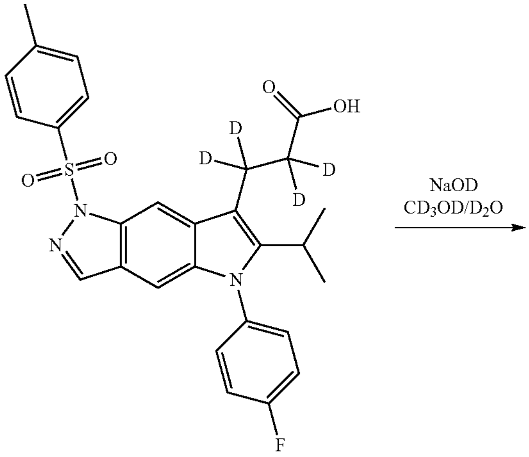
C163

-continued

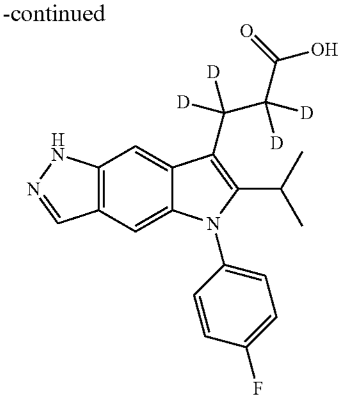

171

Step 1. Synthesis of 3-[5-(4-fluorophenyl)-6-isopropyl-1-(p-tolylsulfonyl)pyrrolo[2,3-f]indazol-7-yl]prop-2-yn-1-ol (C160)

A vial containing 5-(4-fluorophenyl)-7-iodo-6-isopropyl-1-(p-tolylsulfonyl)pyrrolo[2,3-f]indazole C159 (320 mg, 0.56 mmol), $K_2CO_3$ (156 mg, 1.13 mmol) and DME (5 mL). The flask was purged three times with Ar before the addition of prop-2-yn-1-ol (200 µL, 3.44 mmol), $Pd(PPh_3)_2Cl_2$ (39 mg, 0.06 mmol) and CuI (23 mg, 0.12 mmol). The flask was sealed and the reaction mixture was stirred at 90° C. overnight. The mixture was then concentrated and diluted with dichloromethane, and washed with water. The organic layers were passed through a phase separator and concentrated to dryness under reduced pressure. Purification by silica gel chromatography (Gradient: 0-100% EtOAc in heptane) afforded the product. 3-[5-(4-fluorophenyl)-6-isopropyl-1-(p-tolylsulfonyl)pyrrolo[2,3-f]indazol-7-yl]prop-2-yn-1-ol (44 mg, 16%). $^1$H NMR (300 MHz, DMSO-$d_6$) δ 8.46 (d, J=0.9 Hz, 1H), 8.23-8.13 (m, 1H), 7.74-7.65 (m, 2H), 7.63-7.53 (m, 2H), 7.48 (t, J=8.7 Hz, 2H), 7.35 (d, J=8.1 Hz, 2H), 7.29 (d, J=1.0 Hz, 1H), 5.42 (t, J=5.9 Hz, 1H), 4.50 (d, J=5.9 Hz, 2H), 2.92 (p, J=7.0 Hz, 1H), 2.29 (s, 3H), 1.40 (d, J=7.0 Hz, 6H). LCMS m/z 501.93 [M+H]$^+$.

Step 2. Synthesis of 2,2,3,3-tetradeuterio-3-[5-(4-fluorophenyl)-6-isopropyl-1-(p-tolylsulfonyl)pyrrolo[2,3-f]indazol-7-yl]propan-1-ol (C161)

3-[5-(4-fluorophenyl)-6-isopropyl-1-(p-tolylsulfonyl)pyrrolo[2,3-f]indazol-7-yl]prop-2-yn-1-ol C160 (45 mg, 0.09 mmol) was added to a round bottle flask, to which, 10% Pd on carbon (approximately 9.7 mg, 0.009 mmol) was added under nitrogen, followed by EtOAc (7.0 mL) and Methanol-$d_4$ (5.64 mL). A three way adaptor with one side connected with a balloon of $D_2$ was added on the round bottle, exhausted the system with vacuum and refill with $D_2$, repeated three times and the mixture was stirred under $D_2$ balloon at room temperature for 4 h. The catalyst was filtered off over Celite®, washed with EtOAc and methanol. The organic layers were concentrated the organics to dryness under reduced pressure to give 2,2,3,3-tetradeuterio-3-[5-(4-fluorophenyl)-6-isopropyl-1-(p-tolylsulfonyl)pyrrolo[2,3-f]indazol-7-yl]propan-1-ol (45 mg, 65%) which was used without further purification. LCMS m/z 510.24 [M+H]$^+$.

Step 3. Synthesis of 2,2,3,3-tetradeuterio-3-[5-(4-fluorophenyl)-6-isopropyl-1-(p-tolylsulfonyl)pyrrolo[2,3-f]indazol-7-yl]propanal (C162)

To a solution of 2,2,3,3-tetradeuterio-3-[5-(4-fluorophenyl)-6-isopropyl-1-(p-tolylsulfonyl)pyrrolo[2,3-f]indazol-7-yl]propan-1-ol C161 (51 mg, 0.10 mmol) in dichloromethane (1 mL) was added Dess Martin periodinane (47 mg, 0.11 mmol). The reaction mixture was stirred at room temperature for 30 minutes, then washed with water. The organic layer was passed through a phase separator and concentrated to dryness under reduced pressure. Purification by silica gel chromatography (Gradient: 0-100% EtOAc in heptane) afforded the product. 2,2,3,3-tetradeuterio-3-[5-(4-fluorophenyl)-6-isopropyl-1-(p-tolylsulfonyl)pyrrolo[2,3-f]indazol-7-yl]propanal (40.7 mg, 81%). LCMS m/z 508.17 [M+H]$^+$.

Step 4. Synthesis of 2,2,3,3-tetradeuterio-3-[5-(4-fluorophenyl)-6-isopropyl-1-(p-tolylsulfonyl)pyrrolo[2,3-f]indazol-7-yl]propanoic Acid (C163)

NaClO (80 mg, 0.71 mmol) in water (300 µL) was added to a stirred mixture of 2,2,3,3-tetradeuterio-3-[5-(4-fluorophenyl)-6-isopropyl-1-(p-tolylsulfonyl)pyrrolo[2,3-f]indazol-7-yl]propanal C162 (40.7 mg, 0.08 mmol) and $NaH_2PO_4$ (80 mg, 0.70 mmol) in tert-butanol (1.4 µL) at room temperature. 2-methylbut-2-ene (200 µL of 2 M, 0.4 mmol) in THF was then added. The pale brown mixture was stirred at room temperature for 5 hours. The solution was diluted with water and EtOAc, separated the layers and extracted the aqueous phase with EtOAc. The combined organics were washed with brine, dried over sodium sulfate and concentrated under reduced pressure. Purification by silica gel chromatography (Gradient: 0-10% methanol in dichloromethane) afforded the product. 2,2,3,3-tetradeuterio-3-[5-(4-fluorophenyl)-6-isopropyl-1-(p-tolylsulfonyl)pyrrolo[2,3-f]indazol-7-yl]propanoic acid (23 mg, 53%). $^1$H NMR (300 MHz, Chloroform-d) δ 8.31-8.25 (m, 1H), 8.13 (d, J=0.8 Hz, 1H), 7.90-7.83 (m, 2H), 7.35-7.29 (m, 2H), 7.27-7.18 (m, 4H), 7.02 (d, J=1.0 Hz, 1H), 3.12 (p, J=7.2 Hz, 1H), 2.34 (s, 3H), 1.32 (d, J=7.2 Hz, 6H). LCMS m/z 524.24 [M+H]$^+$.

Step 5. Synthesis of 2,2,3,3-tetradeuterio-3-[5-(4-fluorophenyl)-6-isopropyl-1H-pyrrolo[2,3-f]indazol-7-yl]propanoic Acid (171)

2,2,3,3-tetradeuterio-3-[5-(4-fluorophenyl)-6-isopropyl-1-(p-tolylsulfonyl)pyrrolo[2,3-f]indazol-7-yl]propanoic acid C163 (22 mg, 0.04 mmol) was dissolved in trideuterio (deuteriooxy)methane (1 mL) and THF (1 mL). Added $D_2O$ (0.2 mL) and aqueous [$^2$H]O (Sodium salt) (44 µL of 40% w/v, 0.43 mmol) and stirred over 1 hours at 65° C. The mixture was concentrated to dryness under reduced pressure, dissolved in a DMSO/water and purified by reversed-phase chromatography (Column: C18. Gradient: 10-100% MeCN in water with 0.1% TFA) to afford the product. 2,2,3,3-tetradeuterio-3-[5-(4-fluorophenyl)-6-isopropyl-1H-pyrrolo[2,3-f]indazol-7-yl]propanoic acid (Trifluoroacetate salt) (13.7 mg, 61%). $^1$H NMR (300 MHz, DMSO-$d_6$) δ 12.61 (s, 1H), 7.95 (d, J=1.0 Hz, 1H), 7.51-7.43 (m, 5H), 7.01 (d, J=1.1 Hz, 1H), 3.01 (p, J=7.1 Hz, 1H), 1.25 (d, J=7.2 Hz, 6H). LCMS m/z 370.15 [M+H]$^+$.

Compound 172

2,2-dideuterio-3-[3-deuterio-5-(4-fluorophenyl)-6-isopropyl-1H-pyrrolo[2,3-f]indazol-7-yl]propanoic Acid (172)

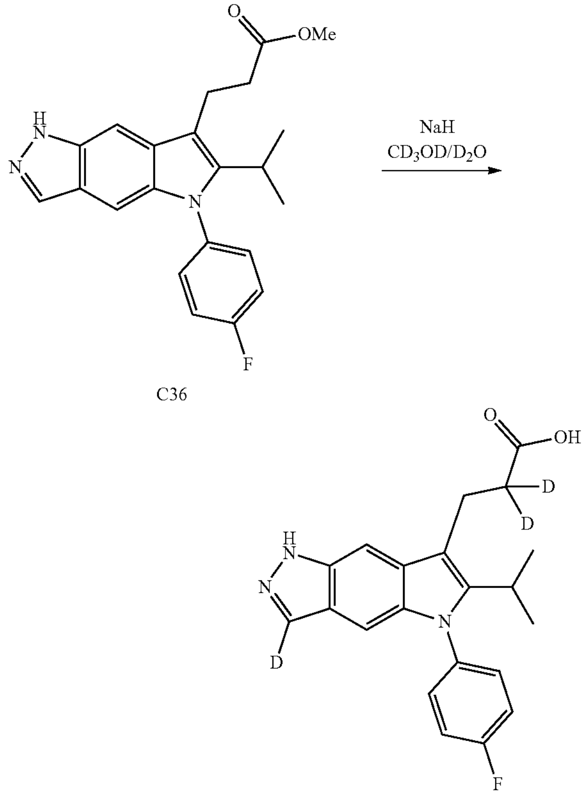

C36

172

Preparation of 2,2-dideuterio-3-[3-deuterio-5-(4-fluorophenyl)-6-isopropyl-1H-pyrrolo[2,3-f]indazol-7-yl]propanoic Acid (172)

To a solution of methyl 3-[5-(4-fluorophenyl)-6-isopropyl-1H-pyrrolo[2,3-f]indazol-7-yl]propanoate C36 (26 mg, 0.07 mmol) in trideuterio(deuteriooxy)methane (1.5 mL) was added NaH (10 mg, 0.25 mmol). The reaction vessel was flushed with nitrogen and sealed, and heated over the weekend at 70° C. The reaction mixture was concentrated to dryness and retreated with trideuterio(deuteriooxy)methane (1.5 mL). The mixture was heated at 70° C. for a further 24 hours. $D_2O$ (0.5 mL) was added and the mixture was heated at 70° C. for 1 hour. The mixture was concentrated, and under reduced pressure. Diluted with DMSO-$d_6$ (1 mL) and $D_2O$ (0.5 mL). Purification by reversed-phase chromatography (Column: C18. Gradient: 20-100% MeCN in water with 0.1% formic acid) afforded the product. 2,2-dideuterio-3-[3-deuterio-5-(4-fluorophenyl)-6-isopropyl-1H-pyrrolo[2,3-f]indazol-7-yl]propanoic acid (18.8 mg, 75%). $^1H$ NMR (300 MHz, DMSO-d6) δ 12.60 (s, 1H), 12.27 (s, 1H), 7.52-7.39 (m, 5H), 7.01 (d, J=1.1 Hz, 1H), 3.11 (s, 2H), 3.01 (p, J=7.1 Hz, 1H), 1.25 (d, J=7.2 Hz, 6H). LCMS m/z 369.11 $[M+H]^+$.

Compound 173

(2S,3S,4S,5R)-6-[3-[5-(4-fluorophenyl)-6-isopropyl-1H-pyrrolo[2,3-f]indazol-7-yl]propanoyloxy]-3,4,5-trihydroxy-tetrahydropyran-2-carboxylic Acid (173)

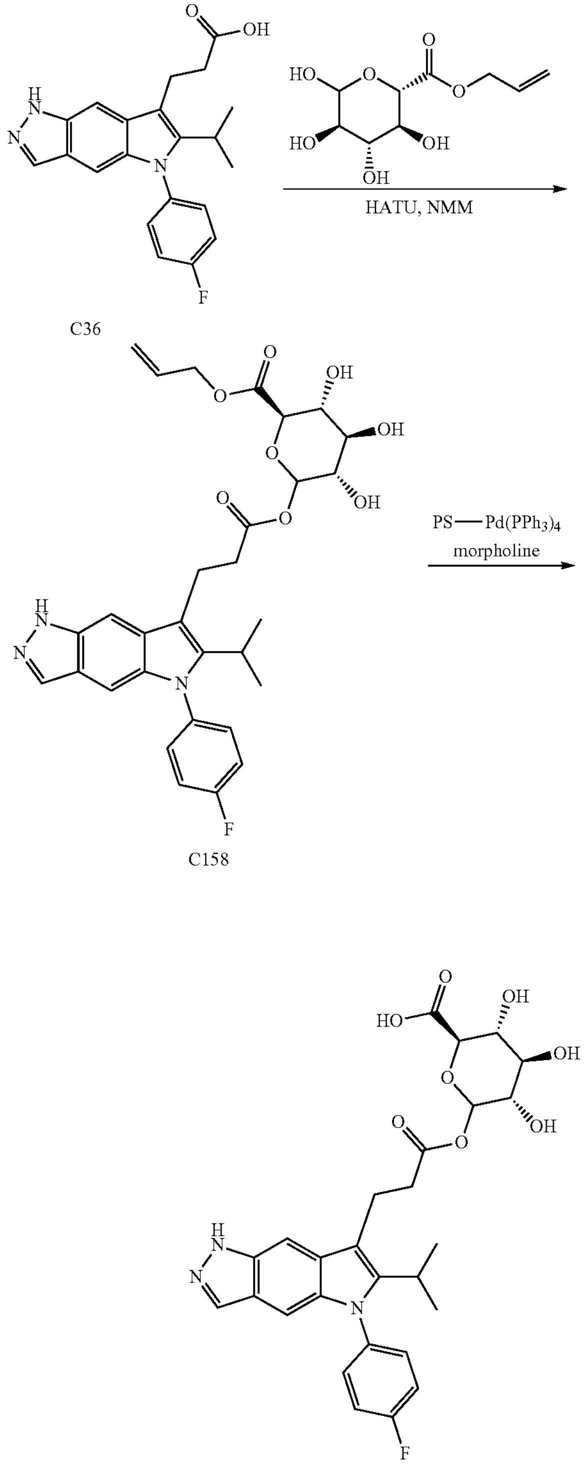

C36

C158

173

Step 1. Synthesis of allyl (2S,3S,4S,5R)-6-[3-[5-(4-fluorophenyl)-6-isopropyl-1H-pyrrolo[2,3-f]indazol-7-yl]propanoyloxy]-3,4,5-trihydroxy-tetrahydropyran-2-carboxylate (C158)

3-[5-(4-fluorophenyl)-6-isopropyl-1H-pyrrolo[2,3-f]indazol-7-yl]propanoic acid C36 (53 mg, 0.14 mmol), allyl (2S,3S,4S,5R)-3,4,5,6-tetrahydroxytetrahydropyran-2-carboxylate (34 mg, 0.15 mmol), and HATU (55 mg, 0.14 mmol) were dissolved in acetonitrile (1.4 mL). NMM (32 μL, 0.29 mmol) was added and the mixture was stirred overnight at room temperature. The reaction mixture was diluted with dichloromethane and washed with 50% saturated sodium bicarbonate. The mixture was passed through a phase separator and concentrated to dryness under reduced pressure. Silica gel chromatography (Gradient: 0-10% MeOH in dichloromethane) afforded the product. Allyl (2S,3S,4S,5R)-6-[3-[5-(4-fluorophenyl)-6-isopropyl-1H-pyrrolo[2,3-f]indazol-7-yl]propanoyloxy]-3,4,5-trihydroxy-tetrahydropyran-2-carboxylate (20.1 mg, 21%). LCMS m/z 582.33 $[M+H]^+$.

Step 2. Synthesis of (2S,3S,4S,5R)-6-[3-[5-(4-fluorophenyl)-6-isopropyl-1H-pyrrolo[2,3-f]indazol-7-yl]propanoyloxy]-3,4,5-trihydroxy-tetrahydropyran-2-carboxylic Acid (173)

To a solution of allyl (2S,3S,4S,5R)-6-[3-[5-(4-fluorophenyl)-6-isopropyl-1H-pyrrolo[2,3-f]indazol-7-yl]propanoyloxy]-3,4,5-trihydroxy-tetrahydropyran-2-carboxylate C158 (194 mg, 0.32 mmol) in dichloromethane (12 mL) at room temperature was added morpholine (60 μL, 0.69 mmol). The solution was bubbled through with nitrogen for 5 minutes, then $PS-PPh_3-Pd$ (443 mg of 0.11 mmol/g, 0.05 mmol) was added. The reaction was allowed to stir for 30 minutes. MP-TMT was added to the reaction mixture with a few drops of methanol for solubility. The mixture was stirred for 4 hours. The mixture was concentrated in vacuo. Purification by reversed-phase chromatography (Column: C18. Gradient: 10-100% MeCN in water with 0.1% formic acid) afforded the product. (2S,3S,4S,5R)-6-[3-[5-(4-fluorophenyl)-6-isopropyl-1H-pyrrolo[2,3-f]indazol-7-yl]propanoyloxy]-3,4,5-trihydroxy-tetrahydropyran-2-carboxylic acid (44.3 mg, 25%). $^1H$ NMR (300 MHz, DMSO-d6) δ 12.90 (s, 1H), 12.59 (s, 1H), 7.95 (d, J=0.9 Hz, 1H), 7.56-7.39 (m, 5H), 7.01 (d, J=1.1 Hz, 1H), 5.52-5.23 (m, 4H), 3.80 (d, J=9.1 Hz, 1H), 3.39 (d, J=8.9 Hz, 2H), 3.26-3.10 (m, 3H), 3.02 (p, J=7.1 Hz, 1H), 2.81-2.68 (m, 2H), 1.25 (d, J=7.1 Hz, 6H). LCMS m/z 542.15 $[M+H]^+$.

Compound 174

7-(azetidin-3-yl)-5-(4-fluorophenyl)-6-isopropyl-1H-pyrrolo[2,3-f]indazole (174)

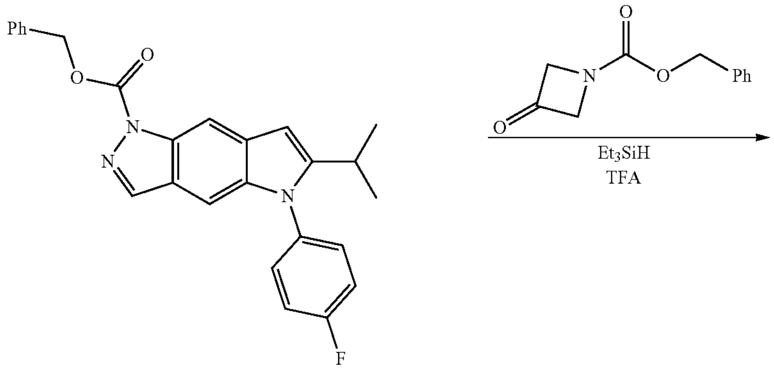

S4

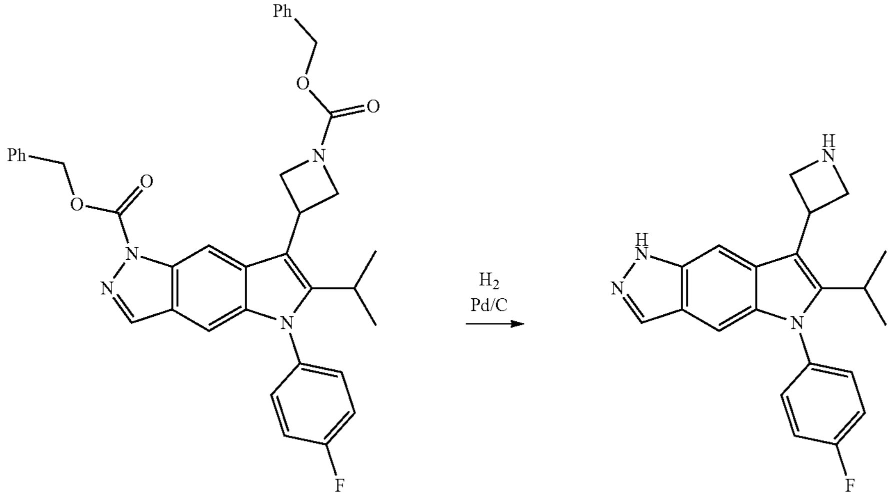

C165

174

Compound 174 was prepared in two steps from S4 by reductive coupling using $Et_3SiH$ and TFA then Cbz removal by hydrogenation, as described in the preparation of compound 32. 7-(azetidin-3-yl)-5-(4-fluorophenyl)-6-isopropyl-1H-pyrrolo[2,3-f]indazole (16 mg, 49%). $^1H$ NMR (300 MHz, DMSO-d6) δ 12.64 (s, 1H), 8.39-8.33 (m, 1H), 7.96 (s, 1H), 7.51-7.39 (m, 4H), 7.03 (d, J=1.0 Hz, 1H), 4.39 (p, J=8.0 Hz, 1H), 4.09-4.01 (m, 2H), 3.95 (dd, J=9.0, 7.3 Hz, 2H), 2.93 (p, J=7.2 Hz, 1H), 1.22 (d, J=7.2 Hz, 6H). LCMS m/z 349.0 $[M+H]^+$.

Compound 175-183

Compounds 175-183 (Table 10) were prepared from C169 or C170 (see scheme) by reductive coupling with the appropriate acetal or aldehyde, followed by deprotection of the phenyl sulfonyl or Cbz protecting group. Any modifications to this procedure are noted in the table footnotes.

Preparation of Intermediates 1-(benzenesulfonyl)-5-(4-fluorophenyl)-6-(2-methoxy-1,1-dimethyl-ethyl)pyrrolo[2,3-f]indazole C169 and benzyl 5-(4-fluoro-phenyl)-6-(2-methoxy-1,1-dimethyl-ethyl)pyrrolo[2,3-f]indazole-1-carboxylate C170

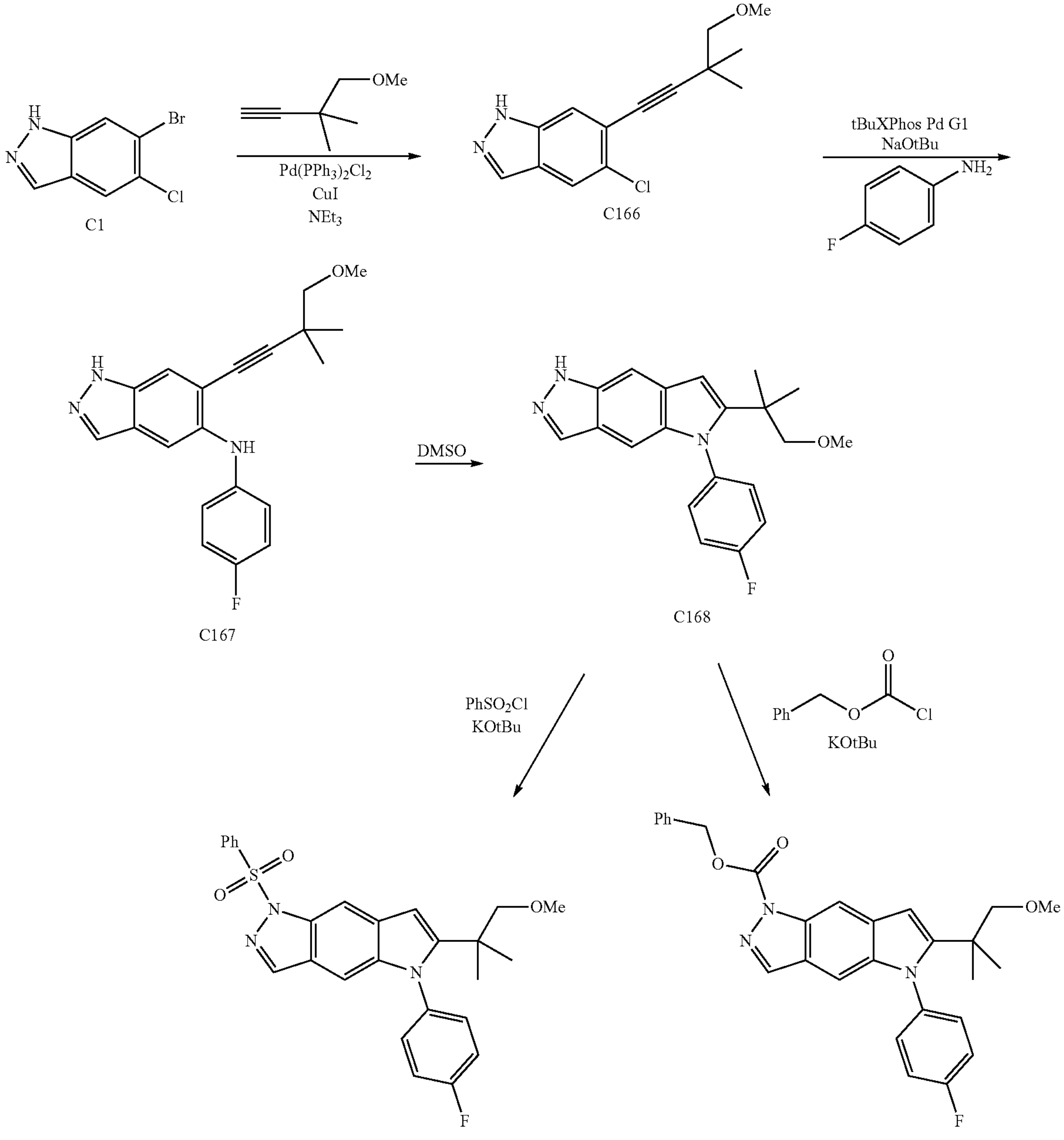

C1

C166

C167

C168

C169

C170

Step 1. Synthesis of 5-chloro-6-(4-methoxy-3,3-dimethyl-but-1-ynyl)-1H-indazole (C166)

A solution of 6-bromo-5-chloro-1H-indazole C1 (5.2 g, 22.5 mmol), $PPh_3$ (355 mg, 1.4 mmol), $Pd(PPh_3)_2Cl_2$ (473 mg, 0.67 mmol), CuI (257 mg, 1.3 mmol) and $Et_3N$ (40 mL) in 1,4-dioxane (40 mL) was purged with nitrogen. 4-methoxy-3,3-dimethyl-but-1-yne (3.5 g, 31.5 mmol) was added and the reaction was heated at 110° C. for 1.5 h. A white solid precipitated upon cooling. The reaction was filtered through Celite®, washing with EtOAc. The filtrate was concentrated and purified by silica gel chromatography (Gradient: 0-80% EtOAc/heptane) to afford the product as a brown solid (3.5 g, 59%). $^1$H NMR (300 MHz, Chloroform-d) δ 10.27 (s, 1H), 8.00 (s, 1H), 7.78 (d, J=0.5 Hz, 1H), 7.63 (s, 1H), 3.49 (s, 3H), 3.42 (s, 2H), 1.38 (s, 6H). LCMS m/z 263.1 $[M+H]^+$.

Step 2. Synthesis of N-(4-fluorophenyl)-6-(4-methoxy-3,3-dimethyl-but-1-ynyl)-1H-indazol-5-amine (C167)

A suspension of 5-chloro-6-(4-methoxy-3,3-dimethyl-but-1-ynyl)-1H-indazole C166 (4.3 g, 16.37 mmol), 4-fluoroaniline (2.5 mL, 26.4 mmol), NaOtBu (4.09 g, 42.6 mmol) in tBuOH (60 mL) were purged with nitrogen. tBuXPhos Pd G1 (563 mg, 0.82 mmol) was added and the mixture purged with nitrogen for an additional 10 min. The mixture was heated at 90° C. for 1 h. An additional 1.4% of tBuXPhos Pd G1 catalyst (~150 mg) was added, and the mixture heated to reflux for another 1 h. Then a further portion of tBuXPhos Pd G1 (80 mg) catalyst was added, and the mixture heated to reflux for 1.5 h. The mixture was concentrated in vacuo, and then saturated $NH_4Cl$ and EtOAc were added. The layers were separated and the aqueous layer extracted with further EtOAc. Combined organic layers dried, and concentrated in vacuo. Purification by silica gel chromatography (Gradient: 0-80% EtOAc/heptane) afforded the product. LCMS m/z 338.0 $[M+H]^+$.

Step 3. Synthesis of 5-(4-fluorophenyl)-6-(2-methoxy-1,1-dimethyl-ethyl)-1H-pyrrolo[2,3-f]indazole (C168)

A solution of C167 in DMSO (26 mL) was heated at 160° C. for 2 h. Upon cooling, 50% saturated $NaHCO_3$ solution (120 mL) was added. The mixture was extracted with EtOAc (×2). The organic layer was concentrated to afford the product as a grey solid which was used without further purification (5 g, 91%). $^1$H NMR (300 MHz, Chloroform-d) δ 9.89 (s, 1H), 7.99 (s, 1H), 7.54 (t, J=1.1 Hz, 1H), 7.47-7.36 (m, 2H), 7.28-7.19 (m, 2H), 6.88 (s, 1H), 6.57 (d, J=0.7 Hz, 1H), 3.27 (s, 3H), 3.23 (s, 2H), 1.33 (s, 6H). LCMS m/z 422.3 $[M+H]^+$.

Preparation of 1-(benzenesulfonyl)-5-(4-fluorophenyl)-6-(2-methoxy-1,1-dimethyl-ethyl)pyrrolo[2,3-f]indazole (C169)

5-(4-fluorophenyl)-6-(2-methoxy-1,1-dimethyl-ethyl)-1H-pyrrolo[2,3-f]indazole C168 (150 mg, 0.43 mmol) was dissolved in THF (1.8 mL). KOtBu (63 mg, 0.56 mmol) was added and stirred for 10 minutes. The reaction was cooled in an ice bath. benzenesulfonyl chloride (75 μL, 0.58 mmol) was added dropwise over 2 h. The mixture was stirred at 0° C. for an additional 2 h. An aqueous solution of $NH_4Cl_{(sat)}$, water and dichloromethane were added. The phases were separated on a phase separator. Purification by silica gel chromatography (Eluent: Ethyl acetate in dichloromethane). 1-(benzenesulfonyl)-5-(4-fluorophenyl)-6-(2-methoxy-1,1-dimethyl-ethyl)pyrrolo[2,3-f]indazole (185 mg, 72%). $^1$H NMR (400 MHz, DMSO) δ 8.42 (s, 1H), 8.20 (s, 1H), 7.84 (d, J=7.8 Hz, 2H), 7.64 (t, J=7.5 Hz, 1H), 7.60-7.36 (m, 6H), 6.92 (s, 1H), 6.72 (s, 1H), 3.15 (d, J=2.5 Hz, 5H), 1.25 (s, 7H). LCMS m/z 478.41 $[M+H]^+$.

Preparation of benzyl 5-(4-fluorophenyl)-6-(2-methoxy-1,1-dimethyl-ethyl)pyrrolo[2,3-f]indazole-1-carboxylate (C170)

Compound C170 was prepared from C168 using the method described for the preparation of S2.

Benzyl 5-(4-fluorophenyl)-6-(2-methoxy-1,1-dimethyl-ethyl)pyrrolo[2,3-f]indazole-1-carboxylate (833.4 mg, 67%). $^1$H NMR (300 MHz, DMSO-$d_6$) δ 8.33 (d, J=0.9 Hz, 1H), 8.26-8.20 (m, 1H), 7.58-7.37 (m, 9H), 7.01-6.96 (m, 1H), 6.67 (d, J=0.8 Hz, 1H), 5.51 (s, 2H), 3.17 (s, 2H), 3.15 (s, 3H), 1.25 (s, 6H). LCMS m/z 472.49 $[M+H]^+$.

TABLE 10

Method of Preparation, structure and physicochemical data for compound 175-183

| Compound | Aldehyde or acetal | Product | $^1$HNMR; LC m/z $[M + H]^+$. structure comment |
|---|---|---|---|
| 175[1] | 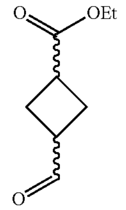 [SMILES: CCOC(=O)C1CC(C=O)C1] | 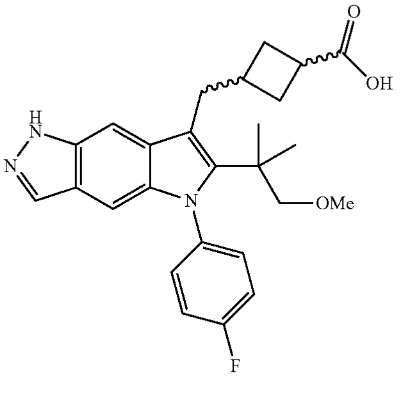 [SMILES: COCC(C)(C)c1c(CC2CC(C(=O)O)C2)c2cc3[nH]ncc3cc2n1-c1ccc(F)cc1] | $^1$H NMR (300 MHz, DMSO-$d_6$) δ 12.57 (s, 1H), 12.06 (s, 1H), 7.93-7.88 (m, 1H), 7.58-7.50 (m, 1H), 7.45-7.35 (m, 4H), 6.67 (d, J = 0.9 Hz, 1H), 3.23 (d, J = 1.6 Hz, 2H), 3.17-3.09 (m, 4H), 3.03 (d, J = 6.8 Hz, 1H), 2.86 (t, J = 8.6 Hz, 1H), 2.30-1.98 (m, 5H), 1.29 (d, J = 1.5 Hz, 6H). LCMS m/z 450.34 $[M + H]^+$. |

TABLE 10-continued

Method of Preparation, structure and physicochemical data for compound 175-183

| Compound | Aldehyde or acetal | Product | $^1$HNMR; LC m/z $[M + H]^+$. structure comment |
|---|---|---|---|
| 176[1] | 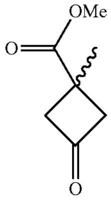 | 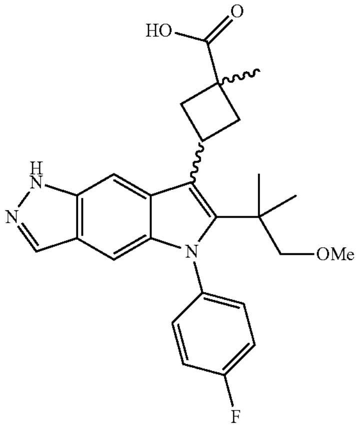 [SMILES: COCC(C)(C)c1c(C2CC(C)(C(=O)O)C2)c2cc3[nH]ncc3cc2n1-c1ccc(F)cc1] | $^1$H NMR (300 MHz, Methanol-$d_4$) δ 8.01 (t, J = 1.1 Hz, 1H), 7.91 (d, J = 1.0 Hz, 1H), 7.38-7.22 (m, 4H), 6.90 (d, J = 1.1 Hz, 1H), 4.41 (p, J = 9.8 Hz, 1H), 3.45 (s, 2H), 3.22 (s, 3H), 2.99-2.88 (m, 2H), 2.75 (td, J = 9.3, 2.7 Hz, 2H), 1.71 (s, 3H), 1.26 (s, 6H). LCMS m/z 450.3 $[M + H]^+$. |
| 177[1] | 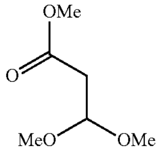 | 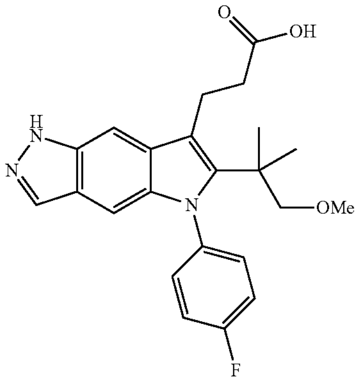 [SMILES: COCC(C)(C)c1c(CCC(=O)O)c2cc3[nH]ncc3cc2n1-c1ccc(F)cc1] | $^1$H NMR (300 MHz, DMSO-$d_6$) δ 12.60 (s, 1H), 12.52-12.2 (bs, 1H), 7.93 (d, J = 1.0 Hz, 1H), 7.50-7.46 (m, 1H), 7.44-7.38 (m, 4H), 6.71 (d, J = 1.1 Hz, 1H), 3.27 (s, 2H), 3.25-3.18 (m, 2H), 3.16 (s, 3H), 2.61-2.53 (m, 2H), 1.27 (s, 6H). LCMS m/z 410.29 $[M + H]^+$. |
| 178[2] | 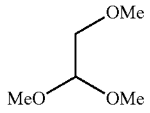 | 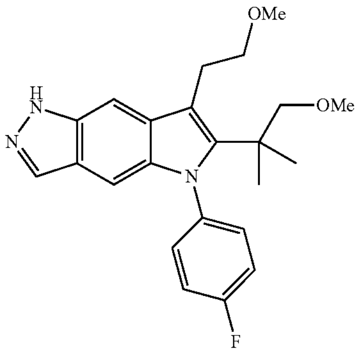 [SMILES: COCCc1c(C(C)(C)COC)n(-c2ccc(F)cc2)c2cc3cn[nH]c3cc12] | $^1$H NMR (400 MHz, Methanol-$d_4$) δ 7.98 (d, J = 1.1 Hz, 1H), 7.63 (t, J = 1.1 Hz, 1H), 7.48-7.42 (m, 2H), 7.41-7.33 (m, 2H), 6.84 (d, J = 1.1 Hz, 1H), 3.79 (dd, J = 8.6, 7.1 Hz, 2H), 3.51 (s, 3H), 3.41 (m, 4H), 3.30 (s, 3H), 1.44 (s, 6H). LCMS m/z 396.28 $[M + H]^+$. |
| 179[2,3] | 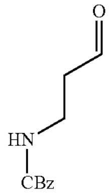 | 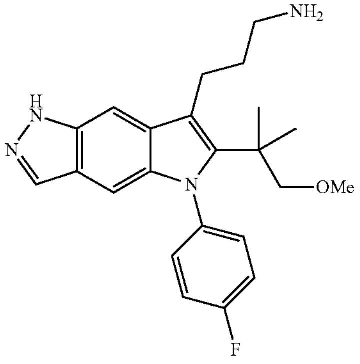 [SMILES: COCC(C)(C)c1c(CCCN)c2cc3[nH]ncc3cc2n1-c1ccc(F)cc1] | $^1$H NMR (400 MHz, DMSO-$d_6$) δ 12.66 (s, 1H), 8.38 (s, 2H), 7.94 (s, 1H), 7.52 (s, 1H), 7.41 (d, J = 6.7 Hz, 4H), 6.71 (s, 1H), 3.25 (s, 2H), 3.15 (s, 3H), 3.03-2.92 (m, 4H), 1.97-1.85 (m, 2H), 1.29 (s, 6H). LCMS m/z 395.14 $[M + H]^+$. |

TABLE 10-continued

| Method of Preparation, structure and physicochemical data for compound 175-183 | | | |
|---|---|---|---|
| Compound | Aldehyde or acetal | Product | $^{1}$HNMR; LC m/z $[M + H]^+$. structure comment |
| 180[2,4] | From compound 179 | 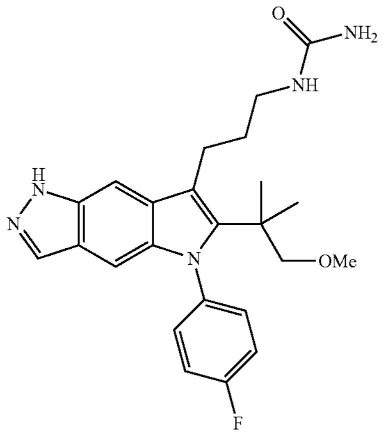 [SMILES: COCC(C)(C)c1c(CCCNC(N)=O)c2cc3[nH]ncc3cc2n1-c1ccc(F)cc1] | $^{1}$H NMR (400 MHz, Methanol-$d_4$) δ 7.89 (s, 1H), 7.53 (s, 1H), 7.42-7.35 (m, 2H), 7.32-7.26 (m, 2H), 6.76 (s, 1H), 3.34-3.29 (m, 4H), 3.22 (s, 3H), 3.08-3.01 (m, 2H), 1.93 (p, J = 7.1 Hz, 2H), 1.35 (s, 6H). LCMS m/z 438.15 $[M + H]^+$. |
| 181[2,5] | 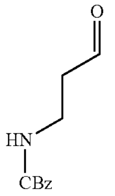 | 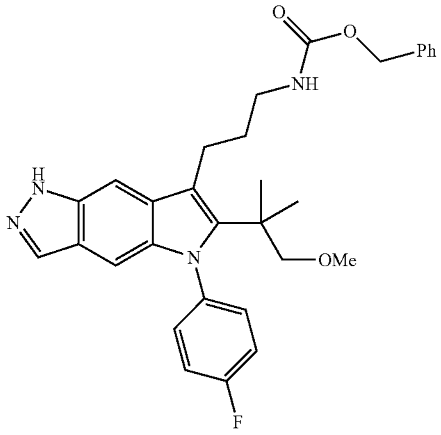 [SMILES: COCC(C)(C)c1c(CCCNC(=O)OCc2ccccc2)c2cc3[nH]ncc3cc2n1-c1ccc(F)cc1] | $^{1}$H NMR (400 MHz, DMSO-$d_6$) δ 12.60 (s, 1H), 7.92 (s, 1H), 7.47 (s, 2H), 7.41 (d, J = 6.8 Hz, 4H), 7.38-7.27 (m, 5H), 6.70 (s, 1H), 5.05 (s, 2H), 3.29-3.18 (m, 4H), 3.14 (s, 3H), 2.97-2.89 (m, 2H), 1.88-1.77 (m, 2H), 1.25 (s, 6H). LCMS m/z 529.18 $[M + H]^+$. |
| 182[2] | 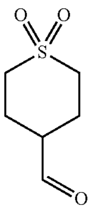 | 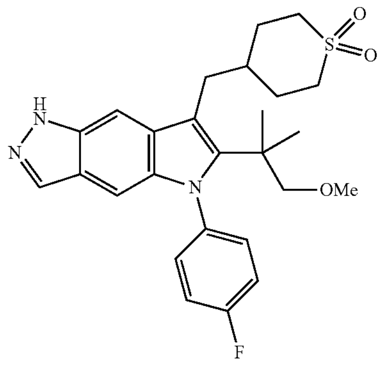 [SMILES: COCC(C)(C)c1c(CC2CCS(=O)(=O)CC2)c2cc3[nH]ncc3cc2n1-c1ccc(F)cc1] | $^{1}$H NMR (400 MHz, Methanol-$d_4$) δ 7.85 (d, J = 1.0 Hz, 1H), 7.50 (t, J = 1.1 Hz, 1H), 7.41-7.31 (m, 2H), 7.31-7.21 (m, 2H), 6.70 (d, J = 1.1 Hz, 1H), 3.23 (s, 2H), 3.18 (s, 3H), 3.11-2.89 (m, 6H), 2.12 (m, 3H), 1.93 (m, 2H), 1.35 (s, 6H). LCMS m/z 484.23 $[M + H]^+$. |

TABLE 10-continued

| Method of Preparation, structure and physicochemical data for compound 175-183 | | | |
|---|---|---|---|
| Compound | Aldehyde or acetal | Product | $^1$HNMR; LC m/z $[M + H]^+$. structure comment |
| 183[1] | From compound 210 | 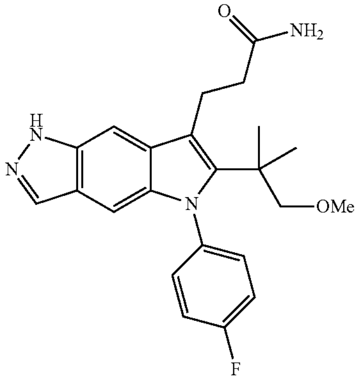 [SMILES: COCC(C)(C)c1c(CCC(N)=O)c2cc3[nH]ncc3cc2n1-c1ccc(F)cc1] | LCMS m/z 409.37 $[M + H]^+$. |

[1]Prepared from compound C170.

[2]Prepared from compound C169.

[3]Compound 179 was prepared from C169 by reductive alkylation, phenyl sulfonyl group deprotection using NaOH, then CBz protecting group removal by transfer hydrogenation with ammonium formate and palladium on carbon.

[4]Compound 180 was prepared from 179 using the method described for the preparation of compound 155.

[5]Compound 181 was prepared as for compound 179, omitting the final hydrogenation step.

Compound 184 and 185

(2S)-1-[6-[5-(3,4-difluorophenyl)-6-tetrahydropyran-4-yl-1H-pyrrolo[2,3-f]indazol-7-yl]-2-azaspiro[3.3]heptan-2-yl]-2-hydroxy-propan-1-one (184) and (2R)-1-[6-[5-(3,4-difluorophenyl)-6-tetrahydropyran-4-yl-1H-pyrrolo[2,3-f]indazol-7-yl]-2-azaspiro[3.3]heptan-2-yl]-2-hydroxy-propan-1-one (185)

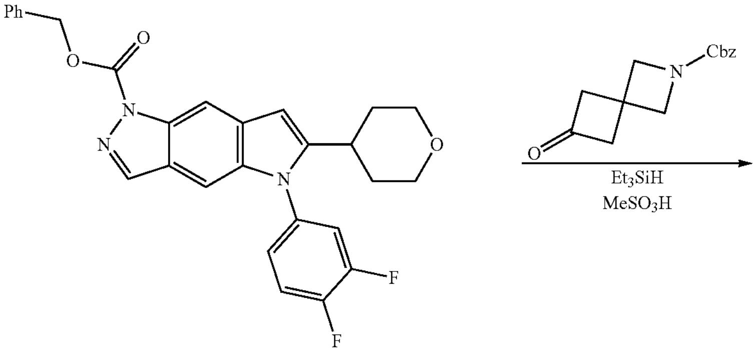

S10

-continued
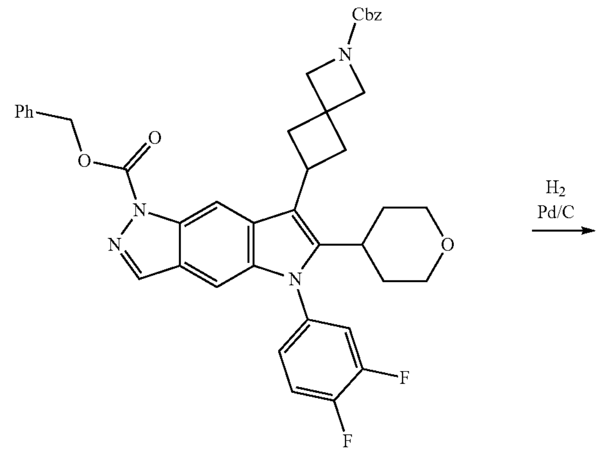
C171
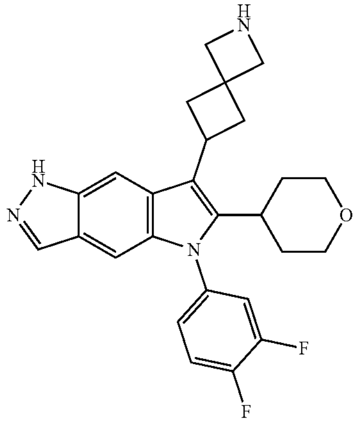
C172
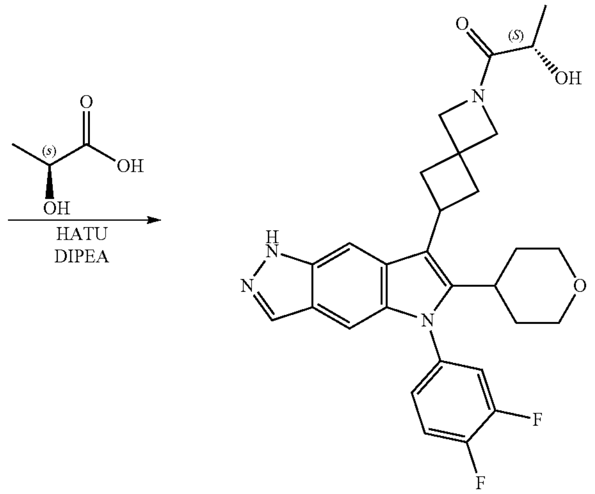
184
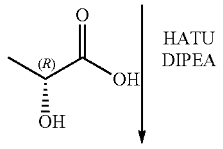
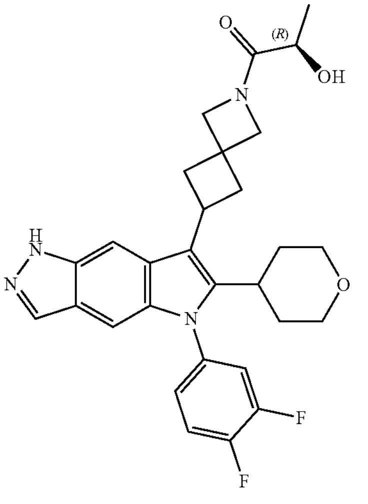
185

7-(2-azaspiro[3.3]heptan-6-yl)-5-(3,4-difluorophenyl)-6-tetrahydropyran-4-yl-1H-pyrrolo[2,3-f]indazole (Trifluoroacetate salt) C172 was prepared in two steps from S10 by reductive coupling and hydrogenation using the method described for the preparation of compound 16. Compound 184 and 185 were prepared by HATU coupling of (2S)-2-hydroxypropanoic acid or (2R)-2-hydroxypropanoic acid using the method described in the preparation of compound 4. (2S)-1-[6-[5-(3,4-difluorophenyl)-6-tetrahydropyran-4-yl-1H-pyrrolo[2,3-f]indazol-7-yl]-2-azaspiro[3.3]heptan-2-yl]-2-hydroxy-propan-1-one (Trifluoroacetate salt) 184 (2.0 mg, 42%). $^1$H NMR (400 MHz, DMSO-$d_6$) δ 12.63 (s, 1H), 7.97 (s, 1H), 7.69 (dd, J=12.0, 7.9 Hz, 3H), 7.31 (d, J=8.7 Hz, 1H), 7.11 (d, J=1.7 Hz, 1H), 4.65-3.64 (m, 8H, water overlaps), 3.24 (d, J=12.9 Hz, 2H), 2.94 (s, 2H), 2.81 (s, 1H), 2.64 (t, J=10.4 Hz, 2H), 1.90 (d, J=13.2 Hz, 2H), 1.67 (s, 2H), 1.21 (d, J=6.7 Hz, 4H). LCMS m/z 520.08 [M+H]$^+$.

(2R)-1-[6-[5-(3,4-difluorophenyl)-6-tetrahydropyran-4-yl-1H-pyrrolo[2,3-f]indazol-7-yl]-2-azaspiro[3.3]heptan-2-yl]-2-hydroxy-propan-1-one (Trifluoroacetate salt) 185 (2.0 mg, 43%). $^1$H NMR (400 MHz, DMSO-$d_6$) δ 12.63 (s, 1H), 7.97 (s, 1H), 7.69 (dd, J=12.1, 7.8 Hz, 3H), 7.31 (d, J=8.9 Hz, 1H), 7.11 (d, J=1.7 Hz, 1H), 4.61-3.79 (m, 8H, water overlaps), 3.33-3.15 (m, 2H), 2.97 (d, J=21.2 Hz, 2H), 2.81 (s, 1H), 2.64 (t, J=10.4 Hz, 2H), 1.90 (d, J=13.0 Hz, 2H), 1.67 (s, 2H), 1.21 (d, J=6.7 Hz, 4H). LCMS m/k 520.24 [M+H]$^+$.

Compound 186

6-[3-cyano-5-(3,4-difluorophenyl)-6-tetrahydropyran-4-yl-1H-pyrrolo[2,3-f]indazol-7-yl]spiro[3.3]heptane-2-carboxylic Acid (186)

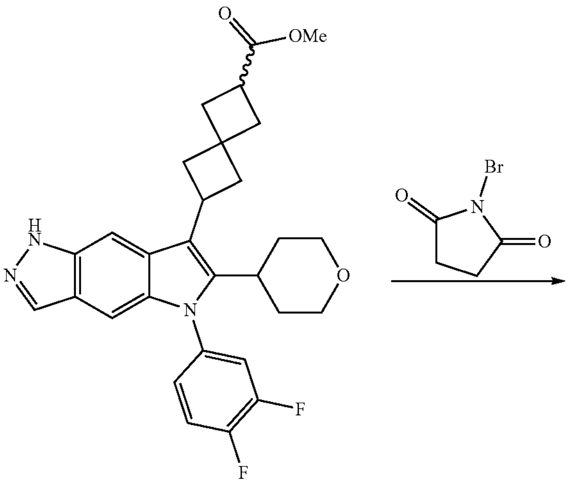

C173

-continued

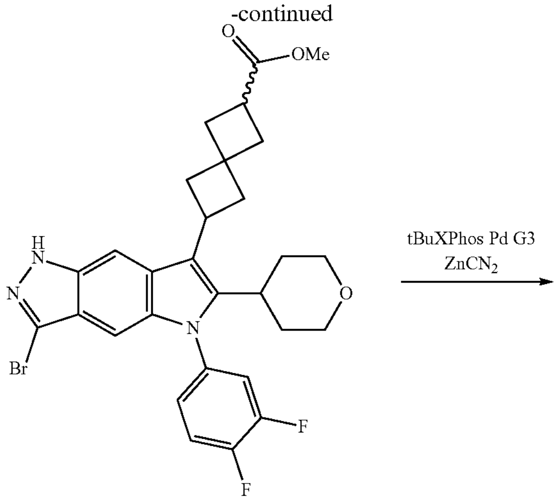

C174

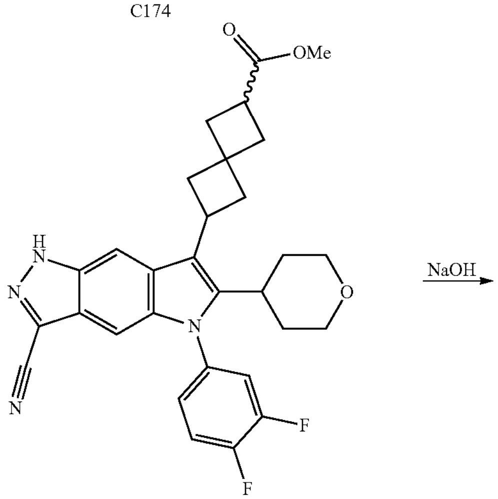

C175

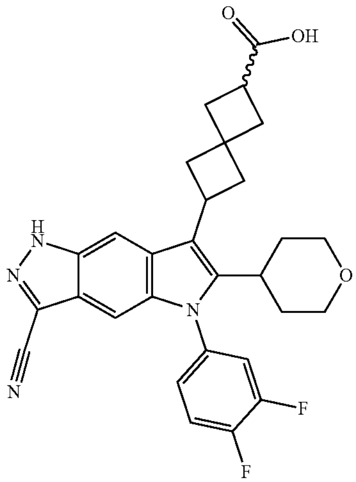

186

Step 1. Synthesis of methyl 6-[3-bromo-5-(3,4-difluorophenyl)-6-tetrahydropyran-4-yl-1H-pyrrolo[2,3-f]indazol-7-yl]spiro[3.3]heptane-2-carboxylate (C174)

At 0° C., to a solution of methyl 6-[5-(3,4-difluorophenyl)-6-tetrahydropyran-4-yl-1H-pyrrolo[2,3-f]indazol-7-yl]

spiro[3.3]heptane-2-carboxylate C173 (300 mg, 0.59 mmol) in DMF (2 mL) was added NaOH (26 mg, 0.63 mmol). The reaction was stirred for 10 minutes at 0° C. and a solution of NBS (111 mg, 0.62 mmol) in DMF (2 mL) was added slowly. The reaction was stirred for 10 minutes at 0° C., quenched with a saturated solution of $NH_4Cl$, and diluted with additional dichloromethane. The phases were separated and the aqueous phase was extracted twice with dichloromethane. The combined organic layers were dried over $Na_2SO_4$, filtered and evaporated. Purification by silica gel chromatography (Gradient: 0-100% EtOAc in dichloromethane) yielded the product. Methyl 6-[3-bromo-5-(3,4-difluorophenyl)-6-tetrahydropyran-4-yl-1H-pyrrolo[2,3-f]indazol-7-yl]spiro[3.3]heptane-2-carboxylate (251 mg, 64%). $^1H$ NMR (400 MHz, Chloroform-d) δ 11.11 (s, 1H), 7.78 (d, J=0.8 Hz, 1H), 7.43-7.32 (m, 1H), 7.20-7.04 (m, 2H), 6.94-6.89 (m, 1H), 4.05-3.84 (m, 3H), 3.69 (s, 3H), 3.31 (td, J=11.7, 5.5 Hz, 2H), 3.19-3.05 (m, 1H), 2.85-2.75 (m, 3H), 2.56-2.32 (m, 6H), 2.12-1.97 (m, 2H), 1.66-1.58 (m, 2H). LCMS m/z 584.33 $[M+H]^+$.

Step 2. Synthesis of methyl 6-[3-cyano-5-(3,4-difluorophenyl)-6-tetrahydropyran-4-yl-1H-pyrrolo[2,3-f]indazol-7-yl]spiro[3.3]heptane-2-carboxylate (C175)

methyl 6-[3-bromo-5-(3,4-difluorophenyl)-6-tetrahydropyran-4-yl-1H-pyrrolo[2,3-f]indazol-7-yl]spiro[3.3]heptane-2-carboxylate C174 (30 mg, 0.05 mmol), dicyanozinc (4 mg, 0.03 mmol) and tBuXPhos Pd G3 (2 mg, 0.003 mmol) were placed in a vial under nitrogen. The vial was purged with one cycle of vacuum/nitrogen. THF (150 μL), followed by water (150 μL) was added. The reaction was heated overnight at 50° C. The reaction was diluted with dichloromethane. The phases were separated and the aqueous phase was extracted twice with dichloromethane. The combined organic layers were dried over $Na_2SO_4$, filtered and evaporated.

Purification by silica gel chromatography (Gradient: 0-100% EtOAc in dichloromethane) yielded the product. Methyl 6-[3-cyano-5-(3,4-difluorophenyl)-6-tetrahydropyran-4-yl-1H-pyrrolo[2,3-f]indazol-7-yl]spiro[3.3]heptane-2-carboxylate (15 mg, 16%). LCMS m/z 531.5 $[M+H]^+$.

Step 3. Synthesis of 6-[3-cyano-5-(3,4-difluorophenyl)-6-tetrahydropyran-4-yl-1H-pyrrolo[2,3-f]indazol-7-yl]spiro[3.3]heptane-2-carboxylic Acid (186)

To a solution of methyl 6-[3-cyano-5-(3,4-difluorophenyl)-6-tetrahydropyran-4-yl-1H-pyrrolo[2,3-f]indazol-7-yl]spiro[3.3]heptane-2-carboxylate C175 (15 mg, 0.03 mmol) in THF (1.9 mL) and methanol (950 μL) was added NaOH (85 μL of 2 M, 0.17 mmol). The reaction mixture was stirred overnight at room temperature. The reaction was quenched with HCl (33 μL of 6 M, 0.12 mmol) and diluted with an excess of dichloromethane. The phases were separated and the aqueous phase was extracted twice with dichloromethane. The combined organic layers were dried over $Na_2SO_4$, filtered and evaporated. Purification by reversed-phase HPLC. Method: C18 Waters Sunfire column (30×150 mm, 5 micron). Gradient: MeCN in $H_2O$ with 0.1% trifluoroacetic acid afforded the product. 6-[3-cyano-5-(3,4-difluorophenyl)-6-tetrahydropyran-4-yl-1H-pyrrolo[2,3-f]indazol-7-yl]spiro[3.3]heptane-2-carboxylic acid (4 mg, 27%). LCMS m/z 517.21 $[M+H]^+$.

Compound 187

3-[6-isopropyl-5-(2,3,5,6-tetradeuterio-4-fluorophenyl)-1H-pyrrolo[2,3-f]indazol-7-yl](1,2,3-$^{13}$C3)propanoic Acid (187)

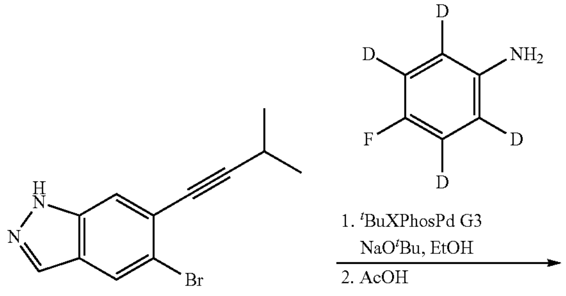

C8

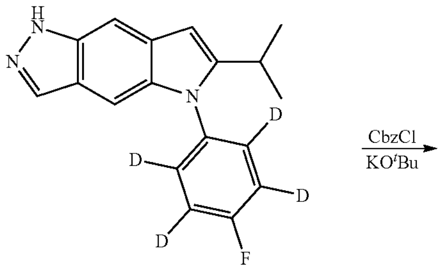

C176

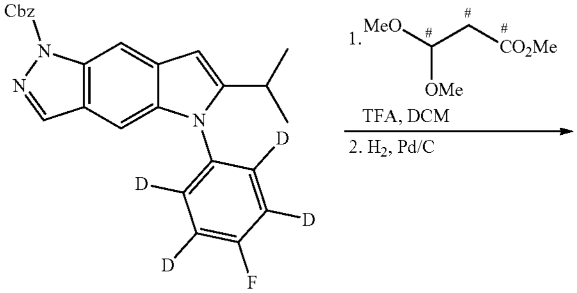

C177

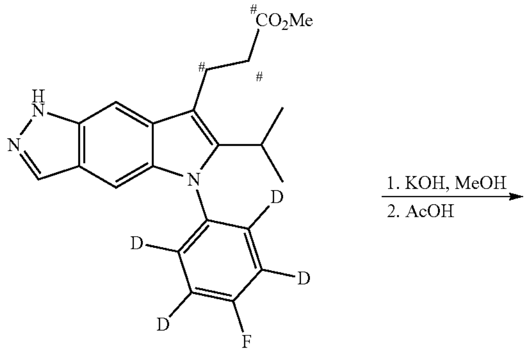

C178

-continued

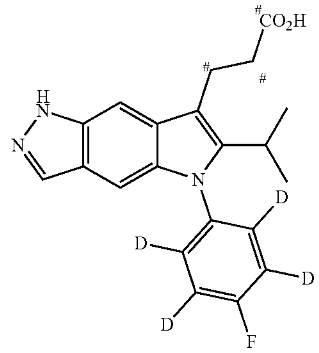

C187

# = $^{13}$C

Step 1. Synthesis of 5-(4-fluorophenyl-2,3,5,6-d4)-6-isopropyl-1,5-dihydropyrrolo[2,3-f]indazole (C176)

To starting indazole C8 (63 g, 239 mmol) and [$D_4$]-4-fluoroaniline (30 g, 261 mmol) in EtOH (370 ml) at 4° C. was added sodium t-butoxide (46 g, 479 mmol), rinsing in with EtOH (20 ml) [exotherm to 23° C.]. The mixture was re-cooled to 10° C. and 5× vacuum/nitrogen cycles were performed to de-oxygenate the mixture. $^{t}$BuXPhosPd-G3 (4.9 g, 6.2 mmol) was added and one additional vacuum/nitrogen cycle was performed. The mixture was heated to 58° C. over one hour and held at 58° C. for 90 minutes (TLC after 60 minutes indicated reaction complete). Acetic acid (50 ml, 870 mmol) was added over 3 minutes [exotherm to 63° C.] and the mixture was stirred at 62-64° C. for 2.5 hours. TLC showed 90-95% conversion to the ring-closed product. Additional acetic acid (10 ml, 174 mmol) was added and the mixture stirred at 64° C. for 90 minutes. Water (780 ml) was added over 24 minutes while allowing the mixture to cool to 44° C. The slurry was cooled to 20° C., filtered and washed with water. The solids were dried in a vacuum oven at 45° C. to afford 5-(4-fluorophenyl-2,3,5,6-$d_4$)-6-isopropyl-1,5-dihydropyrrolo[2,3-f]indazole (74.3 g, assume 239 mmol, 100% yield) as a brown solid.

Step 2. Synthesis of benzyl 5-(4-fluorophenyl-2,3,5,6-d4)-6-isopropylpyrrolo[2,3-f]indazole-1(5H)-carboxylate (C177)

To 5-(4-fluorophenyl-2,3,5,6-d4)-6-isopropyl-1,5-dihydropyrrolo[2,3-f]indazole C176 (74.3 g, assume 239 mmol) in THF (1 L) at −10° C. was added potassium t-butoxide (30.8 g, 274 mmol) in one portion [exotherm to −4° C.]. The mixture was re-cooled to −7° C. over 5 minutes then Cbz-Cl (46.7 g, 274 mmol) was added over 10 minutes [kept <+3° C.]. The mixture was allowed to warm to 16° C. over 75 minutes then quenched with 30 ml 10% $KHCO_3$ followed by 200 ml water. The biphasic thin slurry was concentrated under vacuum to a thick slurry (563 g) then diluted with 200 ml methanol and 200 ml water. The slurry was triturated at 40° C., cooled to 16° C. then filtered and washed with water (2×50 ml) then methanol (3×80 ml). The solids were dried under vacuum at 40° C. to afford benzyl 5-(4-fluorophenyl-2,3,5,6-d4)-6-isopropylpyrrolo[2,3-f]indazole-1(5H)-carboxylate (98 g, 227 mol, 95%) as a pale brown solid.

Step 3. Synthesis of methyl 3-(5-(4-fluorophenyl-2,3,5,6-d4)-6-isopropyl-1,5-dihydropyrrolo[2,3-f]indazol-7-yl)propanoate (C178)

To benzyl 5-(4-fluorophenyl-2,3,5,6-d4)-6-isopropylpyrrolo[2,3-f]indazole-1(5H)-carboxylate C177 (25.9 g, 60.0 mmol) and [$^{13}C_3$] methyl 3,3-dimethoxypropionate (10 g, 66 mmol) in dichloromethane (200 ml) was added TFA (20 ml, 261 mmol). The mixture was heated to 37-38° C. for 25 hours [monitored by HPLC] then cooled to room temperature. The mixture was slowly added to sodium bicarbonate (30 g, 349 mmol) in water (330 ml) [gas evolved], rinsing in with dichloromethane (20 ml). The layers were mixed well and then separated. The aqueous layer was re-extracted with dichloromethane (50 ml). The combined organic layers were dried over $MgSO_4$ (9 g), silica (9 g) and magensol 9 g) then filtered through a pad of silica (9 g), washing with dichloromethane (110 ml). The filtrate was evaporated and the residue was taken up in MTBE (60 ml) at 45° C. [crystals formed on stirring]. n-Heptane (45 ml) was gradually added and the slurry was cooled to room temperature, filtered and washed with 2:1 heptane:MTBE (40 ml). The solids were dried under vacuum at 40° C. to afford methyl (E)-3-(5-(4-fluorophenyl-2,3,5,6-d4)-6-isopropyl-1,5-dihydropyrrolo[2,3-f]indazol-7-yl)acrylate (25.4 g, 49.0 mmol, 82%) as a yellow-tan solid. To methyl (E)-3-(5-(4-fluorophenyl-2,3,5,6-d4)-6-isopropyl-1,5-dihydropyrrolo[2,3-f]indazol-7-yl) acrylate (25.4 g, 49.0 mmol), 10% Pd/C (~60% water, 4.0 g), TMEDA (16 ml) and THF (85 ml) was hydrogenated at 40 psi and room temperature for 8 hours [HPLC indicated 96% completion]. Additional 10% Pd/C (~60% water, 1.0 g) was added and the mixture hydrogenated at 40 psi and room temperature for 7.5 hours [HPLC indicated complete conversion]. The mixture was filtered through a pad of Solkafloc, washing with THF, and the filtrate was evaporated and azeotroped with methanol (25 ml). The residue was taken up in methanol (30 ml) at 45° C. (crystals form) and the slurry was triturated at 45° C., cooled to 15° C., filtered and washed with cold methanol. The solids were dried under vacuum at 40° C. to afford 13.6 g of a pale yellow-tan solid. The solid was dissolved in dichloromethane (70 ml) and treated with mercaptopropyl ethyl sulfide silica (PhosphonicS SPM32f, 1 mmol/g, 1.4 g) for 90 minutes. The slurry was filtered and washed with dichloromethane. The filtrate was evaporated to a solid and triturated with n-heptane (50 ml) at 45° C. The slurry was cooled to 20° C., filtered and washed with n-heptane. The solids were dried under vacuum at 40° C. to afford methyl 3-(5-(4-fluorophenyl-2,3,5,6-d4)-6-isopropyl-1,5-dihydropyrrolo[2,3-f]indazol-7-yl)propanoate (13.1 g, 33.9 mmol, 69%) as a pale tan solid.

Preparation of 3-(5-(4-Fluoro-phenyl-2,3,5,6-$d_4$)-6-isopropyl-1,5-dihydropyrrolo[2,3-f]indazol-7-yl) [$^{13}C_3$]propanoic Acid (187)

To methyl 3-(5-(4-fluorophenyl-2,3,5,6-d4)-6-isopropyl-1,5-dihydropyrrolo[2,3-f]indazol-7-yl)propanoate C178 (13.1 g, 33.9 mmol) in methanol (60 ml) at 26° C. was added 45% KOH (8.0 ml, 94 mmol) in water (28 ml). The mixture was heated to 46-48° C. for 110 minutes [monitored by HPLC] then cooled to 20° C. Acetic acid (5.9 ml) was added over 2 minutes [kept <24° C.] and the mixture stirred for 8 minutes during which time crystals start to form. Water (32 ml) was added over 10 minutes and the slurry was stirred at 20° C. for 2 hours then filtered and washed with water. The solids were dried in a vacuum oven at 45° C. to afford 3-(5-(4-Fluoro-phenyl-2,3,5,6-d4)-6-isopropyl-1,5-dihydropyrrolo[2,3-f]indazol-7-yl)[$^{13}C3$]propanoic acid (12.24 g, 32.9 mmol, 97%) as a pale tan solid. $^{1}$H-NMR (500 MHz, DMSO-$d_6$) δ 12.52 (bs, 1H), 7.96 (s, 1H), 7.51 (s, 1H), 7.02 (s, 1H), 3.14 (d, J=123.4 Hz, 2H), 3.02 (heptet, J=7.3 Hz, 1H), 2.59 (d, J=128.6 Hz 2H), 1.26 (d, J=6.9 Hz, 6H).

Compound 188

3-[6-isopropyl-5-(2,3,5,6-tetradeuterio-4-fluoro-phenyl)-1H-pyrrolo[2,3-f]indazol-7-yl]propanoic Acid (188)

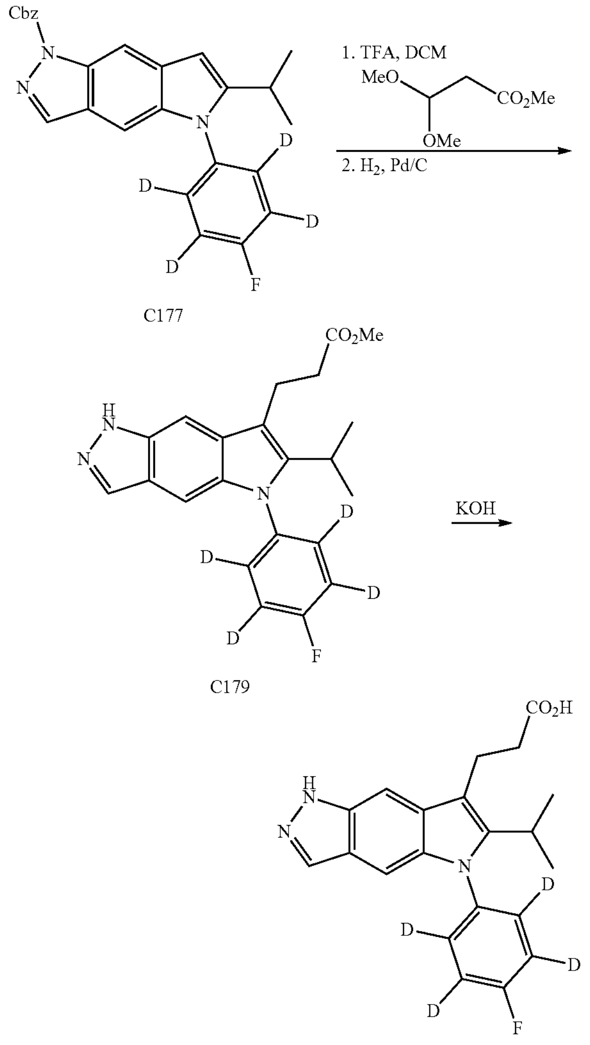

C177

C179

C188

Preparation of Methyl 3-(5-(4-fluoro-phenyl-2,3,5,6-$d_4$)-6-isopropyl-1,5-dihydropyrrolo[2,3-f]indazol-7-yl)propionate (C179)

To benzyl 5-(4-fluorophenyl-2,3,5,6-d4)-6-isopropylpyrrolo[2,3-f]indazole-1(5H)-carboxylate (C177) (29.6 g, 68.6 mmol) and methyl 3,3-dimethoxypropionate (11 ml, 77.6 mmol) in dichloromethane (220 ml) was added TFA (23 ml, 300 mmol). The mixture was heated to 37-38° C. for 40 hours, then cooled to room temperature. The mixture was slowly added to sodium bicarbonate (35 g, 417 mmol) in water (380 ml) [gas evolved], rinsing in with dichloromethane (30 ml). The layers were mixed well and then separated. The aqueous layer was re-extracted with dichloromethane (60 ml). The combined organic layers were dried over $MgSO_4$ (10 g), silica (10 g) and magensol 10 g) then filtered through a pad of silica (10 g), washing with dichloromethane (120 ml). The filtrate was evaporated and the residue was taken up in MTBE (60 ml) at 45° C. [crystals formed on stirring]. n-Heptane (60 ml) was gradually added and the slurry was cooled to 15° C., filtered and washed with 2:1 heptane:MTBE (60 ml). The solids were dried under vacuum at 40° C. to afford methyl (E)-3-(5-(4-fluorophenyl-2,3,5,6-d4)-6-isopropyl-1,5-dihydropyrrolo[2,3-f]indazol-7-yl)acrylate (29.8 g, 57.8 mmol, 84%) as a yellow-brown solid.

Methyl (E)-3-(5-(4-fluorophenyl-2,3,5,6-$d_4$)-6-isopropyl-1,5-dihydropyrrolo[2,3-f]indazol-7-yl)acrylate (29.8 g, 57.8 mmol), 10% Pd/C (~60% water, 3.3 g), TMEDA (19 ml) and THF (100 ml) was hydrogenated at 40 psi and room temperature for 5 hours [HPLC indicated all Cbz removed and 67% reduction of the olefin]. Additional 10% Pd/C (~60% water, 1.7 g) was added and the mixture hydrogenated at 40 psi and room temperature for 6 hours [HPLC indicated 97% completion]. Additional 10% Pd/C (~60% water, 0.9 g) was added and the mixture hydrogenated at 40 psi and room temperature for 8 hours [HPLC indicated complete conversion]. The mixture was filtered through a pad of Solkafloc, washing with THF, and the filtrate was evaporated and azeotroped with methanol (30 ml). The residue was taken up in methanol (30 ml) at 50° C. (crystals form) and the slurry was triturated at 50° C., cooled to 15° C., filtered and washed with cold methanol. The solids were dried under vacuum at 40° C. to afford 16.27 g of a pale yellow solid. $^{1}$H-NMR and HPLC were very clean for desired product. The solid was dissolved in dichloromethane (80 ml) and treated with mercaptopropyl ethyl sulfide silica (PhosphonicS SPM32f, 1 mmol/g, 1.6 g) for 90 minutes. The slurry was filtered and washed with dichloromethane. The filtrate was evaporated to a solid and triturated with n-heptane (50 ml) at 45° C. The slurry was cooled to 20° C., filtered and washed with n-heptane. NMR of the solids after prolonged drying still indicated ~15 mol % dichloromethane. The filtrate (after evaporation to a solid) and the solids were re-combined and evaporated from 60 ml methanol. The material was triturated in methanol (40 ml) at 50° C. for 45 minutes, cooled to 6° C., filtered and washed with cold methanol. The solids were dried under vacuum at 40° C. to afford methyl 3-(5-(4-fluoro-phenyl-2,3,5,6-$d_4$)-6-isopropyl-1,5-dihydropyrrolo [2,3-f]indazol-7-yl)propionate (14.11 g, 36.8 mmol, 64%) as a pale yellow solid. $^{1}$H-NMR (500 MHz, $CDCl_3$) δ 9.93 (s, 1H), 8.01 (s, 1H), 7.52 (s, 1H), 7.10 (s, 1H), 3.75 (s, 3H), 3.26 (t, J=8.3 Hz, 2H), 3.07 (heptet, J=7.3 Hz, 1H), 2.74 (t, J=8.3 Hz, 2H), 1.30 (d, J=7.3 Hz, 6H).

Preparation of 3-(5-(4-fluorophenyl-2,3,5,6-$d_4$)-6-isopropyl-1,5-dihydropyrrolo[2,3-f]indazol-7-yl) propanoic Acid (188)

To methyl 3-(5-(4-fluoro-phenyl-2,3,5,6-$d_4$)-6-isopropyl-1,5-dihydropyrrolo[2,3-f]indazol-7-yl)propionate (C179) (9.15 g, 23.9 mmol) in THF (65 ml) was added a mixture of 45% KOH (9.5 ml, 111 mmol) in water (33 ml). The mixture was stirred at room temperature for 44 hours [monitored by HPLC]. The layers were separated and the organic layer was treated with 6M HCl (5.5 ml) [to pH ~2]. The layers were separated and the organic layer was washed with saturated brine (6 ml) plus extra NaCl (0.65 g) [the salt goes in to solution]. The aqueous layers were sequentially re-extracted with THF (15 ml). The combined organic layers were dried over $MgSO_4$, filtered and evaporated to a yellow foam. The residue was triturated in ethyl acetate (30 ml) at 45° C., diluted with cyclohexane (30 ml) and cooled to 15° C. The slurry was filtered, washed with 2:1 cyclohexane:EtOAc then cyclohexane, and dried in a vacuum oven at 45° C. overnight and then at 65° C. for two hours to afford 3-(5-(4-fluorophenyl-2,3,5,6-d4)-6-isopropyl-1,5-dihydropyrrolo[2,3-f]indazol-7-yl)propanoic acid (8.64 g, 23.4 mmol, 98%) as an off-white to pale yellow solid. $^1H$-NMR (500 MHz, DMSO-$d_6$) δ 12.55 (bs, 1H), 7.96 (s, 1H), 7.51 (s, 1H), 7.02 (s, 1H), 3.14 (t, J=8.3 Hz, 2H), 3.02 (heptet, J=7.3 Hz, 1H), 2.59 (t, J=8.3 Hz, 2H), 1.26 (d, J=7.3 Hz, 6H).

Compound 189

2,2-dideuterio-3-[3,4,8-trideuterio-6-(1-deuterio-1-methyl-ethyl)-5-(4-fluorophenyl)-1H-pyrrolo[2,3-f]indazol-7-yl]propanoic Acid (189)

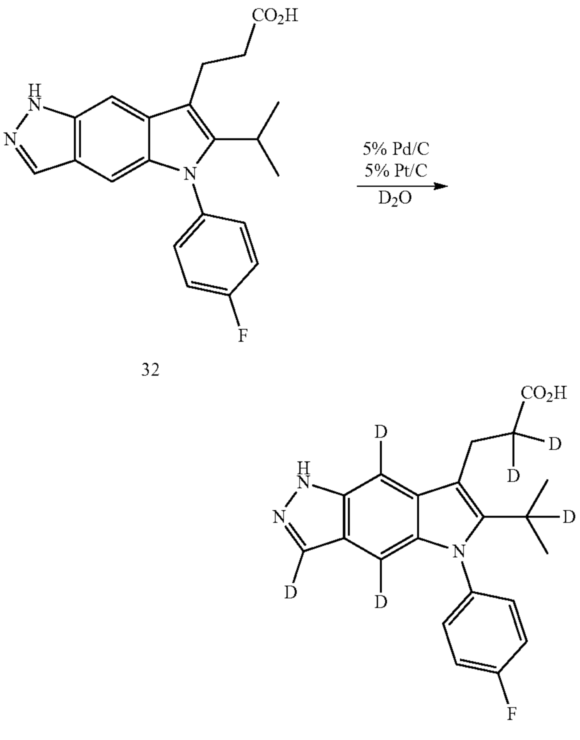

32

189

Synthesis of 2,2-dideuterio-3-[3,4,8-trideuterio-6-(1-deuterio-1-methyl-ethyl)-5-(4-fluorophenyl)-1H-pyrrolo[2,3-f]indazol-7-yl]propanoic Acid (189)

3-[5-(4-fluorophenyl)-6-isopropyl-1H-pyrrolo[2,3-f]indazol-7-yl]propanoic acid 32 (300 mg, 0.81 mmol), 5% Pd on carbon (60 mg, 0.5638 mmol), and 5% Pt on carbon (60 mg, 0.24 mmol) were weighed into a microwave vial. $D_2O$ (10 mL) was added. The mixture was flushed with nitrogen. A $H_2$ balloon atmosphere was placed over the reaction, and the mixture was a very gently place under vacuum, then flushed with $H_2$ (×3). The mixture was heated under a hydrogen atmosphere at 180° C. for 18 h under microwave conditions. $D_2O$ was added and the mixture was heated for 3 hours. The mixture was diluted with dichloromethane and water, and the water was acidified with HCl. The organic layer was passed through a phase separator and concentrated to dryness under reduced pressure. Silica gel chromatography (Gradient: 0-10% MeOH in dichloromethane), then purification by reversed-phase chromatography (Column: C18. Gradient: 10-100% MeCN in water with 0.1% formic acid) afforded the product. 2,2-dideuterio-3-[3,4,8-trideuterio-6-(1-deuterio-1-methyl-ethyl)-5-(4-fluorophenyl)-1H-pyrrolo[2,3-f]indazol-7-yl]propanoic acid (53.9 mg, 18%). $^1H$ NMR (300 MHz, DMSO-$d_6$) δ 12.59 (s, 1H), 12.26 (s, 1H), 7.52-7.36 (m, 4H), 3.17-3.04 (m, 2H), 2.61-2.52 (m, 0.7H), 1.25 (s, 6H). LCMS m/z 372.17 $[M+H]^+$.

Compound 190

3-[6-(2-cyano-1,1-dimethyl-ethyl)-5-(4-fluorophenyl)-1H-pyrrolo[2,3-f]indazol-7-yl]propanoic Acid (190)

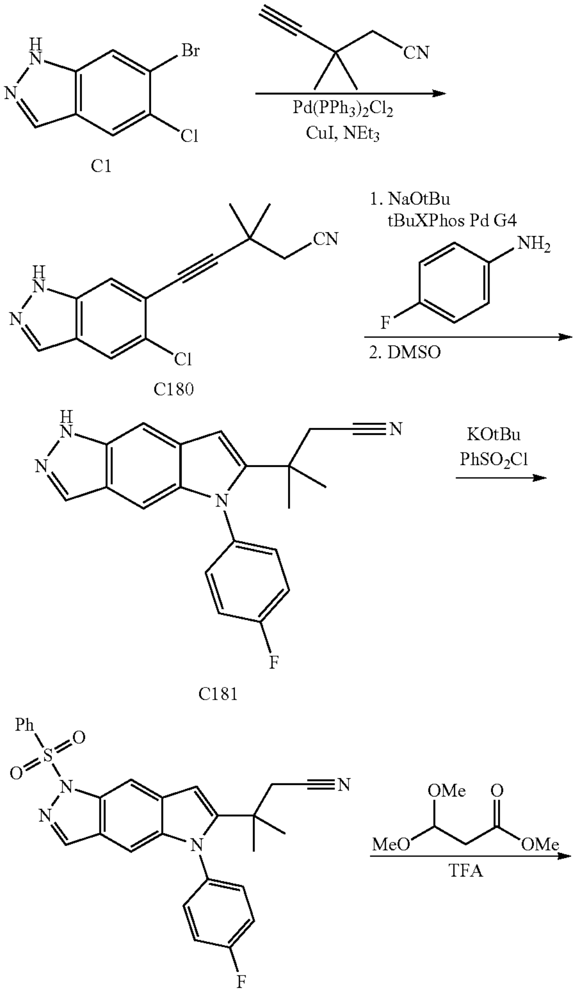

C1

C180

C181

C182

-continued

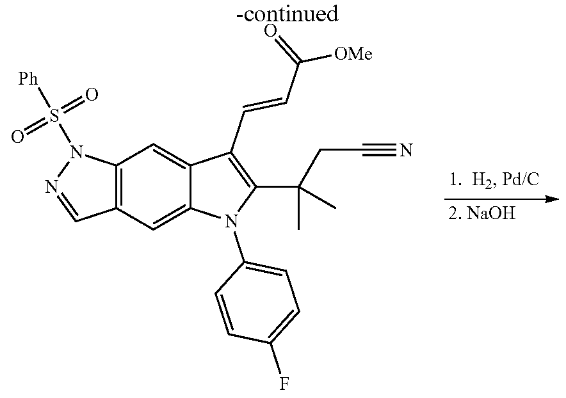

C183

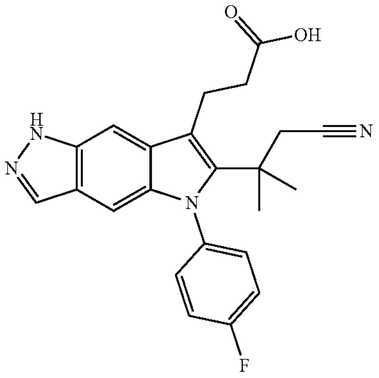

190

Compound 190 was prepared from C1 using an analogous method to that described in the preparation of compound 38. tBuXPhos Pd G4 was used in the Buchwald amination step. Phenyl sulfonyl was used as the protecting group. Purification by reversed-phase chromatography (Column: C18. Gradient: 10-100% MeCN in water with 0.1% formic acid) afforded the product. Concentrated the desired peaks to dryness under reduced pressure to give 3-[6-(2-cyano-1,1-dimethyl-ethyl)-5-(4-fluorophenyl)-1H-pyrrolo[2,3-f]indazol-7-yl]propanoic acid (89.9 mg, 74%). $^1$H NMR (400 MHz, DMSO-d6) δ 12.68 (s, 1H), 12.35 (s, 1H), 7.96 (d, J=1.0 Hz, 1H), 7.56-7.52 (m, 1H), 7.51-7.41 (m, 4H), 6.76 (d, J=1.1 Hz, 1H), 3.33-3.23 (m, 2H), 2.85 (s, 2H), 2.67-2.59 (m, 2H), 1.42 (s, 6H). LCMS m/z 405.21 [M+H]$^+$.

Compound 191

3-[6-(2-cyano-1,1-dimethyl-ethyl)-5-(4-fluorophenyl)-1H-pyrrolo[2,3-f]indazol-7-yl]propanamide (191)

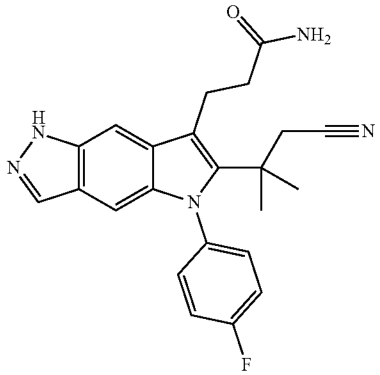 [SMILES: CC(C)(CC#N)c1c(CCC(N)=O)c2cc3[nH]ncc3cc2n1-c1ccc(F)cc1]

Compound 191 was prepared from compound 190 using the method described for the preparation of compound 193. $^1$H NMR (400 MHz, DMSO-$d_6$) δ 12.70 (s, 1H), 7.96 (s, 1H), 7.58 (s, 1H), 7.46 (q, J=4.7, 3.3 Hz, 5H), 6.91 (s, 1H), 6.76 (s, 1H), 3.23 (t, J=8.3 Hz, 2H), 2.88 (s, 2H), 2.48 (d, J=9.6 Hz, 2H), 1.42 (s, 6H). LCMS 404.35 [M+H]$^+$.

Compound 192

3-[5-(4-fluorophenyl)-6-isopropenyl-1H-pyrrolo[2,3-f]indazol-7-yl]propanoic Acid (192)

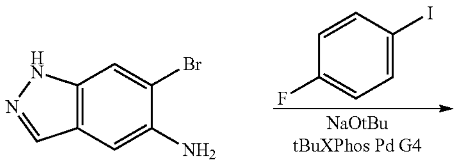

C61

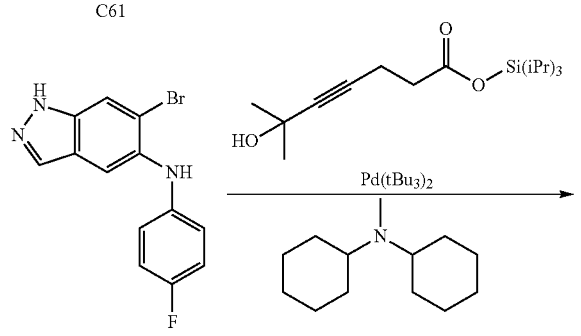

C184

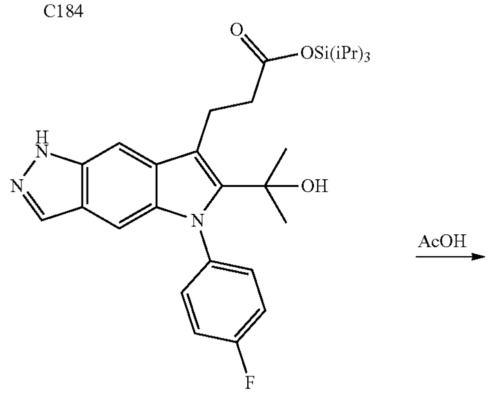

C185

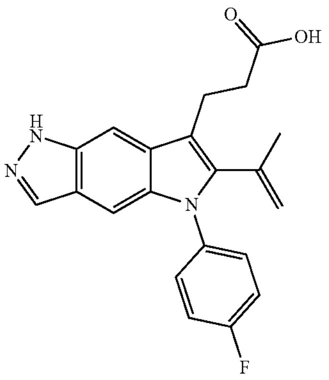

192

Synthesis of 6-bromo-N-(4-fluorophenyl)-1H-indazol-5-amine (C184)

A solution of 1-fluoro-4-iodo-benzene (1.6 mL, 13.9 mmol), 6-bromo-1H-indazol-5-amine C61 (2000 mg, 9.4 mmol), NaOtBu (3.9 g, 40 mmol), and tBuXPhos Pd G4 (432 mg, 0.48 mmol) tBuOH (50 mL) degassed and purged with nitrogen. The mixture was allowed to stir at room temperature for 5 h. The mixture was diluted with ethyl acetate, washed with 50% saturated sodium bicarbonate, and then by brine. The organic layer was dried over with sodium sulfate, filtered and concentrated in vacuo. Silica gel chromatography (Gradient: 0-100% EtOAc in heptane) afforded the product (1.8 g, 62%). $^1$H NMR (400 MHz, DMSO) δ 13.06 (s, 1H), 7.99 (s, 1H), 7.89 (s, 1H), 7.59 (s, 1H), 7.48 (d, J=1.7 Hz, 1H), 7.09-6.88 (m, 2H), 6.80 (dd, J=8.1, 4.7 Hz, 2H). LCMS m/z 305.9 $[M+H]^+$.

3-[5-(4-fluorophenyl)-6-isopropenyl-1H-pyrrolo[2,3-f]indazol-7-yl]propanoic Acid (192)

Part A. Triisopropylsilyl 6-hydroxy-6-methyl-hept-4-ynoate (80 mg, 0.26 mmol), 6-bromo-N-(4-fluorophenyl)-1H-indazol-5-amine C184 (40 mg, 0.13 mmol), and N-cyclohexyl-N-methyl-cyclohexanamine (70 μL, 0.33 mmol) were added to a 30 mL vial with a stir bar. The mixture was placed under vacuum, and then flushed with nitrogen. 1,4-dioxane (1 mL) was added and the mixture was placed under vacuum and flushed with nitrogen (×3). $Pd(tBu_3)_2$ (7 mg, 0.014 mmol) and was added, and the mixture was placed under vacuum, flushed with nitrogen. The vial was sealed and heated to 80° C. overnight. Triisopropylsilyl 3-[5-(4-fluorophenyl)-6-(1-hydroxy-1-methyl-ethyl)-1H-pyrrolo[2,3-f]indazol-7-yl]propanoate. LCMS m/z 364.16 $[M+H]^+$.

Part B. Upon cooling to room temperature, acetic acid (500 μL, 8.8 mmol) was added directly to the reaction mixture. The mixture was heated to 80° C. over 4 hours. Purification by reversed-phase chromatography (Column: C18. Gradient: 10-100% MeCN in water with 0.1% TFA) afforded the product. 3-[5-(4-fluorophenyl)-6-isopropenyl-1H-pyrrolo[2,3-f]indazol-7-yl]propanoic acid (Trifluoroacetate salt) (11.8 mg, 17%). $^1$H NMR (300 MHz, DMSO-$d_6$) δ 12.72 (s, 2H), 8.02 (d, J=1.0 Hz, 1H), 7.61 (d, J=1.1 Hz, 1H), 7.51-7.35 (m, 5H), 5.45 (t, J=2.0 Hz, 1H), 5.27 (s, 1H), 3.06 (dd, J=9.2, 6.7 Hz, 2H), 2.59 (t, J=7.9 Hz, 2H), 1.66 (s, 3H). LCMS m/z 364.16 $[M+H]^+$.

Compound 193

3-[5-(4-fluorophenyl)-6-[1,2,2,2-tetradeuterio-1-(trideuteriomethyl)ethyl]-1H-pyrrolo[2,3-f]indazol-7-yl]propanoic Acid (193)

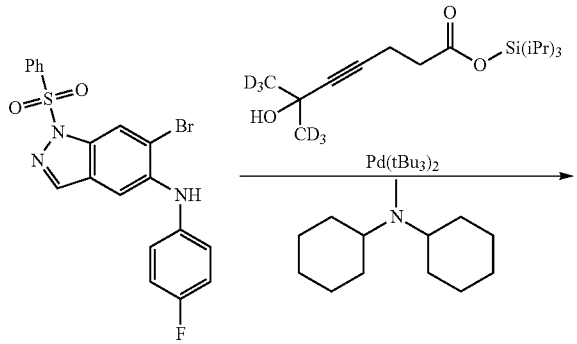

C186

-continued

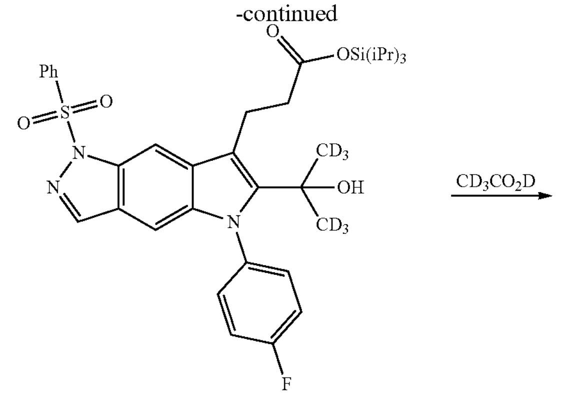

C187

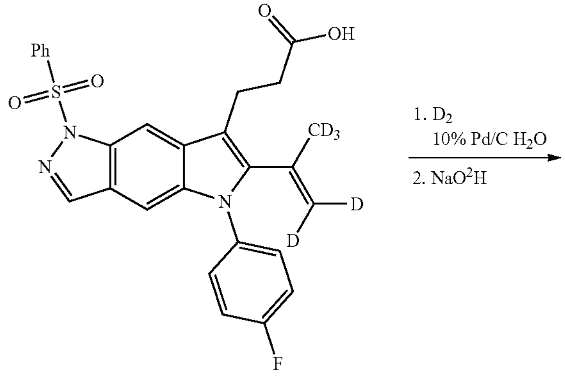

C188

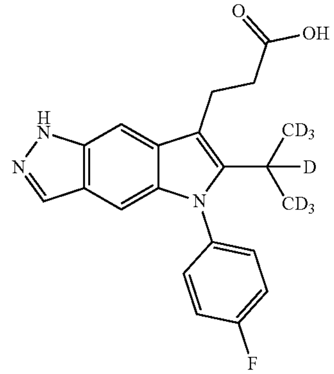

193

Preparation of 1-(benzenesulfonyl)-6-bromo-N-(4-fluorophenyl)indazol-5-amine (C186)

Part A. A solution of 1-(benzenesulfonyl)-6-bromo-5-nitro-indazole (6.97 g, 18.24 mmol) and $NH_4Cl$ (490 mg, 9.16 mmol) in EtOH (65 mL), water (20 mL) and THF (40 mL) was heated to reflux, around 70° C. Iron (4.2 g, 75.21 mmol) portion wisely over 30 min. The mixture was heated at reflux for an additional 30 minutes. The mixture was filtered through a pad of Celite® washing with EtOAc and 2-MeTHF. The mixture was concentrated. Purification by silica gel chromatography (Gradient: 0-100% EtOAc in heptane) yielded the product. 1-(benzenesulfonyl)-6-bromo-indazol-5-amine (6.22 g, 97%). $^1$H NMR (400 MHz, Methanol-$d_4$) δ 8.28-8.21 (m, 1H), 8.11 (d, J=0.9 Hz, 1H), 7.94-7.86 (m, 2H), 7.67-7.58 (m, 1H), 7.55-7.47 (m, 2H), 7.08 (s, 1H). LCMS m/z 351.88 $[M+1]^+$.

Part B. A 1 L flask equipped with a stirrer bar, loaded with 4 Å molecular sieves (24.2 g, dried at 230° C. under vacuum for 18 hours and cooled to ambient temperature under dry nitrogen atmosphere 60 min before use). 1-(benzenesulfonyl)-6-bromo-indazol-5-amine was dried at 50° C. for 48 hours before use. At ambient temperature, a 1 L RBF equipped with stir bar and sieves was charged with 1-(benzenesulfonyl)-6-bromo-indazol-5-amine (20.5 g, 58.2 mmol), (4-fluorophenyl)boronic acid (16.7 g, 119.1 mmol) and copper (II) acetate (21.7 g, 119.2 mmol). Anhydrous dichloromethane (310 mL) was added and the dark blue slurry was stirred under nitrogen atmosphere for 25 min. At 0° C., $NEt_3$ (41 mL, 294.2 mmol) was added drop-wise and oxygen gas was purged through the blue slurry for 15 min, then ice bath was removed. The mixture was agitated at 20-25° C. under an oxygen atmosphere overnight. Dichloromethane (160 mL) was added then temperature cooled to 0° C. 250 mL of 6% $NH_4OH$ was added while keeping internal temperature below 5° C. (very exothermic). The crude mixture was filtered through a pad of Celite®, washing with dichloromethane (250 mL). Phases were separated and the organic layers washed with 6% $NH_4OH$ (2×250 mL), then sat. $NH_4Cl$ (2×400 mL). The aqueous layer was extracted with dichloromethane (250 mL) and combined organic phases washed with brine (300 mL), dried over $MgSO_4$, filtered and concentrated to dryness to afford a dark brown thick oil. Dichloromethane was added (3 vol, 75 mL per product) and heptane (8 vol, 200 mL) added to give a fine precipitate which was left undisturbed at ambient temperature overnight. The mixture was concentrated to dryness and 4 vol THF (100 mL) was added. Heptane was added until a white precipitate formed (~300 mL). The resulting slurry was partially concentrated and solid isolated by filtration. The solid was rinsed with TBME:Heptane=25:75 (100 mL), then heptane (100 mL). Purification by silica gel chromatography (Gradient: 0-30% EtOAc in heptane, containing 10% dichloromethane) yielded the product. 1-(benzenesulfonyl)-6-bromo-N-(4-fluorophenyl)indazol-5-amine (24.13 g, 93%). $^1H$ NMR (300 MHz, Chloroform-d) δ 8.45 (d, J=0.9 Hz, 1H), 8.00-7.92 (m, 3H), 7.63-7.54 (m, 1H), 7.52-7.43 (m, 2H), 7.19-7.10 (m, 3H), 7.10-7.00 (m, 2H), 6.01 (s, 1H). LCMS m/z 446.07 $[M+1]^+$.

Step 1. Synthesis of triisopropylsilyl 3-[1-(benzenesulfonyl)-5-(4-fluorophenyl)-6-[2,2,2-trideuterio-1-hydroxy-1-(trideuteriomethyl)ethyl]pyrrolo[2,3-f]indazol-7-yl]propanoate (C187)

Compound C187 was prepared from triisopropylsilyl 7,7,7-trideuterio-6-hydroxy-6-(trideuteriomethyl)hept-4-ynoate and 1-(benzenesulfonyl)-6-bromo-N-(4-fluorophenyl)indazol-5-amine C186 using the method described in the preparation of compound 225. Triisopropylsilyl 3-[1-(benzenesulfonyl)-5-(4-fluorophenyl)-6-[2,2,2-trideuterio-1-hydroxy-1-(trideuteriomethyl)ethyl]pyrrolo[2,3-f]indazol-7-yl]propanoate (81 mg, 50%). $^1H$ NMR (300 MHz, DMSO-$d_6$) δ 8.43 (d, J=0.8 Hz, 1H), 8.18-8.14 (m, 1H), 7.84-7.82 (m, 1H), 7.82-7.79 (m, 1H), 7.65 (t, J=7.5 Hz, 1H), 7.51 (t, J=7.7 Hz, 2H), 7.43-7.37 (m, 4H), 6.92 (d, J=0.9 Hz, 1H), 5.34 (s, 1H), 3.47-3.38 (m, 2H), 2.84-2.76 (m, 2H), 1.32-1.23 (m, 3H), 1.08 (s, 9H), 1.05 (s, 9H). LCMS m/z 684.53 $[M+H]^+$.

Step 2. Synthesis of 3-[1-(benzenesulfonyl)-6-[2,2-dideuterio-1-(trideuteriomethyl)vinyl]-5-(4-fluorophenyl)pyrrolo[2,3-f]indazol-7-yl]propanoic Acid (C188)

To a solution of triisopropylsilyl 3-[1-(benzenesulfonyl)-5-(4-fluorophenyl)-6-[2,2,2-trideuterio-1-hydroxy-1-(trideuteriomethyl)ethyl]pyrrolo[2,3-f]indazol-7-yl]propanoate C187 (80 mg, 0.12 mmol) in THF (2 mL) was added deuterio 2,2,2-trideuterioacetate (500 μL, 8.7 mmol). The mixture was stirred in a sealed vial for 2 days, then concentrated. Purification by reversed-phase chromatography (Column: C18. Gradient: 0-100% MeCN in water with 0.1% TFA) afforded the product. 3-[1-(benzenesulfonyl)-6-[2,2-dideuterio-1-(trideuteriomethyl)vinyl]-5-(4-fluorophenyl)pyrrolo[2,3-f]indazol-7-yl]propanoic acid (31 mg, 53%). $^1H$ NMR (300 MHz, Chloroform-d) δ 8.37 (t, J=0.9 Hz, 1H), 8.19 (d, J=0.9 Hz, 1H), 8.02-7.96 (m, 2H), 7.57-7.49 (m, 1H), 7.47-7.40 (m, 2H), 7.38-7.32 (m, 3H), 7.25-7.18 (m, 2H), 3.36-3.25 (m, 2H), 2.84 (t, J=7.8 Hz, 2H). LCMS m/z 509.3 $[M+H]^+$.

Step 3 and 4: Synthesis of 3-[5-(4-fluorophenyl)-6-[1,2,2,2-tetradeuterio-1-(trideuteriomethyl)ethyl]-1H-pyrrolo[2,3-f]indazol-7-yl]propanoic Acid (193)

Compound 193 was prepared from 3-[1-(benzenesulfonyl)-6-[2,2-dideuterio-1-(trideuteriomethyl)vinyl]-5-(4-fluorophenyl)pyrrolo[2,3-f]indazol-7-yl]propanoic acid C188 (31 mg, 0.06 mmol) by hydrogenation with $D_2$, then removal of the phenyl sulfonyl protecting group by hydrolysis with $NaO^2H$ as described in the preparation of compound 168. 3-[5-(4-fluorophenyl)-6-[1,2,2,2-tetradeuterio-1-(trideuteriomethyl)ethyl]-1H-pyrrolo[2,3-f]indazol-7-yl]propanoic acid (Trifluoroacetic Acid) (8.8 mg, 35%). $^1H$ NMR (300 MHz, DMSO-$d_6$) δ 12.61 (s, 1H), 12.44-12.06 (bs, 1H), 7.95 (d, J=0.9 Hz, 1H), 7.51-7.37 (m, 5H), 7.01 (d, J=1.1 Hz, 1H), 3.18-3.06 (m, 2H), 2.62-2.54 (m, 2H). LCMS m/z 373.25 $[M+H]^+$.

Compound 194

3-[5-(4-fluorophenyl)-7-isopropyl-1H-pyrrolo[2,3-f]indazol-6-yl]propanoic Acid (227)

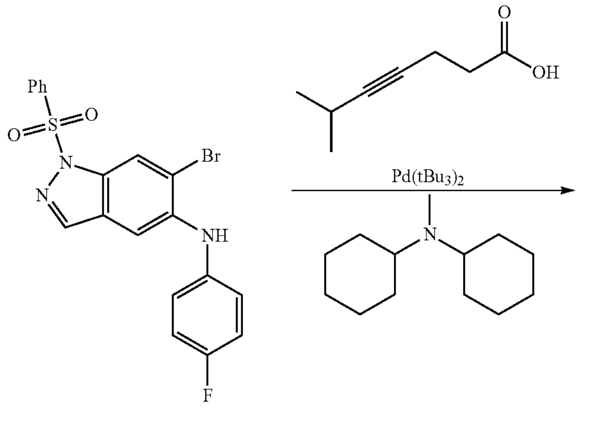

C186

-continued

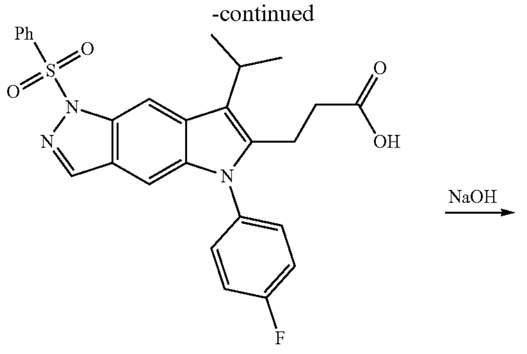

C189

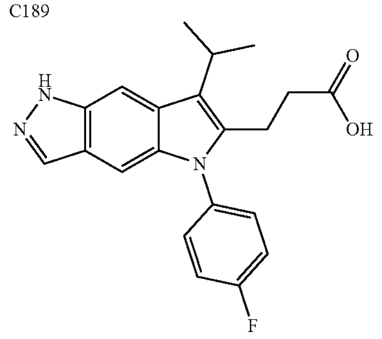

194

Step 1. Synthesis of 3-[1-(benzenesulfonyl)-5-(4-fluorophenyl)-7-isopropyl-pyrrolo[2,3-f]indazol-6-yl]propanoic Acid (C189)

Compound C189 was prepared from 1-(benzenesulfonyl)-6-bromo-N-(4-fluorophenyl)indazol-5-amine C186 (61 mg, 0.14 mmol), and 6-methylhept-4-ynoic acid (25 mg, 0.18 mmol) using the method described for the preparation of Compound 226. 3-[1-(benzenesulfonyl)-5-(4-fluorophenyl)-7-isopropyl-pyrrolo[2,3-f]indazol-6-yl]propanoic acid (25 mg, 36%). $^1$H NMR (400 MHz, Chloroform-d) δ 8.49 (t, J=1.0 Hz, 1H), 8.15 (d, J=0.9 Hz, 1H), 8.03-7.92 (m, 2H), 7.60-7.48 (m, 1H), 7.48-7.37 (m, 2H), 7.38-7.23 (m, 4H), 7.14 (d, J=1.0 Hz, 1H), 3.36 (hept, J=7.2 Hz, 1H), 3.14-2.97 (m, 2H), 2.44-2.35 (m, 2H), 1.60 (d, J=7.1 Hz, 6H). LCMS m/z 506.0 $[M+H]^+$. Note: 3-[1-(benzenesulfonyl)-5-(4-fluorophenyl)-6-isopropyl-pyrrolo[2,3-f]indazol-7-yl]propanoic acid was also obtained.

Step 2. Synthesis of 3-[5-(4-fluorophenyl)-7-isopropyl-1H-pyrrolo[2,3-f]indazol-6-yl]propanoic Acid (194)

Compound 194 was prepared from 1-(benzenesulfonyl)-6-bromo-N-(4-fluorophenyl)indazol-5-amine C189 by hydrolysis with NaOH as described for the preparation of compound 190. Purification by reversed-phase chromatography (Column: C18. Gradient: 10-100% MeCN in water with 0.2% formic acid) afforded the product. 3-[5-(4-fluorophenyl)-7-isopropyl-1H-pyrrolo[2,3-f]indazol-6-yl]propanoic acid (7.8 mg, 41%). The compound was lyophilized overnight to get white solid. $^1$H NMR (400 MHz, DMSO-$d_6$) δ 12.56 (s, 1H), 12.23 (s, 1H), 7.95 (d, J=1.0 Hz, 1H), 7.64 (t, J=1.1 Hz, 1H), 7.58-7.33 (m, 4H), 7.15 (d, J=1.1 Hz, 1H), 3.48-3.21 (m, 1H), 2.90 (dd, J=9.1, 6.8 Hz, 2H), 2.32-2.17 (m, 2H), 1.47 (d, J=7.0 Hz, 6H). LCMS m/z 366.12 $[M+H]^+$.

Compound 195

3-[5-(4-fluoro-3-methyl-phenyl)-6-isopropyl-1-methyl-pyrrolo[2,3-f]indazol-7-yl]propanoic Acid (195)

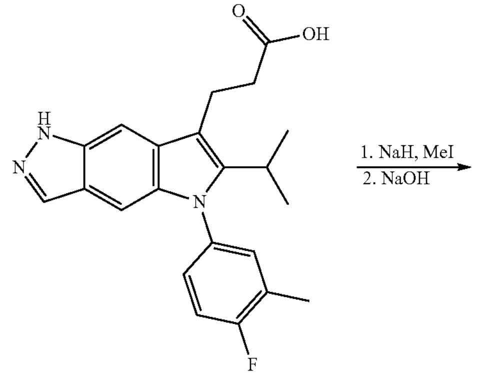

16

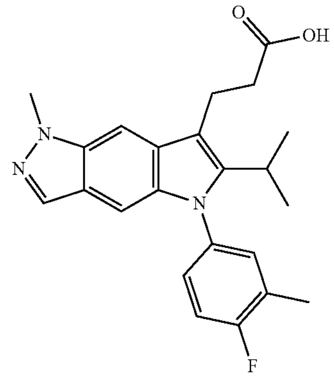

195

Step 1. Synthesis of methyl 3-[5-(4-fluoro-3-methyl-phenyl)-6-isopropyl-1-methyl-pyrrolo[2,3-f]indazol-7-yl]propanoate 3-[5-(4-fluoro-3-methyl-phenyl)-6-isopropyl-1H-pyrrolo[2,3-f]indazol-7-yl]propanoic acid 16 (30 mg, 0.07907 mmol) was dissolved in DMF (1.5 mL). Sodium hydride (6.6 mg, 0.17 mmol) was added, and after 5 minutes iodomethane (10 μL, 0.16 mmol) was added. The mixture was stirred for 48 h. The volatiles were removed on a rotary evaporator. Water and dichloromethane were added. The phases were separated on a phase separator. Purification by silica gel chromatography (Eluent: Ethyl acetate/heptanes) afforded the product. Methyl 3-[5-(4-fluoro-3-methyl-phenyl)-6-isopropyl-1-methyl-pyrrolo[2,3-f]indazol-7-yl]propanoate (15 mg, 47%). $^1$H NMR (400 MHz, DMSO-$d_6$) δ 7.91 (s, 1H), 7.61 (s, 1H), 7.42-7.29 (m, 2H), 7.26 (q, J=6.3, 5.1 Hz, 1H), 7.01 (s, 1H), 4.05 (s, 3H), 3.66 (s, 3H), 3.24-3.11 (m, 2H), 3.01 (p, J=6.9 Hz, 1H), 2.79-2.64 (m, 2H), 2.32 (s, 3H), 1.26 (d, J=7.2 Hz, 6H). LCMS m/z 408.23 $[M+H]^+$.

Step 2. Synthesis of 3-[5-(4-fluoro-3-methyl-phenyl)-6-isopropyl-1-methyl-pyrrolo[2,3-f]indazol-7-yl]propanoic Acid (195)

Methyl 3-[5-(4-fluoro-3-methyl-phenyl)-6-isopropyl-1-methyl-pyrrolo[2,3-f]indazol-7-yl]propanoate (15 mg, 0.04 mmol) was dissolved in methanol (200 μL) and THF (400 μL). Sodium hydroxide (200 μL of 1 M, 0.2 mmol) was added. The mixture was heated to 50° C. for 3 h. The volatiles were removed on a rotary evaporator. Water was added and the pH adjusted to 3-4 with 1M HCl. Water and dichloromethane were added. The phases were separated on a phase separator. The volatiles were removed on a rotary evaporator to afford. 3-[5-(4-fluoro-3-methyl-phenyl)-6-isopropyl-1-methyl-pyrrolo[2,3-f]indazol-7-yl]propanoic acid (12.3 mg, 78%). $^1$H NMR (400 MHz, DMSO-$d_6$) δ 7.91 (s, 1H), 7.61 (s, 1H), 7.43-7.31 (m, 2H), 7.26 (d, J=3.2 Hz, 1H), 7.00 (s, 1H), 4.05 (s, 3H), 3.14 (t, J=8.3 Hz, 2H), 3.01 (q, J=7.1 Hz, 1H), 2.62 (t, J=8.2 Hz, 2H), 2.32 (d, J=1.9 Hz, 3H), 1.26 (d, J=7.9 Hz, 7H). LCMS m/z 394.28 [M+H]$^+$.

Compound 196

6-(5-propyl-6-tetrahydropyran-4-yl-1H-pyrrolo[2,3-f]indazol-7-yl)spiro[3.3]heptane-2-carboxylic Acid (196)

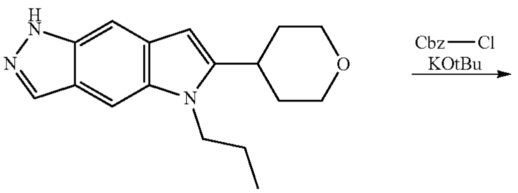

C190

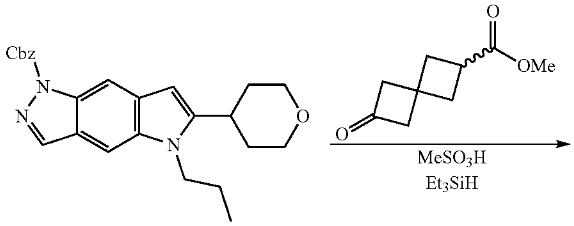

C191

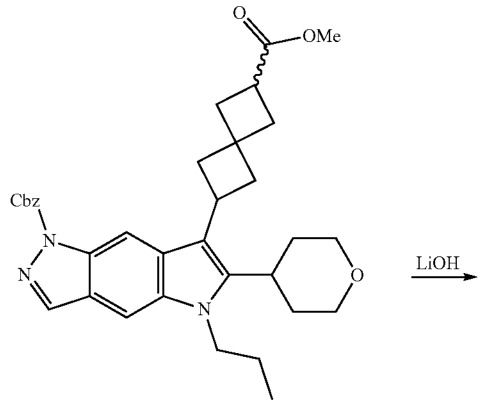

C192

-continued

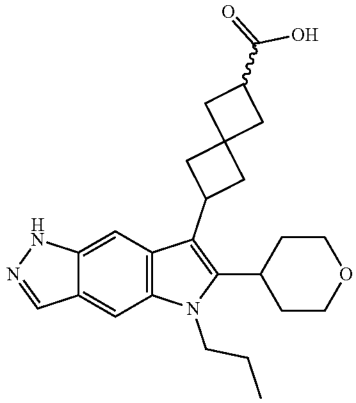

196

Compound 196 was prepared from 5-propyl-6-tetrahydropyran-4-yl-1H-pyrrolo[2,3-f]indazole C190 in three steps using the method described for the preparation of preparation S7 and compound 34. Purification by reversed-phase chromatography (Column: C18. Gradient: 0-100% MeCN in water with 0.1% trifluoroacetic acid) afforded the product. 6-(5-propyl-6-tetrahydropyran-4-yl-1H-pyrrolo[2,3-f]indazol-7-yl)spiro[3.3]heptane-2-carboxylic acid (124 mg, 81%). $^1$H NMR (400 MHz, DMSO-$d_6$) δ 12.49 (s, 1H), 12.08 (s, 1H), 8.01 (s, 1H), 7.65 (s, 2H), 4.13 (t, J=7.7 Hz, 2H), 4.06-3.91 (m, 2H), 3.85 (t, J=9.1 Hz, 1H), 3.48 (t, J=11.7 Hz, 2H), 3.15 (s, 1H), 3.10-2.97 (m, 1H), 2.71 (dt, J=23.1, 10.4 Hz, 2H), 2.32 (q, J=14.7, 11.8 Hz, 4H), 2.03 (d, J=13.3 Hz, 1H), 1.64 (d, J=13.3 Hz, 5H), 0.93 (t, J=7.4 Hz, 3H). LCMS m/z 422.37 [M+H]$^+$.

Compound 197

5-(4-fluorophenyl)-6-(3-methyloxetan-3-yl)-7-methylsulfonyl-1H-pyrrolo[2,3-f]indazole (197)

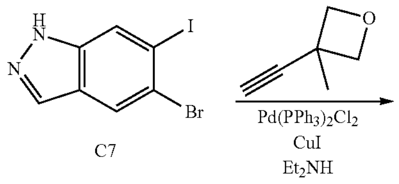

C7

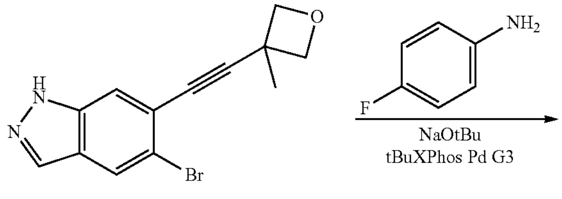

C193

-continued
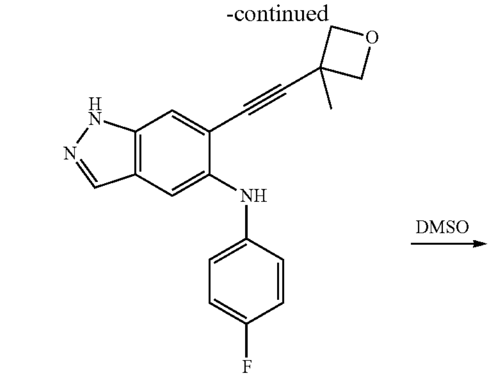
C194
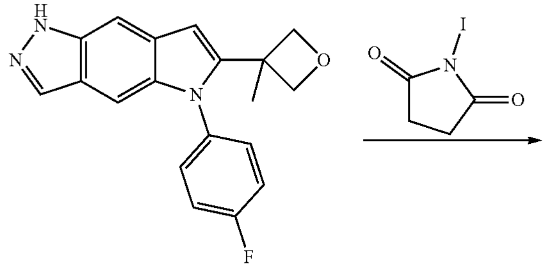
C195
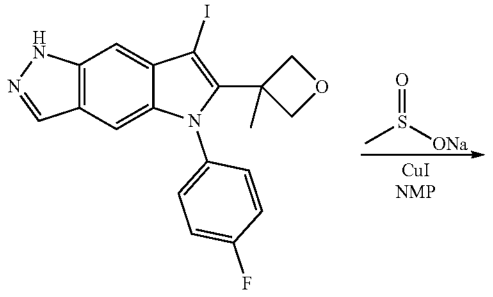
C196
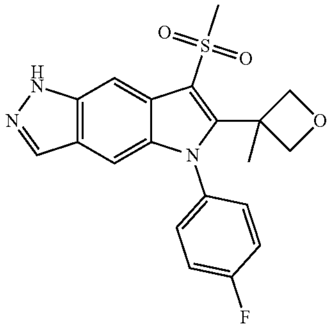
197
Compound 197 was prepared from 5-bromo-6-iodo-1H-indazole (C7) using the method described by the preparation of compound 139. 5-(4-fluorophenyl)-6-(3-methyloxetan-3-yl)-7-methylsulfonyl-1H-pyrrolo[2,3-f]indazole (7.9 mg, 28%). $^1$H NMR (300 MHz, DMSO-$d_6$) δ 12.93 (s, 1H), 8.08 (t, J=1.3 Hz, 1H), 7.90 (t, J=1.1 Hz, 1H), 7.83-7.60 (m, 2H), 7.50 (t, J=8.5 Hz, 2H), 7.17 (d, J=1.0 Hz, 1H), 5.01-4.69 (m, 2H), 3.32-3.30 (m, 5H), 1.99 (s, 3H). LCMS m/z 400.29 [M+H]$^+$.
Compound 198
3-[6-(azetidin-3-yl)-5-(4-fluorophenyl)-1H-pyrrolo[2,3-f]indazol-7-yl]propanoic Acid (198)
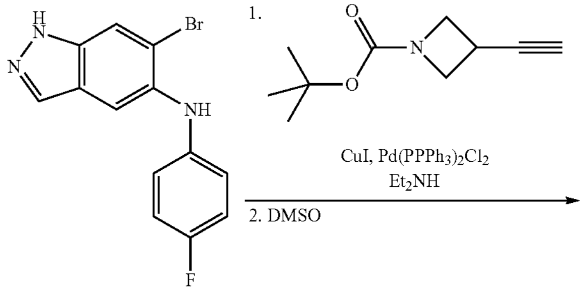
C184
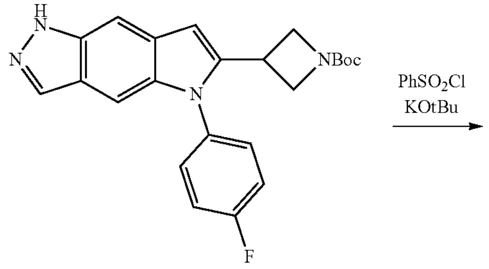
C197
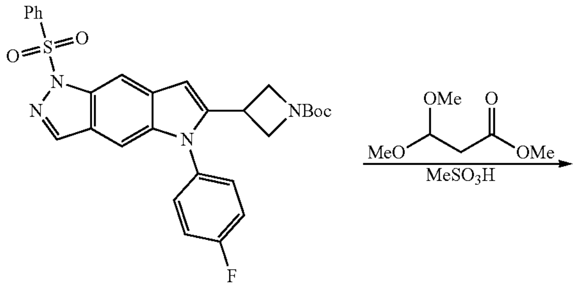
C198
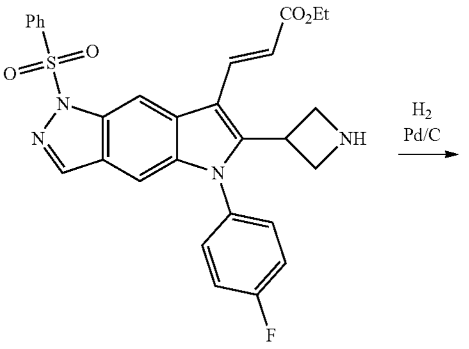
C199

-continued

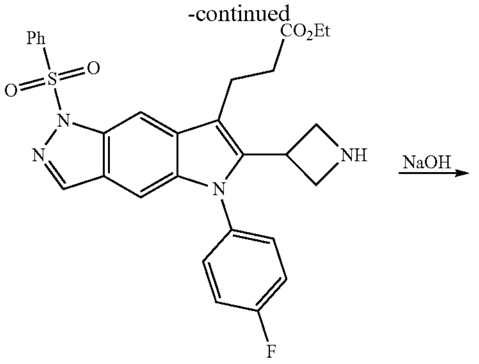

C200

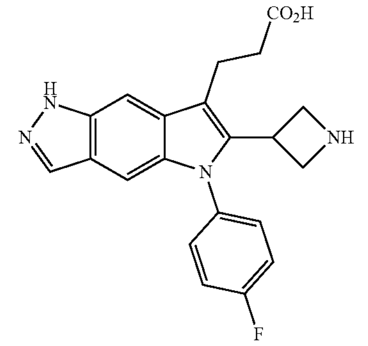

198

Step 1 & 2. tert-butyl 3-[5-(4-fluorophenyl)-1H-pyrrolo[2,3-f]indazol-6-yl]azetidine-1-carboxylate (C197)

A mixture of 6-bromo-N-(4-fluorophenyl)-1H-indazol-5-amine C184 (565 mg, 1.79 mmol) and diethylamine (577 μL, 5.58 mmol) in DMF (4.3 mL) was degassed with nitrogen for 10 minutes. $PdCl_2(PPh_3)_2$ (67 mg, 0.10 mmol) and CuI (24 mg, 0.13 mmol) were added and degassing continued. tert-Butyl 3-ethynylazetidine-1-carboxylate (482 mg, 2.7 mmol) was added and heated and the reaction to 50° C. overnight. The mixture was then concentrated to dryness onto Celite® under reduced pressure. Purification by silica gel chromatography (Gradient: 0-100% EtOAc in heptane) yielded an inseparable mixture of tert-butyl 3-[2-[5-(4-fluoroanilino)-1H-indazol-6-yl]ethynyl]azetidine-1-carboxylate and tert-butyl 3-[5-(4-fluorophenyl)-1H-pyrrolo[2,3-f]indazol-6-yl]azetidine-1-carboxylate (490 mg, 63%). LCMS m/z 407.32 $[M+H]^+$. tert-butyl 3-[5-(4-fluorophenyl)-1H-pyrrolo[2,3-f]indazol-6-yl]azetidine-1-carboxylate (517 mg, 0.92 mmol) was dissolved in DMSO (1.5 mL). The solution was stirred and heated to 150° C. for 30 minutes. The mixture was cooled to room temperature and diluted with Ethyl Acetate (50 mL). Washed with 50% saturated sodium bicarbonate, water and brine. Dried the organics with sodium sulfate, filtered and concentrated to dryness under reduced pressure. Purification by silica gel chromatography (Gradient: 0-100% EtOAc in heptane) yielded tert-butyl 3-[5-(4-fluorophenyl)-1H-pyrrolo[2,3-f]indazol-6-yl]azetidine-1-carboxylate (347 mg, 84%). $^1H$ NMR (400 MHz, DMSO-$d_6$) δ 12.66 (s, 1H), 7.99 (t, J=1.3 Hz, 1H), 7.60 (t, J=1.1 Hz, 1H), 7.53-7.41 (m, 4H), 7.27-7.22 (m, 1H), 6.79-6.73 (m, 1H), 4.00-3.90 (m, 4H), 3.82 (p, J=8.3, 7.6 Hz, 1H), 1.37 (s, 9H). LCMS m/z 407.32 $[M+H]^+$.

Steps 3-5. methyl 3-[6-(azetidin-3-yl)-1-(benzenesulfonyl)-5-(4-fluorophenyl)pyrrolo[2,3-f]indazol-7-yl]propanoate (C200)

Compound C200 was prepared from tert-butyl 3-[5-(4-fluorophenyl)-1H-pyrrolo[2,3-f]indazol-6-yl]azetidine-1-carboxylate C197 in three steps by protection with a phenyl sulfonyl group, reductive coupling, then hydrogenation as using the method described for the preparation of compound 16.

Step 6. Synthesis of 3-[6-(azetidin-3-yl)-5-(4-fluorophenyl)-1H-pyrrolo[2,3-f]indazol-7-yl]propanoic Acid (198)

An aqueous solution of NaOH (554 μL of 2 M, 1.108 mmol) was added to a solution of methyl 3-[6-(azetidin-3-yl)-1-(benzenesulfonyl)-5-(4-fluorophenyl)pyrrolo[2,3-f]indazol-7-yl]propanoate C200 (61 mg, 0.11 mmol) in THF (2 mL), piperazine (29 mg, 0.33 mmol) and methanol (2 mL). The reaction was stirred at 65° C. for 2 hours. The mixture was concentrated in vacuo to dryness. Purification by reversed-phase chromatography (Column: C18. Gradient: 10-100% MeCN in water with 0.1% TFA) afforded the desired product. 3-[6-(azetidin-3-yl)-5-(4-fluorophenyl)-1H-pyrrolo[2,3-f]indazol-7-yl]propanoic acid (Trifluoroacetate salt) (31.2 mg, 46%). $^1H$ NMR (400 MHz, DMSO-$d_6$) δ 12.73 (s, 1H), 8.00 (d, J=1.0 Hz, 1H), 7.59 (t, J=1.2 Hz, 1H), 7.55-7.44 (m, 5H), 7.24 (d, J=1.1 Hz, 1H), 4.52-4.40 (m, 2H), 4.13 (t, J=10.1 Hz, 2H), 3.84-3.78 (m, 2H), 3.05 (t, J=7.7 Hz, 2H), 2.69-2.65 (m, 2H). LCMS m/z 379.19 $[M+H]^+$.

Compound 199

5-(4-fluoro-3-methyl-phenyl)-6-isopropyl-7-methylsulfonyl-1H-pyrrolo[2,3-f]benzotriazole (199)

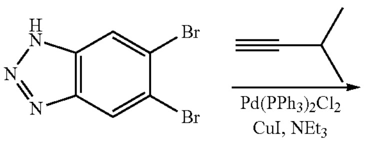

C201

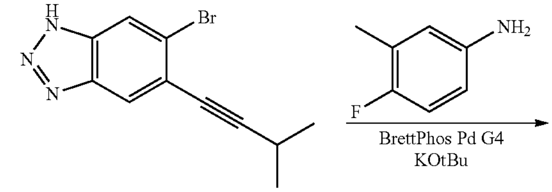

C202

-continued

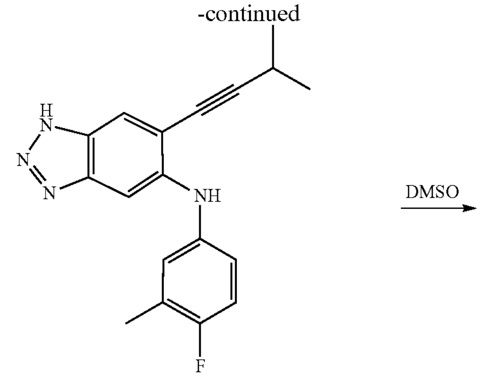

C203

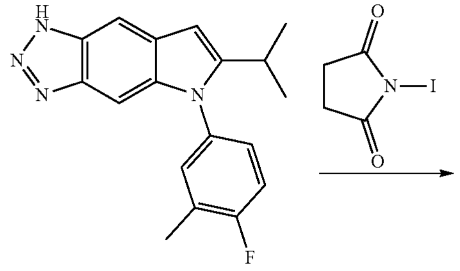

C204

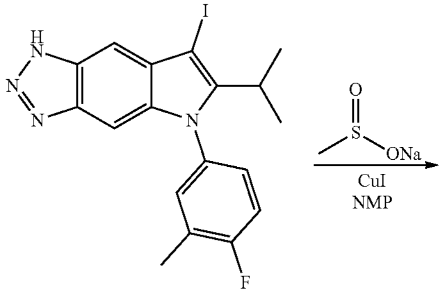

C205

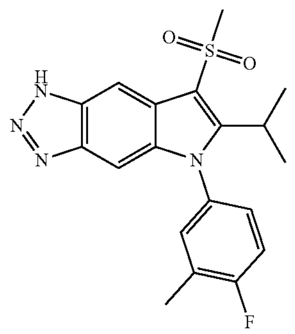

199

Compound 199 was prepared in five steps from 5,6-dibromo-1H-benzotriazole C201 using the method described for the preparation of compound 197. BrettPhos Pd G4 was used in the Buchwald coupling step. Purification by reversed-phase chromatography (Column: C18. Gradient: 10-100% MeCN in water with 0.1% trifluoroacetic acid) afforded the product. 5-(4-fluoro-3-methyl-phenyl)-6-isopropyl-7-methylsulfonyl-1H-pyrrolo[2,3-f]benzotriazole (20.2 mg, 21%). $^{1}H$ NMR (300 MHz, DMSO-$d_6$) δ 15.48 (s, 1H), 8.34 (s, 1H), 7.58 (d, J=7.3 Hz, 1H), 7.51-7.44 (m, 2H), 7.10 (s, 1H), 3.84-3.60 (m, 1H), 3.29 (s, 3H), 2.39-2.31 (m, 3H), 1.28 (d, J=7.2 Hz, 6H). LCMS m/z 387.24 $[M+H]^+$.

Compound 200

3-[1-(4-fluorophenyl)-2-isopropyl-5H-pyrrolo[2,3-f]indol-3-yl]propanoic Acid (200)

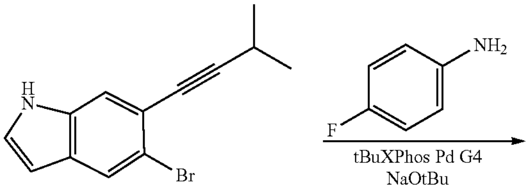

C206

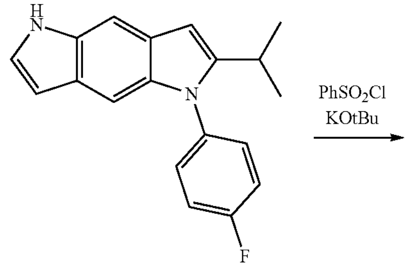

C207

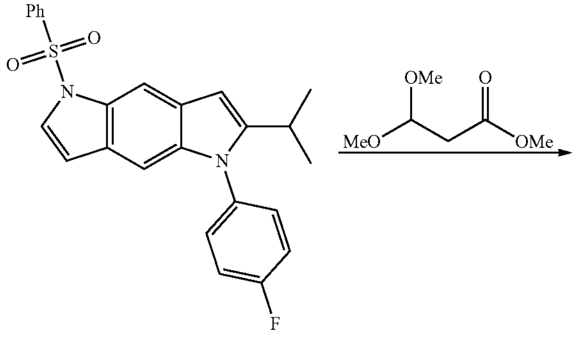

C208

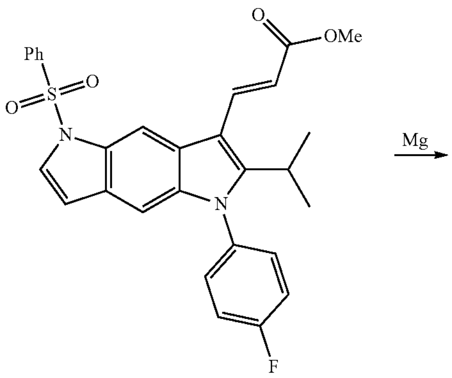

C209

-continued

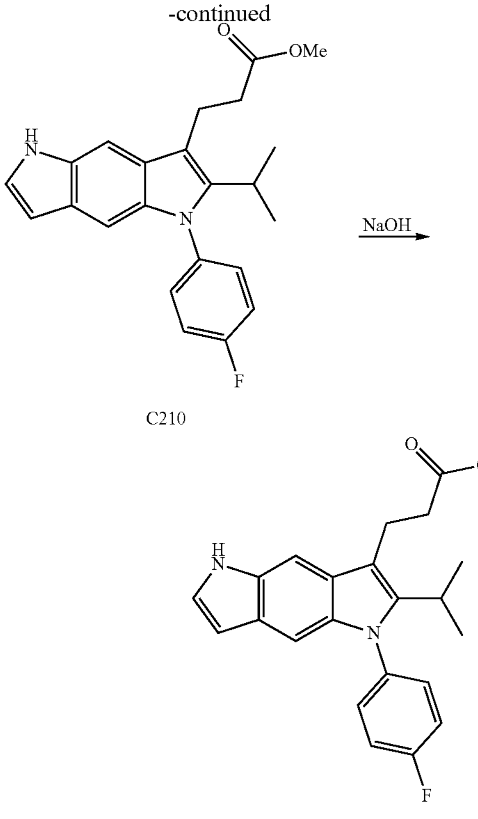

C210

200

Compound 200 was prepared in five steps from 5-bromo-6-(3-methylbut-1-ynyl)-1H-indole C206 using the method described for the preparation of compound 190. Methyl 3-[1-(4-fluorophenyl)-2-isopropyl-5H-pyrrolo[2,3-f]indol-3-yl]propanoate (C210) was prepared from methyl (E)-3-[5-(benzenesulfonyl)-1-(4-fluorophenyl)-2-isopropyl-pyrrolo[2,3-f]indol-3-yl]prop-2-enoate C209 by reduction with Mg.

Synthesis of methyl 3-[1-(4-fluorophenyl)-2-isopropyl-5H-pyrrolo[2,3-f]indol-3-yl]propanoate (C210)

Methanol (6 mL) and THF (2 mL) were added to methyl (E)-3-[5-(benzenesulfonyl)-1-(4-fluorophenyl)-2-isopropyl-pyrrolo[2,3-f]indol-3-yl]prop-2-enoate C209 (150 mg, 0.29 mmol). Magnesium (72 mg, 2.96 mmol) chips were added and the vial sealed and heated to 50° C. for 90 minutes. The mixture was diluted with dichloromethane (50 mL) and washed with a 50% saturated ammonium chloride solution. The organic layers were passed through a phase separator and concentrated to dryness under reduced pressure. Purification by silica gel chromatography (Gradient: 0-100% EtOAc in heptane) yielded methyl 3-[1-(4-fluorophenyl)-2-isopropyl-5H-pyrrolo[2,3-f]indol-3-yl]propanoate (65.7 mg, 59%). $^1$H NMR (400 MHz, DMSO-$d_6$) δ 10.64 (s, 1H), 7.47-7.40 (m, 4H), 7.40-7.36 (m, 1H), 7.25 (dd, J=3.1, 2.4 Hz, 1H), 6.82 (s, 1H), 6.33-6.26 (m, 1H), 3.65 (s, 3H), 3.18-3.09 (m, 2H), 2.99 (p, J=7.1 Hz, 1H), 2.70-2.63 (m, 2H), 1.24 (d, J=7.1 Hz, 6H). LCMS m/z 379.24 $[M+H]^+$.

Compound 190. 3-[1-(4-fluorophenyl)-2-isopropyl-5H-pyrrolo[2,3-f]indol-3-yl]propanoic acid (19.8 mg, 31%). $^1$H NMR (400 MHz, DMSO-$d_6$) δ 12.24 (s, 1H), 10.64 (s, 1H), 7.48-7.35 (m, 5H), 7.30-7.21 (m, 1H), 6.82 (s, 1H), 6.31-6.25 (m, 1H), 3.16-3.05 (m, 2H), 2.99 (p, J=7.2 Hz, 1H), 2.60-2.54 (m, 2H), 1.25 (d, J=7.1 Hz, 6H). LCMS m/z 365.29 $[M+H]^+$.

Compound 201

3-[7-(4-fluorophenyl)-6-isopropyl-1H-pyrrolo[3,2-f]indazol-5-yl]propanoic Acid (201)

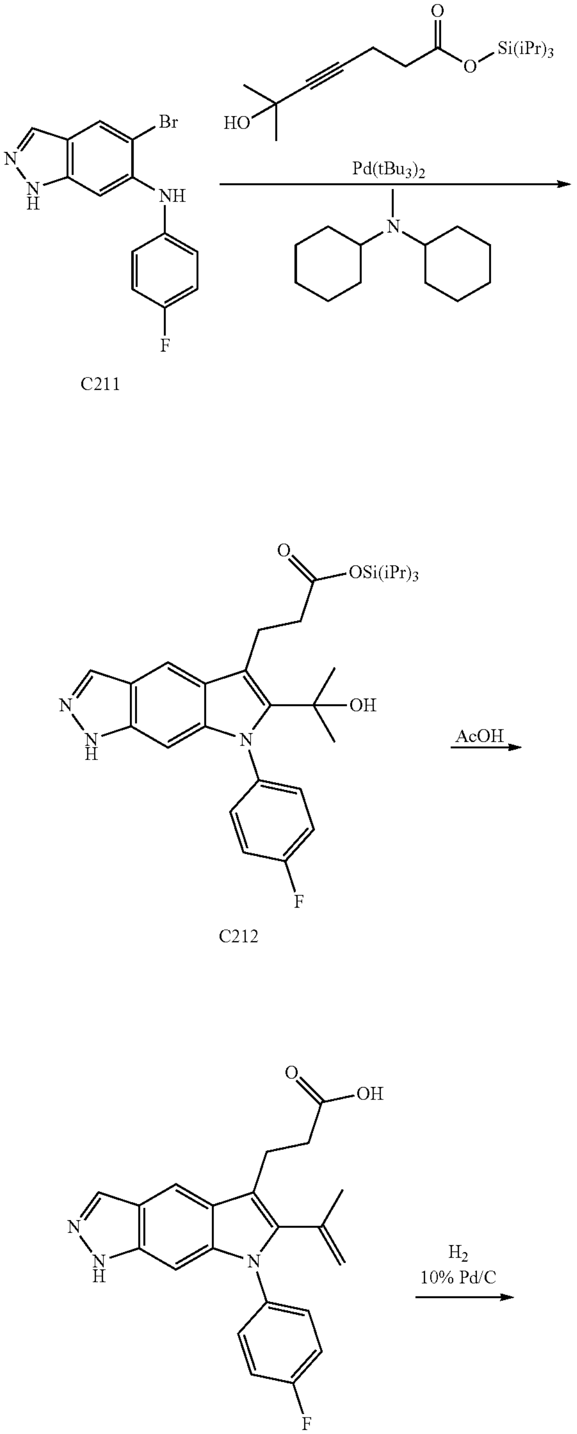

C211

C212

C213

-continued

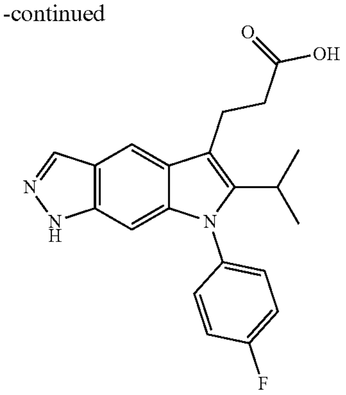

201

Compound 201 was prepared from 5-bromo-N-(4-fluorophenyl)-1H-indazol-6-amine C211 and triisopropylsilyl 3-[7-(4-fluorophenyl)-6-(1-hydroxy-1-methyl-ethyl)-1H-pyrrolo[3,2-f]indazol-5-yl]propanoate using the method described for the preparation of compound 192, and palladium catalyzed hydrogenation as described for compound 16 or 32. Purification by silica gel chromatography (Gradient: 0-10% methanol in dichloromethane) yielded 3-[7-(4-fluorophenyl)-6-isopropyl-1H-pyrrolo[3,2-f]indazol-5-yl] propanoic acid (11.5 mg, 19%). $^{1}H$ NMR (300 MHz, DMSO-$d_6$) δ 12.37 (s, 2H), 8.06 (d, J=1.0 Hz, 1H), 7.83 (d, J=1.1 Hz, 1H), 7.53-7.39 (m, 4H), 6.69-6.60 (m, 1H), 3.14 (dd, J=14.6, 7.1 Hz, 2H), 3.00 (p, J=7.1 Hz, 1H), 2.65-2.54 (m, 2H), 1.24 (d, J=7.2 Hz, 6H). LCMS m/z 366.28 $[M+H]^+$.

Compound 202

3-[4-(4-fluorophenyl)-5-isopropyl-2,4,10,11-tetrazatricyclo[7.3.0.03,7]dodeca-1,3(7),5,8,11-pentaen-6-yl]propanoic Acid (202)

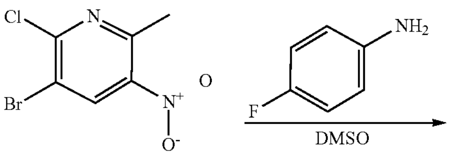

C214

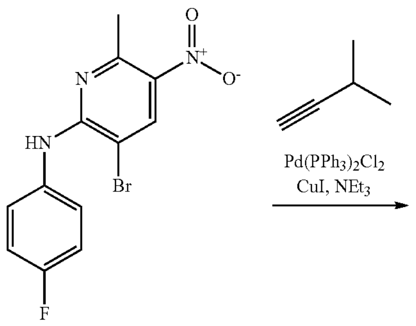

C215

-continued

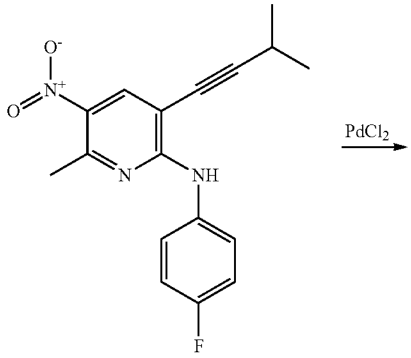

C216

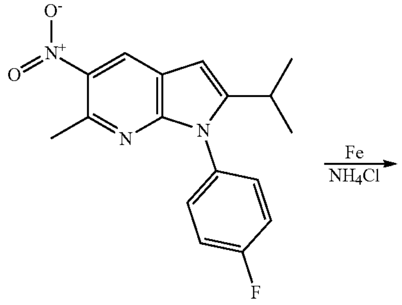

C217

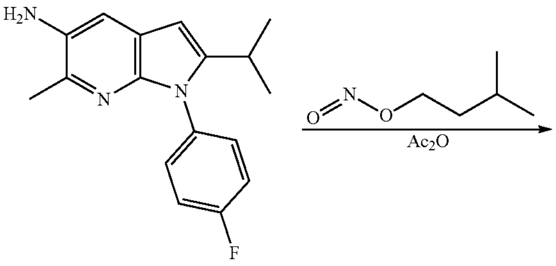

C218

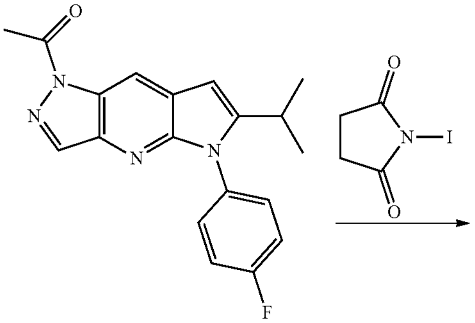

C219

-continued

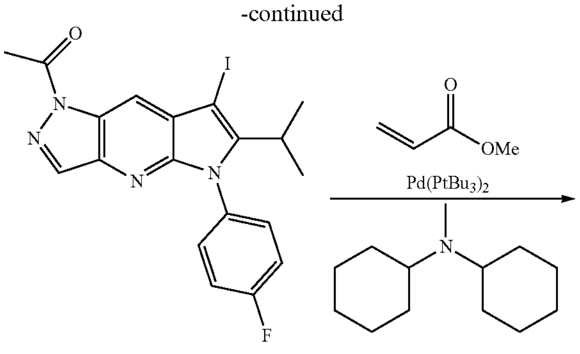

C220

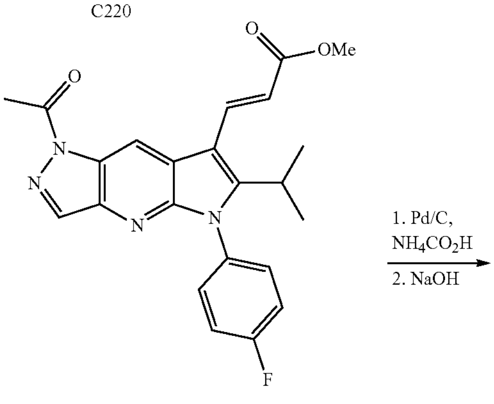

C221

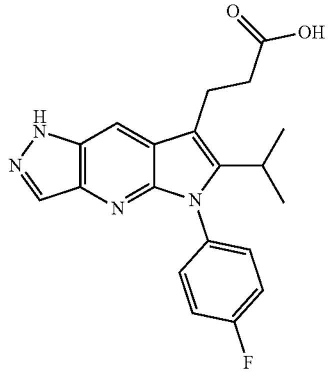

202

Step 1. Synthesis of 3-bromo-N-(4-fluorophenyl)-6-methyl-5-nitro-pyridin-2-amine (C215)

A 100 mL round bottom flask was charged with 3-bromo-2-chloro-6-methyl-5-nitro-pyridine C214 (2.69 g, 10.7 mmol) and dissolved in DMSO (22 mL). 4-fluoroaniline (3 mL, 31.7 mmol) was added, and the reaction was heated to 120° C. for 30 minutes. The reaction mixture was allowed to cool to room temperature, and was poured into water (500 mL), forming a green precipitate. This precipitate was collected by vacuum filtration and washed with excess water. The crude material was purified by column chromatography (Gradient: 0-20% EtOAc in Heptane) to afford the product. 3-bromo-N-(4-fluorophenyl)-6-methyl-5-nitro-pyridin-2-amine (3.2 g, 89%). $^1$H NMR (400 MHz, DMSO-$d_6$) δ 9.14 (s, 1H), 8.56 (s, 1H), 7.66 (ddd, J=9.1, 5.0, 1.7 Hz, 2H), 7.21 (td, J=8.8, 1.7 Hz, 2H), 2.61 (s, 3H). LCMS m/z 325.9 $[M+H]^+$.

Step 2. Synthesis of N-(4-fluorophenyl)-6-methyl-3-(3-methylbut-1-ynyl)-5-nitro-pyridin-2-amine (C216)

Compound C216 was prepared from 3-bromo-N-(4-fluorophenyl)-6-methyl-5-nitro-pyridin-2-amine and 3-methyl-but-1-yne by Sonagashira coupling as described in the preparation of C2 in preparation S1. N-(4-fluorophenyl)-6-methyl-3-(3-methylbut-1-ynyl)-5-nitro-pyridin-2-amine (1.2965 g, 86%). $^1$H NMR (400 MHz, DMSO-d6) δ 8.87 (s, 1H), 8.22 (d, J=1.6 Hz, 1H), 7.69 (dt, J=9.6, 3.4 Hz, 2H), 7.26-7.18 (m, 2H), 2.92 (hept, J=7.1 Hz, 1H), 2.64 (s, 3H), 1.27 (dd, J=6.9, 1.6 Hz, 6H). LCMS m/z 314.02 $[M+H]^+$.

Step 3. Synthesis of 1-(4-fluorophenyl)-2-isopropyl-6-methyl-5-nitro-pyrrolo[2,3-b]pyridine (C217)

A 100 mL round bottom flask was charged with N-(4-fluorophenyl)-6-methyl-3-(3-methylbut-1-ynyl)-5-nitro-pyridin-2-amine C216 (1.12 g, 3.44 mmol) and $PdCl_2$ (161 mg, 0.91 mmol). MeCN (35 mL) was added, and the reaction was heated to 50° C. for 24 hours. The solvent was evaporated, and the crude reaction was purified by column chromatography (Gradient: 0-20% EtOAc in Heptane) to afford the product. 1-(4-fluorophenyl)-2-isopropyl-6-methyl-5-nitro-pyrrolo[2,3-b]pyridine (672 mg, 62%). $^1$H NMR (400 MHz, DMSO-$d_6$) δ 8.71 (s, 1H), 7.55 (dd, J=8.6, 5.0 Hz, 2H), 7.45 (t, J=8.5 Hz, 2H), 6.64 (s, 1H), 2.92 (hept, J=7.1 Hz, 1H), 2.68 (s, 3H), 1.16 (d, J=6.7 Hz, 6H). LCMS m/z 314.34 $[M+H]^+$.

Step 4. Synthesis of 1-(4-fluorophenyl)-2-isopropyl-6-methyl-pyrrolo[2,3-b]pyridin-5-amine (C218)

A 10-20 mL microwave vial was charged with 1-(4-fluorophenyl)-2-isopropyl-6-methyl-5-nitro-pyrrolo[2,3-b]pyridine C217 (600 mg, 1.91 mmol), $NH_4Cl$ (1.42 g, 26.6 mmol), and iron (985 mg, 17.6 mmol). MeOH (10 mL) was added and the reaction was heated at 80° C. overnight. The reaction mixture was filtered and washed with MeOH and dichloromethane. The solvent was evaporated and the mixture was purified by reverse phase chromatography (C18 column. Gradient: 10-100% acetonitrile in water with 0.2% formic acid). 1-(4-fluorophenyl)-2-isopropyl-6-methyl-pyrrolo[2,3-b]pyridin-5-amine (561.7 mg, 85%) LCMS m/z 284.38 $[M+H]^+$.

Step 5. Synthesis of 1-[4-(4-fluorophenyl)-5-isopropyl-2,4,10,11-tetrazatricyclo[7.3.0.03,7]dodeca-1(9),2,5,7,11-pentaen-10-yl]ethanone (C219)

A mixture of 1-(4-fluorophenyl)-2-isopropyl-6-methyl-pyrrolo[2,3-b]pyridin-5-amine C218 (22 mg, 0.08 mmol) and KOAc (10 mg, 0.10 mmol) in chloroform (800 μL) was added and the mixture was stirred at 60° C. for 20 minutes. Then, acetic anhydride (22 μL, 0.23 mmol) was added dropwise, followed by isoamyl nitrite (21 μL, 0.16 mmol) and 1,4,7,10,13,16-hexaoxacyclooctadecane (4 mg, 0.015 mmol). The mixture was allowed to stir overnight. The solution was washed with sat. $NaHCO_3$, and the mixture was passed through a phase separator. The organic phase was collected, and the solvent was evaporated. Purification by silica gel chromatography (Gradient: 0-30% EtOAc in heptane) afforded the product. 1-[4-(4-fluorophenyl)-5-isopropyl-2,4,10,11-tetrazatricyclo[7.3.0.03,7]dodeca-1,3(7),5,8,11-pentaen-10-yl]ethanone (15.1 mg, 56%). $^1$H NMR (400 MHz, DMSO-$d_6$) δ 8.79 (s, 1H), 8.54 (s, 1H), 7.64-7.52 (m, 2H), 7.45 (td, J=8.7, 1.8 Hz, 2H), 6.73 (s, 1H), 3.09-2.94 (m, 1H), 2.73 (d, J=1.6 Hz, 3H), 1.20 (dd, J=6.9, 1.6 Hz, 6H). LCMS m/z 337.06 $[M+H]^+$.

Step 6. Synthesis of 1-[4-(4-fluorophenyl)-6-iodo-5-isopropyl-2,4,10,11-tetrazatricyclo[7.3.0.03,7]dodeca-1(9),2,5,7,11-pentaen-10-yl] ethanone (C220)

1-[4-(4-fluorophenyl)-6-iodo-5-isopropyl-2,4,10,11-tetrazatricyclo[7.3.0.03,7]dodeca-1(9),2,5,7,11-pentaen-10-yl] ethanone (C220) was prepared from 1-[4-(4-fluorophenyl)-5-isopropyl-2,4,10,11-tetrazatricyclo[7.3.0.03,7]dodeca-1,3(7),5,8,11-pentaen-10-yl]ethanone C219 by iodination with N-iodosucinimide using the method described for compound 1. 1-[4-(4-fluorophenyl)-6-iodo-5-isopropyl-2,4,10,11-tetrazatricyclo[7.3.0.03,7]dodeca-1,3(7),5,8,11-pentaen-10-yl]ethanone (206.3 mg, 68%). $^1H$ NMR (400 MHz, DMSO-$d_6$) δ 8.62 (d, J=0.8 Hz, 1H), 8.53 (d, J=0.8 Hz, 1H), 7.58 (ddt, J=8.4, 5.7, 2.7 Hz, 2H), 7.50-7.42 (m, 2H), 3.21-3.02 (m, 1H), 2.75 (s, 3H), 1.36 (d, J=7.1 Hz, 6H). LCMS m/z 462.95 $[M+H]^+$.

Step 7. Synthesis of methyl (E)-3-[10-acetyl-4-(4-fluorophenyl)-5-isopropyl-2,4,10,11-tetrazatricyclo[7.3.0.03,7]dodeca-1(9),2,5,7,11-pentaen-6-yl]prop-2-enoate (C221)

A 2-5 mL microwave vial was charged with 1-[4-(4-fluorophenyl)-6-iodo-5-isopropyl-2,4,10,11-tetrazatricyclo[7.3.0.03,7]dodeca-1,3(7),5,8,11-pentaen-10-yl]ethanone C220 (100 mg, 0.1972 mmol) and DMA (2 mL). methyl acrylate (40 μL, 0.44 mmol) and N-cyclohexyl-N-methyl-cyclohexanamine (90 μL, 0.42 mmol) were added, and the solution was degassed with nitrogen for 10 minutes. $Pd(PtBu_3)_2$ (12 mg, 0.02 mmol) was added, and the reaction was sealed and heated to 80° C. for 1 hour. Water (5 mL) and dichloromethane (5 mL) were added, and the mixture was passed through a phase separator. The organic phase was collected, and the solvent was evaporated. Purification by silica gel chromatography (Gradient: 0-40% EtOAc in Heptane) afforded the product. Methyl (E)-3-[10-acetyl-4-(4-fluorophenyl)-5-isopropyl-2,4,10,11-tetrazatricyclo[7.3.0.03,7]dodeca-1,3(7),5,8,11-pentaen-6-yl]prop-2-enoate (78.8 mg, 91%). $^1H$ NMR (400 MHz, DMSO-$d_6$) δ 9.05 (s, 1H), 8.65 (s, 1H), 8.17 (d, J=15.9 Hz, 1H), 7.68-7.57 (m, 2H), 7.49 (t, J=8.7 Hz, 2H), 6.44 (d, J=15.9 Hz, 1H), 3.79 (s, 3H), 3.29-3.13 (m, 1H), 2.77 (s, 3H), 1.36 (d, J=7.2 Hz, 6H). LCMS m/z 421.1 $[M+H]^+$.

Step 8. Synthesis of 3-[4-(4-fluorophenyl)-5-isopropyl-2,4,10,11-tetrazatricyclo[7.3.0.03,7]dodeca-1,3(7),5,8,11-pentaen-6-yl]propanoic Acid (202)

A 20 mL scintillation vial was charged with methyl (E)-3-[10-acetyl-4-(4-fluorophenyl)-5-isopropyl-2,4,10,11-tetrazatricyclo[7.3.0.03,7]dodeca-1,3(7),5,8,11-pentaen-6-yl]prop-2-enoate C221 (70 mg, 0.16 mmol), palladium on carbon (103 mg, 0.97 mmol), and ammonium formate (112 mg, 1.78 mmol). MeOH (4 mL) was added, and the reaction was heated to 60° C. for 30 minutes. The solution was filtered through a pad of Celite® and washed with MeOH and dichloromethane. The filtrate was evaporated, and the crude material was dissolved in THF (3 mL) and MeOH (1.5 mL). NaOH (3.2 mL of 1 M, 3.2 mmol) was added and the reaction was heated to 50° C. The solvent was evaporated, and the residue was dissolved in minimal water. HCl (3.2 mL of 1 M, 3.200 mmol) was added, forming a precipitate.

The solvent was evaporated and taken up in minimal DMSO. Purification by reversed phase chromatography (C18 column Gradient: 10-100% acetonitrile in water with 0.2% formic acid) afforded the product. 3-[4-(4-fluorophenyl)-5-isopropyl-2,4,10,11-tetrazatricyclo[7.3.0.03,7]dodeca-1,3(7),5,8,11-pentaen-6-yl]propanoic acid (38.6 mg, 64%). $^1H$ NMR (400 MHz, DMSO-$d_6$) δ 12.95 (s, 1H), 8.07 (s, 1H), 8.02 (s, 1H), 7.51-7.32 (m, 4H), 3.09-2.99 (m, 1H), 1.60-1.50 (m, 2H), 1.26 (d, J=7.2 Hz, 6H), 1.11-1.02 (m, 2H). LCMS m/z 367.11 $[M+H]^+$.

Compound 203

3-[10-(4-fluorophenyl)-11-isopropyl-2,4,5,10-tetrazatricyclo[7.3.0.03,7]dodeca-1,3(7),5,8,11-pentaen-12-yl]propanoic Acid (203)

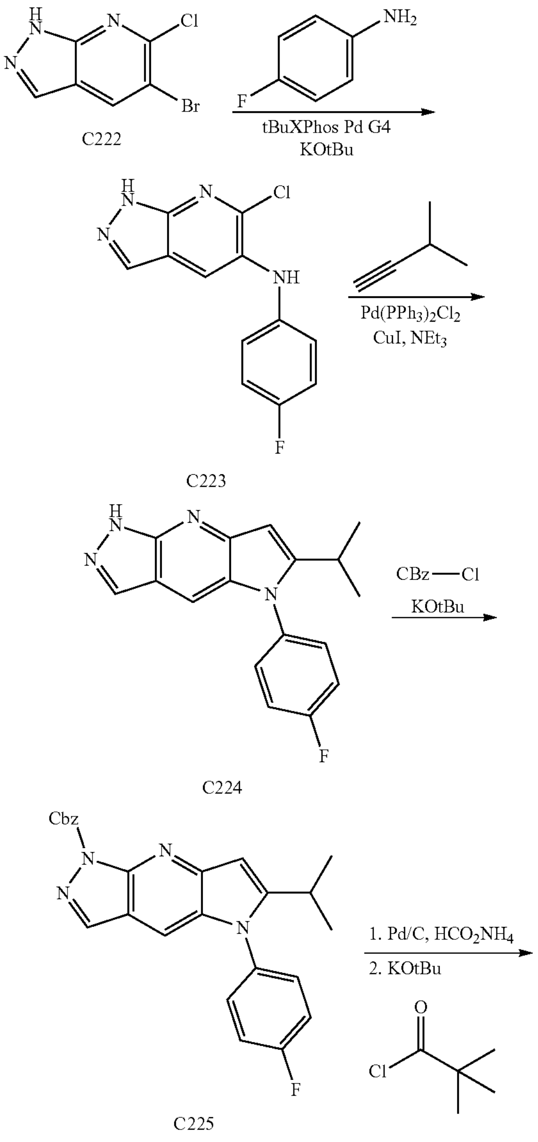

C222

C223

C224

C225

-continued

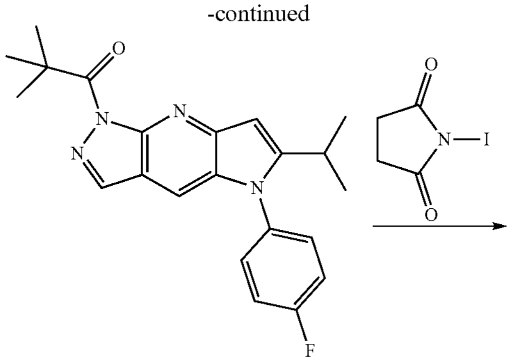

C226

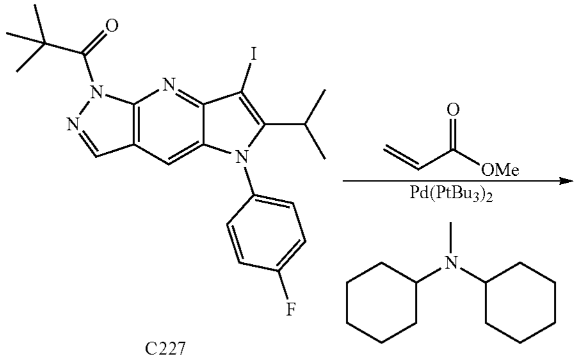

C227

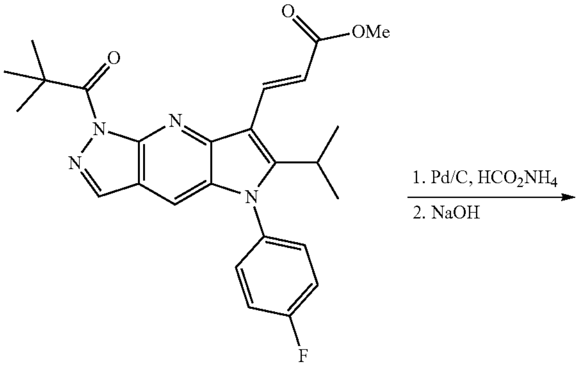

C228

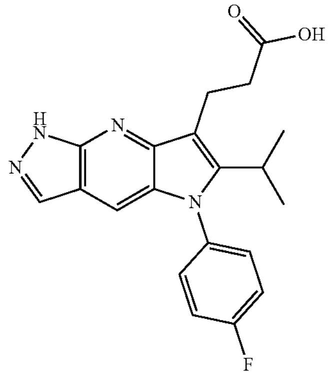

203

Compound 203 was prepared from 5-bromo-6-chloro-1H-pyrazolo[3,4-b]pyridine C222 in nine steps using an analogous method to that described for the preparation of 202. In this example, CBz protected intermediate C225 was used to prepare C226. Compound C225 was prepared by Buchwald amination with 4-fluoraniline, Sonagashira coupling with 3-methylbut-1-yne, then CBz protection (as described in preparation S2). CBz protecting group was exchanged for a tBu carbonyl group by transfer hydrogenation, then acylation as described in the preparation of compound 189. Purification by reverse phase chromatography (C18 column. Gradient: 10-100% acetonitrile in water with 0.2% formic acid) afforded the product. 3-[10-(4-fluorophenyl)-11-isopropyl-2,4,5,10-tetrazatricyclo[7.3.0.03,7]dodeca-1,3(7),5,8,11-pentaen-12-yl]propanoic acid (9.9 mg, 78%). LCMS m/z 367.02 [M+H]+.

Compound 204

3-[10-(4-fluorophenyl)-11-isopropyl-2,4,5,8,10-pentazatricyclo[7.3.0.03,7]dodeca-1,3(7),5,8,11-pentaen-12-yl]propanoic Acid (204)

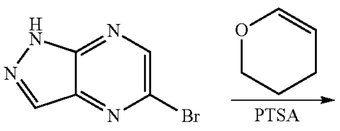

C229

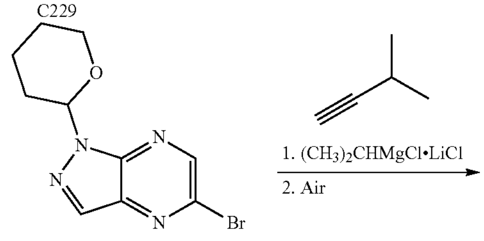

C230

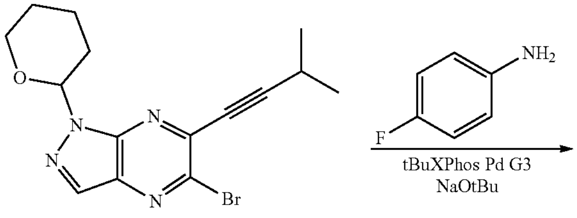

C231

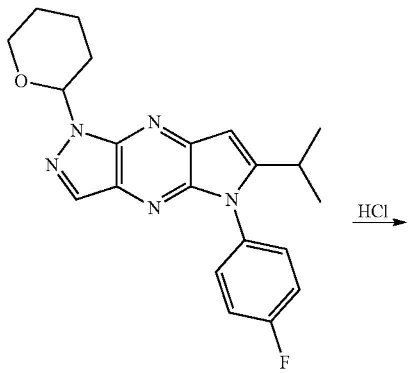

C232

-continued

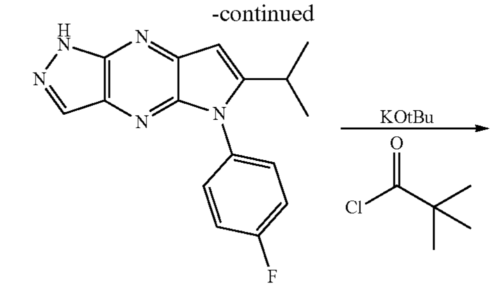

C233

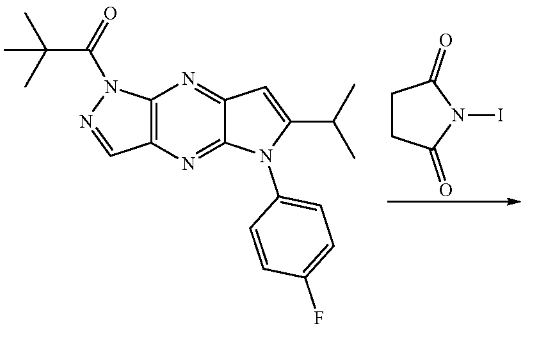

C234

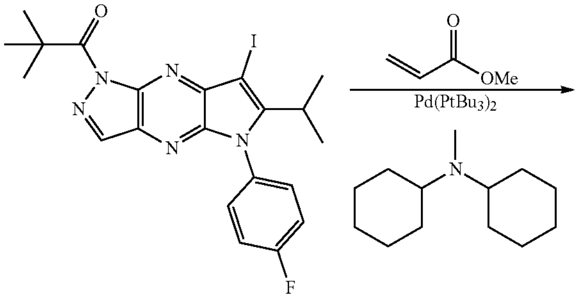

C235

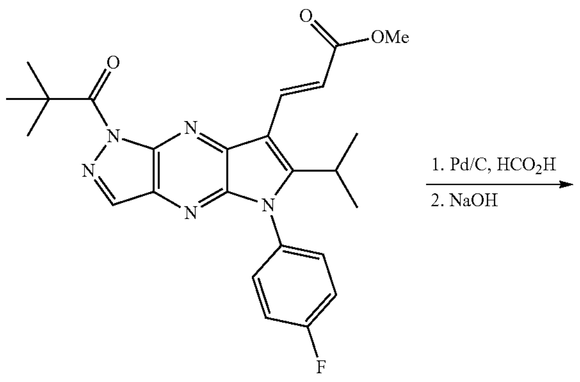

C236

-continued

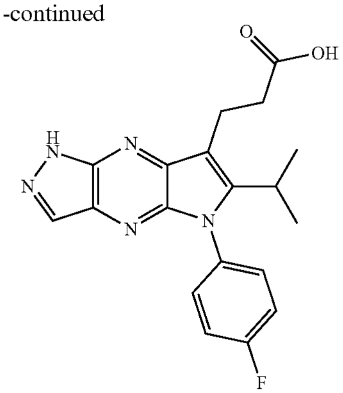

204

Preparation of 5-bromo-1-tetrahydropyran-2-yl-pyrazolo[3,4-b]pyrazine C230

The THP protecting group was added to the starting material C229 as described in the preparation of compound 38.

Preparation of 5-bromo-6-(3-methylbut-1-ynyl)-1-tetrahydropyran-2-yl-pyrazolo[3,4-b]pyrazine (C231)

To a solution of 3-methylbut-1-yne (72 mg, 1.06 mmol) in THF (1.0 mL) was slowly added chloro(isopropyl)magnesium chlorolithium (598 μL of 1.3 M, 0.78 mmol). Upon stirring the mixture for 15 min, the reaction was heated at 40° C. for 45 min and cooled down to −78° C. A solution of 5-bromo-1-tetrahydropyran-2-yl-pyrazolo[3,4-b]pyrazine C229 (100 mg, 0.35 mmol) in THF (1.0 mL) was added dropwise. The reaction was stirred 30 min at −78° C., then warmed to 0° C., stirred for 30 min, warmed to room temperature, stirred 1 h. then heated at 65° C. for 45 minutes. The reaction was cooled to room temperature, the cap was removed and the solution was stirred open to the air for 45 minutes. The reaction was quenched with 1 M HCl and diluted with dichloromethane. The phases were separated and the aqueous phase was extracted with dichloromethane (×2). The combined organic layers were dried over $Na_2SO_4$, filtered and evaporated. Purification by silica gel chromatography (Gradient: 0-100% EtOAc in heptane) gave 5-bromo-6-(3-methylbut-1-ynyl)-1-tetrahydropyran-2-yl-pyrazolo[3,4-b]pyrazine (83 mg, 64%). $^1$H NMR (400 MHz, Chloroform-d) δ 8.22 (d, J=0.6 Hz, 1H), 6.04 (dd, J=10.4, 2.6 Hz, 1H), 4.16-4.05 (m, 1H), 3.80 (td, J=11.5, 2.6 Hz, 1H), 2.95 (hept, J=6.9 Hz, 1H), 2.67-2.55 (m, 1H), 2.15 (d, J=10.9 Hz, 1H), 2.00-1.91 (m, 1H), 1.86-1.72 (m, 2H), 1.68-1.61 (m, 1H), 1.38 (d, J=6.9 Hz, 6H). LCMS m/z 345.11 $[M+H]^+$.

Preparation of 3-[10-(4-fluorophenyl)-11-isopropyl-2,4,5,8,10-pentazatricyclo[7.3.0.03,7]dodeca-1,3(7),5,8,11-pentaen-12-yl]propanoic Acid (204)

Compound 204 was prepared from 5-bromo-6-(3-methylbut-1-ynyl)-1-tetrahydropyran-2-yl-pyrazolo[3,4-b]pyrazine C231 using the method described for the preparation of compound 203.

Purification by reversed-phase HPLC. (Method: C18 Waters Sunfire column (30×150 mm, 5 micron). Gradient:

MeCN in $H_2O$ with 0.2% formic acid) afforded 3-[10-(4-fluorophenyl)-11-isopropyl-2,4,5,8,10-pentazatricyclo [7.3.0.03,7]dodeca-1,3(7),5,8,11-pentaen-12-yl]propanoic acid (8.8 mg, 23%). $^1$H NMR (400 MHz, DMSO-$d_6$) δ 13.60 (s, 1H), 12.32 (s, 1H), 8.22 (s, 1H), 7.53 (dd, J=8.5, 5.0 Hz, 2H), 7.44 (t, J=8.5 Hz, 2H), 3.17 (s, 2H), 3.11 (dd, J=14.3, 7.3 Hz, 1H), 2.72 (t, J=8.1 Hz, 2H), 1.31 (d, J=7.1 Hz, 6H). LCMS m/z 368.19 [M+H]$^+$.
Compound 205
3-[5-(4-fluorophenyl)-6-isopropyl-1H-pyrrolo[3,2-f] indazol-7-yl]propanoic Acid (205)
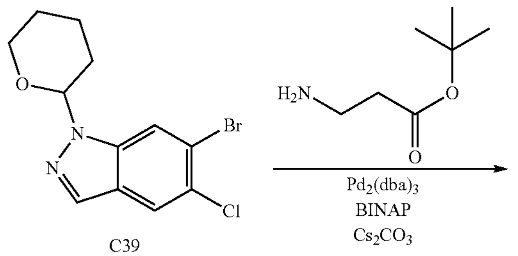
C39
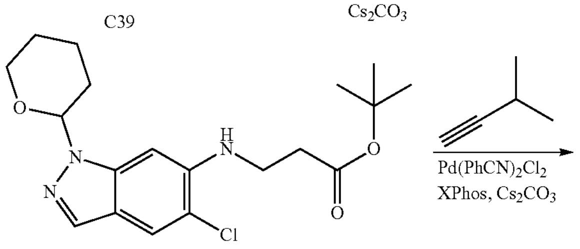
C237
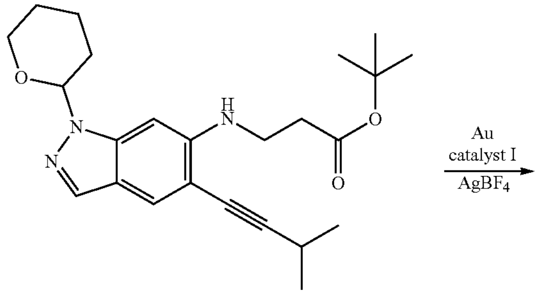
C238
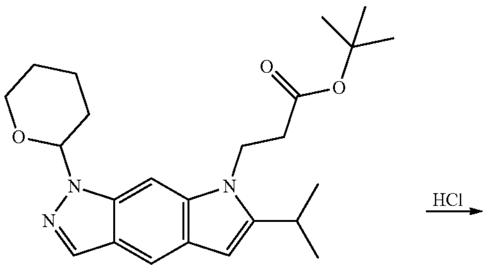
C239
-continued
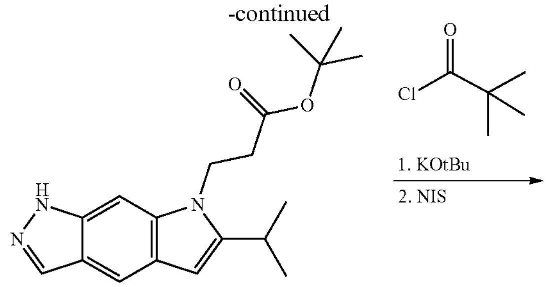
C240
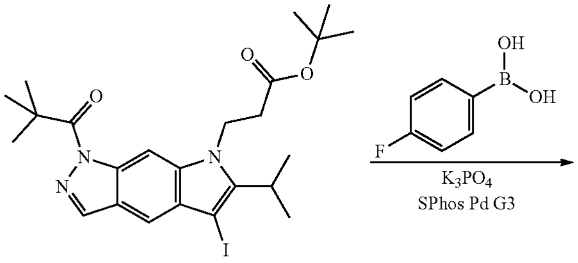
C241
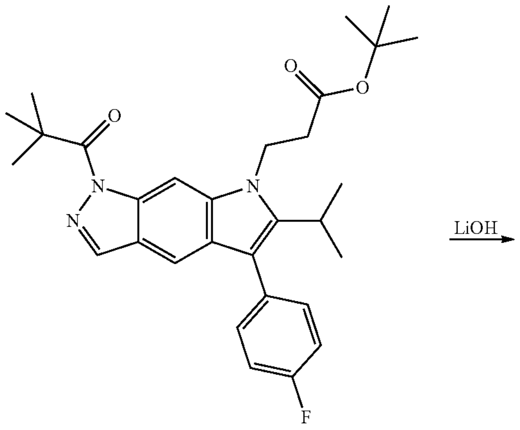
C242
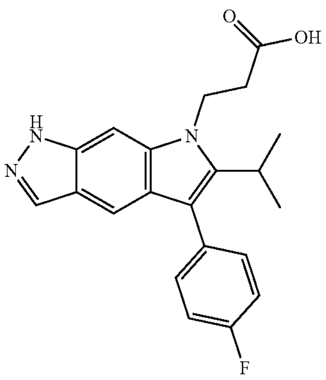
205

-continued

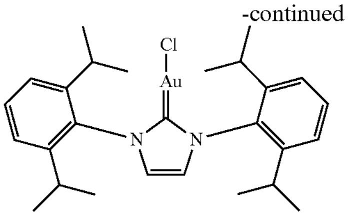

Au catalyst I

Step 1. Synthesis of tert-butyl 3-[(5-chloro-1-tetrahydropyran-2-yl-indazol-6-yl)amino]propanoate (C237)

In a 30 mL microwave vial was loaded 6-bromo-5-chloro-1-tetrahydropyran-2-yl-indazole C39 (420 mg, 1.331 mmol), tert-butyl 3-aminopropanoate (250 mg, 1.72 mmol), $Pd_2(dba)_3$ (60 mg, 0.07 mmol), rac-BINAP (43 mg, 0.07 mmol) and $Cs_2CO_3$ (668 mg, 2.10 mmol). THF (12 mL) was added. The mixture was bubbled with $N_2$. The vial was sealed and heated at 80° C. for 16 h. The mixture was cooled to room temperature, partitioned in EtOAc and water, extracted with EtOAc (3×). The organic phase was dried over $Na_2SO_4$, filtered and evaporated. Purification by silica gel chromatography (Gradient: 0-50% EtOAc in heptane) yielded the product. tert-butyl 3-[(5-chloro-1-tetrahydropyran-2-yl-indazol-6-yl)amino]propanoate (420 mg, 83%). $^1H$ NMR (300 MHz, Chloroform-d) δ 7.74 (d, J=0.8 Hz, 1H), 7.54 (d, J=0.4 Hz, 1H), 6.55 (s, 1H), 5.53 (dd, J=9.2, 2.8 Hz, 1H), 4.03-3.83 (m, 1H), 3.68 (ddd, J=11.5, 9.9, 3.2 Hz, 1H), 3.45 (t, J=6.5 Hz, 2H), 2.58 (t, J=6.5 Hz, 2H), 2.54-2.37 (m, 1H), 2.21-1.85 (m, 2H), 1.81-1.46 (m, 3H), 1.41 (s, 9H). LCMS m/z 380.18 $[M+H]^+$.

Step 2. Synthesis of tert-butyl 3-[[5-(3-methylbut-1-ynyl)-1-tetrahydropyran-2-yl-indazol-6-yl]amino]propanoate (C238)

In a 30 mL microwave tube was loaded $PdCl_2(PhCN)_2$ (33 mg, 0.09 mmol), X-Phos (100 mg, 0.21 mmol), $Cs_2CO_3$ (910 mg, 2.80 mmol) and acetonitrile (2 mL). The mixture was bubbled with $N_2$. tert-butyl 3-[(5-chloro-1-tetrahydropyran-2-yl-indazol-6-yl)amino]propanoate C237 (420 mg, 1.11 mmol) in acetonitrile (8 mL) was added. After 5 minutes, 3-methylbut-1-yne (202 mg, 2.96 mmol) in acetonitrile (2 mL) was added. The vial was sealed and heated at 80° C. for 2.5 h. The mixture was concentrated. The residue was suspended in saturated $NH_4Cl$, extracted with dichloromethane (3×). The organic phase was dried over $Na_2SO_4$, filtered and evaporated. Purification by silica gel chromatography (Gradient: 0-50% EtOAc in heptane) yielded the product. tert-butyl 3-[[5-(3-methylbut-1-ynyl)-1-tetrahydropyran-2-yl-indazol-6-yl]amino]propanoate (400 mg, 88%). LCMS m/z 411.78 $[M+H]^+$.

Step 3. Synthesis of tert-butyl 3-(6-isopropyl-1-tetrahydropyran-2-yl-pyrrolo[3,2-f]indazol-7-yl)propanoate (C239)

A mixture of tert-butyl 3-[[5-(3-methylbut-1-ynyl)-1-tetrahydropyran-2-yl-indazol-6-yl]amino]propanoate C238 (186 mg, 0.42 mmol), [1,3-bis(2,6-diisopropylphenyl)imidazol-2-ylidene]-chloro-gold (14 mg, 0.02 mmol) and $AgBF_4$ (12 mg, 0.06 mmol) in heptane (10 mL) was stirred at 50° C. for 6 h, then at 60° C. over 36 hours. Purification by silica gel chromatography (Gradient: 0-50% EtOAc in heptane) yielded the product. tert-butyl 3-(6-isopropyl-1-tetrahydropyran-2-yl-pyrrolo[3,2-f]indazol-7-yl)propanoate (111 mg, 65%). $^1H$ NMR (300 MHz, Chloroform-d) δ 8.09 (d, J=0.8 Hz, 1H), 7.80 (d, J=1.0 Hz, 1H), 7.30 (d, J=1.0 Hz, 1H), 6.33 (d, J=0.8 Hz, 1H), 5.79 (dd, J=9.1, 2.7 Hz, 1H), 4.55-4.31 (m, 2H), 4.06 (ddd, J=10.3, 4.2, 2.5 Hz, 1H), 3.82 (ddd, J=11.4, 9.8, 3.1 Hz, 1H), 3.24-3.02 (m, 1H), 2.89-2.61 (m, 3H), 2.40-2.05 (m, 2H), 1.94-1.63 (m, 3H), 1.47 (s, 9H), 1.38 (dd, J=6.8, 3.4 Hz, 6H).

Step 4. Synthesis of tert-butyl 3-(6-isopropyl-1H-pyrrolo[3,2-f]indazol-7-yl)propanoate (C240)

To a solution of tert-butyl 3-(6-isopropyl-1-tetrahydropyran-2-yl-pyrrolo[3,2-f]indazol-7-yl)propanoate C239 (193 mg, 0.45 mmol) in MeOH (10 mL) was added methanol (Hydrochloride salt) (3 mL of 1.25 M, 3.75 mmol) (HCl in MeOH). The mixture was stirred at 50° C. for 3 h. The mixture was cooled with dry ice. KOtBu (1.5 mL of 1 M, 1.5 mmol) was added to adjust the pH to ~pH 9. The mixture was evaporated. The residue was dissolve in dichloromethane, brine was added. The mixture was extracted with dichloromethane (3×). The organic phase was dried over $Na_2SO_4$, filtered and evaporated. Purification by silica gel chromatography (Gradient: 0-50% EtOAc in heptane) yielded the product. tert-butyl 3-(6-isopropyl-1H-pyrrolo[3,2-f]indazol-7-yl)propanoate (80 mg, 54%). $^1H$ NMR (300 MHz, Chloroform-d) δ 10.02 (s, 1H), 8.14 (d, J=1.0 Hz, 1H), 7.84 (d, J=1.1 Hz, 1H), 7.27 (d, J=1.0 Hz, 1H), 6.34 (d, J=0.8 Hz, 1H), 4.47-4.37 (m, 2H), 3.18-3.06 (m, 1H), 2.74-2.65 (m, 2H), 1.46 (s, 9H), 1.39 (d, J=6.8 Hz, 6H). LCMS m/z 328.29 $[M+H]^+$.

Step 5. Synthesis of tert-butyl 3-[1-(2,2-dimethylpropanoyl)-5-iodo-6-isopropyl-pyrrolo[3,2-f]indazol-7-yl]propanoate (C241)

Compound C240 was prepared by pivaloyl protection as described for compound 188, then iodination with N-iodosuccinimide as described in the preparation of compound 1 afforded C241. tert-butyl 3-[1-(2,2-dimethylpropanoyl)-5-iodo-6-isopropyl-pyrrolo[3,2-f]indazol-7-yl]propanoate (93 mg, 71%). $^1H$ NMR (300 MHz, Chloroform-d) δ 8.40 (t, J=0.9 Hz, 1H), 8.18 (d, J=0.8 Hz, 1H), 7.70 (d, J=0.9 Hz, 1H), 4.62-4.40 (m, 2H), 3.48 (p, J=7.2 Hz, 1H), 2.82-2.64 (m, 2H), 1.60 (s, 9H), 1.53 (d, J=7.2 Hz, 6H), 1.47 (s, 9H). LCMS m/z 537.22 $[M+H]^+$.

Step 6. Synthesis of tert-butyl 3-[1-(2,2-dimethylpropanoyl)-5-(4-fluorophenyl)-6-isopropyl-pyrrolo[3,2-f]indazol-7-yl]propanoate (C242)

A 5 mL microwave vial was charged with tert-butyl 3-[1-(2,2-dimethylpropanoyl)-5-iodo-6-isopropyl-pyrrolo[3,2-f]indazol-7-yl]propanoate C241 (46 mg, 0.09 mmol), (4-fluorophenyl)boronic acid (37 mg, 0.26 mmol), 1,4-dioxane (2.5 mL) and water (150 μL). The solution was bubbled with $N_2$. $K_3PO_4$ (70 mg, 0.33 mmol) and SPhos G3 (5 mg, 0.006 mmol) were added. The vial was sealed and heated at 80° C. under microwave for 1 h. The mixture was evaporated. The residue was suspended in water, extracted with dichloromethane (3×). The organic phase was dried over $Na_2SO_4$, filtered and evaporated. Purification by silica gel chromatography (Gradient: 0-30% EtOAc in heptane) yielded the product. tert-butyl 3-[1-(2,2-dimethylpropanoyl)-5-(4-fluorophenyl)-6-isopropyl-pyrrolo[3,2-f]indazol-7-yl]propanoate (33 mg, 76%). $^1$H NMR (300 MHz, Chloroform-d) δ 8.45 (t, J=0.9 Hz, 1H), 8.09 (d, J=0.7 Hz, 1H), 7.57 (d, J=0.9 Hz, 1H), 7.47-7.30 (m, 2H), 7.24-7.10 (m, 2H), 4.76-4.49 (m, 2H), 3.40 (p, J=7.2 Hz, 1H), 2.96-2.73 (m, 2H), 1.62 (s, 9H), 1.52 (s, 9H), 1.35 (d, J=7.2 Hz, 6H). LCMS m/z 506.34 [M+H]$^+$.

Step 6. Synthesis of 3-[5-(4-fluorophenyl)-6-isopropyl-1H-pyrrolo[3,2-f]indazol-7-yl]propanoic Acid (205)

A mixture of tert-butyl 3-[1-(2,2-dimethylpropanoyl)-5-(4-fluorophenyl)-6-isopropyl-pyrrolo[3,2-f]indazol-7-yl] propanoate C242 (33 mg, 0.07 mmol) and LiOH (130 μL of 5 M, 0.65 mmol) in THF (2 mL) and $H_2O$ (0.5 mL) was stirred at 50° C. for 18 h. Another 0.2 mL 1M LiOH was added and stirred at 65° C. for 1 h. The mixture was concentrated. The residue was dissolved in MeOH (1 mL), acidified with 6 M HCl, diluted with DMSO (1 mL). Purification by reversed-phase chromatography (Column: C18. Gradient: 0-90% MeCN in water with 0.1% trifluoroacetic acid) afforded the product. 3-[5-(4-fluorophenyl)-6-isopropyl-1H-pyrrolo[3,2-f]indazol-7-yl]propanoic acid (Trifluoroacetate salt) (23.8 mg, 68%). $^1$H NMR (300 MHz, DMSO-$d_6$) δ 12.64 (s, 1H), 8.01 (d, J=0.9 Hz, 1H), 7.48 (d, J=1.0 Hz, 1H), 7.45-7.37 (m, 3H), 7.36-7.17 (m, 2H), 4.51 (dd, J=8.9, 6.4 Hz, 2H), 3.36 (p, J=7.2 Hz, 1H), 2.89-2.63 (m, 2H), 1.28 (d, J=7.2 Hz, 6H). LCMS m/z 366.1 [M+H]$^+$.

Compound 206

3-[5-(4-chlorophenyl)-6-isopropyl-1H-pyrrolo[3,2-f]indazol-7-yl]propanoic Acid (206)

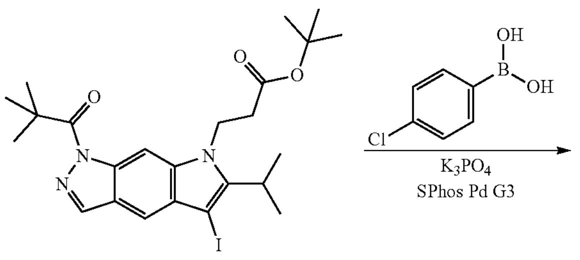

C241

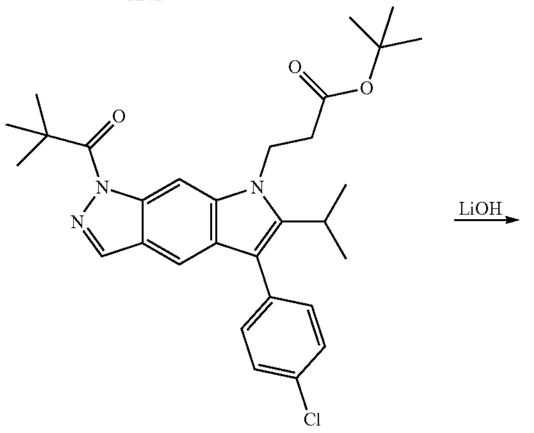

C243

-continued

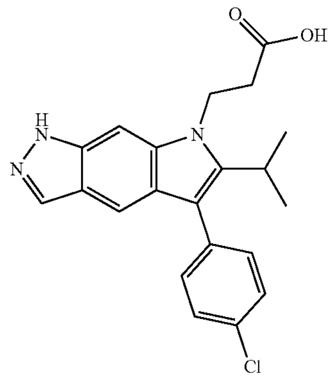

206

Compound 206 was prepared from tert-butyl 3-[1-(2,2-dimethylpropanoyl)-5-iodo-6-isopropyl-pyrrolo[3,2-f]indazol-7-yl]propanoate C241 and 4-chloroboronic acid as described for the preparation of compound 205. Purification by reversed-phase chromatography (Column: C18. Gradient: 0-90% MeCN in water with 0.1% trifluoroacetic acid) afforded the product. 3-[5-(4-chlorophenyl)-6-isopropyl-1H-pyrrolo[3,2-f]indazol-7-yl]propanoic acid (Trifluoroacetate salt) (18.3 mg, 50%). $^1$H NMR (300 MHz, DMSO-$d_6$) δ 12.66 (s, 1H), 8.00 (d, J=0.9 Hz, 1H), 7.56-7.49 (m, 3H), 7.44-7.38 (m, 3H), 4.59-4.32 (m, 2H), 3.38 (p, J=7.1 Hz, 1H), 2.74 (dd, J=8.9, 6.3 Hz, 2H), 1.29 (d, J=7.2 Hz, 6H). LCMS m/z 382.12 [M+H]$^+$.

Compound 207 and 208 methyl 3-[5-(4-fluorophenyl)-6-isopropenyl-1H-pyrrolo[2,3-f]indazol-7-yl]bicyclo[1.1.1]pentane-1-carboxylate (207) and 3-[5-(4-fluorophenyl)-6-isopropenyl-1H-pyrrolo[2,3-f]indazol-7-yl]bicyclo[1.1.1]pentane-1-carboxylic Acid (208)

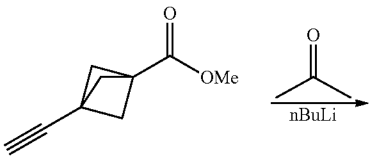

C244

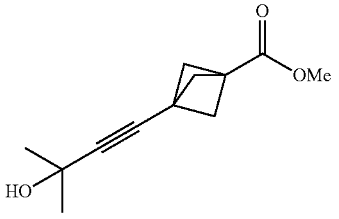

C245

-continued

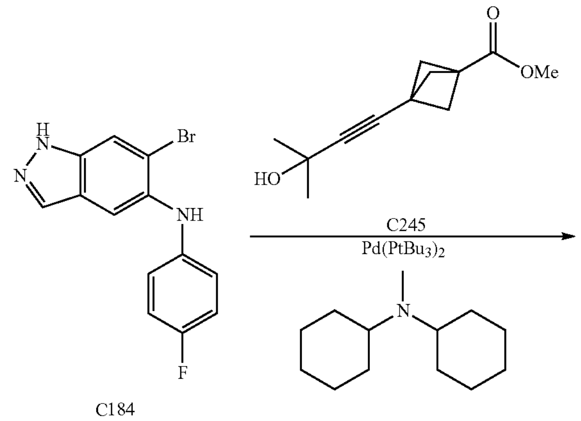

C184

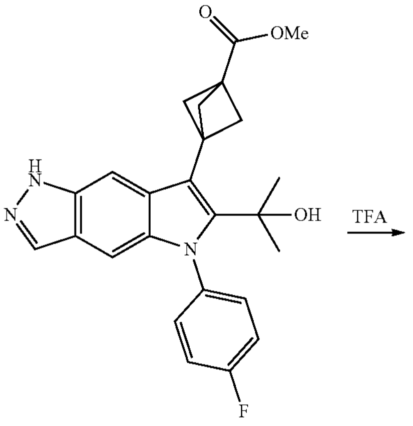

C246

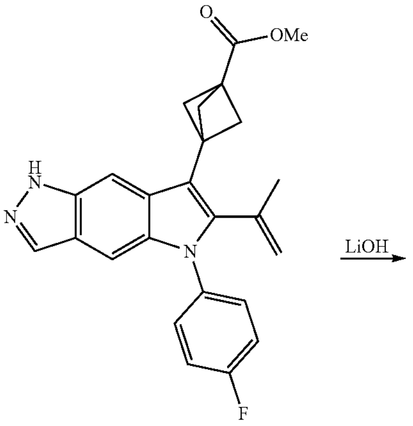

207

-continued

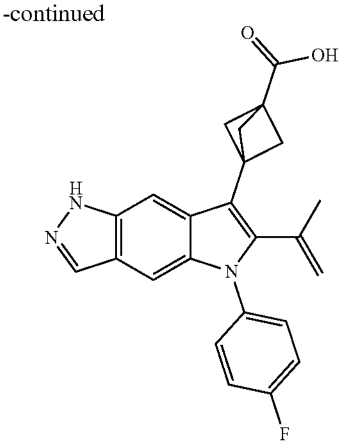

208

Step 1. Synthesis of methyl 3-(3-hydroxy-3-methyl-but-1-ynyl)bicyclo[1.1.1]pentane-1-carboxylate (C245)

A solution of methyl 1-ethynylbicyclo[1.1.1]pentane-3-carboxylate C244 (375 mg, 2.50 mmol) in THF (11.4 mL) was cooled to −78° C. (dry ice/acetone bath) under Na. After 15 minutes butyllithium (1.7 mL of 1.6 M, 2.72 mmol) was added dropwise. The reaction was allowed to stir for 30 minutes, after which acetone (1.8 mL, 24.51 mmol) (dried over 4 A mol sieves) was added to the solution drop-wise. After 30 min, the cooling bath was removed and the reaction was warmed to room temperature and stirred for 30 minutes. The reaction mixture was cooled to 0° C. and quenched with aqueous sat. $NH_4Cl$ solution, then extracted with EtOAc. The organic phase was washed with brine, dried over $MgSO_4$, filtered, and concentrated. Purification by silica gel chromatography (Gradient: 0-30% EtOAc in heptane, then 30-70% EtOAc in heptane) yielded the product. Methyl 3-(3-hydroxy-3-methyl-but-1-ynyl)bicyclo[1.1.1]pentane-1-carboxylate (175 mg, 34%). $^1H$ NMR (400 MHz, Chloroform-d) δ 3.69 (s, 3H), 2.31 (s, 6H), 1.52 (s, 6H).

Step 2. Synthesis of methyl 3-[5-(4-fluorophenyl)-6-(1-hydroxy-1-methyl-ethyl)-1H-pyrrolo[2,3-f]indazol-7-yl]bicyclo[1.1.1]pentane-1-carboxylate (C246)

In a 30 mL microwave vial, a solution of 6-bromo-N-(4-fluorophenyl)-1H-indazol-5-amine (250 mg, 0.79 mmol), methyl 3-(3-hydroxy-3-methyl-but-1-ynyl)bicyclo[1.1.1]pentane-1-carboxylate C245 (210 mg, 1.01 mmol) and N-cyclohexyl-N-methyl-cyclohexanamine (0.43 mL, 2.0 mmol) in 1,4-dioxane (6 mL) was bubbled with $N_2$. $Pd(PtBu_3)_2$ (43 mg, 0.08414 mmol) was added. The vial was sealed and heated at 60° C. for 2 h and then heated at 80° C. for 44 h. The mixture was concentrated. The residue was suspended in 20% MeOH/dichloromethane, adsorbed onto silica gel was evaporated to dryness, and purified by silica gel chromatography (0-50% EtOAc in heptane) to afford the product. Methyl 3-[5-(4-fluorophenyl)-6-(1-hydroxy-1-methyl-ethyl)-1H-pyrrolo[2,3-f]indazol-7-yl]bicyclo[1.1.1]pentane-1-carboxylate (218 mg, 47%). LCMS m/z 434.28 $[M+H]^+$.

Step 3. Synthesis of methyl 3-[5-(4-fluorophenyl)-6-isopropenyl-M-pyrrolo[2,3-f]indazol-7-yl]bicyclo[1.1.1]pentane-1-carboxylate (207)

A dark solution of methyl 3-[5-(4-fluorophenyl)-6-(1-hydroxy-1-methyl-ethyl)-1H-pyrrolo[2,3-f]indazol-7-yl]bicyclo[1.1.1]pentane-1-carboxylate C246 (200 mg, 0.46 mmol) in TFA (2 mL, 25.96 mmol) was stirred at room temperature for 90 minutes. The mixture was evaporated. The residue was dissolved in dichloromethane, washed with saturated $NaHCO_3$. The aq. phase was re-extracted with dichloromethane (2×). The organic phase was dried over $Na_2SO_4$, filtered and evaporated. Silica gel chromatography (Gradient: 0-30% EtOAc in dichloromethane) afforded the product. Methyl 3-[5-(4-fluorophenyl)-6-isopropenyl-1H-pyrrolo[2,3-f]indazol-7-yl]bicyclo[1.1.1]pentane-1-carboxylate (110 mg, 57%). $^1$H NMR (400 MHz, Chloroform-d) δ 10.41 (s, 1H), 8.07 (d, J=1.1 Hz, 1H), 7.74 (t, J=1.2 Hz, 1H), 7.41-7.35 (m, 3H), 7.25-7.14 (m, 2H), 5.50-5.38 (m, 1H), 5.30 (dd, J=2.2, 1.1 Hz, 1H), 3.76 (s, 3H), 2.61 (s, 6H), 2.40 (s, 3H). LCMS 416.32 $[M+H]^+$.

Step 4. Synthesis of 3-[5-(4-fluorophenyl)-6-isopropenyl-1H-pyrrolo[2,3-f]indazol-7-yl]bicyclo[1.1.1]pentane-1-carboxylic Acid (208)

methyl 3-[5-(4-fluorophenyl)-6-isopropenyl-1H-pyrrolo[2,3-f]indazol-7-yl]bicyclo[1.1.1]pentane-1-carboxylate 207 (59 mg) in THF (2 mL), MeOH (1 mL) and LiOH (200 µL of 5 M, 1.0 mmol) was heated at 50° C. for 2 h. The mixture was cooled to room temperature, 1 mL 1M HCl was added and the mixture was concentrated. Purification by reversed-phase HPLC (Method: C18 Waters Sunfire column (30×150 mm, 5 micron). Gradient: MeCN in $H_2O$ with 0.2% formic acid) afforded the product. 3-[5-(4-fluorophenyl)-6-isopropenyl-1H-pyrrolo[2,3-f]indazol-7-yl]bicyclo[1.1.1]pentane-1-carboxylic acid (36 mg, 31%). $^1$H NMR (400 MHz, DMSO-$d_6$) δ 12.64 (s, 1H), 12.42 (s, 1H), 8.00 (d, J=1.1 Hz, 1H), 7.68 (t, J=1.1 Hz, 1H), 7.47 (ddd, J=8.5, 5.2, 2.7 Hz, 2H), 7.40 (t, J=8.8 Hz, 2H), 7.29 (d, J=1.1 Hz, 1H), 5.48 (t, J=2.0 Hz, 1H), 5.28 (dd, J=2.2, 1.1 Hz, 1H), 2.46 (s, 6H), 1.68 (d, J=1.2 Hz, 3H). LCMS m/z 402.32 $[M+H]^+$.

Compound 209

3-[5-(4-fluorophenyl)-6-tetrahydropyran-4-yl-1H-pyrrolo[2,3-f]indazol-7-yl]bicyclo[1.1.1]pentane-1-carboxylic Acid (209)

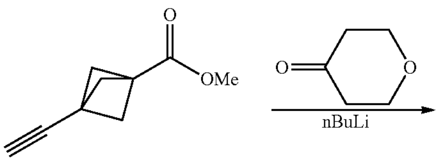

C244

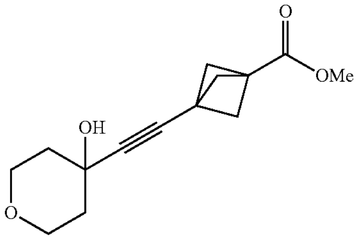

C247

-continued

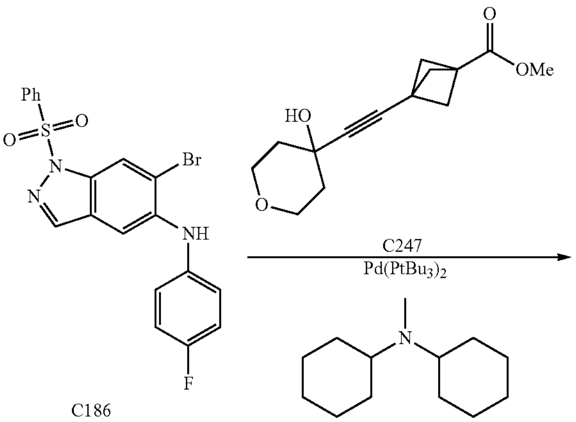

C186

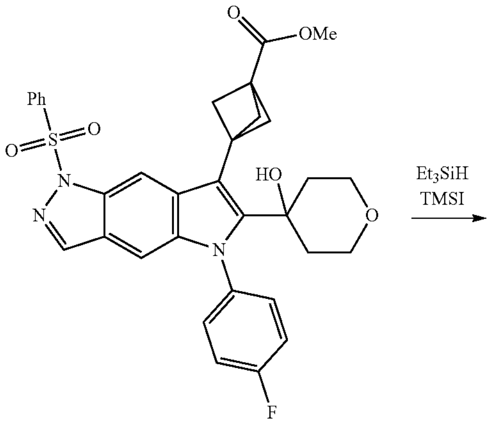

C248

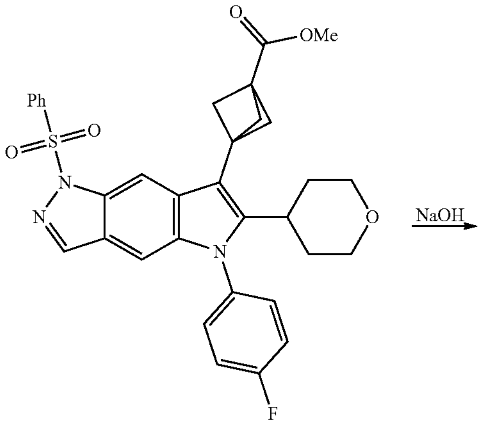

C249

-continued

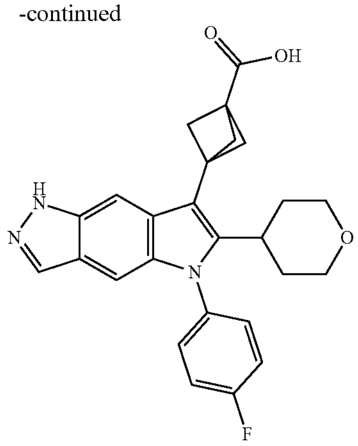

209

Step 1. Synthesis of methyl 3-[2-(4-hydroxytetrahydropyran-4-yl)ethynyl]bicyclo[1.1.1]pentane-1-carboxylate (C247)

A solution of methyl 3-ethynylbicyclo[1.1.1]pentane-1-carboxylate C244 (491 mg, 3.27 mmol) in THF (15 mL) was cooled with dry ice-acetone bath under $N_2$. After 15 min, n-butyllithium (2.2 mL of 1.6 M, 3.46 mmol) in hexanes was added drop-wise. After 30 min, tetrahydropyran-4-one (1.25 mL, 13.5 mmol) was added. After 30 min, the cooling bath was removed. The mixture was stirred at room temperature for 1 hour. The reaction mixture was partitioned between aqueous sat. $NH_4Cl$ solution and EtOAc. Organic phase was separated, washed with brine, dried over $Na_2SO_4$, filtered and concentrated. Silica gel chromatography (Gradient: 0-100% EtOAc in heptane). Methyl 3-[2-(4-hydroxytetrahydropyran-4-yl)ethynyl]bicyclo[1.1.1]pentane-1-carboxylate (290 mg, 35%).

$^1$H NMR (400 MHz, Chloroform-d) δ 3.90 (dt, J=11.7, 4.8 Hz, 2H), 3.70 (s, 3H), 3.65 (ddd, J=11.7, 8.7, 3.0 Hz, 2H), 2.33 (s, 6H), 2.02 (d, J=1.3 Hz, 1H), 1.96-1.88 (m, 2H), 1.79 (ddd, J=12.8, 8.8, 3.9 Hz, 2H). LCMS m/z 251.14 [M+H]$^+$.

Step 2. Synthesis of methyl 3-[1-(benzenesulfonyl)-5-(4-fluorophenyl)-6-(4-hydroxytetrahydropyran-4-yl)pyrrolo[2,3-f]indazol-7-yl]bicyclo[1.1.1]pentane-1-carboxylate (C248)

Methyl 3-[2-(4-hydroxytetrahydropyran-4-yl)ethynyl]bicyclo[1.1.1]pentane-1-carboxylate C247 (75 mg, 0.30 mmol), 1-(benzenesulfonyl)-6-bromo-N-(4-fluorophenyl) indazol-5-amine C186 (100 mg, 0.15 mmol), and N-cyclohexyl-N-methyl-cyclohexanamine (85 μL, 0.40 mmol) were combined in a 4 mL vial. The mixture was placed under vacuum and flushed with nitrogen. 1,4-Dioxane (1.0 mL) was added and the mixture gently pulled under vacuum and flushed with nitrogen (3×). Palladium tritert-butylphosphane (8 mg, 0.02 mmol) was added the mixture was again and placed under vacuum and flushed with nitrogen. The mixture was heated to 80° C. overnight. Upon cooling to room temperature and dilution with THF, Celite® was added and the mixture was concentrated to dryness under reduced pressure. Purification by silica gel chromatography (Gradient: 0-100% EtOAc in heptane) yielded methyl 3-[1-(benzenesulfonyl)-5-(4-fluorophenyl)-6-(4-hydroxytetrahydropyran-4-yl)pyrrolo[2,3-f]indazol-7-yl]bicyclo[1.1.1]pentane-1-carboxylate (99 mg, 107%). $^1$H NMR (400 MHz, DMSO-d6) δ 8.54 (t, J=1.0 Hz, 1H), 8.43 (d, J=0.8 Hz, 1H), 7.84-7.79 (m, 2H), 7.68-7.61 (m, 1H), 7.58-7.51 (m, 2H), 7.48-7.39 (m, 4H), 6.93 (d, J=0.9 Hz, 1H), 5.37 (s, 1H), 3.77-3.70 (m, 2H), 3.69 (s, 3H), 3.52 (dd, J=11.0, 4.5 Hz, 2H), 2.76 (s, 6H), 1.72 (td, J=12.7, 4.8 Hz, 2H), 1.59 (d, J=12.9 Hz, 2H). LCMS m/z 616.49 [M+H]$^+$.

Step 3. Synthesis of methyl 3-[1-(benzenesulfonyl)-5-(4-fluorophenyl)-6-tetrahydropyran-4-yl-pyrrolo[2,3-f]indazol-7-yl]bicyclo[1.1.1]pentane-1-carboxylate (C249)

To a solution of methyl 3-[1-(benzenesulfonyl)-5-(4-fluorophenyl)-6-(4-hydroxytetrahydropyran-4-yl)pyrrolo[2,3-f]indazol-7-yl]bicyclo[1.1.1]pentane-1-carboxylate C248 (50 mg, 0.08 mmol) and triethylsilane (64 μL, 0.40 mmol) in acetonitrile (2 mL) was added iodo(trimethyl)silane (60 μL, 0.42 mmol) at room temperature and then the reaction was heated at 50° C. for 30 minutes. Methanol and Celite® were added and the mixture was concentrated to dryness. Purification by silica gel chromatography (Gradient: 0-100% EtOAc in heptane) yielded methyl 3-[1-(benzenesulfonyl)-5-(4-fluorophenyl)-6-tetrahydropyran-4-yl-pyrrolo[2,3-f]indazol-7-yl]bicyclo[1.1.1]pentane-1-carboxylate (18.4 mg, 38%). $^1$H NMR (300 MHz, Chloroform-d) δ 8.49 (t, J=1.0 Hz, 1H), 8.11 (d, J=0.9 Hz, 1H), 8.01-7.94 (m, 2H), 7.57-7.49 (m, 1H), 7.46-7.38 (m, 2H), 7.34-7.29 (m, 2H), 7.28-7.21 (m, 2H), 6.89 (d, J=1.0 Hz, 1H), 3.96 (dd, J=11.4, 3.8 Hz, 2H), 3.81 (s, 3H), 3.46-3.29 (m, 3H), 2.80 (s, 6H), 1.76 (qd, J=12.5, 12.0, 4.2 Hz, 2H), 1.64 (s, 2H). LCMS m/z 600.42 [M+H]$^+$.

Step 4. Synthesis of 3-[5-(4-fluorophenyl)-6-tetrahydropyran-4-yl-1H-pyrrolo[2,3-f]indazol-7-yl]bicyclo[1.1.1]pentane-1-carboxylic Acid (209)

An aqueous solution of NaOH (150 μL of 2 M, 0.30 mmol) was added to a solution of methyl 3-[1-(benzenesulfonyl)-5-(4-fluorophenyl)-6-tetrahydropyran-4-yl-pyrrolo[2,3-f]indazol-7-yl]bicyclo[1.1.1]pentane-1-carboxylate C249 (18.4 mg, 0.031 mmol) and piperidine (30 μL, 0.30 mmol) in THF (1 mL) and methanol (0.1 mL). The reaction was stirred at 65° C. for 1 hour. The mixture was concentrated in vacuo to dryness. Purification by reversed-phase chromatography (Column: C18. Gradient: 10-100% MeCN in water with 0.1% TFA) afforded the product. 3-[5-(4-fluorophenyl)-6-tetrahydropyran-4-yl-1H-pyrrolo[2,3-f]indazol-7-yl]bicyclo[1.1.1]pentane-1-carboxylic acid (Trifluoroacetic Acid (0.5)) (3.7 mg, 23%). $^1$H NMR (300 MHz, Acetone-$d_6$) δ 11.93-10.72 (bs, 2H), 7.94 (d, J=1.1 Hz, 1H), 7.83 (t, J=1.1 Hz, 1H), 7.56-7.49 (m, 2H), 7.48-7.39 (m, 2H), 6.93 (d, J=1.2 Hz, 1H), 3.85 (dd, J=11.2, 4.0 Hz, 2H), 3.51 (ddt, J=12.1, 8.3, 3.9 Hz, 1H), 3.40 (td, J=11.5, 2.5 Hz, 2H), 2.70 (s, 6H), 1.82-1.62 (m, 4H). LCMS m/z 446.38 [M+1]$^+$.

Compound 210

3-(5-(4-fluorophenyl)-6-isopropyl-1,5-dihydropyrrolo[2,3-f]indazol-7-yl)bicyclo[1.1.1]pentane-1-carboxylic Acid (210)

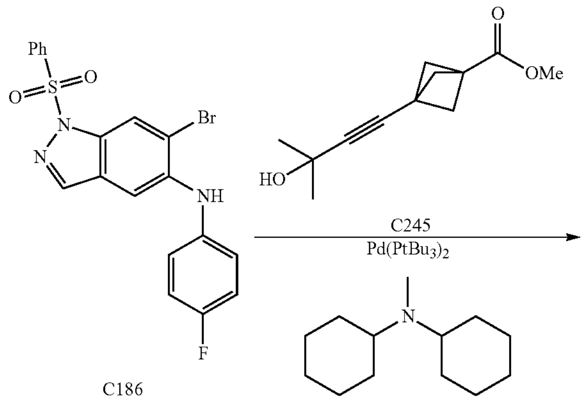

C186

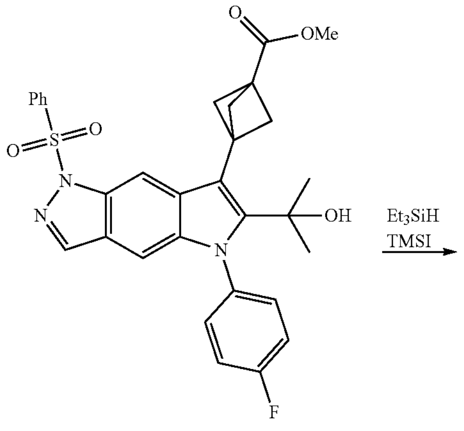

C250

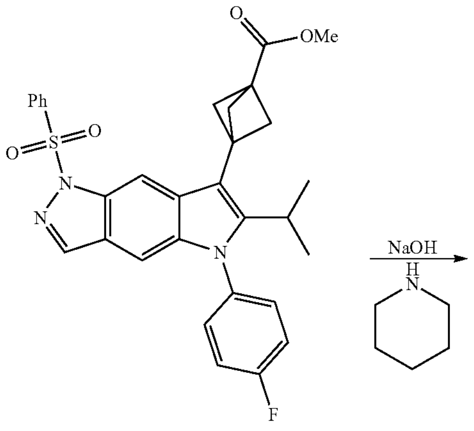

251

-continued

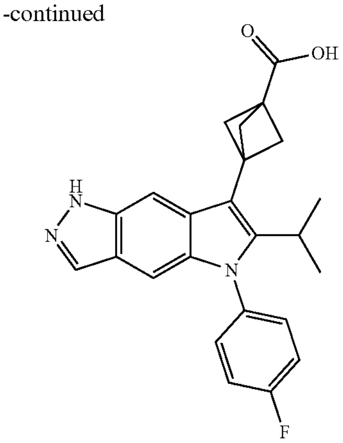

210

Compound 210 was prepared from C186 using the method described for the preparation of compound 209. 3-[5-(4-fluorophenyl)-6-isopropyl-1H-pyrrolo[2,3-f]indazol-7-yl]bicyclo[1.1.1]pentane-1-carboxylic acid (37.9 mg, 29%). $^1$H NMR (400 MHz, DMSO-d6) δ 12.56 (s, 2H), 7.93 (d, J=1.0 Hz, 1H), 7.64 (t, J=1.1 Hz, 1H), 7.56-7.33 (m, 4H), 6.86 (d, J=1.1 Hz, 1H), 3.50 (q, J=7.3 Hz, 1H), 2.57 (s, 6H), 1.09 (d, J=7.3 Hz, 6H). LCMS m/z 404.31 [M+H]$^+$.

Compound 211

3-[5-(4-fluorophenyl)-6-isopropyl-1H-pyrrolo[2,3-f]indazol-7-yl]-N-[(3S,4R)-4-hydroxy-2-oxo-pyrrolidin-3-yl]propanamide (211)

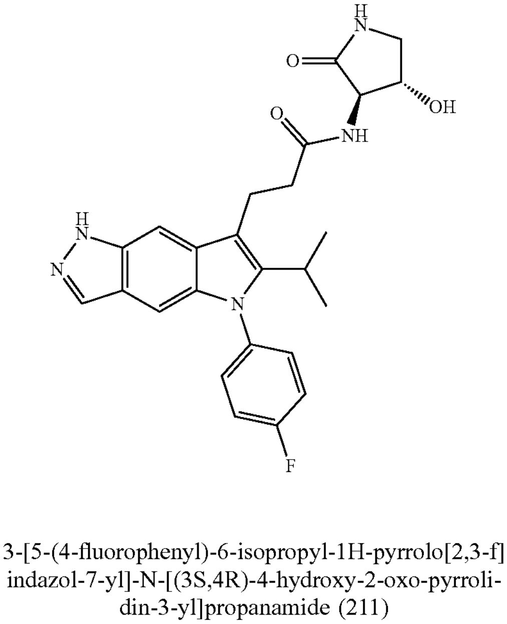

3-[5-(4-fluorophenyl)-6-isopropyl-1H-pyrrolo[2,3-f]indazol-7-yl]-N-[(3S,4R)-4-hydroxy-2-oxo-pyrrolidin-3-yl]propanamide (211)

To a mixture of 3-[5-(4-fluorophenyl)-6-isopropyl-1H-pyrrolo[2,3-f]indazol-7-yl]propanoic acid (60 mg, 0.16 mmol) and (3S,4R)-3-amino-4-hydroxy-pyrrolidin-2-one (24 mg, 0.2 mmol) in DMSO (1.5 mL) was added TEA (70 µL, 0.50 mmol) and HATU (80 mg, 0.21 mmol). The mixture was allowed to stir at room temperature for –2 h. Purification by reverse phase chromatography (C18 column. Gradient. 20-90% MeCN in water containing formic acid). 3-[5-(4-fluorophenyl)-6-isopropyl-1H-pyrrolo[2,3-f]indazol-7-yl]-N-[(3S,4R)-4-hydroxy-2-oxo-pyrrolidin-3-yl]propanamide (45 mg, 56%). $^1$H NMR (300 MHz, Methanol-$d_4$) δ 7.93 (d, J=1.0 Hz, 1H), 7.61 (t, J=1.1 Hz, 1H), 7.48-7.22 (m, 4H), 7.05 (d, J=1.1 Hz, 1H), 4.41 (q, J=7.5 Hz, 1H), 4.30 (d, J=7.9 Hz, 1H), 3.59 (dd, J=9.9, 7.6 Hz, 1H), 3.18-3.05 (m, 2H), 2.74-2.62 (m, 2H), 1.33 (d, J=7.2 Hz, 6H). LCMS m/z 464.25 [M+H]$^+$.

Compound 212

1-[(3R,4R)-3,4-dihydroxypyrrolidin-1-yl]-3-[5-(4-fluorophenyl)-6-isopropyl-1H-pyrrolo[2,3-f]indazol-7-yl]propan-1-one (212)

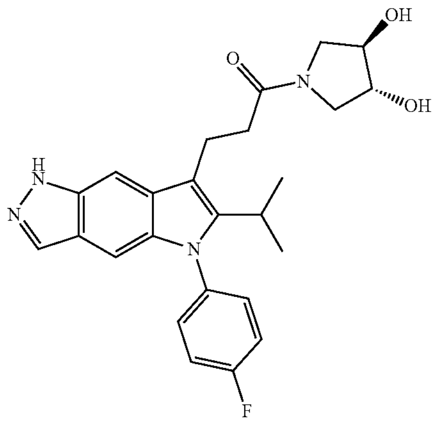 [SMILES: CC(C)c1c(CCC(=O)N2C[C@@H](O)[C@H](O)C2)c2cc3[nH]ncc3cc2n1-c1ccc(F)cc1]

1-[(3R,4R)-3,4-dihydroxypyrrolidin-1-yl]-3-[5-(4-fluorophenyl)-6-isopropyl-1H-pyrrolo[2,3-f]indazol-7-yl]propan-1-one (212)

To a mixture of 3-[5-(4-fluorophenyl)-6-isopropyl-1H-pyrrolo[2,3-f]indazol-7-yl]propanoic acid (60 mg, 0.16 mmol) and (3R,4R)-pyrrolidine-3,4-diol (21 mg, 0.19 mmol) in DMSO (1.5 mL) was added TEA (70 μL, 0.50 mmol) and HATU (80 mg, 0.21 mmol). The mixture was allowed to stir at room temperature for ~2 h. Purification by reverse phase chromatography (C18 column. Gradient. 20-90% MeCN in water containing formic acid). 1-[(3R,4R)-3,4-dihydroxypyrrolidin-1-yl]-3-[5-(4-fluorophenyl)-6-isopropyl-1H-pyrrolo[2,3-f]indazol-7-yl]propan-1-one (16 mg, 21%). $^1$H NMR (300 MHz, Methanol-$d_4$) δ 8.08 (s, 1H), 7.92 (d, J=1.0 Hz, 1H), 7.58 (t, J=1.1 Hz, 1H), 7.41-7.20 (m, 4H), 7.03 (d, J=1.1 Hz, 1H), 4.03 (tq, J=3.3, 1.7 Hz, 2H), 3.65-3.45 (m, 3H), 3.26 (dd, J=9.9, 7.3 Hz, 3H), 3.09 (hept, J=7.2 Hz, 1H), 2.85-2.69 (m, 2H), 1.28 (d, J=7.2 Hz, 6H). LCMS m/z 451.74 [M+H]$^+$.

Compound 213

1-[(3S)-3-[[5-(4-fluorophenyl)-6-tetrahydropyran-4-yl-1H-pyrrolo[2,3-f]indazol-7-yl]methyl]pyrrolidin-1-yl]ethanone (213)

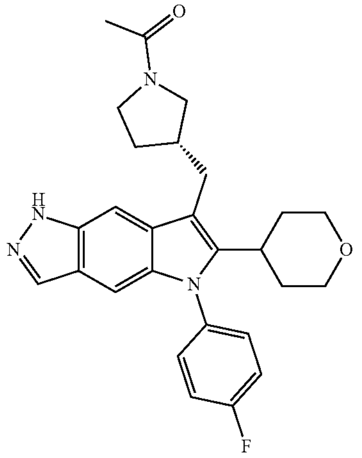 [SMILES: CC(=O)N1CC[C@@H](Cc2c(C3CCOCC3)n(-c3ccc(F)cc3)c3cc4cn[nH]c4cc23)C1]

Compound 213 was prepared in three steps from compound S7 and benzyl (3S)-3-formylpyrrolidine-1-carboxylate using the method described for the preparation of compound 153. In this example, methyl(diphenyl)silane and methane sulfonic acid were used in the reductive alkylation step. In step 2, transfer hydrogenation with ammonium formate and palladium on carbon was used to remove the two Cbz protecting groups. 1-[(3S)-3-[[5-(4-fluorophenyl)-6-tetrahydropyran-4-yl-1H-pyrrolo[2,3-f]indazol-7-yl]methyl]pyrrolidin-1-yl]ethanone (3.4 mg, 6%). $^1$H NMR (400 MHz, DMSO-$d_6$) δ 12.64 (d, J=5.3 Hz, 1H), 7.96 (s, 1H), 7.55 (m, 1H), 7.54-7.40 (m, 4H), 6.96 (d, J=4.8 Hz, 1H), 3.90-3.77 (m, 2H), 3.66-3.43 (m, 3H), 3.31-3.20 (m, 3H), 3.13-2.89 (m, 4H), 2.06 (m, 1H), 1.92 (m, 3H), 1.89-1.54 (m, 5H). LCMS m/z 461.28 [M+1]$^+$.

Compound 214

3-(5-(4-fluorophenyl)-6-isopropyl-3,5-dihydro-[1,2,3]triazolo[4,5-f]indol-7-yl)propanoic Acid (214)

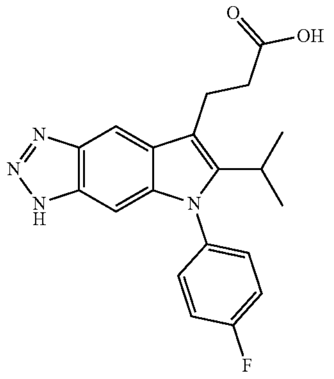 [SMILES: CC(C)c1c(CCC(=O)O)c2cc3nn[nH]c3cc2n1-c1ccc(F)cc1]

Compound 214 was prepared from 5-(4-fluorophenyl)-6-isopropyl-3,5-dihydro-[1,2,3]triazolo[4,5-f]indole using the method analogous to that described for compound 40. 5-(4-fluorophenyl)-6-isopropyl-3,5-dihydro-[1,2,3]triazolo[4,5-f]indole was prepared as described for compound 199. $^1$H NMR (300 MHz, DMSO-$d_6$) δ 12.23 (s, 1H), 7.97 (s br, 1H), 7.56-7.41 (m, 4H), 6.97 (s br, 1H), 3.22-3.10 (m, 2H), 3.02 (hept, J=7.2 Hz, 1H), 2.66-2.55 (m, 2H), 1.25 (d, J=7.2 Hz, 6H). LCMS m/z 367.15 $[M+H]^+$.

Compound 215

4-[2-[5-(4-fluorophenyl)-6-tetrahydropyran-4-yl-1H-pyrrolo[2,3-f]indazol-7-yl]ethynyl]benzoic Acid (215)

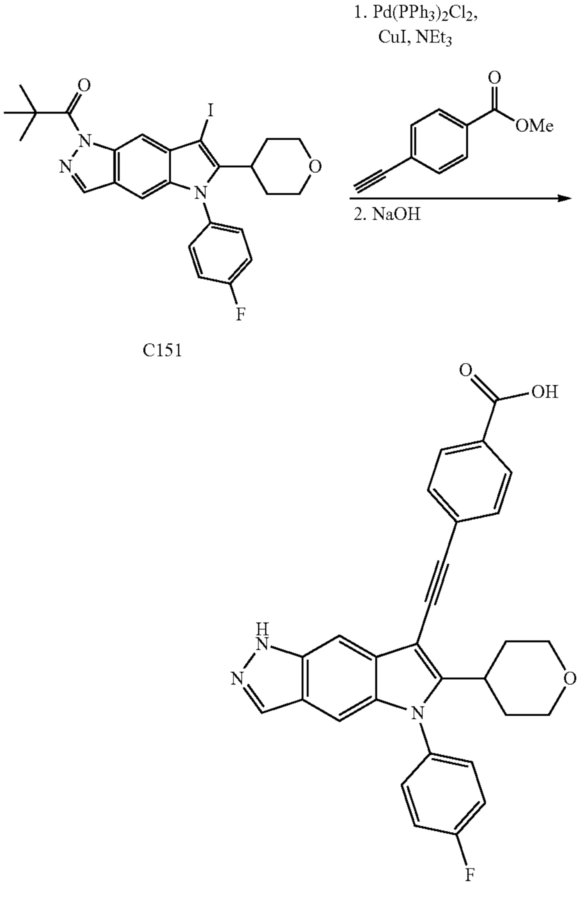

C151

215

A microwave vial was charged with 1-[5-(4-fluorophenyl)-7-iodo-6-tetrahydropyran-4-yl-pyrrolo[2,3-f]indazol-1-yl]-2,2-dimethyl-propan-1-one C151 (254 mg, 0.41 mmol) and methyl 4-ethynylbenzoate (93 mg, 0.58 mmol), and dissolved in DMF (1 mL) and TEA (1 μL). The mixture was degassed with $N_2$ for 10 minutes. Then, $Pd(PPh_3)_2Cl_2$ (12 mg, 0.02 mmol) and CuI (12 mg, 0.06 mmol) were added and the reaction was heated to 90° C. overnight. The reaction mixture was cooled to room temperature and diluted with water (50 mL) and dichloromethane (50 mL). The mixture was passed through a phase separator and the solvent was evaporated.

Purification by silica gel chromatography (Gradient: 0-25% EtOAc in heptane), then by reversed-phase HPLC. Method: C18 Waters Sunfire column (30×150 mm, 5 micron). Gradient: MeCN in $H_2O$ with 0.1% trifluoroacetic acid afforded methyl 4-[2-[5-(4-fluorophenyl)-6-tetrahydropyran-4-yl-1H-pyrrolo[2,3-f]indazol-7-yl]ethynyl]benzoate (34 mg). This material was dissolved in THF (1000 μL) and MeOH (500 μL), then NaOH (413 μL of 1 M, 0.41 mmol) was added and the mixture was heated to 60° C. for 30 minutes. The solvent was evaporated and the crude material was dissolved in minimal water. HCl (413 μL of 1 M, 0.41 mmol) was added, to form a precipitate. The solvent was evaporated and purification by reversed-phase chromatography (Column: C18. Gradient: 0-100% MeCN in water with 0.1% formic acid), then SFC to afford the product. 4-[2-[5-(4-fluorophenyl)-6-tetrahydropyran-4-yl-1H-pyrrolo[2,3-f]indazol-7-yl]ethynyl]benzoic acid (6 mg, 3%). $^1$H NMR (400 MHz, Chloroform-d) δ 7.89-7.81 (m, 3H), 7.63 (s, 1H), 7.47 (d, J=7.8 Hz, 2H), 7.23-7.13 (m, 4H), 7.04 (s, 1H), 3.93-3.87 (m, 2H), 2.77-2.68 (m, 1H), 2.55-2.41 (m, 2H), 1.59 (d, J=13.2 Hz, 2H). LCMS m/z 480.13 $[M+1]^+$.

Example 2. Assays for Detecting and Measuring AAT Modulator Properties of Compounds

A. AAT Function Assay (MSD Assay NL20-SI Cell Line)

Alpha-1 antitrypsin (AAT) is a SERPIN (serine protease inhibitor) that inactivates enzymes by binding to them covalently. This assay measured the amount of functionally active AAT in a sample in the presence of the disclosed compounds 1-215 by determining the ability of AAT to form an irreversible complex with human neutrophil Elastase (hNE). In practice, the sample (cell supernatant, blood sample, or other) was incubated with excess hNE to allow AAT-Elastase complex to be formed with all functional AAT in the sample. This complex was then captured to a microplate coated with an anti-AAT antibody. The complex captured to the plate was detected with a labeled anti-Elastase antibody and quantitated using a set of AAT standards spanning the concentration range present in the sample. Meso Scale Discovery (MSD) plate reader, Sulfo-tag labeling, and microplates were used to provide high sensitivity and wide dynamic range.

Materials:

| Reagents/Plates | Concentration |
|---|---|
| Goat anti-human Alpha-1-Antitrypsin Polyclonal Antibody<br>Use at 5 μg/mL in phosphate buffered saline (PBS) | 1 mL @ 1 mg/mL |
| Human Neutrophil Elastase<br>Stock at 3.4 μM (0.1 mg + 1 mL PBS)<br>Working at 1 μg/mL (34 nm) in MSD Assay buffer (1% bovine serum albumin (BSA)) | 100 μg lyophilized |
| Mouse anti-human Neutrophil Elastase Monoclonal Antibody Sulfo-tagged @ 12:1 using MSD Gold Sulfo-tag N-hydroxysuccinimide (NHS) ester; use at 0.45 μg/mL in MSD Assay buffer (1% BSA) | 900 μg/mL |
| M-AAT (Alpha-1-Antitrypsin) | 5 mg lyophilized |
| MSD Blocker A (BSA)<br>5% solution in PBS for blocking<br>1% solution in PBS for assay buffer | 250 mL |
| MSD Read Buffer T (4X) with Surfactant | 1 L or 250 mL |
| MSD 384 high bind plates | |
| Polypropylene for dilution 384 well plate | |
| Tissue culture treated black well 384 well plate | |

Instrument(s):
Meso Sector S600
Bravo
Washer dispenser
Multidrop Combi
Assay Protocol
Day 1 Cell Culture
1. Harvest NL20 human bronchial epithelial cells expressing human Z-AAT in OptiMEM™ containing Pen/Strep (P/S)
2. Seed at 16,000 cells/well in 30 µL (384 well plate)
3. Centrifuge plates briefly up to speed (1200 rpm) and place into 37° C. incubator overnight
Day 2: Compound Addition and Coating Plates with Capture Antibody Compound Addition:
1. Dispense 40 µL of OptiMEM™ (P/S) with doxycycline (1:1000 stock=0.1 µM final) to each well of the compound plate using a multidrop Combi in hood
2. Remove cell plate from incubator, flip/blot and take immediately to Bravo to transfer compounds
3. Return plates to incubator overnight
Coat MSD Plates
1. Dilute capture antibody (Polyclonal Goat anti-AAT) to 5 µg/mL (1:200) in PBS (no BSA).
2. Dispense 25 µL of diluted capture antibody into all wells of MSD 384-well High Bind plate using the Multidrop equipped with a standard cassette.
3. Incubate overnight at 4° C.
Prepare Blocker A (BSA) Solutions
1. Prepare solution of 5% MSD Blocker A (BSA) following the manufacturer's instructions.
2. Further dilute the 5% MSD Blocker A in PBS to 1% (Blocker A) as needed.
Day 3: Run MSD Assay
Block Plates
1. Wash plate 1× with 50 µL Wash buffer (PBS+0.5% Tween 20), and adds 35 µL 5% Block A buffer to block non-specific binding on washer dispenser
2. Rotate plates on shaker for 1 hour at 600 rpm
Prepare M-AAT Standards
1. Dilute M-AAT stock to 1.6 µg/mL in 1% BSA Blocker A (Stock in −70° C.); then prepare 12×1:2 serial dilutions in 1% Blocker A
2. The top starting final concentration on MSD plate is 320 ng/mL. These dilutions correspond to a final concentration of 320, 160, 80, 40, 20, 10, 5, 2.5, 1.25, 0.625, 0.312, 0.156 ng/mL.
Dilution Plate
1. Add 80 µL of 1% Assay buffer to all wells except columns 1/24 (standards) with Multidrop Combi
2. Add diluted standards to columns 1 and 24
3. Centrifuge dilution plates 1200 rpm briefly
Cell Plate
1. Aspirate columns which will have the standards from the cell plates in the hood using 16-pin aspirator
Prepare Human Neutrophil Elastase (hNE)
1. Prepare 1 µg/mL Human Neutrophil Elastase by diluting in 1% Blocker A.
a. Small 100 µg vial—add 1 mL PBS (100 µg/mL)
i. This can then be diluted 1:100 in 1% Assay Buffer for a final 1 µg/mL concentration
MSD—Add hNE (20 µL/well)
1. After the MSD plate has blocked for at least 1 hour, wash plate 1× with 50 µL Wash buffer (PBS+0.5% Tween 20) and then add 20 µL hNE to each well
Bravo—Cell Plate—Dilution Plate—MSD Plate
Using the Bravo aspirate 10 µL from the cell plate, transfer to the dilution plate (9-fold dilution)
1. Mix 25 µL 3×, then aspirate 5 µL, transfer to MSD plate (5-fold dilution)
2. Mix 10 µL 3×. Total dilution is 45 fold.
3. Shake plates at 600 rpm for 1.5 hours
Add Functional detection hNE antibody
1. Wash plate 1× with wash buffer
2. Add 25 µL Sulfo-tagged anti-Elastase Monoclonal Mouse anti-Elastase) diluted to 0.45 µg/mL (1:2000) in 1% Blocker A into all wells of the functional activity MSD plates using the washer/dispenser
Note: The dilution required for sufficient signal must be determined for each new lot of labeled antibody.
3. Incubate at RT shaking at 600 rpm for 1 hour.
Final Wash and MSD Imager Read
1. Wash the plate 1×, and add 25 µL of Wash Buffer to the plate.
2. Make 2× Read buffer
3. Remove wash buffer from MSD plate
4. Transfer 35 µL 2× Read Buffer to MSD plate using Bravo and take to MSD to read immediately
Data analysis in MSD Discovery Workbench 4.0 software and EC50 values were determined using Genedata. See Table 8 for data.
B. Biochemical Assay (Z-AAT Elastase Activity Assay)
This assay measured the modulation of compounds 1-215 on Z-AAT SERPIN activity using purified Z-AAT protein and purified human neutrophil elastase (hNE). Normally, when active monomeric Z-AAT encounters a protease such as trypsin or elastase, it forms a 1:1 covalent "suicide" complex in which both the AAT and protease are irreversibly inactivated. However, compounds binding to Z-AAT can lead to a decrease in SERPIN activity. In such cases, when a protease encounters compound-bound Z-AAT, the protease cleaves and inactivates Z-AAT without itself being inactivated.
Materials
Reagents
PBS buffer (media prep)+0.01% BRIJ35 detergent (Calbiochem catalog #203728) Opti-MEM media (Fisher 11058-021)
Human neutrophil elastase (hNE, Athens Research #16-14-051200)
3.4 µM stock (0.1 mg/mL) prepared in 50 mM Na Acetate, pH 5.5, 150 mM NaCl, stored at −80° C.
Elastase substrate V (ES V, fluorescent peptide substrate MeOSuc-Ala-Ala-Pro-Val-AMC, Calbiochem catalog #324740)
20 mM stock in DMSO, stored at −20° C.
Purified Z-AAT protein from human plasma;
12.9 µM (0.67 mg/mL) Z-AAT Vertex Cambridge Sample 4942, from patient #061-SSN, stored at −80 C
Plates
Corning 4511 (384 well black low volume)
Instruments
PerkinElmer® EnVision™
Assay Protocol
Pre-Incubation of Z-AAT with Compounds
1. 7.5 µL of Z-AAT (20 nM) was incubated with compounds 1-215 in a GCA plate for 1 hour at room temperature
Addition of hNE
1. 7.5 µL of HNE solution (3 nM in PBS+0.01% BRIJ35) added into GCA plate 2. Incubate plate for 30 minutes to allow Z-AAT/HNE suicide complex formation.

Addition of Substrate and Read Plate on PE Envision 1. 7.5 μL of substrate (300 μM solution of elastase substrate (ES V) in PBS+0.01% BRIJ35) dispensed per well into GCA plate 2. Immediately read on Envision.

Compounds 1-87, 89-140, 143-151, 154, 158, 160, 164-167, 170, 171, 173-183, 186, 189-208, and 210-215 had an $IC_{50}/EC_{50}$ ratio of greater than 10 or an $IC_{50}$ of greater than 10 μM. Compounds 161, 162, 163, 172, and 209 had an $IC_{50}$ of greater than 3.33 μM.

C. EC50 Data for Compounds 1-215

The compounds of formula (I) are useful as modulators of AAT activity. Table 8 below illustrates the $EC_{50}$ of the compounds 1-215 using procedures described above (assays described above in Example 2A). In Table 8 below, the following meanings apply. For $EC_{50}$: "+++" means <1.16 μM; "++" means between 1.16 μM and 3.0 μM; "+" means greater than 3.0 μM. "N/A" means activity not assessed.

TABLE 8

EC50 data for Compounds 1-215

| Compound No. | NL20 Func. (EC50) |
|---|---|
| 1 | ++ |
| 2 | + |
| 3 | ++ |
| 4 | + |
| 5 | + |
| 6 | + |
| 7 | + |
| 8 | + |
| 9 | + |
| 10 | + |
| 11 | ++ |
| 12 | + |
| 13 | +++ |
| 14 | +++ |
| 15 | + |
| 16 | ++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | + |
| 31 | ++ |
| 32 | ++ |
| 33 | +++ |
| 34 | +++ |
| 35 | +++ |
| 36 | +++ |
| 37 | + |
| 38 | ++ |
| 39 | ++ |
| 40 | + |
| 41 | ++ |
| 42 | ++ |
| 43 | + |
| 44 | + |
| 45 | + |
| 46 | + |
| 47 | + |
| 48 | + |
| 49 | + |
| 50 | + |

TABLE 8-continued

EC50 data for Compounds 1-215

| Compound No. | NL20 Func. (EC50) |
|---|---|
| 51 | ++ |
| 52 | +++ |
| 53 | +++ |
| 54 | + |
| 55 | +++ |
| 56 | ++ |
| 57 | ++ |
| 58 | ++ |
| 59 | +++ |
| 60 | + |
| 61 | + |
| 62 | + |
| 63 | ++ |
| 64 | + |
| 65 | + |
| 66 | ++ |
| 67 | +++ |
| 68 | +++ |
| 69 | + |
| 70 | +++ |
| 71 | + |
| 72 | ++ |
| 73 | +++ |
| 74 | ++ |
| 75 | +++ |
| 76 | +++ |
| 77 | +++ |
| 78 | +++ |
| 79 | ++ |
| 80 | +++ |
| 81 | ++ |
| 82 | + |
| 83 | ++ |
| 84 | ++ |
| 85 | ++ |
| 86 | + |
| 87 | ++ |
| 88 | ++ |
| 89 | + |
| 90 | +++ |
| 91 | +++ |
| 92 | +++ |
| 93 | ++ |
| 94 | ++ |
| 95 | ++ |
| 96 | +++ |
| 97 | +++ |
| 98 | ++ |
| 99 | + |
| 100 | ++ |
| 101 | + |
| 102 | + |
| 103 | + |
| 104 | +++ |
| 105 | ++ |
| 106 | +++ |
| 107 | + |
| 108 | ++ |
| 109 | ++ |
| 110 | ++ |
| 111 | ++ |
| 112 | + |
| 113 | ++ |
| 114 | + |
| 115 | ++ |
| 116 | + |
| 117 | ++ |
| 118 | + |
| 119 | ++ |
| 120 | +++ |
| 121 | ++ |
| 122 | ++ |
| 123 | ++ |
| 124 | ++ |
| 125 | + |
| 126 | ++ |

TABLE 8-continued

| EC50 data for Compounds 1-215 | |
|---|---|
| Compound No. | NL20 Func. (EC50) |
| 127 | +++ |
| 128 | ++ |
| 129 | + |
| 130 | +++ |
| 131 | +++ |
| 132 | +++ |
| 133 | +++ |
| 134 | +++ |
| 135 | +++ |
| 136 | +++ |
| 137 | +++ |
| 138 | + |
| 139 | + |
| 140 | + |
| 141 | + |
| 142 | + |
| 143 | + |
| 144 | +++ |
| 145 | +++ |
| 146 | ++ |
| 147 | ++ |
| 148 | ++ |
| 149 | ++ |
| 150 | ++ |
| 151 | ++ |
| 152 | ++ |
| 153 | ++ |
| 154 | ++ |
| 155 | + |
| 156 | + |
| 157 | + |
| 158 | + |
| 159 | ++ |
| 160 | + |
| 161 | + |
| 162 | ++ |
| 163 | ++ |
| 164 | + |
| 165 | ++ |
| 166 | + |
| 167 | ++ |
| 168 | ++ |
| 169 | ++ |
| 170 | ++ |
| 171 | +++ |
| 172 | ++ |
| 173 | + |
| 174 | + |
| 175 | ++ |
| 176 | +++ |
| 177 | ++ |
| 178 | ++ |
| 179 | + |
| 180 | ++ |
| 181 | + |
| 182 | ++ |
| 183 | + |
| 184 | + |
| 185 | ++ |
| 186 | + |
| 187 | N/A |
| 188 | ++ |
| 189 | ++ |
| 190 | + |
| 191 | + |
| 192 | ++ |
| 193 | ++ |
| 194 | + |
| 195 | + |
| 196 | + |
| 197 | + |
| 198 | + |
| 199 | + |
| 200 | + |
| 201 | + |
| 202 | + |
| 203 | + |
| 204 | + |
| 205 | ++ |
| 206 | ++ |
| 207 | + |
| 208 | +++ |
| 209 | + |
| 210 | +++ |
| 211 | + |
| 212 | + |
| 213 | + |
| 214 | + |
| 215 | +++ |

Example 3: Alternative Preparation of Compound 32

Compound 32

3-[5-(4-fluorophenyl)-6-isopropyl-1H-pyrrolo[2,3-f]indazol-7-yl]propanoic Acid

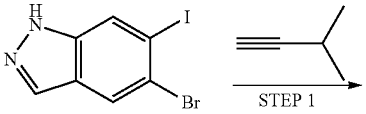

C7

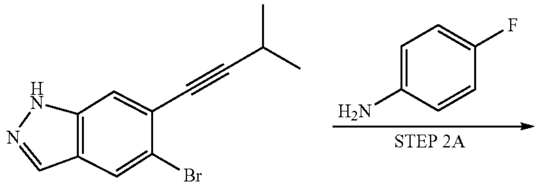

C8

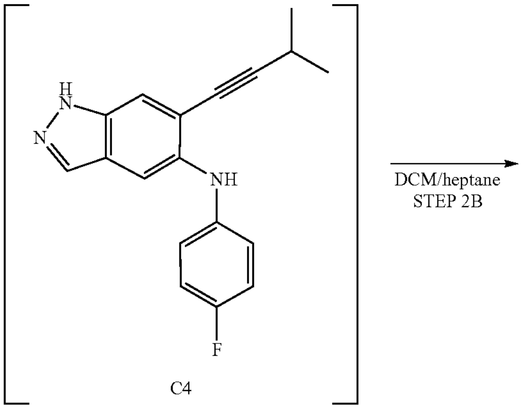

C4

-continued

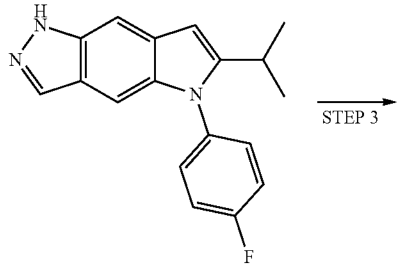

S3

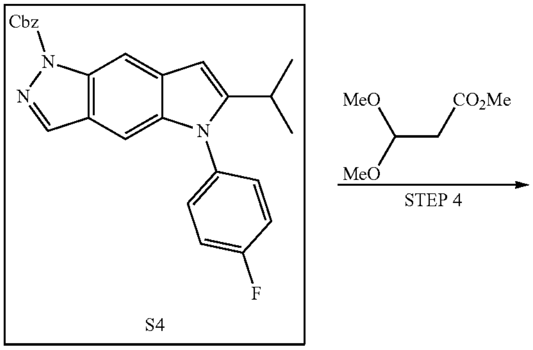

S4

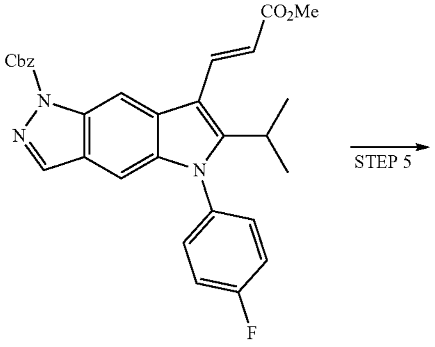

C35

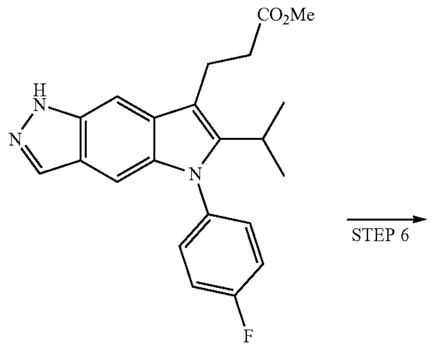

C36

-continued

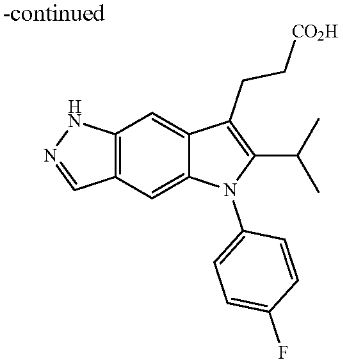

32

Step 1: Synthesis of 5-bromo-6-(3-methylbut-1-yn-1-yl)-1H-indazole (C8)

C7 (300 g, 0.93 mol) was charged to a reactor, to which was then charged $Pd(PPh_3)_2Cl_2$ (32.6 g, 0.046 mol), and CuI (12.4 g, 0.07 mol). MTBE (3 L, 10 vol) was then charged, and agitation was started. Diethylamine (210.6 g, 2.88 mol) was charged to the reactor. The reaction mixture was stirred at 20° C. 3-methyl-1-butyne (75.94 g, 1.11 mol) was charged to the reactor, which was sealed. The reactor was heated to 54° C. internal temperature. After four hours, the reactor was cooled to 25° C., and MTBE (1.5 L, 5 vol) was charged. Aqueous ammonium chloride solution (20 wt %, 2.9 L, 9.7 vol) was charged to the reactor. The mixture was stirred for 30 minutes at 25° C. Agitation was discontinued, the layers were separated for 30 minutes, and the aqueous layer was drained. 0.1 M HCl (1.4 L, 4.5 vol) was charged to the reactor, and the mixture was stirred for 30 minutes. Agitation was discontinued, the layers were separated for 30 minutes, and the aqueous layer was drained. Water (1.62 L, 5 vol) was charged, and the mixture was stirred for 30 minutes. Agitation was discontinued, the layers were separated for 30 minutes, and the aqueous layer was drained. The organic phase was distilled to –2-3 volumes. MTBE (1.5 L, 5 vol) was charged to the reactor, and the mixture was concentrated to ~2-3 volumes. MTBE (1.5 L, 5 vol) was charged to the reactor, and the mixture was concentrated to –2-3 volumes. n-Heptane (1.5 L, 5 vol) was charged to the reactor, and the mixture was concentrated to ~2-3 volumes. n-Heptane (1.5 L, 5 vol) was charged to the reactor, and the mixture was concentrated to ~2-3 volumes. Dichloromethane (300 mL, 1 vol) was charged to the reactor. The reactor was heated to 35° C. internal temperature and stirred for 1 hour. n-Heptane (300 mL, 1 vol) was charged, and the mixture was stirred for 30 minutes. The reactor was cooled to 15° C. over four hours. The slurry was stirred for 30 minutes and then filtered. The reactor was washed with 1:1 dichloromethane: n-heptane (300 mL, 1 vol). The rinse was transferred to the wet cake. The wet cake was dried in a vacuum oven with nitrogen bleed at 40° C. The yield was 80-85% with a purity of >99 A %.

Step 2: Synthesis of 5-(4-fluorophenyl)-6-isopropyl-1,5-dihydropyrrolo[2,3-f]indazole (S3)

Ethanol (16 L, 3.7 vol) was charged to a reactor, and the reactor was cooled to 0-5° C. Sodium tert-butoxide (3320 g, 34.54 mol) was charged to the reactor. Ethanol (10 L, 2.3 vol) was charged to the reactor, and the reactor jacket temperature was adjusted to 20° C. C8 (4.324 kg, 16.43 mol) was charged to the reactor at 20° C. 4-Fluoroaniline (2.06 kg, 18.49 mol) was charged to the reactor at 20° C. A vacuum and nitrogen purge cycle was performed three times. Chloro(2-di-t-butylphosphino-2',4',6'-tri-1-propyl-1, 1'-biphenyl)[2-(2-aminoethyl)phenyl]palladium (II) (283 g, 0.41 mol) was charged at 20° C. The reactor was heated to 65° C. internal temperature. After 1-2 hours, the reactor was cooled to 55-60° C. Acetic acid (3.7 kg, 61.62 mol) was charged at 55-60° C. The reaction mixture was stirred at 60-65° C. for 2-4 hours. Water (26 L, 6 vol) was charged to the reactor over 2-3 hours. The reactor was cooled to 50° C. over 1 hour. Water (26 L, 6 vol) was charged to the reactor over 3-4 hours. The reaction mixture was agitated for 1 hour at 50° C. The reactor was cooled to 20-25° C. over 5-6 hours. The reaction mixture was agitated for 30 minutes at 20-25° C. The slurry was filtered. The reactor was rinsed with 1:1 EtOH:water (4.4 L, 1 vol), and the rinse was transferred to the wet cake. The wet cake was transferred to a vacuum oven set to 60° C. The resulting crude S3 was charged to a reactor. THF (11 vol) was charged to the reactor. Charcoal (14 wt %, 0.61 kg) and MP-TMT (macroporous polystyrene-bound trimercaptotriazine) (23 wt %, 0.99 kg) were charged to the reactor. The reactor was heated to 40° C., and the mixture was agitated for 3 hours. The mixture was filtered over a bed of Celite. The reactor was rinsed with THF (8.7 L, 2 vol), and the rinse was transferred to the Celite cake. The filtrate was distilled to 2-3 volumes. The slurry was stirred for 1 hour. The slurry was filtered. The reactor was rinsed with THF (1 vol), and the rinse was transferred to the wet cake. The wet cake was dried under vacuum at 50° C. with nitrogen bleed. The yield was approximately 85% and the purity was >99 A %.

Step 3: Synthesis of benzyl 5-(4-fluorophenyl)-6-isopropylpyrrolo[2,3-f]indazole-1(5H)-carboxylate (S4)

S3 (4.63 kg, 15.78 mol) was charged to a reactor. Anhydrous THF (65 L, 14 vol) was charged to the reactor, agitated was started, and the reactor was cooled to 0-5° C. Sodium tert-pentoxide (12.4 L, 1.91 kg, 17.36 mol) was charged to the reactor at 5° C. The mixture was agitated for 30 minutes at 0-5° C. Benzyl chloroformate (2.7 L, 18.98 mol) was charged to the reactor at 0-10° C. The mixture was stirred for 30 minutes at 5° C. The reactor was warmed to 20° C. Water (15 L, 3 vol) was charged to the reactor. MTBE (15 L, 3 vol) was charged to the reactor, and the mixture was stirred for 30 minutes. The aqueous layer was drained. MTBE (15 L, 3 vol) was charged to the reactor, and the mixture was stirred for 30 minutes. The aqueous layer was drained. The organic layer was distilled to 2-3 volumes. Methanol (23 L, 5 vol) was charged to the reactor, and the mixture was distilled to 2-3 volume. Methanol (23 L, 5 vol) was charged to the reactor, and the mixture was distilled to 2-3 volume. Methanol (10 L, 2.2 vol) was charged to the reactor, and the mixture was stirred for 30 minutes. The reactor was cooled to 10° C. over 2 hours, and the mixture was stirred for 30 minutes. The slurry was filtered. The reactor was rinsed with methanol (4.6 L, 1 vol), and the rinse was transferred to the wet cake. The material was dried under vacuum at 45° C. with nitrogen bleed. S4 (5.958 kg) was charged to a reactor. THF (66 L, 11 vol) was charged to the reactor, and agitation was started. The slurry was heated to 45° C. internal temperature. MP-TMT (macroporous polystyrene-bound trimercaptotriazine) resin (1.2 kg, 20% wt equiv.) and charcoal (600 g, 10% wt equiv.) were charged to the reactor. The mixture was agitated for 3 hours. The mixture was filtered through a pad of Celite while hot. The reactor was washed with THF (12 L, 2 vol), and the rinse was transferred to the Celite cake. The filtrate was distilled to 3 volumes. n-Heptane (~8 L, 1.3 vol) was charged over 1 hour. The slurry was agitated for 20 minutes. The reactor was cooled to 10° C. internal temperature, and the mixture was agitated for 30 minutes. The slurry was filtered. The reactor was rinsed with 1:1 THF:Heptane (6 L, 1 vol). The rinse was transferred to the wet cake. The wet cake was dried under vacuum at 45° C. with nitrogen bleed. The yield was 75% and the purity was >99 A %.

Step 4: Synthesis of benzyl 5-(4-fluorophenyl)-6-isopropyl-7-[(E)-3-methoxy-3-oxo-prop-1-enyl]pyrrolo[2,3-f]indazole-1-carboxylate (C35)

S4 (7.6 kg, 17.78 mol) was charged to a reactor. p-Toluenesulfonic acid monohydrate (10.15 kg, 53.34 mol) was charged to the reactor. Dichloromethane (50.9 L, 67.7 kg, 6.7 vol) was charged to the reactor, and agitation was started at 20° C. Methyl-3,3-dimethoxypropionate (3.23 L, 3.4 kg) was charged to the reactor at 20° C. The transfer line was rinsed with dichloromethane (2.3 L, 3.0 kg, 0.3 vol), and the rinse was transferred to the reactor. The reactor was heated to 35±3° C. The mixture was agitated for 4 hours. The reactor was cooled to 15° C. An aqueous ~7% sodium bicarbonate solution was prepared by dissolving sodium bicarbonate (6.72 kg, 80.0 mol) in water (92 L, 91.7 kg). A portion of this sodium bicarbonate solution (67.8 kg) was charged to the reactor at 25° C. The mixture was agitated for 30 minutes. The agitation was stopped, and the phases were allowed to separate for 30 minutes. The organic layer was drained. The aqueous layer was drained. The organic layer was charged to the reactor. The transfer line was rinsed with dichloromethane (7.6 L, 1 vol), and the rinse was charged to the reactor. 30.6 kg of the 7 wt. % sodium bicarbonate solution was charged to the reactor, and the mixture was stirred for 30 minutes at 20° C. The agitation was stopped, and the phases were allowed to separate for 30 minutes. The organic layer was drained. The aqueous layer was drained. The organic layer was charged to the reactor, rinsing with dichloromethane (3.8 L, 0.5 vol). The reactor content was distilled under reduced pressure to 2-3 volumes. Ethyl acetate (34.3 kg, 5 vol) was charged to the reactor, and the mixture was distilled to 2-3 volumes. Ethyl acetate (34.3 kg, 5 vol) was charged to the reactor, and the mixture was distilled to 2-3 volumes. Ethyl acetate (34.3 kg, 5 vol) was charged to the reactor. The reactor was heated to 75° C. n-Heptane (22.8 L, 18.1 kg, 3 vol) was charged to the reactor, and the temperature was maintained at 75±5° C. The internal temperature was adjusted to 60° C., and the mixture was agitated for 1 hour. n-Heptane (97.3 L, 77.1 kg, 15 vol) was charged to the reactor over 4 hours while maintaining the temperature at 60° C. The reactor was cooled to 20° C. over 6 hours, and the mixture was agitated at 20° C. for 1 hour. The reactor contents were filtered. The reactor was rinsed with 2.5:1 v/v n-heptane:ethyl acetate (26.6 L, 21.8 kg, 3 vol), and the rinse was transferred to the wet cake. The wet cake was dried under vacuum at 50° C. with nitrogen bleed. The yield was ~85%.

Optional Recrystallization: The crude C35 was transferred to a reactor. Ethyl acetate (5 vol) was charged to the reactor. The reactor was heated to 75° C. internal temperature to obtain a solution. The reactor is cooled to 58° C. internal temperature. The mixture was stirred for 1 hour to obtain a seed bed. The reactor was cooled to 20° C. over 6 hours, and the mixture was agitated for 1 hour. The reactor contents were filtered. The reactor was rinsed with ethyl acetate (1 vol), and the rinse was transferred to the wet cake. The wet cake was dried under vacuum at 50° C. with nitrogen bleed. The recovery was ~80%.

Step 5: Synthesis of methyl 3-[5-(4-fluorophenyl)-6-isopropyl-1H-pyrrolo[2,3-f]indazol-7-yl]propanoate (C36)

C35 (1.82 kg) was charged to a reactor. The reactor was evacuated and purged with nitrogen three times. 5% Pd/C catalyst (Johnson Matthey Type A405032-5 or Type A405028-5, 381 g, 10% wt (dry basis)) was charged to the reactor. The reactor was evacuated and purged with nitrogen three times. THF (6.4 L, 3.5 vol) was charged to the reactor. The reactor was evacuated and purged with nitrogen six times. TMEDA (1.18 L) was charged to the reactor. The reactor was evacuated and purged with nitrogen three times. The reactor was heated to 25° C., and the reactor was pressurized to 3 bar with hydrogen gas. The mixture was agitated for ~7-10 hours. The reaction mixture was filtered using filter aid to remove Pd/C. The reactor was rinsed twice with THF (2 L, 1.1 vol), and the rinse was transferred onto the cake. The solution was transferred to a reactor, rinsing the lines with THF (2×1 L). The solution was distilled under vacuum at 35° C. to 2-3 volumes. Ethyl acetate (7.3 L, 4 vol) was charged to the reactor, and the mixture was distilled to 2-3 volumes. Ethyl acetate (7.3 L, 4 vol) was charged to the reactor, and the mixture was distilled to 2-3 volumes. Ethyl acetate (7.3 L, 4 vol) was charged to the reactor, and the mixture was distilled to 2-3 volumes. Ethyl acetate (7.3 L, 4 vol) was charged to the reactor. The reactor was heated to 70-75° C. The reactor was cooled to 60° C. n-Heptane (3.6 L, 2.0 vol) was charged to the reactor over 30 minutes at 60° C. The beatch was stirred for 1 hour to obtain a seed bed. n-Heptane (20 L, 1.1 vol) was charged over 4 hours while maintaining a temperature of 60° C. The mixture was stirred at 60° C. for 4 hours. The reactor was cooled to 20° C. over 5 hours. The mixture was stirred at 20° C. for 1 hour. The batch was filtered. The reactor was rinsed with n-heptane (2.7 L, 1.5 vol) and ethyl acetate (0.9 L, 0.5 vol), and the rinse was transferred to the wet cake. The wet cake was dried under vacuum at 50-55° C.

Step 6: Synthesis of 3-[5-(4-fluorophenyl)-6-isopropyl-M-pyrrolo[2,3-f]indazol-7-yl]propanoic Acid (32)

C36 (2.34 kg) was charged to a reactor. Ethanol (30.4 L, 13 vol) was charged to the reactor, and agitation was started. Potassium hydroxide aqueous solution (40% w/v, 2.34 L) was charged to the reactor over 30 minutes at not more than 25° C. The mixture was stirred for 3 hours at 25° C. The mixture was polish filtered through a 0.45 micron inline filter. Acetic acid (1 L) was charged through a polish filter to the batch while maintaining a temperature of not more than 25° C. The reaction was heated to 50° C. Purified water (29 L, 12.4 vol) was charged through a polish filter to the reactor over 2 hours. The reactor was cooled to 20° C. internal temperature over 5 hours. The batch was filtered. A solution of ethanol (2.3 L, 1.0 vol) and water (2.3 L, 1.0 vol) was charged to the reactor through a polish filter. The rinse was transferred to the wet cake. The wet cake was washed with purified water (4.6 L, 2.0 vol). The wet cake was dried under vacuum at 50° C. The yield was ~90%, and the purity was >99.8 A %.

Example 4: Morphological Studies of Compound 32

General Considerations

Bruker-Biospin 400 MHz wide-bore spectrometer equipped with Bruker-Biospin 4 mm HFX probe was used. Samples were packed into 4 mm $ZrO_2$ rotors and spun under Magic Angle Spinning (MAS) condition with spinning speed typically set to 12.5 kHz. The proton relaxation time was measured using $^{1}H$ MAS $T_1$ saturation recovery relaxation experiment in order to set up proper recycle delay of the $^{13}C$ cross-polarization (CP) MAS experiment. The fluorine relaxation time was measured using $^{19}F$ MAS $T_1$ saturation recovery relaxation experiment in order to set up proper recycle delay of the $^{19}F$ MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Both carbon and fluorine spectra were recorded with proton decoupling using TPPM15 decoupling sequence with the field strength of approximately 100 kHz.

Mixture of Crystalline Form A of Compound 32 and Crystalline Form C of Compound 32

Synthetic Procedure: C36 (2.34 kg, 1.0 equiv) was charged to a 90 L reactor. Then EtOH (30.4 L, 13 vol) was charged to the same reactor. After that, 40% w/v KOH (2.33 L, 2.7 eq) was charged over 30 min while the temperature was maintained at no more than (NMT) 25° C. The reaction mixture was stirred at 25° C. for 3 hrs. Upon completion of reaction, AcOH (1 L, 2.85 eq) was charge while the temperature was maintained at NMT 25° C. The reaction mixture was then heated to 50° C. Subsequently, water (29 L, 12.4 vol) was charged to the reactor over 2 hrs. Next, the reactor was cooled to 20° C. over 5 hrs. The solids were filtered. The filtered cake was washed with a solution of EtOH (2.3 L, 1.0 vol) and water (2.3 L, 1.0 vol), and an additional time with water (4.6 L, 2.0 vol). The filter cake was dried under vacuum at 50° C. to give a mixture of Crystalline Form A of Compound 32 and Crystalline Form C of Compound 32 (2.05 kg, 91% yield, 99.8% purity by HPLC).

X-Ray Powder Diffraction (XRPD): The powder x-ray powder diffraction diffractogram of a mixture of Crystalline Form A of Compound 32 and Crystalline Form C of Compound 32 was acquired at room temperature using the PANalytical Empyrean diffractometer equipped with a PIXcel 1D detector. FIG. 1 depicts an XRPD diffractogram of a mixture of Crystalline Form A of Compound 32 and Crystalline Form C of Compound 32. Table 11 provides XRPD peaks, angle, and intensity % for a mixture of Crystalline Form A of Compound 32 and Crystalline Form C of Compound 32.

TABLE 11

| XRPD Peaks | Angle (Degrees 2-Theta ± 0.2) | Intensity % |
|---|---|---|
| 1 | 20.3 | 166.0 |
| 2 | 17.6 | 61.4 |
| 3 | 18.0 | 53.2 |
| 4 | 24.4 | 40.3 |
| 5 | 18.5 | 34.4 |
| 6 | 28.4 | 33.2 |
| 7 | 28.7 | 33.0 |
| 8 | 29.2 | 29.9 |
| 9 | 24.6 | 29.6 |

TABLE 11-continued

| XRPD Peaks | Angle (Degrees 2-Theta ± 0.2) | Intensity % |
|---|---|---|
| 10 | 21.4 | 28.8 |
| 11 | 18.8 | 25.8 |
| 12 | 15.4 | 25.6 |
| 13 | 21.8 | 24.8 |
| 14 | 14.9 | 23.9 |
| 15 | 23.6 | 21.9 |
| 16 | 15.0 | 21.9 |
| 17 | 26.7 | 19.3 |
| 18 | 13.8 | 16.9 |
| 19 | 10.9 | 15.6 |
| 20 | 22.6 | 14.9 |
| 21 | 22.1 | 12.3 |
| 22 | 10.1 | 12.2 |
| 23 | 25.7 | 10.1 |

Figure 2:
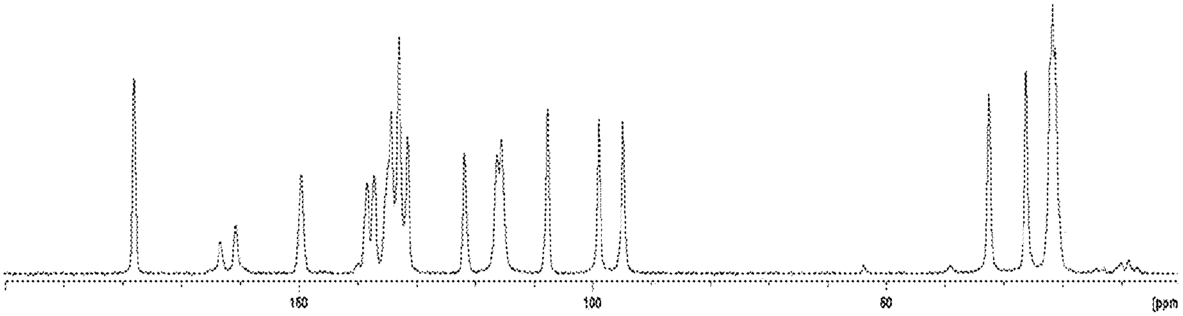
FIG. 2 depicts a solid state $^{13}C$ NMR spectrum for a mixture of crystalline Form A of Compound 32 and crystalline Form C of Compound 32.

Solid State NMR: FIG. 2 depicts a solid state NMR spectrum for a mixture of Crystalline Form A of Compound 32 and Crystalline Form C of Compound 32. Table 12 recites 13C NMR chemical shift data for a mixture of Crystalline Form A of Compound 32 and Crystalline Form C of Compound 32.

TABLE 12

| Peak # | Chem Shift [ppm] | Intensity [rel] |
|---|---|---|
| 1 | 178.1 | 72.4 |
| 2 | 163.4 | 11.9 |
| 3 | 160.8 | 18.2 |
| 4 | 149.5 | 37.2 |
| 5 | 140.1 | 3.2 |
| 6 | 138.4 | 33.8 |
| 7 | 137.2 | 36.3 |
| 8 | 134.3 | 60.5 |
| 9 | 133 | 88 |
| 10 | 131.5 | 51.1 |
| 11 | 121.8 | 45.0 |
| 12 | 116.3 | 44 |
| 13 | 115.5 | 49.8 |
| 14 | 107.7 | 61.1 |
| 15 | 98.9 | 57.2 |
| 16 | 94.8 | 56.7 |
| 17 | 32.5 | 66.8 |
| 18 | 26.2 | 75.0 |
| 19 | 21.7 | 100.0 |
| 20 | 21.2 | 83.8 |

Figure 3:
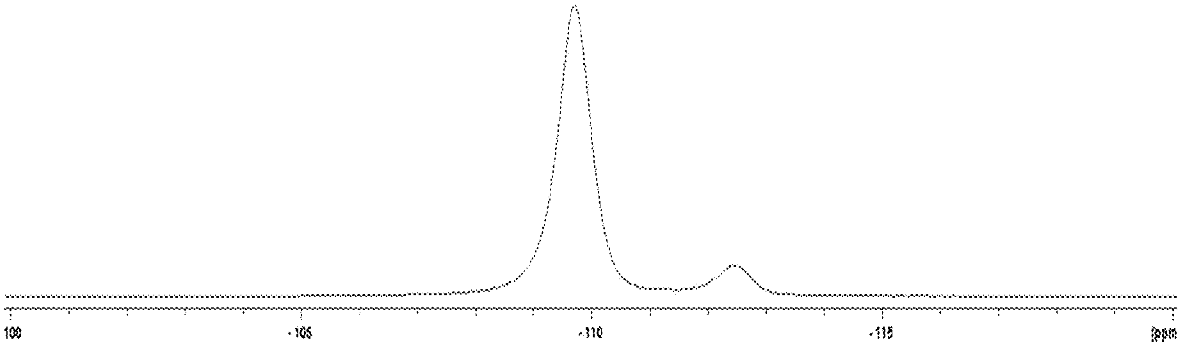
FIG. 3 depicts a $^{19}F$ MAS (magnetic angle spinning) spectrum for a mixture of crystalline Form A of Compound 32 and crystalline Form C of Compound 32.

FIG. 3 depicts a 19F MAS (magnetic angle spinning) spectrum for a mixture of Crystalline Form A of Compound 32 and Crystalline Form C of Compound 32. Table 13 recites 19F chemical shift data for a mixture of Crystalline Form A of Compound 32 and Crystalline Form C of Compound 32.

TABLE 13

| Peak # | Chem Shift [ppm] | Intensity [rel] |
|---|---|---|
| 1 | −109.7 | 12.5 |
| 2 | −112.5 | 1.3 |

Figure 4:
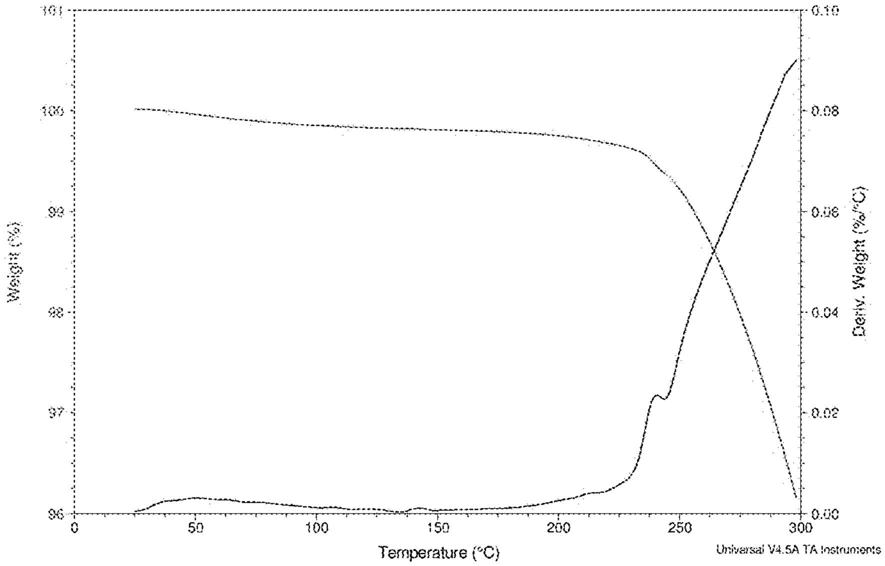
FIG. 4 depicts a TGA thermogram of a mixture of crystalline Form A of Compound 32 and crystalline Form C of Compound 32.

Thermogravimetric Analysis (TGA): Thermal gravimetric analysis of a mixture of Crystalline Form A of Compound 32 and Crystalline Form C of Compound 32 was measured using the TA Instruments Q5000. FIG. 4 depicts a TGA thermogram of a mixture of Crystalline Form A of Compound 32 and Crystalline Form C of Compound 32, and the thermogram shows 0.2% wt. loss from ambient to 150° C.

Figure 5:
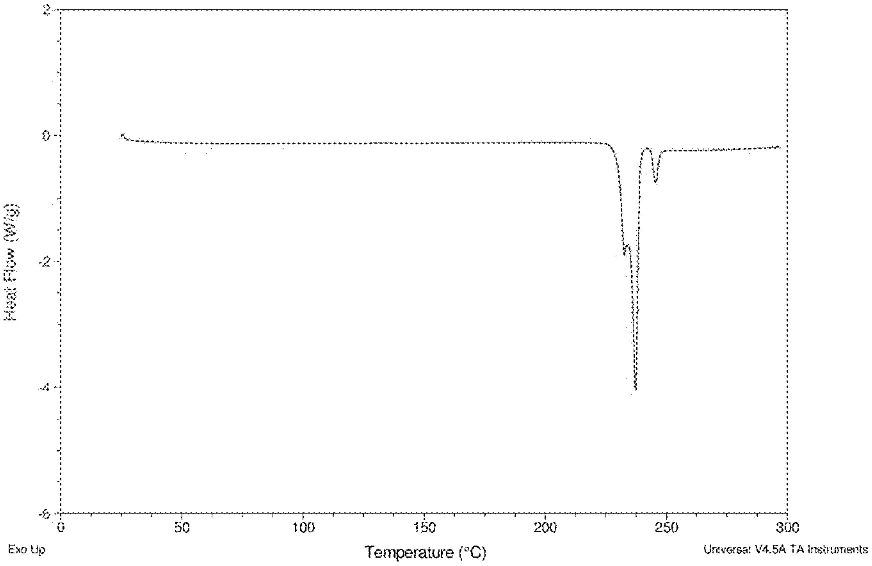
FIG. 5 depicts a DSC thermogram of a mixture of crystalline Form A of Compound 32 and crystalline Form C of Compound 32.

Differential Scanning Calorimetry (DSC) Analysis: The melting point of a mixture of Crystalline Form A of Compound 32 and Crystalline Form C of Compound 32 was measured using the TA Instruments Discovery DSC. FIG. 5 depicts a DSC thermogram of a mixture of Crystalline Form A of Compound 32 and Crystalline Form C of Compound 32, which shows an melting onset of 234° C. with a peak due to melting/decomposition at 237° C.

Figure 6:
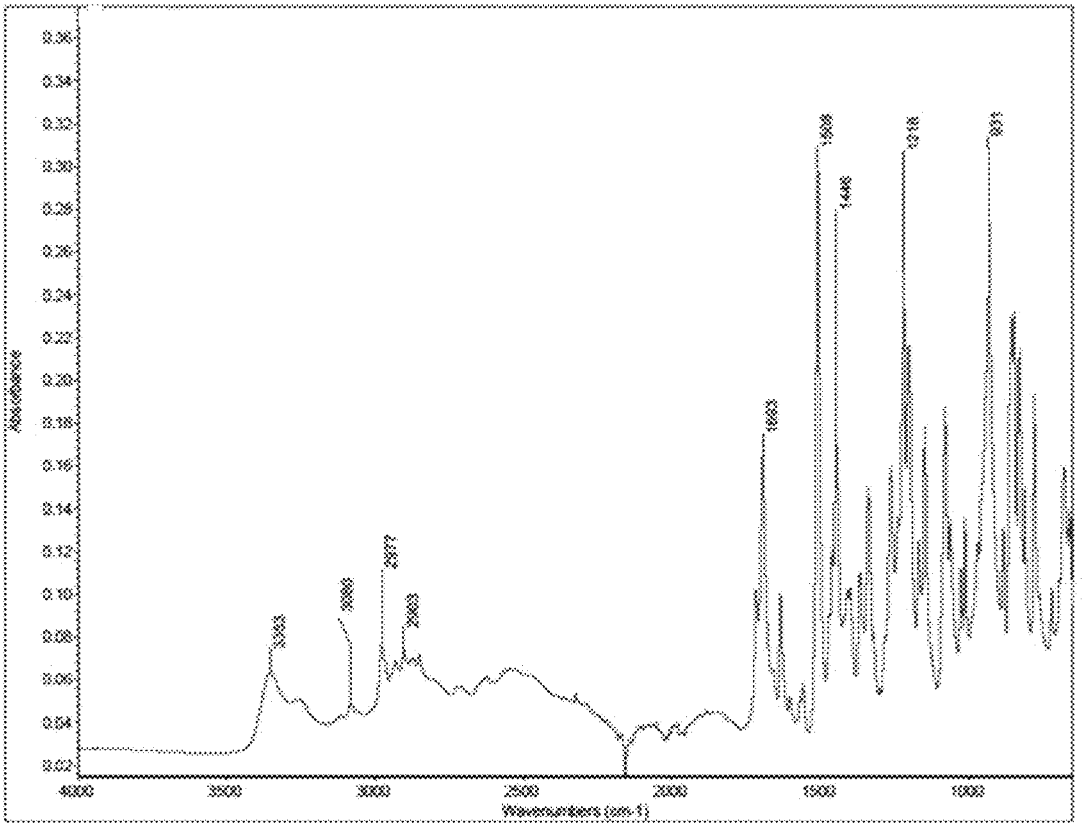
FIG. 6 depicts an IR spectrum of a mixture of crystalline Form A of Compound 32 and crystalline Form C of Compound 32.

Infrared (IR) Spectroscopy: The IR spectrum of a mixture of Crystalline Form A of Compound 32 and Crystalline Form C of Compound 32 was collected using the Thermo Scientific Nicolet iS50 Spectrometer equipped with a diamond ATR sampling accessory. Table 14 recites IR frequencies and interpretations thereof for a mixture of Crystalline Form A of Compound 32 and Crystalline Form C of Compound 32. FIG. 6 depicts an IR spectrum of a mixture of Crystalline Form A of Compound 32 and Crystalline Form C of Compound 32.

TABLE 14

| Frequency ($cm^{-1}$) | Moiety | Vibration |
|---|---|---|
| 3353 | OH | Stretch |
| 3080 | Aromatic CH | Stretch |
| 2977, 2903 | Aliphatic CH | Stretch |
| 1693 | Acid CO | Stretch |
| 1508 | Aromatic and heteroaromatic ring | Stretch |
| 1446 | Aliphatic $CH_2$ | Scissor |
| 1218 | Aromatic CF | Stretch |
| 931 | Heteroaromatic | Ring deformation |

Crystalline Form A of Compound 32

Synthetic Procedure: ~500 mg of a mixture of crystalline Form A of Compound 32 and crystalline Form C of Compound 32 was slurried in ~6-8 ml 100% EtOH at ambient temperature. Sample was vortexed periodically. Pure Compound 32 Form A was obtained when sample was filtered and dried after ~1 month of stirring at 200 rpm.

Figure 7:
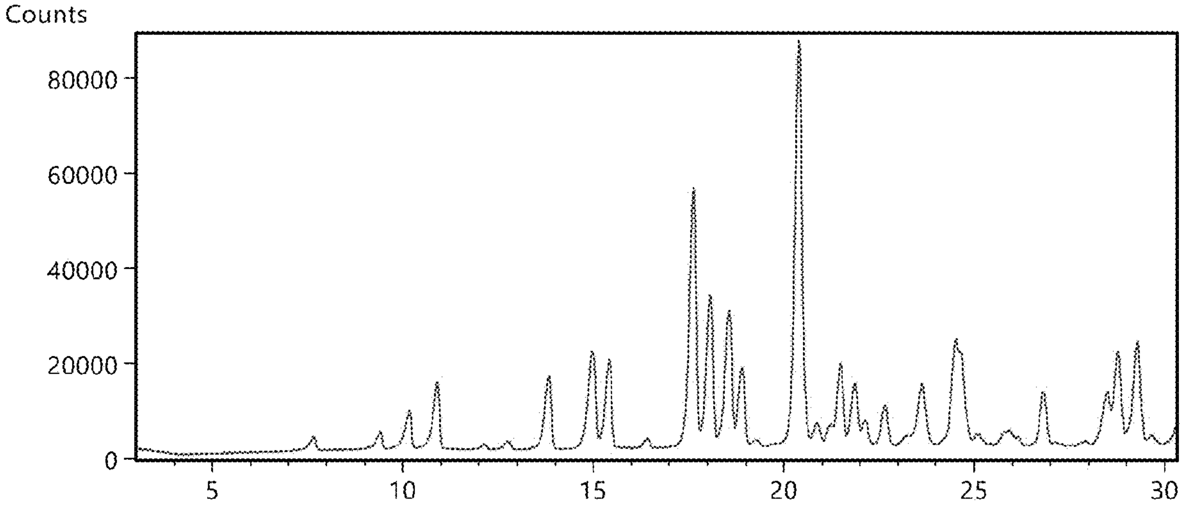
FIG. 7 depicts an XRPD diffractogram of Crystalline Form A of Compound 32.

X-Ray Powder Diffraction: The powder x-ray powder diffraction diffractogram of Crystalline Form A of Compound 32 was acquired at room temperature using the PANalytical Empyrean diffractometer equipped with a PIXcel 1D detector. FIG. 7 depicts an XRPD diffractogram of Crystalline Form A of Compound 32. Table 15 recites XRPD data for Crystalline Form A of Compound 32.

TABLE 15

| XRPD Peaks | Angle (Degrees 2-Theta ± 0.2) | Intensity % |
|---|---|---|
| 1 | 20.4 | 100.0 |
| 2 | 17.6 | 64.1 |
| 3 | 18.1 | 38.2 |
| 4 | 18.6 | 34.4 |
| 5 | 24.5 | 27.6 |
| 6 | 29.3 | 27.1 |
| 7 | 15.0 | 24.5 |
| 8 | 28.8 | 24.4 |
| 9 | 24.7 | 23.4 |
| 10 | 15.4 | 22.5 |
| 11 | 21.5 | 21.6 |
| 12 | 18.9 | 20.9 |
| 13 | 13.8 | 18.6 |
| 14 | 10.9 | 16.9 |
| 15 | 21.9 | 16.9 |
| 16 | 23.6 | 16.7 |
| 17 | 28.5 | 14.8 |
| 18 | 26.8 | 14.7 |
| 19 | 22.7 | 11.4 |
| 20 | 10.2 | 10.0 |

Single Crystal Elucidation: Single crystals of crystalline Form A of Compound 32 were grown from t-butylmethyl ether. X-ray diffraction data were acquired at 100K on a Bruker diffractometer equipped with Cu $K_\alpha$ radiation (λ=1.54178 Å) and a CMOS detector. The structure was solved and refined using SHELX programs (Sheldrick, G. M., Acta Cryst., (2008) A64, 112-122) and results are summarized in Table 16 below.

TABLE 16

| Crystal System | Monoclinic |
|---|---|
| Space Group | $P2_1/c$ |
| a (Å) | 9.3274(5) |
| b (Å) | 22.8131(12) |
| c (Å) | 8.5512(5) |
| α (°) | 90 |
| β (°) | 94.673(3) |
| γ (°) | 90 |
| V (Å$^3$) | 1813.53(17) |
| Z/Z' | 4/1 |
| Temperature | 100 K |

Figure 8:
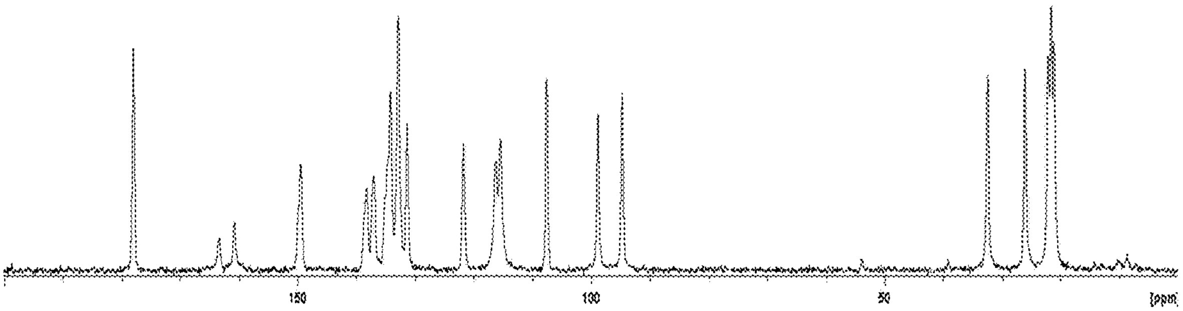
FIG. 8 depicts a solid state NMR spectrum of Crystalline Form A of Compound 32.

Solid State NMR: FIG. 8 depicts a solid state NMR spectrum of Crystalline Form A of Compound 32. Table 17 recites $^{13}$C NMR chemical shift data for Crystalline Form A of Compound 32. Underlined peaks are unique within the spectra of unsolvated crystalline Forms of the free base of Compound 32.

TABLE 17

| Peak # | Chem Shift [ppm] | Intensity [rel] |
|---|---|---|
| 1 | 178.0 | 83.2 |
| 2 | 163.3 | 11.2 |
| 3 | 160.8 | 17.6 |
| 4 | 149.5 | 39.1 |
| 5 | 138.3 | 30.4 |
| <u>6</u> | <u>137.1</u> | <u>35.2</u> |
| 7 | 134.2 | 67.1 |
| 8 | 132.9 | 95.3 |
| <u>9</u> | <u>131.4</u> | <u>54.1</u> |
| <u>10</u> | <u>121.7</u> | <u>47</u> |
| 11 | 116.2 | 41 |
| 12 | 115.4 | 49 |
| <u>13</u> | <u>107.6</u> | <u>72.3</u> |
| <u>14</u> | <u>98.8</u> | <u>58.9</u> |
| 15 | 94.7 | 66.0 |
| 16 | 32.5 | 72.7 |
| 17 | 26.1 | 75.6 |
| 18 | 22.1 | 80.1 |
| 19 | 21.6 | 100.0 |
| 20 | 21.1 | 85.6 |

Figure 9:
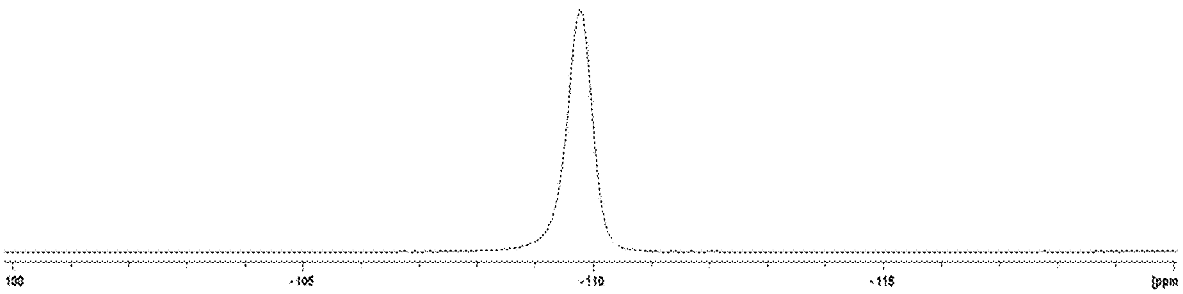
FIG. 9 depicts a 19F NMR spectrum of Crystalline Form A of Compound 32.

FIG. 9 depicts a $^{19}$F NMR spectrum of Crystalline Form A of Compound 32. Table 18 recites $^{19}$F chemical shift data for Crystalline Form A of Compound 32.

TABLE 18

| Peak # | Chem Shift [ppm] | Intensity [rel] |
|---|---|---|
| 1 | −109.8 | 12.5 |

Figure 10:
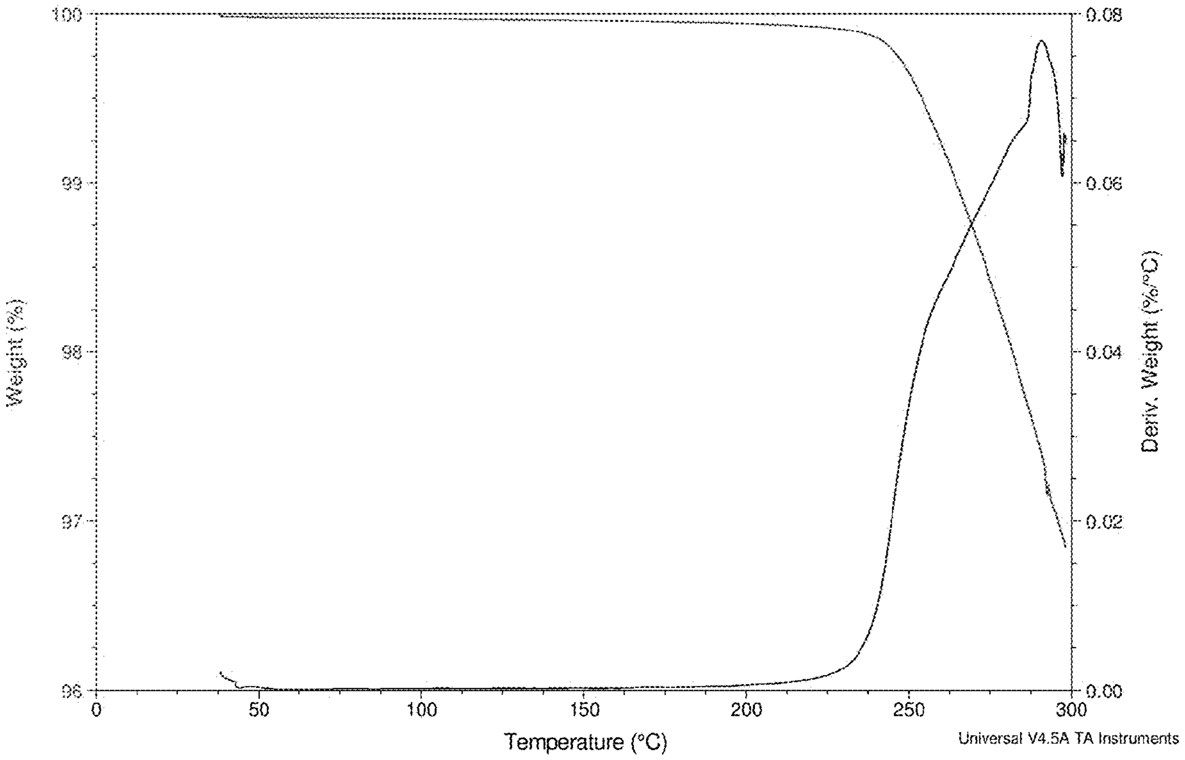
FIG. 10 depicts a TGA thermogram of Crystalline Form A of Compound 32.

Thermogravimetric Analysis: Thermal gravimetric analysis (TGA) of Crystalline Form A of Compound 32 was measured using the TA Instruments Q5000. FIG. 10 depicts a TGA thermogram of Crystalline Form A of Compound 32, which shows ~0.05% wt. loss from ambient to 200° C.

Differential Scanning Calorimetry Analysis: The melting point of Crystalline Form A of Compound 32 was measured using the TA Instruments Discovery DSC. FIG. 11 depicts a DSC thermogram of Crystalline Form A of Compound 32, which shows a melting point ~234° C.

Figure 12:
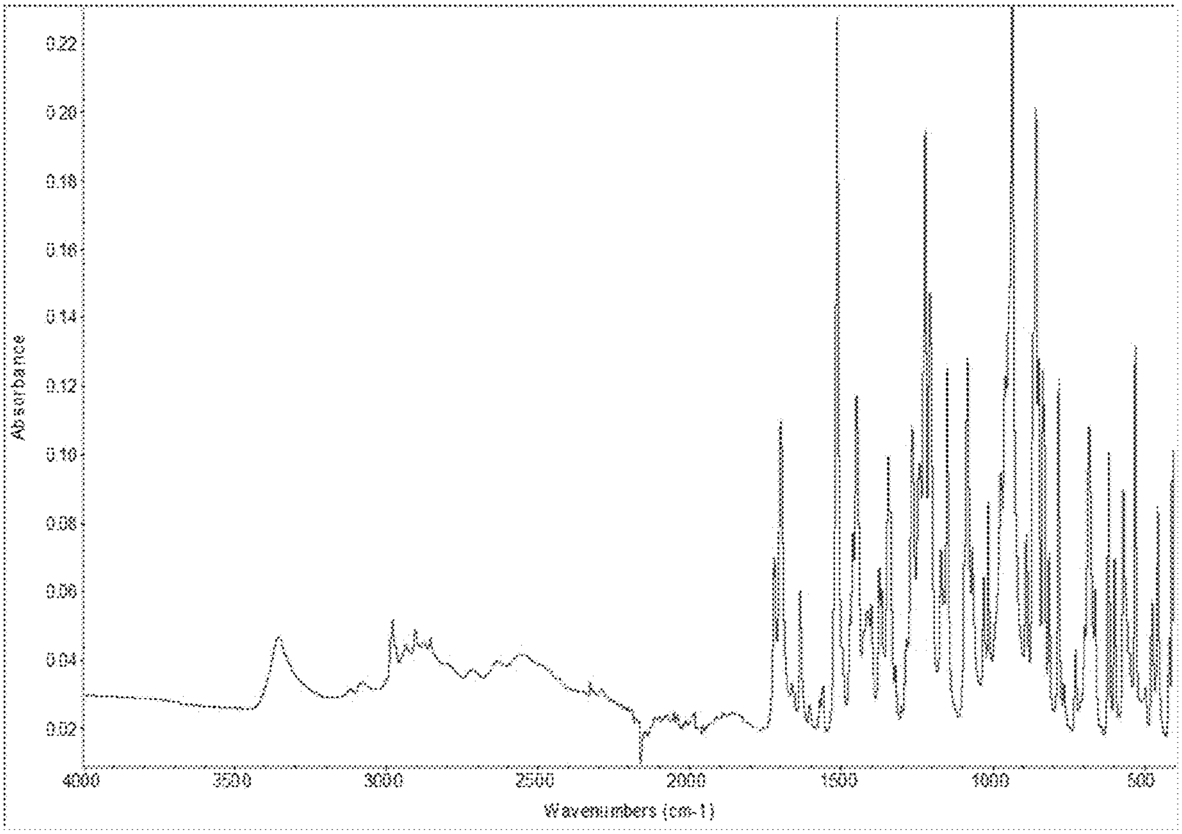
FIG. 12 depicts an IR spectrum of Crystalline Form A of Compound 32.

Infrared Spectroscopy: The IR spectrum of Crystalline Form A of Compound 32 was collected using the Thermo Scientific Nicolet iS50 Spectrometer equipped with a diamond ATR sampling accessory. The following wavenumbers (cm$^{-1}$) were chosen as distinguishing from Crystalline Form C of Compound 32: 969, 956, 855, 493. The following wavenumbers (cm$^{-1}$) are also representative of the frequency bands in the spectrum of Crystalline Form A of Compound 32: 3352, 2976, 1694, 1509, 1446, 1218, 931, 680. FIG. 12 depicts an IR spectrum of Crystalline Form A of Compound 32.

Crystalline Form B of Compound 32

Synthetic Procedure: Tetrahydrofuran (44.74 mL) and methanol (31.96 mL) were added to a 500 mL round bottom flask containing methyl 3-[5-(4-fluorophenyl)-6-isopropyl-1,5-dihydropyrrolo[2,3-f]indazol-7-yl]propanoate, (6.2 g, 16 mmol). A solution of lithium hydroxide (2.76 g, 65.8 mmol) in water (38.4 mL) was added. The mixture was stirred for 2 h. The mixture was acidified to pH 2 with 6M HCl and 0.1N HCl. The mixture was diluted with ethyl acetate (200 mL) and the layers were separated. The aqueous layer was extracted with ethyl acetate (50 mL). The pooled organic layers were dried with sodium sulfate, filtered and concentrated in vacuo. The solid was suspended in ethyl acetate (100 mL) heated, sonicated and concentrated. The solid was again suspended in ethyl acetate (20 mL) filtered, washed with small amounts of ethyl acetate (2×5 mL). The solid was air dried via suction filtration to 5.1 g, transferred to a scintillation vial and then dried in the vacuum oven at 60° C. overnight to give 4.9 g of 3-[5-(4-fluorophenyl)-6-isopropyl-1,5-dihydropyrrolo[2,3-f]indazol-7-yl]propanoic acid, (yield=82%) as an off-white solid.

Figure 13:
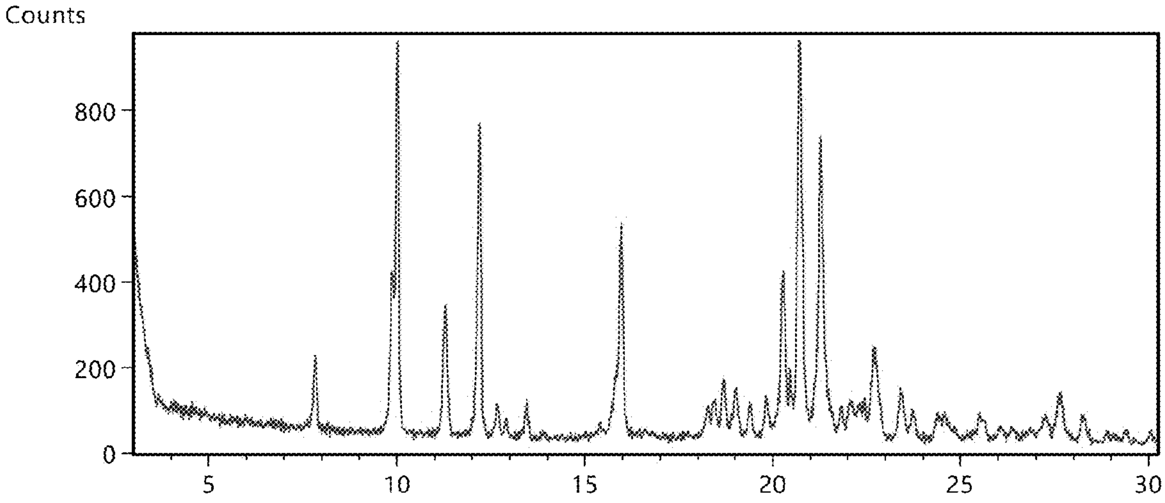
FIG. 13 depicts an XRPD spectrum of Crystalline Form B of Compound 32.

X-Ray Powder Diffraction: X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Mass.). The X-Ray generator operated at a voltage of 45 kV and a current of 40 mA with copper radiation (1.54060 A). The powder sample was placed on a 96 well sample holder with mylar film and loaded into the instrument. The sample was scanned over the range of about 3° to about 40° 2θ with a step size of 0.0131303° and 49 s per step. FIG. 13 depicts an XRPD spectrum of Crystalline Form B of Compound 32. Table 19 recites XRPD data for Crystalline Form B of Compound 32.

TABLE 19

| XRPD Peaks | Angle (Degrees 2-Theta ± 0.2) | Intensity % |
|---|---|---|
| 1 | 20.7 | 100.0 |
| 2 | 10.0 | 97.9 |
| 3 | 12.2 | 74.7 |
| 4 | 21.3 | 73.4 |
| 5 | 16.0 | 53.7 |
| 6 | 20.3 | 41.8 |
| 7 | 9.9 | 39.0 |
| 8 | 11.3 | 31.7 |
| 9 | 22.7 | 21.9 |
| 10 | 7.8 | 18.6 |
| 11 | 20.5 | 18.1 |

TABLE 19-continued

| XRPD Peaks | Angle (Degrees 2-Theta ± 0.2) | Intensity % |
|---|---|---|
| 12 | 18.7 | 14.2 |
| 13 | 23.4 | 12.5 |
| 14 | 19.0 | 11.5 |
| 15 | 27.6 | 10.9 |

Figure 14:
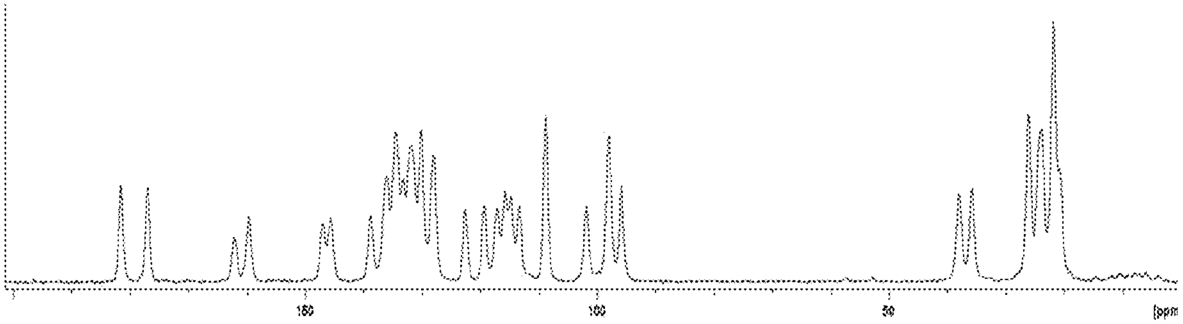
FIG. 14 depicts a 13C NMR spectrum of Crystalline Form B of Compound 32.

Solid State NMR: FIG. 14 depicts a $^{13}$C NMR spectrum of Crystalline Form B of Compound 32. Table 20 recites $^{13}$C NMR chemical shift data for Crystalline Form B of Compound 32. Underlined peaks are unique within the spectra of unsolvated crystalline Forms of the free base of Compound 32.

TABLE 20

| Peak # | Chem Shift [ppm] | Intensity [rel] |
|---|---|---|
| <u>1</u> | <u>181.5</u> | <u>37.0</u> |
| 2 | 177.0 | 36.7 |
| <u>3</u> | <u>162.1</u> | <u>17.2</u> |
| <u>4</u> | <u>159.6</u> | <u>25.2</u> |
| 5 | 147 | 22.5 |
| <u>6</u> | <u>145.6</u> | <u>24.4</u> |
| 7 | 138.8 | 25.5 |
| <u>8</u> | <u>136.1</u> | <u>40.2</u> |
| 9 | 134.4 | 57.6 |
| 10 | 133.2 | 39.4 |
| 11 | 131.9 | 52.1 |
| <u>12</u> | <u>130.1</u> | <u>57.9</u> |
| <u>13</u> | <u>128.0</u> | <u>48.5</u> |
| <u>14</u> | <u>122.6</u> | <u>27.5</u> |
| <u>15</u> | <u>119.3</u> | <u>29.5</u> |
| <u>16</u> | <u>117.2</u> | <u>28.1</u> |
| 17 | 115.7 | 34.2 |
| <u>18</u> | <u>114.8</u> | <u>32.9</u> |
| <u>19</u> | <u>113.3</u> | <u>28.8</u> |
| <u>20</u> | <u>108.8</u> | <u>63.9</u> |
| <u>21</u> | <u>101.8</u> | <u>28.9</u> |
| <u>22</u> | <u>98.0</u> | <u>56.4</u> |
| <u>23</u> | <u>95.8</u> | <u>36.9</u> |
| <u>24</u> | <u>38.0</u> | <u>33.7</u> |
| 25 | 35.8 | 35.7 |
| 26 | 26.1 | 64.1 |
| <u>27</u> | <u>23.9</u> | <u>58.3</u> |
| 28 | 21.8 | 100.0 |

Figure 15:
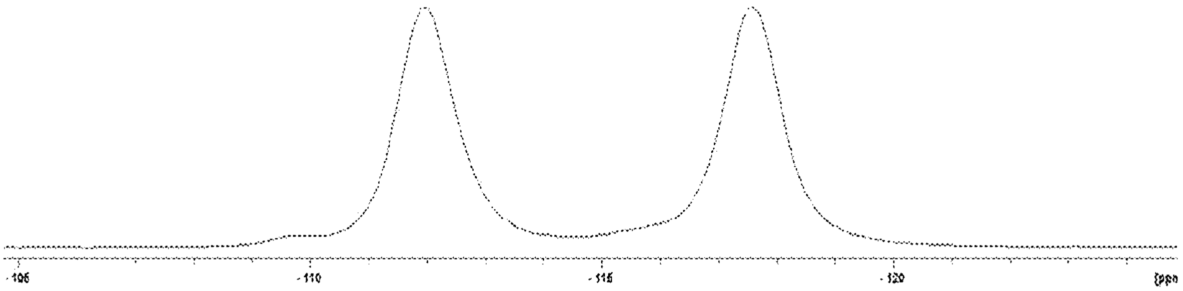
FIG. 15 depicts a 19F NMR spectrum of Crystalline Form B of Compound 32.

FIG. 15 depicts a $^{19}$F NMR spectrum of Crystalline Form B of Compound 32. Table 21 recites $^{19}$F chemical shift data for Crystalline Form B of Compound 32.

TABLE 21

| Peak # | Chem Shift [ppm] | Intensity [rel] |
|---|---|---|
| 1 | −112.0 | 12.5 |
| 2 | −117.6 | 12.5 |

Figure 16:
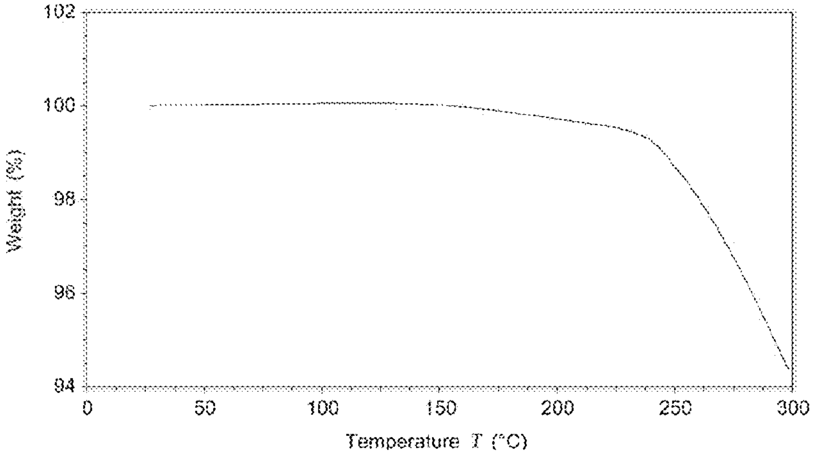
FIG. 16 depicts a TGA thermogram of Crystalline Form B of Compound 32.

Thermogravimetric Analysis: TGA data were collected on a TA Discovery Thermogravimetric Analyzer (TA Instruments, New Castle, Del.). A sample with weight of approximately 1-10 mg was scanned from 25° C. to 300° C. at a heating rate of 10° C./min. Data were collected and analyzed by Trios Analysis software (TA Instruments, New Castle, Del.). FIG. 16 depicts a TGA thermogram of Crystalline Form B of Compound 32, which shows ~0.5% wt. loss from ambient to ~~230° C.

Differential Scanning Calorimetry Analysis: The melting point of Crystalline Form B of Compound 32 was measured using the TA Instruments Discovery DSC. FIG. 17 depicts a DSC thermogram of Crystalline Form B of Compound 32, which shows a melting point ~246° C.

Crystalline Form C of Compound 32

Synthetic Procedure: ~110 mg of a mixture of crystalline Form A of Compound 32 and crystalline Form C of Compound 32 and EtOH solvate was slurried in 1 mL EtOH at 70° C. for 24 hours. The resulted solid is Crystalline Form C of Compound 32.

Figure 18:
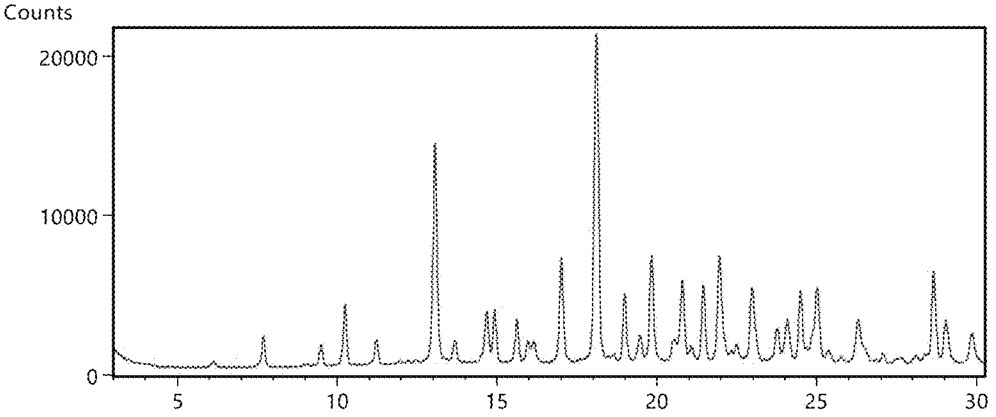
FIG. 18 depicts an XRPD diffractogram of Crystalline Form C of Compound 32.

X-Ray Powder Diffraction: XRPD were acquired at room temperature in reflection mode using a Bruker Advance diffractometer equipped with Vantec-1 detector. Sample was analyzed on a silicon sample holder from 3-40° 2-theta on continuous mode with step size of 0.0144531° and time per step of 0.25 seconds. Sample was spinning at 15 rpm. FIG. 18 depicts an XRPD diffractogram of Crystalline Form C of Compound 32. Table 22 recites XRPD data for Crystalline Form C of Compound 32.

TABLE 22

| XRPD Peaks | Angle (Degrees 2-Theta ± 0.2) | Intensity % |
|---|---|---|
| 1 | 18.1 | 100.0 |
| 2 | 13.1 | 67.3 |
| 3 | 19.8 | 33.4 |
| 4 | 22.0 | 33.4 |
| 5 | 17.0 | 32.9 |
| 6 | 28.7 | 28.7 |
| 7 | 20.8 | 26.2 |
| 8 | 21.5 | 24.5 |
| 9 | 25.0 | 24.1 |
| 10 | 23.0 | 24.0 |
| 11 | 24.5 | 22.9 |
| 12 | 19.0 | 22.0 |
| 13 | 10.2 | 19.0 |
| 14 | 14.9 | 17.3 |
| 15 | 14.7 | 17.1 |
| 16 | 15.6 | 14.6 |
| 17 | 24.1 | 14.5 |
| 18 | 26.3 | 14.3 |
| 19 | 29.0 | 14.1 |
| 20 | 23.8 | 11.9 |
| 21 | 29.9 | 10.5 |

Single Crystal Elucidation: Single crystals of crystalline Form C of Compound 32 were grown from ethanol. X-ray diffraction data were acquired at 100K on a Bruker diffractometer equipped with Cu K$_\alpha$ radiation (λ=1.54178 Å) and a CMOS detector. The structure was solved and refined using SHELX programs (Sheldrick, G. M., Acta Cryst., (2008) A64, 112-122) and results are summarized in Table 23 below.

TABLE 23

| Crystal System | Orthorhombic |
|---|---|
| Space Group | Pbca |
| a (Å) | 22.9530(8) |
| b (Å) | 8.5273(4) |
| c (Å) | 37.5510(12) |
| α (°) | 90 |
| β (°) | 90 |
| γ (°) | 90 |
| V (Å$^3$) | 7349.7(5) |
| Z/Z' | 6/2 |
| Temperature | 100 K |

Figure 19:
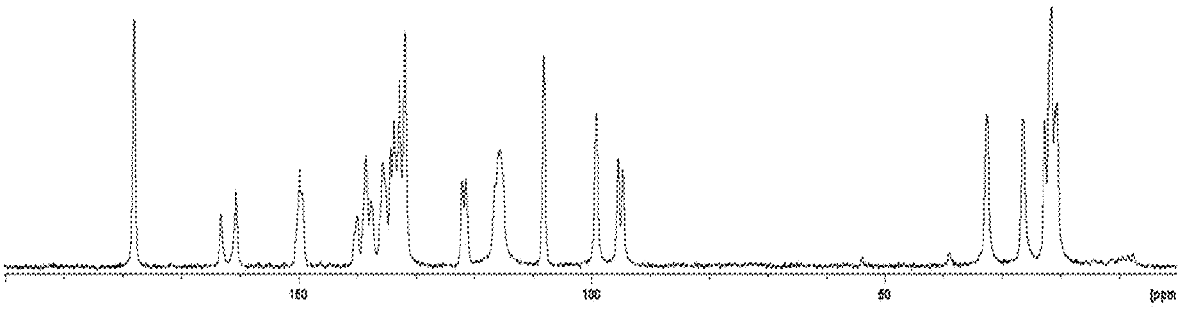
FIG. 19 depicts a 13C NMR spectrum of Crystalline Form C of Compound 32.

Solid State NMR: FIG. 19 depicts a $^{13}$C NMR spectrum of Crystalline Form C of Compound 32. Table 24 recites $^{13}$C NMR chemical shift data for Crystalline Form C of Compound 32. Underlined peaks are unique within the spectra of unsolvated crystalline Forms of the free base of Compound 32.

TABLE 24

| Peak # | Chem Shift [ppm] | Intensity [rel] |
|---|---|---|
| 1 | 178.1 | 95.5 |
| 2 | 163.2 | 19.8 |
| 3 | 160.7 | 29.3 |
| 4 | 149.8 | 38 |
| 5 | 140.0 | 19.4 |
| 6 | 138.5 | 42.0 |
| 7 | 137.5 | 24.7 |
| 8 | 135.6 | 39.9 |
| 9 | 134.3 | 45.4 |
| 10 | 133.7 | 56.3 |
| 11 | 132.8 | 71.4 |
| 12 | 131.9 | 90.4 |
| 13 | 122.1 | 33.0 |
| 14 | 121.4 | 33.0 |
| 15 | 115.5 | 44.8 |
| 16 | 108.1 | 80.6 |
| 17 | 99.2 | 58.8 |
| 18 | 95.5 | 41.3 |
| 19 | 94.6 | 37.5 |
| 20 | 32.5 | 58.5 |
| 21 | 26.3 | 56.8 |
| 22 | 22.7 | 57.3 |
| 23 | 21.6 | 100.0 |
| 24 | 20.9 | 59.9 |
| 25 | 20.6 | 63.1 |

Figure 20:
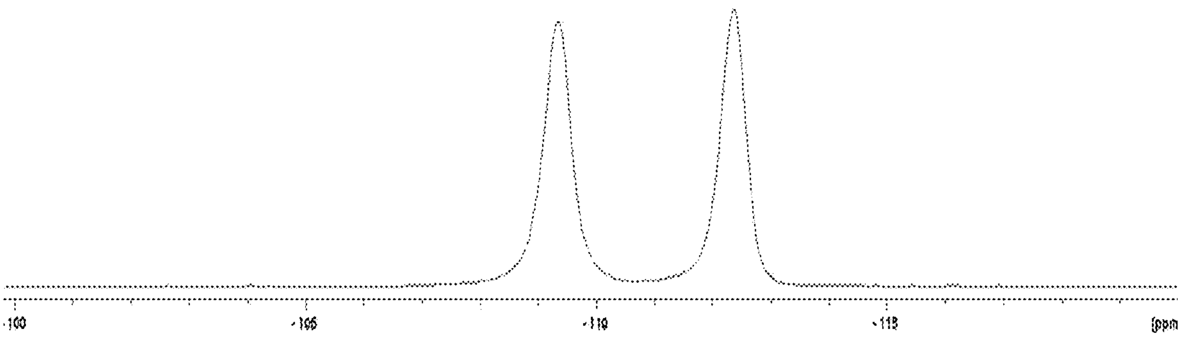
FIG. 20 depicts a 19F NMR spectrum of Crystalline Form C of Compound 32.

FIG. 20 depicts a $^{19}F$ NMR spectrum of Crystalline Form C of Compound 32. Table 25 recites $^{19}F$ NMR chemical shift data for Crystalline Form C of Compound 32.

TABLE 25

| Peak # | Chem Shift [ppm] | Intensity [rel] |
|---|---|---|
| 1 | −109.3 | 12.0 |
| 2 | −112.4 | 12.5 |

Figure 21:
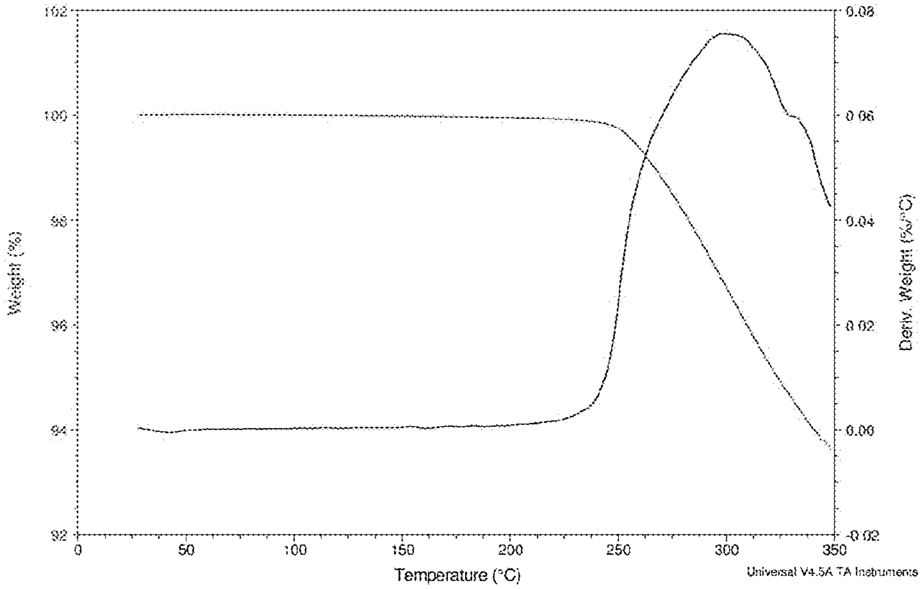
FIG. 21 depicts a TGA thermogram of Crystalline Form C of Compound 32.

Thermogravimetric Analysis: Thermal gravimetric analysis of Crystalline Form C of Compound 32 was measured using the TA Instruments Q5000. FIG. 21 depicts a TGA thermogram of Crystalline Form C of Compound 32, which shows ~0.06% wt. loss from ambient to ~200° C.

Differential Scanning Calorimetry Analysis: The melting point of Crystalline Form C of Compound 32 was measured using the TA Instruments Discovery DSC. FIG. 22 depicts a thermogram of Crystalline Form C of Compound 32, which shows a melting point ~239° C.

Figure 23:
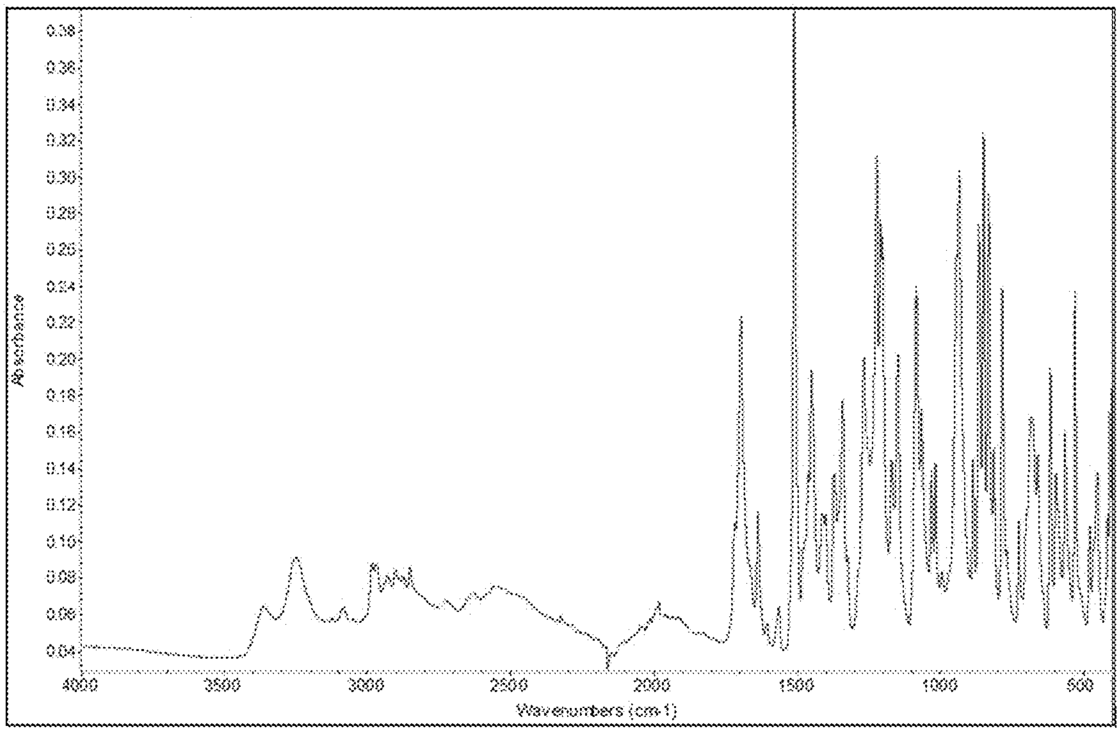
FIG. 23 depicts an IR spectrum of Crystalline Form C of Compound 32.

Infrared Spectroscopy: The IR spectrum of Crystalline Form C of Compound 32 was collected using the Thermo Scientific Nicolet iS50 Spectrometer equipped with a diamond ATR sampling accessory. The following wavenumbers ($cm^{-1}$) were chosen as distinguishing from Crystalline Form A of Compound 32: 3247, 1479, 1208, 1201. The following wavenumbers ($cm^{-1}$) are also representative of the frequency bands in the spectrum of Crystalline Form C of Compound 32: 2967, 1693, 1508, 1448, 1220, 933, 863. FIG. 23 depicts an IR spectrum of Crystalline Form C of Compound 32.

Compound 32 Ethanol Solvate

Synthetic Procedure: ~36 mg Compound 32 was dissolved in 1 mL of 3:1 EtOH/heptane (v/v) at 85° C. The solution was air cooled to ambient temperature. The solid precipitated was Compound 32 ethanol solvate.

Figure 24:
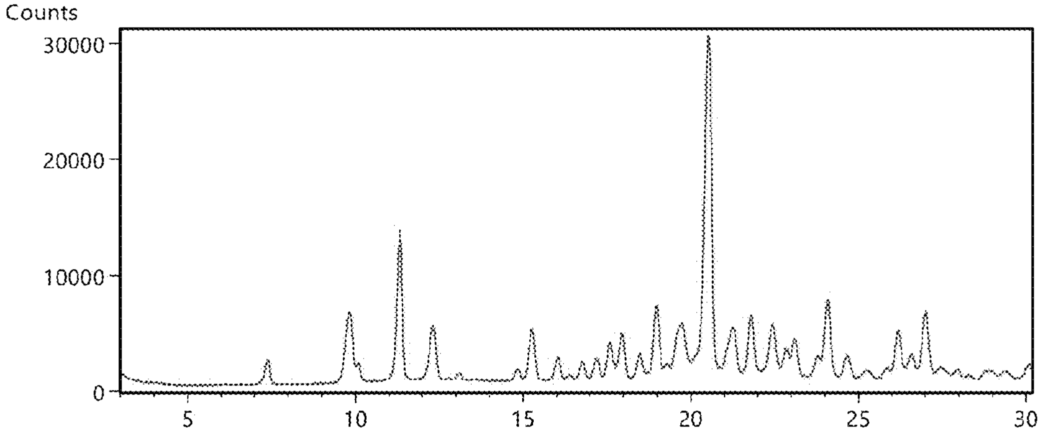
FIG. 24 depicts an XRPD diffractogram of Compound 32 ethanol solvate.

X-Ray Powder Diffraction: XRPD were acquired at room temperature in reflection mode using a Bruker Advance equipped with Vantec-1 detector. Sample was analyzed on a silicon sample holder from 3-40° 2-theta on continuous mode with step size of 0.0144531° and time per step of 0.25 seconds. Sample was spinning at 15 rpm. FIG. 24 depicts an XRPD diffractogram of Compound 32 ethanol solvate. Table 26 recites XRPD data for Compound 32 ethanol solvate.

TABLE 26

| XRPD Peaks | Angle (Degrees 2-Theta ± 0.2) | Intensity % |
|---|---|---|
| 1 | 20.5 | 100.0 |
| 2 | 11.3 | 44.2 |
| 3 | 24.1 | 24.3 |
| 4 | 19.0 | 22.7 |
| 5 | 27.0 | 20.9 |
| 6 | 9.8 | 20.7 |
| 7 | 21.8 | 19.9 |
| 8 | 9.8 | 18.3 |
| 9 | 19.7 | 17.5 |
| 10 | 22.4 | 17.4 |
| 11 | 12.3 | 16.9 |
| 12 | 21.3 | 16.3 |
| 13 | 15.3 | 15.6 |
| 14 | 26.2 | 15.4 |
| 15 | 18.0 | 14.6 |
| 16 | 19.6 | 13.5 |
| 17 | 21.2 | 13.2 |
| 18 | 23.1 | 13.0 |
| 19 | 17.6 | 12.2 |
| 20 | 22.9 | 10.5 |

Single Crystal Elucidation: Single crystals of Compound 32 ethanol solvate of Compound 32 were grown from ethanol. X-ray diffraction data were acquired at 100K on a Bruker diffractometer equipped with Cu $K_{\alpha}$ radiation ($\lambda$=1.54178 Å) and a CMOS detector. The structure was solved and refined using SHELX programs (Sheldrick, G. M., Acta Cryst., (2008) A64, 112-122) and results are summarized in Table 27 below.

TABLE 27

| Crystal System | Triclinic |
|---|---|
| Space Group | P-1 |
| a (Å) | 9.2391(6) |
| b (Å) | 14.5469(9) |
| c (Å) | 15.4547(9) |
| α (°) | 73.566(5) |
| β (°) | 75.558(5) |
| γ (°) | 88.683(5) |
| V ($Å^3$) | 1926.8(2) |
| Z/Z' | 2/2 |
| Temperature | 100 K |

Figure 25:
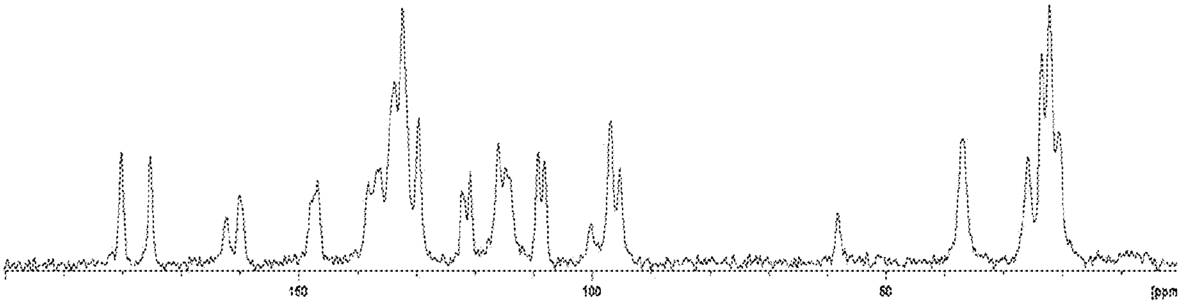
FIG. 25 depicts a 13C NMR spectrum of Compound 32 ethanol solvate.

Solid State NMR: FIG. 25 depicts a $^{13}C$ NMR spectrum of Compound 32 ethanol solvate. Table 28 recites $^{13}C$ NMR chemical shift data for Compound 32 ethanol solvate. Underlined peaks are unique.

TABLE 28

| Peak # | Chem Shift [ppm] | Intensity [rel] |
|---|---|---|
| 1 | 180.1 | 42.5 |
| 2 | 175.2 | 41.4 |
| 3 | 162.3 | 17.7 |
| 4 | 160.1 | 26.1 |
| 5 | 147.9 | 23.9 |

TABLE 28-continued

| Peak # | Chem Shift [ppm] | Intensity [rel] |
|---|---|---|
| 6 | 146.8 | 31.7 |
| 7 | 138.1 | 31.2 |
| 8 | 136.1 | 36.3 |
| 9 | 133.7 | 70.1 |
| 10 | 132.3 | 98.0 |
| 11 | 129.6 | 55.9 |
| 12 | 122.1 | 27.5 |
| 13 | 120.8 | 35.3 |
| 14 | 116.0 | 45.9 |
| 15 | 114.8 | 36.3 |
| 16 | 114.1 | 33.0 |
| 17 | 109.3 | 42.8 |
| 18 | 108.1 | 39.2 |
| 19 | 100.2 | 15.3 |
| 20 | 96.9 | 55.0 |
| 21 | 95.3 | 37.0 |
| 22 | 58.2 | 19.5 |
| 23 | 36.9 | 47.8 |
| 24 | 25.8 | 41.0 |
| 25 | 23.5 | 81.2 |
| 26 | 22.2 | 100.0 |
| 27 | 20.5 | 50.7 |

Figure 26:
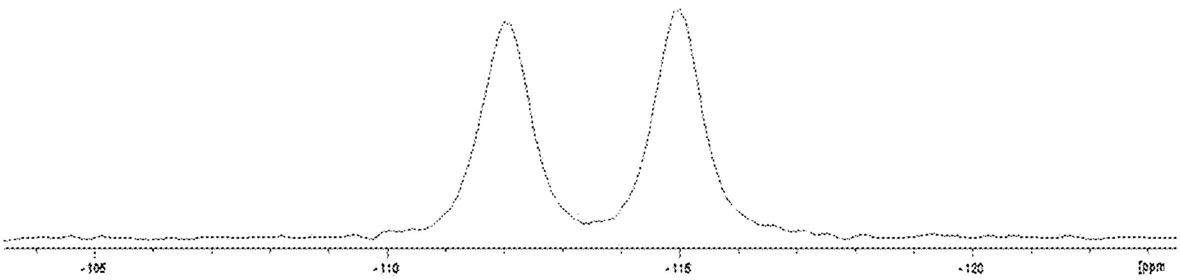
FIG. 26 depicts a 19F NMR spectrum of Compound 32 ethanol solvate.

FIG. 26 depicts a $^{19}F$ NMR spectrum of Compound 32 ethanol solvate. Table 29 recites $^{19}F$ NMR chemical shift data for Compound 32 ethanol solvate.

TABLE 29

| Peak # | Chem Shift [ppm] | Intensity [rel] |
|---|---|---|
| 1 | −112.0 | 11.8 |
| 2 | −115.0 | 12.5 |

Figure 27:
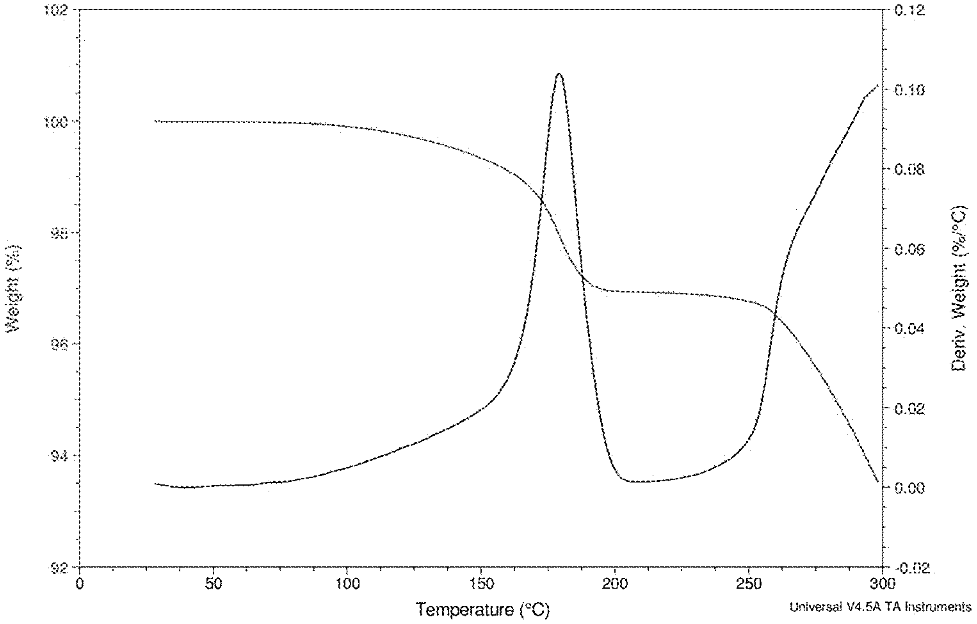
FIG. 27 depicts a TGA thermogram of Compound 32 ethanol solvate.

Thermogravimetric Analysis: Thermal gravimetric analysis of Compound 32 ethanol solvate was measured using the TA Instruments Q5000. FIG. 27 depicts a TGA thermogram of Compound 32 ethanol solvate, which shows ~3.1% weight loss from ambient to 225° C.

Differential Scanning Calorimetry Analysis: A DSC thermogram of Compound 32 ethanol solvate was obtained using TA Instruments DSC Q2000. Sample was heated at 10° C./min from 30° C. to 350° C. FIG. 28 depicts a DSC thermogram of Compound 32 ethanol solvate, which shows multiple endothermic peaks, a broad one ~181° C., and one at ~248° C.

Compound 32 Monohydrochloride Salt

Synthetic Procedure: Stoichiometric ratio of 1N HCl and a mixture of Crystalline Form A of Compound 32 and Crystalline Form C of Compound 32 was mixed and stirred in a solvent at 2 mL scale. The mixture was stirred at ambient temperature protected from light for 24 h. The solid isolated by filtration is Compound 32 HCl salt.

Figure 29:
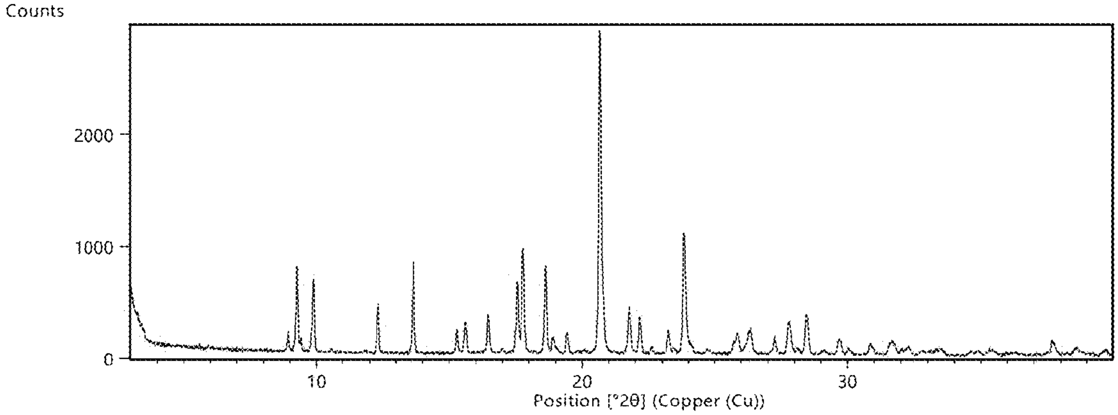
FIG. 29 depicts an XRPD diffractogram of Compound 32 Mono HCl Salt.

X-Ray Powder Diffraction: X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Mass.). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step. FIG. 29 depicts an XRPD diffractogram of Compound 32 Monohydrochloride Salt. Table 30 recites XRPD data for Compound 32 Monohydrochloride Salt.

TABLE 30

| XRPD Peaks | Angle (Degrees 2-Theta ± 0.2) | Intensity % |
|---|---|---|
| 1 | 20.7 | 100.0 |
| 2 | 23.8 | 36.8 |
| 3 | 17.8 | 32.6 |
| 4 | 13.6 | 28.4 |
| 5 | 18.6 | 26.9 |
| 6 | 9.3 | 26.0 |
| 7 | 9.9 | 22.4 |
| 8 | 17.6 | 22.1 |
| 9 | 12.3 | 15.1 |
| 10 | 21.8 | 14.7 |
| 11 | 28.4 | 12.4 |
| 12 | 16.5 | 12.0 |
| 13 | 22.2 | 11.6 |
| 14 | 27.8 | 10.0 |

Single Crystal Elucidation: Single crystals having the Compound 32 (Monohydrochloride salt) structure were grown. X-ray diffraction data were acquired at 100K on a Bruker diffractometer equipped with Cu $K_{\alpha}$ radiation ($\lambda$=1.54178 Å) and a CMOS detector. The structure was solved and refined using SHELX programs (Sheldrick, G. M., Acta Cryst., (2008) A64, 112-122) and results are summarized in Table 31 below.

TABLE 31

| Crystal System | Monoclinic |
|---|---|
| Space Group | $P2_1/n$ |
| a (Å) | 12.184(3) |
| b (Å) | 18.603(5) |
| c (Å) | 17.974(4) |
| α (°) | 90 |
| β (°) | 101.975(8) |
| γ (°) | 90 |
| V (Å$^3$) | 3985.3(16) |
| Z/Z' | 2/2 |
| Temperature | 100 K |

Differential Scanning Calorimetry: A DSC thermogram of Compound 32 Monohydrochloride Salt was obtained using TA Instruments DSC Q2000. Sample was heated at 10° C./min from 30° C. to 300° C. FIG. 30 depicts a DSC thermogram of Compound 32 Monohydrochloride Salt, which shows multiple endothermic peaks, a broad one ~226° C., and a sharp one at ~245° C.

Compound 32 Hemihydrochloride Salt Hemi Hydrate

Synthetic Procedure: ~436 mg of a mixture of Crystalline Form A of Compound 32 and Crystalline Form C of Compound 32 was dissolved in 5 mL of THF. 1.2 mL of 1N HCl (~1 eq) was added to the solution. The resulted solution was put in MTBE vapor over a weekend. The solid obtained is Compound 32 Hemihydrochloride Hemihydrate, which could dehydrate to different forms upon drying.

Figure 31:
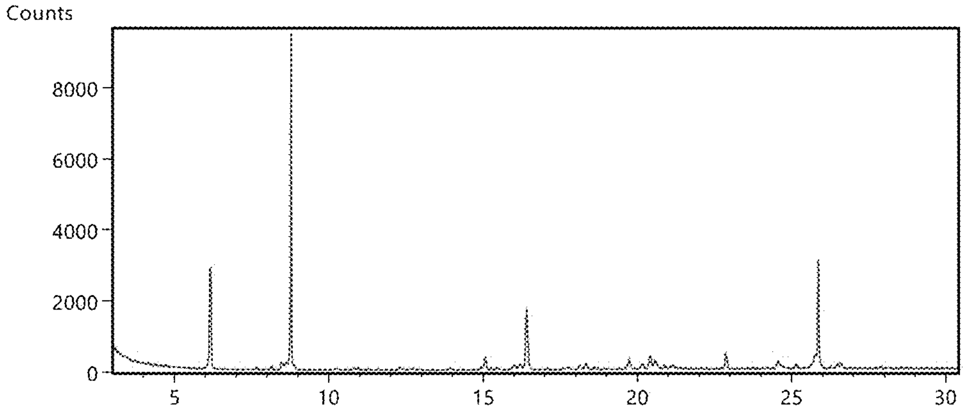
FIG. 31 depicts an XRPD diffractogram of a wet sample of Compound 32 Hemi HCl Salt Hemi Hydrate.
Figure 32:
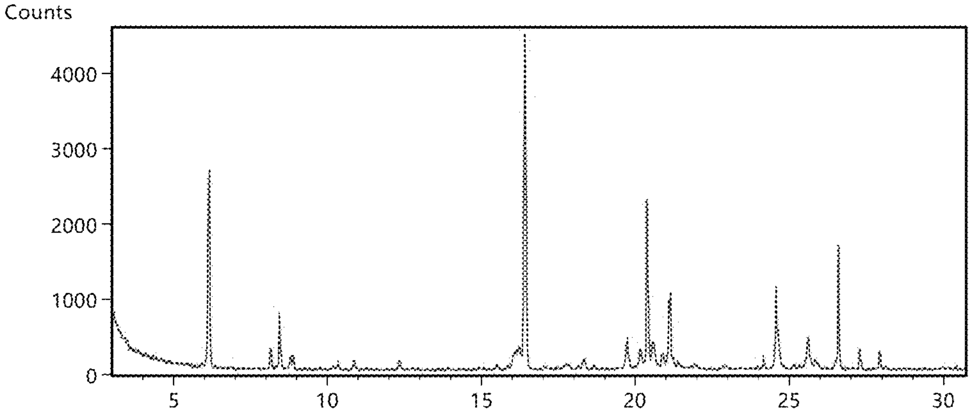
FIG. 32 depicts an XRPD diffractogram of an air-dried sample of Compound 32 Hemi HCl Salt Hemi Hydrate.
Figure 33:
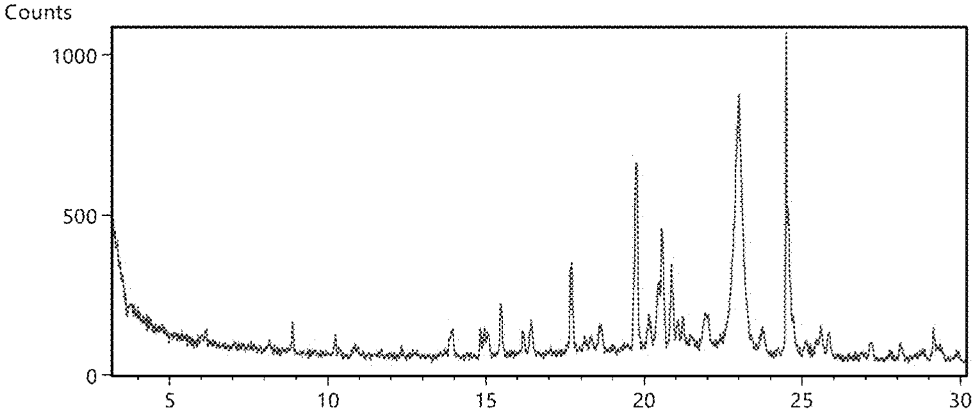
FIG. 33 depicts an XRPD diffractogram of a vacuum-dried sample of Compound 32 Hemi HCl Hemi Salt Hydrate.

X-Ray Powder Diffraction: X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Mass.). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step. FIG. 31 depicts an XRPD diffractogram of a wet sample of Compound 32 Hemihydrochloride Hemihydrate. Table 32 recites XRPD data for a wet sample of Compound 32 Hemihydrochloride Hemihydrate. FIG. 32 depicts an XRPD diffractogram of an air-dried sample of Compound 32 Hemihydrochloride Hemihydrate. Table 33 recites XRPD data for an air-dried sample of Compound 32 Hemihydrochloride Hemihydrate. FIG. 33 depicts an XRPD diffractogram of a vacuum-dried sample of Compound 32 Hemihydrochloride Hemihydrate. Table 34 recites XRPD data for a vacuum-dried sample of Compound 32 Hemihydrochloride Hemihydrate.

TABLE 32

| XRPD Peaks | Angle (Degrees 2-Theta ± 0.2) | Intensity % |
|---|---|---|
| 1 | 8.8 | 100.0 |
| 2 | 25.9 | 32.3 |
| 3 | 6.2 | 31.2 |
| 4 | 16.4 | 18.5 |

TABLE 33

| XRPD Peaks | Angle (Degrees 2-Theta ± 0.2) | Intensity % |
|---|---|---|
| 1 | 16.4 | 100.0 |
| 2 | 6.2 | 59.1 |
| 3 | 20.4 | 50.4 |
| 4 | 26.6 | 34.6 |
| 5 | 24.6 | 24.6 |
| 6 | 21.15 | 21.7 |
| 7 | 21.09 | 21.1 |
| 8 | 8.4 | 16.5 |

TABLE 34

| XRPD Peaks | Angle (Degrees 2-Theta ± 0.2) | Intensity % |
|---|---|---|
| 1 | 24.5 | 100.0 |
| 2 | 23.0 | 77.0 |
| 3 | 19.8 | 59.6 |
| 4 | 20.6 | 39.8 |
| 5 | 20.9 | 29.4 |
| 6 | 17.7 | 29.1 |
| 7 | 22.0 | 13.3 |
| 8 | 20.2 | 12.5 |

Single Crystal Elucidation: Single crystals of Compound 32 (Hemihydrochloride Hemihydrate) structure were grown from diffusion of MTBE into a THF/water/1N HCl solution of the API. X-ray diffraction data were acquired at 100K on a Bruker diffractometer equipped with Cu K$_\alpha$ radiation (λ=1.54178 Å) and a CMOS detector. The structure was solved and refined using SHELX programs (Sheldrick, G. M., Acta Cryst., (2008) A64, 112-122) and results are summarized in Table 35.

TABLE 35

| Crystal System | Triclinic |
|---|---|
| Space Group | P-1 |
| a (Å) | 10.4223(7) |
| b (Å) | 13.9638(10) |
| c (Å) | 14.3472(10) |

TABLE 35-continued

| Crystal System | Triclinic |
|---|---|
| Space Group | P-1 |
| α (°) | 102.211(3) |
| β (°) | 91.676(4) |
| γ (°) | 107.715(3) |
| V (Å$^3$) | 1934.2(2) |
| Z/Z' | 2/2 |
| Temperature | 100 K |

Figure 34:
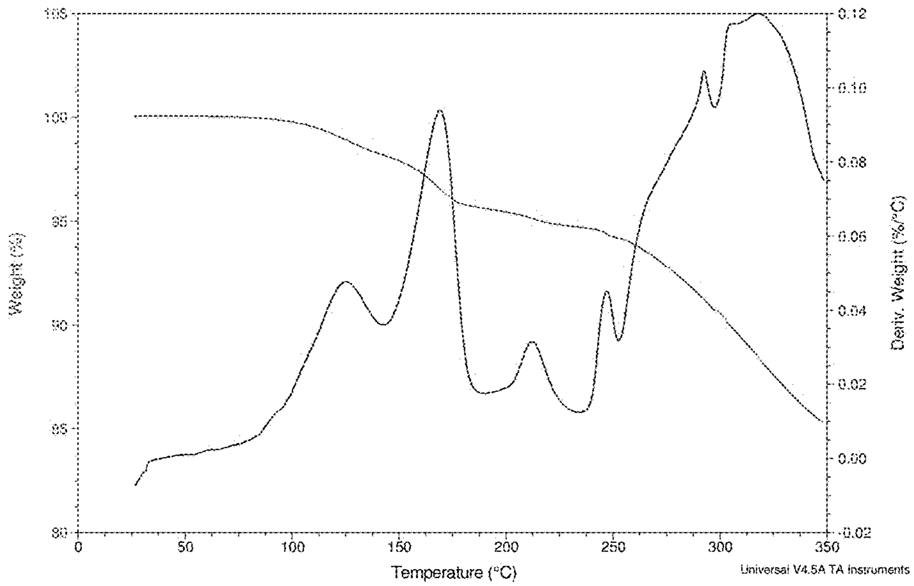
FIG. 34 depicts a TGA thermogram of Compound 32 Hemi HCl Hemi Salt Hydrate.

Thermogravimetric Analysis: Thermal gravimetric analysis of Compound 32 Hemihydrochloride Hemihydrate vacuum dried sample was measured using the TA Instruments Q5000. FIG. 34 depicts a TGA thermogram of Compound 32 Hemihydrochloride Hemihydrate, which shows multiple step weight loss from ambient to ~250° C.

Differential Scanning calorimetry Analysis: Modulated Differential Scanning calorimetry Analysis of Compound 32 Hemihydrochloride Hemihydrate vacuum dried sample was measured using the TA Instruments Discovery DSC. FIG. 35 depicts a DSC thermogram of Compound 32 Hemihydrochloride Hemihydrate, which shows multiple endothermic peaks from ambient to ~250° C.

Amorphous Compound 32

Synthetic Procedure: 4.8 g of Compound 32 was weighed into a 100 ml bottle. 100 ml of 90:10 Acetone water was added. The bottle was capped and the contents were stirred for 1 h at ambient temperature when a clear solution resulted. This solution was then spray dried to make neat amorphous Compound 32.

Figure 36:
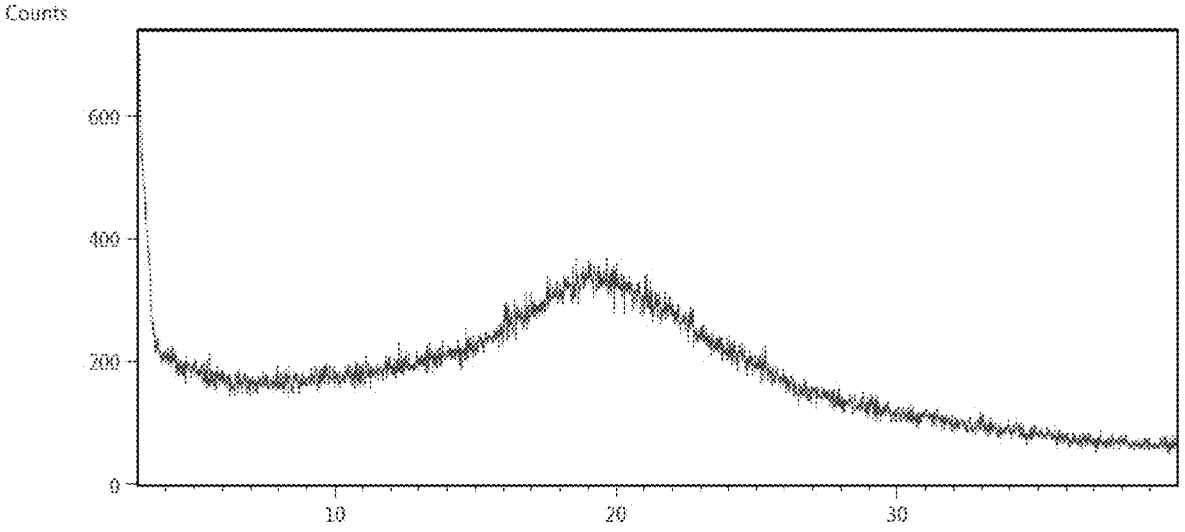
FIG. 36 depicts an XRPD diffractogram of a wet sample of Amorphous Form of Compound 32.

X-Ray Powder Diffraction: X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Mass.). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step. FIG. 36 depicts an XRPD diffractogram of a wet sample of Amorphous Compound 32.

Figure 37:
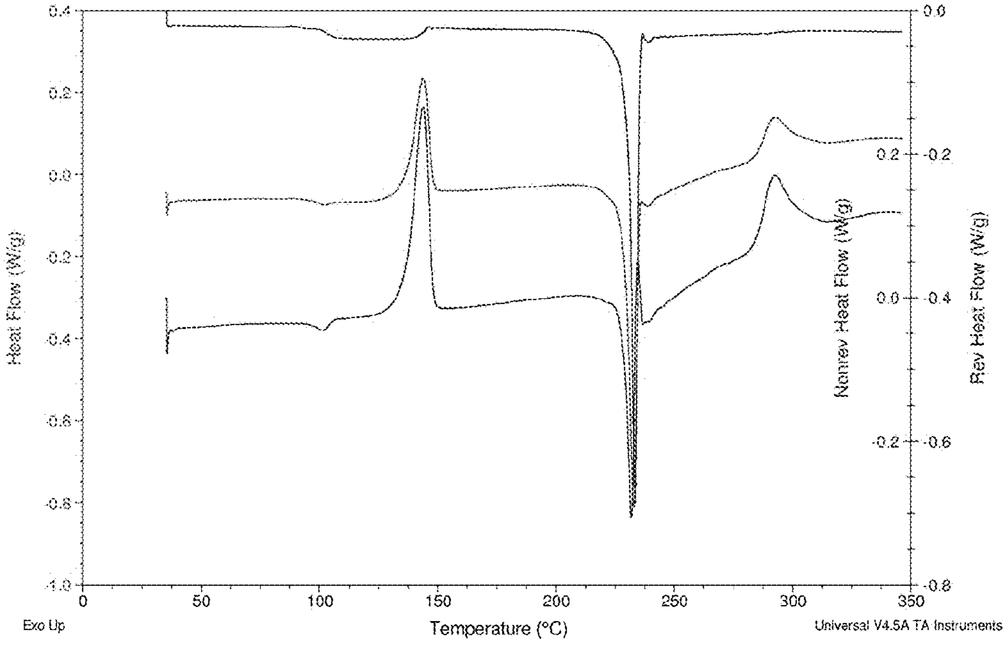
FIG. 37 depicts a DSC thermogram of Amorphous Form of Compound 32.

Differential Scanning Calorimetry: Modulated Differential Scanning Calorimetry Analysis of Compound 32 Neat Amorphous was carried out using the TA Instruments Discovery DSC. FIG. 37 depicts a DSC thermogram of Compound 32 Neat Amorphous, which shows a glass transition at ~104° C., a recrystallization at ~144° C. and a melt endotherm at ~233° C.

Figure 38:
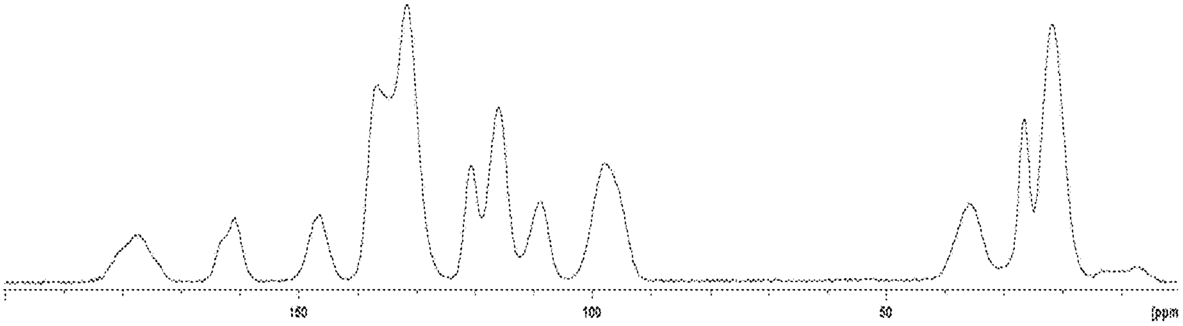
FIG. 38 depicts a 13C NMR spectrum of Amorphous Form of Compound 32.

Solid State NMR: FIG. 38 depicts a $^{13}$C NMR spectrum of Amorphous Compound 32. Table 36 recites $^{13}$C NMR chemical shift data for Amorphous Compound 32. Underlined peaks are unique within the spectra of unsolvated crystalline Forms of the free base of Compound 32.

TABLE 36

| Peak # | Chem Shift [ppm] | Intensity [rel] |
|---|---|---|
| 1 | 177.2 | 16.8 |
| 2 | 163.2 | 14.5 |
| 3 | 160.9 | 22.8 |
| <u>4</u> | <u>146.5</u> | <u>24.2</u> |
| 5 | 136.8 | 71.2 |
| 6 | 131.6 | 100.0 |

TABLE 36-continued

| Peak # | Chem Shift [ppm] | Intensity [rel] |
|---|---|---|
| 7 | 120.6 | 42.0 |
| 8 | 115.9 | 63.2 |
| 9 | 108.7 | 28.6 |
| 10 | 98.0 | 42.5 |
| 11 | 35.7 | 28.4 |
| 12 | 26.6 | 59.2 |
| 13 | 21.7 | 92.9 |

Figure 39:
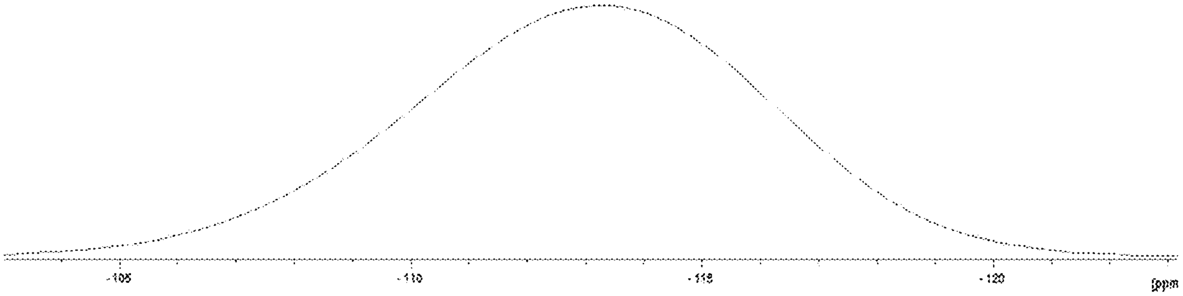
FIG. 39 depicts a 19F NMR spectrum of Amorphous Form of Compound 32.

FIG. 39 depicts a $^{19}F$ NMR spectrum of Amorphous Compound 32. Table 37 recites $^{19}F$ NMR chemical shift data for Amorphous Compound 32.

TABLE 37

| Peak # | Chem Shift [ppm] | Intensity [rel] |
|---|---|---|
| 1 | −113.3 | 12.5 |

Other Embodiments

This disclosure provides merely exemplary embodiments of the invention. One skilled in the art will readily recognize from the disclosure and accompanying figures and claims, that various changes, modifications and variations can be made therein without departing from the spirit and scope of the invention as defined in the following claims.

The invention claimed is:

1. A compound of formula (I):

(I)

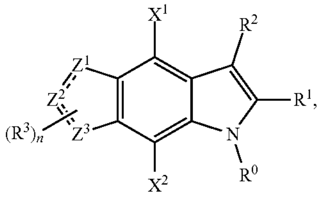

a tautomer thereof, a pharmaceutically acceptable salt of the compound or the tautomer, or a deuterated derivative of the compound, the tautomer, or the pharmaceutically acceptable salt;

wherein:

(i) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents chosen from halogens and methoxy;

(ii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iii) $R^2$ is chosen from:

hydrogen, cyano, halogens, alkylamide groups, $C_1$-$C_8$ linear, branched, and cyclic alkyl groups optionally substituted with one or more groups independently chosen from:

an oxo group, a $C_1$-$C_8$ linear, branched, and cyclic alkoxy group, a 5- or 6-membered heteroaryl group, a cyano group, an amino group, an aminoalkyl group, an alkylamide group, an alkylsulfonyl group, an alkylsulfonamide group, an alkylsulfoxide group, a group

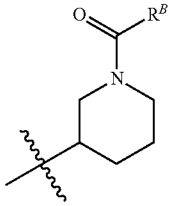

or

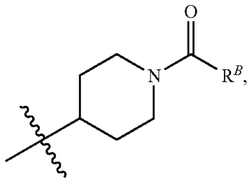

wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group, a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group, a

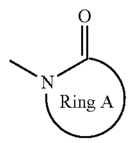

group, wherein the Ring A is chosen from 4-8 membered rings optionally containing one or two heteroatoms in addition to the Ring A nitrogen, and a carboxylic acid group esterified with a uronic acid, $C_2$-$C_6$ linear, branched, and cyclic alkenyl groups, $C_2$-$C_6$ linear, branched, and cyclic alkynyl groups, A-$CO_2R^4$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, and $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, A-C(O)$NH_2$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, and $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and C(O)$NR^6R^7$ wherein $R^6$ and $R^7$ are independently chosen from hydrogen, $C_1$-$C_8$ linear, branched, and cyclic alkyl groups, $C_2$-$C_6$ linear, branched, and cyclic alkenyl groups, 4- to 8-membered heterocycles optionally substituted by one or more substituents chosen from cyano and halogens, $C_1$-$C_8$ linear, branched, and cyclic alkyl groups, and $C_2$-$C_6$ linear, branched, and cyclic alkenyl groups, or $R^6$ and $R^7$ together with the nitrogen to which they are attached form a 4-8 membered ring optionally containing one or two heteroatoms in addition to the nitrogen to which they are attached, and which 4-8 membered ring is optionally substituted with a substituent chosen from halogens, cyano, hydroxy, and $C_1$-$C_6$ linear, branched, and cyclic alkyl groups, and $SO_2R^5$ groups wherein $R^5$ is chosen from $C_1$-$C_8$ linear, branched, and cyclic alkyl groups, and $C_2$-$C_6$ linear, branched, and cyclic alkenyl groups, and

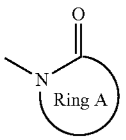

groups, wherein the Ring A is a 4-8 membered ring optionally containing one or two heteroatoms in addition to the Ring A nitrogen;

(iv) $X^1$ and $X^2$ are independently chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(v) each ═══ represents a single or double bond, provided that no more than one ═══ is a double bond;

(vi) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and the linear, branched, and cyclic alkoxy groups are optionally substituted with 1-4 halogens;

(vii) n is an integer chosen from 0, 1, 2, and 3; and (viii) $Z^1$ and $Z^2$ are nitrogen, and $Z^3$ is chosen from carbon and nitrogen, wherein the valences of carbon and nitrogen are completed with hydrogen atoms, $C_1$-$C_8$ linear, branched, and cyclic alkyls, or cyano.

2. The compound of claim 1, a tautomer thereof, a pharmaceutically acceptable salt of the compound or the tautomer, or a deuterated derivative of the compound, the tautomer, or the pharmaceutically acceptable salt, wherein $R^1$ is chosen from:

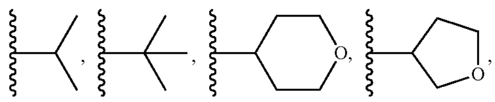

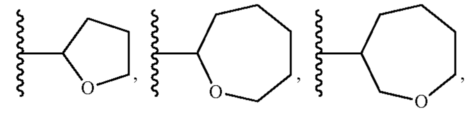

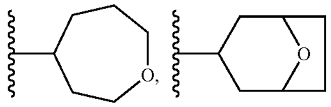

and

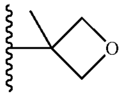

.

3. The compound of claim 1, chosen from compounds of Formulae 1-6, 3-4, 3-5, 3-6, 4-3, 5-3, 6-4, 7-4, 8-4, 12-1, and 12-2:

1-6

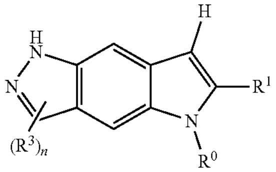

3-4

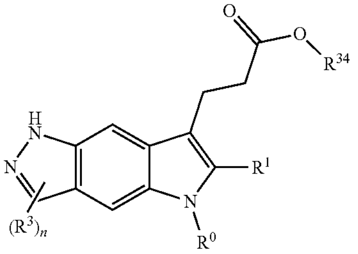

3-5

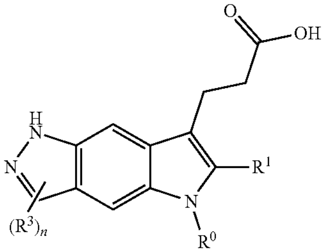

3-6

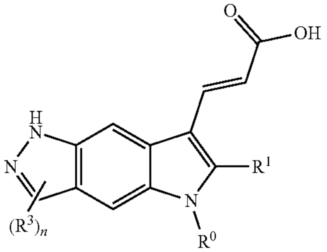

4-3

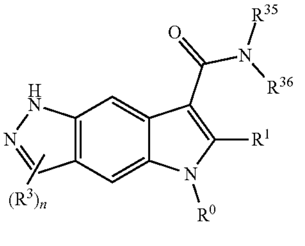

5-3

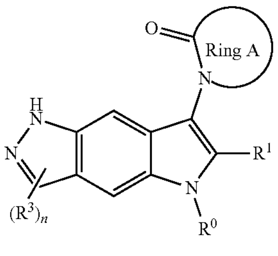

-continued 6-4

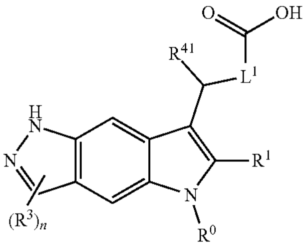

7-4

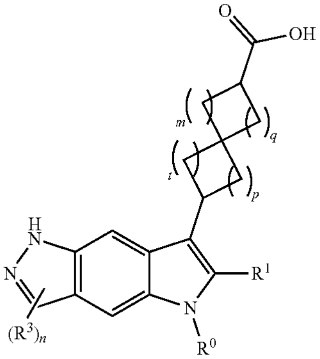

8-4

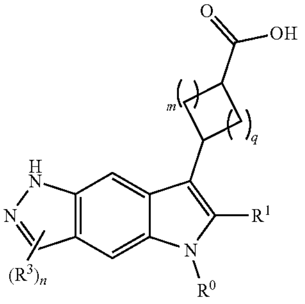

12-1

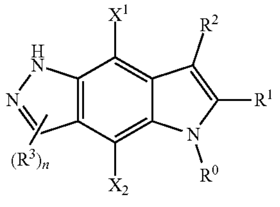

12-2

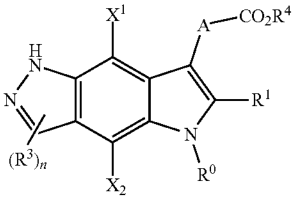

a tautomer thereof, a pharmaceutically acceptable salt of the compound or the tautomer, or a deuterated derivative of the compound, the tautomer, or the pharmaceutically acceptable salt, wherein:

$R^0$, $R^1$, $R^2$, $R^3$, $R^4$, $X^1$, $X^2$, A, and n are defined for compounds of Formula (I), $R^{34}$ is chosen from $C_1$-$C_6$ linear, branched, and cyclic alkyl groups, $R^{35}$ and $R^{36}$ are chosen from $C_1$-$C_6$ linear, branched, and cyclic alkyl groups; or $R^{35}$ and $R^{36}$, taken together with the N atom to which they are bound, form a 4 to 6 membered ring, optionally substituted with $C_1$-$C_6$ linear, branched, and cyclic alkyl groups;

$R^{41}$ is chosen from H, $C_1$-$C_6$ linear, branched, and cyclic alkyl groups;

$L^1$ is chosen from:

$C_1$-$C_8$ linear, branched, and cyclic alkyl groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, and $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of $L^1$ are optionally substituted with 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, m is an integer chosen from 0-3, and q is an integer chosen from 0-3, provided that:

(i) if m is 0, then q is at least 1; and (ii) if q is 0, then m is at least 1;

and t is an integer chosen from 0-3, and p is an integer chosen from 0-3, provided that:

(i) if t is 0, then p is at least 2; and (ii) if p is 0, then t is at least 2.

4. A compound of formula (II):

(II)

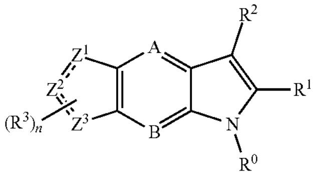

a tautomer thereof, a pharmaceutically acceptable salt of the compound or the tautomer, or a deuterated derivative of the compound, the tautomer, or the pharmaceutically acceptable salt;

wherein:

(i) A and B are each independently chosen from N and C—$X^1$ (ii) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents chosen from halogens and methoxy;

(iii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iv) $R^2$ is chosen from:

hydrogen, cyano, halogens, alkylamide groups, $C_1$-$C_8$ linear, branched, and cyclic alkyl groups optionally substituted with one or more groups independently chosen from:

an oxo group, a $C_1$-$C_8$ linear, branched, and cyclic alkoxy group, a 5- or 6-membered heteroaryl group, a cyano group, an amino group, an aminoalkyl group, an alkylamide group, an alkylsulfonyl group, an alkylsulfonamide group, an alkylsulfoxide group, a group

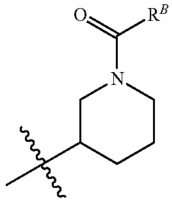

or

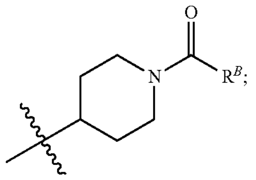

or wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group, a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group, a

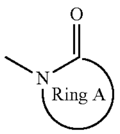

group, wherein the Ring A is chosen from 4-8 membered rings optionally containing one or two heteroatoms in addition to the Ring A nitrogen, and a carboxylic acid group esterified with a uronic acid, $C_2$-$C_6$ linear, branched, and cyclic alkenyl groups, $C_2$-$C_6$ linear, branched, and cyclic alkynyl groups, A-$CO_2R^4$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, and $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, A-C(O)$NH_2$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, and $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and C(O)$NR^6R^7$ wherein $R^6$ and $R^7$ are independently chosen from hydrogen, $C_1$-$C_8$ linear, branched, and cyclic alkyl groups, $C_2$-$C_6$ linear, branched, and cyclic alkenyl groups, 4- to 8-membered heterocycles optionally substituted by one or more substituents chosen from cyano and halogens, $C_1$-$C_8$ linear, branched, and cyclic alkyl groups, and $C_2$-$C_6$ linear, branched, and cyclic alkenyl groups, or $R^6$ and $R^7$ together with the nitrogen to which they are attached form a 4-8 membered ring optionally containing one or two heteroatoms in addition to the nitrogen to which they are attached, and which 4-8 membered ring is optionally substituted with a substituent chosen from halogens, cyano, hydroxy, and $C_1$-$C_6$ linear, branched, and cyclic alkyl groups, and $SO_2R^5$ groups wherein $R^5$ is chosen from $C_1$-$C_8$ linear, branched, and cyclic alkyl groups, and $C_2$-$C_6$ linear, branched, and cyclic alkenyl groups, and

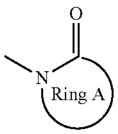

groups, wherein the Ring A is a 4-8 membered ring optionally containing one or two heteroatoms in addition to the Ring A nitrogen;

(v) $X^1$ is chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(vi) each ═══ represents a single or double bond, provided that no more than one ═══ is a double bond;

(vii) each $R^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and the linear, branched, and cyclic alkoxy groups are optionally substituted with 1-4 halogens;

(viii) n is an integer chosen from 0, 1, 2, and 3; and (ix) $Z^1$ and $Z^2$ are nitrogen, and $Z^3$ is chosen from carbon and nitrogen, wherein the valences of carbon and nitrogen are completed with hydrogen atoms, $C_1$-$C_8$ linear, branched, and cyclic alkyls, or cyano.

5. A compound of formula (III):

(III)

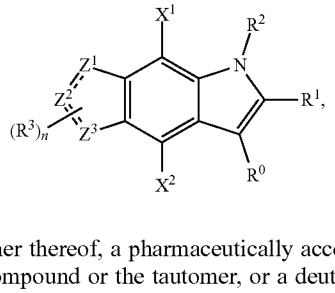

a tautomer thereof, a pharmaceutically acceptable salt of the compound or the tautomer, or a deuterated derivative of the compound, the tautomer, or the pharmaceutically acceptable salt;

wherein:

(i) $R^0$ is chosen from (a) $C_1$-$C_8$ linear, branched, and cyclic alkyl groups, wherein the alkyl group is optionally substituted with 1-4 $R^A$; and (b) 5- to 10-membered aromatic rings optionally substituted with 1-4 $R^A$, wherein each $R^A$ is independently chosen from halogens, cyano, hydroxy, thiol, sulfonic acid, sulfonamide, sulfinamide, amino, amide, 5- to 10-membered aromatic rings, and $C_1$-$C_6$ linear, branched, and cyclic groups, wherein the $C_1$-$C_6$ linear, branched, and cyclic groups are chosen from alkyl, alkoxy, thioalkyl, alkylsulfoxide, alkylsulfonyl, alkylsulfonamide, alkylsulfinamide, aminoalkyl, and alkylamide, and wherein the 5- to 10-membered aromatic rings and $C_1$-$C_6$ linear, branched, and cyclic groups are optionally substituted with 1-4 substituents chosen from halogens and methoxy;

(ii) $R^1$ is chosen from (a) $C_1$-$C_8$ linear, branched, and cyclic alkyl groups, wherein the alkyl group is optionally substituted with 1-4 substituents chosen from halogens, carboxylic acid, cyano, and $C_1$-$C_6$ linear, branched, and cyclic groups, wherein the $C_1$-$C_6$ linear, branched, and cyclic groups are chosen from alkyl and alkoxy groups, and wherein the $C_1$-$C_6$ linear, branched, and cyclic groups are optionally substituted with 1-4 halogens, (b) $C_1$-$C_8$ linear, branched, and cyclic alkoxy groups optionally substituted with 1-4 substituents chosen from halogens, cyano, and $C_1$-$C_6$ linear, branched, and cyclic alkyl groups that are optionally substituted with 1-4 halogens;

(c) $C_1$-$C_8$ heterocycles, and (d) $C_2$-$C_6$ linear, branched, and cyclic alkenyl groups;

(iii) $R^2$ is chosen from:

hydrogen, cyano, halogens, alkylamide groups, $C_1$-$C_8$ linear, branched, and cyclic alkyl groups optionally substituted with one or more groups independently chosen from:

an oxo group, a $C_1$-$C_8$ linear, branched, and cyclic alkoxy group, a 5- or 6-membered heteroaryl group, a cyano group, an amino group, an aminoalkyl group, an alkylamide group, an alkylsulfonyl group, an alkylsulfonamide group, an alkylsulfoxide group, a group

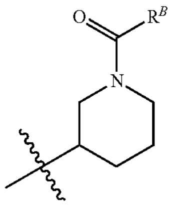

or

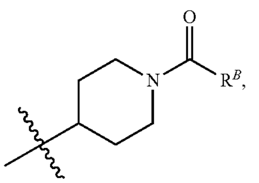

wherein $R^B$ is chosen from amino groups, $C_1$-$C_8$ linear, branched, and cyclic alkyl groups, and O—$R^C$ groups, wherein $R^C$ is chosen from $C_1$-$C_8$ linear, branched, and cyclic alkyl groups substituted with an aryl group, a group N—C(O)—$R^B$ wherein $R^B$ is chosen from amino groups, $C_1$-$C_8$ linear, branched, and cyclic alkyl groups, and O—$R^C$, wherein $R^C$ is chosen from $C_1$-$C_8$ linear, branched, and cyclic alkyl groups substituted with an aryl group, a

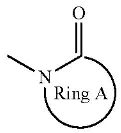

group, wherein the Ring A is chosen from 4-8 membered rings optionally containing one or two heteroatoms in addition to the Ring A nitrogen, and a carboxylic acid group esterified with a uronic acid, $C_2$-$C_6$ linear, branched, and cyclic alkenyl groups, $C_2$-$C_6$ linear, branched, and cyclic alkynyl groups, A-$CO_2R^4$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, and $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and wherein $R^4$ is chosen from hydrogen, $C_1$-$C_8$ linear, branched, and cyclic alkyl groups, and $C_2$-$C_6$ linear, branched, and cyclic alkenyl groups, A-$C(O)NH_2$ groups wherein A is optionally present and if present is chosen from $C_1$-$C_8$ linear, branched, and cyclic alkyl and alkoxy groups, $C_2$-$C_6$ linear, branched, and cyclic alkenyl groups, $C_3$-$C_8$ cycloalkyl linked to $C_1$-$C_8$ linear or branched alkyl groups, $C_1$-$C_8$ linear or branched alkyl linked to $C_3$-$C_8$ cycloalkyl groups, $C_3$-$C_8$ cycloalkyl linked to $C_3$-$C_8$ cycloalkyl groups, and $C_1$-$C_8$ linear, branched, and cyclic alkyl linked to $C_3$-$C_8$ cycloalkyl linked to a $C_1$-$C_8$ linear, branched, and cyclic alkyl groups, wherein up to 3 carbon atoms of A are optionally substituted with 1-4 halogens or 1-3 $C_1$-$C_4$ linear, branched, or cyclic groups, wherein the $C_1$-$C_4$ linear, branched, or cyclic groups are chosen from alkyl and alkoxy groups, and wherein the linear, branched, or cyclic $C_1$-$C_4$ groups are optionally substituted with 1-4 halogens, and C(O)NR$^6$R$^7$ wherein R$^6$ and R$^7$ are independently chosen from hydrogen, $C_1$-$C_8$ linear, branched, and cyclic alkyl groups, $C_2$-$C_6$ linear, branched, and cyclic alkenyl groups, 4- to 8-membered heterocycles optionally substituted by one or more substituents chosen from cyano and halogens, $C_1$-$C_8$ linear, branched, and cyclic alkyl groups, and $C_2$-$C_6$ linear, branched, and cyclic alkenyl groups, or R$^6$ and R$^7$ together with the nitrogen to which they are attached form a 4-8 membered ring optionally containing one or two heteroatoms in addition to the nitrogen to which they are attached, and which 4-8 membered ring is optionally substituted with a substituent chosen from halogens, cyano, hydroxy, and $C_1$-$C_6$ linear, branched, and cyclic alkyl groups, and SO$_2$R$^5$ groups wherein R$^5$ is chosen from $C_1$-$C_8$ linear, branched, and cyclic alkyl groups, and $C_2$-$C_6$ linear, branched, and cyclic alkenyl groups, and

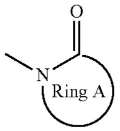

groups, wherein the Ring A is a 4-8 membered ring optionally containing one or two heteroatoms in addition to the Ring A nitrogen;

(iv) X$^1$ and X$^2$ are independently chosen from hydrogen, halogens, cyano, hydroxy, $C_1$-$C_6$ linear, branched, and cyclic groups wherein the $C_1$-$C_6$ linear, branched, and cyclic groups are chosen from alkyl, alkoxy, thioalkyl, and aminoalkyl groups, and wherein the $C_1$-$C_6$ linear, branched, and cyclic groups are optionally substituted by 1-4 halogens;

(v) each  represents a single or double bond, provided that no more than one  is a double bond;

(vi) each R$^3$ is independently chosen from hydrogen, halogens, cyano, $C_1$-$C_6$ linear, branched, and cyclic alkyl groups, and $C_1$-$C_6$ linear, branched, and cyclic alkoxy groups, wherein the linear, branched, and cyclic alkyl and the linear, branched, and cyclic alkoxy groups are optionally substituted with 1-4 halogens;

(vii) n is an integer chosen from 0, 1, 2, and 3; and (viii) Z$^1$ and Z$^2$ are nitrogen, and Z$^3$ is chosen from carbon and nitrogen, wherein the valences of carbon and nitrogen are completed with hydrogen atoms, $C_1$-$C_8$ linear, branched, and cyclic alkyls, or cyano.

6. A compound chosen from formula S3 and formula S6:

S3

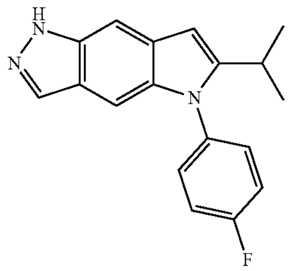

S6

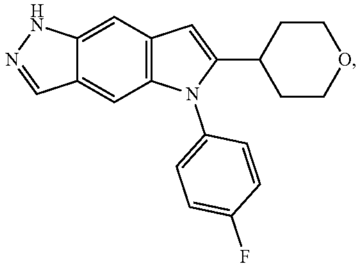

tautomers thereof, salts of the compounds or the tautomers, or deuterated derivatives of the compounds, the tautomers, or the salts.

7. The compound of claim 1, wherein the compound is Compound 32:

(Compound 32)

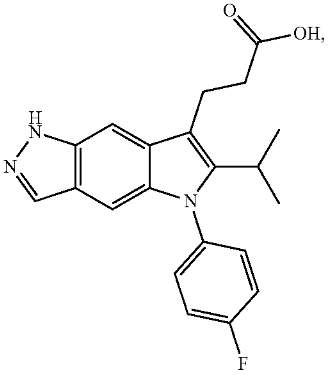

a tautomer thereof, a pharmaceutically acceptable salt of the compound or the tautomer, or a deuterated derivative of the compound, the tautomer, or the pharmaceutically acceptable salt.

8. A composition comprising:

at least one compound according to claim 1, pharmaceutically acceptable salts of the compounds, and deuterated derivatives of the compounds or the pharmaceutically acceptable salts; and at least one pharmaceutically acceptable carrier.

9. A crystalline form of Compound 32:

(32)

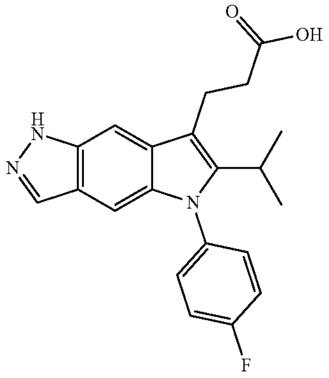

chosen from Crystalline Form A, Crystalline Form B, and Crystalline Form C, wherein:

Crystalline Form A is characterized by an X-ray powder diffractogram having a signal at at least two two-theta values chosen from 15.0±0.2, 15.4±0.2, 17.6±0.2, and 20.4±0.2;

Crystalline Form B is characterized by an X-ray powder diffractogram having a signal at at least two two-theta values chosen from 10.0±0.2, 11.3±0.2, 12.2±0.2, and 20.7±0.2; and Crystalline Form C is characterized by an X-ray powder diffractogram having a signal at at least two two-theta values chosen from 14.7±0.2, 14.9±0.2, and 17.0±0.2.

10. A composition comprising:

at least one of the crystalline forms of Compound 32:

(32)

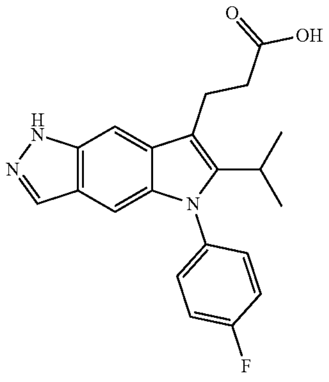

according to claim 9;

and at least one pharmaceutically acceptable carrier.

11. A monohydrochloride salt, a hemihydrochloride hemihydrate, an amorphous form, or an ethanol solvate of Compound 32:

(32)

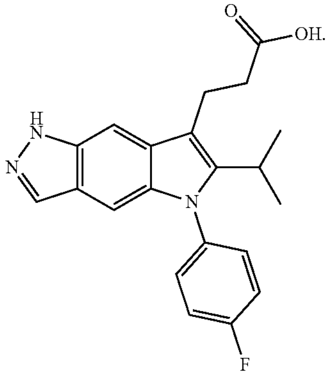

12. A composition comprising the monohydrochloride salt, the hemihydrochloride hemihydrate, the amorphous form, or the ethanol solvate of Compound 32:

(32)

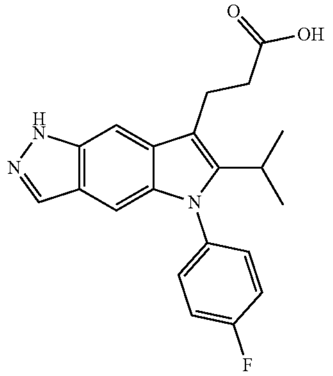

and at least one pharmaceutically acceptable carrier.

13. The compound of claim 6, wherein the compound is chosen from formula S6:

S6

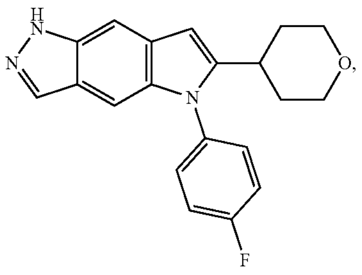

tautomers of the compound, salts of the compound or the tautomers, or deuterated derivatives of the compound, the tautomers, or the salts.

14. A compound chosen from:
1
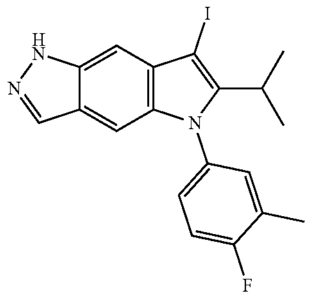
2
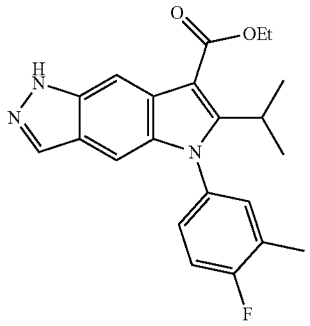
3
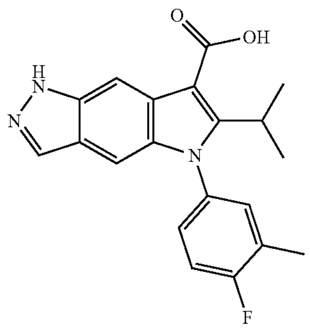
4
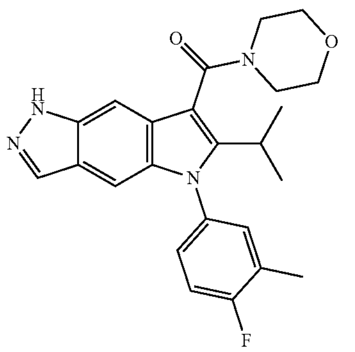
-continued
5
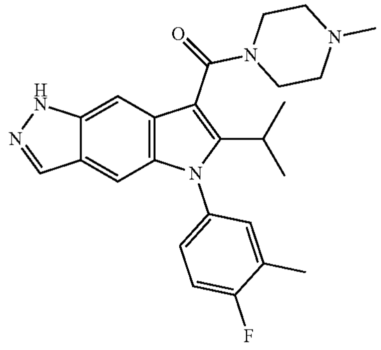
6
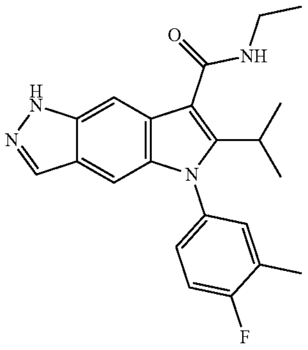
7
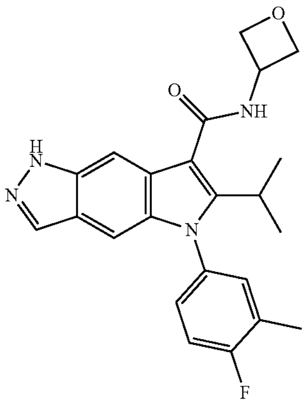
8
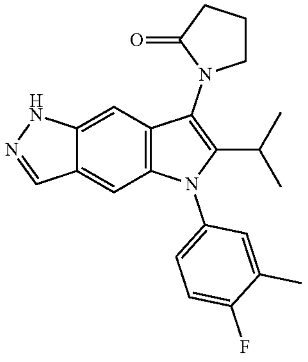

-continued
9
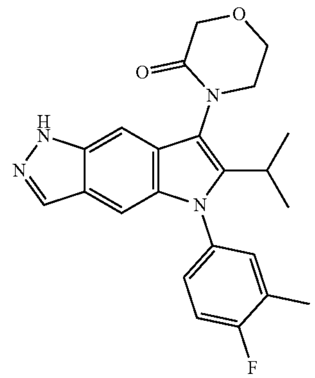
10
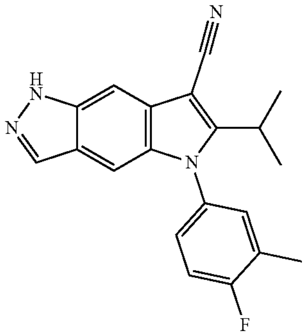
11
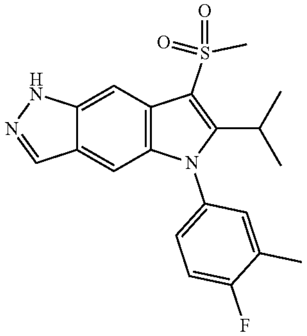
12
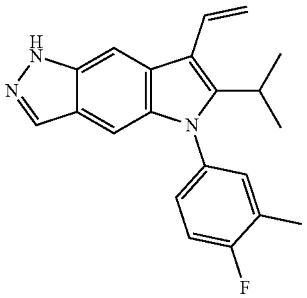
-continued
13
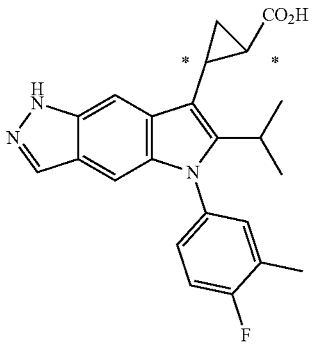
[TRANS
Enantiomer-1]
14
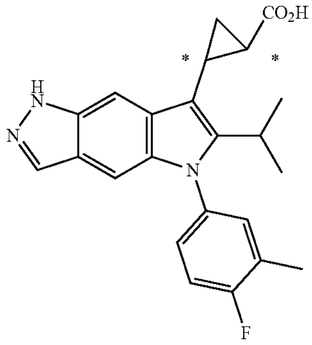
[TRANS
Enantiomer-2]
15
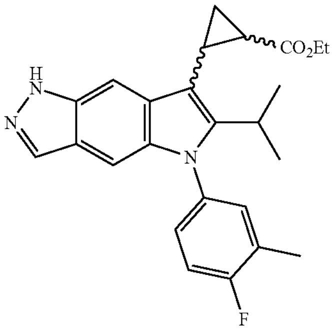
16
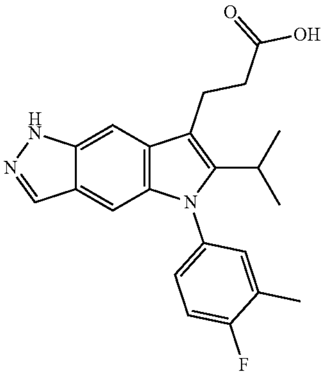

-continued
17
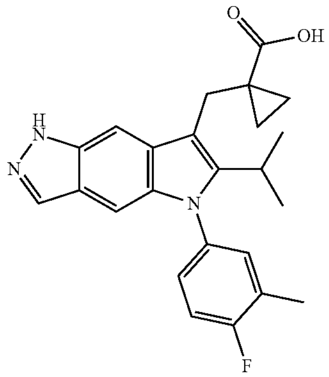
18
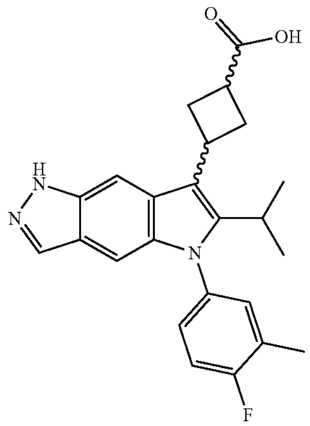
19
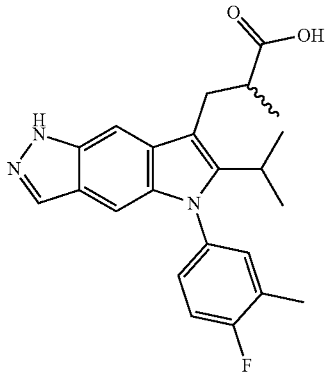
20
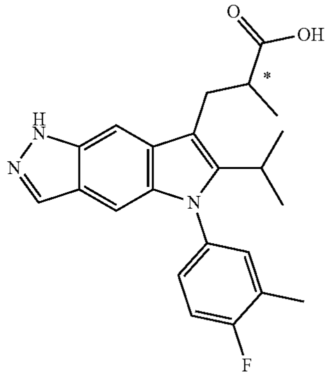
[Enantiomer-1]
-continued
21
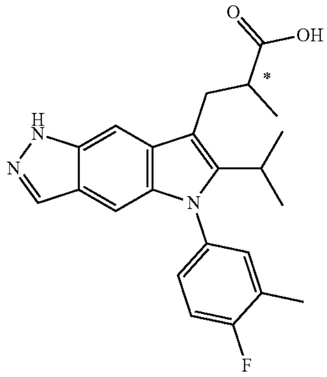
[Enantiomer-2]
22
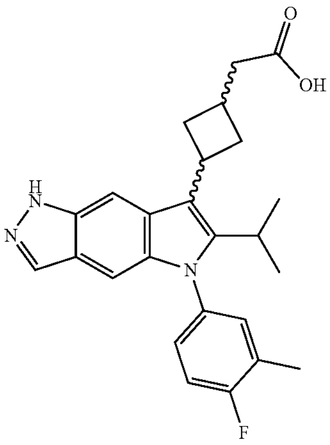
23
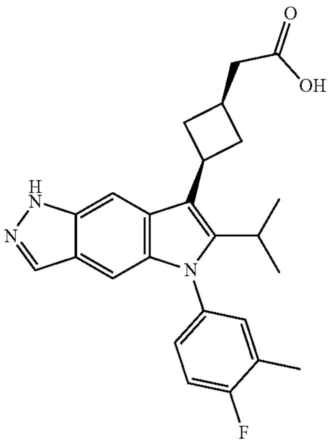

-continued
24
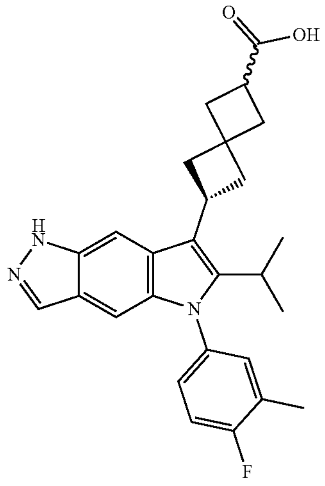
[RAC]
25
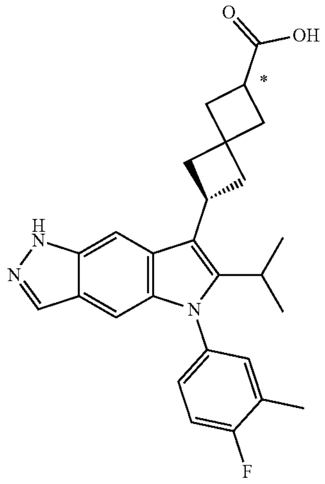
Enantiomer-1
26
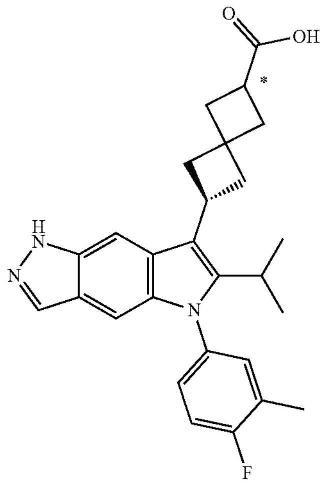
[Enantiomer-2]
-continued
27
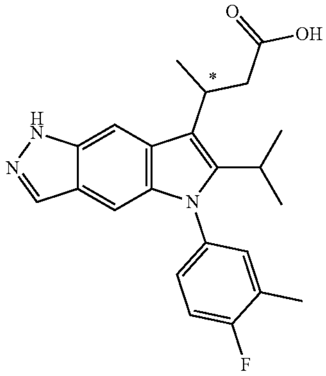
[Enantiomer-1]
28
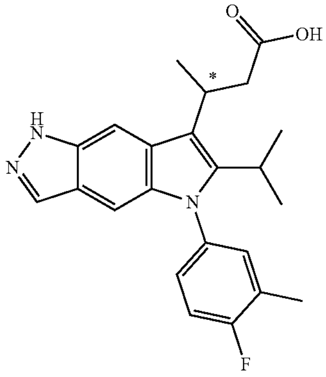
[Enantiomer-2]
29
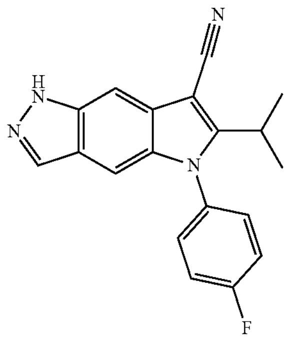
30
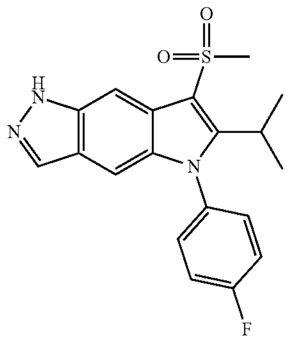

-continued
31
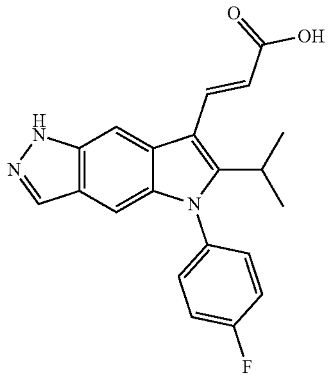
32
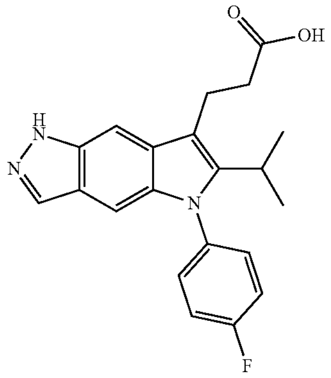
33
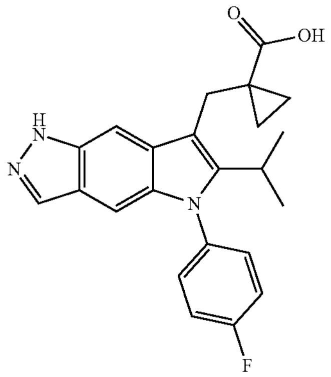
34
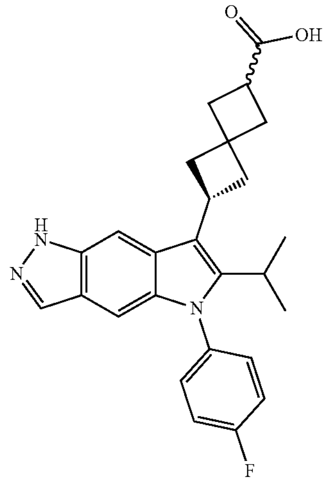
[Racemic]
-continued
35
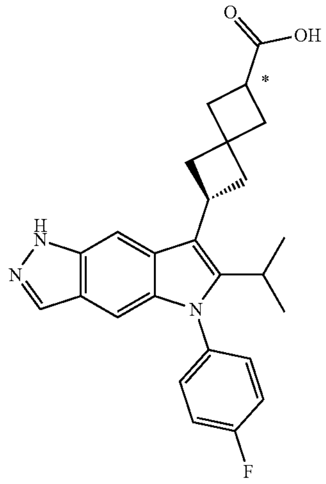
[Enantiomer-1]
36
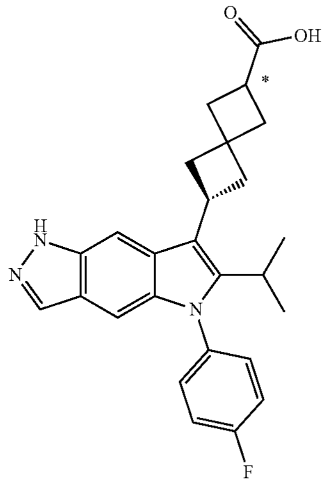
[Enantiomer-2]
37
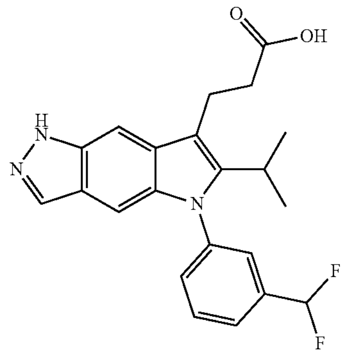

-continued
38
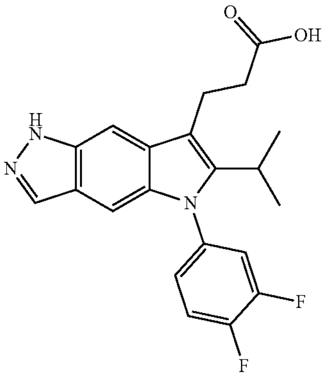
39
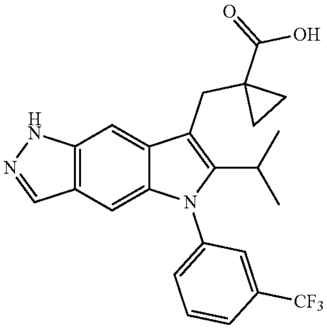
40
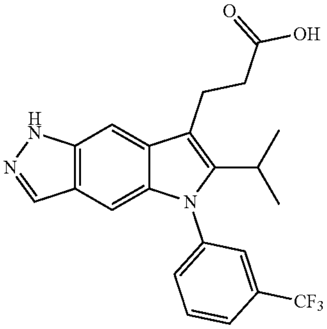
41
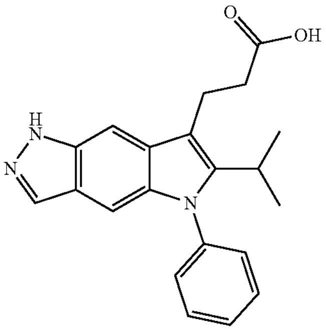
-continued
42
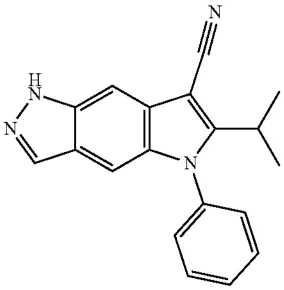
43
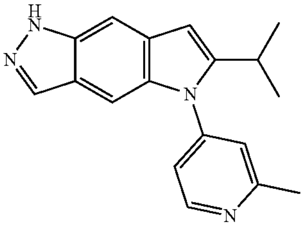
44
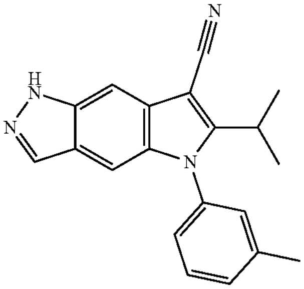
45
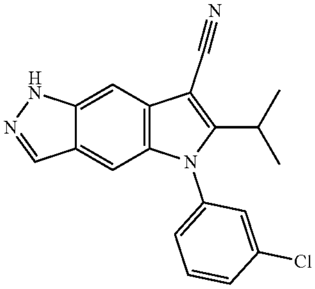
46
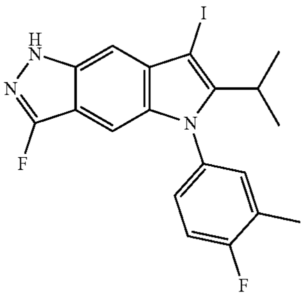

-continued
47
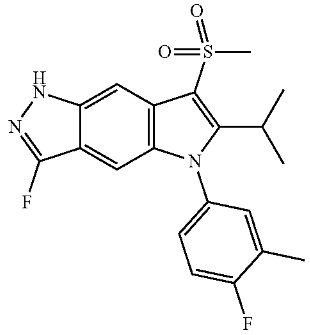
48
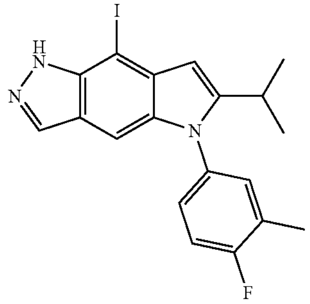
49
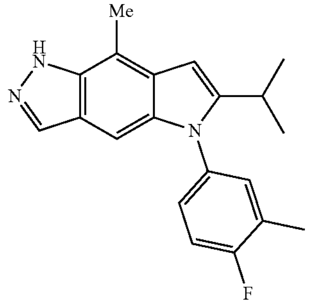
50
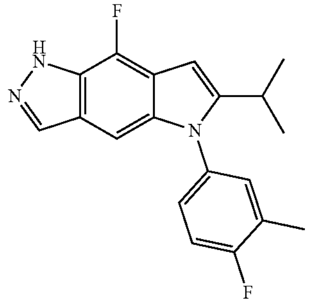
51
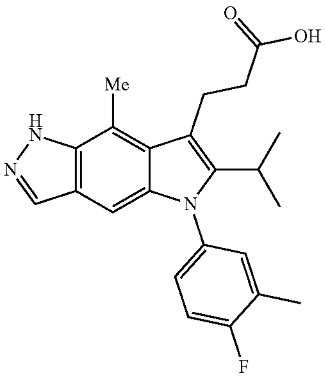
-continued
52
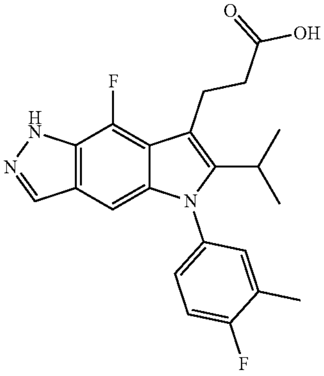
53
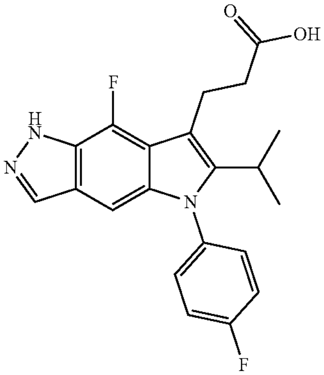
54
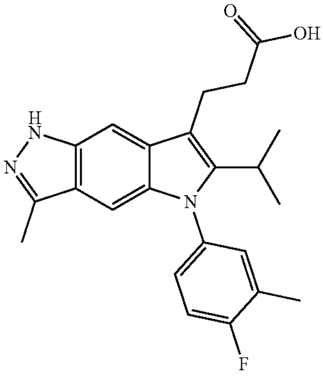
55
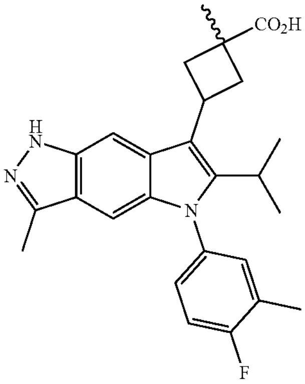

-continued
56
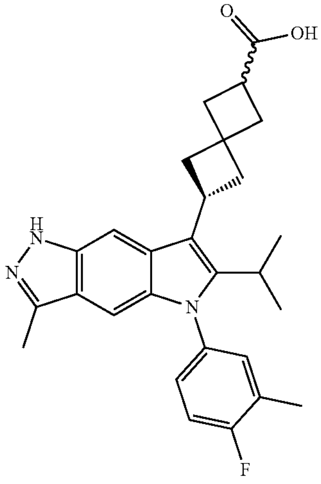
[Racemic]
57
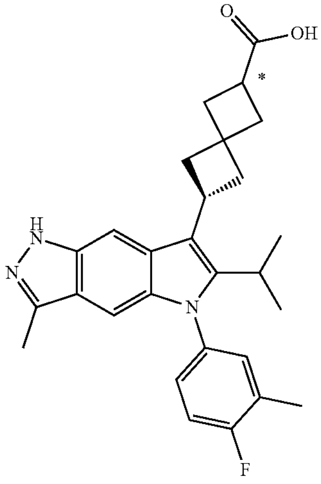
[Enantiomer-1]
58
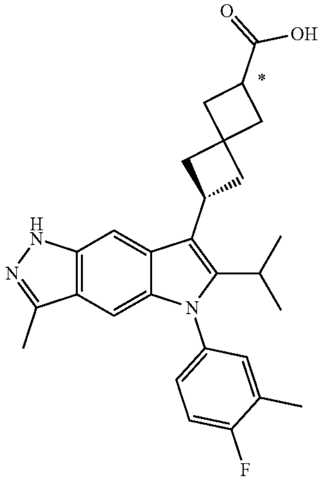
[Enantiomer-2]
-continued
59
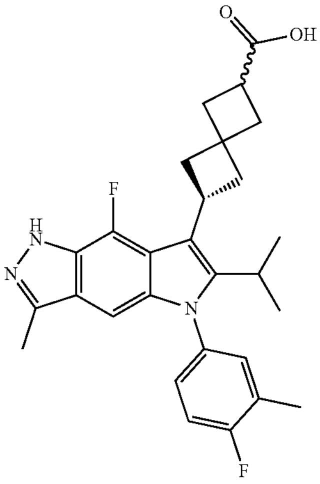
60
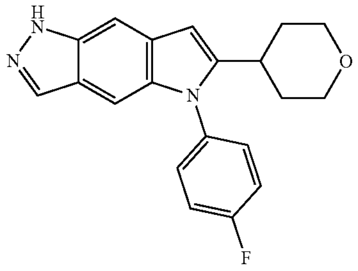
61
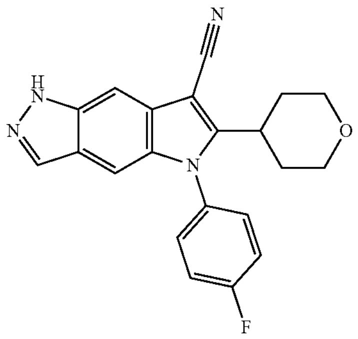
62
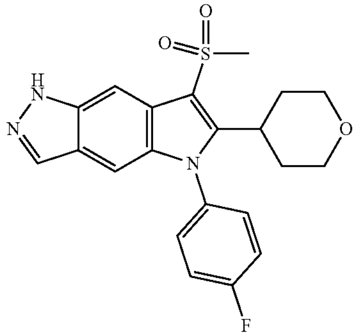

-continued
63
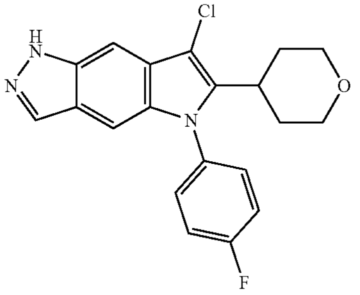
64
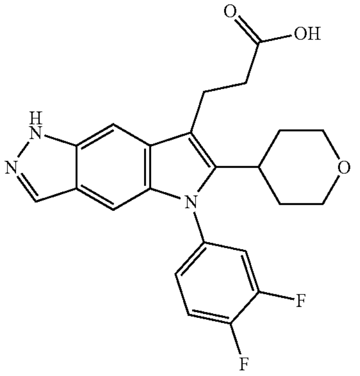
65
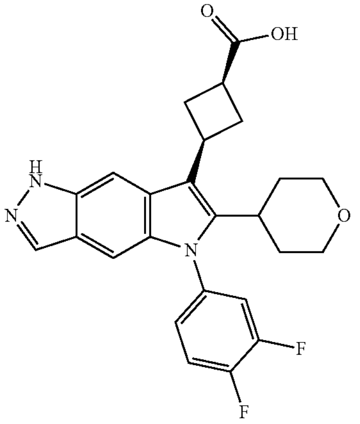
66
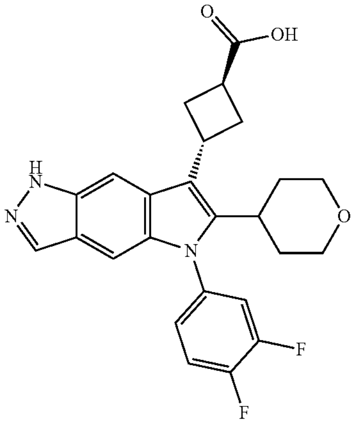
-continued
67
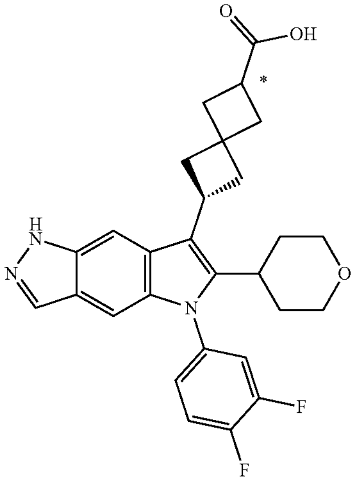
[Enantiomer-1]
68
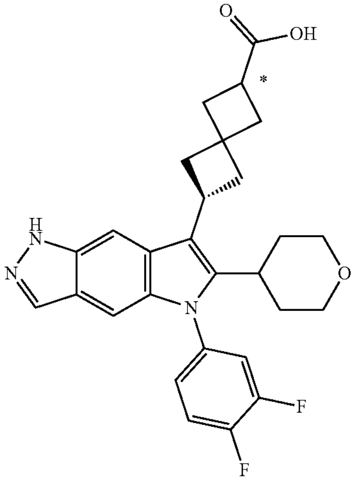
[Enantiomer-2]
69
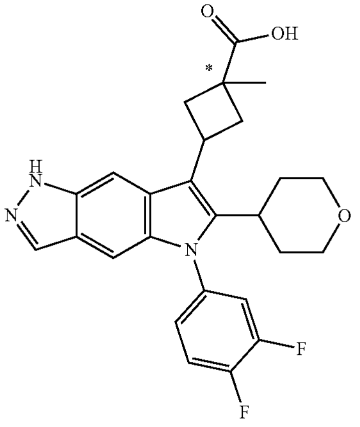
[Isomer-1]

-continued
70
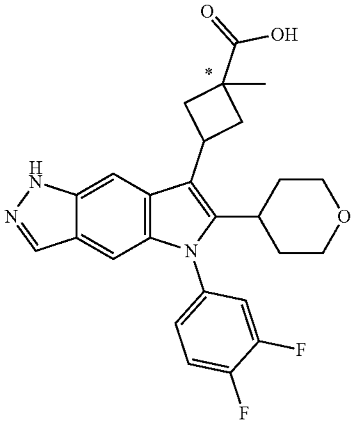
[Isomer-2]
71
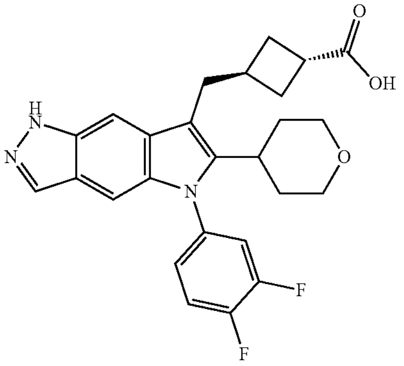
72
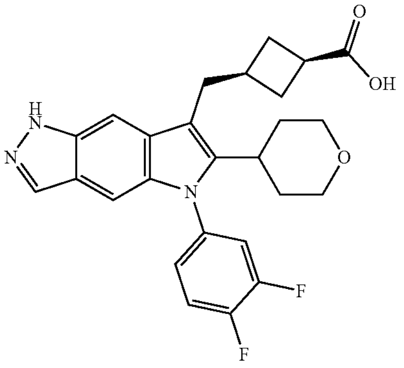
73
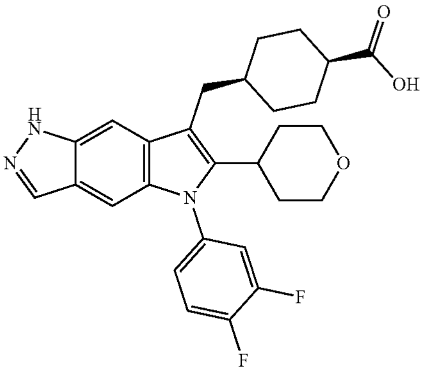
-continued
74
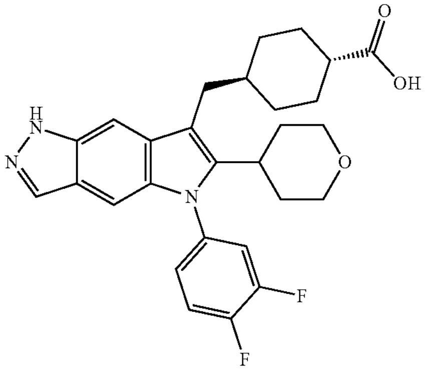
75
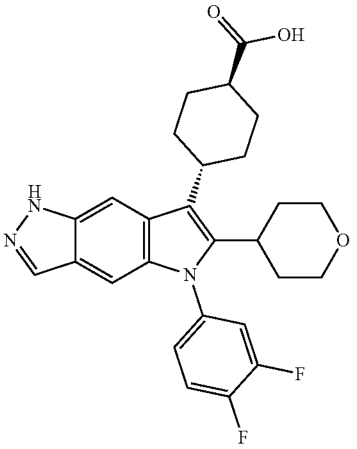
76
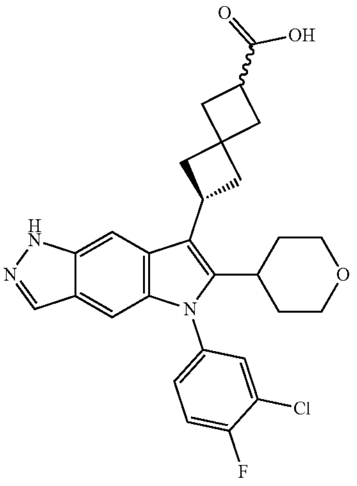
Racemic -continued
77
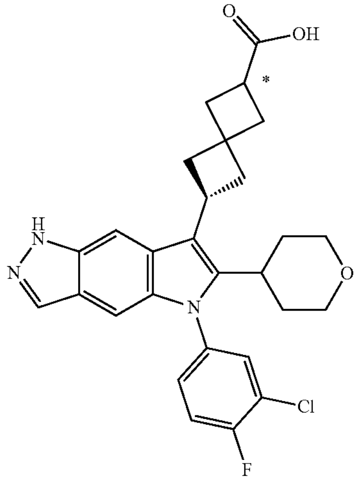
[Enantiomer-1]
78
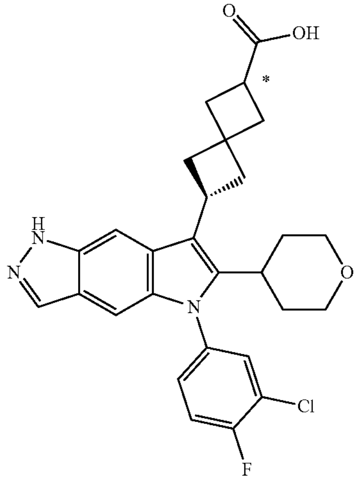
[Enantiomer-2]
79
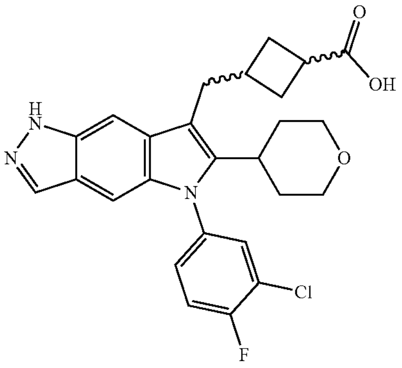
-continued
80
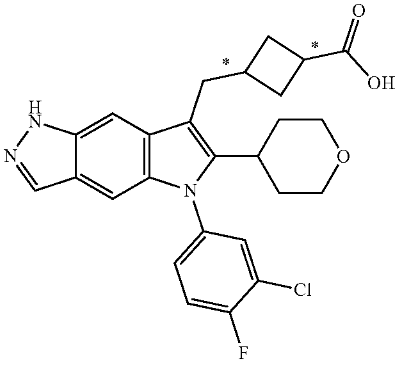
[Isomer-1]
81
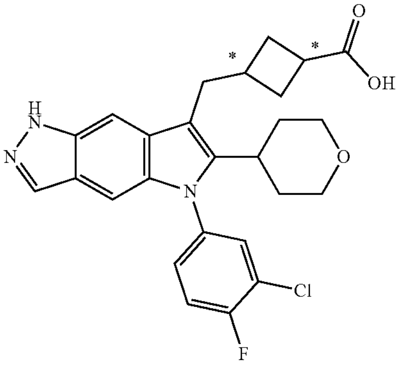
[Isomer-2]
82
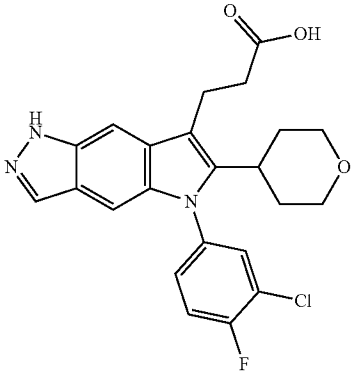
83
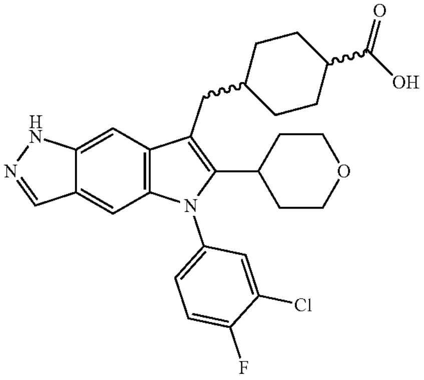

-continued
84
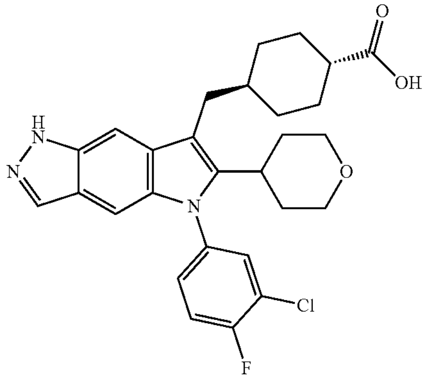
85
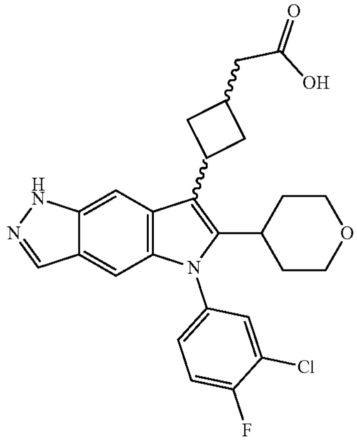
86
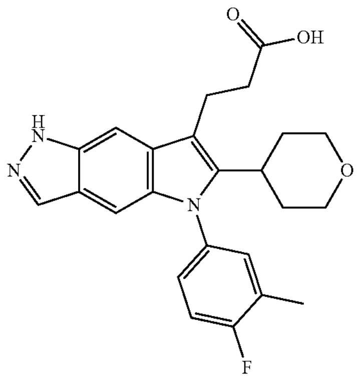
87
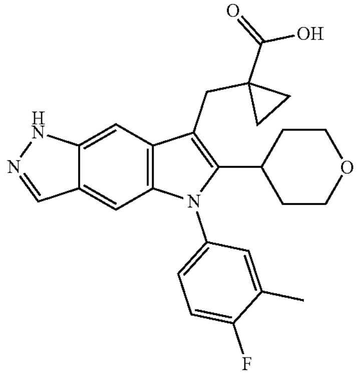
-continued
88
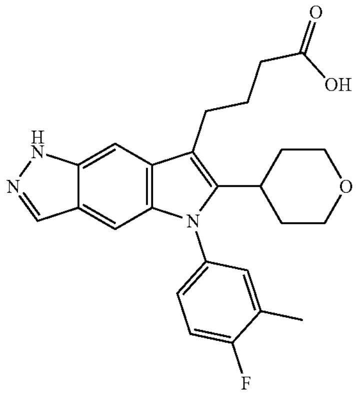
89
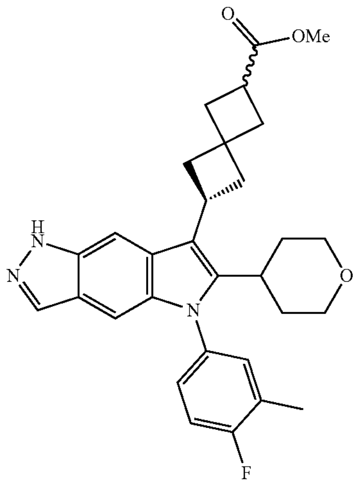
90
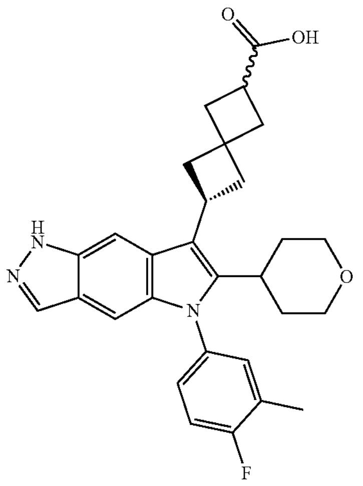

-continued
91
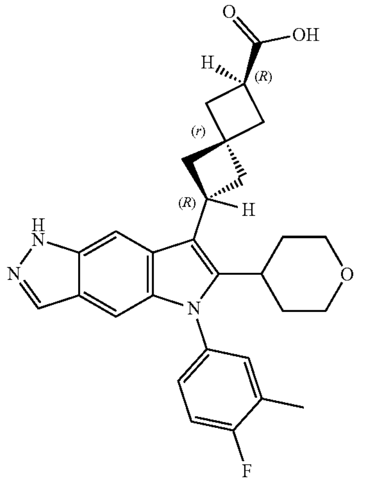
[Enantiomer-1]
92
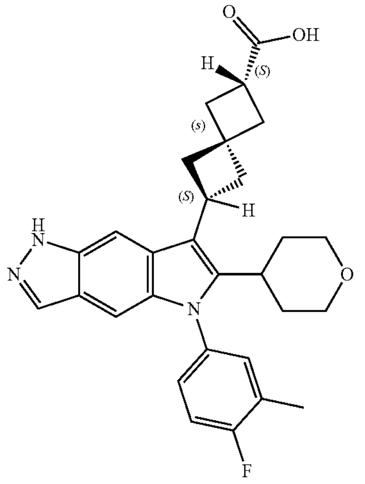
[Enantiomer-2]
93
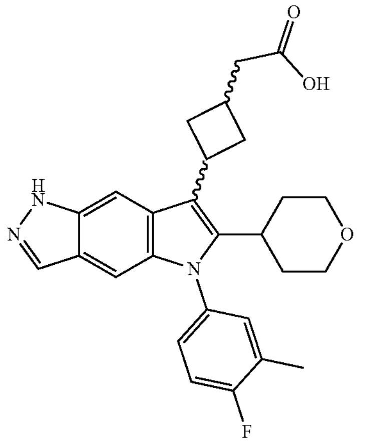
-continued
94
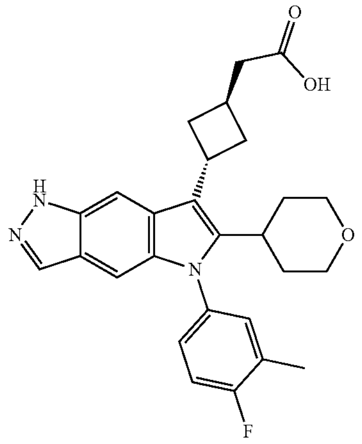
95
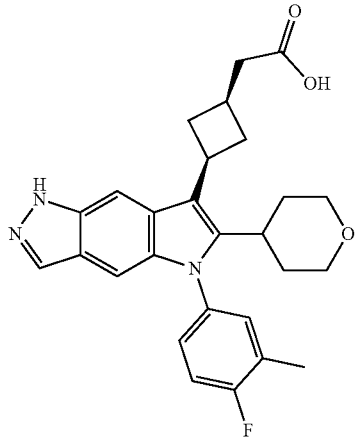
96
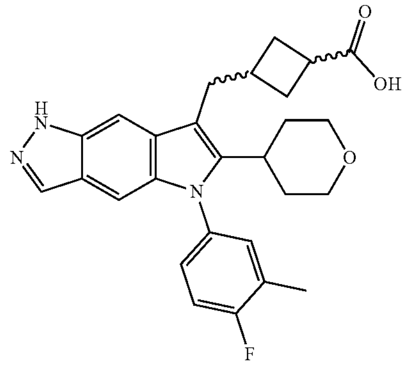
97
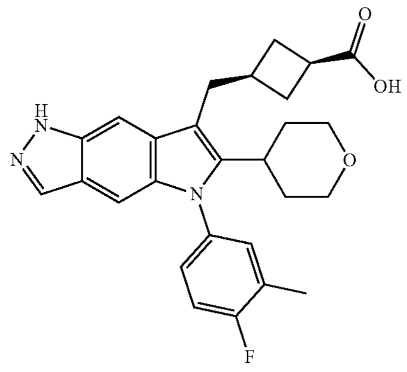

-continued
98
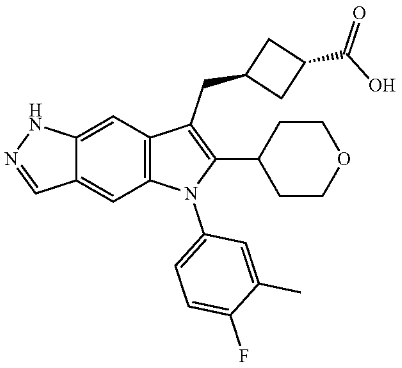
99
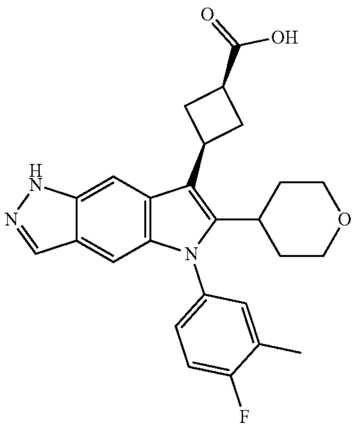
100
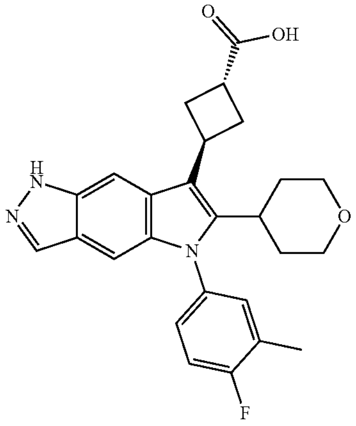
-continued
101
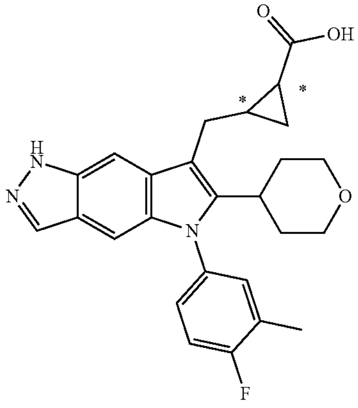
[TRANS-Enantiomer-1]
102
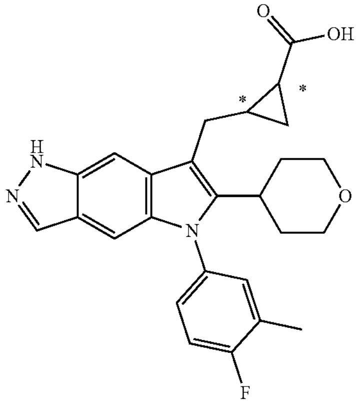
[TRANS-Enantiomer-2]
103
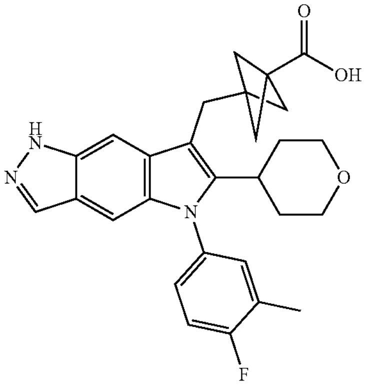

-continued
104
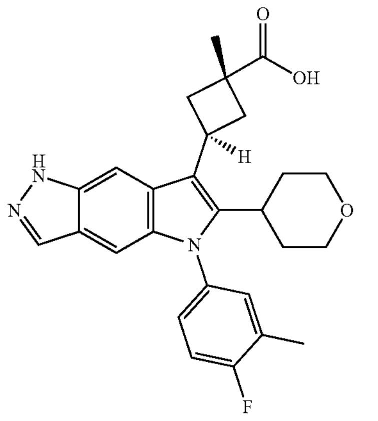
105
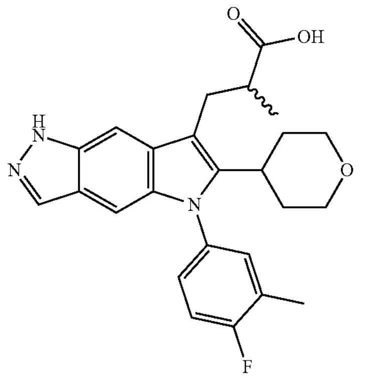
106
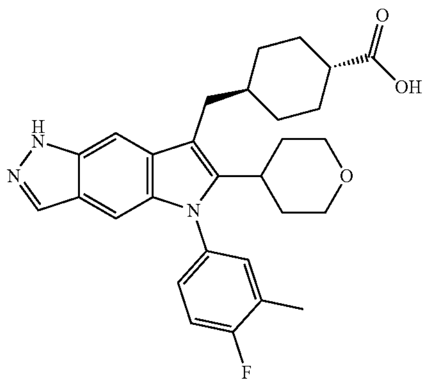
107
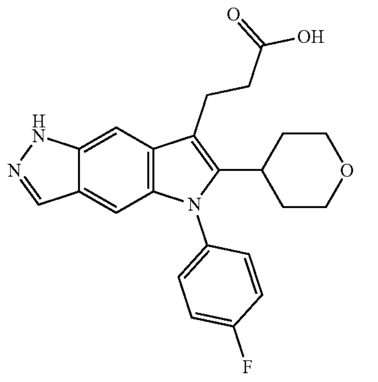
-continued
108
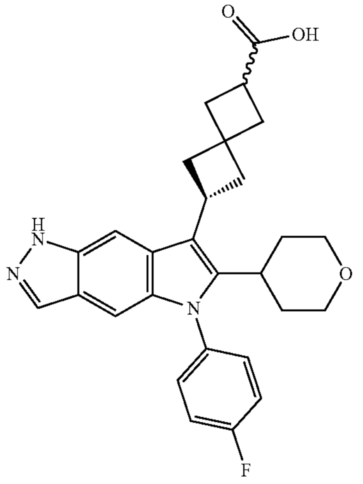
[Racemic]
109
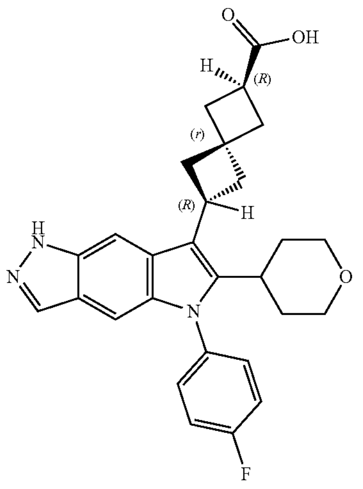
[Enantiomer-1]
110
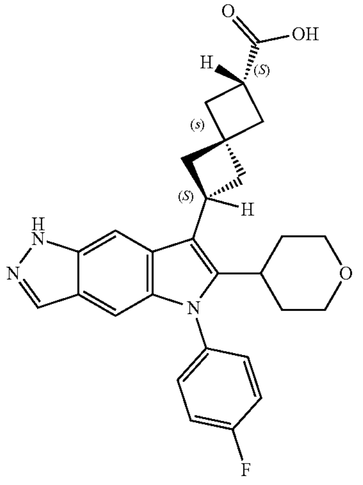
[Enantiomer-2]

-continued
111
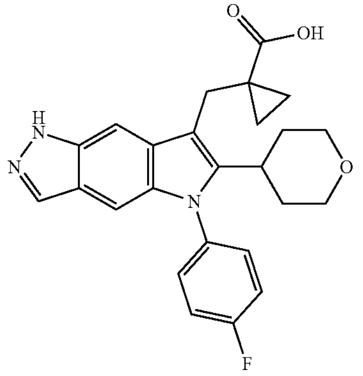
112
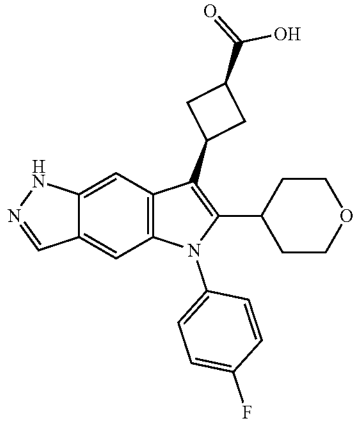
113
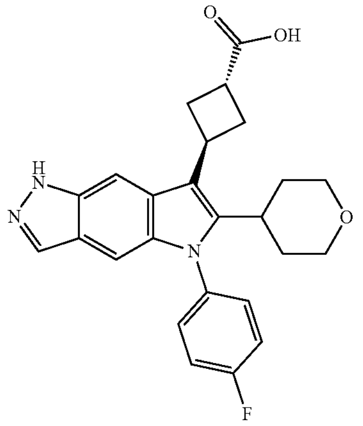
114
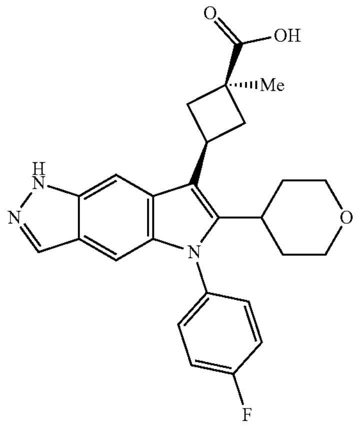
-continued
115
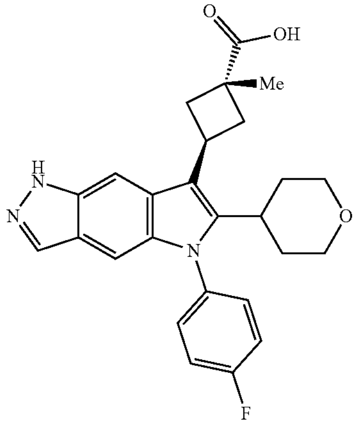
116
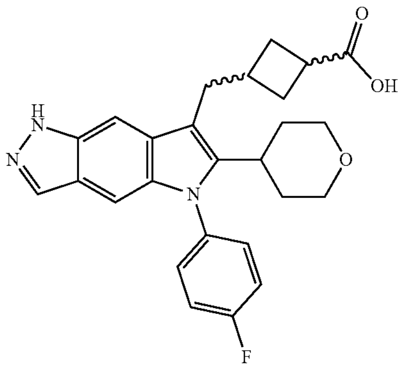
117
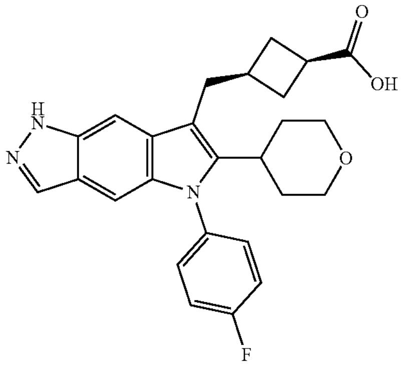
118
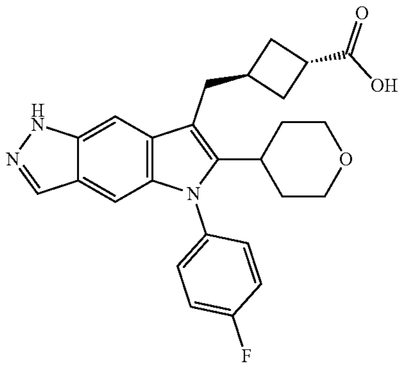

119
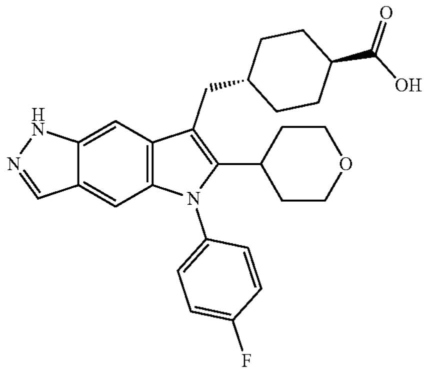
120
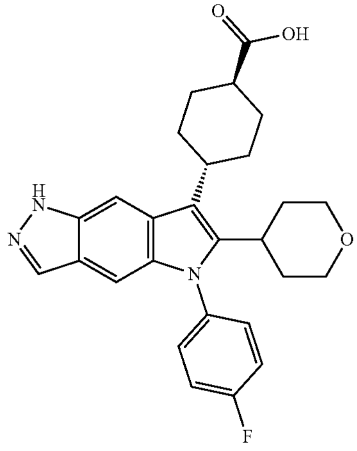
121
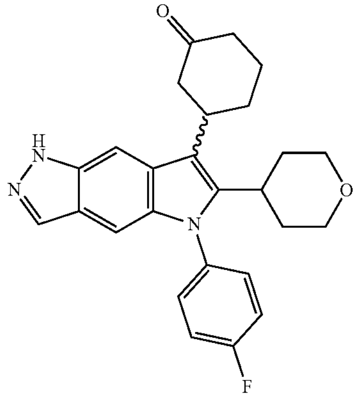
122
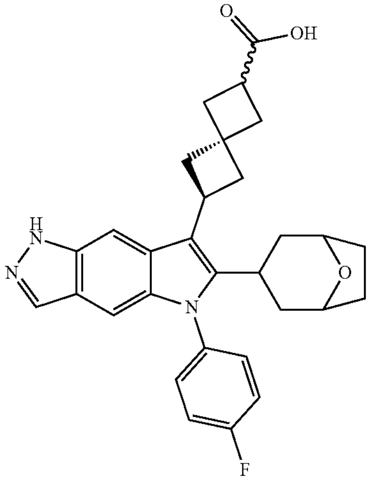
123
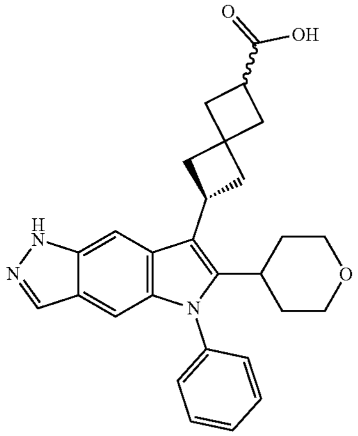
124
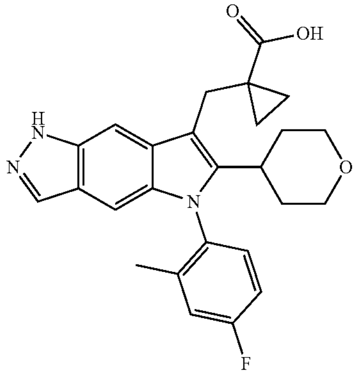

125
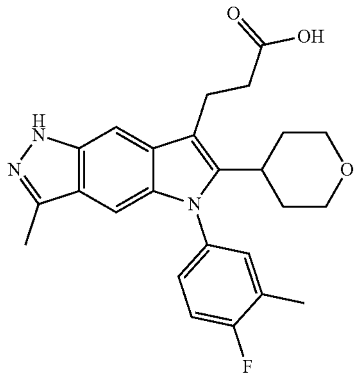
126
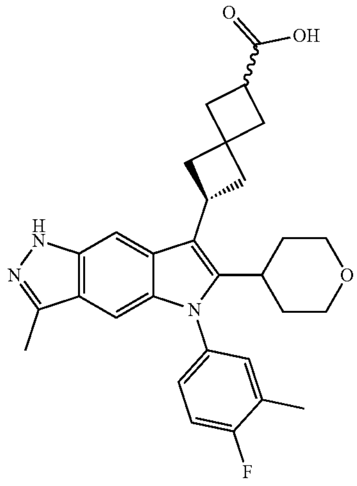
127
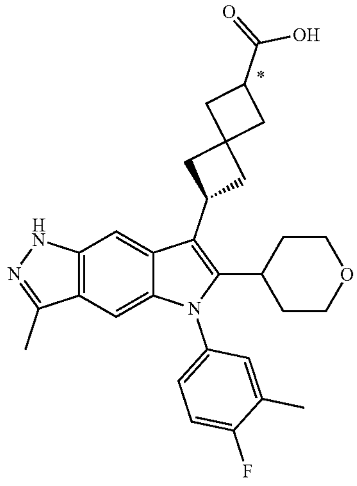
[Enantiomer-1]
128
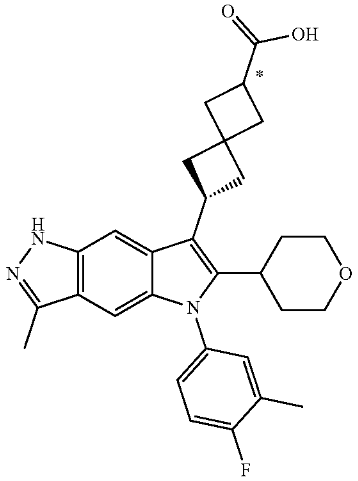
[Enantiomer-2]
129
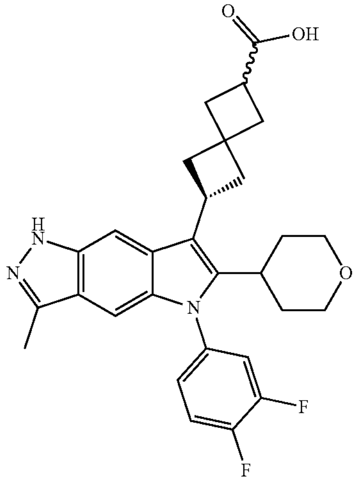
[Racemic]
130
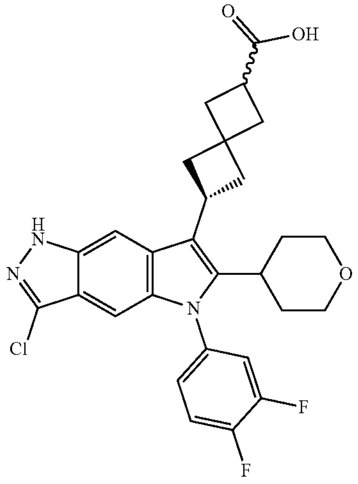

-continued
131
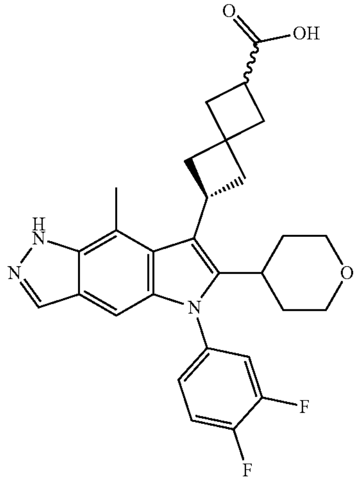
132
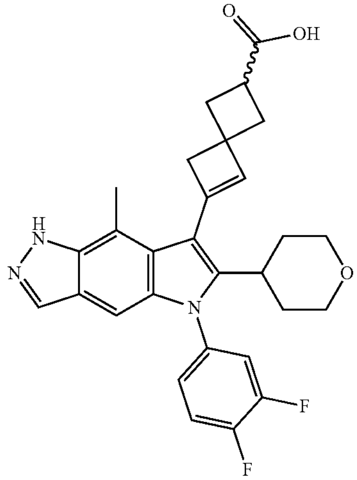
133
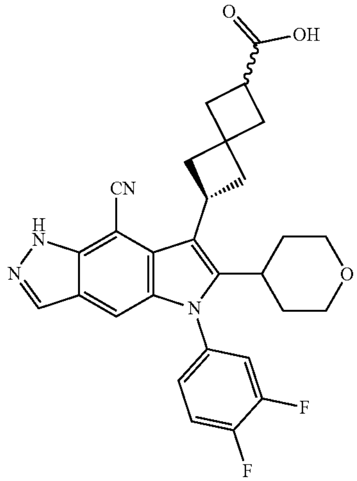
-continued
134
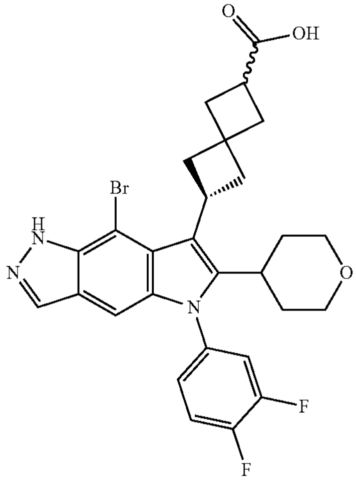
135
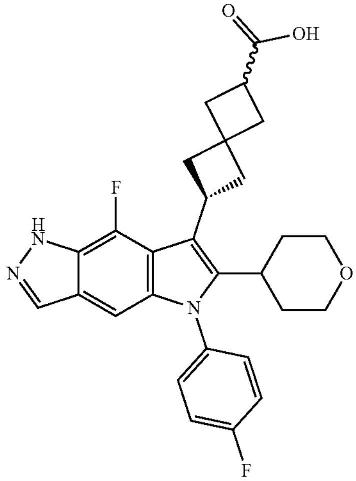
[Racemic]
136
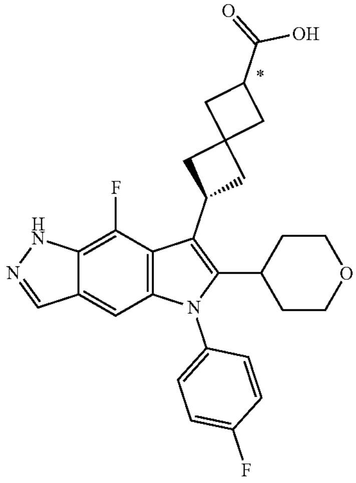
[Enantiomer-1]

-continued
137
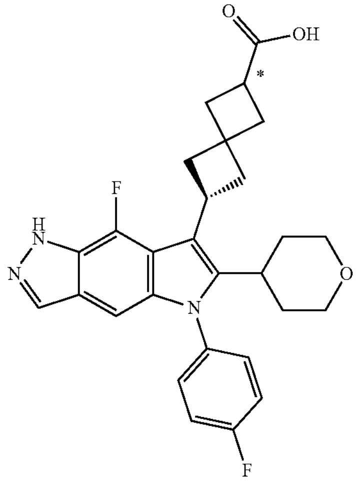
[Enantiomer-2]
138
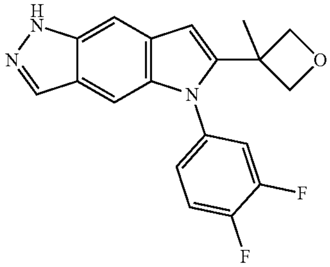
139
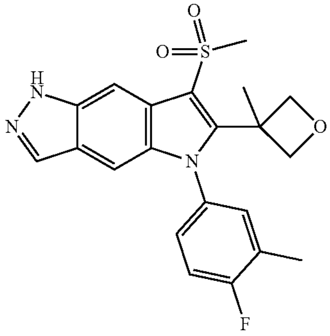
140
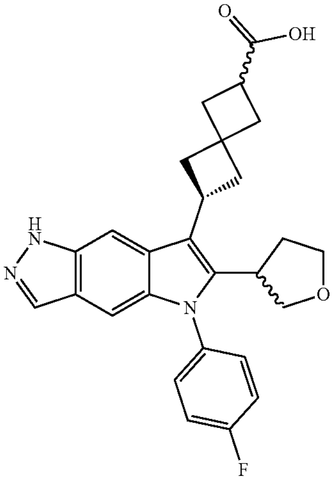
-continued
141
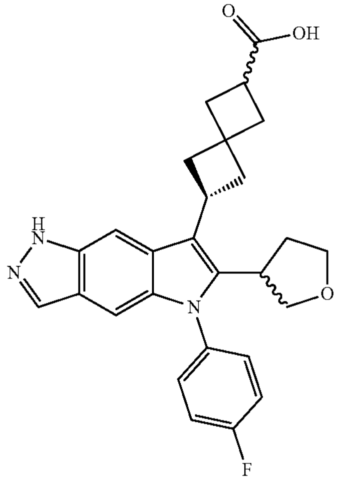
143
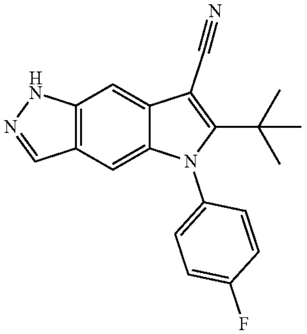
144
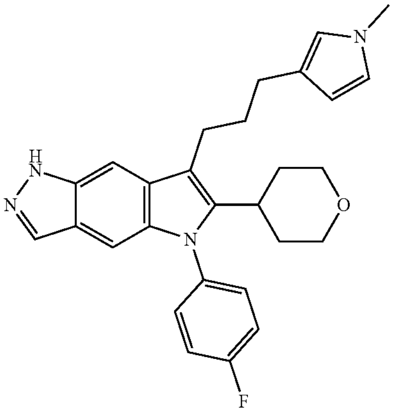
145
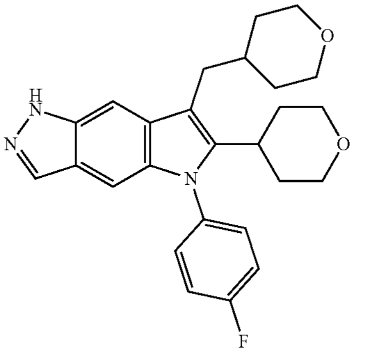

-continued
146
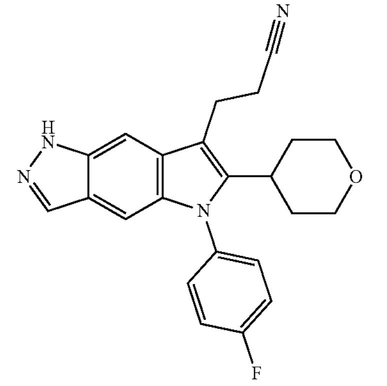
147
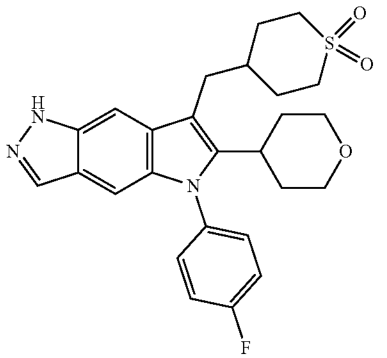
148
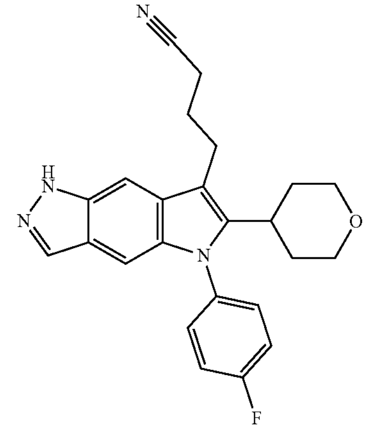
149
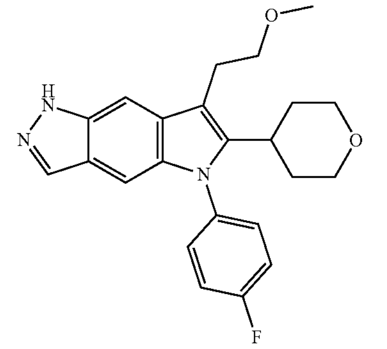
-continued
150
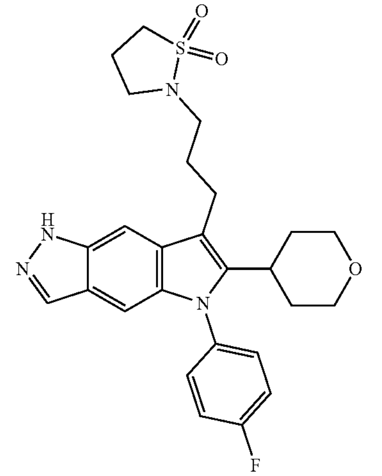
151
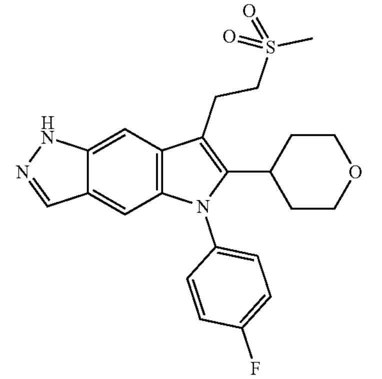
152
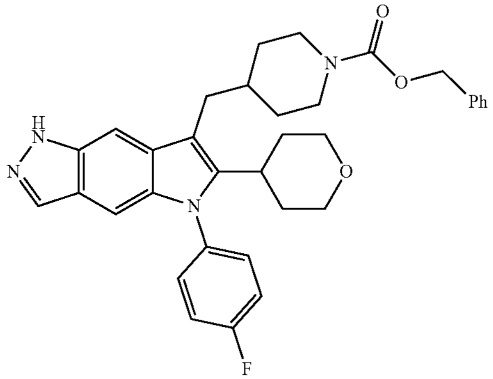
153
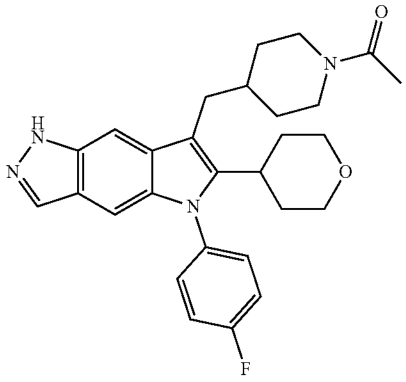

-continued
154
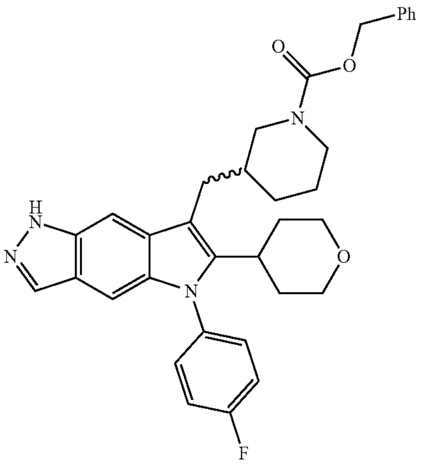
155
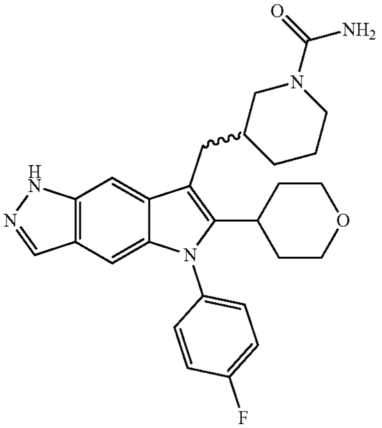
156
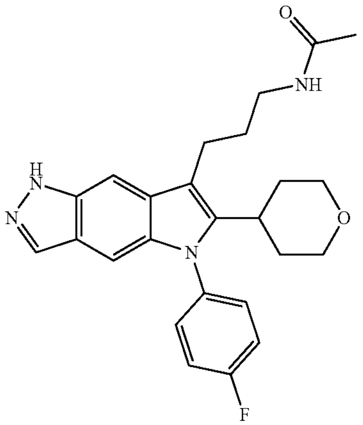
-continued
157
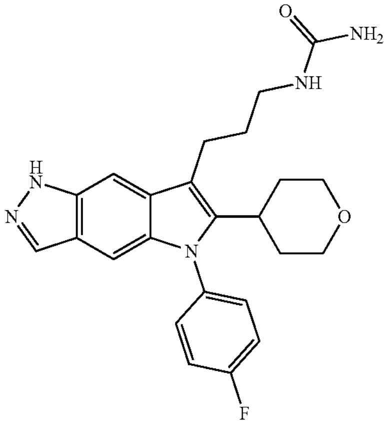
158
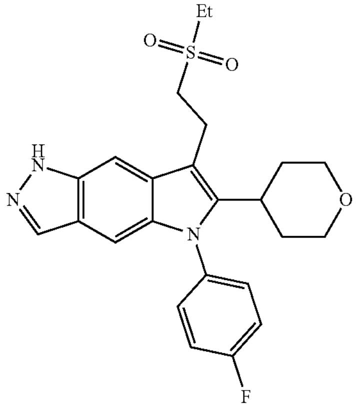
159
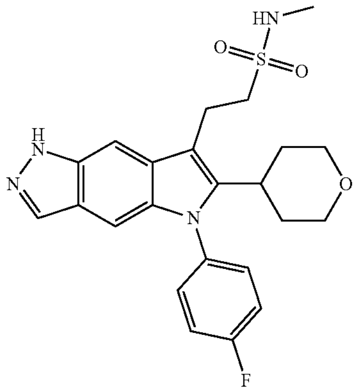
160
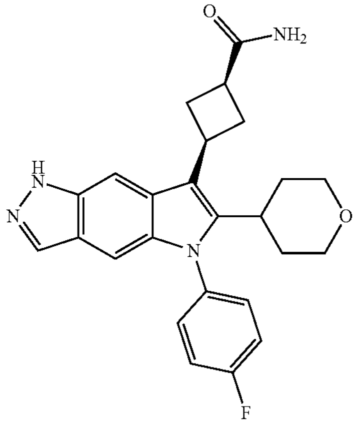

161
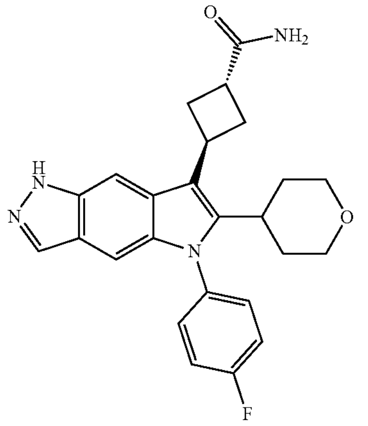
162
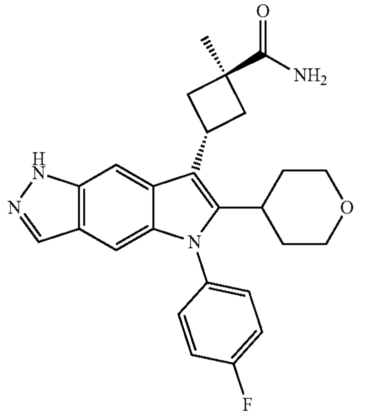
163
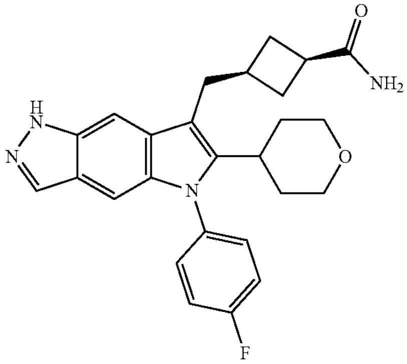
164
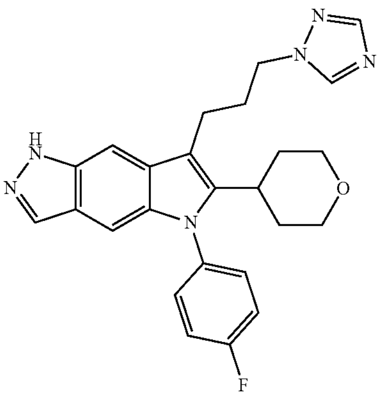
165
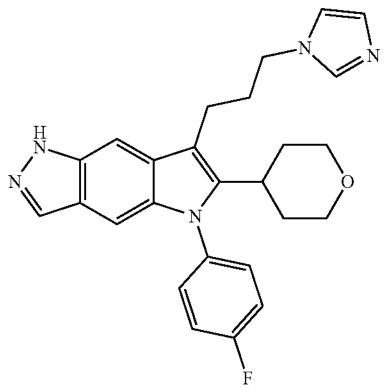
166
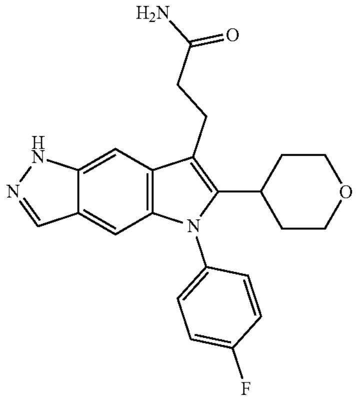
167
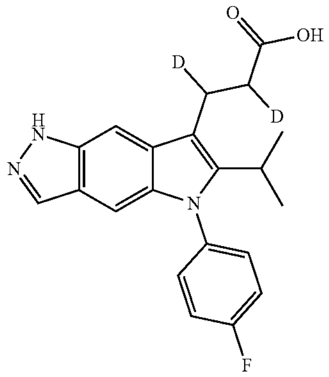
168
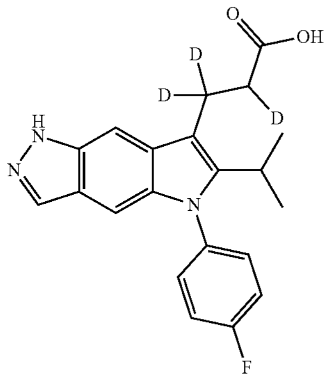

-continued
169
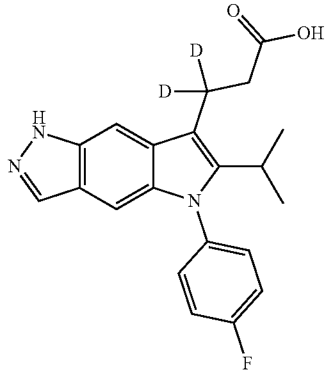
170
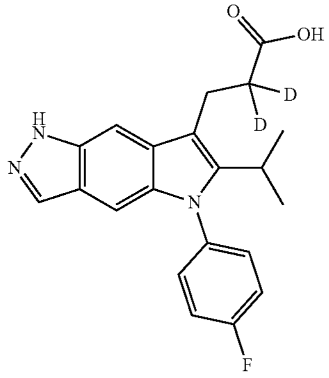
171
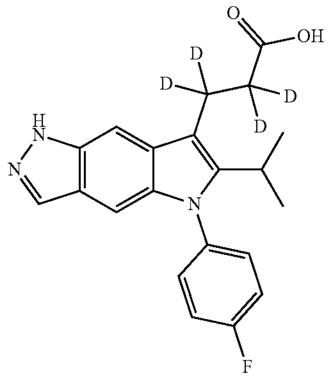
172
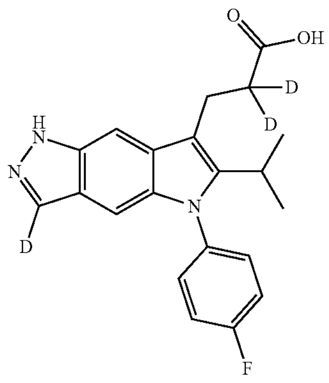
-continued
173
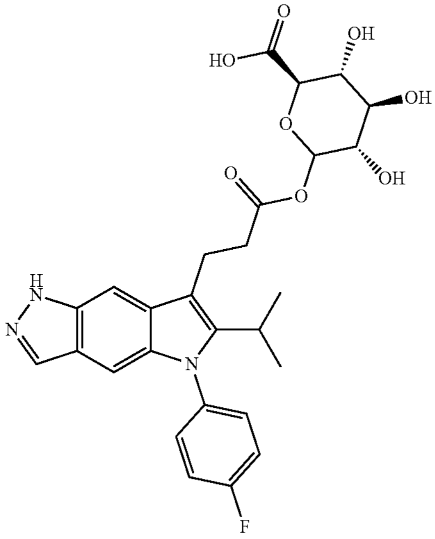
174
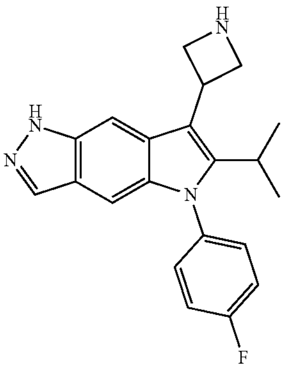
175
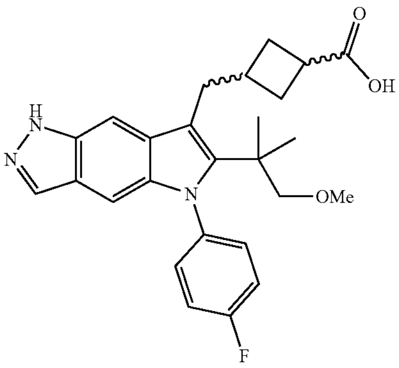

-continued
176
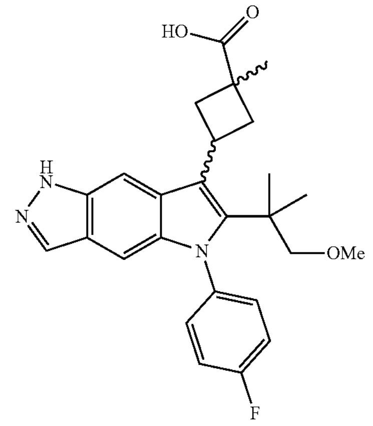
177
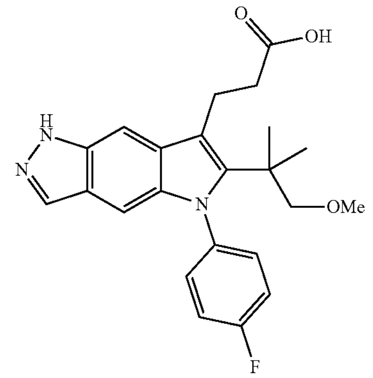
178
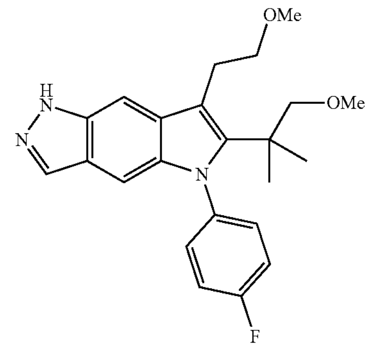
179
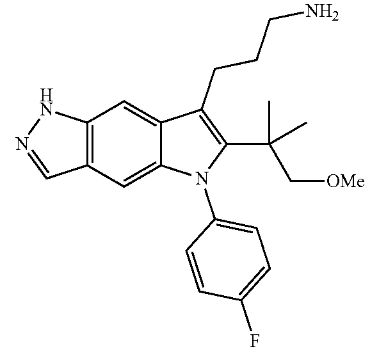
-continued
180
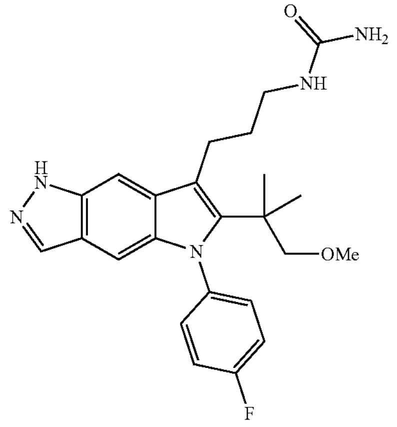
181
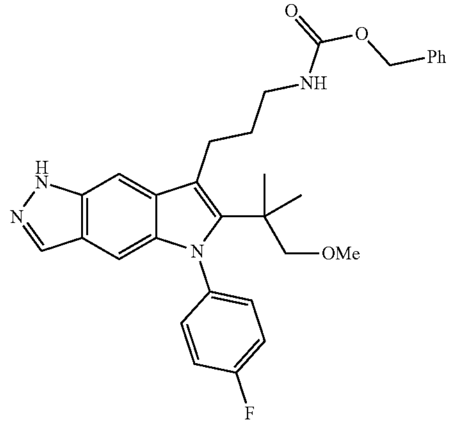
182
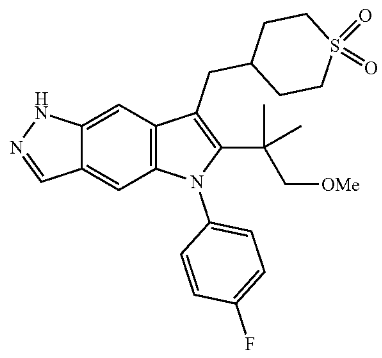
183
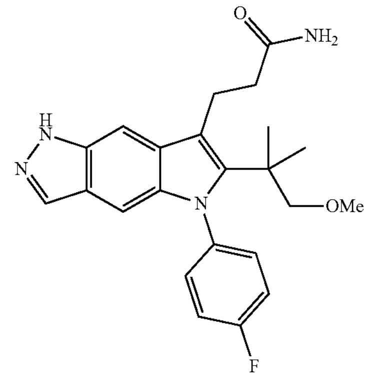

-continued
184
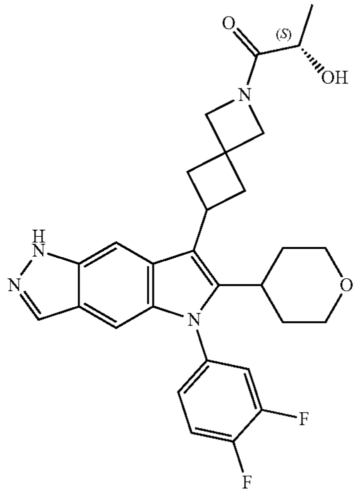
185
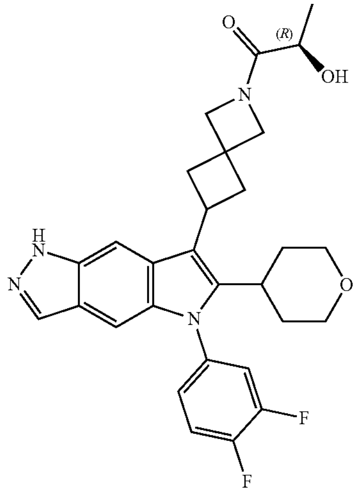
186
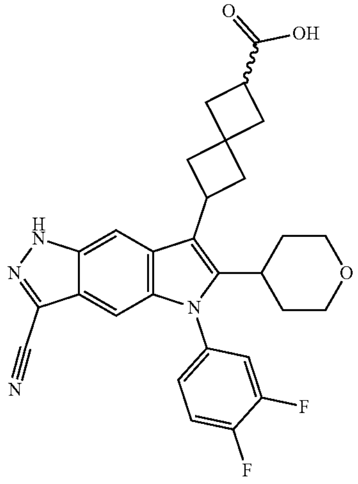
-continued
187
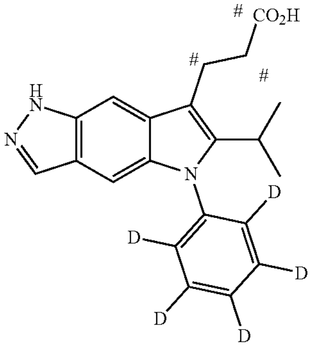
188
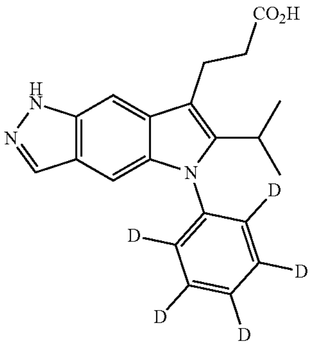
189
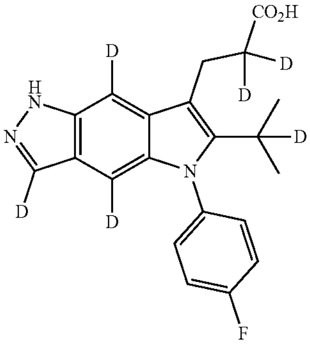
190
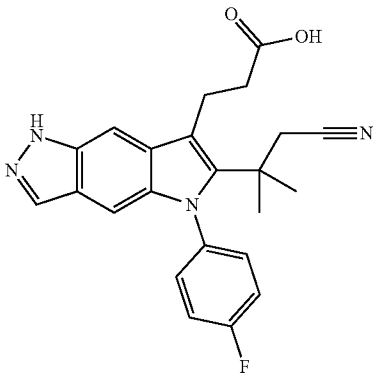

-continued
191
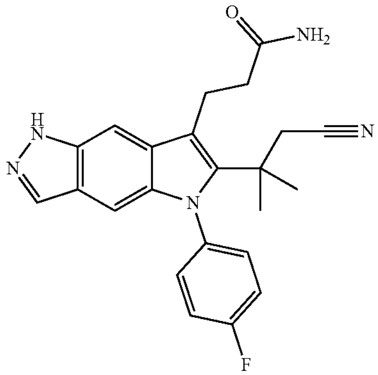
192
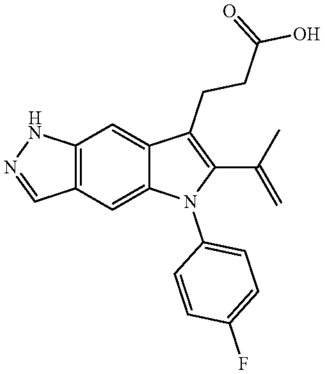
193
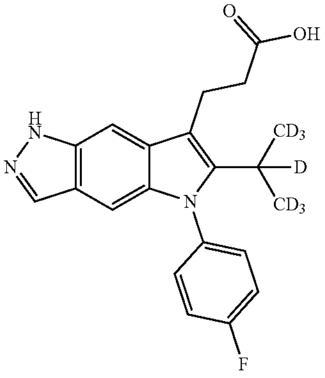
194
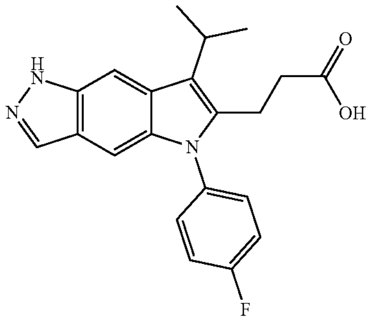
-continued
195
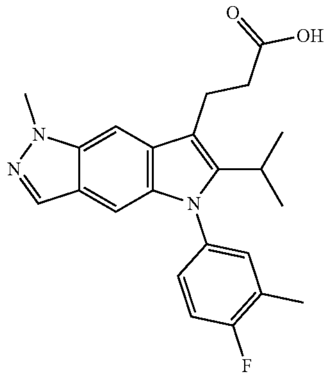
196
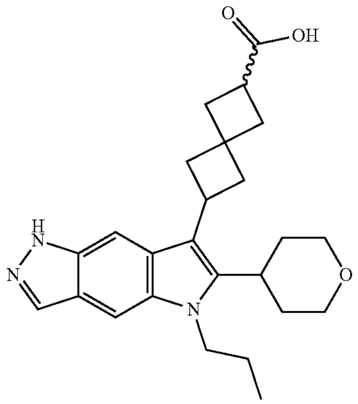
197
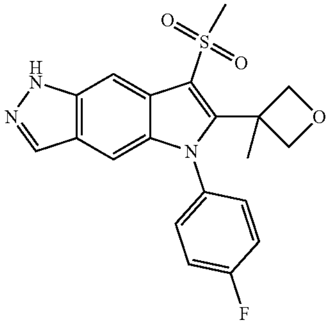
198
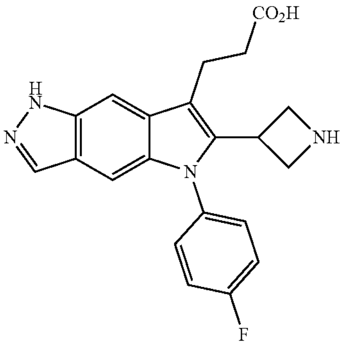

-continued
199
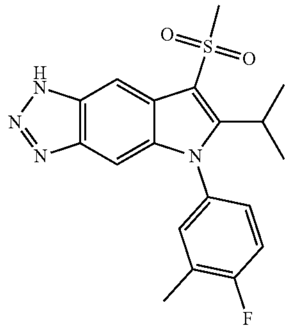
200
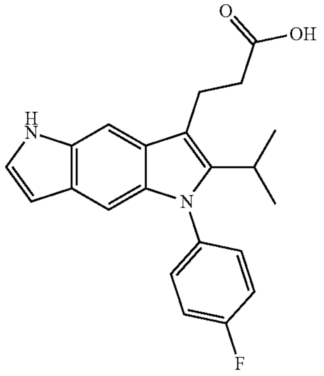
201
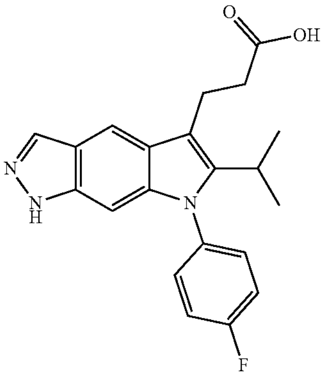
202
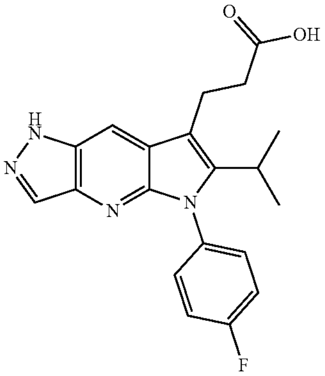
-continued
203
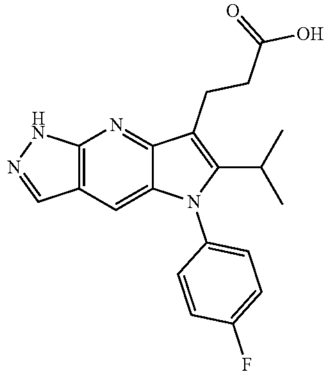
204
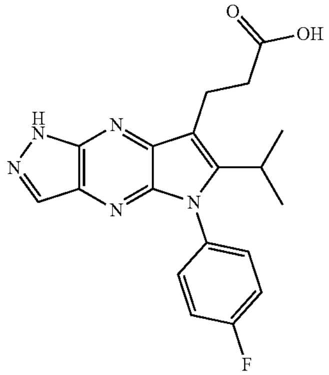
205
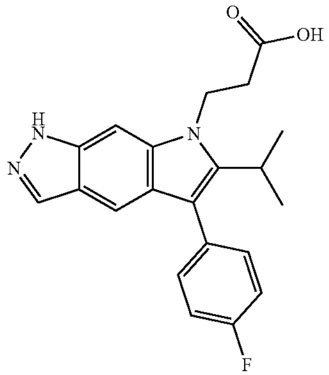
206
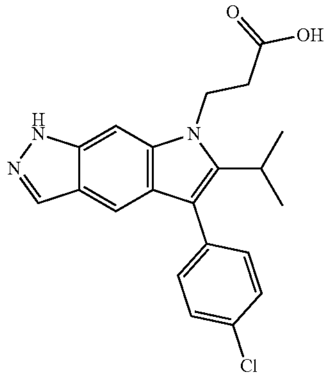

-continued
207
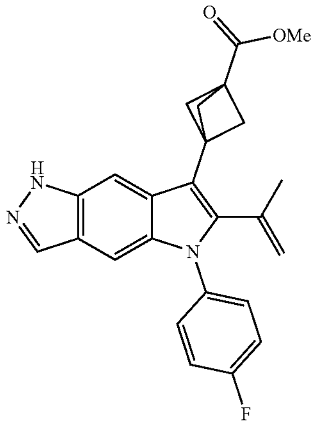
208
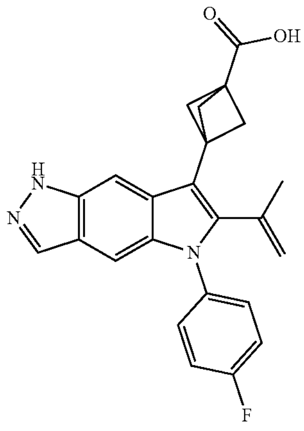
209
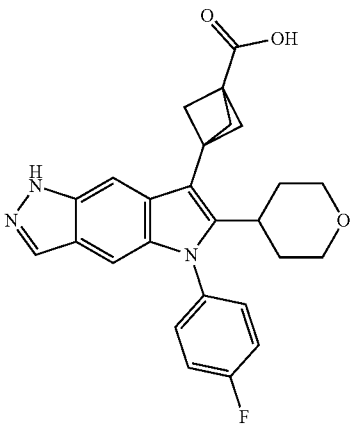
-continued
210
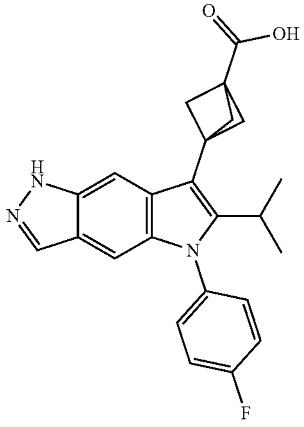
211
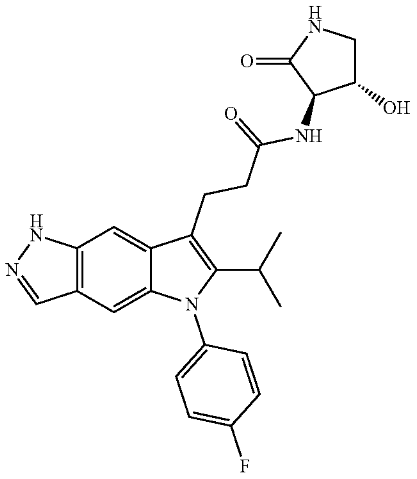
212
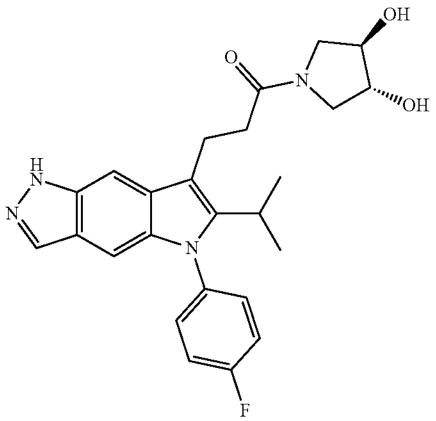

-continued

213

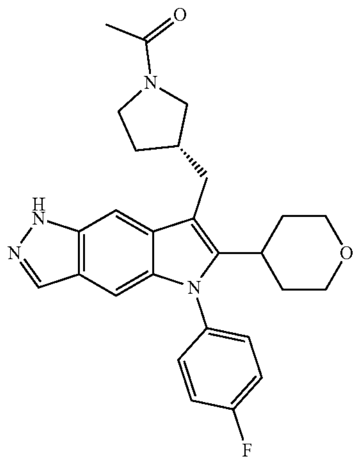

214

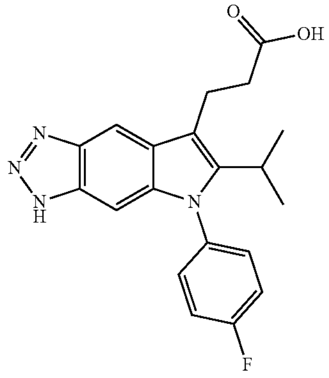

-continued

215

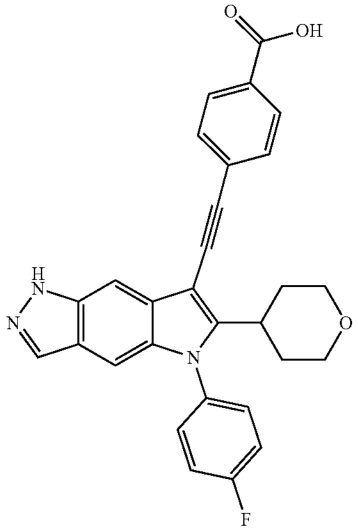

and tautomers thereof, pharmaceutically acceptable salts of the compounds and the tautomers, and deuterated derivatives of the compounds, the tautomers, and the pharmaceutically acceptable salts.

15. A compound selected from:

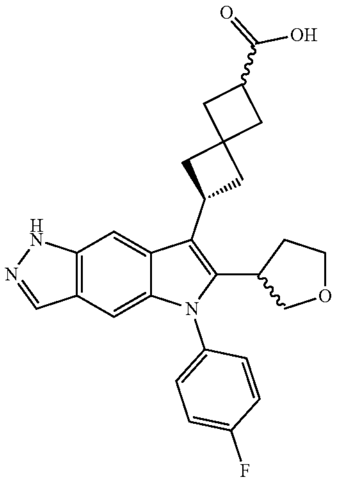

tautomers thereof, salts of the compound or the tautomers, and deuterated derivatives of the compound, the tautomers, or the salts.

* * * * *